(12) United States Patent
Betzig

(10) Patent No.: US 7,894,136 B2
(45) Date of Patent: *Feb. 22, 2011

(54) OPTICAL LATTICE MICROSCOPY USING PEDIODIC INTERFERENCE PATTERNS OF COHERENT WAVES

(76) Inventor: Robert Eric Betzig, 2174 Butternut Dr., Okemos, MI (US) 48864

( * ) Notice: Subject to any disclaimer, the term of this patent is extended or adjusted under 35 U.S.C. 154(b) by 689 days.

This patent is subject to a terminal disclaimer.

(21) Appl. No.: 11/719,928

(22) Filed: May 22, 2007

(65) Prior Publication Data

US 2009/0073563 A1    Mar. 19, 2009

Related U.S. Application Data

(63) Continuation of application No. PCT/US2005/042686, filed on Nov. 23, 2005.

(60) Provisional application No. 60/630,021, filed on Nov. 23, 2004.

(51) Int. Cl.
G02B 27/00 (2006.01)

(52) U.S. Cl. .................. 359/577; 359/578; 359/370

(58) Field of Classification Search .................. None
See application file for complete search history.

(56) References Cited

U.S. PATENT DOCUMENTS

| | | | |
|---|---|---|---|
| 5,731,588 A | 3/1998 | Hell | |
| 5,867,604 A | 2/1999 | Ben-Levy et al. | |
| 6,255,642 B1 | 7/2001 | Cragg et al. | |
| RE38,307 E | 11/2003 | Gustafsson et al. | |
| 7,609,391 B2 * | 10/2009 | Betzig | 356/521 |
| 2004/0114138 A1 | 6/2004 | Hell | |
| 2007/0282030 A1 | 12/2007 | Anderson et al. | |
| 2009/0046298 A1 * | 2/2009 | Betzig | 356/521 |

2009/0135432 A1    5/2009    Betzig

FOREIGN PATENT DOCUMENTS

WO    WO-2006058187 A2    6/2006
WO    WO-2006058187 A3    6/2006

(Continued)

OTHER PUBLICATIONS

E. Betzig, 'Sparse and composite coherent latttices', Phys. Rev. A, vol. 71, 063406, 2005.*

(Continued)

Primary Examiner—Arnel C Lavarias
(74) Attorney, Agent, or Firm—Brake Hughes Bellermann LLP

(57) ABSTRACT

A method for creating a periodic interference pattern of coherent waves in two or three dimensions, D, includes generating at least D+2 waves, where each wave has substantially the same wavelength, $\lambda$, and travels substantially in a unique direction, $k_n$. The waves are directed such that at least a portion of each wave intersects in a common excitation region to create the interface pattern. The directions, $k_n$, of the waves are selected such that the interference pattern within the excitation region forms a Bravais lattice, and at least one wave travels substantially in a direction, $k_i$, such that one or more symmetry operations characteristic of the Bravais lattice map the direction of the wave, $k_i$, onto a direction of a different wave, $k_j$. The directions of the waves, $k_n$, do not all lie on a D-dimensional set of mutually orthogonal axes.

44 Claims, 175 Drawing Sheets

FOREIGN PATENT DOCUMENTS

WO    WO-2006058187 C1    6/2006

OTHER PUBLICATIONS

A. Dwivedi, J. Xavier, J. Joseph, K. Singh, 'Formation of all fourteen Bravais lattices of three-dimensional photonic crystal structures by a dual beam multiple-exposure holographic technique', Appl. Opt., vol. 47, No. 12, Apr. 20, 2008, pp. 1973-1980.*

Y. Ono, T. Ochi, 'All fourteen Bravais lattices can be fabricated by triple exposure of two-beam interference fringes', Proc. SPIE, vol. 6327, 632709, 2006.*

S. Shoji, R. P. Zaccaria, H. Sun, S. Kawata, 'Multi-step multi-beam laser interference patterning of three-dimensional photonic lattices', Opt. Express, vol. 14, No. 6, Mar. 20, 2006, pp. 2309-2316.*

Betzig, E., "Excitation Strategies for Optical Lattice Microscopy", *Optics Express*, 13(8), (Apr. 18, 2005),3021-3036.

Cai, L. Z., et al., "Formation of Three-Dimensional Periodic Microstructures by Interference of Four Noncoplanar Beams", *J. Opt. Soc. Am. A*, 19(11), (Nov. 2002),2238-2244.

Cai, L. Z., et al., "What Kind of Bravais Lattices can be Made by the Interference of Four Umbrella Like Beams?", *Optics Communications*, 224, (Sep. 1, 2003),243-246.

Campbell, M., et al., "Fabrication of Photonic Crystals for the Visible Spectrum by Holographic Lithography", *Nature*, 404, (Mar. 2, 2000),53-56.

Yuan, L., et al., "Arrangements of Four Beams for Any Bravais Lattice", *Optics Letters*, 28(19), (Oct. 1, 2003),1769-1771.

Axelrod, D. et al., "Total internal reflection fluorescent microscopy", Journal of Microscopy 129(1): 19-28, (Jan. 1983),pp. 19-28.

Berger, et al., ""Photonic band gaps and holography"", J. Appl. Physics 82 (1)., (Jul. 1, 1997),60-64.

Betzig, E "Proposed method for molecular optical imaging", vol. 20, No. 3. Optics Letters, (Feb. 1, 1995),pp. 237-239.

Blonk, J. C., et al., "Fluorescence photobleaching recovery in the confocal scanning light microscope", Journal of Microscopy, Vo. 169, Pt. 3, (Mar. 1993),pp. 363-374.

Bobroff, N. et al., "Position measurement with a resolution and noise-limited instrument", Rev. Sci. Instrum., vol. 57, No. 6, (Jun. 1986),1152-1157.

Booth, Martin J., et al., "Adaptive aberration correction in a confocal microscope", PNAS, vol. 99, No. 9, (Apr. 30, 2002),5788-5792.

Cai, et al., "All fourteen Brava is lattices can be formed by interference of four noncoplanar beams", Optics Letters. vol. 27, No. 11, (Jun. 1, 2002),900-902.

Cai, et al., "Formation of a microfiber bundle by interference of three noncoplanar beams", Optics Letters. vol. 26, No. 23., (Dec. 1, 2001),1858-1860.

Chan, et al., "Photonic band gap templating using optical interference lithography", Physical Review E. 71, (Apr. 7, 2005),046605-1-046605-18.

Cheng, Ji-Xin et al., "Laser-Scanning Coherent Anti-Stokes Raman Scattering Microscopy and Applications to Cell Biology", Biophysical Journal, vol. 83, (Jul. 2002),pp. 502-509.

Frohn, Jan T., et al., "True optical resolution beyond the Rayleigh limit achieved by standing wave illumination", PNAS, vol. 97, No. 13, (Jun. 20, 2000),pp. 7232-7236.

Gustafsson, M.. G., et al., "I5M: 3D widefield light microscopy with better than 100nm axial resolution", The Royal Microscopical Society, Journal of Microscopy, 195, (1999),pp. 10-16.

Hell, Stefan W., et al., "Breaking the diffraction resolution limit by stimulated emission: stimulated-emission-depletion fluorescence microscopy", Optics Letters, vol. 19, No. 11, (Jun. 1, 1994),pp. 780-782.

Hess, Samuel T., et al., "Biological and Chemical Applications of Fluorescence Correlation Spectroscopy: A Review", Biochemistry, vol. 41, No. 3, (Jan. 22, 2002),pp. 697-705.

Neil, M. A., et al., "Adaptive aberration correction in a two-photon microscope", J. Microsc., vol. 200, (2000),pp. 105-108.

Petsas, K I., et al., "Crystallography of optical lattices", Phys. Rev. A, vol. 50, No. 6, (Dec. 1994),5173-5189.

Schuler, Benjamin et al., "Probing the free-energy surface for protein folding with single-molecule fluorescence spectroscopy", Nature, vol. 419,, (Oct. 17, 2002),pp. 743-747.

Sharp, ""Photonic crystals for the visible spectrum by holographic lithography"", Optical and Quantum Electronics. 34., (2002),3-12.

So, Peter T., et al., "Resolution enhancement in standing-wave total internal reflection microscopy: a point-spread-function engineering approach", J. Opt. Soc. Am. A, vol. 18, No. 11, (Nov. 2001),pp. 2833-2845.

Timp, G. et al., "Using light as a lens for Submicron, neutral atom lithography", Phys. Rev. Lett., vol. 69, No. 11, (Sep. 14, 1992),pp. 1636-1639.

Wang, et al., "Three-dimensional photonic crystals fabricated by visible light holographic lithography", Applied Physics Letiers. vol. 82, No. 14, (Apr. 7, 2003),2212-2214.

Weiss, S. "Fluorescence Spectroscopy of Single Biomolecules", Science, vol. 283, (Mar. 12, 1999),pp. 1676-1683.

"Notice of Allowance, U.S. Appl. No. 11/719,931, filed on May 22, 2007, Notice of Allowability dated Apr. 27, 2009".

* cited by examiner

OPTICAL LATTICE MICROSCOPY USING PEDIODIC INTERFERENCE PATTERNS OF COHERENT WAVES

CROSS REFERENCE TO RELATED APPLICATIONS

This application is a continuation of International Patent Application No. PCT/US2005/042686, filed Nov. 23, 2005, entitled "OPTICAL LATTICE MICROSCOPY," which itself claims priority to U.S. Patent Application No. 60/630,021, filed Nov. 23, 2004, entitled, OPTICAL LATTICE MICROSCOPY," both of which are incorporated by reference herein in their entirety.

TECHNICAL FIELD

This disruption relates to optical lattices and related components, systems, and methods, and, in particular, to optical lattice microscopy.

BACKGROUND

Optical microscopy is useful for the study of living cells, because of its comparatively weak effect on the intracellular environment and because of the wealth of information that can be extracted from highly developed optical techniques, such as time resolved spectroscopy. Because living cells are three-dimensional (3D) systems that exhibit features on length scales from the atomic to macroscopic and dynamic evolution on time scales over many orders of magnitude, the refinement of optical microscopy to visualize these features and this evolution with ever increasing spatial and temporal resolution remains an area of active interest.

Referring to FIG. 1, a common approach in optical microscopy is to illuminate a sample 102 with light filling the rear pupil 100 of an objective lens 101, and then to collect the light resulting from the interaction of the focused illumination with the sample 102 using either the same lens 101 or a different lens. In widefield microscopy, as shown in FIG. 1, the excitation light 103 from a source 104 impinges on the plane of the rear pupil 100 from a multitude of angles, so that the entire field of view within the sample 102 is illuminated simultaneously. Then, a detector 106 images the collected light 105 representing the signal of interest. Because detection across the entire field of view usually occurs simultaneously, widefield imaging can be quite rapid.

Light 107 emitted near the focal plane 108 of the objective 101 produces a clear, focused image at the detector 106. However, a widefield system also collects light (e.g., 109 and 110) emitted from other planes (e.g., 111 and 112), which can create an out-of-focus background haze in thicker samples 102 and obscure the crisp image data from the focal plane 108.

As shown in FIG. 2, confocal microscopy addresses this issue by: (a) illuminating the objective lens 101 at its rear pupil 100 with a nearly parallel beam of light 200, which, for example, can be created by filtering the excitation light 103 through a pinhole mask 201 and subsequently collimating the light with a lens 205, thereby creating a single, concentrated spot of light 206 within the focal plane 207; and (b) centering a pinhole 208 in an opaque mask 210 at the confocal position in the image plane 207 relative to the focal spot 206. Light 209 emitted from the sample 210 near the focal spot 206 is largely concentrated at the pinhole 208 and is passed to the detector 211. However, light (e.g., 212 and 213) from other focal planes (e.g., 214 and 215) is not well concentrated at the confocal position in the image plane 207 and, therefore, is mostly excluded from passing through the pinhole 208. By scanning the sample 210 and the focal spot 206/detection pinhole 208 combination relative to one another on a point-by-point basis in one, two, or three dimensions, a composite image can be captured by detector 211.

As shown in FIG. 3, the resolution of images created by confocal microscopy techniques (e.g., as shown in FIGS. 3D, 3E, and 3F) are often much sharper than equivalent images created by widefield microscopy techniques (e.g., as shown in FIGS. 3A, 3B, and 3C) due to the significant rejection of out-of-focus background haze that confocal microscopy can achieve. However, confocal microscopy images generally take longer to acquire due to the sequential nature of the point-by-point imaging process.

As shown in FIG. 4, in both widefield microscopy (as shown in FIG. 4A) and confocal microscopy (as shown in FIG. 4B), the light illumination within a sample is not confined to the focal plane 400 or point of interest. Instead, the illumination light in each case extends throughout two solid cones 401 and 402 of incoming and outgoing illumination (relative to the focal plane), where the half-angle of each cone is dictated by the numerical aperture (NA) of the objective lens that focuses the light within the sample. The light within illumination cones 401 and 402 that does not contribute to the focused image increases the possibility of photo-induced damage (also known as "photobleaching") within a sample.

Fluorescence microscopy can be used for intracellular imaging, and a wide variety of site-specific markers have been developed to yield high-contrast images of features of interest. Photobleaching can be problematic in fluorescence microscopy because many fluorescent marker molecules can undergo only a limited number of absorption/emission cycles before permanently photobleaching and becoming useless for creating a fluorescent image. Therefore, excitation of fluorescent marker molecules throughout the illumination cones 410 and 412 of widefield microscopy and confocal microscopy is wasteful, because only a small fraction of the photon budget for each molecule contributes to the desired signal.

Spatial resolution is usually somewhat superior in confocal microscopy, compared to widefield microscopy because the spatial resolution arises from a convolution of the effective excitation region with the effective detection region dictated by the pinhole 204. As shown in FIG. 5, an objective lens 101 can focus incoming monochromatic light 504 to a focal point 505. Because the light is monochromatic, rays of the focused light can have different wavevectors, $k_1$, $k_z$, and $k_2$, not because their wavelengths are different, but because their directions are different. The sharpness of either the effective excitation region or the effective detecting region created by the lens 101, and hence the resolution of the imaging system, is superior in the plane transverse to the objective axis, $\hat{e}_z$ 500, as compared to any plane along $\hat{e}_z$ because the highest spatial frequency in the plane transverse to the objective axis is:

$$(\Delta k_\perp)_{max} = |(k_1 - k_2)\cdot \hat{e}_\perp| = 2k\frac{NA}{n} \quad (1)$$

whereas the highest spatial frequency in the direction along the objective axis is:

$$(\Delta k_z)_{max} = |(k_z - k_1)\cdot \hat{e}_z| = k(1-\sqrt{1-(NA/n)^2}) \quad (2)$$

where, for monochromatic light, $|k_m|=k$ for all values of m, $k_1$ 501 and $k_2$ 502 are wavevectors at opposite edges of the illumination cone of the objective lens 102, $k_z = k\hat{e}_z$ 503, and n is the refractive index in the sample and its surrounding medium. Increased confinement of the excitation and detection regions improves sensitivity as well as resolution of the imaging system, because less spurious signal from effects such as autofluorescence and Rayleigh scattering is generated outside the region of interest, and the remaining spurious signal is more efficiently rejected prior to detection.

Improving the performance of live cell imaging requires consideration of the demanding problem of time resolved three-dimensional imaging of $P \geq 1$ independent optical properties (e.g., polarization and/or wavelength at different three-dimensional positions and at different times). This requires binning the measured photons in hypervoxels of P+4 dimensions (where a "hypervoxel" is a multidimensional pixel), which vastly increases the detected flux necessary to generate statistically significant data, compared to static two-dimensional or even three-dimensional imaging. Increasing the resolution in any of the P+4 dimensions demands further subdivision, thereby only exacerbating the problem. Furthermore, the photons within each hypervoxel originate from a 3D volume that decreases rapidly in size with increasing spatial resolution, making it increasingly difficult to generate the requisite flux in a non-invasive manner. Thus, the issues of image resolution, signal intensity, imaging speed, and sensitivity of the sample to damage by the imaging light are interrelated.

SUMMARY

In a first general aspect, a method of creating a periodic interference pattern of coherent waves in two or three dimensions, D, includes generating at least D+1 waves, each wave having substantially the same wavelength, $\lambda$, and each wave traveling substantially in a unique direction, $k_n$, and positioning said waves such that at least a portion of each wave intersects in a common excitation region to create the interference pattern. The directions of the waves, $k_n$, are selected such that the interference pattern within the excitation region forms a Bravais lattice having a symmetry, a shape to the primitive cell defined by the D-dimensional region closest to any chosen lattice point, and a periodicity relative to the wavelength, $\lambda$, that is larger than the smallest periodicity Bravais lattice having the same symmetry and identically defined primitive cell shape that can be created at the wavelength, $\lambda$. In addition, the directions of the waves, $k_n$, do not all lie on a D-dimensional set of mutually orthogonal axes.

In another general aspect, a method for creating a periodic interference pattern of coherent waves in two or three dimensions, D, includes generating at least D+2 waves, where each wave has substantially the same wavelength, $\lambda$, and travels substantially in a unique direction, $k_n$, and directing the waves such that at least a portion of each wave intersects in a common excitation region to create the interface pattern. The directions, $k_n$, of the waves are selected such that the interference pattern within the excitation region forms a Bravais lattice. At least one wave travels substantially in a direction, $k_i$, such that one or more symmetry operations characteristic of the Bravais lattice map the direction of the wave, $k_i$, onto a direction of a different wave, $k_j$, and the directions of the waves, $k_n$, do not all lie on a D-dimensional set of mutually orthogonal axes.

Implementations can include one or more of the following features. For example, the method can further include controlling an amplitude of at least one wave to enhance an amplitude of a field in the interference pattern at a predetermined point within each primitive cell of the lattice within the excitation region. The method can further include controlling a phase of at least one wave to enhance an amplitude of a field in the interference pattern at a predetermined point within each primitive cell of the lattice within the excitation region. The method can further include controlling a phase of at least two waves to enhance a degree of mutual constructive interference between the two waves at a predetermined point within each primitive cell of the lattice within the excitation region. A phase of substantially all of beams can be controlled to translate the interference pattern. The waves can be electromagnetic waves, and a property (e.g., a polarization, a phase, or an amplitude) of at least one wave can be controlled to enhance an intensity in the interference pattern at a predetermined point in each primitive cell within the excitation region, to enhance a contrast between an intensity at a predetermined point in each primitive cell within the excitation region and an intensity at regions adjacent to the predetermined point within each such primitive cell, or to enhance a predetermined component of the polarization of the electromagnetic interference pattern at a predetermined point in each primitive cell within the excitation region.

The method can also include controlling a complex electric field polarization, $e_n(x,t)$, of at least one wave to enhance a real part of the wave's complex projection, $Re\{e_n^*(x_d,t_d) \cdot e_d\}$, at a time, $t_d$, and at a relative point, $x_d$, in each primitive cell within the excitation region onto a complex electric field vector, $e_d$, describing the desired state of the total electric field in the interference pattern at the same time, $t_d$, and the same position, $x_d$. The electric field vector, $e_d$, can describe a state of linear polarization, or a state of circular polarization.

The method can further include controlling a property of at least one wave to enhance a gradient of a total electric field in the interference pattern, $\partial e(x,t)/\partial x_j$, or the total magnetic field, $\partial h(x,t)/\partial x_j$, in at least one particular direction, $e_j$, at a predetermined point in each primitive cell within the excitation region.

The method can further include controlling a property of at least one wave to enhance a magnitude of a gradient of the total electric field in the interference pattern, $|\nabla e(x,t)|$, or the total magnetic field in the interference pattern, $|\nabla h(x,t)|$, at a predetermined point in each primitive cell within the excitation region.

The method can further include a property of at least one wave to reduce an intensity in the interference pattern at a predetermined point within each primitive cell of the lattice within the excitation region. A property of the at least one wave can be controlled to enhance an intensity in the interference pattern in at least a portion of a region surrounding the predetermined point in each primitive cell where the intensity has been reduced.

The method can further include varying the direction, $k_n$, of each wave such that ratios between the lattice constants of the lattice are changed. The change in the ratios can cause enhance an intensity at a predetermined point in each primitive cell within the excitation region, can enhance a contrast between an intensity at a predetermined point in each primitive cell within the excitation region and an intensity elsewhere within each such primitive cell, or can enhance a magnitude of at least one component of an electric field in the interference pattern at a predetermined point in each primitive cell within the excitation region is enhanced. By varying the direction of each wave an aspect ratio of the lattice can be increased in a direction parallel to an axis defined by the component of the electric field that is enhanced.

The method can further include rotating the direction, $k_n$, of substantially every wave by a substantially identical angle to enhance a magnitude of at least one component of an electric field of the interference pattern at a predetermined point in each primitive cell within the excitation region.

The waves can be acoustic waves. The waves can be composed of particles of matter (e.g., electrons or electrically neutral particles) having a deBroglie wavelength, $\lambda$. The waves can exist at an interface between two dissimilar media (e.g., water and air).

In one implementation, the direction, $k_n$, of each wave forms substantially the same angle, $\theta$, with respect to a fixed axis, $\hat{e}_{2D}$. The method can further include varying the direction, $k_n$, of each wave such that the angle, $\theta$, of each wave with the fixed axis, $\hat{e}_{2D}$, changes and thereby varies the periodicity of the lattice in the plane substantially perpendicular to the fixed axis, $\hat{e}_{2D}$. The waves can travel substantially within a single plane, and the symmetry of the lattice can be a square symmetry, a primitive rectangular symmetry, a centered rectangular symmetry, or a hexagonal symmetry.

In certain implementations, the interference pattern can be a three-dimensional pattern, and the symmetry of the lattice is a simple cubic symmetry, a hexagonal symmetry, a body-centered cubic symmetry, or a face-centered cubic symmetry. The lattice can be a member of the tetragonal crystal group, a member of the orthorhombic crystal group.

The method can further include generating more than D+1 waves, where at least one wave travels substantially in a direction, $k_i$, such that one or more symmetry operations characteristic of the Bravais lattice can map the direction of the wave, $k_i$, onto a direction, $k_j$, of a different wave. For substantially each wave traveling substantially in a unique direction, $k_i$, another wave can exist traveling substantially in a direction, $k_j$, that is determined by applying a combination of symmetry operations associated with the Bravais lattice to the direction of the wave, $k_i$.

The method can further include rotating the optical lattice and its constituent waves together with respect to a longitudinal axis, $\hat{e}_z$, of a lens to increase the number of waves traveling substantially in directions that fall within the solid angle defined by the numerical aperture of the lens.

The method can further include controlling the directions, $k_n$, in which the waves travel to control a ratio of the lattice constants of the lattice and thereby increase the number of waves traveling substantially in directions that fall within a solid angle defined by the numerical aperture of a lens.

In another general aspect, an optical system for generating an optical lattice in two or three dimensions, D, substantially confined to an excitation region, includes a source of electromagnetic radiation having a wavelength, $\lambda$, and one or more optical elements configured to divide the radiation into at least D+1 independent excitation beams. Also included are optical elements configured to direct each excitation beam substantially in a unique direction, $k_n$, such that substantially all the beams intersect to create the optical lattice within the excitation region, and a first lens, having a rear pupil side and an opposite focusing side facing the excitation region The optical elements are adapted and arranged for directing at least two of the excitation beams into the rear pupil of the lens at distinct beam-center positions, $x_n''$, chosen such that the beams exit from the focusing side of the lens in the unique directions, $k_n$, and the directions, $k_n$, of the beams that exit from the focusing side of the lens lie substantially within a solid angle defined by a numerical aperture of the lens.

Implementations may include one or more of the following features. For example, the optical elements can be configured such that the optical lattice includes a Bravais lattice within the excitation region having a symmetry, a shape to the primitive cell defined by the D-dimensional region closest to any chosen lattice point, and a periodicity relative to the wavelength, $\lambda$, that is larger than the smallest periodicity Bravais lattice having the same symmetry and identically defined primitive cell shape that can be created at the wavelength, $\lambda$, and wherein the directions, $k_n$, of all the beams do not lie on a D-dimensional set of mutually orthogonal axes. The optical elements can be configured such that the optical lattice is a Bravais lattice within the excitation region, and at least one beam travels substantially in a direction, $k_i$, such that one or more symmetry operations characteristic of the Bravais lattice can map the direction of the beam, $k_i$, onto a direction, $k_j$, of a different beam, and wherein the directions, $k_n$, of all beams do not lie on a D-dimensional set of mutually orthogonal axes.

The optical system can further include a first optical element (e.g., a substantially opaque mask having a substantially transmissive aperture, a diffractive optical element, or a spatial light modulator) configured to control an effective cross-section at the plane of the rear pupil of a beam. The optical elements can be adapted and arranged to control the cross-sectional extent of at least one beam along the radial axis, $\hat{e}_\rho$, in the plane of the rear pupil intersecting the beam-center position, $x_n''$, and the longitudinal axis, $\hat{e}_z$, of the lens, so that the extent of the focal waist of the beam after it exits from the focusing side of the lens is inversely controlled along the axis, $\hat{e}_\theta$, perpendicular to its direction, $k_n$, and in the plane defined by $k_n$ and $\hat{e}_z$. The optical elements can be are adapted and arranged to control the cross-sectional extent of at least one beam along the tangential axis, $\hat{e}_\phi$, parallel to the plane of the rear pupil and perpendicular to the radial axis, $\hat{e}_\rho$, that lies in this plane and intersects the beam-center position, $x_n''$, and the longitudinal axis, $\hat{e}_z$, of the lens, so that the extent of the focal waist of the beam after it exits from the focusing side of the lens is inversely controlled in the same tangential direction, $\hat{e}_\phi$. The optical elements can be adapted and arranged to control the cross-sectional extent of at least one beam such that the cross-sectional extent of the resulting convergent beam that exits from the focusing side of the lens is substantially similar to the desired cross-sectional extent of the excitation region in a desired plane within said region perpendicular to the direction, $k_n$, of the convergent beam.

The optical system can further include a second optical element (e.g., an attenuating filter, a polarization sensitive optical element, a spatial light modulator) adapted and arranged for controlling the intensity of at least one of the beams entering the lens.

The optical system can further include an optical element (e.g., a reflector mounted on a linear translator, an optical phase modulator, a spatial light modulator) for controlling the phase at the plane of the rear pupil across at least one of the beams entering the lens. The optical element can be a means (e.g., a pivot-mounted reflector) for controlling the phase across the beam at the plane of the rear pupil by tilting the beam direction, $(k_{in})_n$, with respect to the longitudinal axis, $\hat{e}_z$, of the lens. The optical elements can be adapted and arranged to control the tilt of at least one beam that enters the lens, said tilt being controlled in the plane defined by the longitudinal axis, $\hat{e}_z$, of the lens and the direction, $k_n$, of the resulting convergent beam that exits from the focusing side of the lens, such that the position of the focal waist of the convergent beam is controlled along the axis, $\hat{e}_\theta$, in the same plane that is perpendicular to $k_n$. The optical elements can be adapted and arranged to control the tilt of at least one beam that enters the lens, said tilt being controlled perpendicular to the plane defined by the longitudinal axis, $\hat{e}_z$, of the lens and the direction, $k_n$, of the resulting convergent beam that exits from the focusing side of the lens, such that the position of the focal waist of the convergent beam is controlled along the axis, $\hat{e}_\phi$, perpendicular to both the same plane and to $k_n$. The optical element can be adapted and arranged to control the wavefront curvature of at least one beam, such that the position of the focal waist of the resulting convergent beam that exits from the focusing side of the lens is controlled along its direction, $k_n$. The third optical element can be a second lens through which the beam passes prior to entering the first lens.

The system can further include an optical element (e.g., a phase retardation plate, a linear polarizer, or a polarization sensitive beam splitter) adapted and arranged for controlling a polarization of a beam entering the lens. The optical elements can be adapted and arranged to control the magnitude of the electric field of at least one beam along the radial axis, $\hat{e}_\rho$, in the plane of the rear pupil pointing from the center of the lens to the center of the beam, such that the magnitude of the electric field of the beam is controlled along an axis $\hat{e}_\theta$ as it exits from the lens, where $\hat{e}_\theta$ is defined as perpendicular to the direction $k_n$ of the exiting beam and parallel to the plane defined by $k_n$ and the longitudinal axis of the lens. The optical elements can be adapted and arranged to control the magnitude of the electric field of the beam along the tangential axis, $\hat{e}_\phi$, perpendicular to plane defined by the longitudinal axis of the lens and the direction of the beam, $k_n$, as it exits from the lens, such that the magnitude of the electric field of the exiting beam is controlled along $\hat{e}_\phi$.

The optical lattice can be created at least in part by the intersection of substantially all beams substantially traveling in unique directions, $k_n$, that reside within the solid angle defined by the numerical aperture of the lens and that can be found by applying any combination of the symmetry operations of the Bravais lattice to the direction vector $k_m$ of any other constituent beam of the lattice. The optical lattice can be created exclusively by the intersection of beams that reside within the solid angle defined by the numerical aperture of the lens.

The optical system can further include a substrate, a sample at least partially overlapping with the excitation region and mounted to the substrate, and a fifth optical element (e.g., lens or a spatial light modulator) adapted for correcting for aberrations introduced in a beam that passes through the substrate before reaching the sample.

The lens of the optical system can be a high numerical aperture microscope objective having a numerical aperture greater than 0.9. The microscope objective is adapted for collecting light arising from an interaction of the lattice with the sample. The optical system can further include one additional beam contributing to creation of the lattice that reaches the excitation zone from outside the objective. The lattice can be a three-dimensional lattice, oriented such that multiple lattice planes are oriented substantially parallel to a focal plane of the objective. The lattice can be a two-dimensional lattice, and each beam can be directed at substantially the same angle with respect to a longitudinal axis, $\hat{e}_z$, of the objective, and reside within a solid angle defined by the numerical aperture of the lens.

The optical system can further include a second lens having a rear pupil side and an opposite focusing side, where the directing optical elements are adapted and arranged for directing at least two of the excitation beams into the second lens. The focusing sides of the first and second lenses can oppose one another and their longitudinal axes can be substantially parallel. The two lenses can be high numerical aperture microscope objectives having numerical apertures greater than 0.9. The system can further include a sample at least partially overlapping with the excitation region, and wherein the microscope objectives are adapted for collecting light arising from an interaction of the lattice with the sample.

The optical lattice can be created at least in part by the intersection of all beams substantially traveling in unique directions, $k_n$, residing within the total solid angle defined by the numerical apertures of the two objectives and that can be found by applying any combination of the symmetry operations of the Bravais lattice to the direction vector $k_m$ of any other constituent beam of the lattice. At least one additional beam contributing to the creation of the lattice can reach the excitation zone by passing through the space between the two objectives. The lattice can be generated by substantially all beams substantially traveling in unique directions, $k_n$, that can be found by applying any combination of the symmetry operations of the Bravais lattice to the direction, $k_m$, of any other constituent beam of the lattice and that either reside within the total solid angle defined by the numerical apertures of the two objectives or that travel outside the objectives and that can reach the excitation zone without being substantially occluded by the objectives.

The system can further include phase-controlling optical elements adapted and arranged for introducing a controllable, independent overall phase to substantially every beam that contributes to the lattice. At least one of the phase-controlling optical elements can be a reflector mounted on a linear translator or an optical phase modulator or a spatial light modulator. The phase-controlling optical elements can be adapted for translating a basis associated with the lattice by controlling the phase of substantially every beam. The system can further include a sample at least partially overlapping with the excitation region, and a detector adapted for detecting deviations from a desired basis associated with the lattice, where the phase-controlling optical elements are adapted for independently controlling the overall phase of substantially every beam to reduce deviations in the basis by reducing deviations in the phases of the beams relative to one another at a predetermined point within both the sample and the excitation region.

In another general aspect, an optical system includes a source of electromagnetic radiation having a wavelength, $\lambda$ and one or more dividing optical elements configured for dividing the radiation into at least D+1 substantially independent excitation beams. Directing optical elements are configured for directing each excitation beam in a unique direction, $k_n$, such that substantially all the beams overlap within an excitation region to create an optical lattice in two or three dimensions, D. The optical elements are arranged and adapted such that in the excitation region the phase of substantially every beam approximates the phase of a plane wave traveling in the same direction as the beam.

Implementations can include one or more of the following features. For example, the optical elements can be further configured to focus substantially every beam and to control the position or cross-sectional extent of substantially every focused beam waist to control the location and extent of the excitation region. The optical elements can include a lens that focuses exactly one of the beams. One of the optical elements can include a spatial light modulator that focuses at least one of the beams.

The optical lattice can include a Bravais lattice within the excitation region having a symmetry, a shape to the primitive cell defined by the D-dimensional region closest to any chosen lattice point, and a periodicity relative to the wavelength, $\lambda$, that is larger than the smallest periodicity Bravais lattice having the same symmetry and identically defined primitive cell shape that can be created at the wavelength, $\lambda$, and wherein the directions, $k_n$, of all the beams do not lie on a D-dimensional set of mutually orthogonal axes.

The optical lattice can include a Bravais lattice within the excitation region, and a least one beam can travel substantially in a direction, $k_i$, such that one or more symmetry operations characteristic of the Bravais lattice can map the direction of the beam, $k_i$, onto a direction, $k_j$, of a different beam, and wherein the directions, $k_n$, of all beams do not lie on a D-dimensional set of mutually orthogonal axes.

The system can further include second optical elements configured for controlling the intensity of substantially every beam, such that they are of substantially similar intensity at a predetermined point within the excitation region. At least some of the optical elements can be configured for controlling the shape and sharpness of the excitation region by directing multiple beams substantially in the same direction, $k_m$, as one or more beams that make up the lattice, and by controlling the positions of the focal waists of all beams traveling in substantially the same direction so that their foci are offset from one another. The optical elements can include a diffractive optical element configured to create two or more beams of offset foci traveling in substantially the same direction. The optical elements can include a spatial light modulator configured to create two or more beams of offset foci traveling in substantially the same direction.

In another general aspect, an optical system includes a source of electromagnetic radiation, having a first wavelength, $\lambda_1$, and dividing optical elements configured for dividing the radiation from the source into a first set of at least D+1 excitation beams. Directing optical elements are configured for directing each excitation beam in a unique direction, $k_n$, such that the beams intersect within an excitation region to create an interference pattern having a symmetry of a first Bravais lattice in two or three dimensions, D, and a first lattice periodicity. Control optical elements are configured for controlling an electromagnetic field basis associated with the first lattice to produce at least one excitation maximum in each primitive cell of the first lattice, wherein the excitation maximum is substantially confined to a region less than the wavelength, $\lambda_1$, in at least two dimensions. A detector having individual detector elements configured for detecting signal light resulting from an interaction of the lattice with a sample located in the excitation region. The lattice and the directions, $k_n$, of the excitation beams are selected such that the lattice periodicity is large enough for signals from multiple excitation maxima within the sample to be individually resolved and simultaneously measured by separate detector elements.

Implementations can include one or more of the following features. For example, the directing optical elements can be configured for directing the beams in directions, $k_n$, such that the optical Bravais lattice has a shape to the primitive cell defined by the D-dimensional region closest to any chosen lattice point, and a periodicity relative to the wavelength, $\lambda_1$, that is larger than the smallest periodicity Bravais lattice having the same symmetry and identically defined primitive cell shape that can be created at the wavelength, $\lambda_1$, and wherein the directions, $k_n$, of all beams do not lie on a D-dimensional set of mutually orthogonal axes.

The directing optical elements can be configured for directing at least one of the beams in a direction, $k_i$, such that one or more symmetry operations characteristic of the Bravais lattice can map the direction, $k_i$, onto a direction, $k_j$, of a different beam, and wherein the directions $k_n$ of all beams do not lie on a D-dimensional set of mutually orthogonal axes.

The detector can be configured for detecting a fluorescence emission signal arising from the interaction of the electromagnetic radiation with the sample, or for performing time correlated single photon counting of the signal resulting from the interaction of the electromagnetic radiation with the sample.

The source and detector can be configured for generating and detecting a signal resulting from a nonlinear interaction of the electromagnetic radiation with the sample, for generating and detecting light resulting from multiphoton absorption of the electromagnetic radiation by the sample, for generating and detecting light from a multiphoton scattering process (e.g., including second harmonic generation) between the electromagnetic radiation and the sample, for generating and detecting light resulting from Raman scattering of the electromagnetic radiation by the sample.

The source can be configured for emitting pulsed beams of electromagnetic radiation.

The system can further include a source of electromagnetic radiation having a second wavelength, $\lambda_2$, optical elements configured for dividing the radiation into a second set of at least D+1 excitation beams, optical elements configured for directing each excitation beam of the second set in a unique direction, $k_n$, such that the beams intersect within the excitation region to create an interference pattern having a symmetry of a second Bravais lattice in D dimensions, and a second lattice periodicity, and optical elements configured for controlling an electromagnetic field basis associated with the second lattice to produce at least one excitation maximum in each primitive cell of the second lattice, where the excitation maxima are substantially confined to a region less than the wavelength, $\lambda_2$, in at least two dimensions, and where at least a portion of the signal light arises from an interaction of both the first lattice and the second lattice with the sample.

The second lattice can have the same symmetry and substantially the same lattice constants as the first lattice, and the period of the second lattice can be a rational multiple of a period of the first lattice. The first wavelength can be selected to provide pump radiation to the sample and the second wavelength is selected to provide probe radiation to the sample. The sources and the detector can be configured for generating and detecting light resulting from Coherent Anti-Stokes Raman Scattering within the sample.

The system can further include translation optical elements configured for translating the excitation maxima relative to the sample, a memory configured for recording the detected light from each observed excitation maximum at multiple relative positions of the maxima and sample, and a processor configured for generating an image from the recorded detected light. A display can be configured for displaying the image.

The lattice can be a three dimensional lattice, and the optical elements for translating the excitation maxima can be configured for translating the excitation maxima across a volume that includes a primitive cell of the lattice. The lattice can be a three dimensional lattice, and the optical elements can be configured for scanning the excitation maxima relative to the sample in a plane substantially parallel to a lattice plane of the lattice and for scanning each maximum at least over an area defined by an intersection of the lattice plane with a primitive cell of the lattice.

The processor can be configured for generating simultaneously multiple two-dimensional images from excitation maxima within parallel lattice planes.

The lattice can be two-dimensional, and the processor can be adapted for generating a two-dimensional image from signal light detected when the excitation maxima are scanned over an area that includes a primitive cell of the lattice.

A translation stage can translate an optical element that is configured to translate the excitation maxima relative to the sample. The optical elements configured for translating the excitation maxima can include at least one phase shifter for adding an independent overall phase to each excitation beam. The system can further include a translation stage configured for translating the sample relative to the excitation maxima of the Bravais lattice, a memory for recording the detected light from each observed excitation maximum at multiple relative positions of the maxima and sample, and a processor for generating an image from the recorded detected light.

The lattice can be a three-dimensional lattice, and the translation stage can be configured for translating the sample is configured for translating the excitation maxima across a volume that includes a primitive cell of the lattice. The translation stage for translating the sample can be configured for translating the sample in a plane substantially parallel to a lattice plane of the lattice, and for translating the sample at least over an area defined by an intersection of the lattice plane with a primitive cell of the lattice. The processor can be configured for generating simultaneously multiple two dimensional images from excitation maxima within parallel lattice planes.

The lattice can be two-dimensional, and the processor can be adapted for generating a two dimensional image from signal light detected when the sample is translated over an area that includes a primitive cell of the lattice.

The detector can include a microscope objective configured for collecting at least a portion of the signal light. The detector can include a lens configured for imaging signal light beyond the rear pupil of the objective. Detector elements of the detector can be located substantially at an image plane of the lens that images the signal light.

The lattice can be is three-dimensional and oriented such that a family of lattice planes is substantially parallel to the focal plane of the objective, the excitation maxima within at least one lattice plane within the family can reside at least in part within the focal plane.

A numerical aperture of the objective can be selected relative to a separation distance between adjacent lattice planes of the family of lattice planes such that substantially only excitation maxima within a single lattice plane lie within the region of focus defined by the numerical aperture.

The detector can be charged-coupled device ("CCD") camera. The detector can include a substantially opaque mask located at the image plane of the lens that images the signal light, and the mask can contains multiple substantially transmissive apertures located at positions corresponding to projected images onto the image plane of multiple excitation maxima. A lens can refocus a spatially filtered signal transmitted through each aperture onto a distinct element or group of elements in a detector that converts the light into an electrical signal. The numerical aperture of the objective and the sizes of the apertures can be selected such that the signal transmitted through the apertures originates primarily from excitation maxima within the region of focus defined by the numerical aperture of the objective.

The lattice can be two-dimensional and oriented such that the excitation varies primarily in a plane parallel to the focal plane of the objective. The objective can be configured for passing at least one of the excitation beams and can include an optical element for separating an excitation beam from signal light in the region beyond the rear pupil. A phase shifter can be used to control a phase across an aggregate signal beam emerging from the rear pupil of the objective. The phase shifter can include a phase shift mask, a spatial light modulator, or a deformable mirror.

The objective can be infinity corrected and can include a tube lens for creating a magnified image of an excitation maximum at an image plane of the tube lens.

The system can further include a source of electromagnetic radiation having a trapping wavelength, $\lambda_{trap}$, and optical elements configured for directing radiation beams of the trapping wavelength into the sample to create a single or multifocus optical trap for holding the sample substantially at a desired point with respect to the objective. At least a portion of the optical trap can be created with one or more radiation beams of the trapping wavelength that pass through the signal collection of objective, and further comprising an optical element for isolating the signal light from radiation having the trapping wavelength.

The detector of the system can include first and second microscope objectives, with each objective having a rear pupil end, a distal focusing end and a longitudinal axis, where the focusing ends of the two objectives face each another and face the excitation region, and the longitudinal axes of the two objectives are substantially parallel. In such a detector the first lens can be configured for imaging signal light beyond the rear pupil end of the first objective, and the second lens can be configured for imaging signal light beyond the rear pupil end of the second objective. First individual detector elements can be configured for detecting signal light imaged by the first lens, and second individual detector elements configured for detecting signal light imaged by the second lens. At least some excitation maxima can be located within the sample, at least in part within a region of focus of the first or second objective defined by a focal plane and a numerical aperture of the first or second objective.

The lattice can be three-dimensional, with the lattice being oriented such that a lattice plane is substantially parallel to a focal plane of the first or second objective, and where the excitation maxima within at least one lattice plane are located at least in part within the region of focus of the first or second objective. At least one lattice plane can be in the region of focus of the first objective and in the region of focus of the second objective, and signal light from the at least one lattice plane can be detected by the first individual detector elements and by second individual detector elements. A numerical aperture of each objective can be selected relative to a separation distance between adjacent lattice planes, such that only a single lattice plane is within the region of focus of both objectives.

At least one lattice plane can be within the region of focus of the first objective but not within the region of focus of the second objective, and at least one additional lattice plane can be within the region of focus of the second objective but not within the region of focus of the first objective. A numerical aperture of each objective can be selected relative to a separation distance between adjacent lattice planes, such that signal light from excitation maxima within exactly one lattice plane is detected only by the first individual detector elements but not by the second individual detector elements, and signal light from excitation maxima within a second lattice plane is detected only by the second individual detector elements but not by the first individual detector elements.

When at least one excitation beam can be transmitted by each objective, the system can further include optical elements configured for separating excitation beams from the signal light in a region beyond the rear pupil of each objective.

The system can include first and second microscope objectives, with each objective having a rear pupil end, a distal focusing end, and a longitudinal axis, where the focusing ends of the two objectives face each another and face the excitation region, and the longitudinal axes of the two objectives are substantially parallel. The system can also include optical elements configured to coherently combine at least a portion of a first aggregate signal beam emerging from the rear pupil of the first objective with at least a portion of a second aggregate signal beam emerging from the rear pupil of the second objective, and a lens configured to focus the combined signal beam to create an image at an image plane, where signal in focus at the image plane arises from either a first focal plane of the first objective, or from a second focal plane of the second objective. The system can also include optical elements configured to manipulate the polarization and phase of the aggregate signal beams prior to their combination, such that the two orthogonal polarization components of the individual signal beams substantially interfere constructively after combination, and matching optical elements configured to symmetrically match the image produced by focusing the first aggregate signal beam through the lens with the image produced by focusing the second aggregate signal beam through the lens, such that signal from any transverse location in the first focal plane is focused at the same point on the image plane as the signal from the same transverse location on the second focal plane. In such a case, the detector can have individual detector elements substantially located at the image plane, and at least some of the excitation maxima can reside at least in part within both the first focal plane and the second focal plane.

The system can further include a phase shifter configured for controlling the phase across the aggregate signal beam emerging from the rear pupil of at least one of the objectives prior to its combination with the aggregate signal beam from the other objective, such that the first and second focal planes associated with the image plane substantially coincide within the sample. The phase shifter can include a phase shift mask, a movable reflective element, or a phase retardation plate configured to control the phase of one component of the polarization of one of the aggregate signal beams relative to an orthogonal polarization component of the same aggregate signal beam.

The matching optical elements can include a penta prism and a roof prism, where the image produced by focusing the first aggregate signal beam through the lens is symmetrically matched to the image produced by focusing the second aggregate signal beam through the lens by passing one of the aggregate signal beams through the penta prism, and the other aggregate signal beam through the roof prism.

The system can include optical elements configured for controlling a polarization of an excitation beam. The system can include a polarizer configured to substantially isolate at least one of the two orthogonal polarization states of the signal light that emerges from the rear pupil of the objective. The polarizer can be configured to divide the signal light into two polarized beams of orthogonal polarization traveling in substantially different directions, and then the system can further include a first lens configured to image one of the polarized beams at a first image plane, a second lens configured to image the other polarized beam at a second image plane, first individual detector elements for detecting signal light imaged by the first lens, and second individual detector elements for detecting signal light imaged by the second lens. The polarizer can be configured to divide the signal light into two polarized beams of orthogonal polarization traveling in directions tilted slightly with respect to one another, and the system can further include a lens configured to image each of the polarized beams at an image plane, individual detector elements configured for detecting signal light imaged by the lens, where the different detector elements are configured for detecting signal in each of the orthogonal polarization states generated at excitation maxima within the sample.

The system can further include a spatial filter configured to isolate at least one portion of the aggregate signal beam that emerges from the rear pupil of the objective. The system can further include optical elements configured to focus light spatially filtered from two or more distinct portions of the aggregate signal beam such that the light from each portion is focused onto its own distinct group of detection elements. The system can further include a lens and a detector associated with each filtered portion of the aggregate signal beam, where each lens is configured to focus light from its associated filtered portion of the signal beam onto its associated detector.

The system can further include at least one optical element configured to direct light from the distinct filtered portions of the aggregate signal beam in slightly different directions, and a lens configured to focus light from the different portions of the aggregate signal beam onto an image plane, where the detector is located at the image plane, and the light from each portion of the aggregate signal beam is focused onto a different set of elements within the detector at positions determined by the direction imparted on that portion of the aggregate signal beam.

The system can include a spatial light modulator configured to direct two or more portions of the aggregate signal beam in different directions. The spatial light modulator can be configured to isolate the signal from at least one annular portion of the aggregate signal beam. A spatial light modulator can be configured to spatially filter the signal.

The detector can include a spectral filter configured for isolating and spectrally resolving the signal created by at least one of the excitation maxima. The detector can include an optical fiber bundle, a spectrometer, and a lens. The fiber bundle can include a face located at an image plane of the lens and configured to image the signal light and an array of optical fibers having proximal ends located at positions corresponding to positions of imaged signal light from a plurality of excitation maxima within a region of focus defined by the focal plane and numerical aperture of the objective lens and having distal ends substantially arranged in a single column. The a spectrometer can include a two-dimensional multi-element detector, and the lens can be configured for focusing signal light emerging from the array of optical fibers onto an entrance slit of the spectrometer. An aperture mask can be configured for spatially filtering the signal light from the excitation maxima before coupling the signal light into individual optical fibers of the array.

In another general aspect, an optical system includes a substrate adapted for supporting a sample, a source of electromagnetic radiation, a detector, first dividing optical elements, first directing optical elements, and first control optical elements. The substrate has a refractive index, $n_{sub}$, larger than a refractive index of the sample, $n_{sample}$. The source of electromagnetic radiation has a wavelength, $\lambda_o$. The detector has multiple individual detector elements configured for detecting a signal resulting from an interaction of the electromagnetic radiation with the sample. The first dividing optical elements are configured for dividing the electromagnetic radiation from the source into at least three substantially independent excitation beams. The first directing optical elements are configured for directing each excitation beam in a unique direction, $k_n$, through the substrate and incident upon an interface between the substrate an the sample at angles relative to a normal axis to the interface, $\hat{e}_z$, such that each excitation beam is divided into a reflected beam and an evanescent interfacial beam within the sample that travels in the plane of the interface, where the evanescent beams at least partially intersect with each other within at least a portion of the sample to create an excitation region with an interference pattern having a symmetry of a two dimensional interfacial Bravais lattice. The first control optical elements are configured for controlling an electromagnetic field of each excitation beam such that a basis associated with the interfacial Bravais lattice includes a substantially isolated excitation maximum in each primitive cell of the lattice substantially confined to a size less than a substrate wavelength, $\lambda_{sub}=\lambda_o/n_{sub}$, in any direction parallel to the interface. The directions, $k_n$, of the excitation beams are selected such that the periodicity of the lattice in any direction parallel to the interface is large enough for signals from adjacent excitation maxima to be individually resolved and simultaneously measured by separate elements within the detector.

Implementations can include one or more of the following features. For example, the directing and control optical elements can be configured such that the interfacial Bravais lattice has a symmetry, a shape to the primitive cell defined by the region within the interface closest to any chosen lattice point, and a periodicity within the sample that is larger relative to the substrate wavelength, $\lambda_{sub}$, than the smallest such lattice of the same symmetry and identically defined primitive cell shape that can be created at that wavelength, and wherein the directions of the interfacial beams do not all lie on a pair of mutually orthogonal axes.

The directing and control optical elements can be configured such that at least one of the interfacial beams travels substantially in a direction, $k_n^{interface}$, such that one or more symmetry operations characteristic of the lattice can map the direction, $k_n^{interface}$, onto a different direction, $k_m^{interface}$, associated with a different interfacial beam, and wherein the directions of all the interfacial beams do not lie on a pair of mutually orthogonal axes.

The directing and control optical elements can be configured such that for substantially every interfacial beam traveling in a unique direction, $k_n^{interface}$, another interfacial beam exists traveling in a direction, $k_m^{interface}$, that is determined by applying any combination of symmetry operations associated with the interfacial Bravais lattice to the direction $k_n^{interface}$.

The directing and control optical elements can be configured such that the incident excitation beams and the reflected beams intersect within the substrate to form a three-dimensional Bravais lattice oriented such that a lattice plane of the three-dimensional lattice is parallel to the interface.

The directing and control optical elements can be configured such that each incident beam is polarized in its plane of incidence, so that an electric field associated with the interfacial Bravais lattice is substantially polarized perpendicular to the interface.

The substrate can include a substantially transparent material having a refractive index greater than about 2. The substrate can include gallium nitride, gallium phosphide, silicon carbide, aluminum nitride, or aluminum arsenide. The substrate can be substantially hemispherical in shape, where the sample is supported on the flat surface of the hemisphere, and where the excitation beams enter the substrate through the curved surface of the hemisphere.

The system can include a hemisphere of a material having a refractive index, $n_{sphere}$, where the substrate is mounted to the flat surface of the hemisphere, and the directing and control optical elements can be configured such that the excitation beams enter the hemisphere through its curved surface and exit the hemisphere through its flat surface. Thee refractive index of the hemisphere can be selected such that at least a portion of each excitation beam is transmitted through the interface between the hemisphere and the substrate, and the directing and control optical elements can be configured such that the excitation beams enter the hemisphere in directions such that they travel in the substrate in the directions, $k_n$, that generate the interfacial lattice.

The system can include translation optical elements configured for translating the excitation maxima relative to the sample in the plane of the interface, a memory configured for recording a signal from each excitation maximum at multiple relative positions of the maxima and sample, and a processor configured for generating an image of the sample from the recorded signals. A display can be configured for displaying the image. The processor can be further configured for generating a two-dimensional image from signals recorded when the sample and the excitation maxima are scanned relative to another over an area that includes at least one primitive cell of the interfacial lattice.

The detector can include a microscope objective adapted for collecting at least a portion of the signal, and a lens adapted for creating an image of the interface at an image plane beyond a rear pupil of the objective, where the individual detector elements are located substantially at an image plane of the lens, and where a plurality of excitation maxima within the sample are focused upon distinct detector elements. The detector can include a substantially opaque mask located at the image plane having multiple substantially transmissive apertures at positions corresponding to projected image positions on the image plane of a plurality of excitation maxima near the interface and a lens adapted for refocusing signal light transmitted through each aperture onto a distinct detector element or group of detector elements.

The system can include optical elements configured for adjusting the direction, $k_n$, of each excitation beam, so that the projection of each direction, $k_n$, onto the interface can be changed simultaneously by substantially the same amount for each excitation beam.

The processor can be adapted for generating a plurality of images recorded at different incident beam projections onto the interface, and can be adapted for generating a three-dimensional image of the sample from the plurality of images.

The system can include a second source of pulsed electromagnetic radiation, having a second wavelength, $\lambda_{depl}$. Second dividing optical elements can be configured for dividing the radiation from the second source into a second set of at least $D_{depl}+1$ depletion beams of wavelength, $\lambda_{depl}$, second directing optical elements configured for directing each depletion beam of the second set in a unique direction, $k_n^{depl}$, such that a pulse within each beam intersects with a pulse within every other beam of the second set within the excitation region at time $t_0$ create a depletion interference pattern having a symmetry of a Bravais lattice in $D_{depl}$ dimensions, and a depletion lattice periodicity, second control optical elements configured for controlling an electromagnetic field basis associated with the depletion lattice, such that at least one substantially isolated intensity minimum of the depletion lattice at least partially surrounded by a region of higher intensity and substantially confined to a size of less than the wavelength, $\lambda_{depl}$, in at least two dimensions, exists in each primitive cell of the depletion lattice. An optical element can be configured for gating the detector to detect signal at a time, $t>t_0$, after the pulses that intersect at an initial time, $t_0$, have left the excitation region, where the first and second directing and control optical elements are configured such that the symmetry and periodicity of the first Bravais lattice and the depletion Bravais lattice are chosen such that a plurality of excitation maxima within the first Bravais lattice at least partially overlap with a plurality of intensity minima within the depletion lattice. The wavelength, λ, of the first Bravais lattice can be chosen such that the first Bravais lattice raises a selected species of fluorescent emitters within the sample to an excited energy state, and the wavelength, $\lambda_{depl}$ of the depletion lattice can be chosen such that the depletion Bravais lattice lower the fluorescent emitters from the excited state to a lower energy state by a stimulated emission process.

The system can further include a pulse controller for controlling an intensity and a duration of the pulse of depletion beams, such that a desired portion of the emitters near each excitation maximum of the first Bravais lattice is de-excited prior to opening of a gate to the detector, so that a recorded signal arises substantially from a lattice of regions, each significantly smaller than the excitation wavelength in at least two dimensions.

The first and second directing and control optical elements can be configured such that the depletion lattice has the same symmetry and identically defined primitive cell shape as the first Bravais lattice, and wherein the wavelengths, λ and $\lambda_{depl}$, of the two lattices as well as their wavelength-normalized periodicities are chosen so that their absolute periodicities are an integral ratio of one another.

In another general aspect, optical system includes a source of electromagnetic radiation, dividing optical elements, field control optical elements, and intensity control optical elements. The source of electromagnetic radiation has a wavelength, λ. The dividing optical elements are configured for dividing the radiation from the source into at least D+1 excitation beams. The directing optical elements are configured for directing each excitation beam in a unique direction, $k_n$, such that the beams intersect within an excitation region within a photosensitive sample to create an interference pattern in the sample having a symmetry of a Bravais lattice in two or three dimensions, D, and a lattice periodicity. The field control optical elements are configured for controlling an electromagnetic field basis associated with the lattice. The intensity control optical elements configured for controlling the intensity of the excitation beams. The optical elements are configured to produce at least one substantially isolated intensity maximum in each primitive cell of the lattice substantially confined in any direction within at least two dimensions to a size that is less than half the periodicity of the lattice in the same direction.

In another general aspect, an optical system includes, a first source of electromagnetic radiation, first dividing optical elements, first directing optical elements, and first control optical elements. The first source of electromagnetic radiation has a trapping wavelength, $\lambda_{trap}$. The first dividing optical elements are configured for dividing the radiation from the first source into a first set of at least D+1 trapping beams. The first directing optical elements are configured for directing each trapping beam in a unique direction, $k_n$, such that the beams intersect within an trapping region to create an interference pattern having a symmetry of a trapping Bravais lattice in two or three dimensions, D, and a lattice periodicity. The first control optical elements are configured for controlling an electromagnetic field basis associated with the lattice, such that at least one substantially isolated intensity maximum is produced in each primitive cell of the lattice and is substantially confined in any direction within at least two dimensions to a size that is less than half the periodicity of the trapping lattice in the same direction. The control optical elements are configured for controlling the absolute intensity at the maxima in each primitive cell is controlled to produce points of an intensity gradient sufficiently strong for confining matter.

In another general aspect, a method for inducing a photophysical change in a sample at a plurality of isolated regions simultaneously includes generating within the sample a periodic interference pattern of coherent waves from a plurality of mutually intersecting electromagnetic beams of substantially the sample wavelength, λ, wherein the pattern has characteristics of a Bravais lattice in two or three dimensions. The basis associated with the lattice is controlled to produce at least one substantially isolated intensity maximum in each primitive cell of the lattice, with the intensity maximum being substantially confined in at least two dimensions to less than half the periodicity of the lattice defined by the intensity maxima. The intensity and duration of the exposure of the sample to the lattice is controlled to limit the photoinduced physical change in the sample to a desired region centered at each maximum.

In another general aspect, a method of creating a plurality of isolated intensity maxima capable of optically trapping a sample of matter in at least two dimensions includes generating within the matter a periodic interference pattern of coherent waves from a plurality of mutually intersecting electromagnetic beams of substantially the sample wavelength, λ, where the pattern has the characteristics of a Bravais lattice in two or three dimensions. The basis associated with the lattice is controlled to produce at least one substantially isolated intensity maximum in each primitive cell of the lattice, the intensity maxima being substantially confined in at least two dimensions to less than half the periodicity of the lattice defined by the intensity maxima. An absolute intensity at the maxima is controlled to produce an intensity gradient sufficiently strong to trap the matter.

In another general aspect, a microscope includes a source of electromagnetic radiation having a wavelength, $\lambda_1$, dividing optical elements configured for dividing the radiation from the source into multiple excitation beams, directing optical elements, and a detector. The directing optical elements are configured for directing each excitation beam in unique directions, such that the beams intersect in an excitation region within a sample to create a two-dimensional or three-dimensional interference pattern of multiple excitation maxima within the sample. The detector has individual detector elements, and the detector elements are configured for detecting light resulting from an interaction of an individual excitation maximum and the sample.

Implementations can include one or more of the following features. For example, the microscope can include a translation stage configured for translating the sample and the interference patter relative to each other. The detector can be configured to detect simultaneously signals of light resulting from interactions of multiple individual excitation maxima and the sample. The microscope can further include a processor configured for generating an image of the sample from the multiple signals. A spacing of the maxima can be less than the wavelength, $\lambda_1$.

BRIEF DESCRIPTION OF DRAWINGS

FIG. 14A also shows the lattice in relation to surfaces showing surfaces of detection efficiency that are 50% of the maximum detection efficiency due to an associated pinhole array filter.

FIG. 14D also shows the lattice in relation to surfaces showing surfaces of detection efficiency that are 50% of maximum detection efficiency due to an associated pinhole array filter.

FIG. 15A also shows a light intensity surface having 50% of the maximum intensity near the focus of a NA=1.2 water-immersion microscope objective oriented along the z-axis and illuminated with an x-polarized plane wave.

Figure 46A:
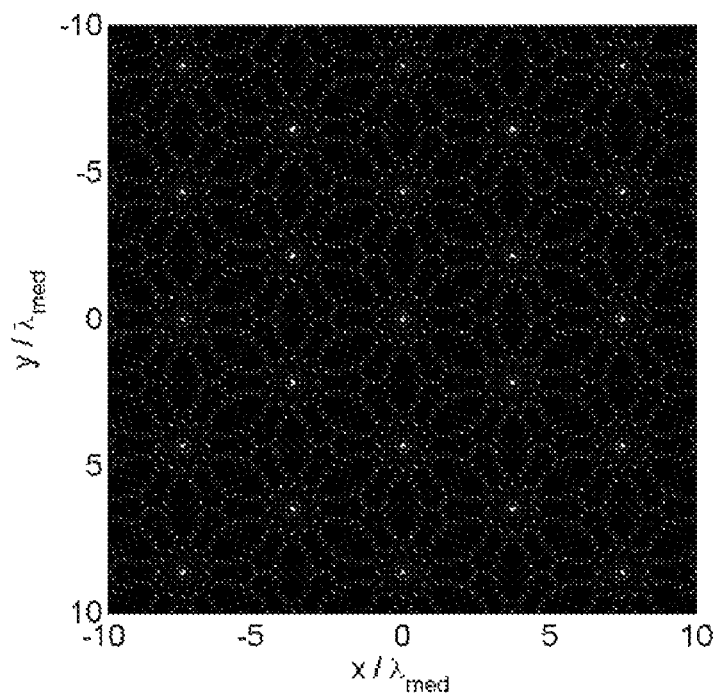
FIG. 46A is a linear grayscale image of the light intensity at the interface between a transparent substrate of refractive index $n_{sub}$=3.4 and a transparent medium of refractive index $n_{med}$=1.33 when illuminated from within the substrate with all twenty-four plane waves of the maximally symmetric two-dimensional hexagonal lattice of minimum intensity period $\sqrt{485}\lambda_{sub}/2$, at a common angle of incidence for all waves of slightly less than 90° (i.e., not quite parallel to the interface), and with polarizations $e_m$ that yield a basis that optimizes the z-component of the field at the intensity maxima within the medium.
Figure 46B:
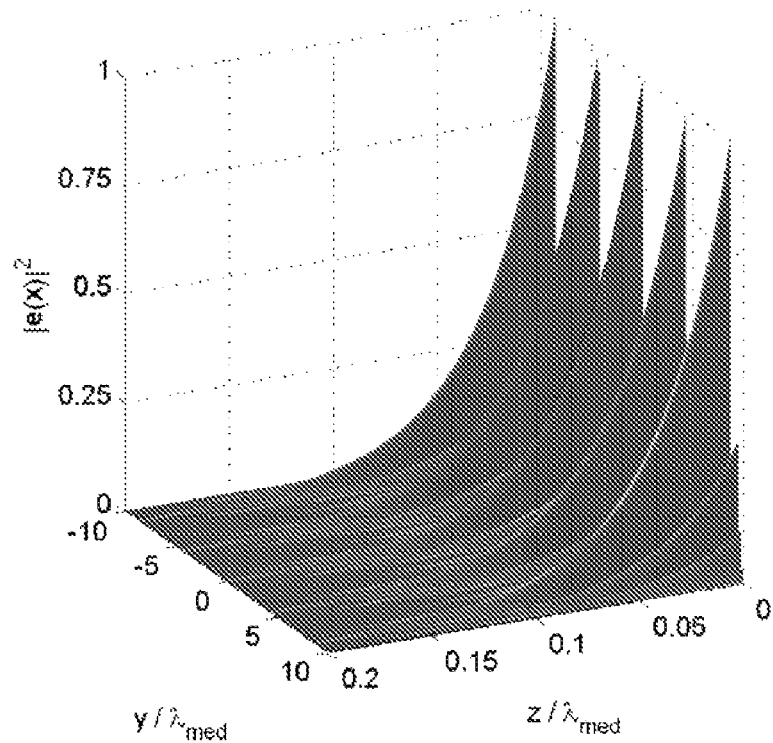
FIG. 46B is a surface plot in the indicating the rate of decay with increasing distance into the medium for points along the y-axis of the intensity pattern in FIG. 46A.
Figure 46C:
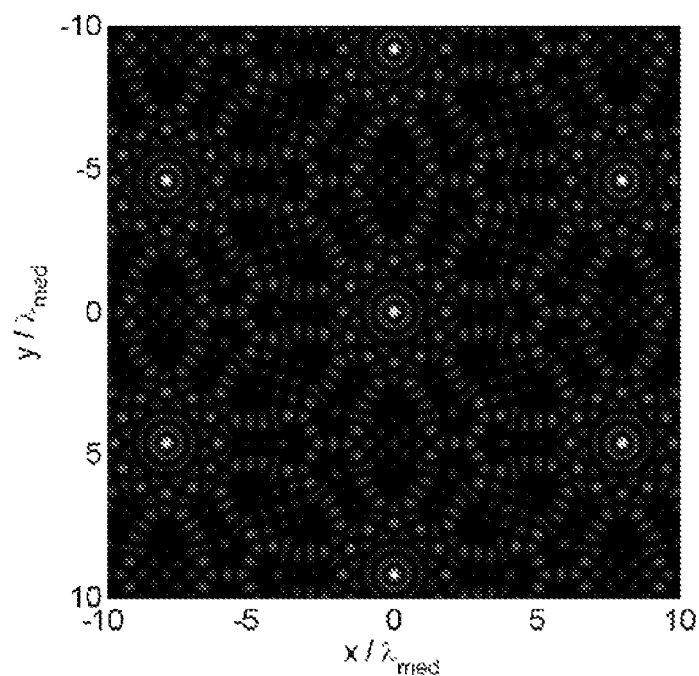

FIG. 46C is a linear grayscale image of the light intensity at the interface between a transparent substrate of refractive index $n_{sub}$=3.4 and a transparent medium of refractive index $n_{med}$=1.33 when illuminated from within the substrate with all twenty-four plane waves of the maximally symmetric two-dimensional hexagonal lattice of minimum intensity period $\sqrt{485}\lambda_{sub}/2$, at a common angle of incidence for all waves of $\theta_m=\sin^{-1}(1.2\sin\theta_{critical})=\sin^{-1}(1.2n_{med}/n_{sub})$ (where $\theta_{critical}$ is the critical angle for total internal reflection at the interface), and with polarizations $e_m$ that yield a basis that optimizes the z-component of the field at the intensity maxima within the medium.

Figure 46D:
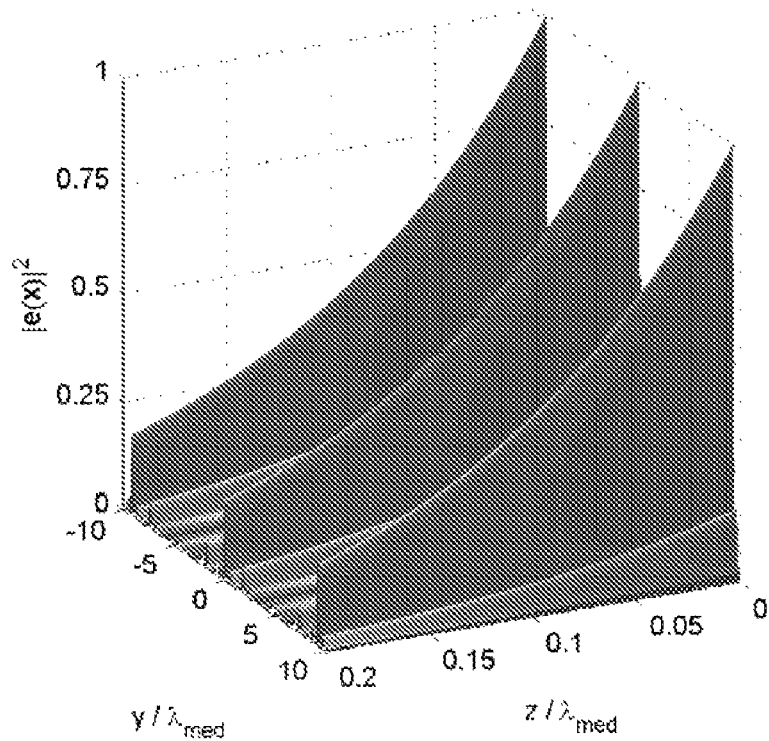

FIG. 46D is a surface plot in the indicating the rate of decay with increasing distance into the medium for points along the y-axis of the intensity pattern in FIG. 46D.

Figure 47A:
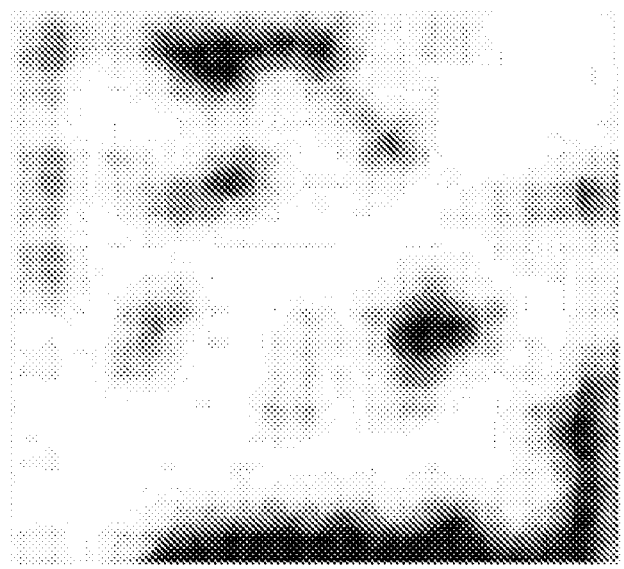

FIG. 47A is a representative S dimensional spatial image of discrete emitters poorly resolved by an optical imaging system.

Figure 47B:
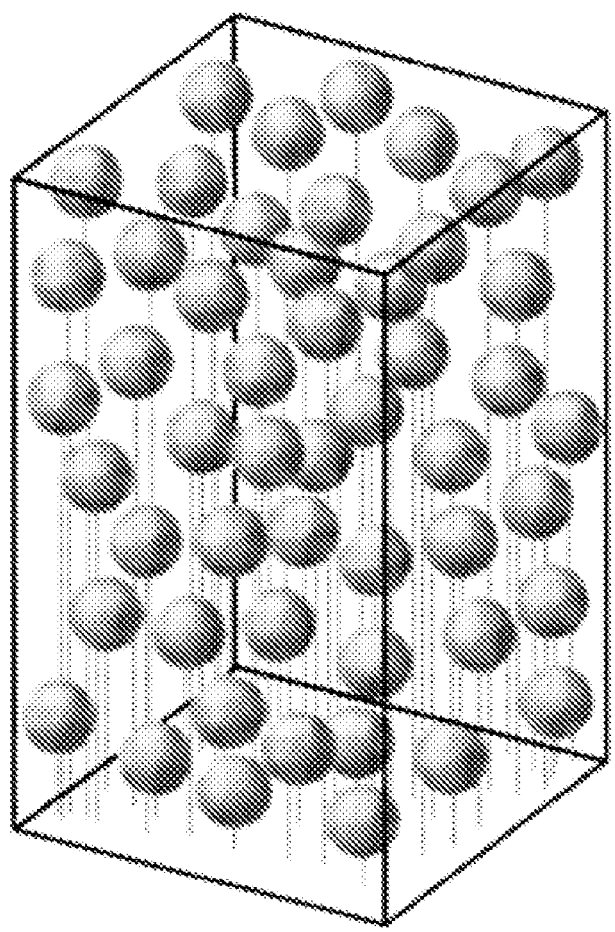

FIG. 47B is a representative S+P dimensional plot of the same emitters as in FIG. 47A, isolated by additional measurement of P independent optical properties at each position in the S dimensional space.

Figure 47C:
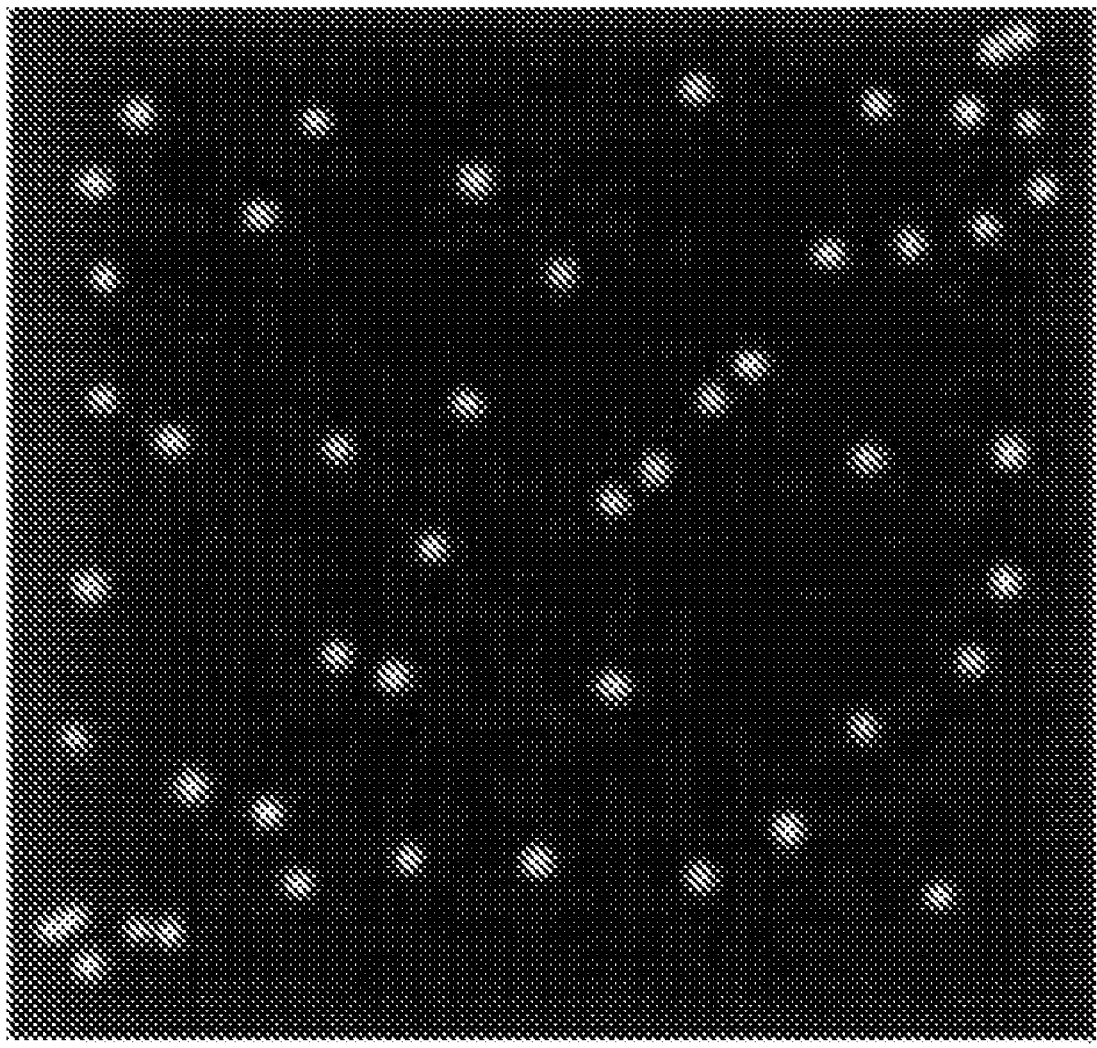

FIG. 47C is a representative S dimensional, high spatial resolution image obtained by determining the spatial position of each isolated emitter in the S+P dimensional hyperspace of FIG. 47B.

Figure 48A:
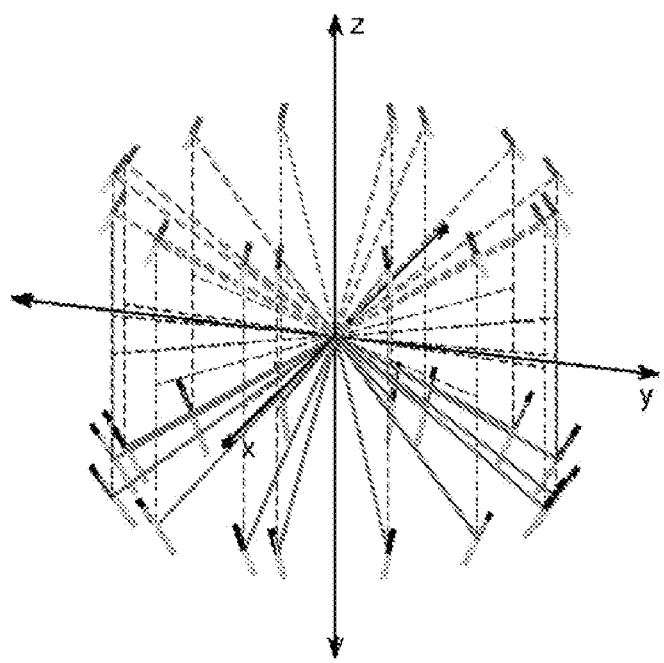

FIG. 48A is a three-dimensional representation of the relative wavevector and electric field directions and real field magnitudes at different times for the plane waves (lower half-space of figure) that comprise a maximally symmetric two-dimensional square composite lattice in a photoresist film with a basis chosen to optimize the z-polarization at a point in the primitive cell, and the additional plane waves (upper half-space) that result from the reflection of these incident waves from a photoresist/silicon interface (refractive indices 1.7 and 1.1+2.6i, respectively, at $\lambda_D$=193 nm).

Figure 48B:
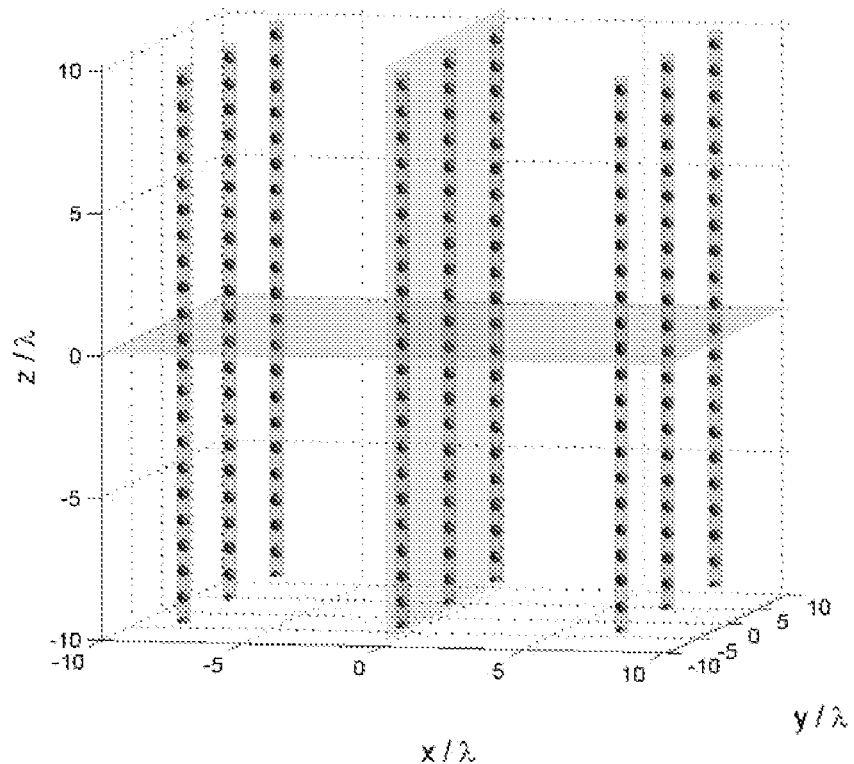

FIG. 48B is a three-dimensional plot of surfaces of 50% of maximum intensity for the two-dimensional lattice (translucent) created with the plane waves in the lower half-space of FIG. 48A, as well as the three-dimensional lattice (opaque) resulting from the interaction of both the incident and reflected waves of FIG. 48A.

Figure 48C:
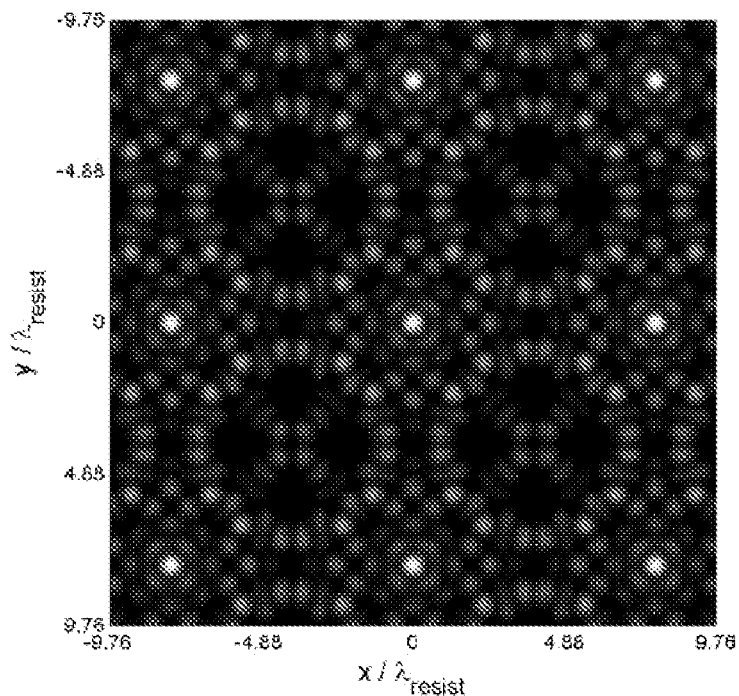
Figure 48D:
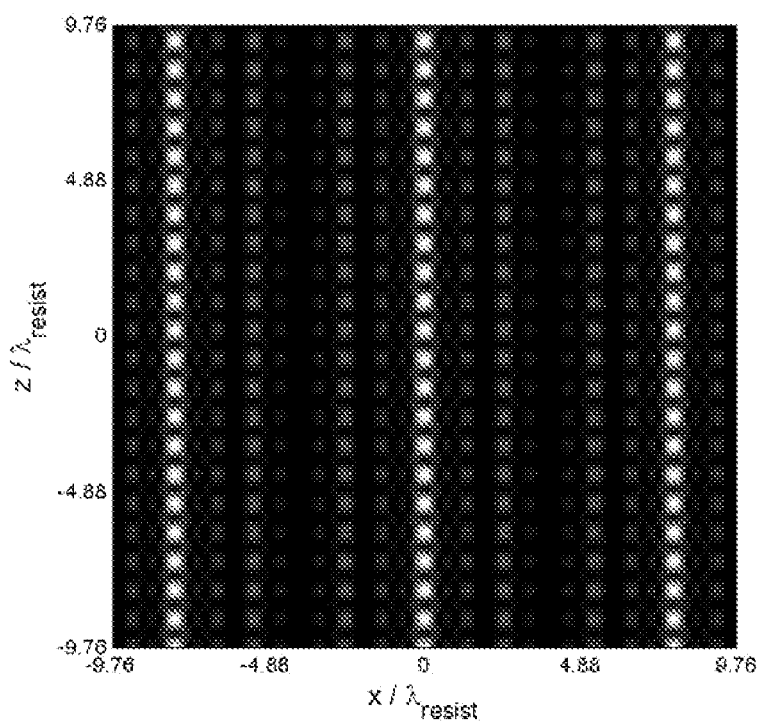

FIGS. 48C and 48D are linear grayscale images of the excitation intensity for the three-dimensional lattice with reflections in the xy, and yz planes, respectively, as shown in FIG. 48B.

Figure 49A:
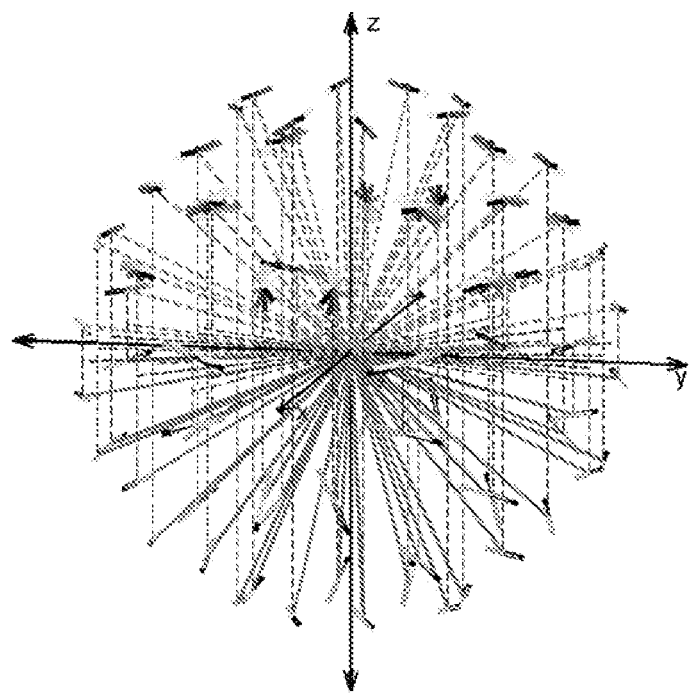

FIG. 49A is a three-dimensional representation of the relative wavevector and electric field directions and real field magnitudes at different times for those plane waves (lower half-space) of the maximally symmetric three-dimensional simple cubic composite lattice of intensity period= $\sqrt{59}\lambda_{resist}/2$ incident from z>0 onto an xy-oriented photoresist/silicon interface (lattice c-axis□$\hat{e}_z$), as well as the remaining plane waves of the maximally composite set (upper half-space) created by reflection of the incident waves from the interface. The basis is chosen to maximize the projection of the electric field of each incident wave along $\hat{e}_x$□α-axis at the interface (z=0).

Figure 49B:
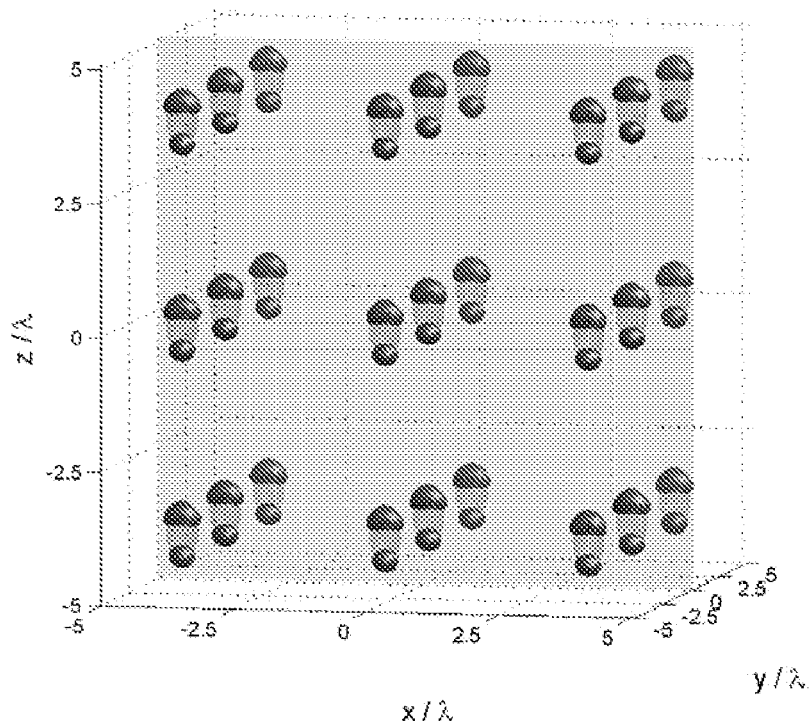

FIG. 49B is a three-dimensional plot of surfaces of 50% of maximum intensity for the half-space subset lattice (translucent) consisting of only the incident waves from FIG. 49A, as well as the lattice (opaque) formed from both the incident and reflected waves.

Figure 49C:
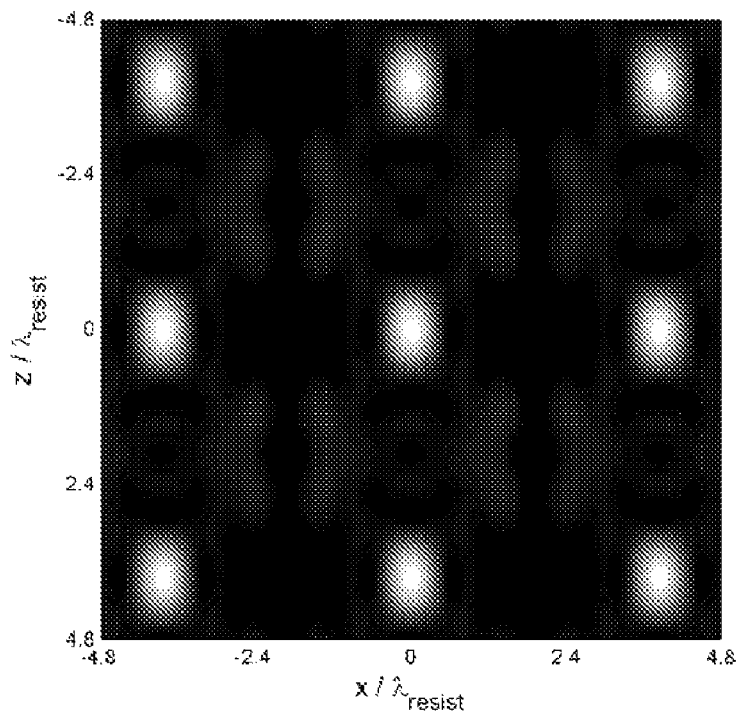
Figure 49D:
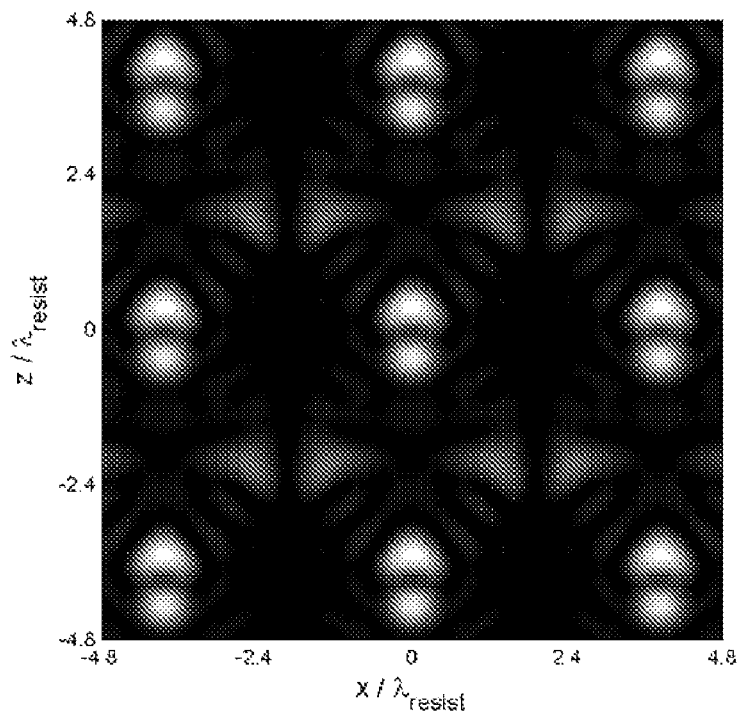

FIGS. 49C and 49D are linear grayscale images of the excitation intensity in the x-z plane shown in FIG. 49B for the lattices formed by the incident waves only and the incident and reflected waves together, respectively.

Figure 50A:
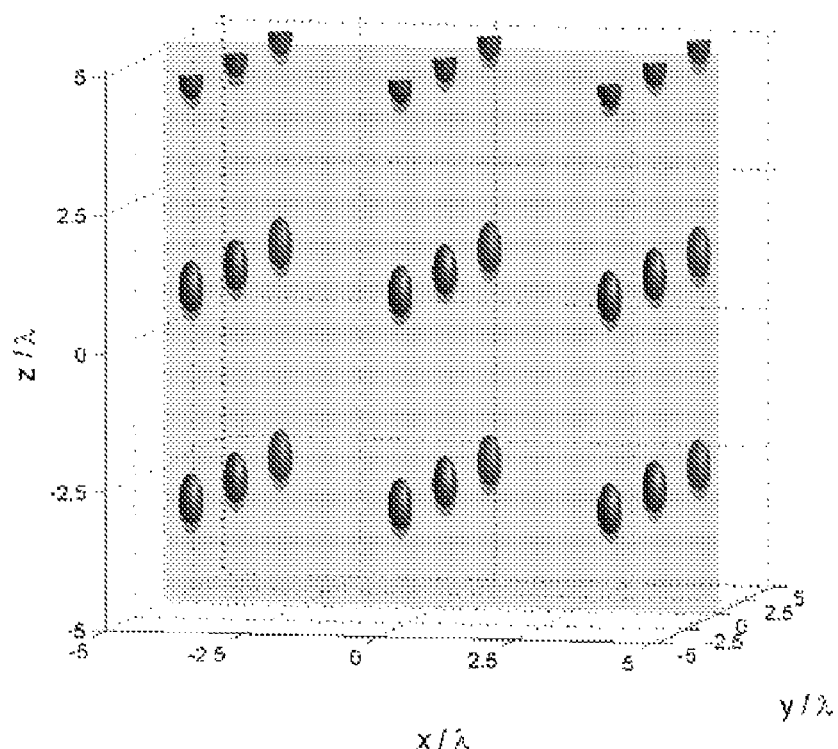

FIG. 50A is a three-dimensional plot of surfaces of 50% of maximum intensity for a three-dimensional simple cubic composite lattice (translucent) of intensity period $\sqrt{59}\lambda_{water}/2$ and c-axis□$\hat{e}_z$ consisting of those plane waves of the associated maximally symmetric lattice incident from z>0 onto an xy-oriented water/glass interface (refractive indices 1.33 and 1.52, respectively) as well as their subsequent reflections, and the related lattice (opaque) formed by the same incident waves and their reflections from a water/glass interface with an intervening $MgF_2$ anti-reflection film. The basis in each case is chosen to maximize the projection of the electric field of each incident wave along $\hat{e}_z$ at a point z=0.25 periods from the water/glass or water/$MgF_2$ interface.

Figure 50B:
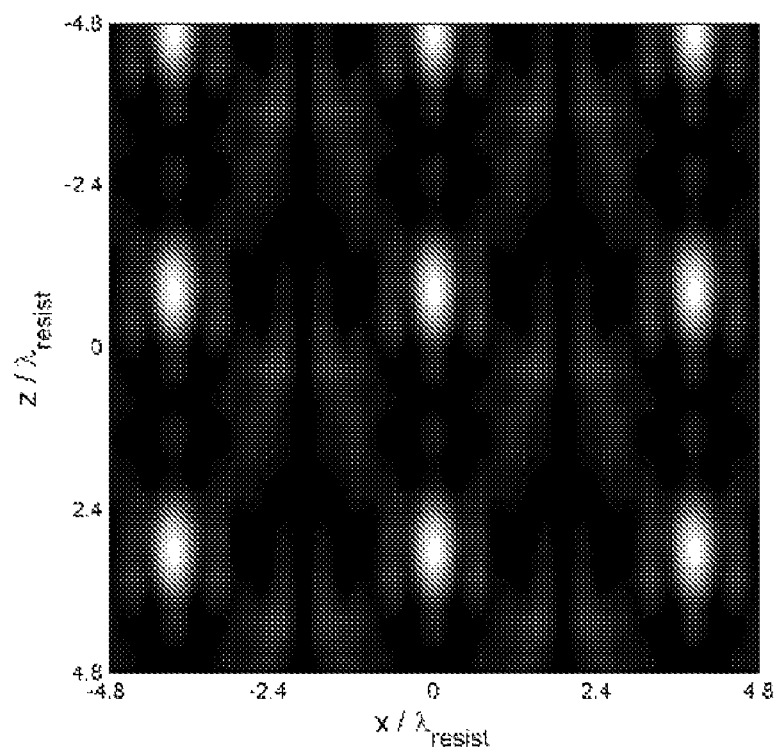
Figure 50C:
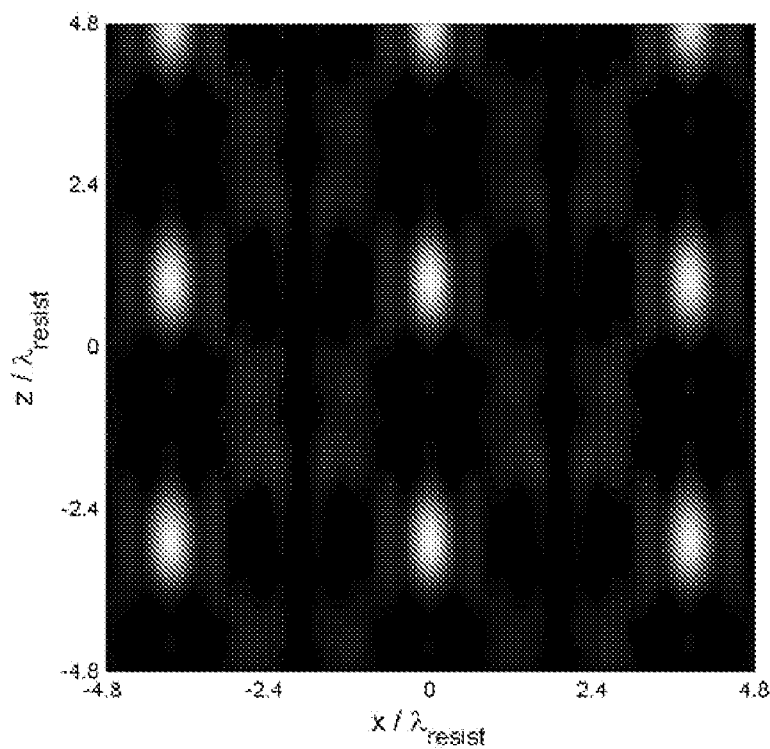
Figure 50D:
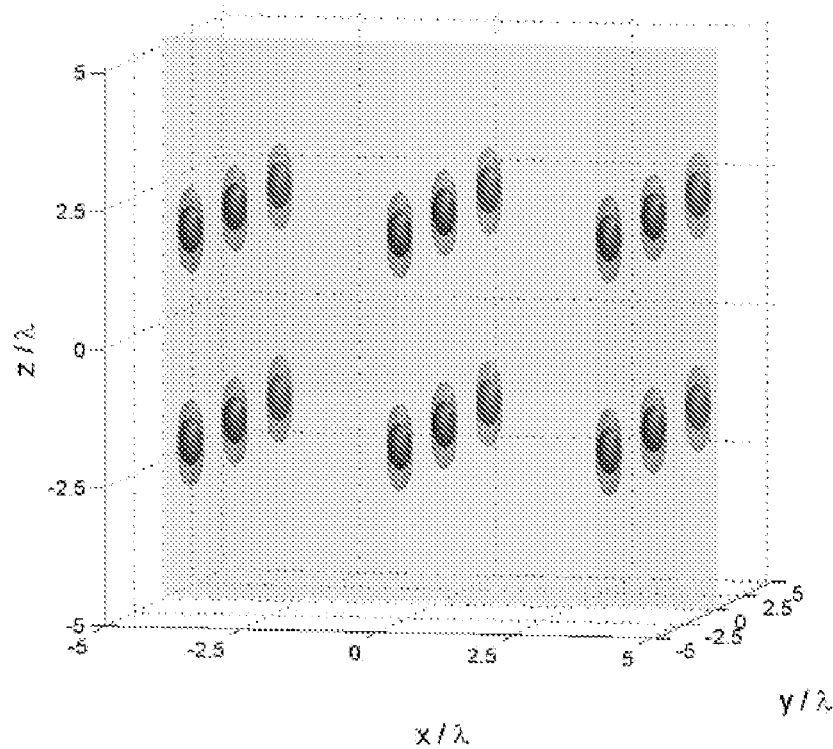

FIG. 50D is a similar plot of the lattice under the same interfacial conditions, but with a basis chosen to maximize the projection of each incident electric field along $\hat{e}_z$ at a distance of z=0.50 periods from the water/glass or water/$MgF_2$ interface.

Figure 50E:
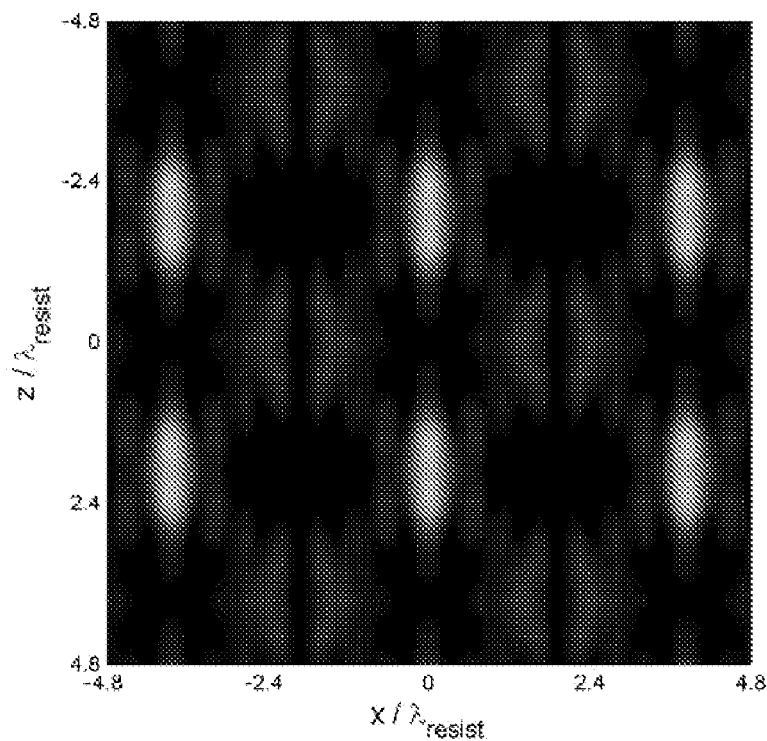

FIGS. 50B and 50E are linear grayscale images of the excitation intensity in the xz plane of FIGS. 50A and 50D, respectively, for the lattice without an anti-reflection film at the interface, revealing significant dependence of the basis under translation of the lattice along $\hat{e}_z$.

Figure 50F:
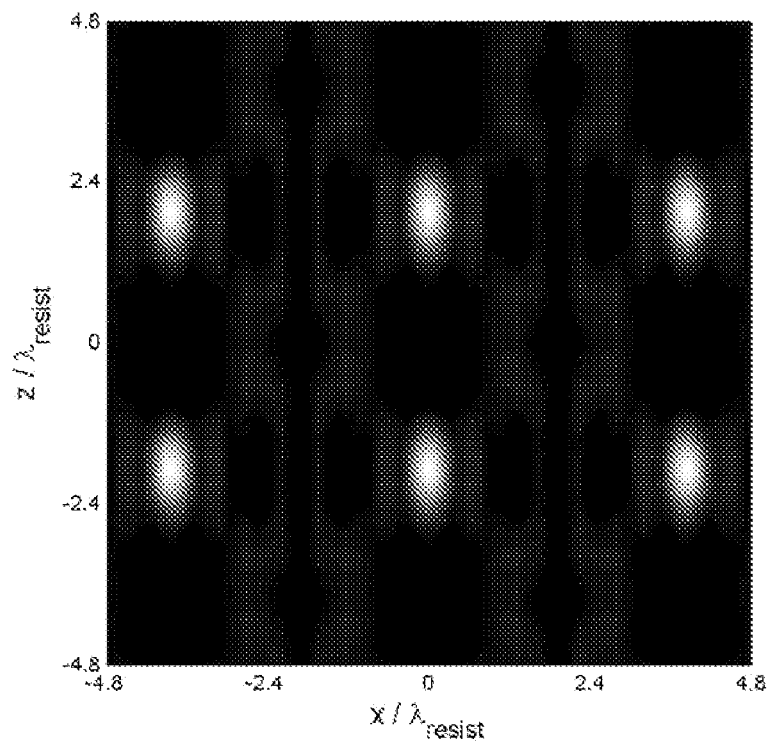

FIGS. 50C and 50F are similar linear grayscale images for the lattice with an anti-reflection film at the interface, demonstrating far less reflection-induced dependence of the basis under translation along $\hat{e}_z$.

Figure 51A:
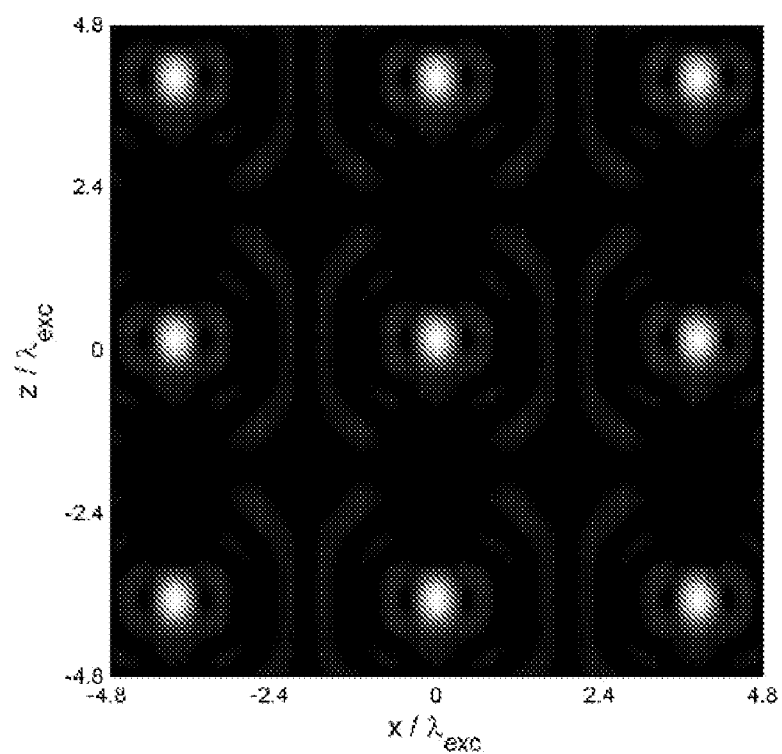
Figure 51B:
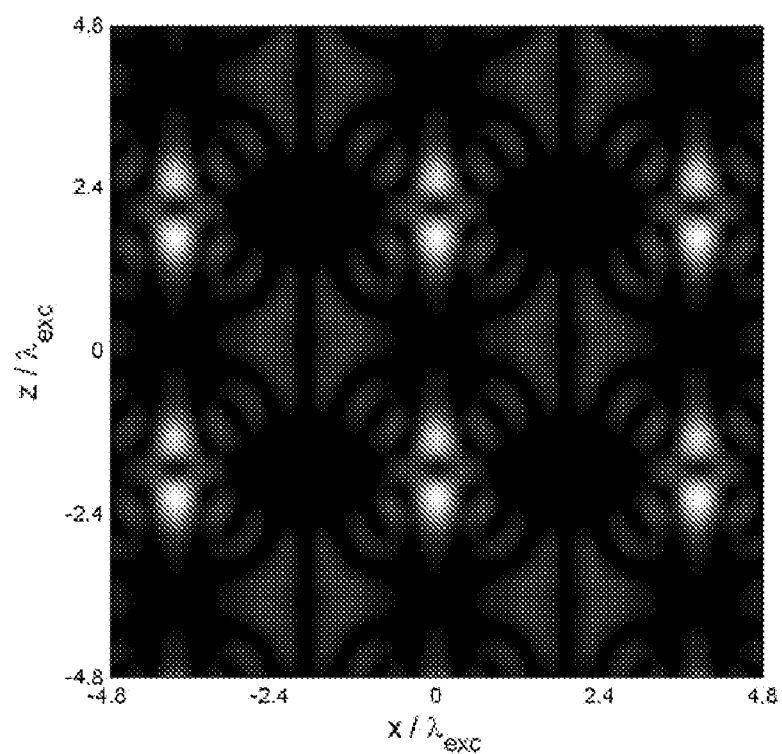

FIGS. 51A and 51B are linear grayscale images of the excitation intensity in the xz plane of a three-dimensional simple cubic composite lattice of intensity period $\sqrt{59}\lambda_{resist}/2$ and c-axis□$\hat{e}_z$ consisting of those plane waves of the associated maximally symmetric lattice incident from z>0 onto an xy-oriented photoresist/silicon interface and their subsequent reflections, with bases chosen to maximize the projection of each incident electric field along $\hat{e}_z$ at a distances of z=0 and z=0.50 periods from the interface, respectively.

Figure 51C:
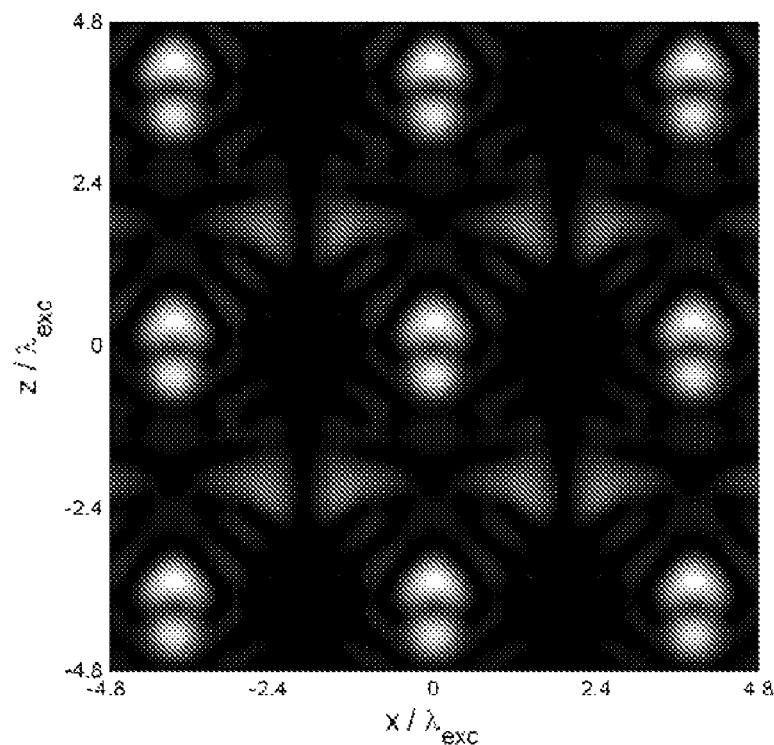
Figure 51D:
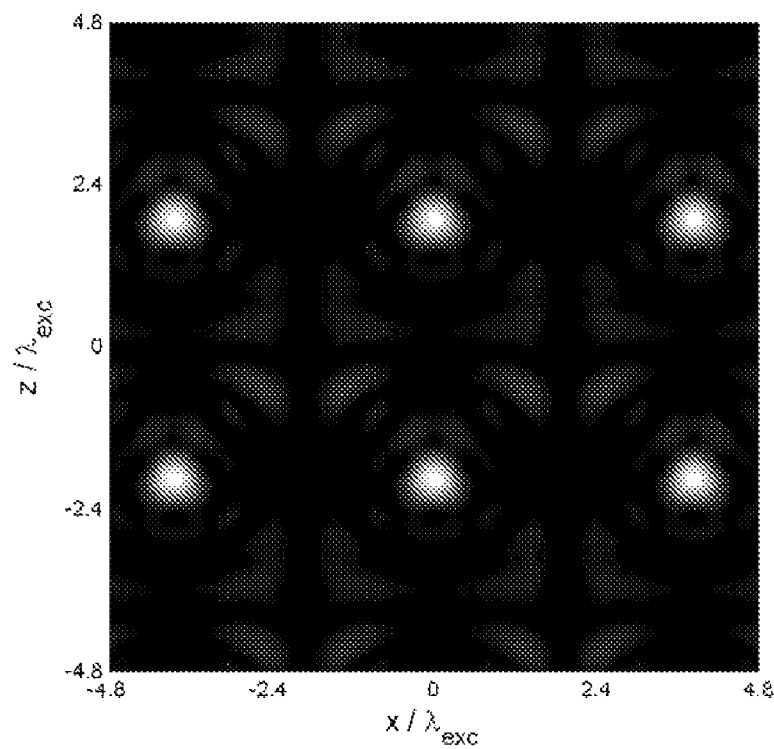

FIGS. 51C and D are similar images of the same lattice near the same interface, but with bases chosen to maximize the projection of each incident electric field along $\hat{e}_z$ at a distances of z=0 and z=0.50 periods from the interface, respectively, demonstrating that different bases provide optimal intensity confinement and contrast at different distances from a partially reflective interface.

Figure 52A:
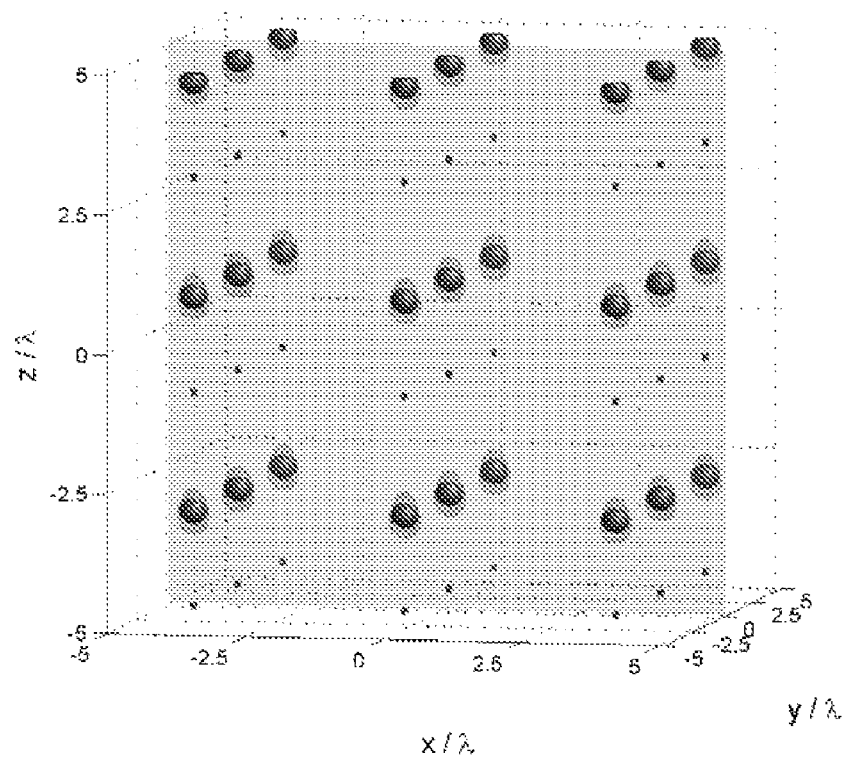

FIG. 52A is a three-dimensional plot of surfaces of 50% of maximum intensity for two three-dimensional simple cubic composite lattices of intensity period $\sqrt{59}\lambda_{resist}/2$ and c-axis□$\hat{e}_z$ consisting of those plane waves of the associated maximally symmetric lattice incident from z>0 onto an xy-oriented photoresist/silicon interface as well as their subsequent reflections, with the basis of the first lattice (translucent) chosen to maximize the projection of each incident electric field along $\hat{e}_x$ at a distance of z=0.20 periods from the interface, and the basis of the second lattice (opaque) chosen to maximize the projection of the superposition of each incident field with its associated reflected field in the same direction and at the same distance from the interface.

Figure 52B:
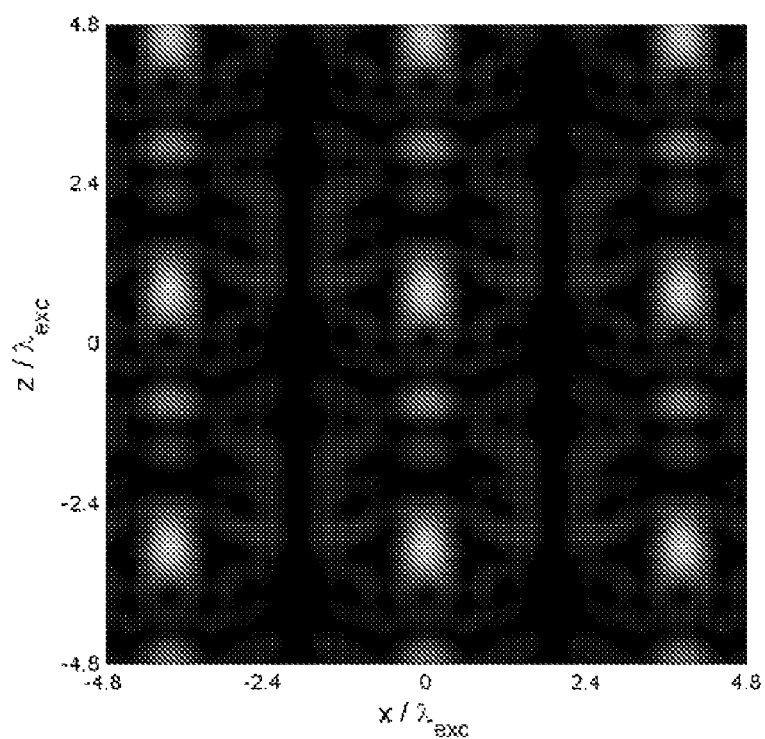
Figure 52C:
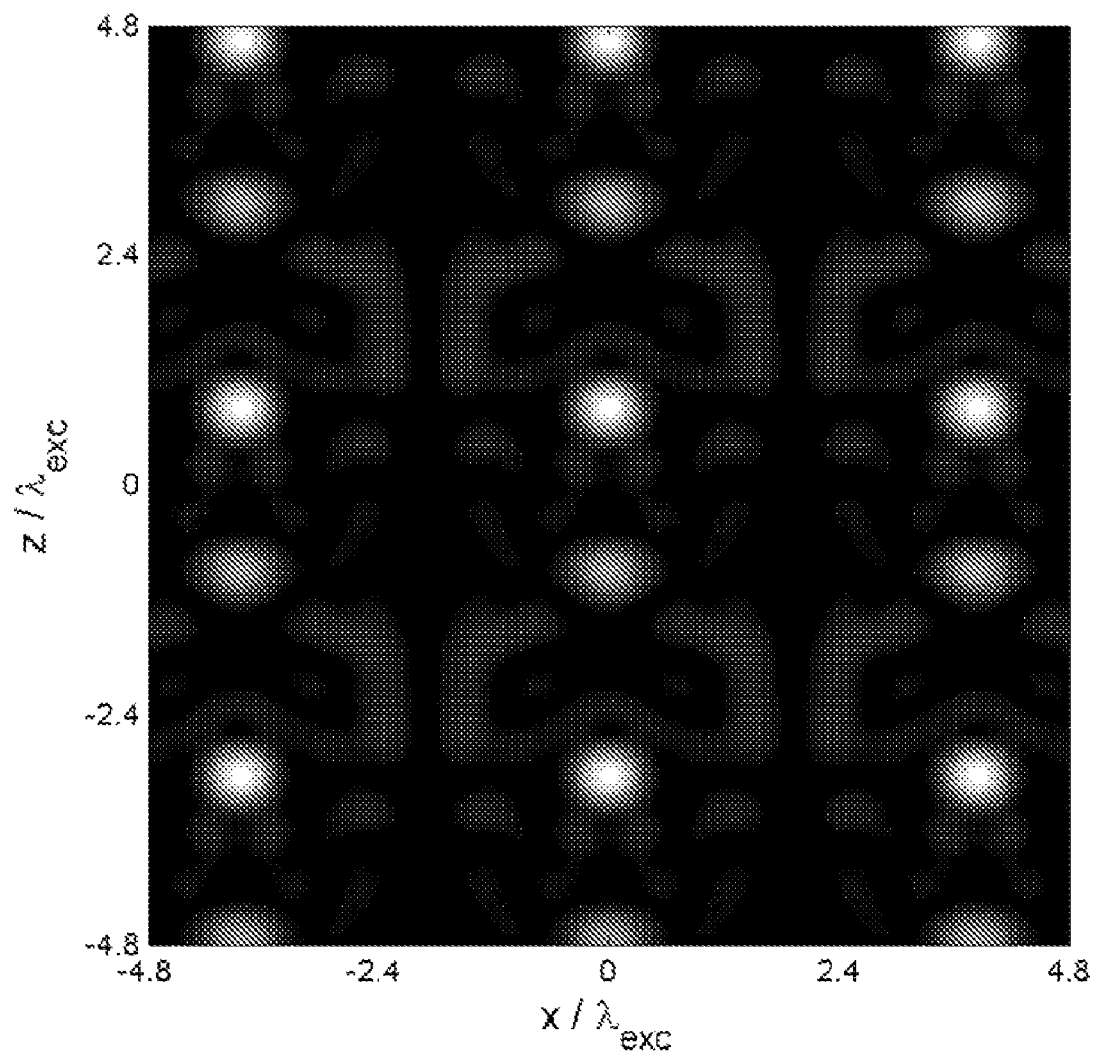

FIGS. 52B and 52C are linear grayscale images of the excitation intensity in the xz plane for the first and second lattices of FIG. 52A, respectively.

Figure 53A:
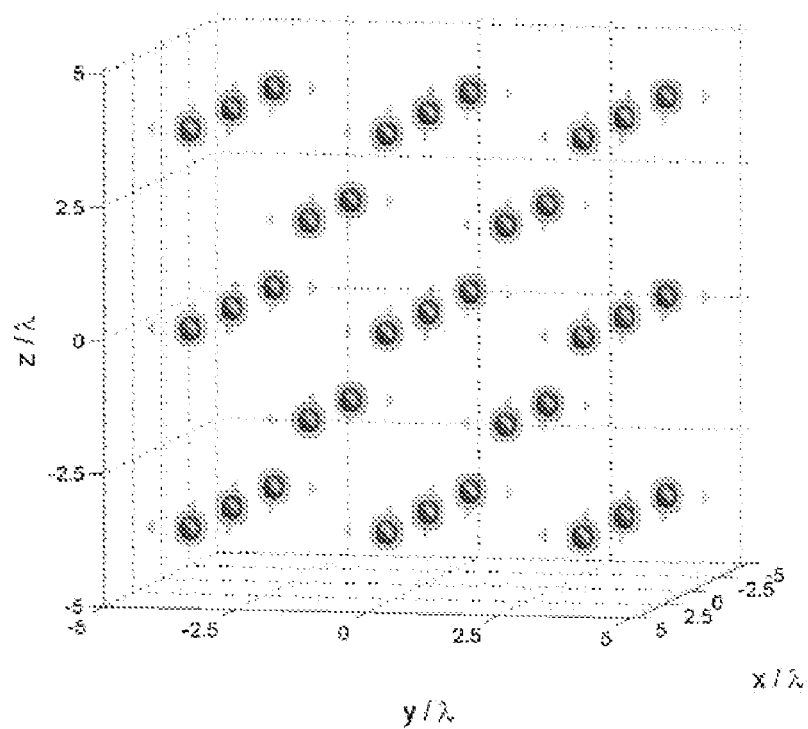

FIG. 53A is a three-dimensional plot of the surfaces of 20% (translucent) and 50% (opaque) of the maximum intensity for a maximally symmetric body-centered cubic lattice of intensity period $\sqrt{14}\lambda$ having a basis that optimizes the z-component of the total basis field at the intensity maxima.

Figure 53B:
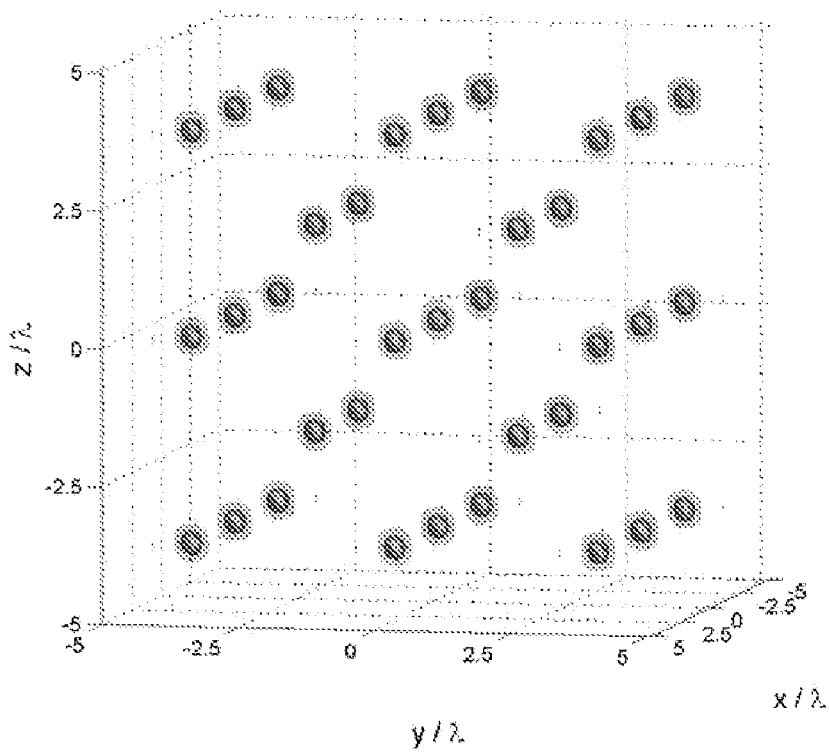

FIG. 53B is a three-dimensional plot of the surfaces of 20% (translucent) and 50% (opaque) of the maximum intensity for the same lattice as in FIG. 53A, but with the basis perturbed by introducing a phase error of 180° in one of the constituent plane waves having the largest projection onto the desired z-polarization state.

Figure 54A:
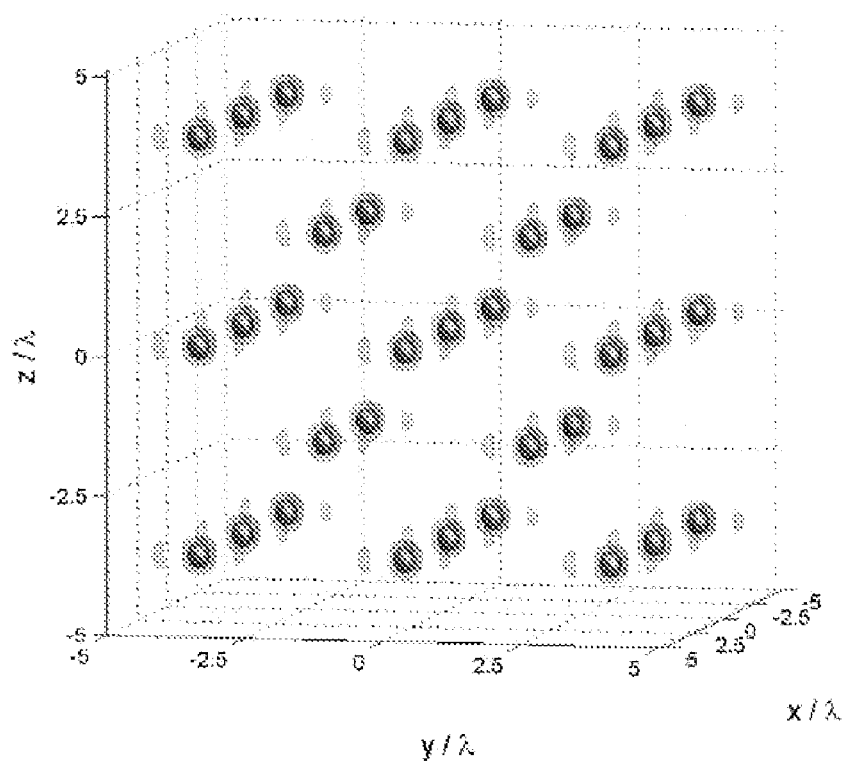
Figure 54B:
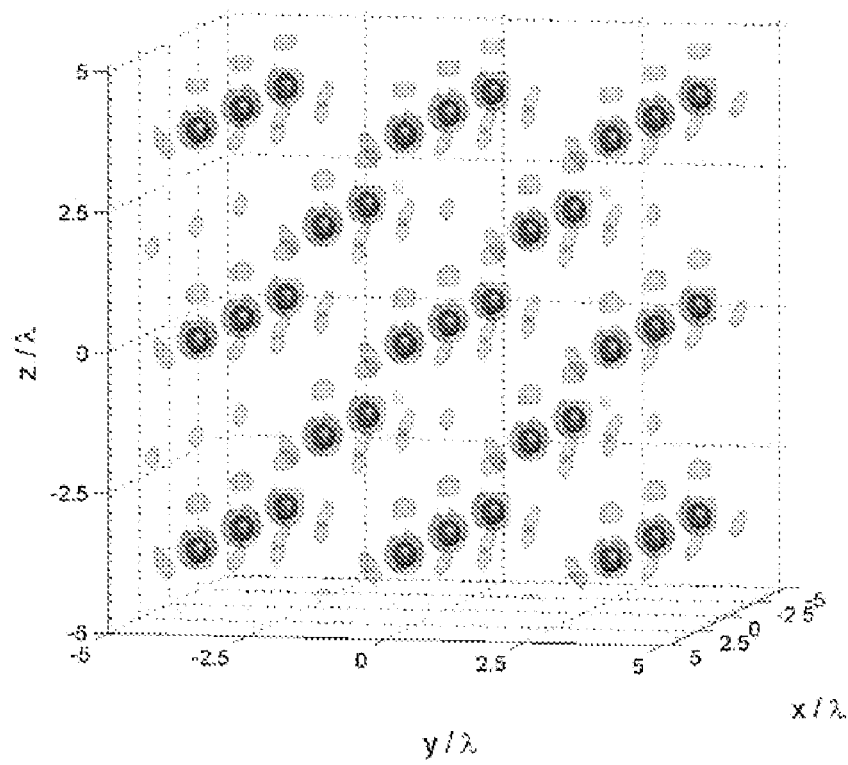
Figure 54C:
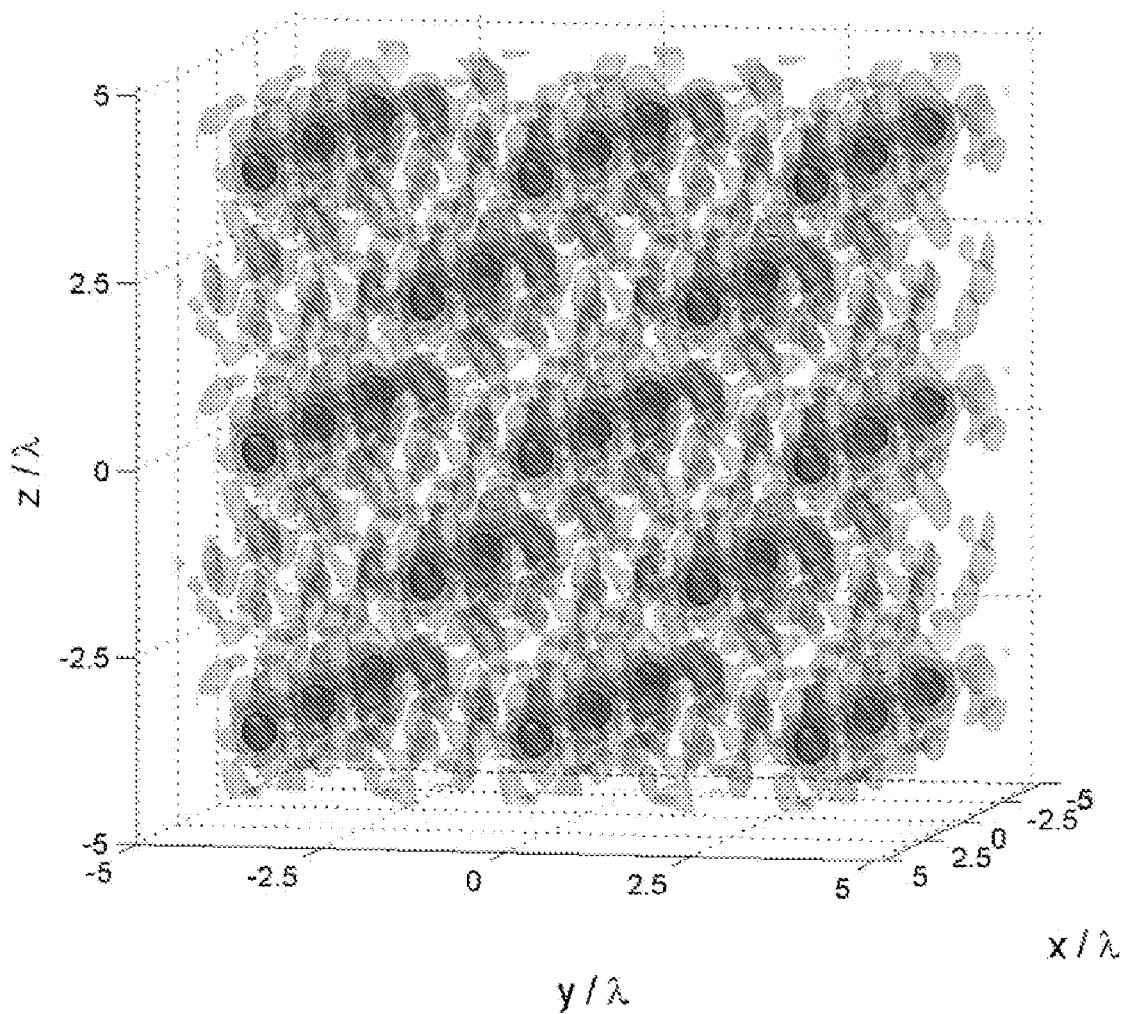

FIGS. 54A, 54B, and 54C are three-dimensional plot of the surfaces of 20% (translucent) and 50% (opaque) of the maximum intensity for the same lattice as in FIG. 53A, but with the basis perturbed by introducing random phase errors in all constituent plane waves, such errors being normally distributed about a mean of 0°, with a standard deviation of 30°, 45°, and 60°, respectively.

Figure 55A:
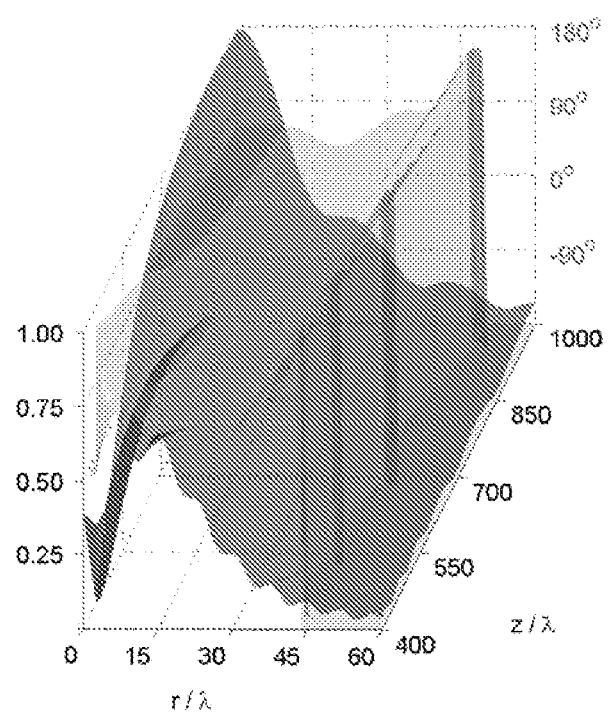
Figure 55B:
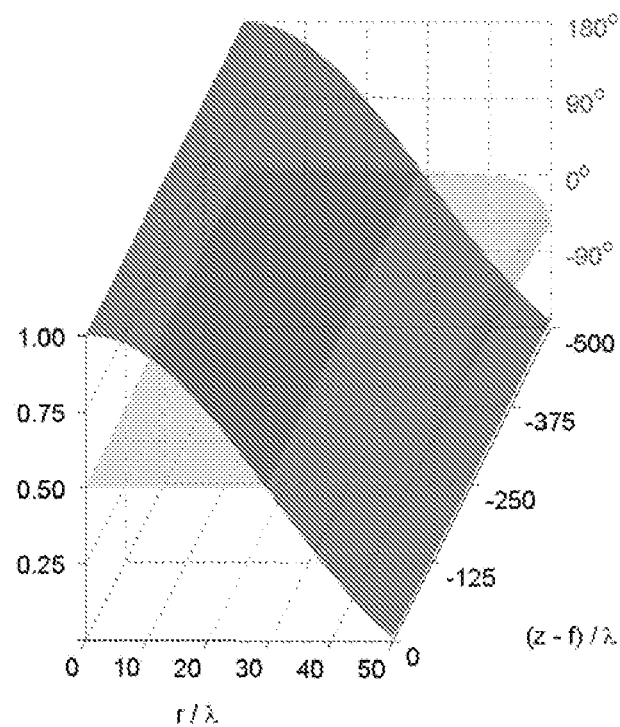

FIG. 55A is a surface plot of the amplitude (dark translucent) and the phase (light translucent) of the complex deviation from plane wave behavior for the diffracted field $e_n(x,t)$ transmitted through an aperture of radius $\alpha=30\lambda$. FIG. 55B is a surface plot of the amplitude (dark translucent) and the phase (light translucent) of the complex deviation from plane wave behavior for the field $e_n(x,t)$ in the neighborhood of the focal point of a lens of focal length f and radius $\alpha=0.012f$.

Figure 56A:
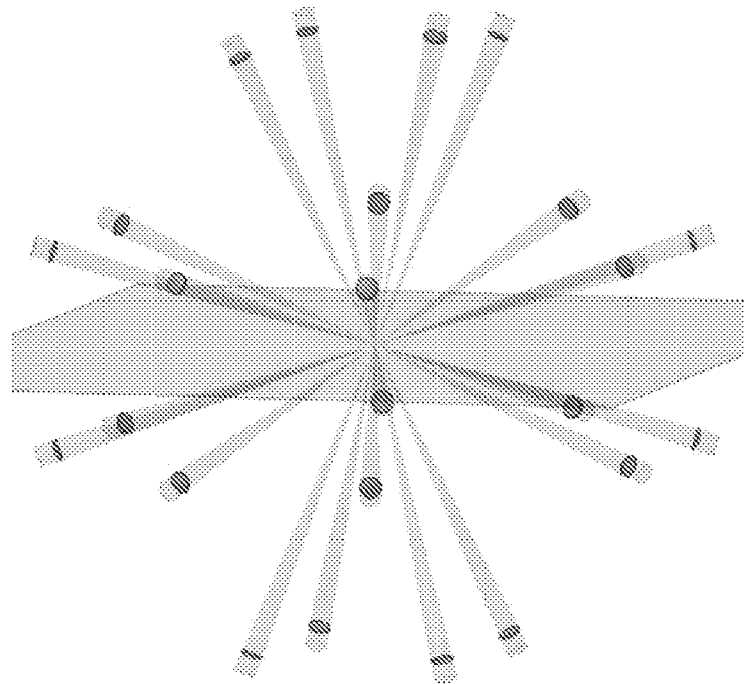
Figure 56B:
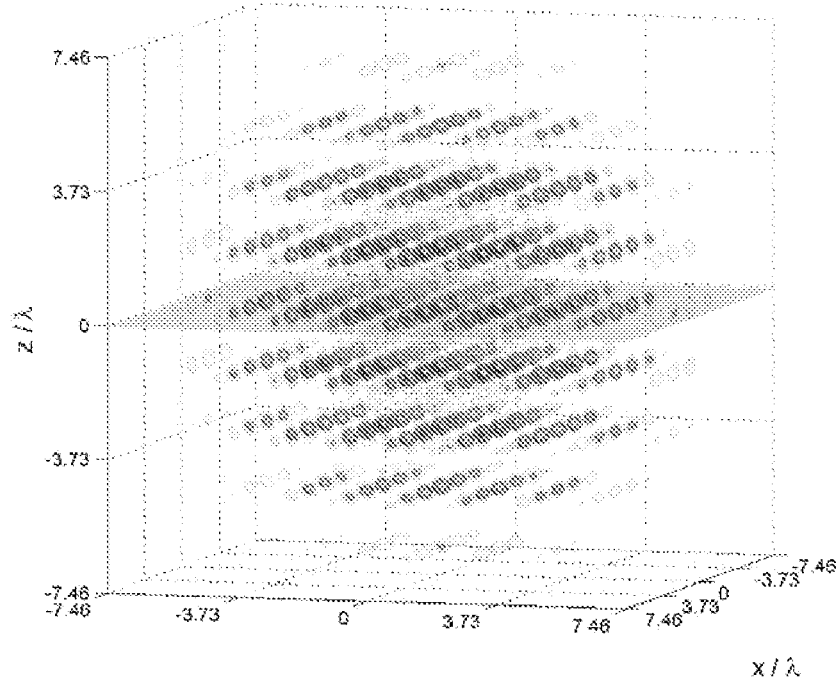
Figure 56C:
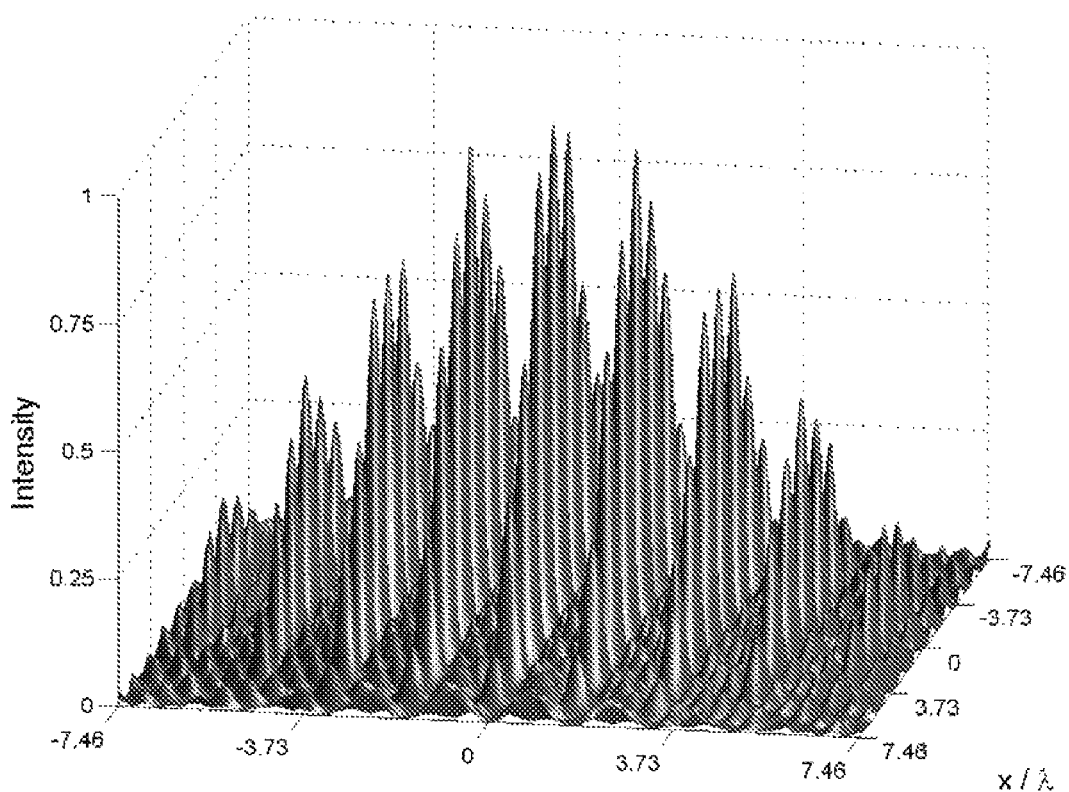

FIG. 56A is a conceptual view of the experimental arrangement of 24 low $n\alpha$ lenses used for the external excitation of a maximally symmetric simple cubic bound lattice of intensity period $\sqrt{11}\lambda/2$. FIG. 56B is a three-dimensional plot of surfaces of 50% (opaque), 20% (medium translucent), and 10% (light translucent) of maximum intensity for the bound lattice generated with the method of FIG. 49A, assuming $n\alpha \approx \alpha/f=0.08$. FIG. 56C is a surface plot of the intensity in the xy-plane through the center of the bound lattice of FIG. 56B.

Figure 57A:
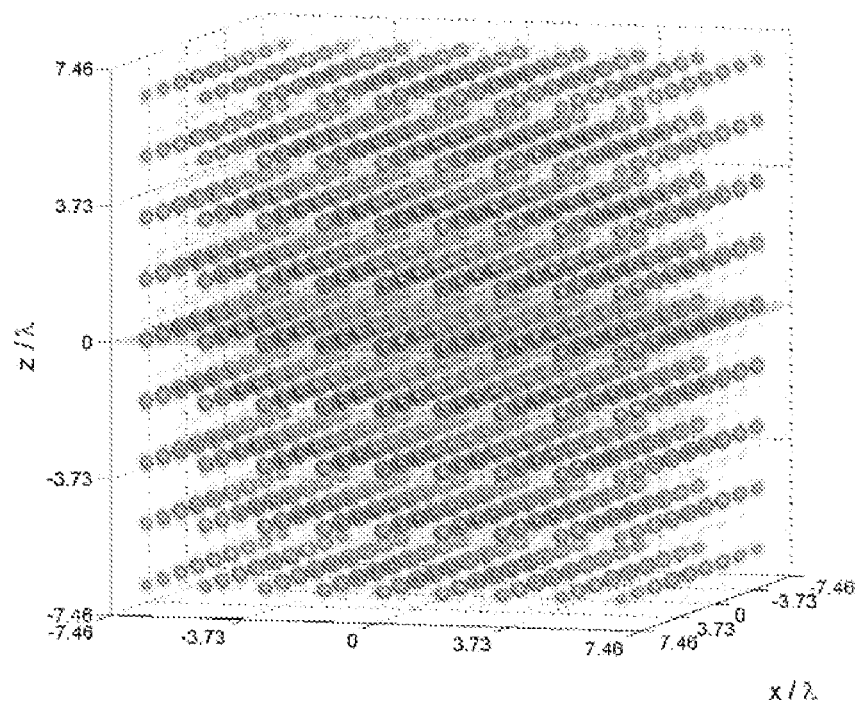
Figure 57B:
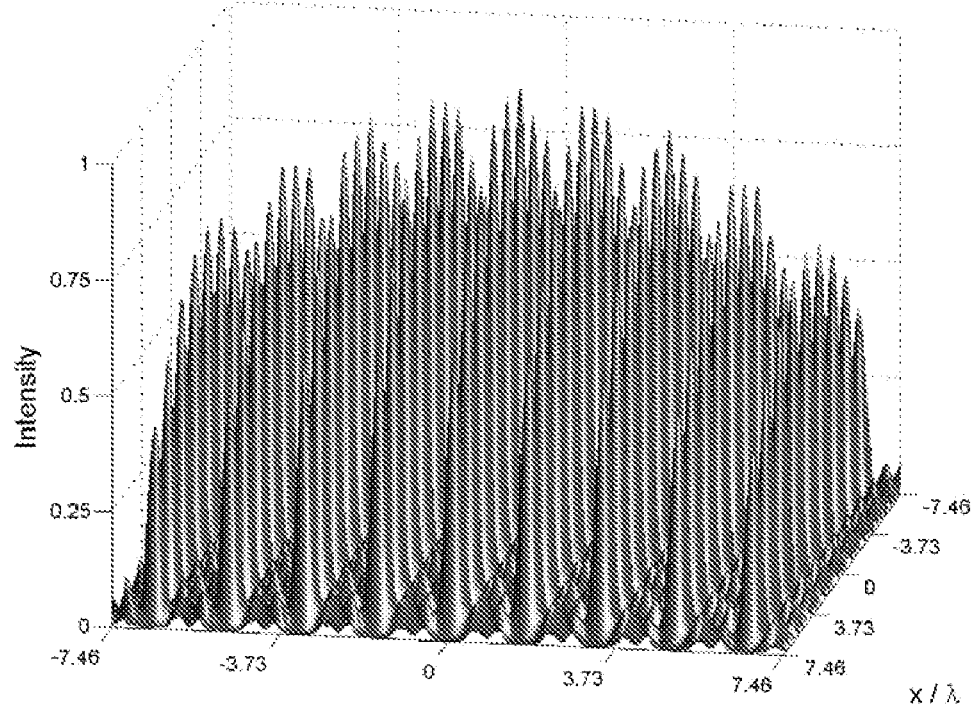
Figure 57C:
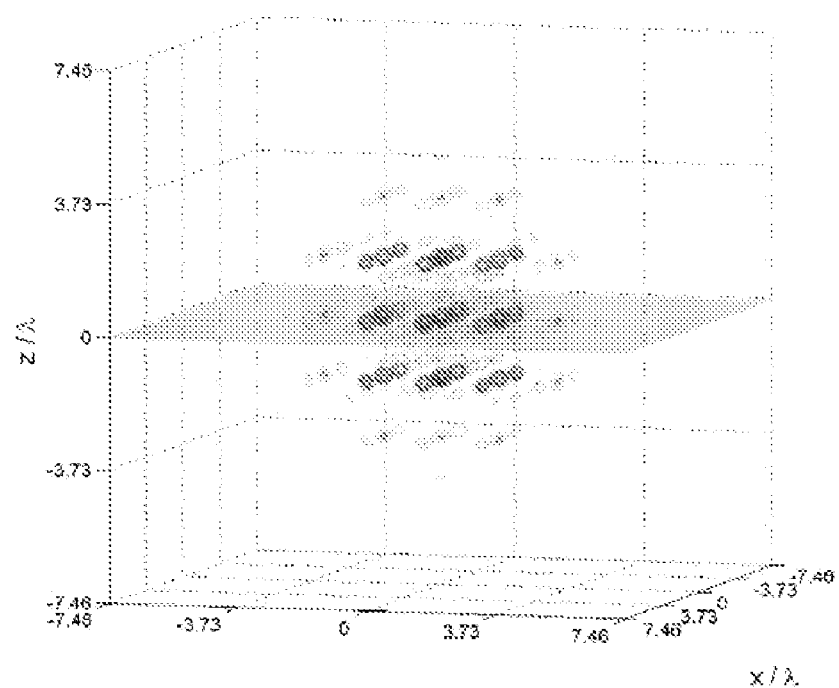
Figure 57D:
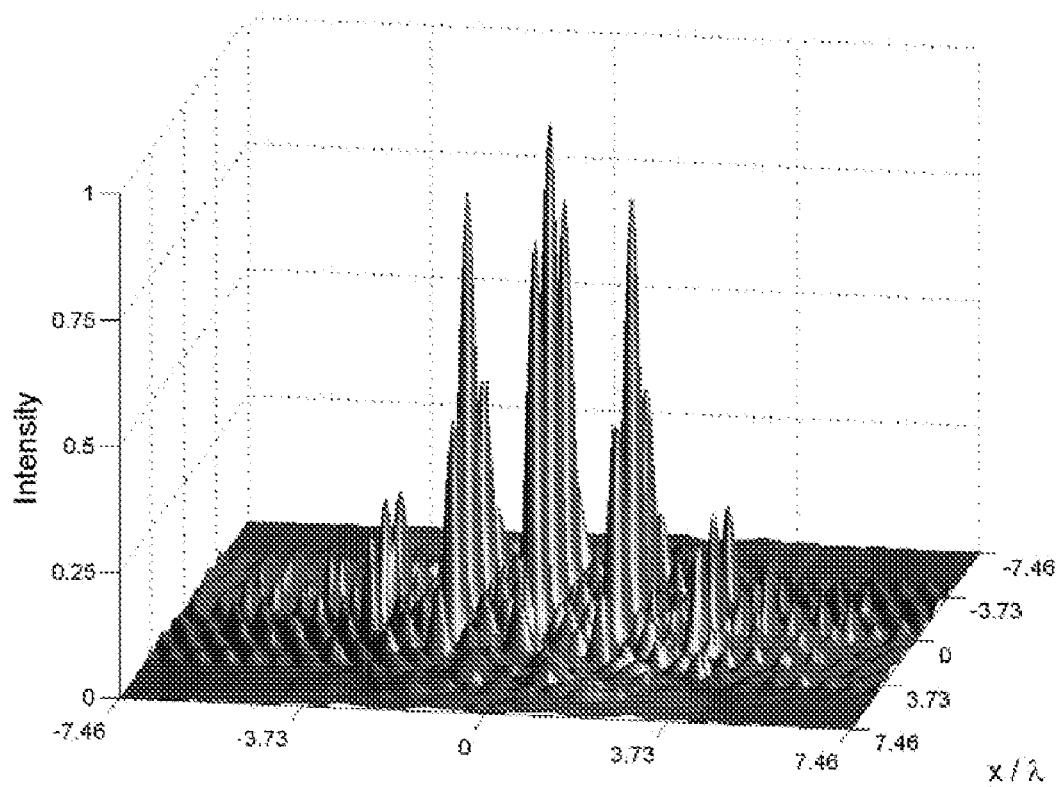
Figure 57E:
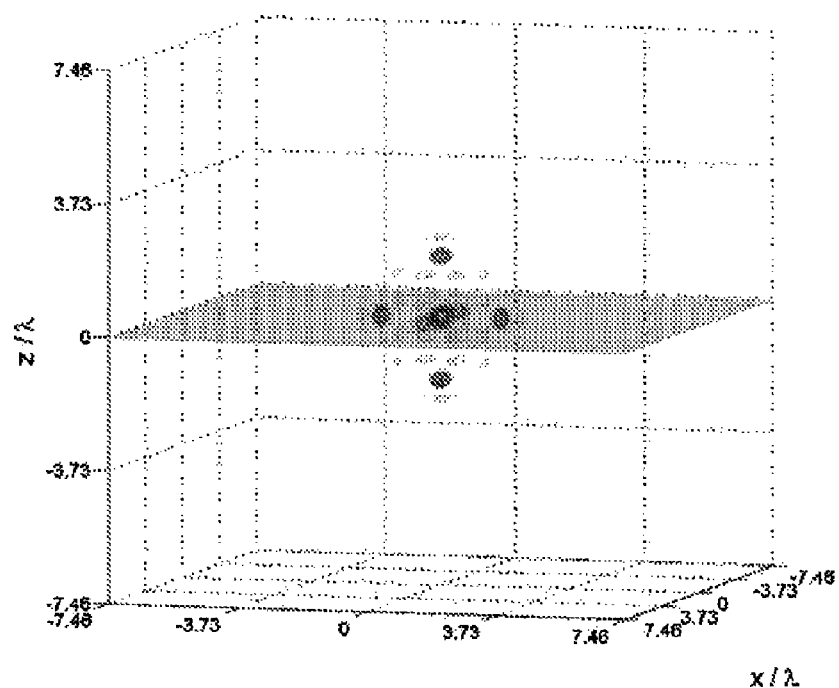
Figure 57F:
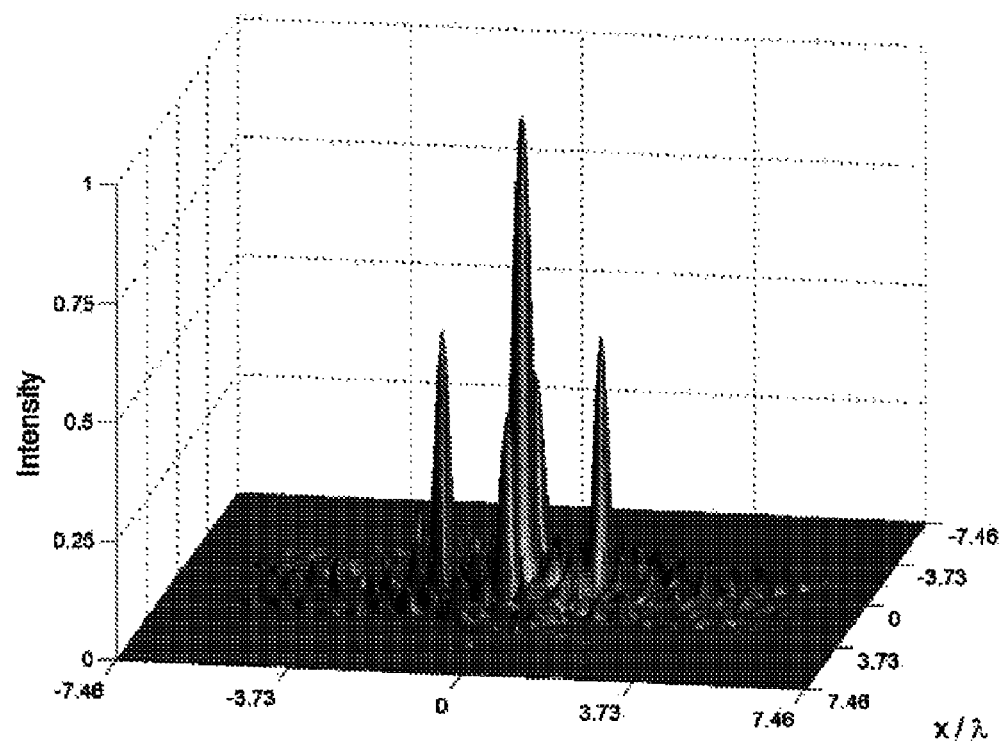

FIGS. 57A, C, and E are three-dimensional plots of surfaces of 50% (opaque), 20% (medium translucent), and 10% (light translucent) of maximum intensity for the bound lattice generated with the method of FIG. 56A, assuming $\alpha/f=-0.04$, 0.16, and 0.32, respectively. FIGS. 57B, D, and F are surface plots of the intensity in the xy-plane through the center of the bound lattice of FIGS. 57A, C, and E, respectively.

Figure 58A:
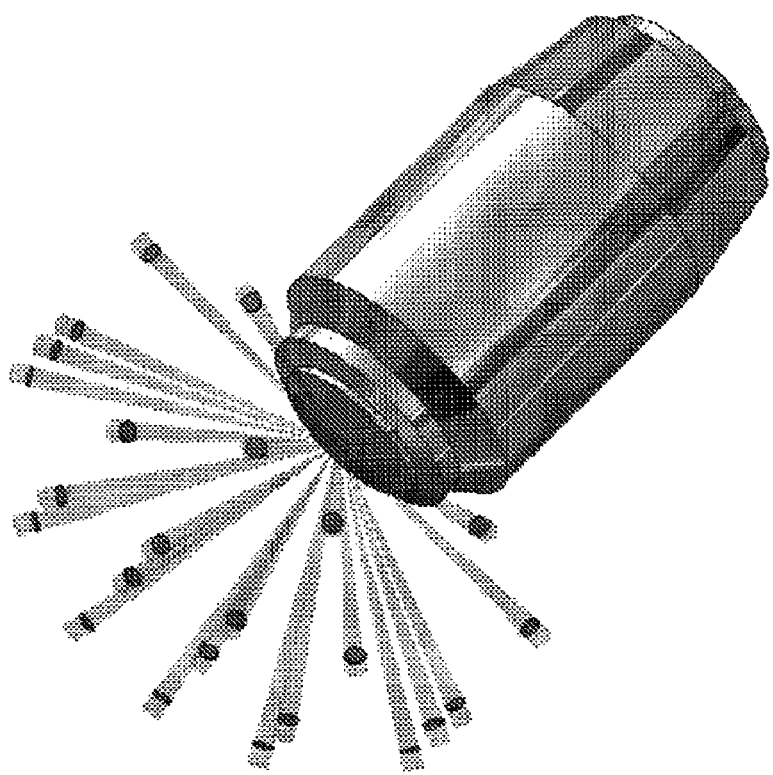
Figure 58B:
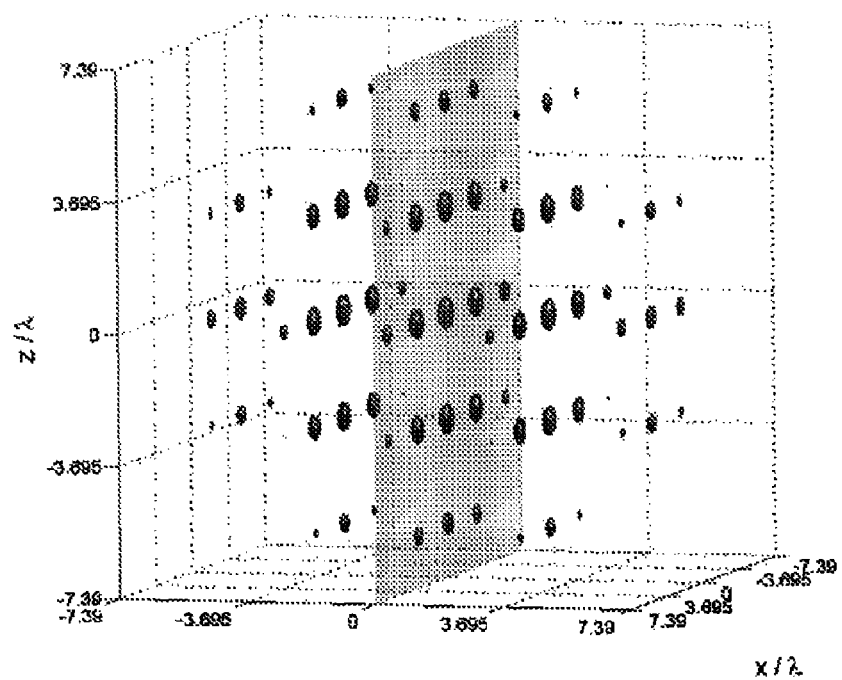
Figure 58C:
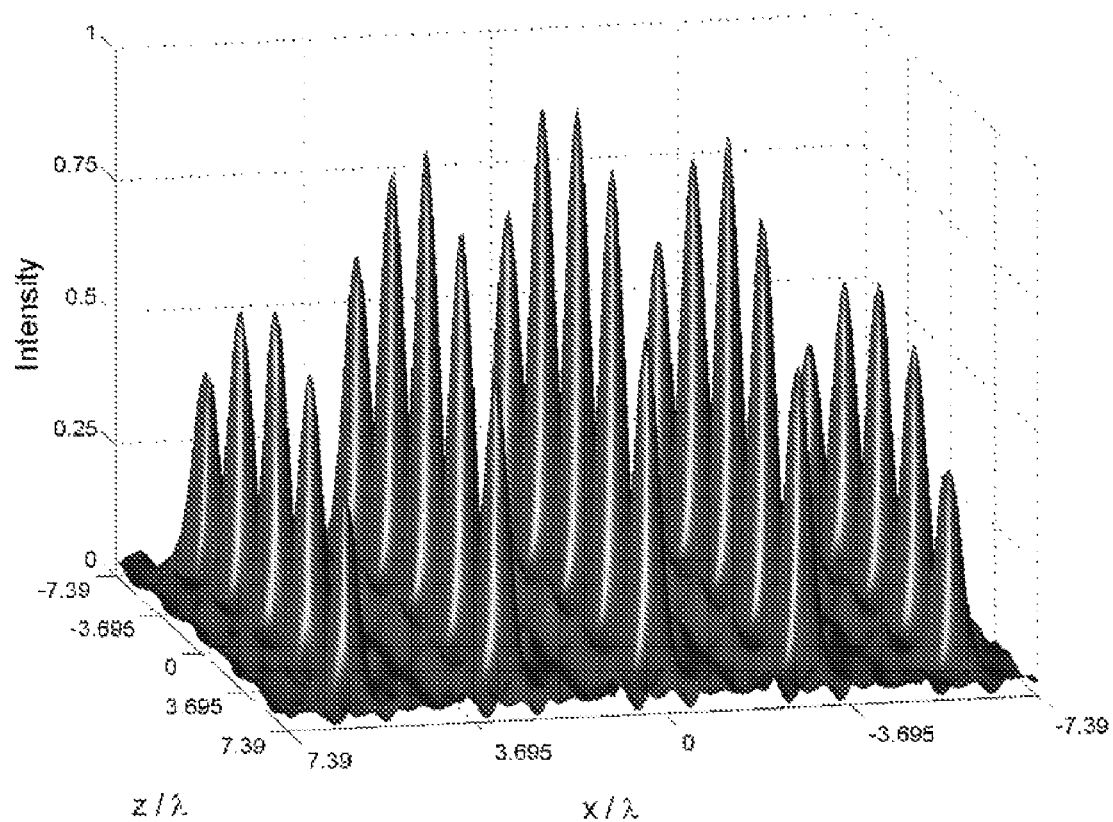

FIG. 58A is a conceptual view of an experimental arrangement for the external excitation of and simultaneous detection of signal from a simple cubic bound subset lattice of intensity period $\sqrt{35}\lambda/2$. Excitation is provided with 24 low $n\alpha$ lenses covering those wavevectors $k_n$ of the corresponding ideal lattice within one half-space, and detection occurs with a single high NA microscope objective in the opposite half-space. FIG. 58B is a three-dimensional plot of surfaces of 50% of maximum intensity for the bound lattice of FIG. 58A (assuming $n\alpha \approx \alpha/f=0.045$), indicating reduced intensity confinement along the axis $\hat{e}_z$ perpendicular to the plane that defines the half-spaces. FIG. 58C is a surface plot of the intensity in the xz-plane through the center of the bound lattice of FIG. 58B.

Figure 59A:
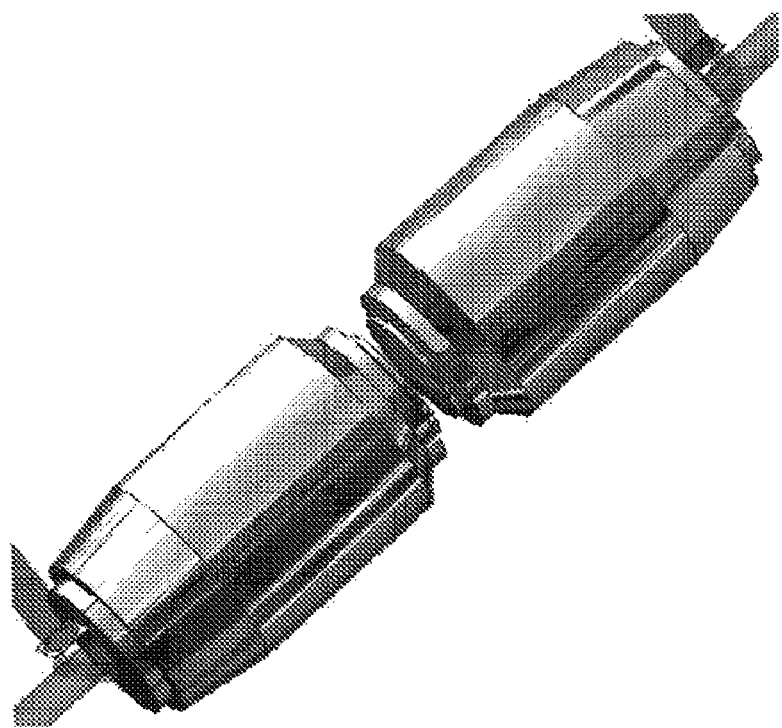
Figure 59B:
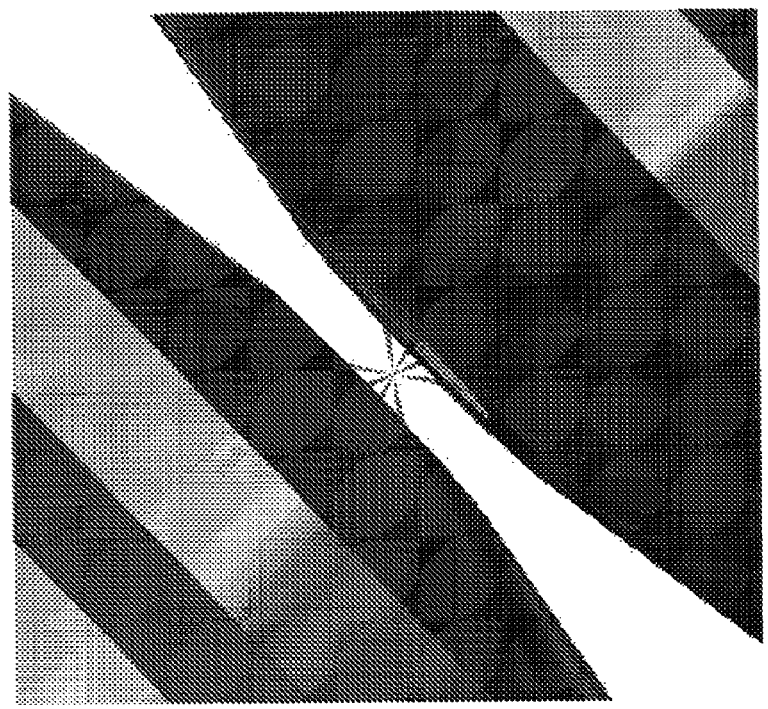
Figure 59C:
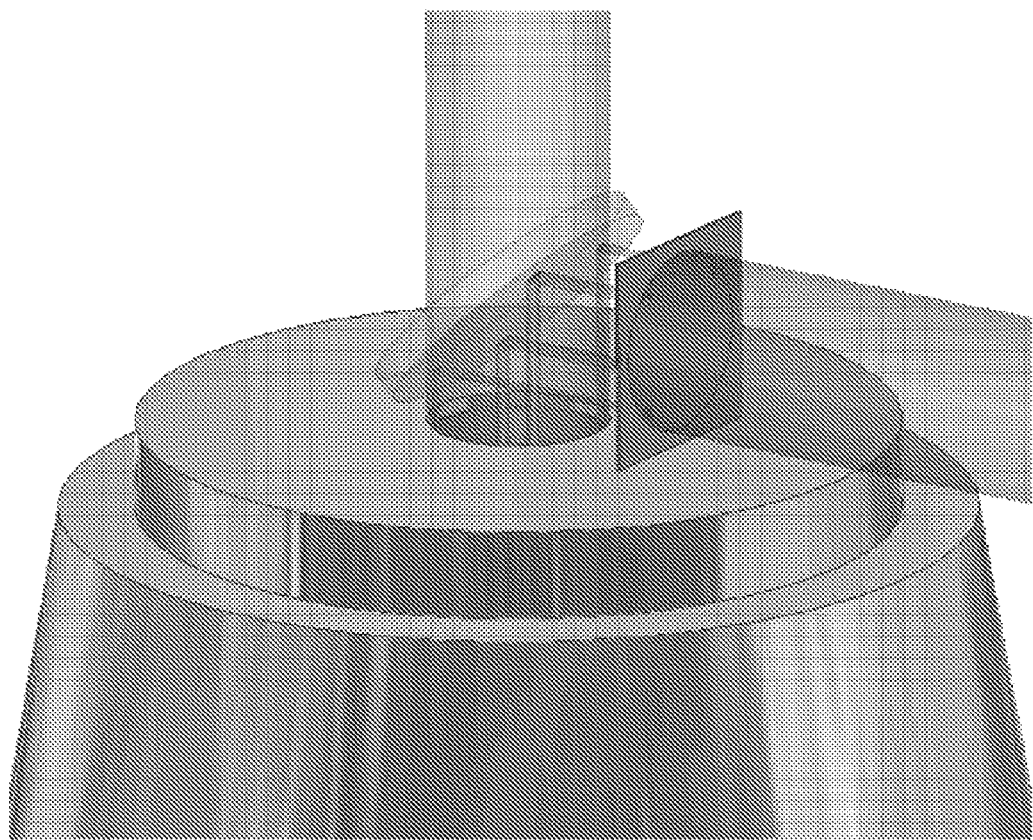

FIGS. 59A, B, and C are conceptual views of an experimental arrangement for the internal excitation of and simultaneous detection of signal from a maximally symmetric simple cubic lattice of intensity period $\sqrt{3}\lambda/2$. FIG. 59A is an overall view, showing the two opposed high NA objectives used. FIG. 59B is a view near the focal point common to the two objectives. FIG. 59C is a view near the rear pupil of one of the objectives, showing an opaque mask with the elliptical apertures that define the necessary input beams.

Figure 60:
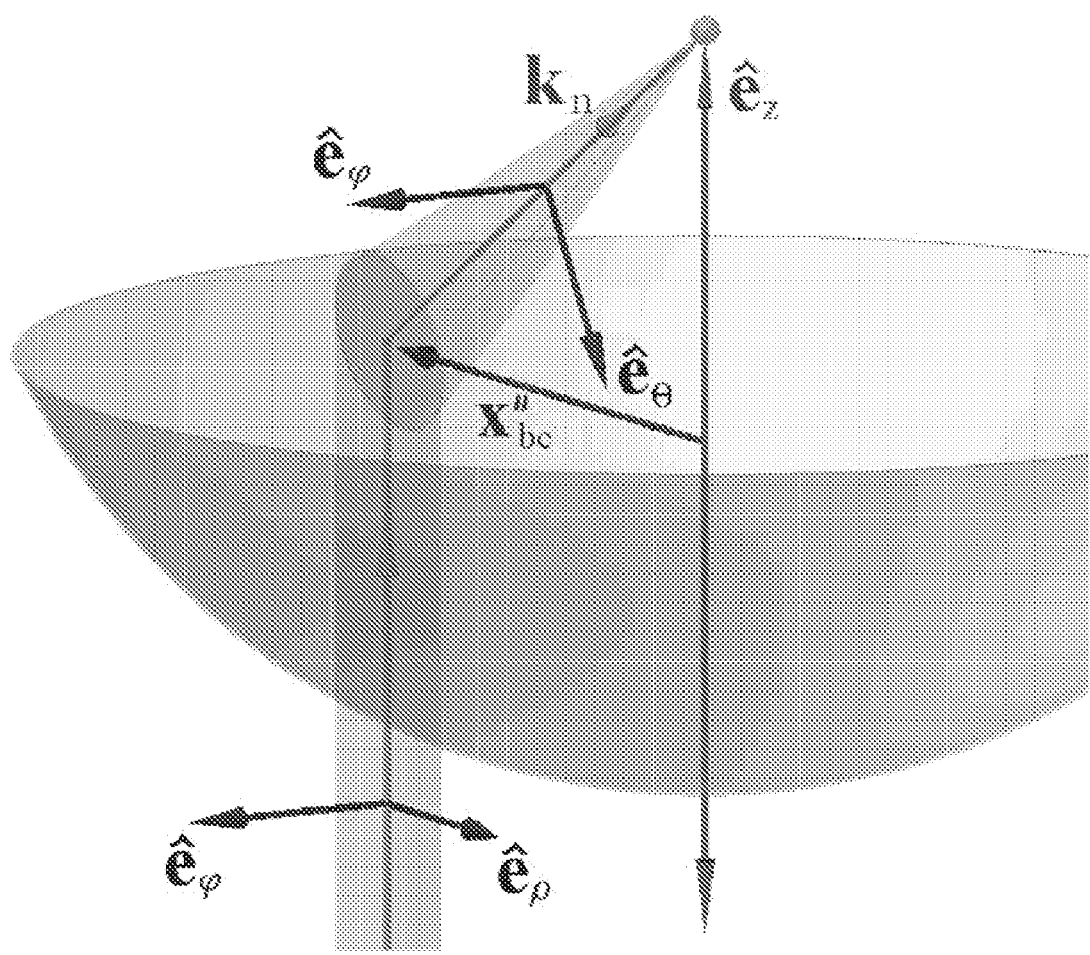

FIG. 60 is a schematic view of the effect on the polarization and beam shape as a confined, off-center circular input beam is transformed into a convergent beam in a high NA microscope objective.

Figure 61A:
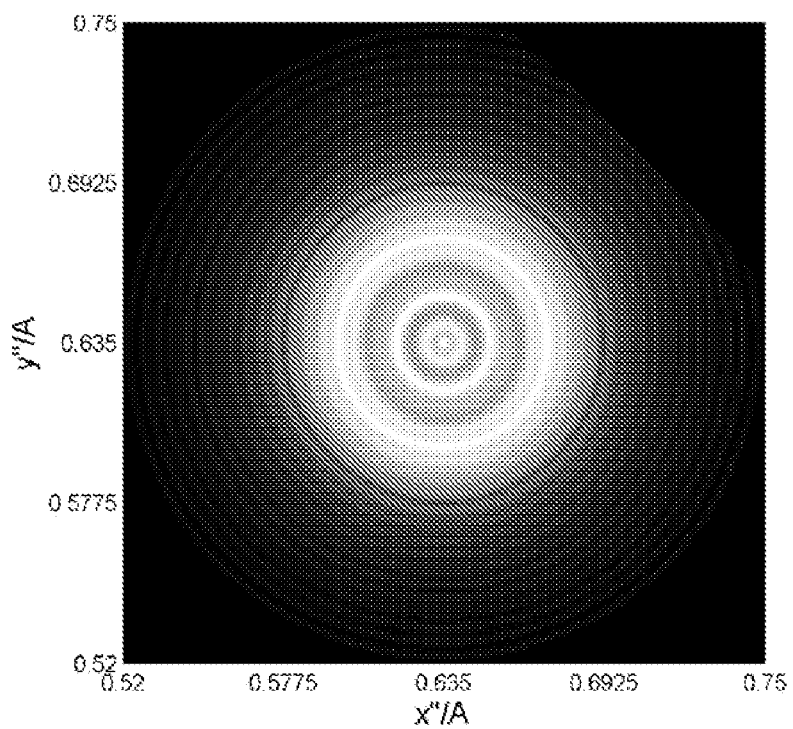
Figure 61B:
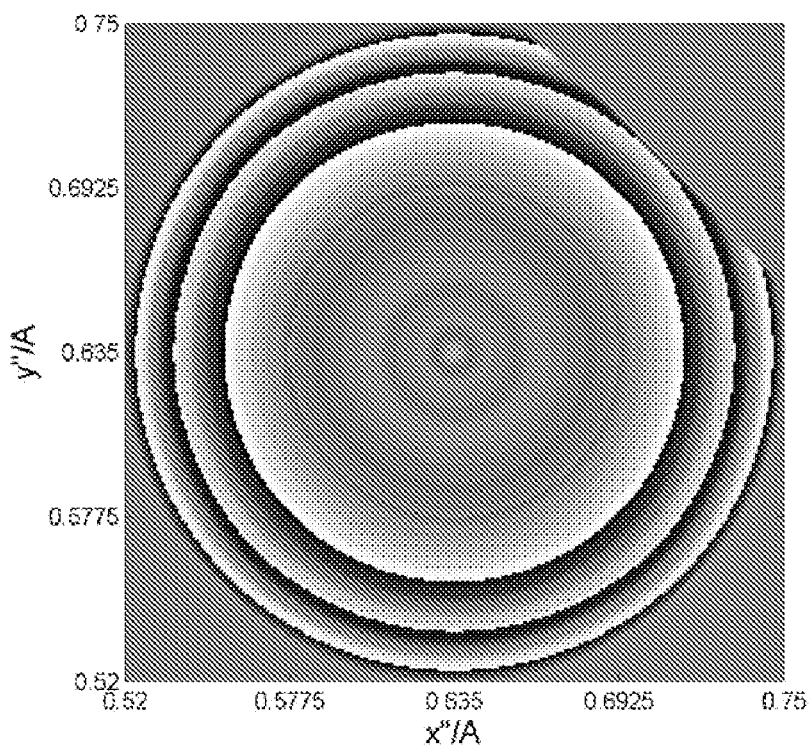
Figure 61C:
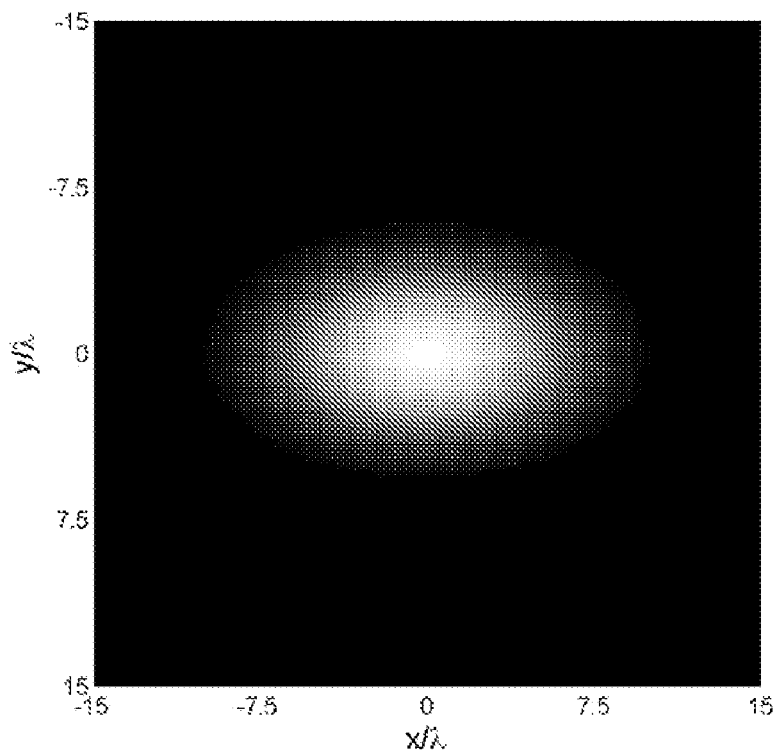
Figure 61D:
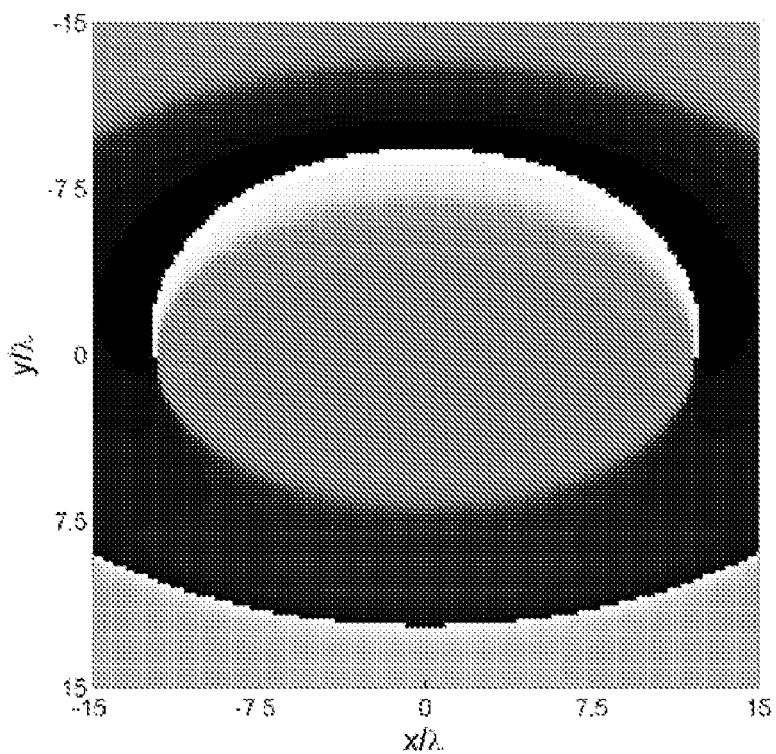
Figure 61E:
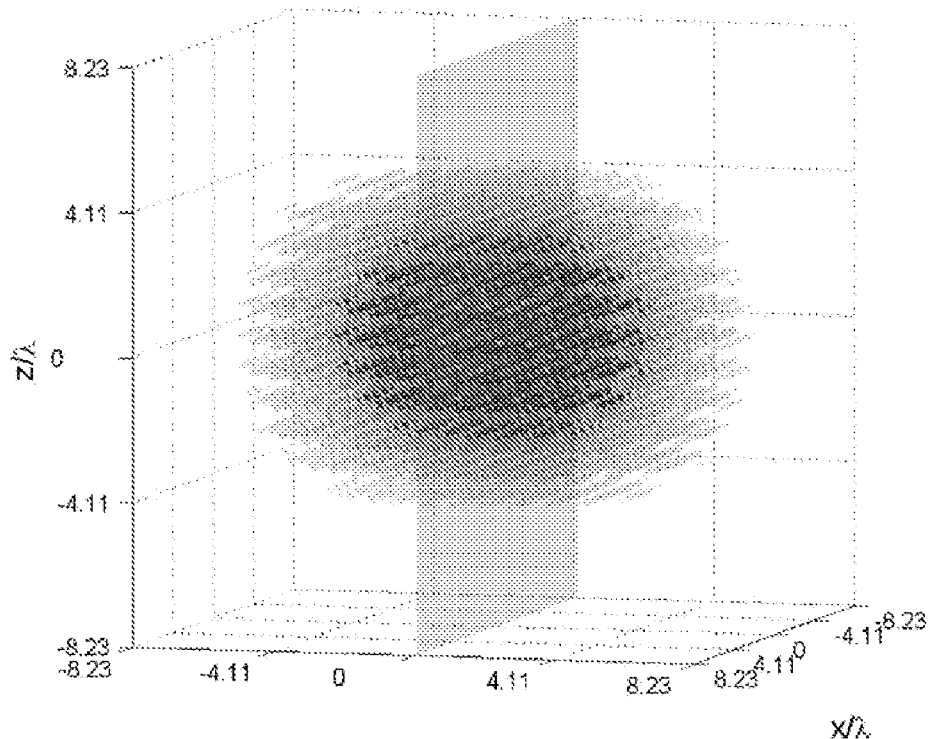

FIGS. 61A and B are linear grayscale maps the amplitude $|\psi(x'')|$ and phase $\arg[\psi(x'')]$ at the rear pupil plane of an NA=1.2 water-immersion objective for an input beam created with a circular aperture of radius $\alpha=0.26\lambda F_o/\rho=333\lambda$ in a mask a distance $z=2 \cdot 10^4 \lambda$ from this plane, in a manner similar to that shown in FIG. 59C. FIGS. 61C and D show the intensity $|e_n(x_\perp,t)|^2$ and phase $\arg[e_n(x_\perp,t) \cdot e_n]$ of the dominant polarization component $e_n$ of the convergent beam associated with the input beam of FIGS. 61A and B. These plots are at points $x_\perp$ in the plane that intersects the focal point of the objective and is perpendicular to the central propagation direction $k_n$ of the convergent beam. FIGS. 61E and F give three-dimensional isosurfaces and a two-dimensional plot in the xz plane, respectively, of the intensity within the maximally symmetric simple cubic bound lattice of intensity period $\sqrt{3}\lambda/2$ created by superimposing eight such convergent beams propagating in the appropriate directions as shown in FIG. 59B.

Figure 62A:
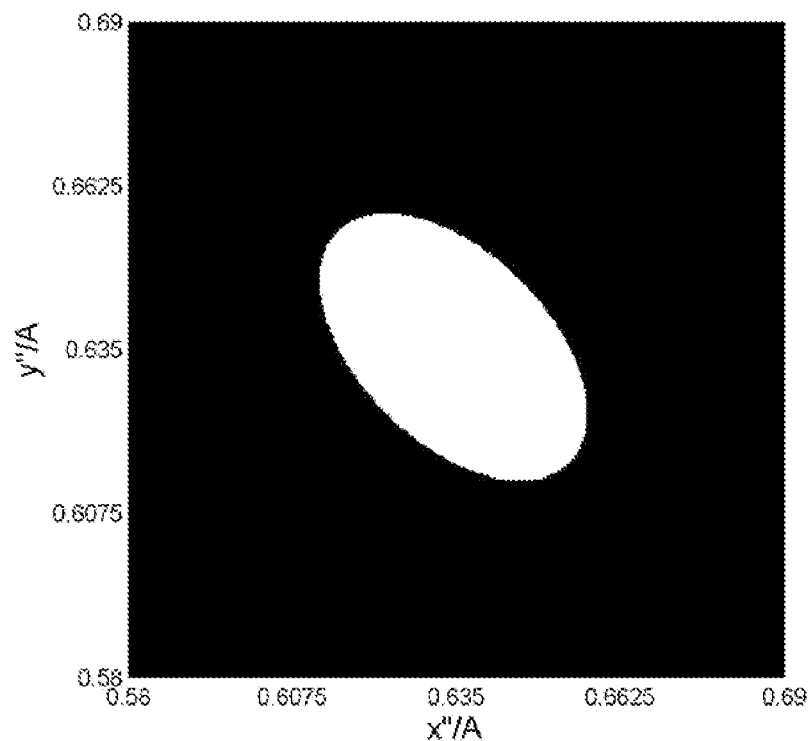
Figure 62B:
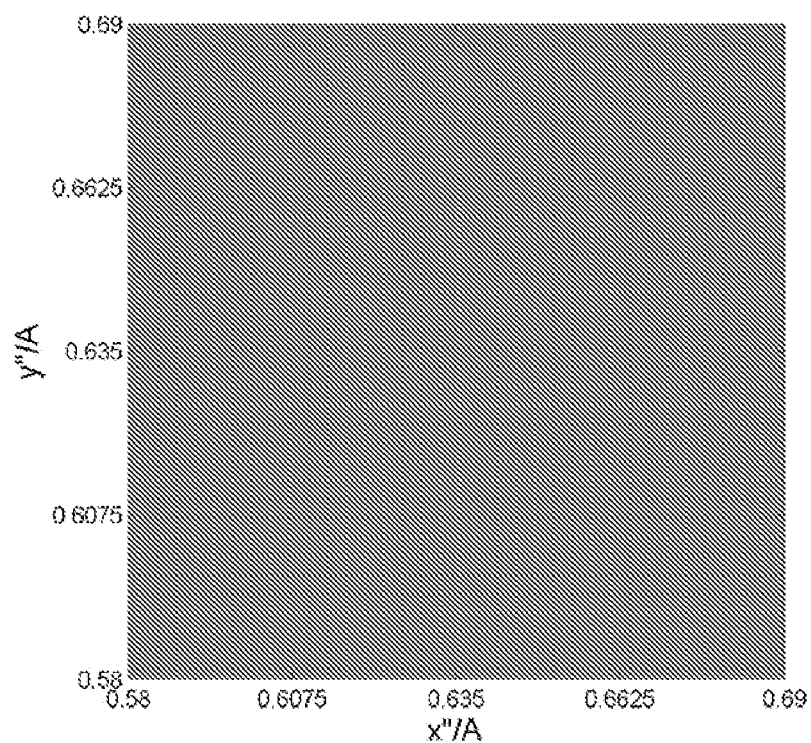
Figure 62C:
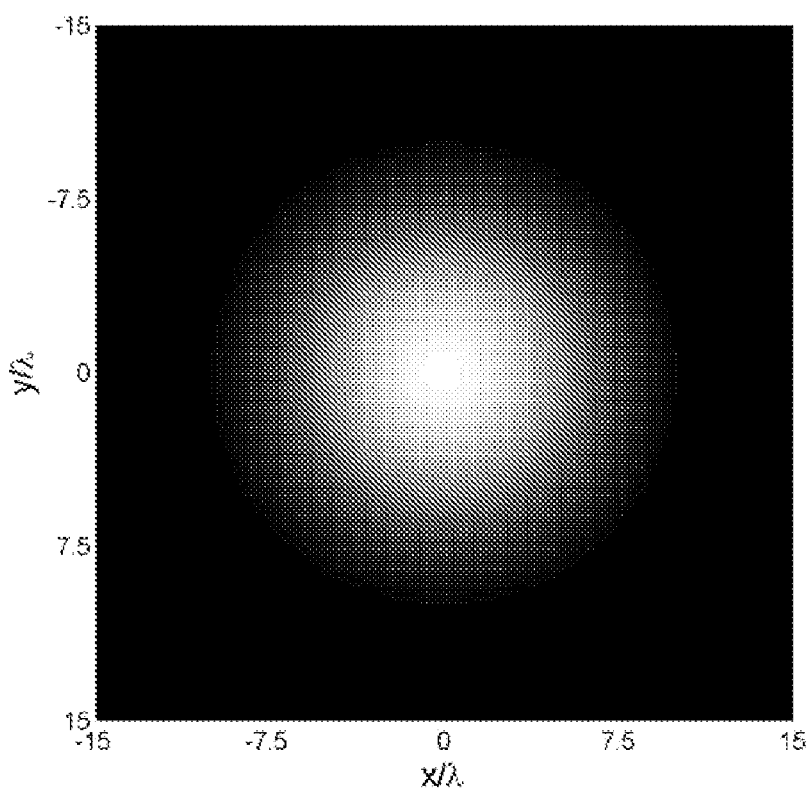
Figure 62D:
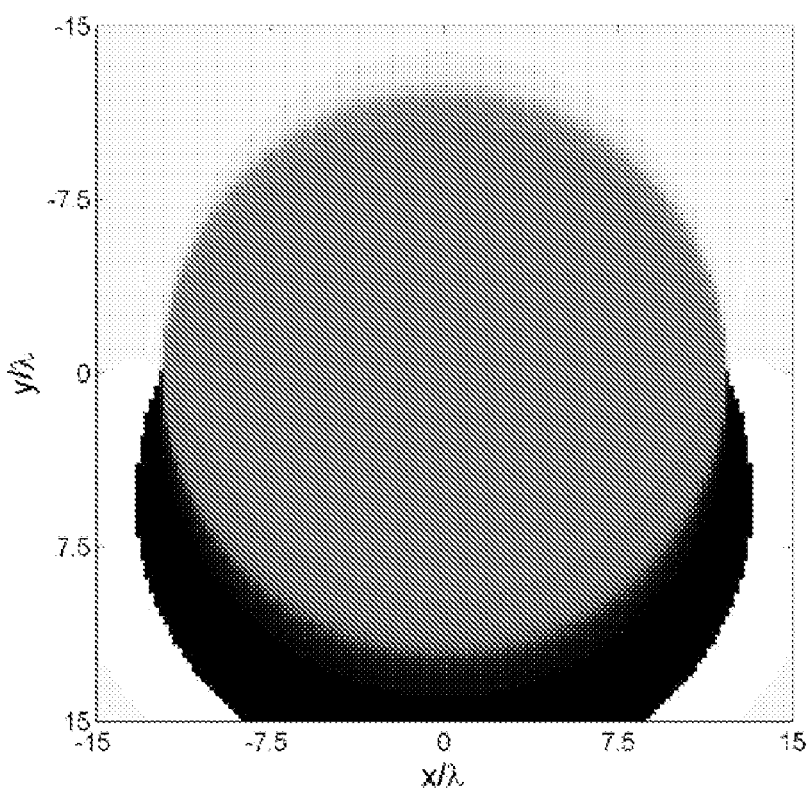
Figure 62E:
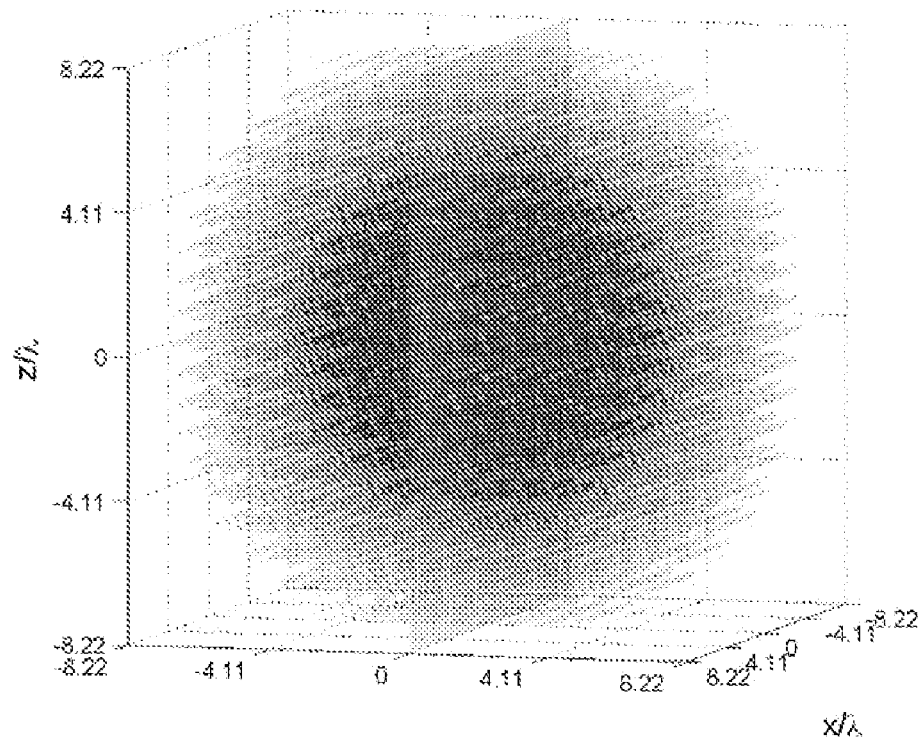
Figure 62F:
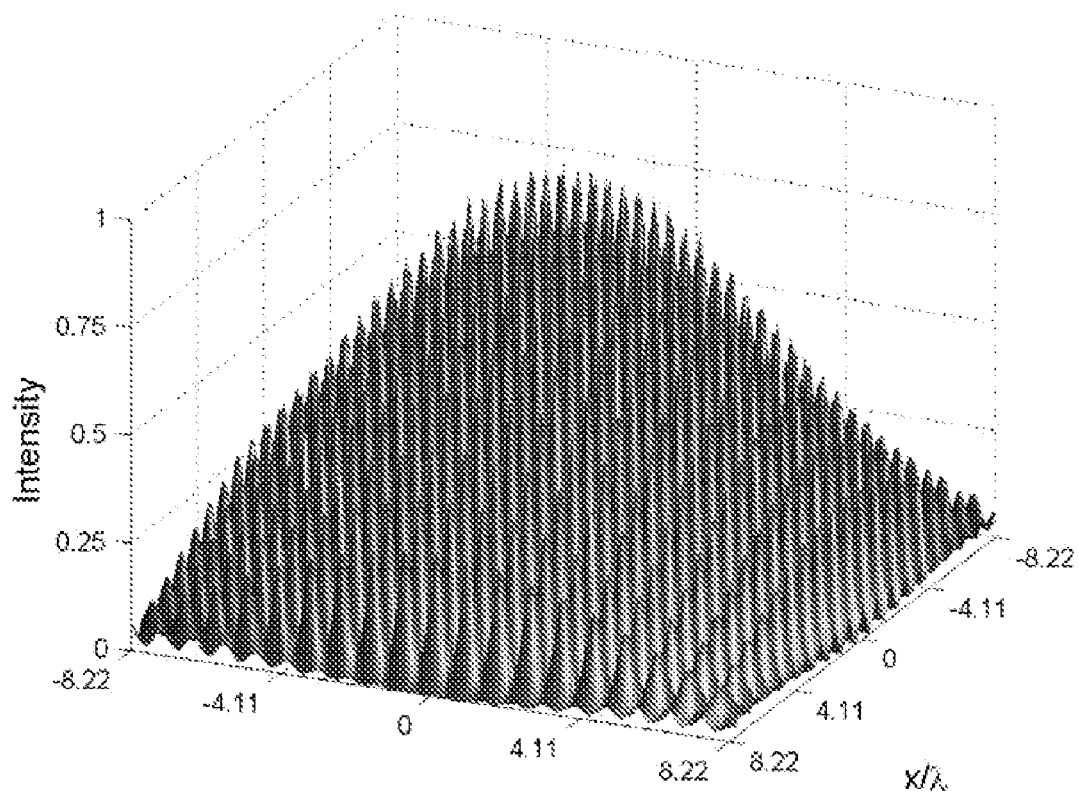

FIGS. 62A and B are linear grayscale maps the amplitude $|\psi(x'')|$ and phase $\arg[\psi(x'')]$ at the rear pupil plane of an NA=1.2 water-immersion objective for an idealized input beam created with an elliptical aperture of major axis half-length $\alpha=0.26\lambda F_o/\rho=333\lambda$ and eccentricity $k_n \cdot \hat{e}_z/k=1/\sqrt{3}$, chosen to compensate for the ellipticity in the resulting convergent beam as observed in FIGS. 60 and 61C. FIGS. 62C and D show the intensity $|e_n(x_\perp,t)|^2$ and phase $\arg[e_n(x_\perp,t) \cdot e_n]$ of the dominant polarization component $e_n$ of the convergent beam associated with the input beam of FIGS. 62A and B. These plots are at points $x_\perp$ in the plane that intersects the focal point of the objective and is perpendicular to the central propagation direction $k_n$ of the convergent beam. FIGS. 62E and F give three-dimensional isosurfaces and a two-dimensional plot in the xz plane, respectively, of the intensity within the maximally symmetric simple cubic bound lattice of intensity period $\sqrt{3}\lambda/2$ created by superimposing eight such convergent beams propagating in the appropriate directions as shown in FIG. 59B.

Figure 63A:
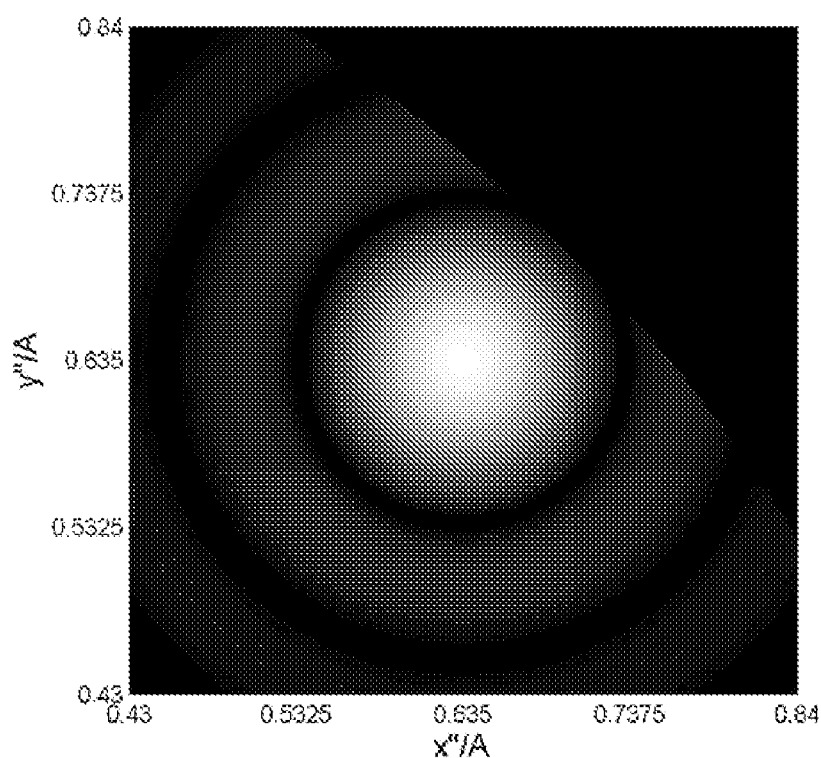
Figure 63B:
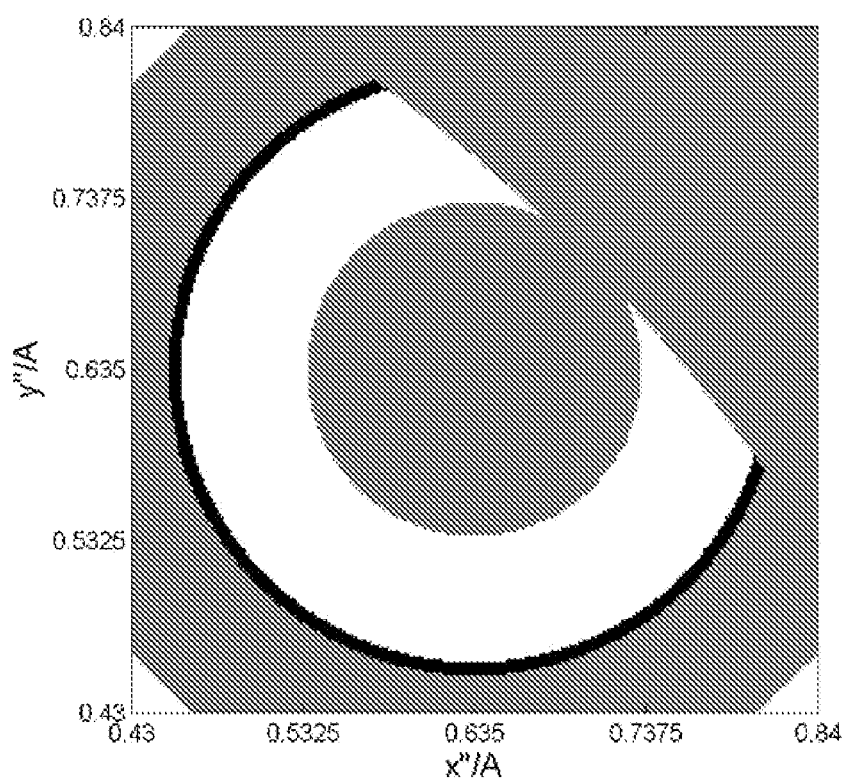
Figure 63C:
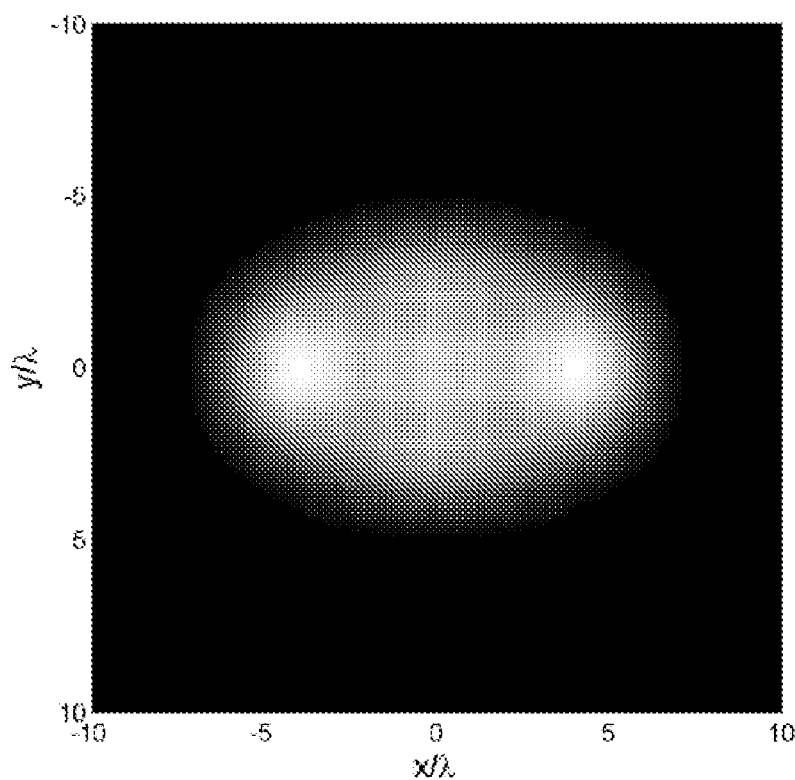
Figure 63D:
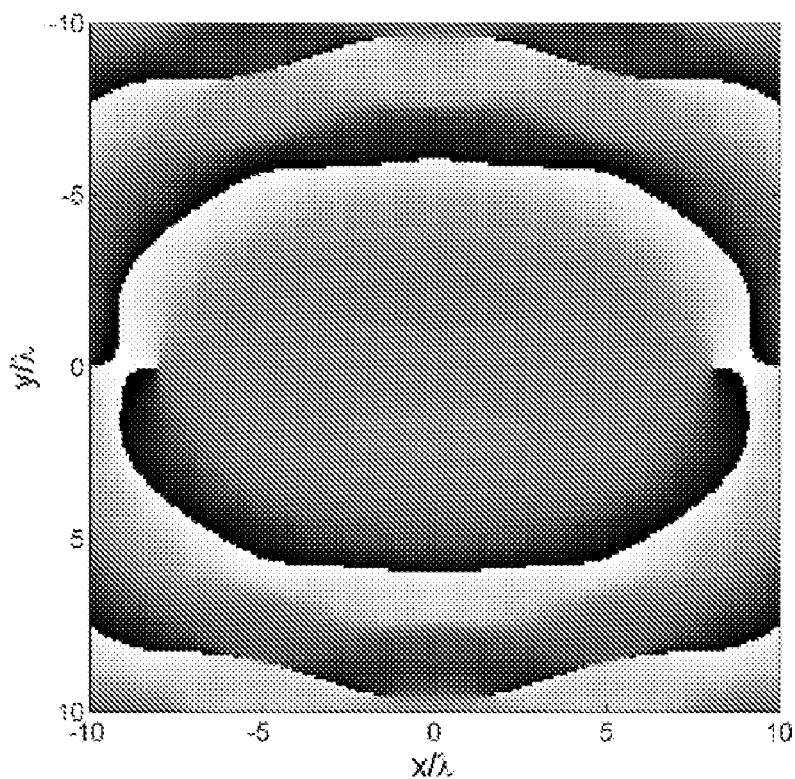
Figure 63E:
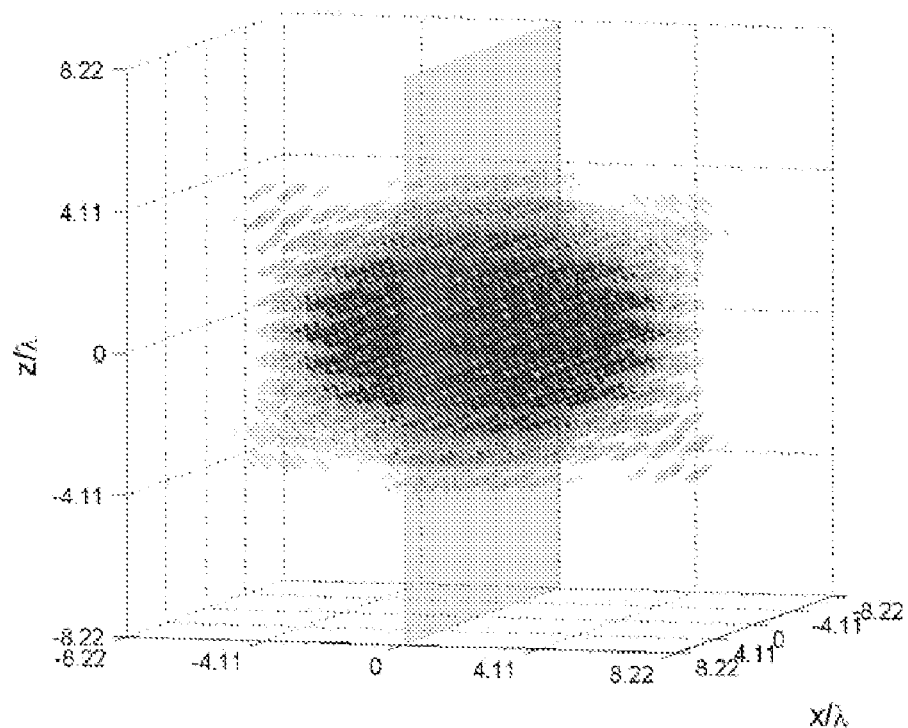

FIGS. 63A and B are linear grayscale maps the amplitude $|\psi(x'')|$ and phase $\arg[\psi(x'')]$ at the rear pupil plane of an NA=1.2 water-immersion objective for an input beam created with an $n\alpha \approx \alpha/f=0.001$ circular lens focused onto this plane. FIGS. 63C and D show the intensity $|e_n(x_\perp,t)|^2$ and phase $\arg[e_N(x_\perp,t) \cdot e_n]$ of the dominant polarization component $e_n$ of the convergent beam associated with the input beam of FIGS. 63A and B. These plots are at points $x_\perp$ in the plane that intersects the focal point of the objective and is perpendicular to the central propagation direction $k_n$ of the convergent beam. FIGS. 63E and F give three-dimensional isosurfaces and a two-dimensional plot in the xz plane, respectively, of the intensity within the maximally symmetric simple cubic bound lattice of intensity period $\sqrt{3}\lambda/2$ created by superimposing eight such convergent beams propagating in the appropriate directions as shown in FIG. 59B.

Figure 64A:
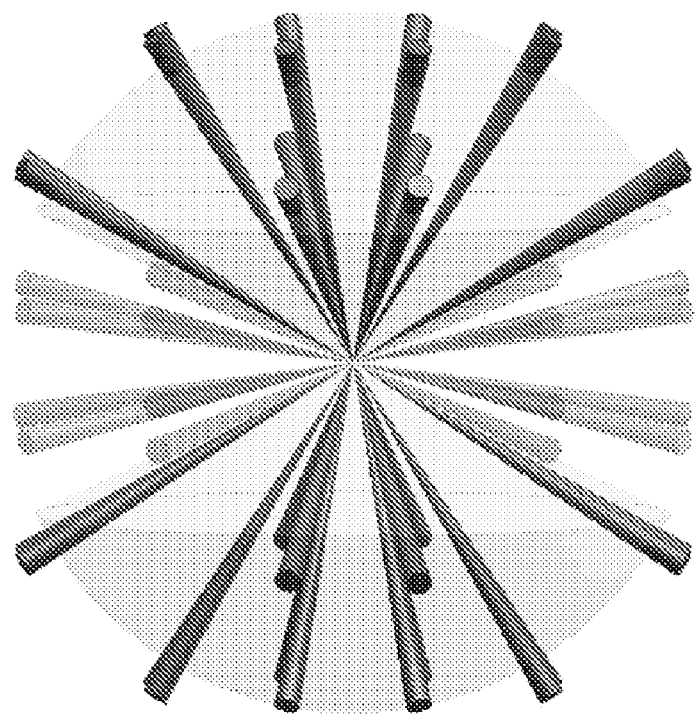
Figure 64B:
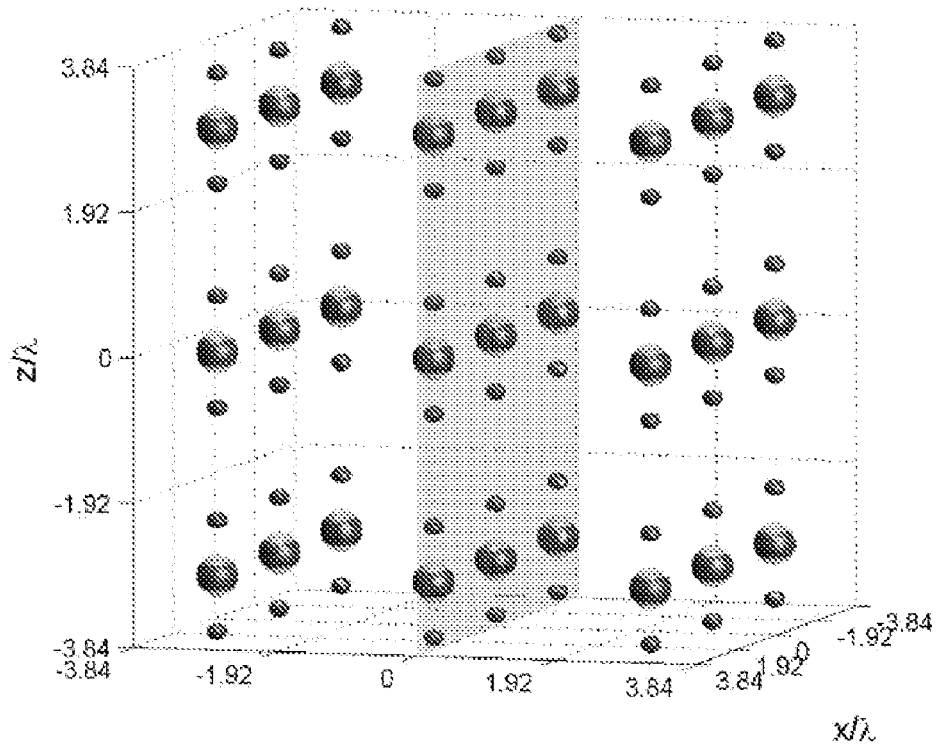
Figure 64C:
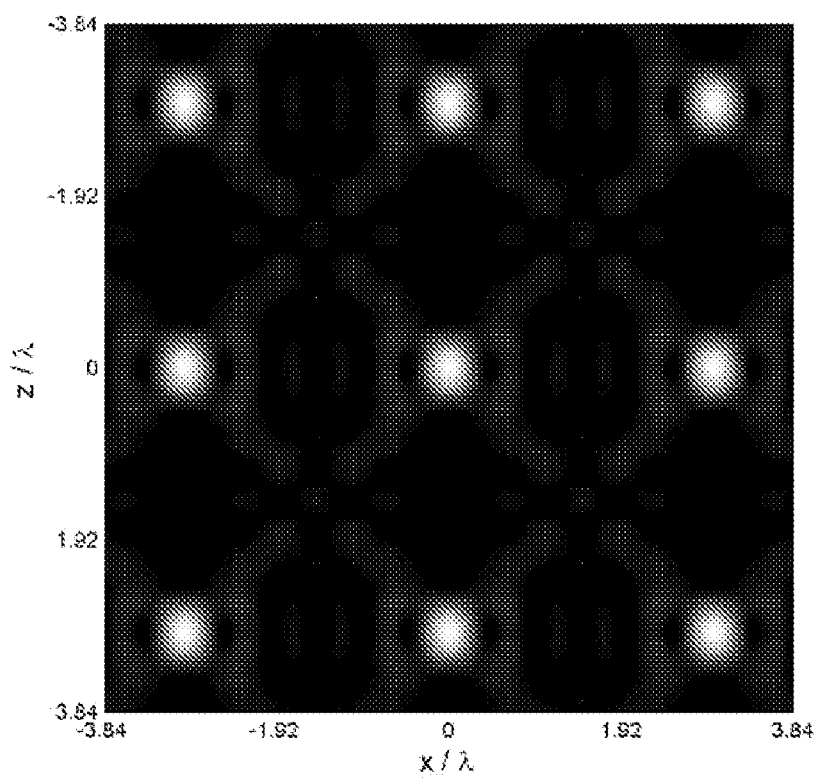

FIG. 64A is a representation of the relative directions of the convergent beams of a maximally symmetric simple cubic bound lattice of intensity period $\sqrt{35}\lambda/2$, indicating the 32 beams (dark opaque) that pass through the acceptance cones (light translucent) of opposed NA=1.2 water-immersion objectives, and the 16 beams (medium translucent) that fall outside these cones and hence cannot contribute to internal excitation of the lattice. FIG. 64B is a three-dimensional plot of the isosurfaces of 40% of maximum intensity for the maximally symmetric ideal lattice containing all 48 beams (light translucent), and the ideal subset lattice containing the 32 beams within the acceptance cones. FIGS. 64C and D are linear grayscale images of the intensity in the xz-plane of FIG. 64B for the maximally symmetric and subset lattices, respectively.

Figure 65A:
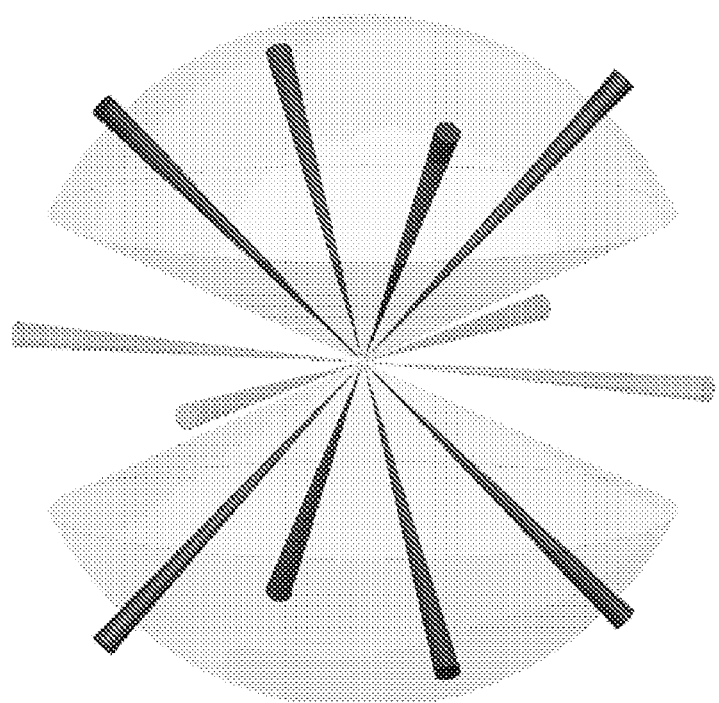
Figure 65B:
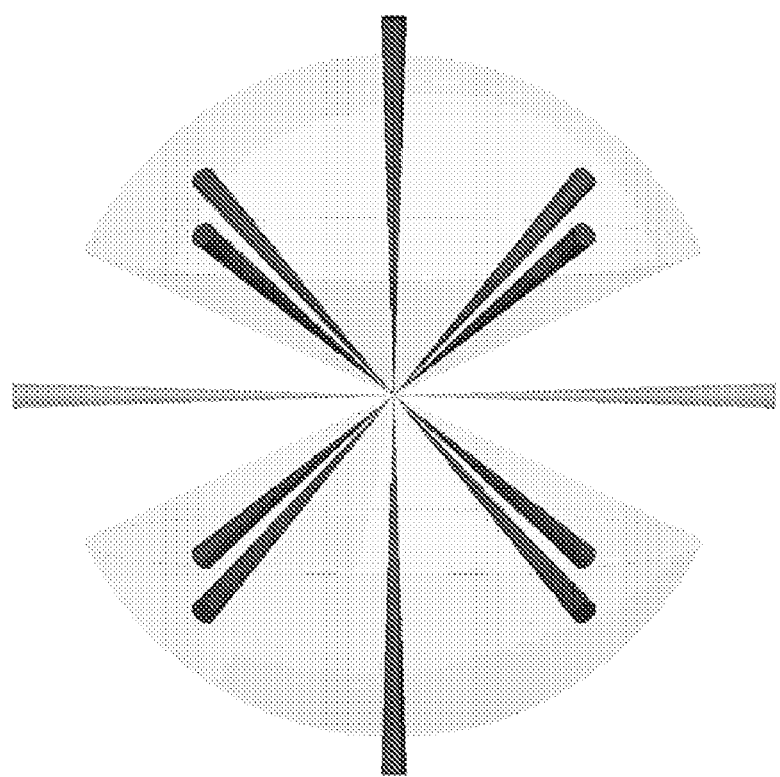
Figure 65C:
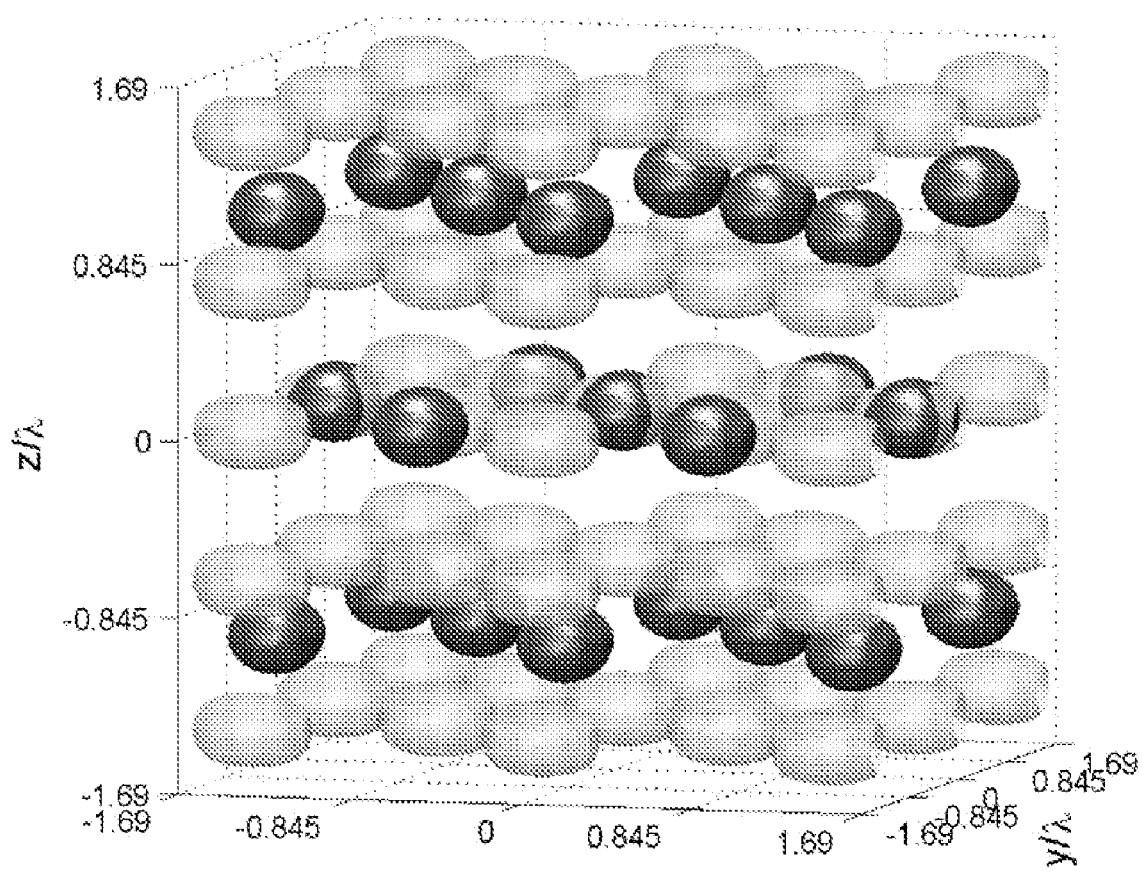

FIG. 65A is a representation of the relative directions of the convergent beams of a maximally symmetric body-centered cubic bound lattice of intensity period $\sqrt{2}\lambda$, assuming the [0 0 1] lattice axis is parallel to the axis $\hat{e}_z$ of opposed NA=1.2 water-immersion objectives. Eight beams (dark opaque) that pass through the acceptance cones (light translucent) of the objectives, and the four beams (medium translucent) do not. FIG. 65B is a similar representation of the same lattice, except rotated so that the [1 1 0] lattice axis is parallel to $\hat{e}_z$, indicating ten beams within the acceptance cones and two beams outside. FIG. 65C is a three-dimensional plot of the isosurfaces of 50% of maximum intensity for the ideal subset lattices obtained using the beams within the acceptance zone for the [0 0 1]∥ê$_z$ (light translucent) and [1 1 0]∥ê$_z$ (dark opaque) orientations, with the basis has been chosen to optimize x-polarization at the maxima in each case.

Figure 66A:
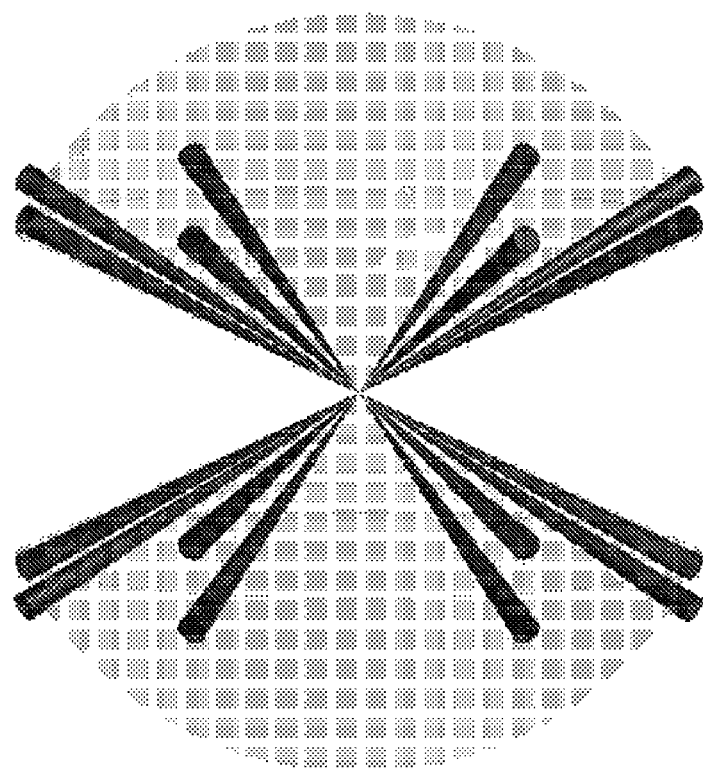
Figure 66B:
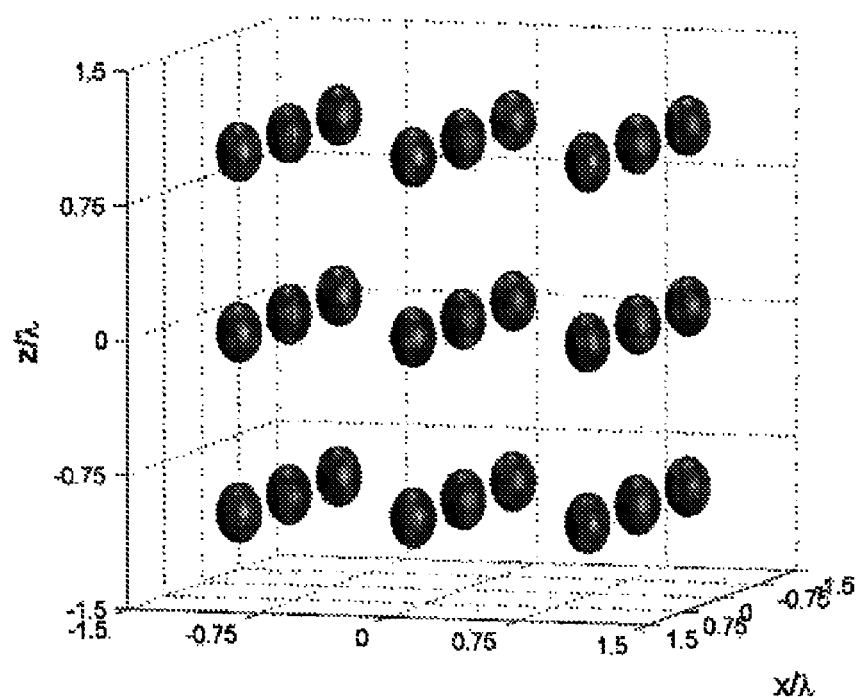

FIG. 66A is a representation of the relative directions of the convergent beams of a maximally symmetric simple tetragonal lattice wherein the aspect ratio; ξ=c/α has been chosen so that all beams (dark opaque) fall just inside the acceptance cones (light translucent) of opposed NA=1.2 water-immersion objectives. FIG. 66B is a three-dimensional plot of surfaces of 50% of maximum intensity for the ideal lattice obtained with the wavevector set indicated by FIG. 66A.

Figure 67A:
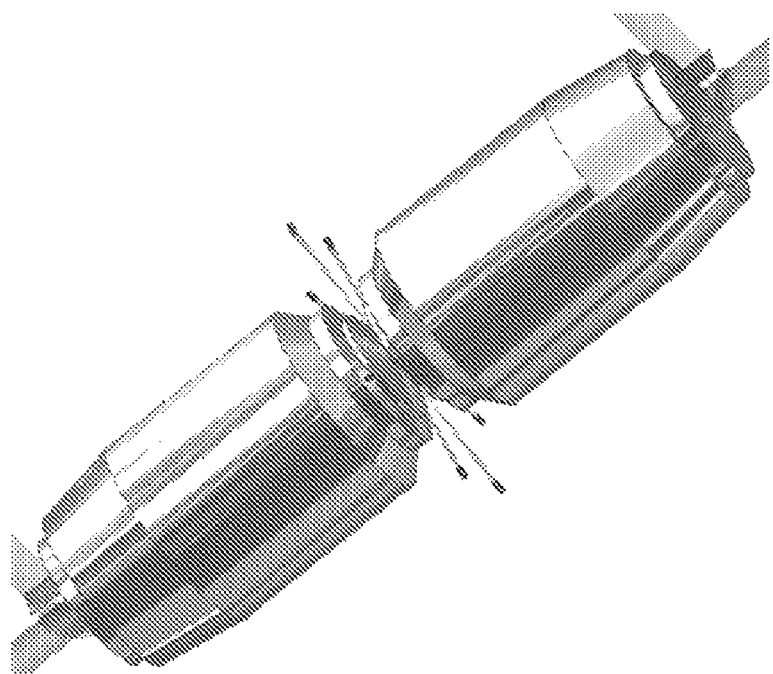
Figure 67B:
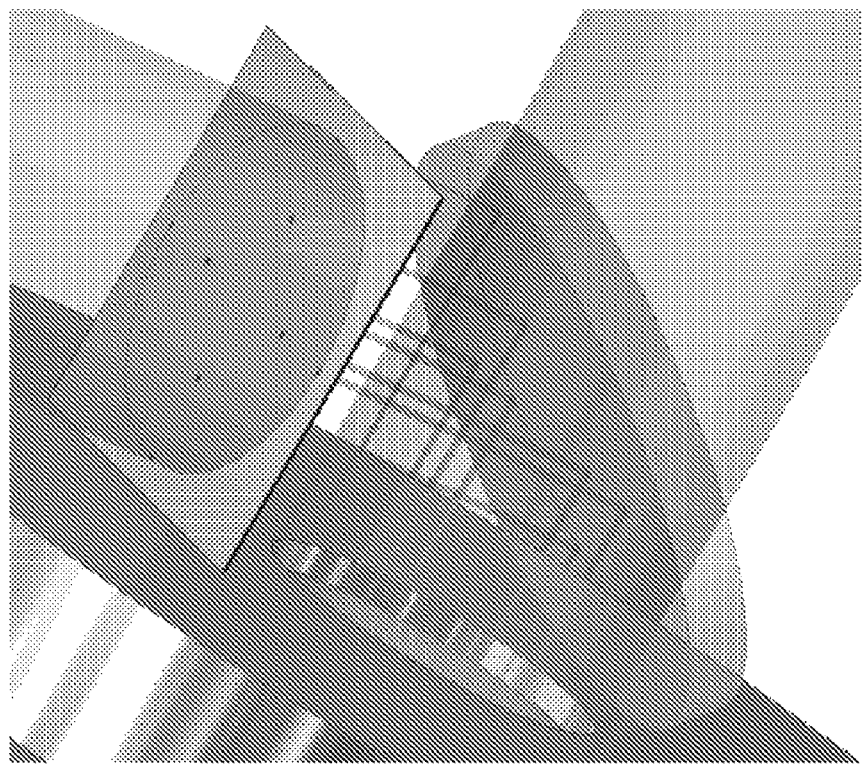
Figure 67C:
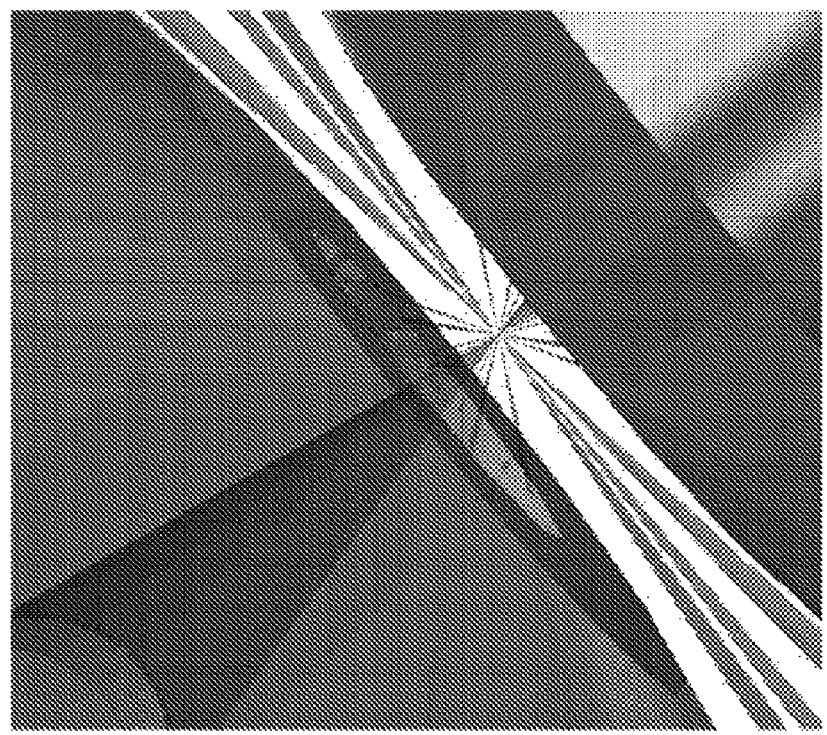
Figure 67D:
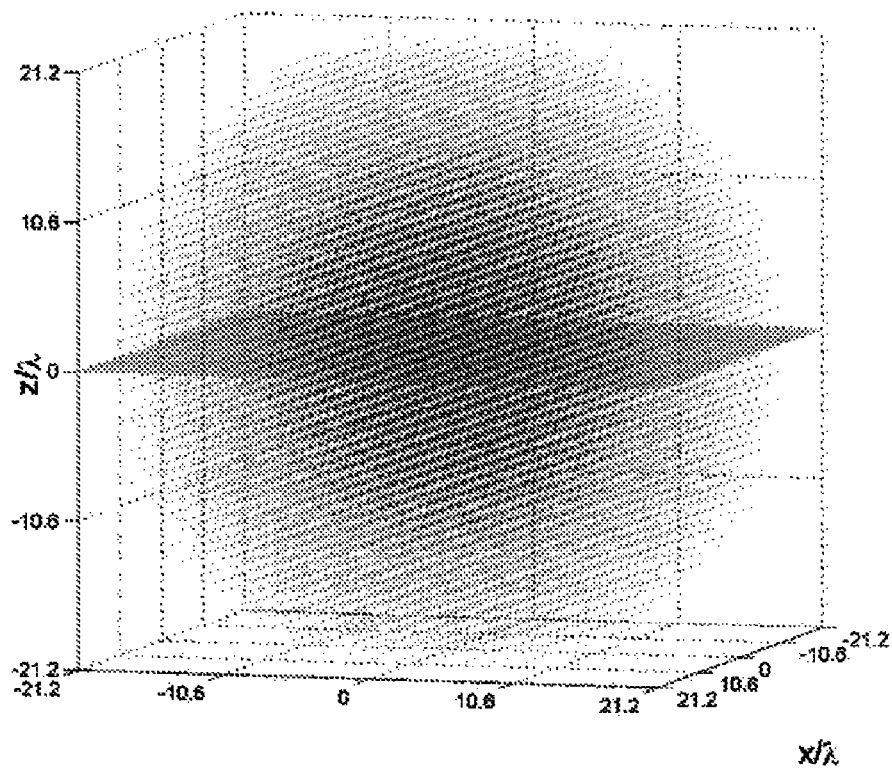
Figure 67E:
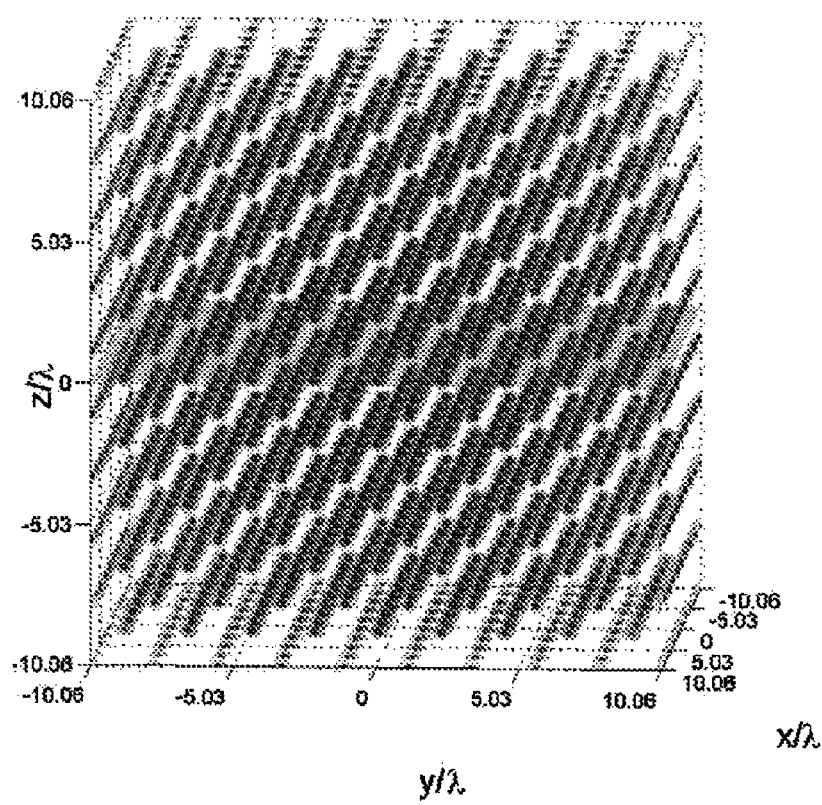
Figure 67F:
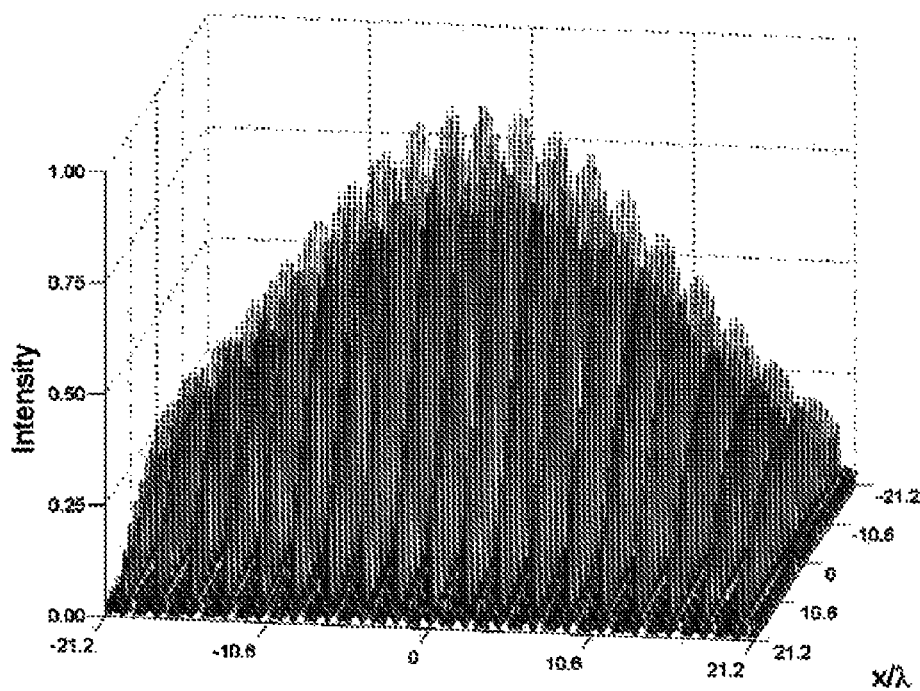

FIGS. 67A, B, and C are conceptual views of an experimental arrangement for the hybrid excitation of and simultaneous detection of signal from a maximally symmetric body-centered cubic lattice of intensity period $\sqrt{5}\lambda$. FIG. 67A is an overall view, showing the two opposed high NA objectives and eight external low nα lenses used. FIG. 67B is a view near the rear pupil of one of the objectives, showing an opaque mask with the elliptical apertures that define the necessary input beams, and the dichroic mirror that separates these beams from the collected signal. FIG. 67C is a view near the common the focal point of all lenses, illustrating the intersection of the internal and external beams at this point. FIG. 67D is a three-dimensional plot of the surfaces of 50% (opaque) and 20% (translucent) of maximum intensity of the resulting bound lattice when all beams are of effective nα≈0.02, and FIG. 67E is an expanded view near the center of the excitation zone. FIG. 67F is a surface plot of the intensity in the xy slice plane at the center of the excitation zone as shown in FIG. 67D.

Figure 68A:
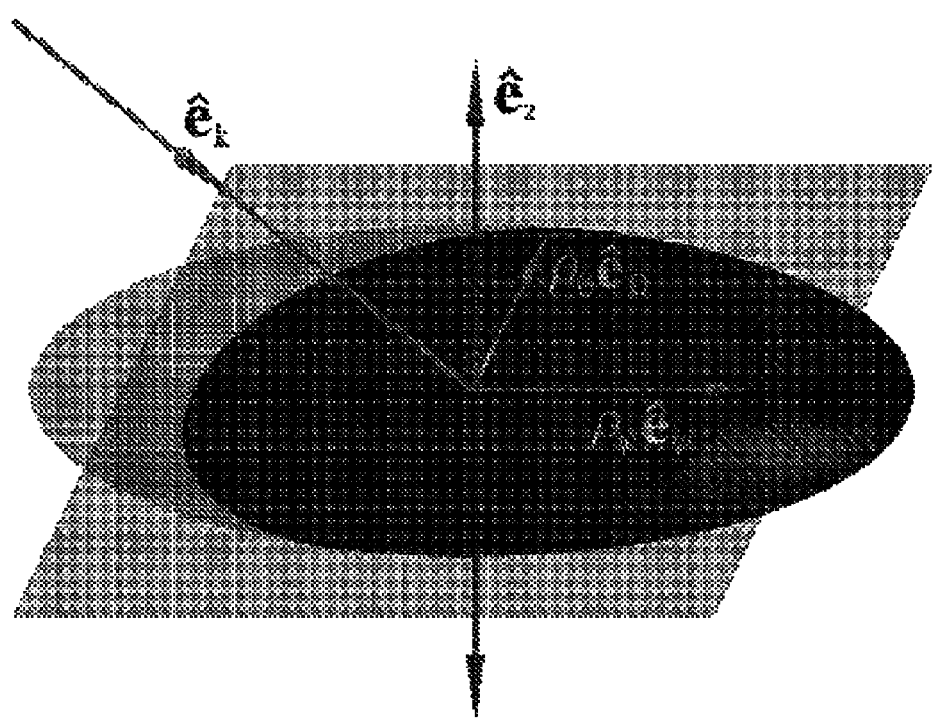
Figure 68B:
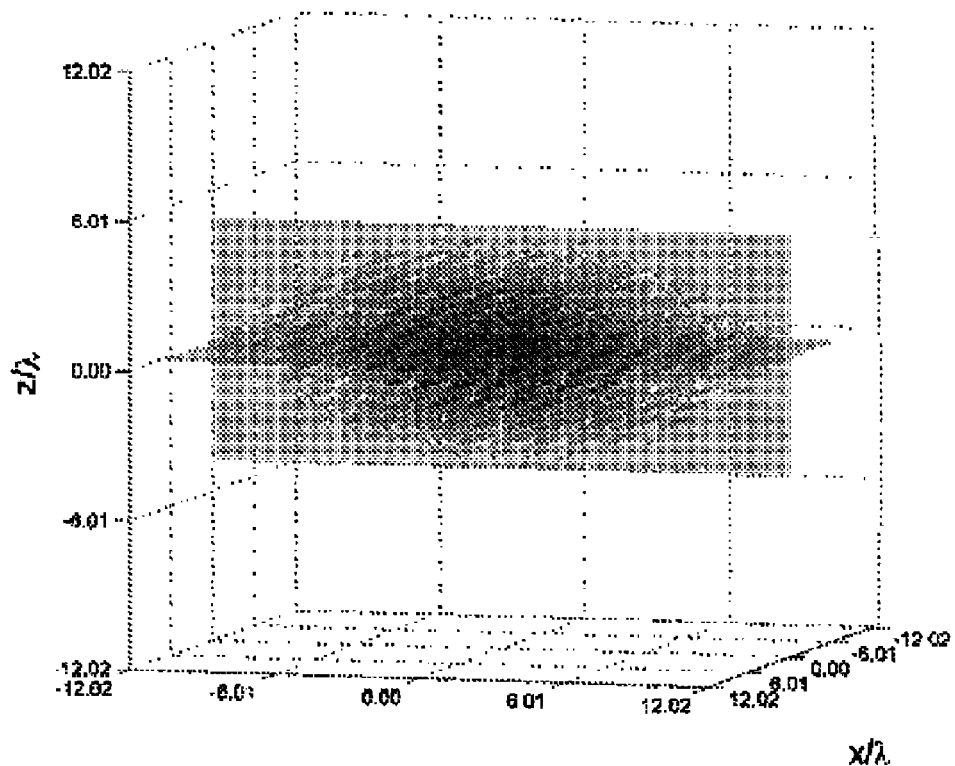
Figure 68C:
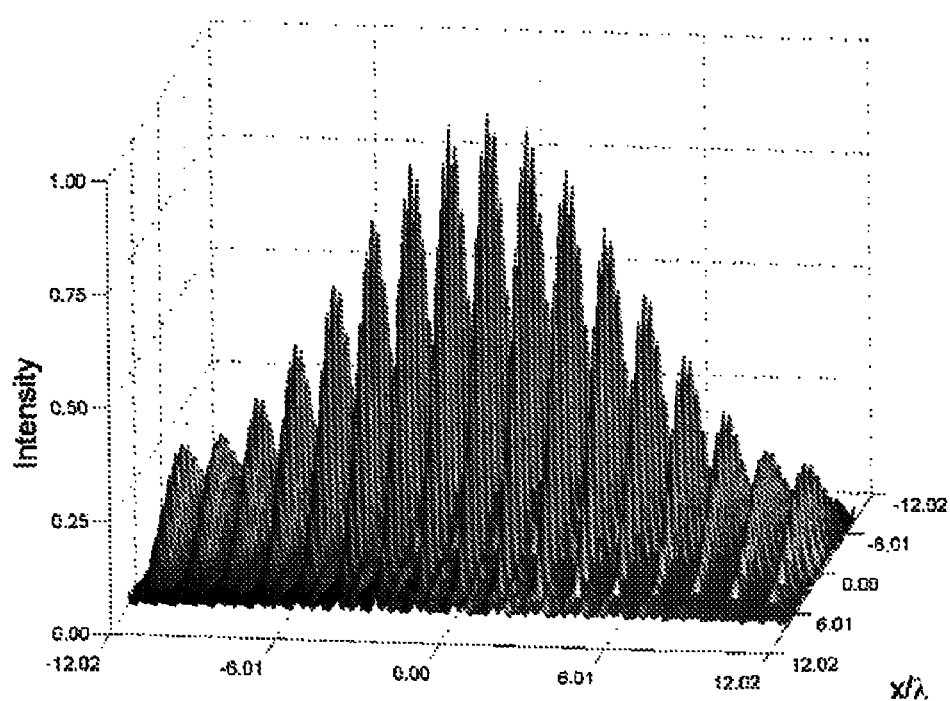

FIG. 68A is a conceptual view of a desired excitation zone (ellipsoid) and the resulting suggested cross-section for a constituent convergent beam of ideal propagation direction ê$_k$. FIG. 68B is a three-dimensional plot of the surfaces of 50% (opaque) and 20% (translucent) of maximum intensity for a hybrid-excited, maximally symmetric, body-centered cubic bound lattice of intensity period $\sqrt{2}\lambda$, wherein the excitation zone was tailored by shaping each constituent convergent beam as suggested by FIG. 68A. FIGS. 68C and D are surface plots of the intensity in xy and yz planes, respectively, through the center of the excitation zone as indicated in FIG. 68B.

Figure 69A:
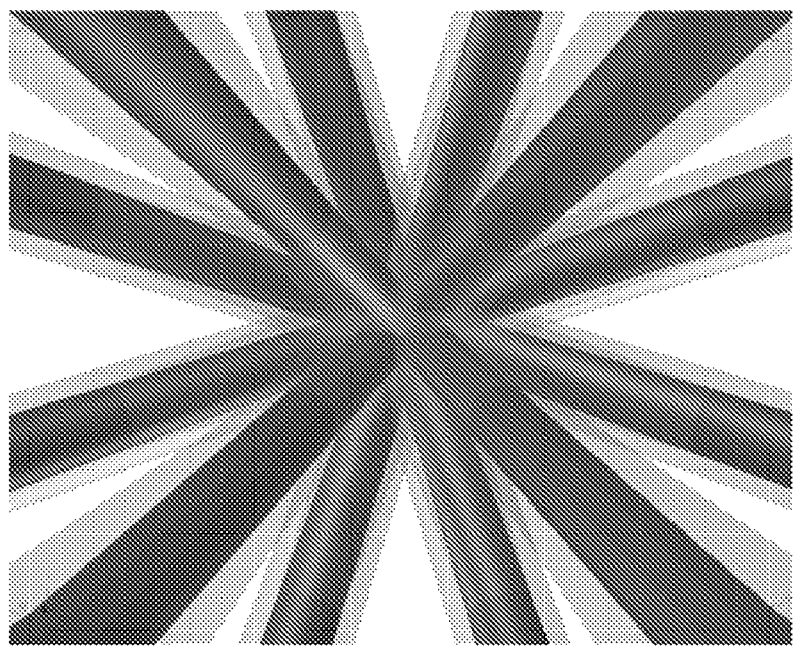
Figure 69B:
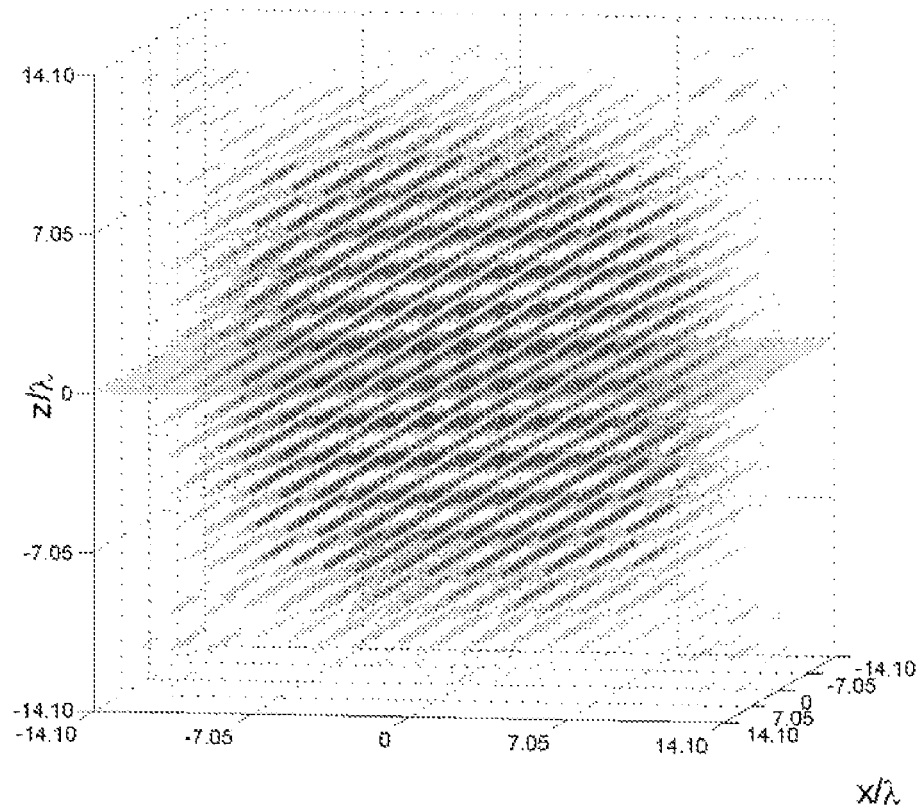
Figure 69C:
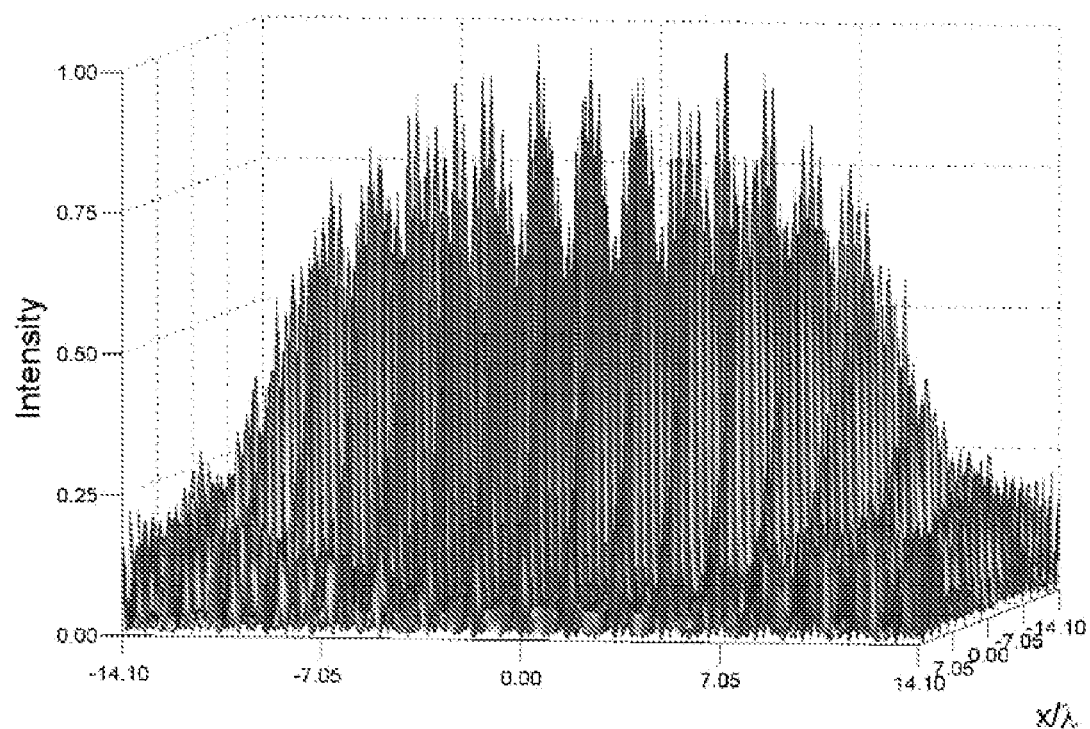

FIG. 69A is a conceptual view in the vicinity of the excitation zone of a bound lattice with confocal external excitation beams (dark), and the larger excitation zone created with axially displaced beams (light). FIG. 69B is a three-dimensional plot of the surfaces of 50% (opaque) and 20% (translucent) of maximum intensity for the same maximally symmetric simple cubic lattice of intensity period $\sqrt{11}\lambda/2$ as in FIG. 56, except with each beam axially displaced by Δz=245λ. FIG. 69C is a surface plot of the intensity in the xy-plane through the center of the excitation zone as shown in FIG. 69B.

Figure 70A:
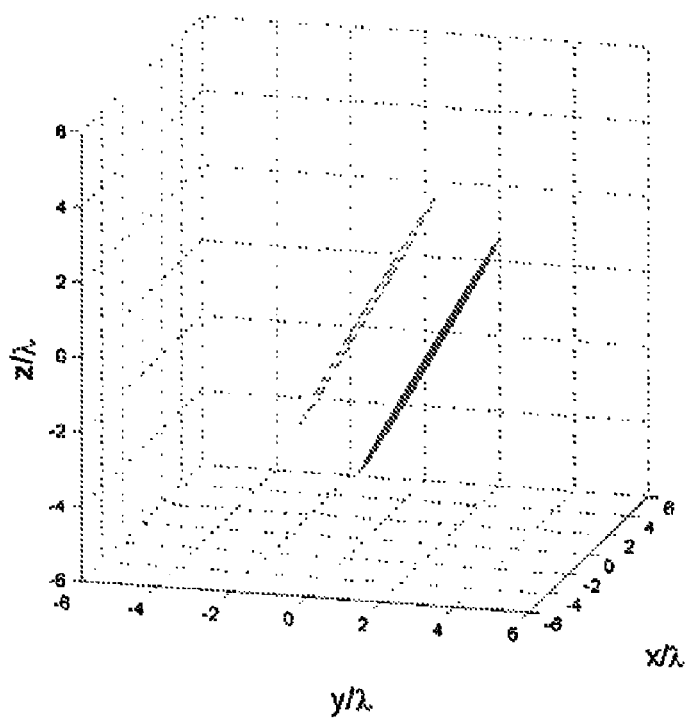
Figure 70B:
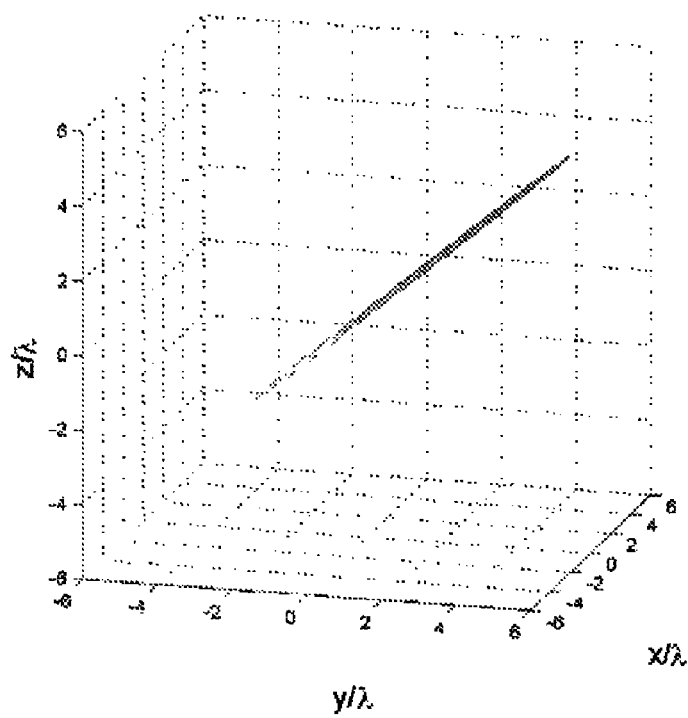
Figure 70C:
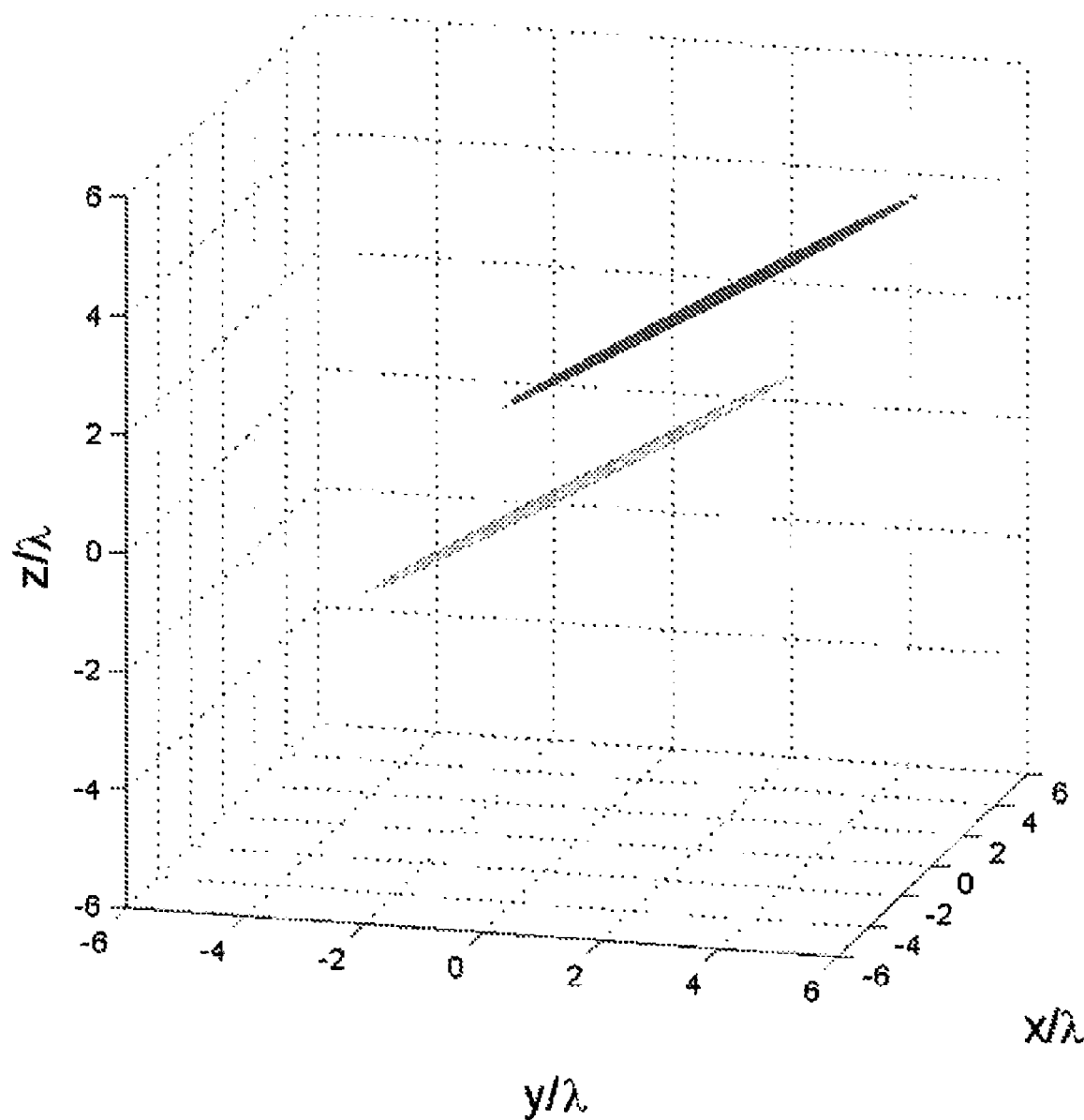

FIG. 70A is a three-dimensional plot of the focal maximum (light) of a convergent beam created with a confined input beam of flat phase offset within the rear pupil of an NA=1.2 water immersion microscope objective (see FIG. 60), and the focal maximum (dark) of a convergent beam similar in all respects, except offset 3λ along ê$_k$ by introducing an appropriate spherical phase dependence to the input beam. FIG. 70B is a three-dimensional plot of the focal maximum (light) of a convergent beam at a different propagation angle (cos$^{-1}$ (ê$_k$·ê$_z$)=30° vs. 50° in FIG. 70A), and the maximum of a related beam (dark) offset 2λ along ê$_θ$ by introducing an appropriate tilt along ê$_ρ$ to the input beam. FIG. 70C is a three-dimensional plot of the focal maximum (light) of a convergent beam propagating at 60° to the objective axis, and the maximum (dark) of a similar convergent beam offset Δx=λ, Δy=2λ, and Δz=3λ by introducing an appropriate combination of curvature and ê$_φ$, ê$_ρ$ tilt corrections to the phase of the input beam.

Figure 71A:
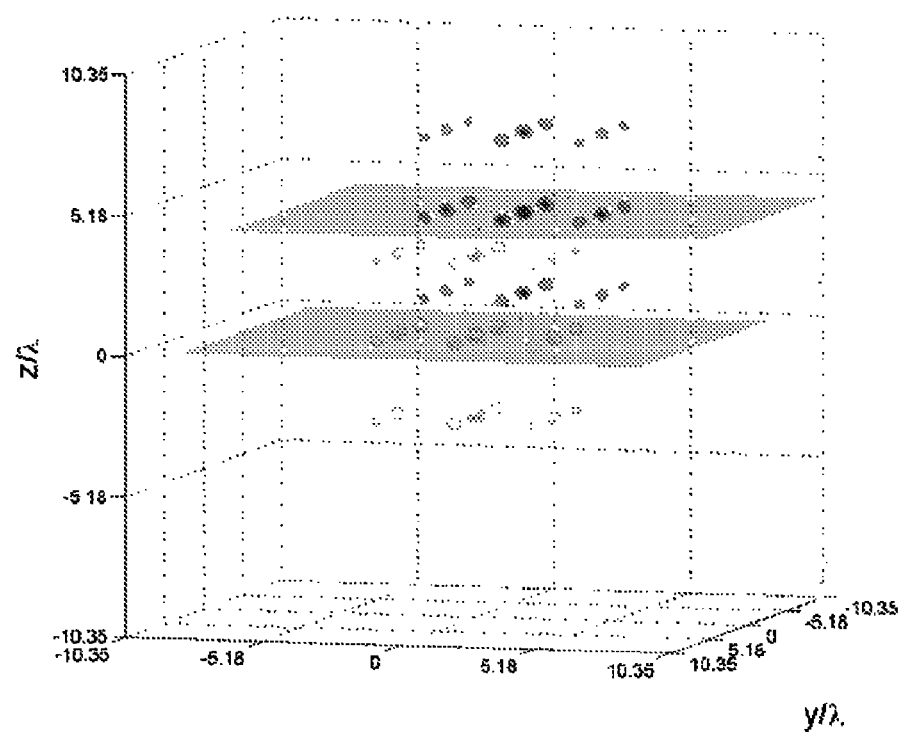
Figure 71B:
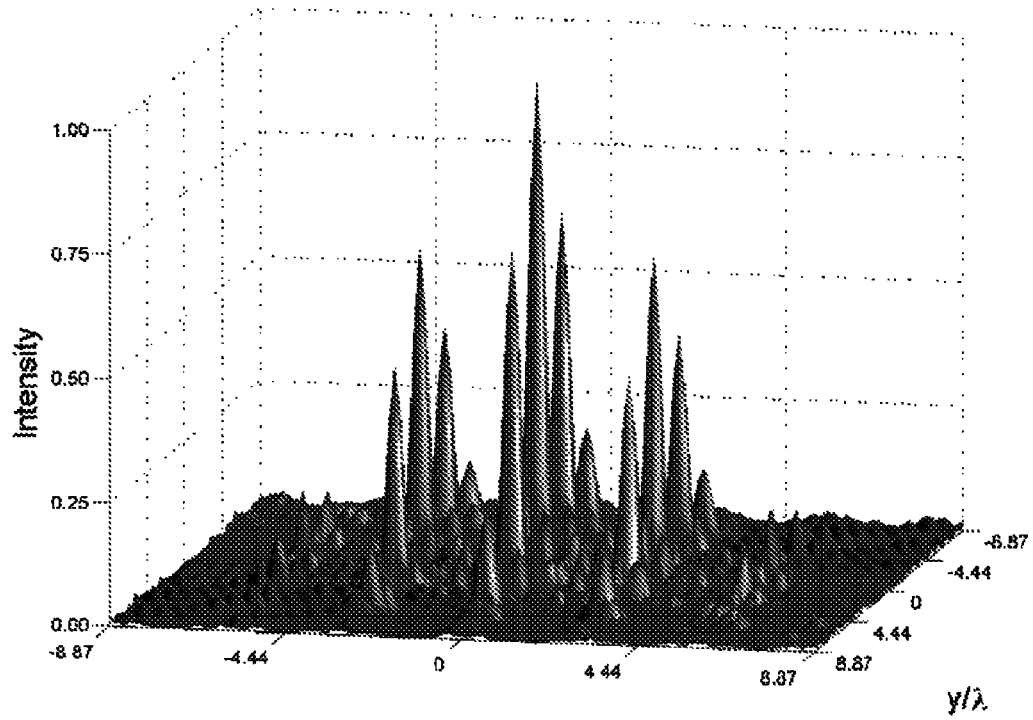

FIG. 71A is a three-dimensional plot of the surfaces of 50% (light opaque) and 20% (light translucent) of maximum intensity for a hybrid-excited, maximally symmetric, simple cubic bound lattice of intensity period $\sqrt{35}\lambda/2$, all 48 input beams thereof exhibiting flat phase, and all convergent beams having nα=0.08. Also shown are the surfaces of 50% (dark opaque) and 20% (dark translucent) of maximum intensity for a bound lattice similar in all respects, except translated by Δx=3λ, Δy=4λ, Δz=5λ via suitable modification of the phase dependence of each input beam. FIGS. 71B and C are surface plots of the intensity in the xy plane through the centers of the original and translated lattices, respectively, as shown in FIG. 71A.

Figure 71C:
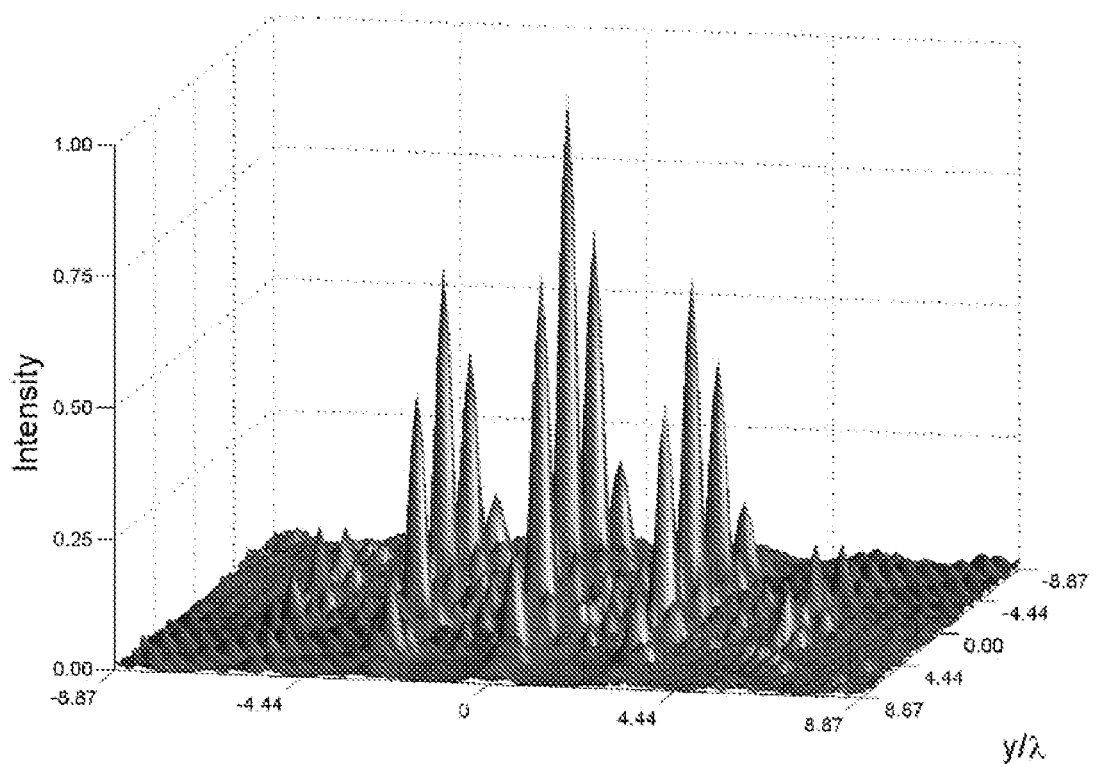
Figure 72A:
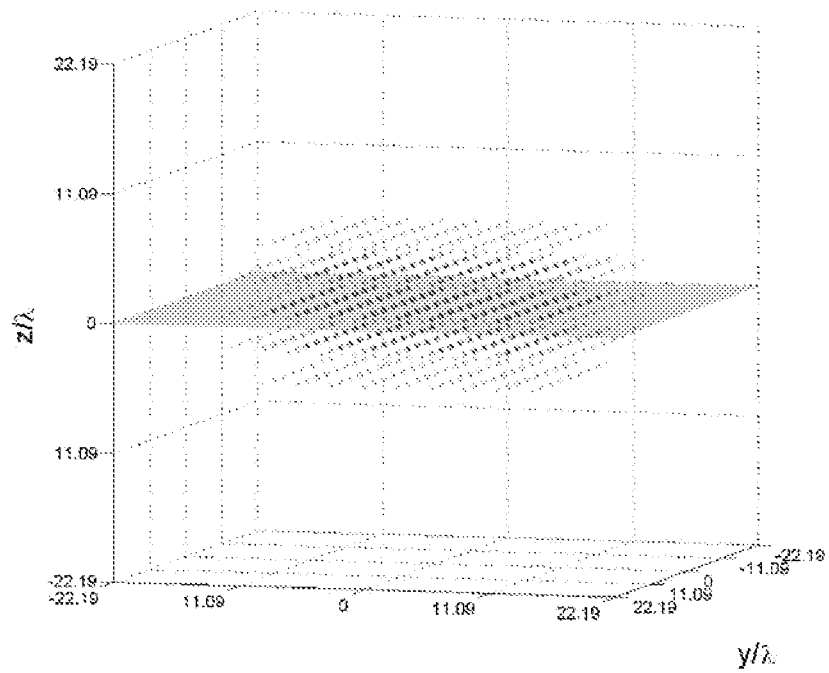
Figure 72B:
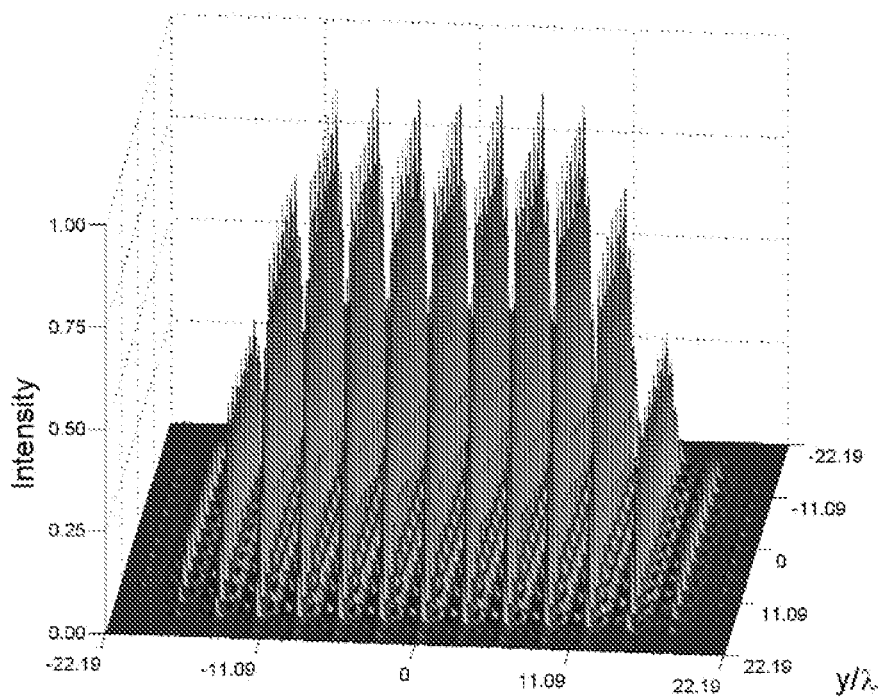

FIG. 72A is a three-dimensional plot of the surfaces of 50% (opaque) and 20% (translucent) of maximum intensity for a lattice of the same properties as in FIG. 71, except with a large, sharply bound excitation zone with uniform response therein created by overlapping an 11×11×5 array of sub-excitation zones similar to those of FIG. 71. FIG. 72B is a surface plot of the intensity in the xy plane through the center of the excitation zone as shown in FIG. 72A.

Figure 73A:
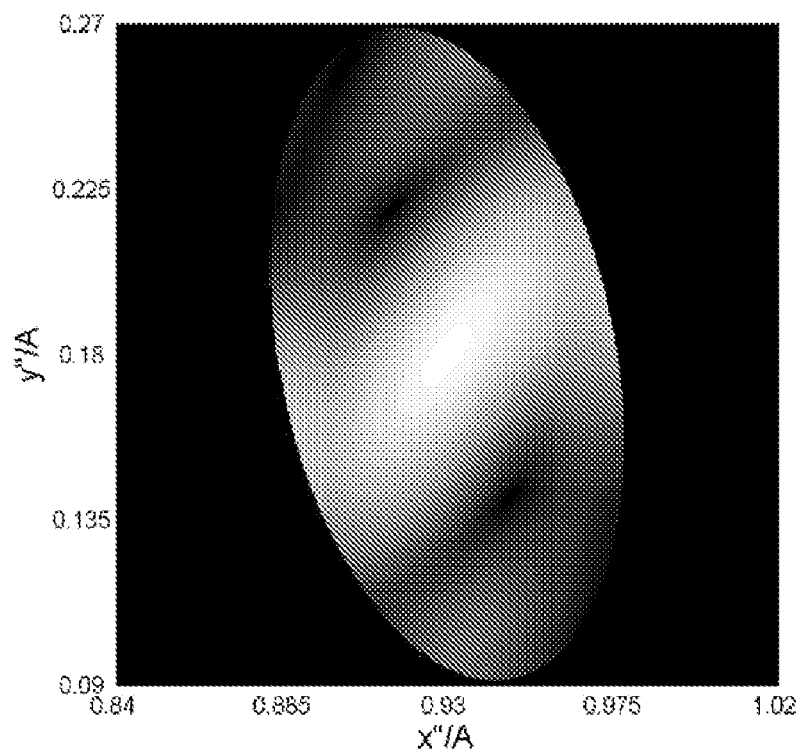
Figure 73B:
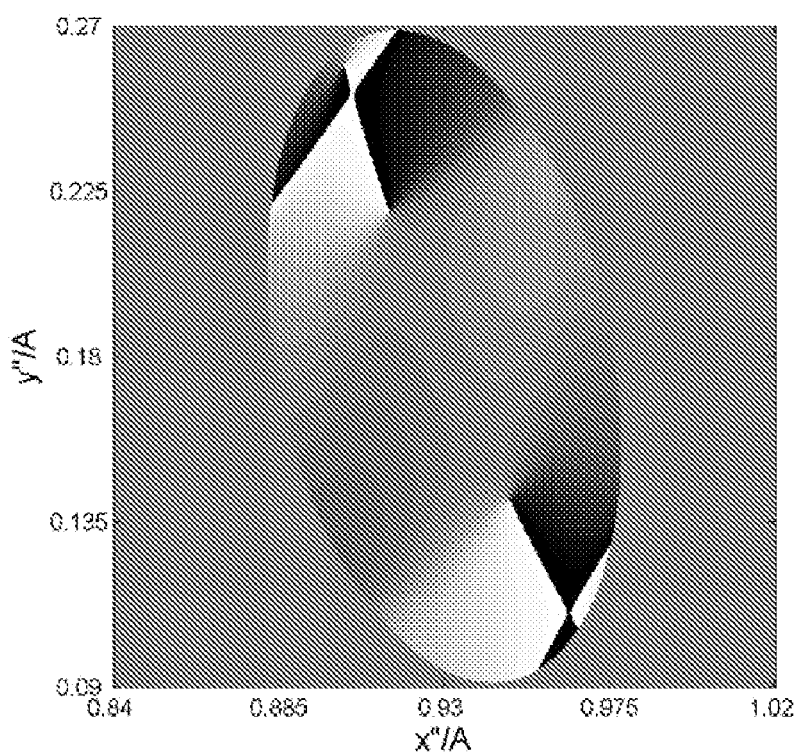
Figure 73C:
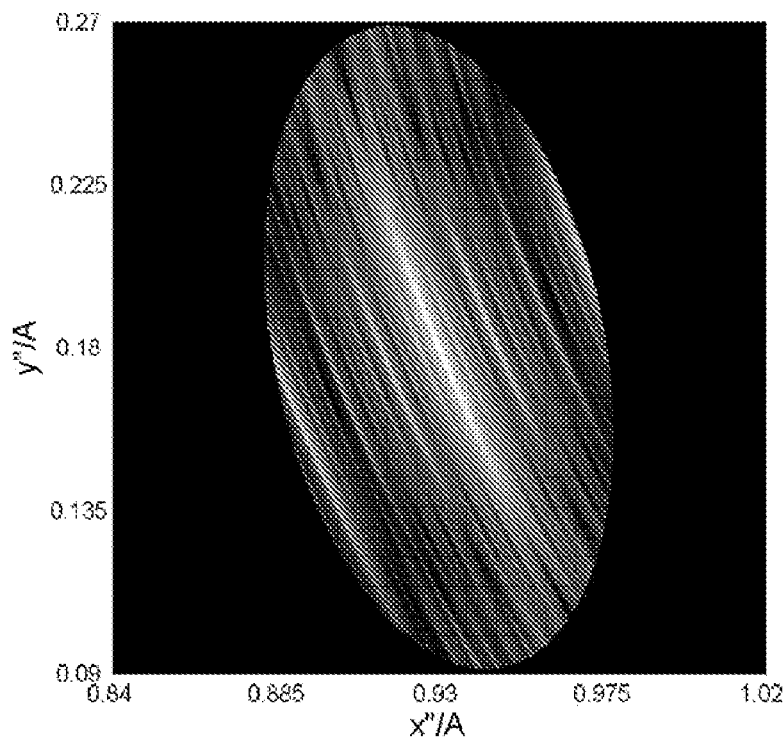
Figure 73D:
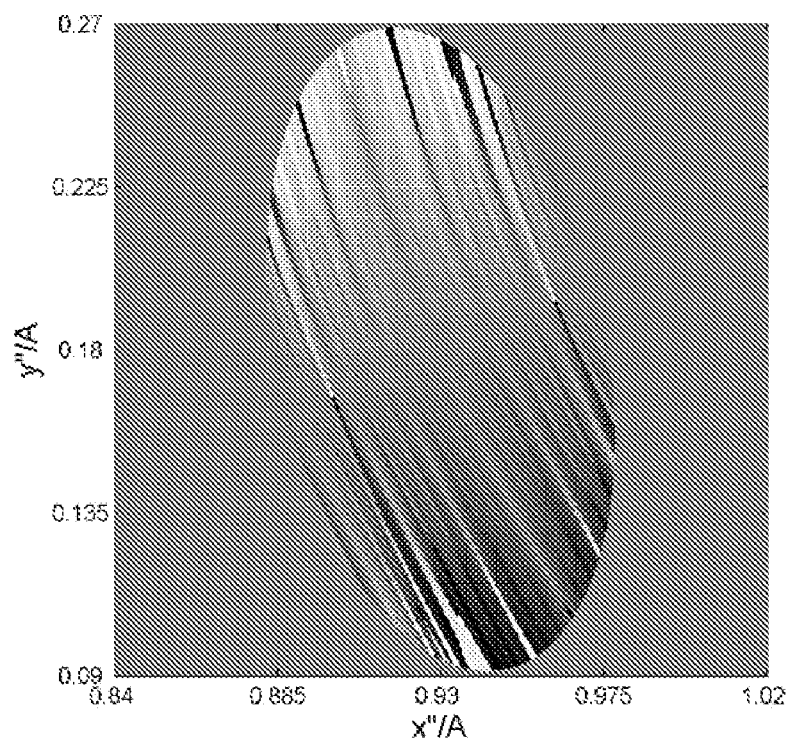
Figure 73E:
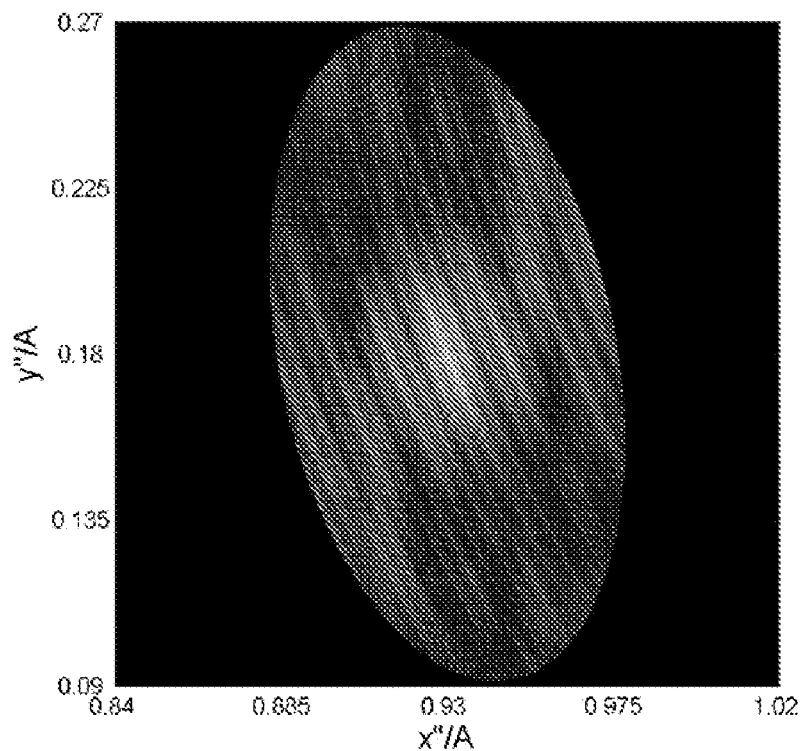
Figure 73F:
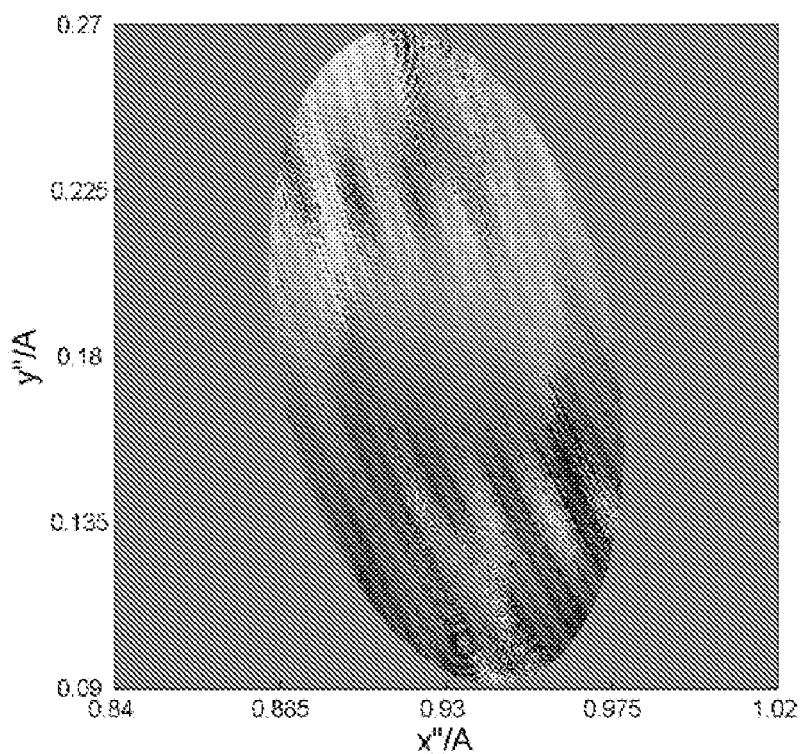

FIGS. 73A and B are linear grayscale images of the amplitude and phase, respectively, at the rear pupil of an NA=1.2 water immersion microscope objective for an internal input beam of ideal wavevector k$_n$=[−5ê$_x$−3ê$_y$+ê$_z$]/($\sqrt{35}$k), used to create an excitation zone consisting of a 1×9×1 array of superimposed sub-zones of the type shown in FIG. 71. FIGS. 73C and D give the amplitude and phase of the same input beam, assuming the excitation zone consists of a 5×5×1 array of such sub-zones. FIGS. 73E and F similarly give the amplitude and phase of the input beam when the excitation zone consists of a 3×5×2 array of sub-zones.

Figure 74A:
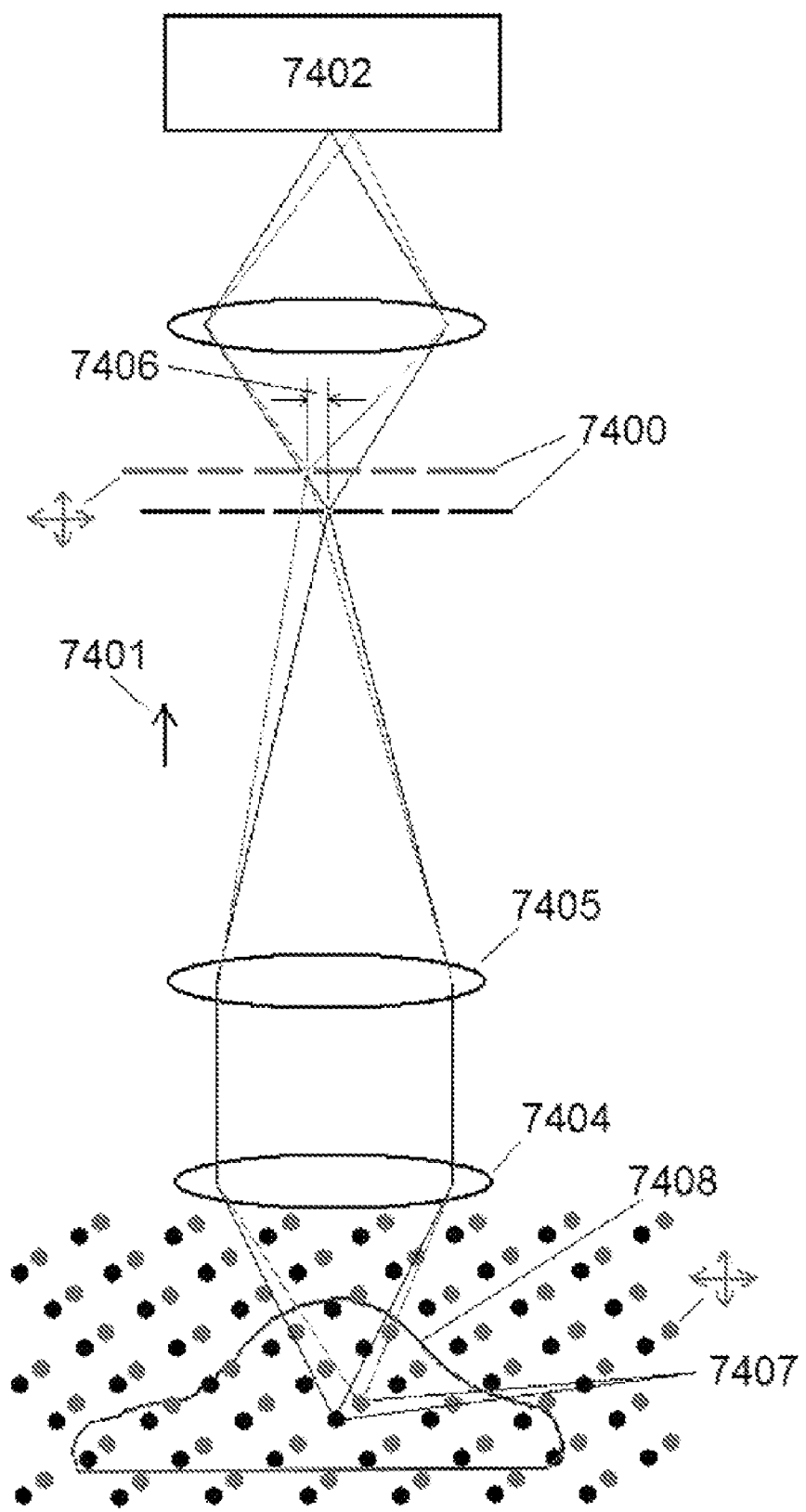

FIG. 74A is a schematic view of a scanning arrangement wherein a lattice and filtering pinhole array are translated in tandem both transversely and axially.

Figure 74B:
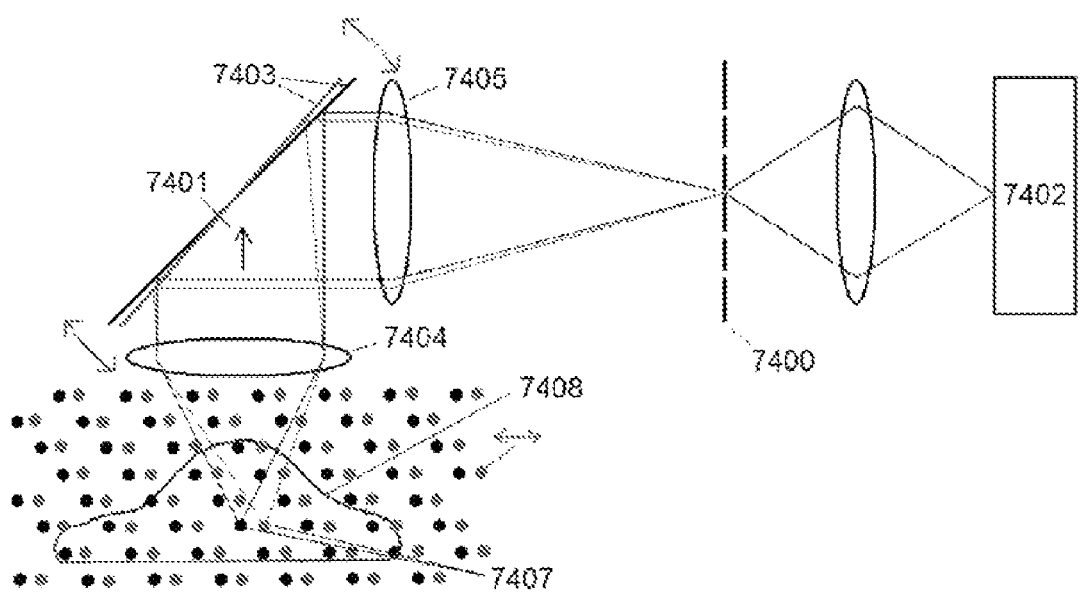

FIG. 74B is a schematic view of a scanning arrangement wherein a lattice is translated axially, and a mirror is tilted simultaneously, to maintain a fixed projection of the lattice at the image plane.

Figure 74C:
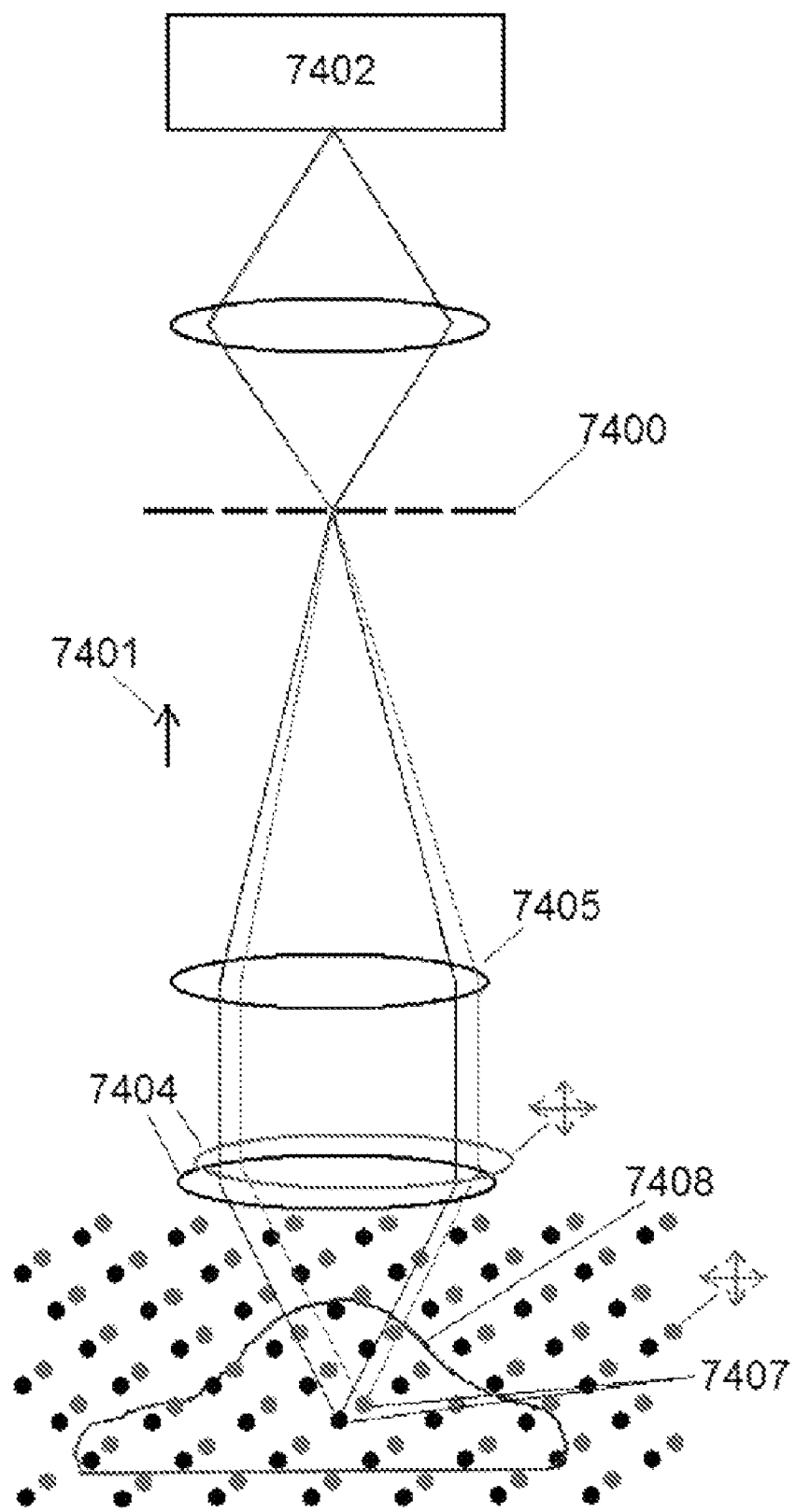

FIG. 74C is a schematic view of a scanning arrangement wherein a lattice and a collection objective are translated in tandem both transversely and axially.

Figure 74D:
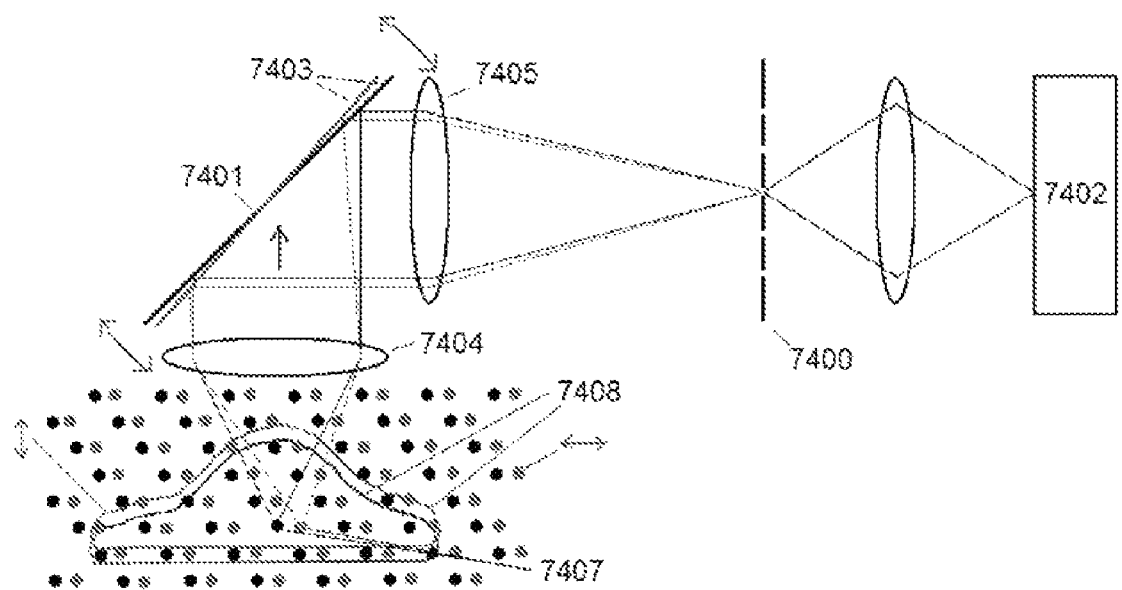

FIG. 74D is a schematic view of a scanning arrangement wherein a lattice is translated transversely, a mirror is tilted in tandem with this motion to maintain a fixed projection of the lattice at the image plane, and a sample is translated axially.

Figure 75A:
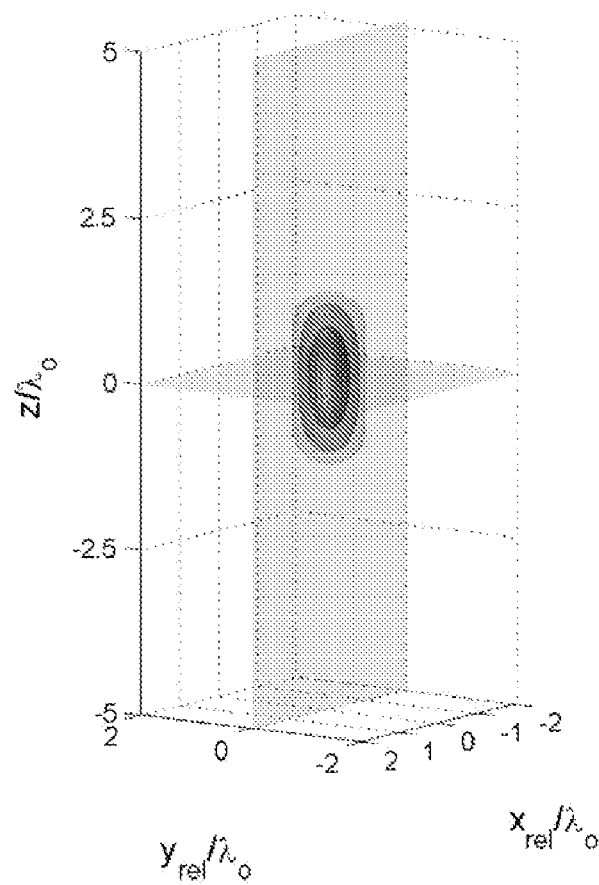
Figure 75B:
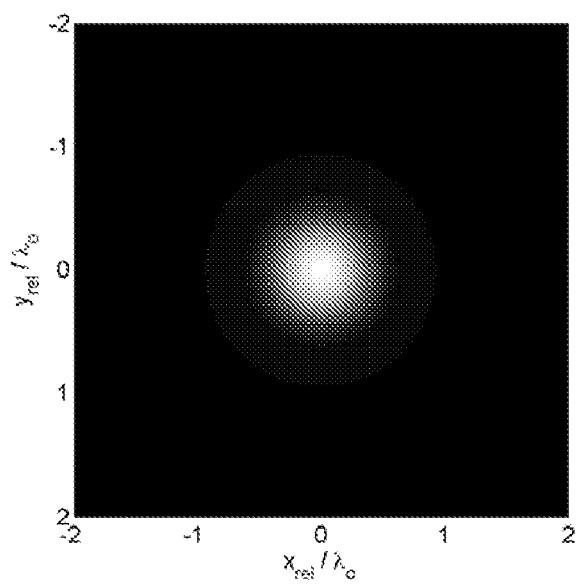
Figure 75C:
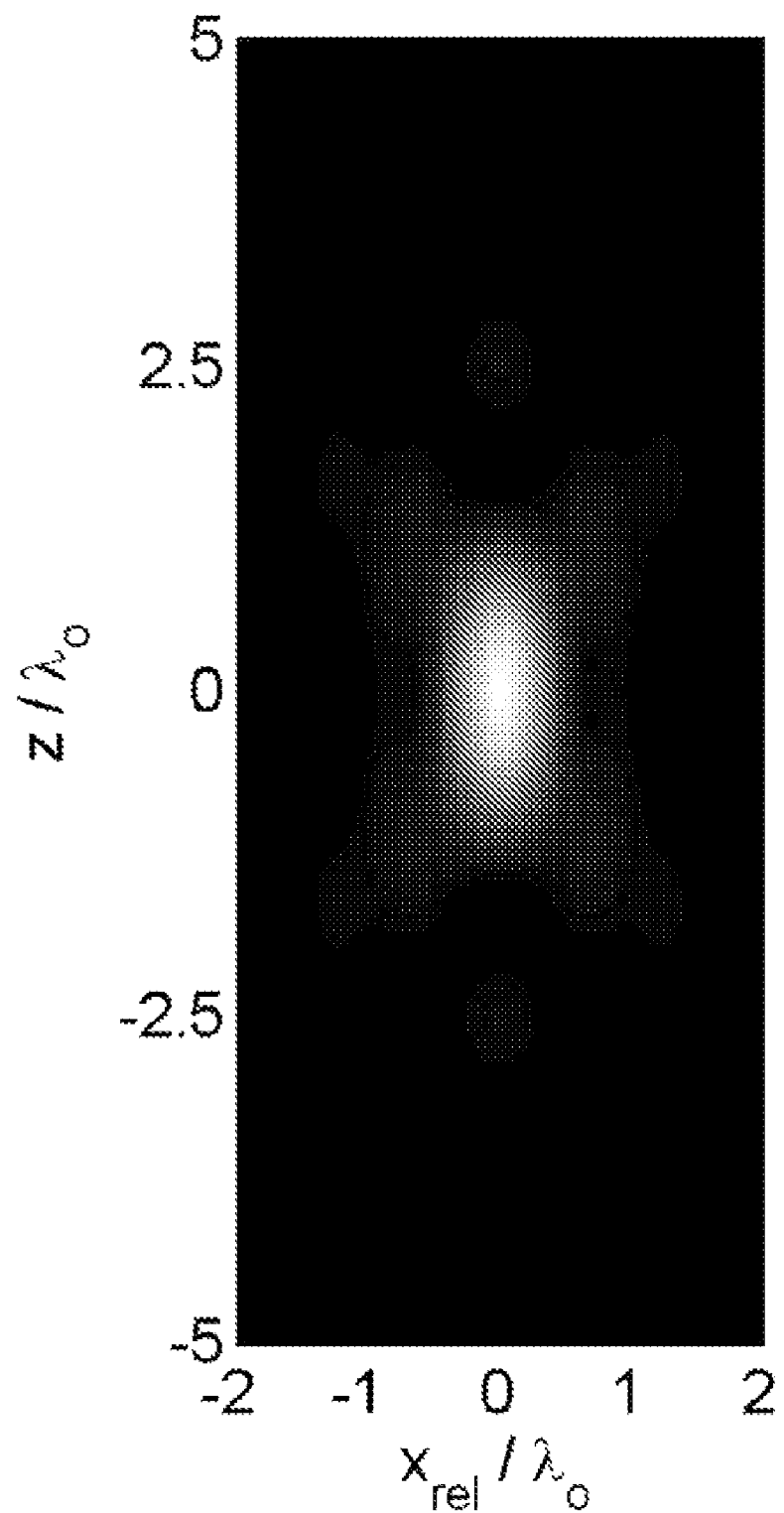
Figure 76A:
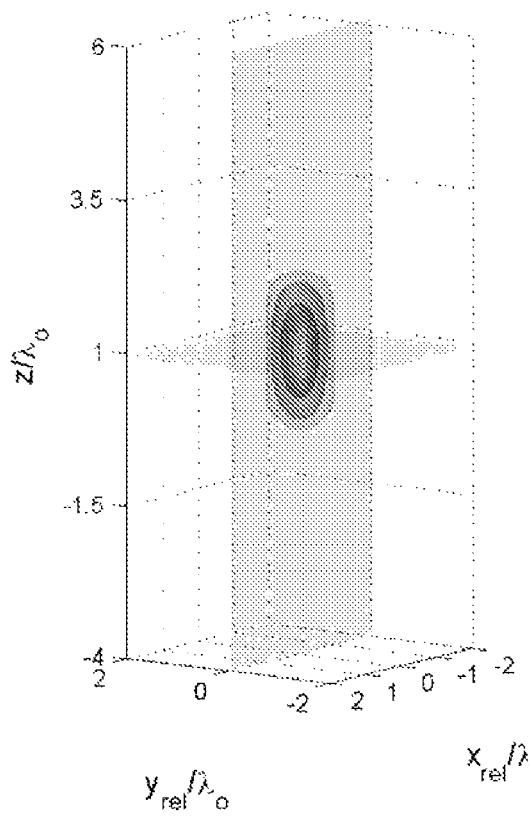
Figure 76B:
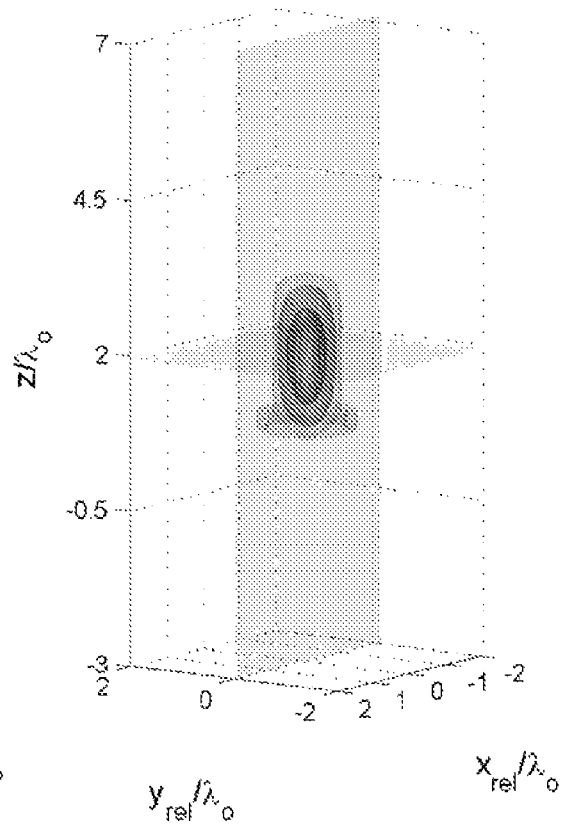
Figure 76C:
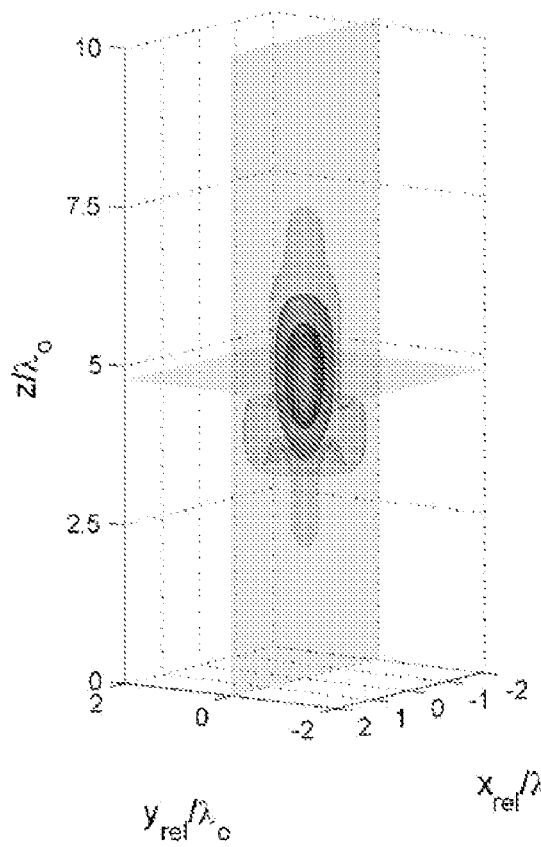
Figure 76D:
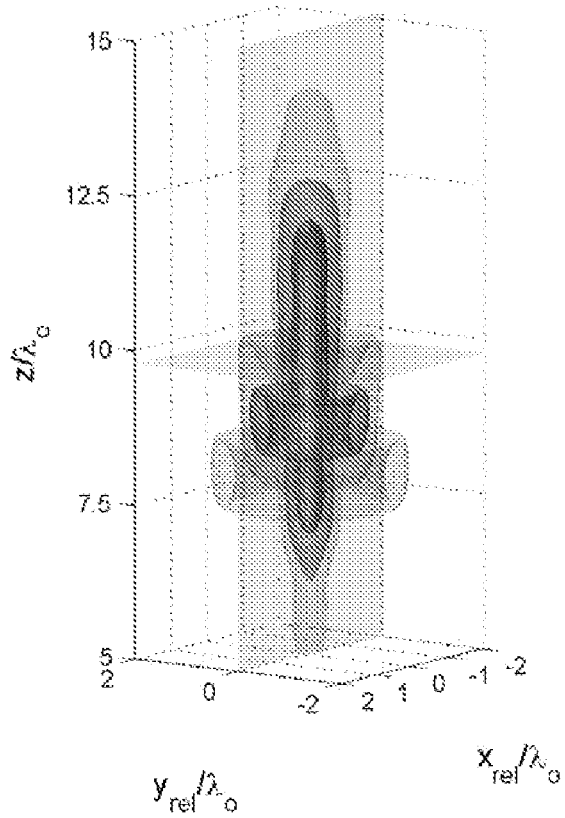
Figure 76E:
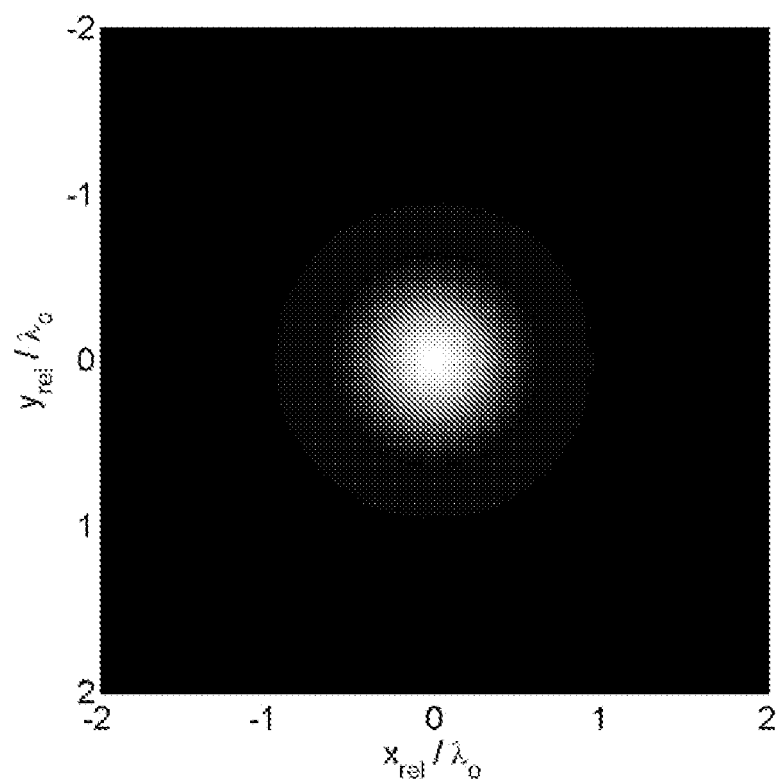
Figure 76F:
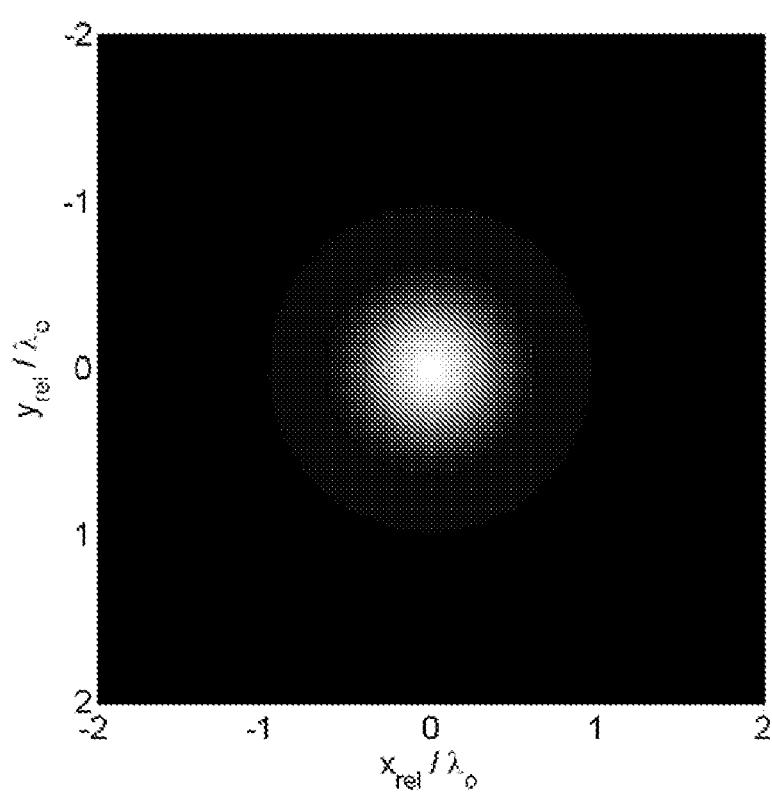
Figure 76G:
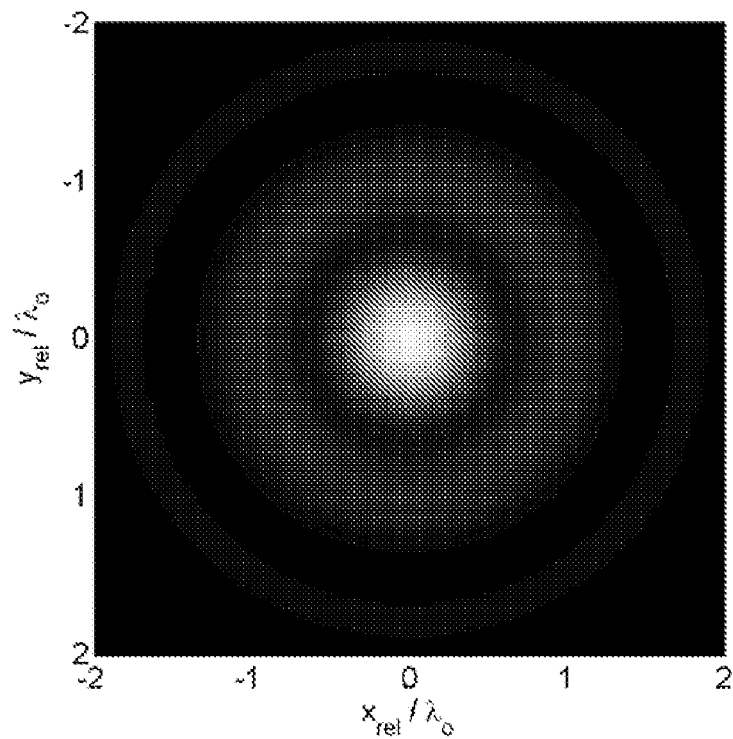
Figure 76H:
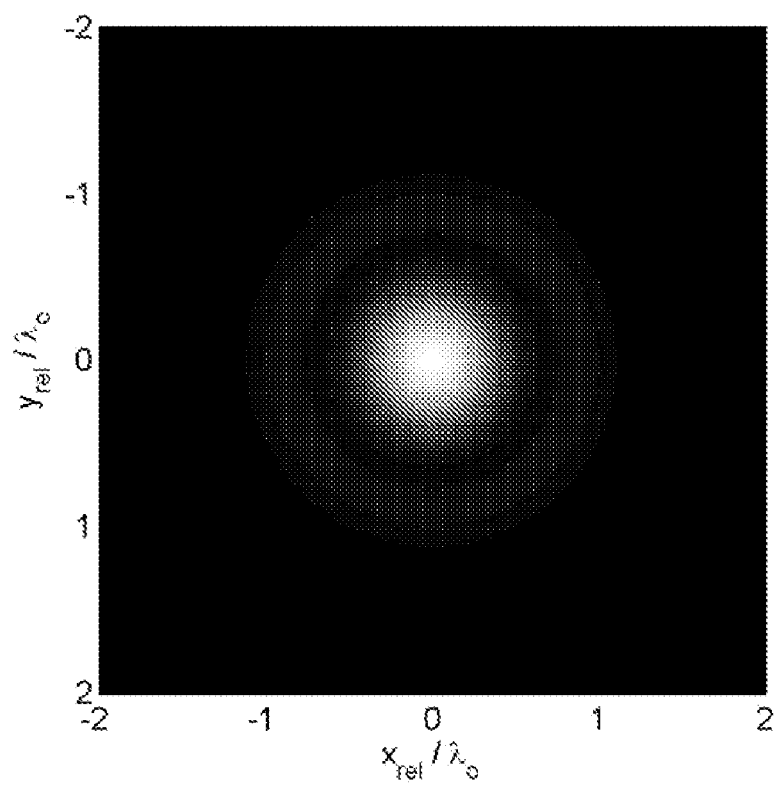
Figure 76I:
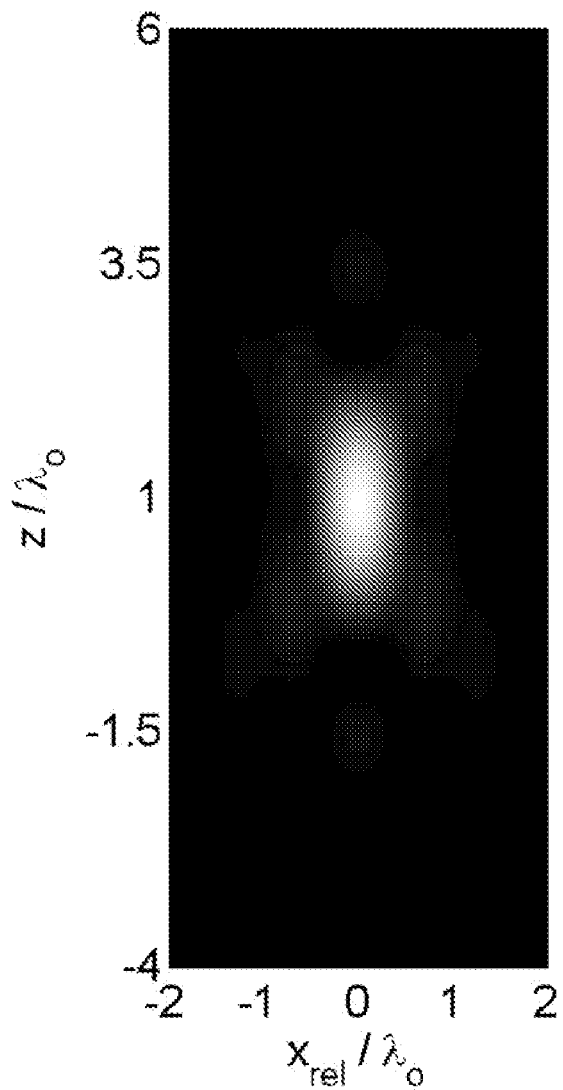
Figure 76J:
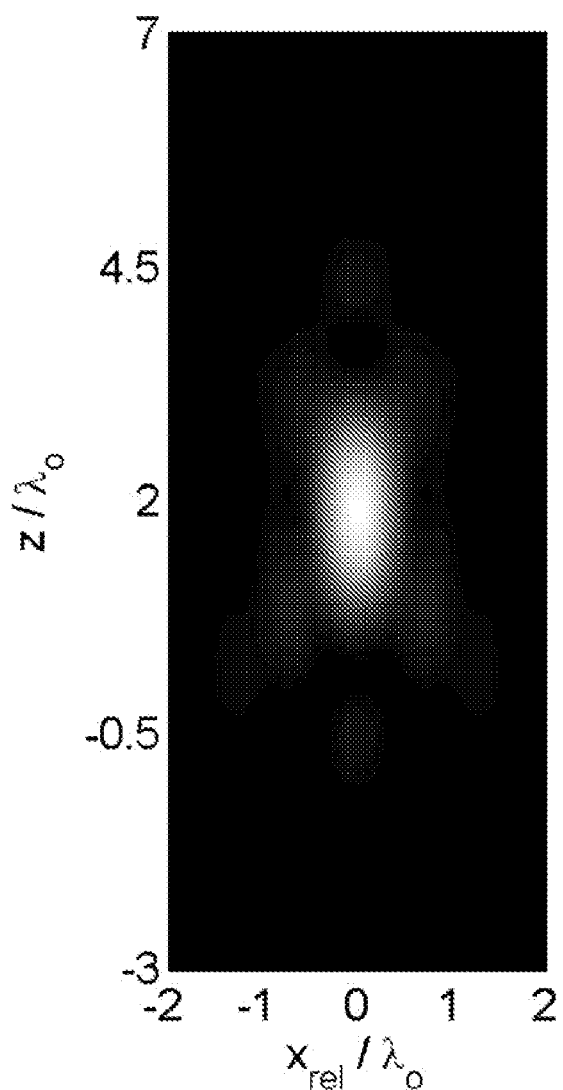
Figure 76K:
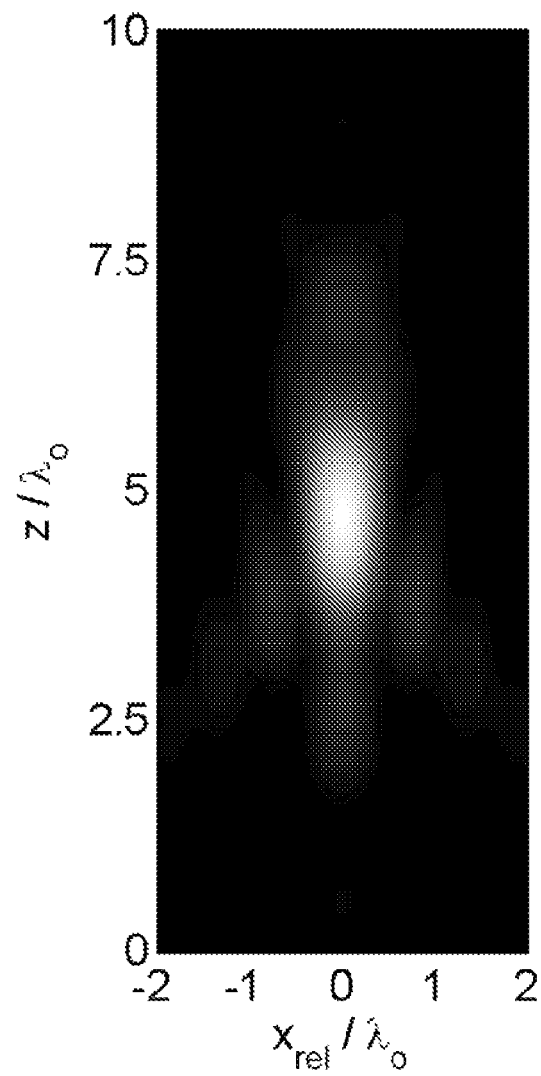
Figure 76L:
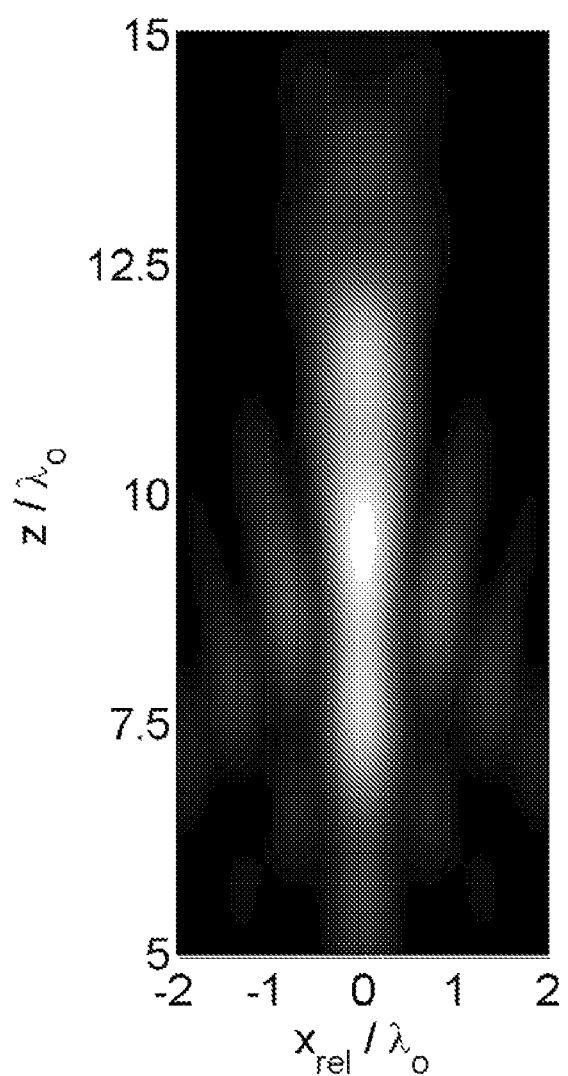
Figure 77A:
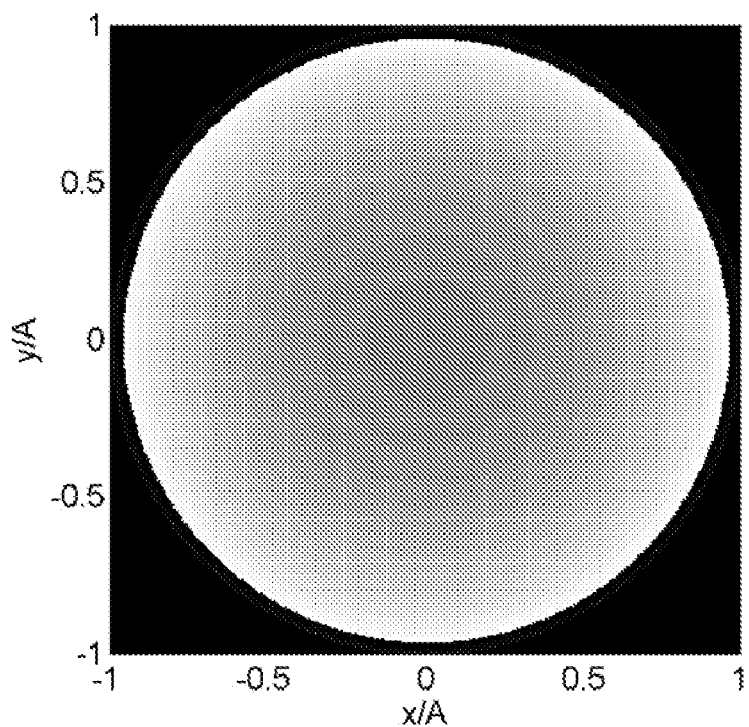
Figure 77B:
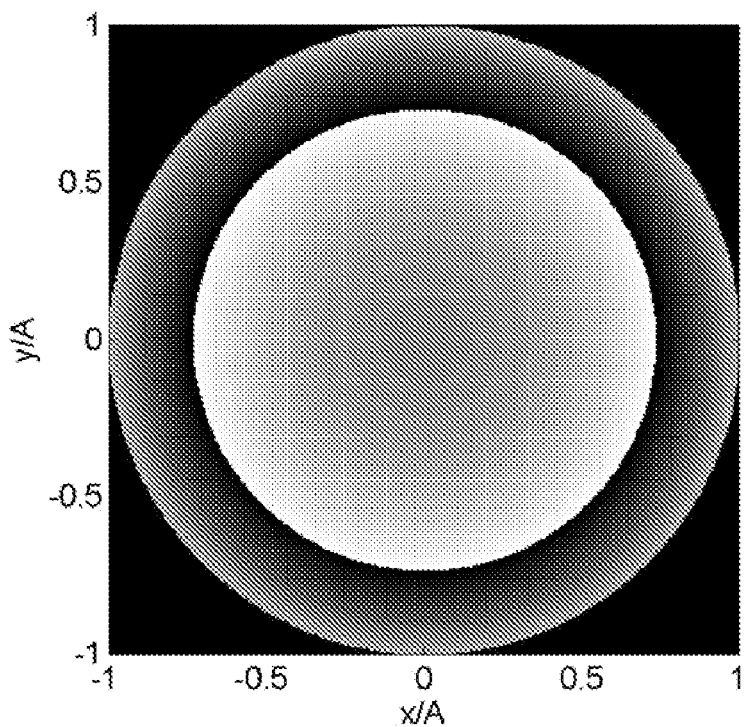
Figure 77C:
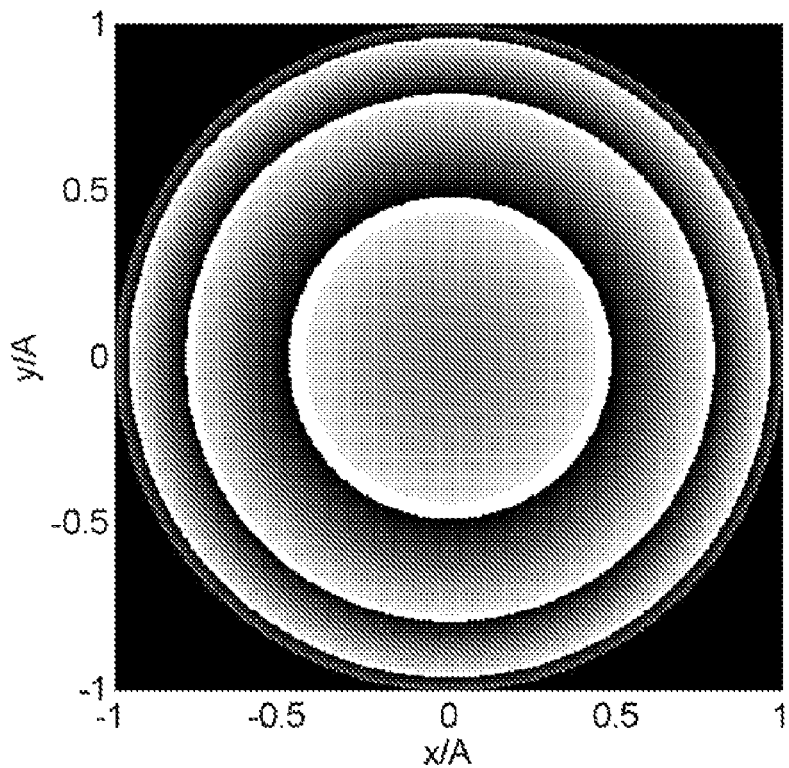
Figure 77D:
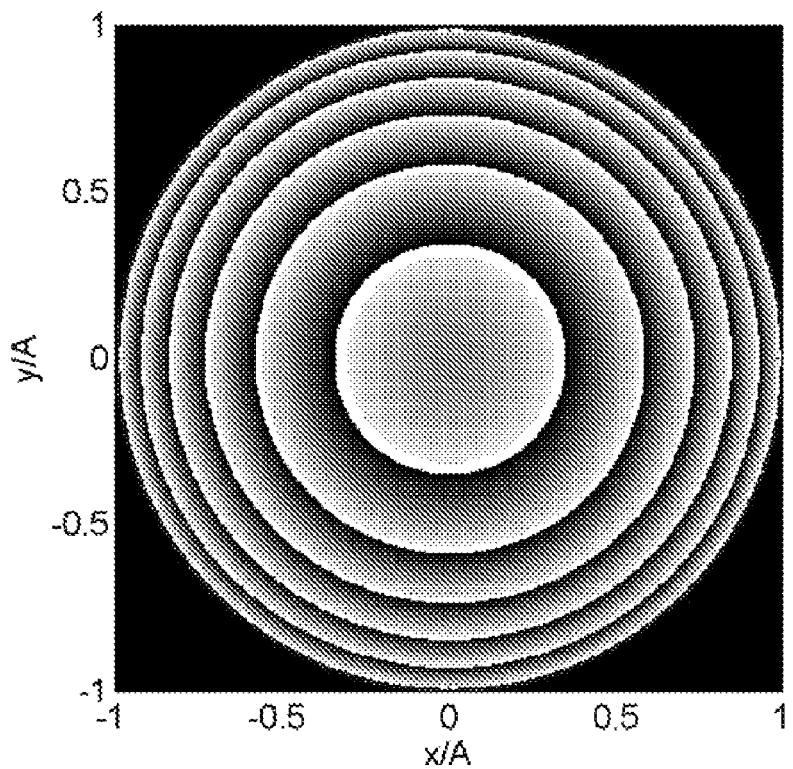

FIG. 75A is a three-dimensional plot of surfaces of 50% (opaque), 20% (medium translucent), and 10% (light translucent) of maximum detection efficiency at a single point in the image plane of a tube lens for a single fluorophore in the corresponding focal plane of a 60×, NA=1.2 infinity corrected water immersion signal collection objective, averaged over all orientations of the fluorophore dipole axis. FIGS. 75B and 75C are two-dimensional plots of the detection efficiency in the x-y and x-z planes, respectively, shown in FIG. 75A.

FIGS. 76A-D are three-dimensional plots of the surfaces of 50% (opaque), 20% (medium translucent), and 10% (light translucent) of maximum detection efficiency for an orientation-averaged fluorophore in the vicinity of the focal point of an objective when a point detector is placed at 2710, 5410, 13500, and 27000 image-space wavelengths, $\lambda_i$, respectively, from the image plane. Lens parameters are the same as in FIG. 75. FIGS. 76E-H are two-dimensional plots of the detection efficiency in the x-y planes and FIGS. 76I-L are similar plots in the x-z planes shown in FIGS. 76A-D, respectively.

FIGS. 77A-D are grayscale plots of the phase variation $\Delta\phi$ across the signal beam (modulo $2\pi$, black for $\Delta\phi=-\pi$, white for $\Delta\phi=+\pi$) emerging from the rear pupil of an NA=1.2 microscope objective for a point source on the longitudinal axis of the objective, but a distance of $\lambda_o$, $2\lambda_o$, $5\lambda_o$, and $10\lambda_o$ object-space wavelengths from its focal point.

Figure 78A:
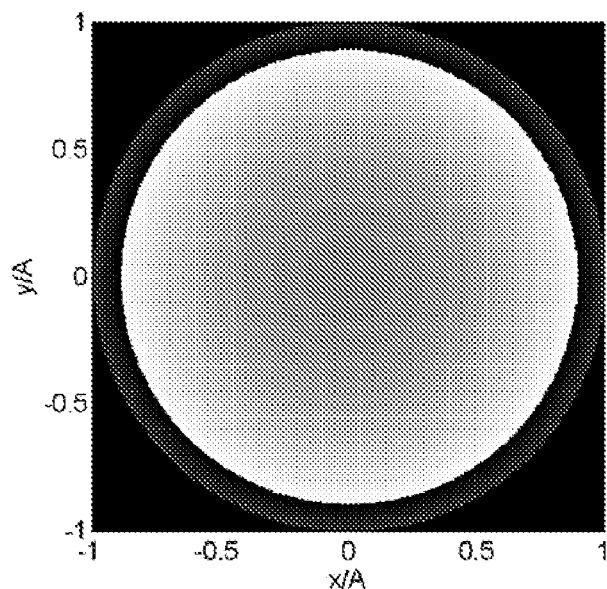
Figure 78B:
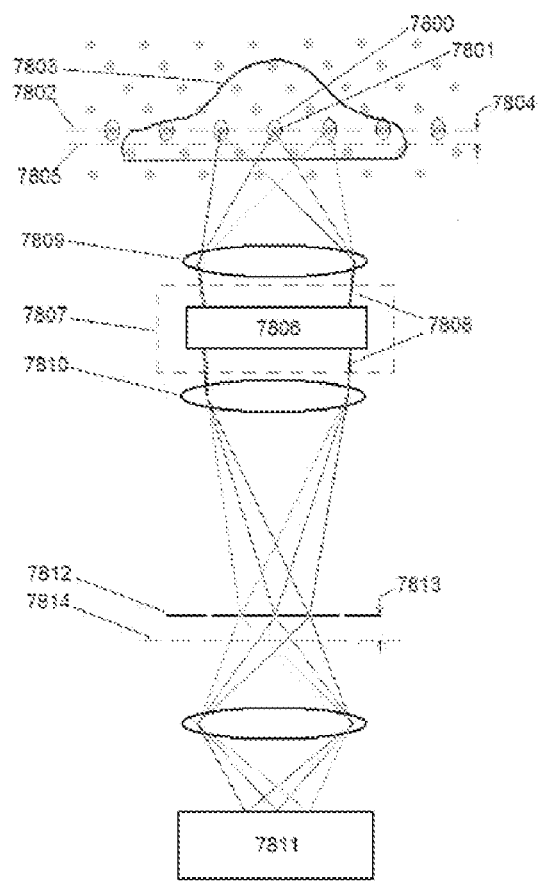
Figure 79A:
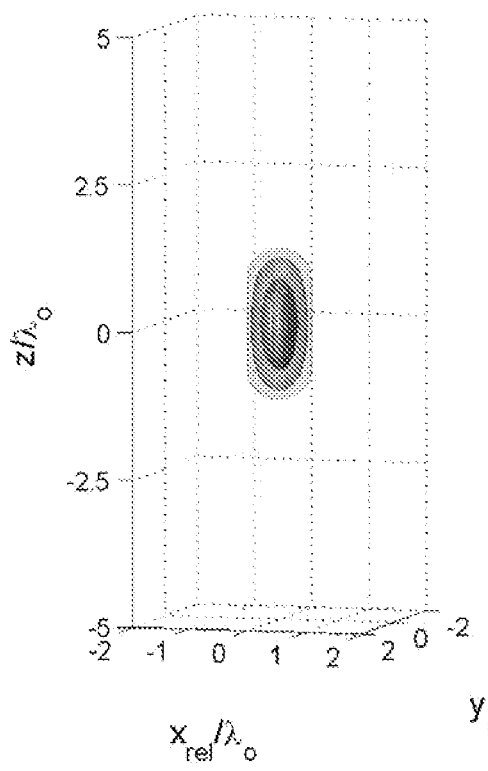
Figure 79B:
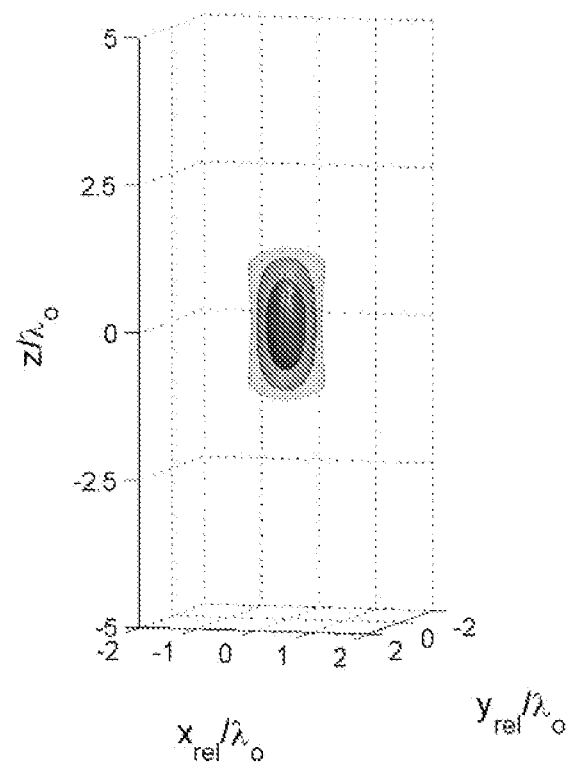
Figure 79C:
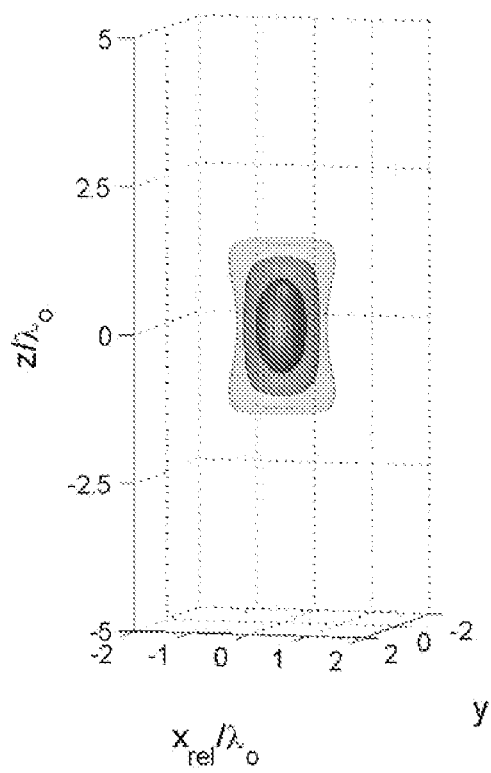
Figure 79D:
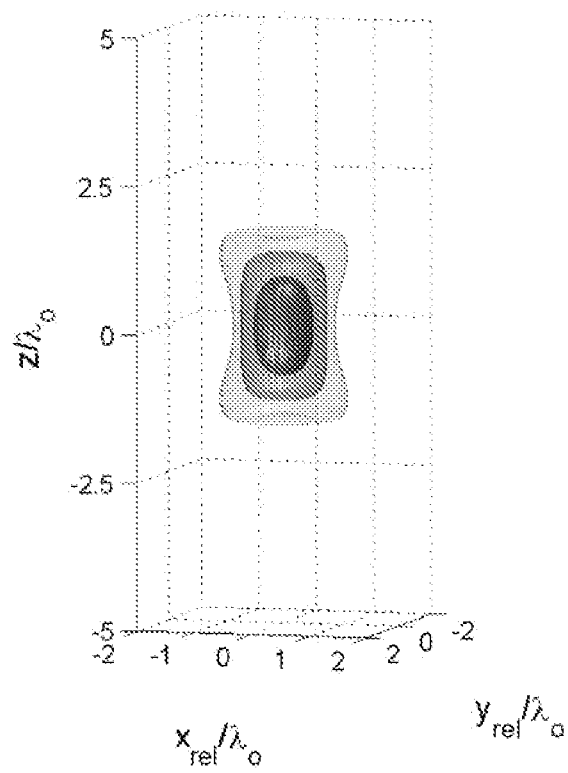
Figure 79E:
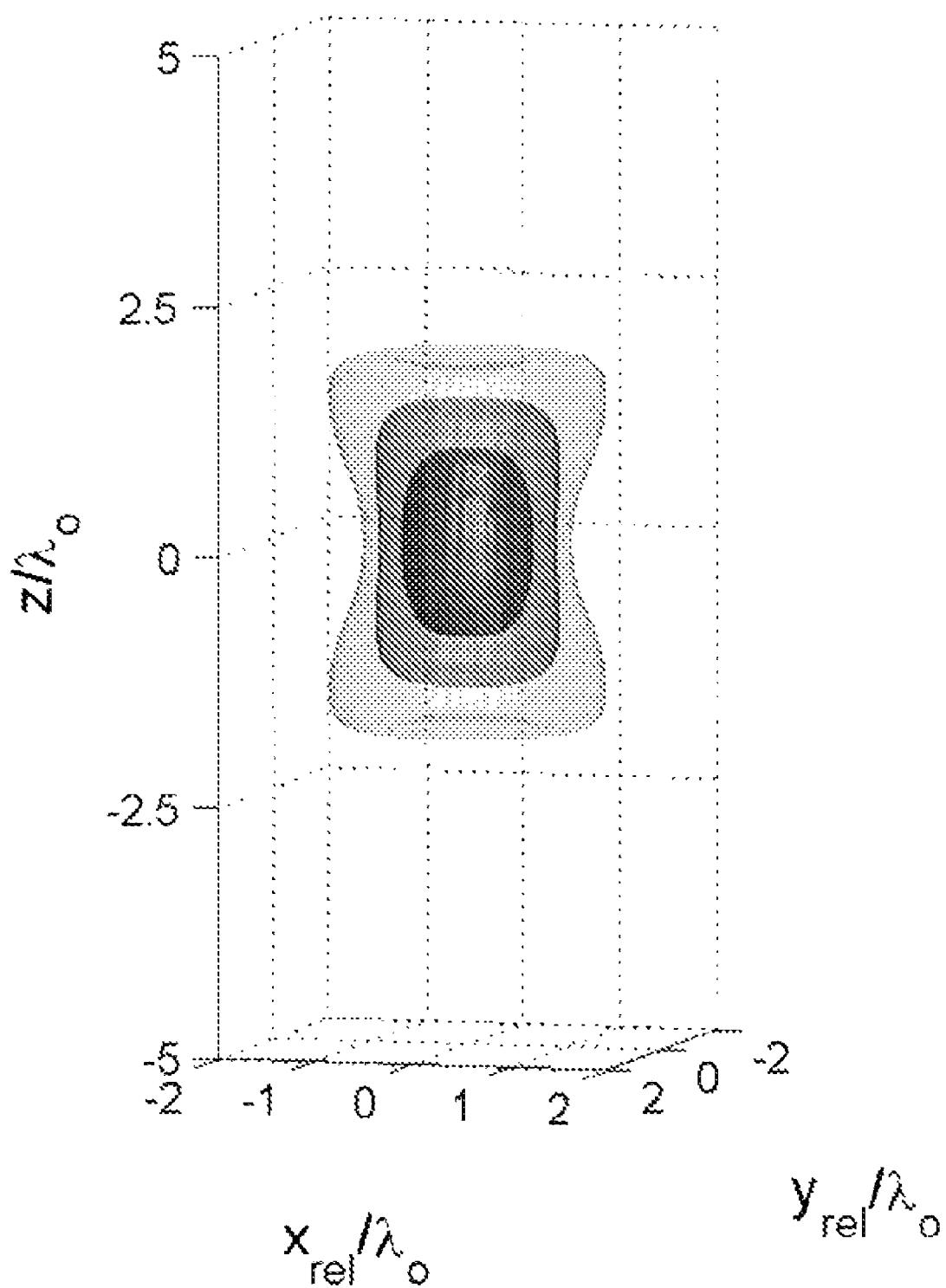

FIG. 78A is a schematic view of an apparatus for detecting the signal from individual excitation maxima in a single plane of a three-dimensional optical lattice, including means to improve the detection efficiency when the lattice plane is offset from the objective focal plane, and a spatial filtering aperture mask is offset from the image plane. FIG. 78B is a plot of the phase correction across the beam emerging from the objective required to optimize the detection when the lattice plane is $\lambda_o$ from the original focal plane and the aperture mask is $600\lambda_i$ from the original image plane.

FIGS. 79A-E are three-dimensional plots of the surfaces of 50% (opaque), 20% (medium translucent), and 10% (light translucent) of maximum detection efficiency for an orientation-averaged fluorophore in the focal plane of a 60×, NA=1.2 infinity corrected water immersion signal collection objective when the focused signal is filtered by an aperture of radius $60\times0.1\lambda_i$, $60\times0.2\lambda_i$, $60\times0.4\lambda_i$, $60\times0.5\lambda_i$, and $60\times0.65\lambda_i$, respectively, centered at the corresponding point in the image plane prior to detection. The percentage of collected signal that is transmitted through the aperture is 5.7%, 20.3%, 54.1%, 64.4%, and 71.9%, respectively.

Figure 80A:
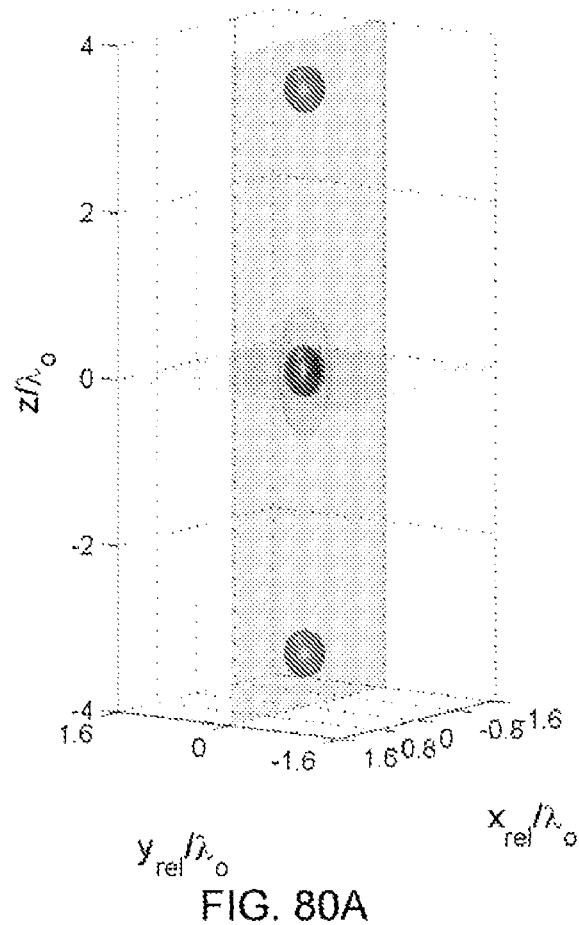
Figure 80B:
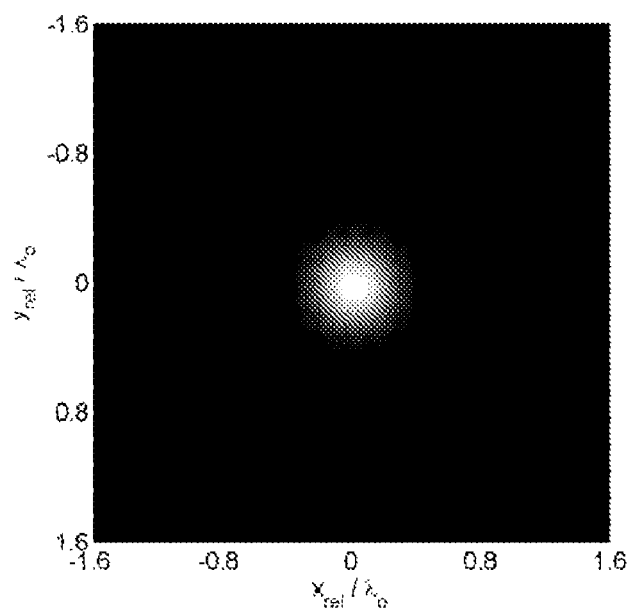
Figure 80C:
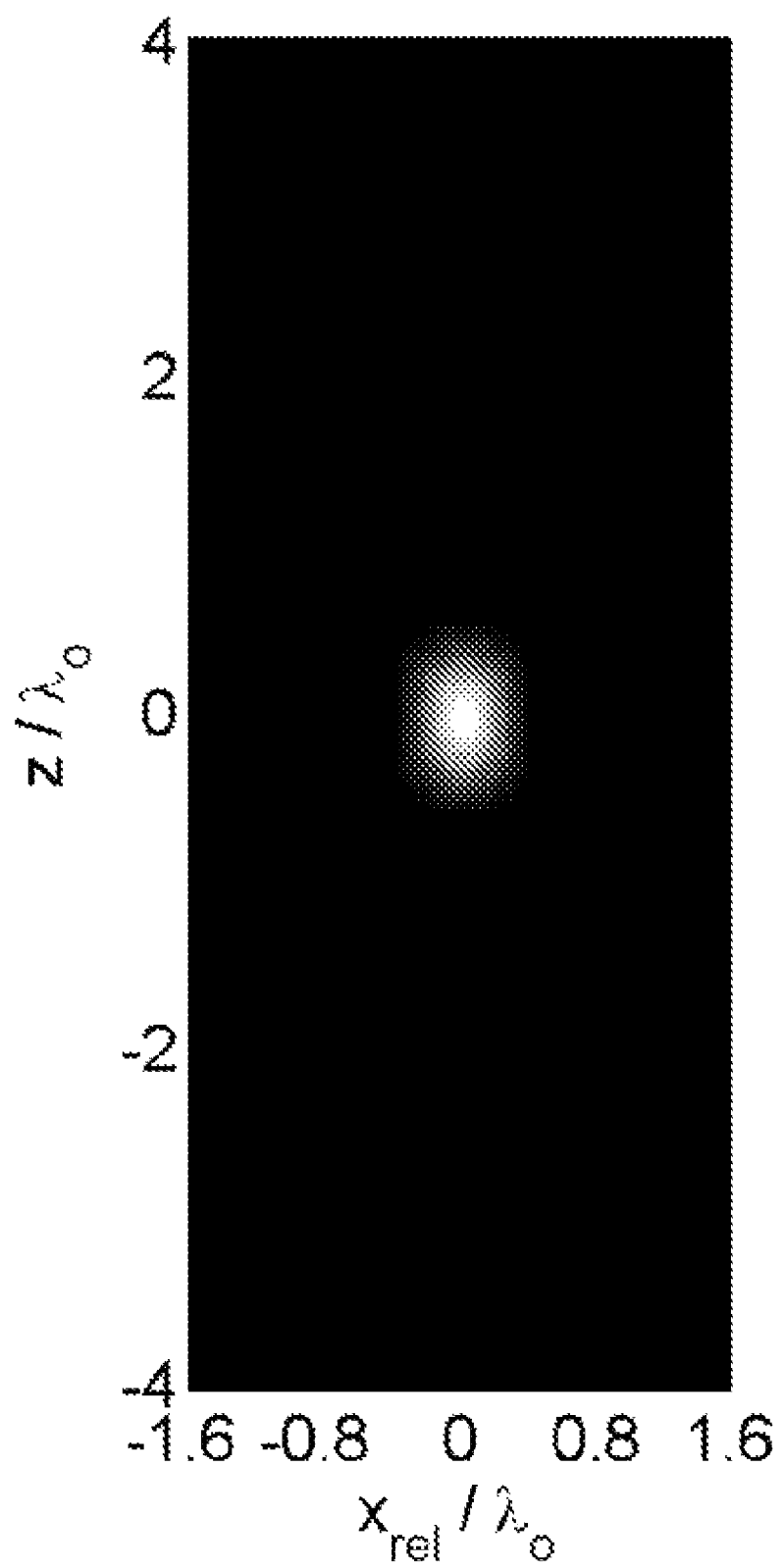

FIG. 80A is a three-dimensional plot of: the surfaces of 50% of maximum intensity for a predominantly z-polarized simple cubic lattice of intensity period $\sqrt{35}\lambda_o/2$ (top, center, and bottom medium translucent surfaces); the surface of 50% of maximum detection efficiency for an orientation-averaged fluorophore located at the central intensity maximum, for the same parameters as FIG. 75 (light translucent); and the surface of 50% of total signal collected (dark opaque surface at center), as given by the product of the excitation and detection efficiency profiles. FIGS. 80B and 80C are two-dimensional plots of the total collected signal for this lattice and objective in both the x-y and x-z planes shown in FIG. 80A. Note in FIG. 80C that the detection system effectively limits the signal collection to a single lattice plane, as desired.

FIGS. 81A-E are three-dimensional plots of the surfaces of 50% (opaque), 20% (medium translucent), and 10% (light translucent) of maximum detection efficiency for an orientation-averaged fluorophore in the focal plane of a 60×, NA=1.2 infinity corrected water immersion signal collection objective when the x-polarized component of the collected signal is focused onto an aperture of ellipticity 1.5 and semi-major axis length $0\lambda_i$ (ideal point detection), $60\times0.1\lambda_i$, $60\times0.2\lambda_i$, $60\times0.4\lambda_i$, and $60\times0.6\lambda_i$, respectively, centered at the corresponding point in the image plane prior to detection. The percentage of collected signal that is transmitted through the aperture is 0%, 6.9%, 23.8%, 59.4%, and 74.1%, respectively.

Figure 82A:
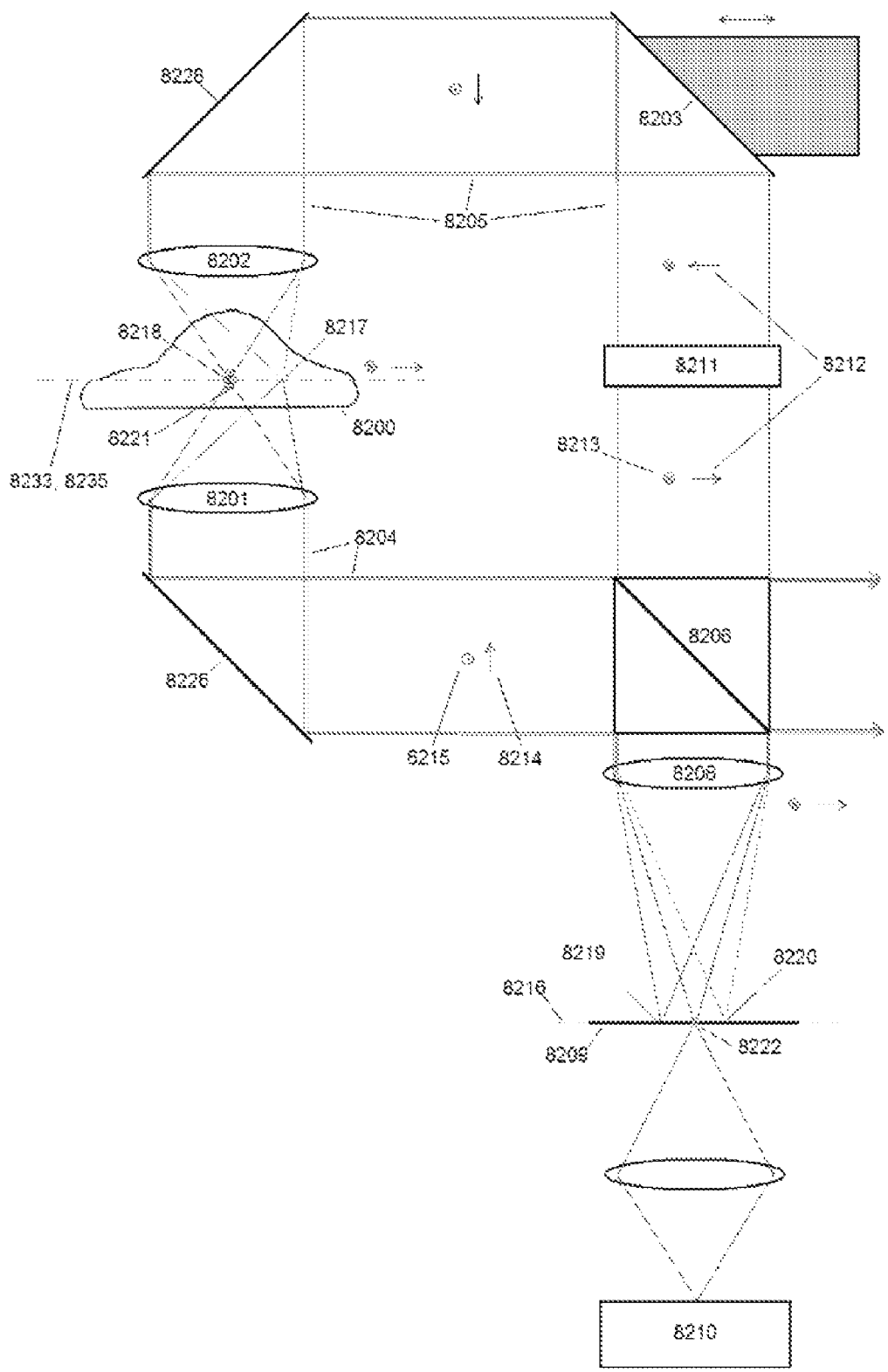
Figure 82B:
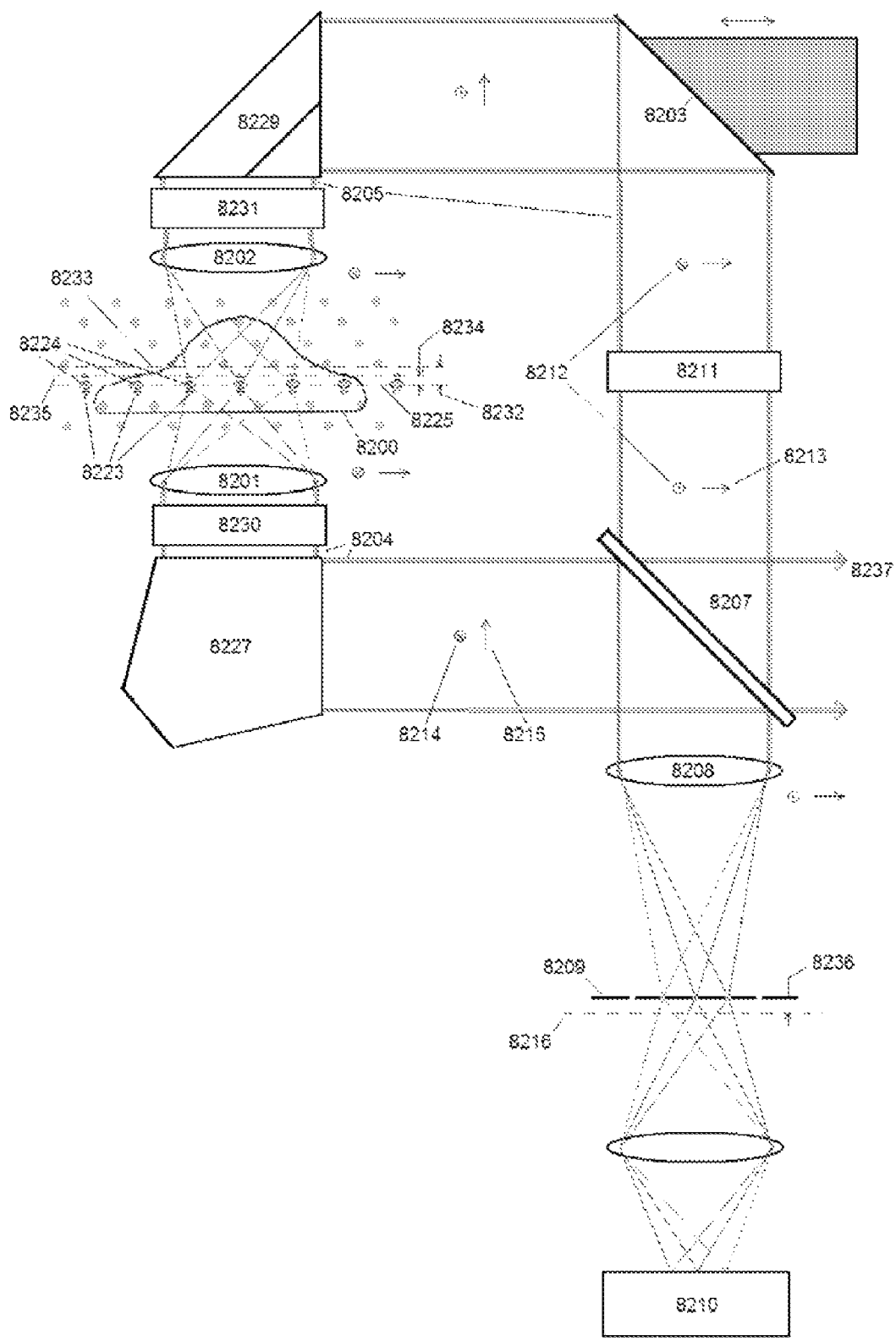

FIG. 82A is a schematic view of a conventional $4\pi$ microscope that coherently detects signal emitted from the common focal point of two opposed objectives. FIG. 82B is a schematic view of an apparatus for the coherent detection of signal from a plurality of excitation maxima in a single lattice plane collected by two opposed objectives, wherein the two focal planes and the lattice plane need not coincide.

Figure 83A:
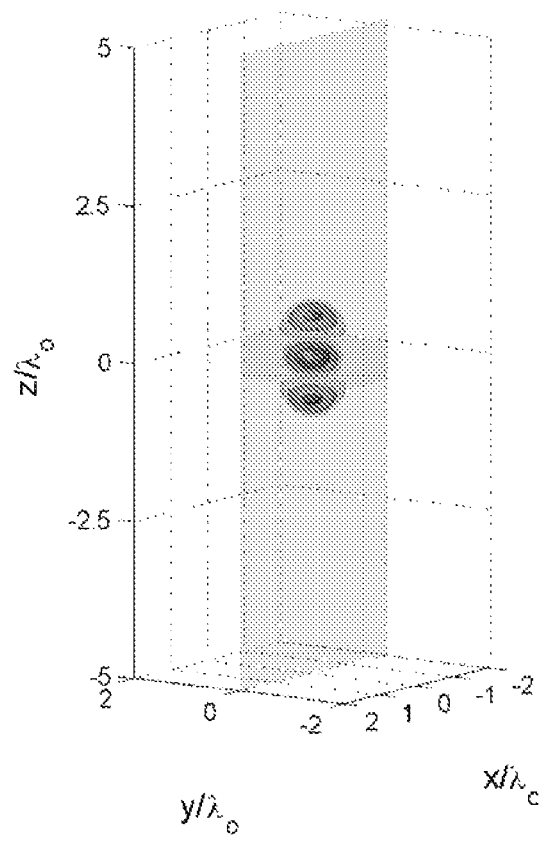
Figure 83B:
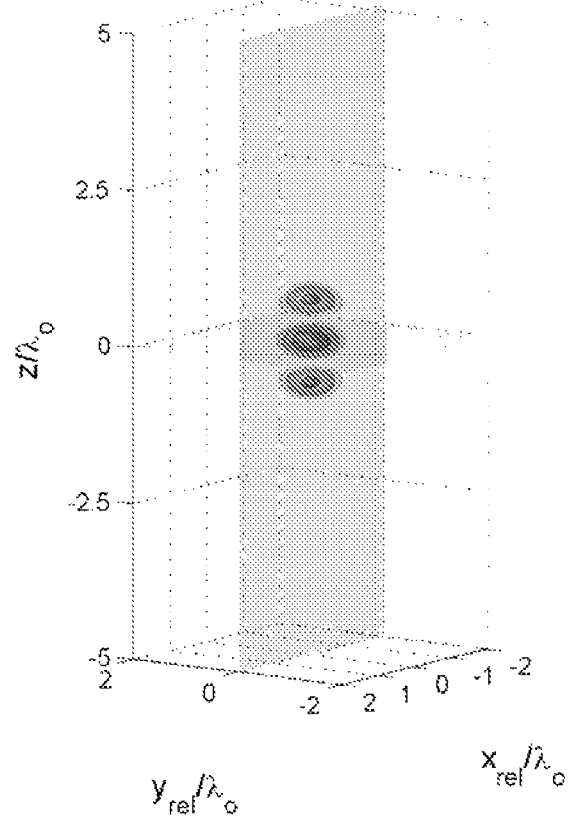
Figure 83C:
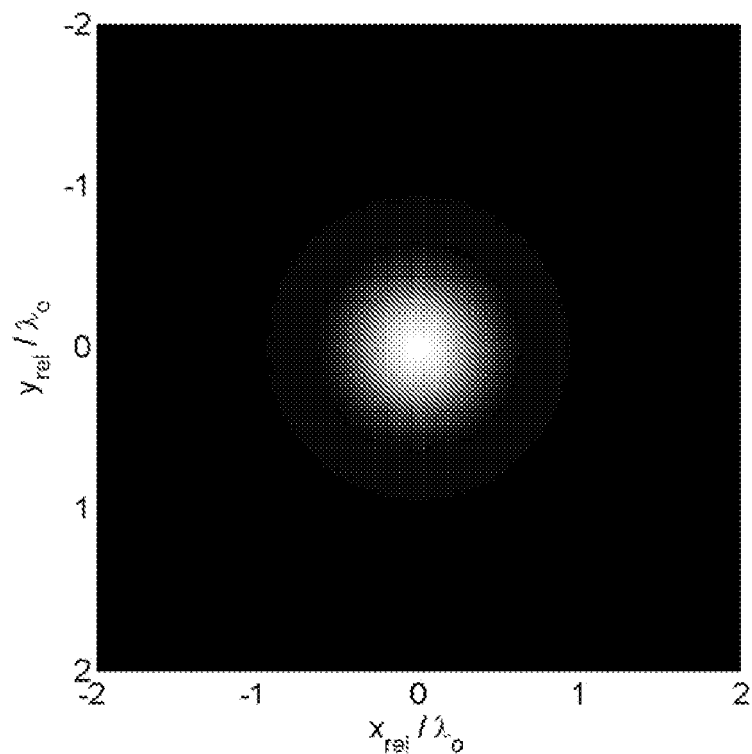

FIG. 83A is a three-dimensional plot of the surfaces of 50% (opaque), 20% (medium translucent), and 10% (light translucent) of maximum detection efficiency for an orientation-averaged fluorophore at the focal point of the $4\pi$ microscope of FIG. 82A. FIG. 83B is a similar plot of detection efficiency surfaces for a fluorophore at any one of the excitation maxima in a chosen lattice plane for the apparatus of FIG. 82B. FIGS. 83C, D and FIGS. 83E, F are two-dimensional plots of the detection efficiency in the x-y and x-z planes, respectively, shown in FIGS. 83A, B.

DETAILED DESCRIPTION

Overview

A sample can be imaged by creating a periodic array of light intensity maxima within the sample. The periodic array can be created though the superposition and interference of a finite set of plane waves, i.e., multiple beams of monochromatic light. Such a construct can be known as an optical lattice. Portions of the sample illuminated by the intensity maxima can be detected and imaged by separate detector elements. The periodic array then can be translated within the sample to illuminate and image different portions of the sample. By translating the array of intensity maxima throughout the sample and imaging the maxima during the translation, an image of the entire sample can be created. Because the array is periodic, the array only needs to be shifted over one unit cell of the array to create an image of the entire sample.

Before three-dimensional optical lattices are described, the simpler cases of one- and two-dimensional optical lattices are described. The concepts that are developed for the one- and two-dimensional cases then are extended to the three-dimensional case.

One-Dimensional Lattices

Figure 1:
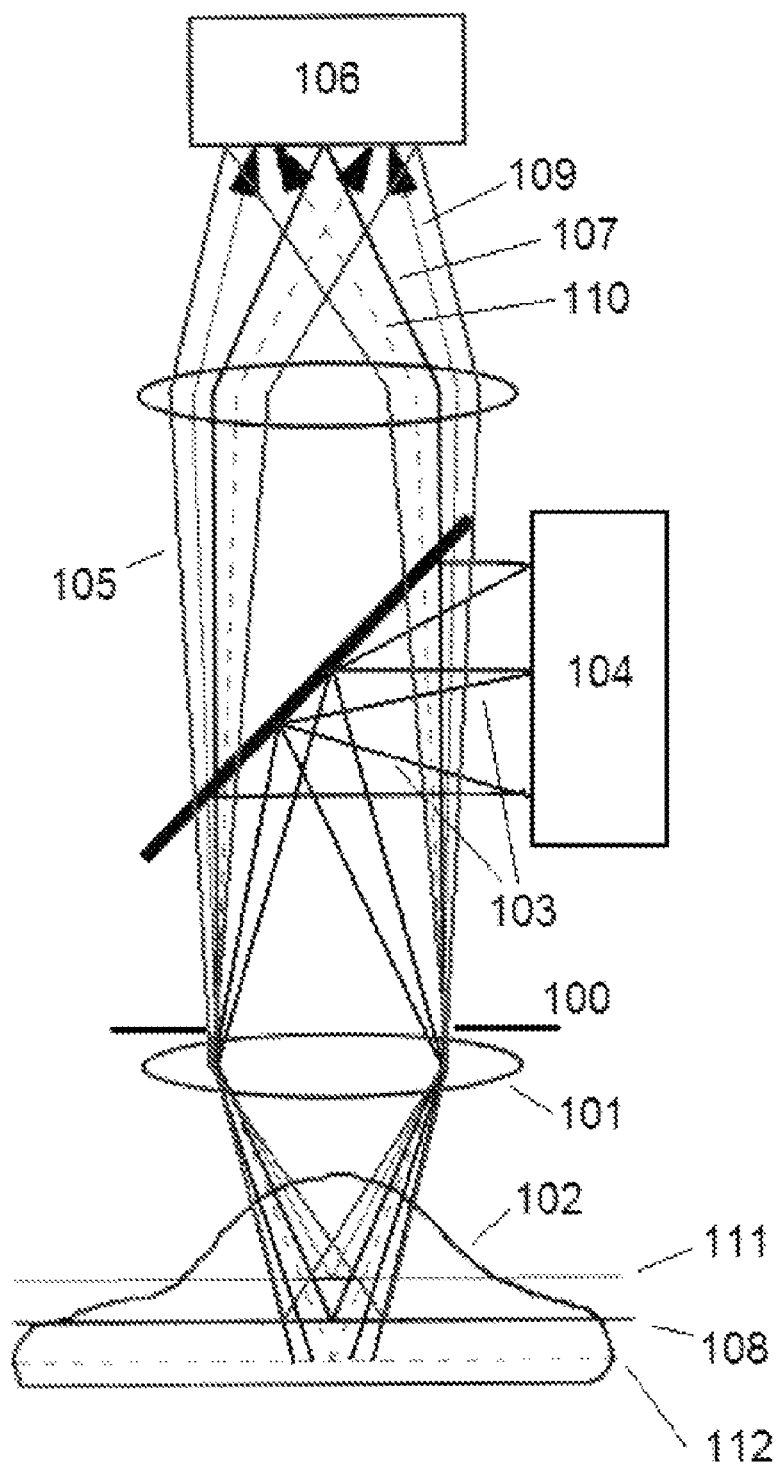
FIG. 1 is a schematic view of a widefield microscopy system.
Figure 2:
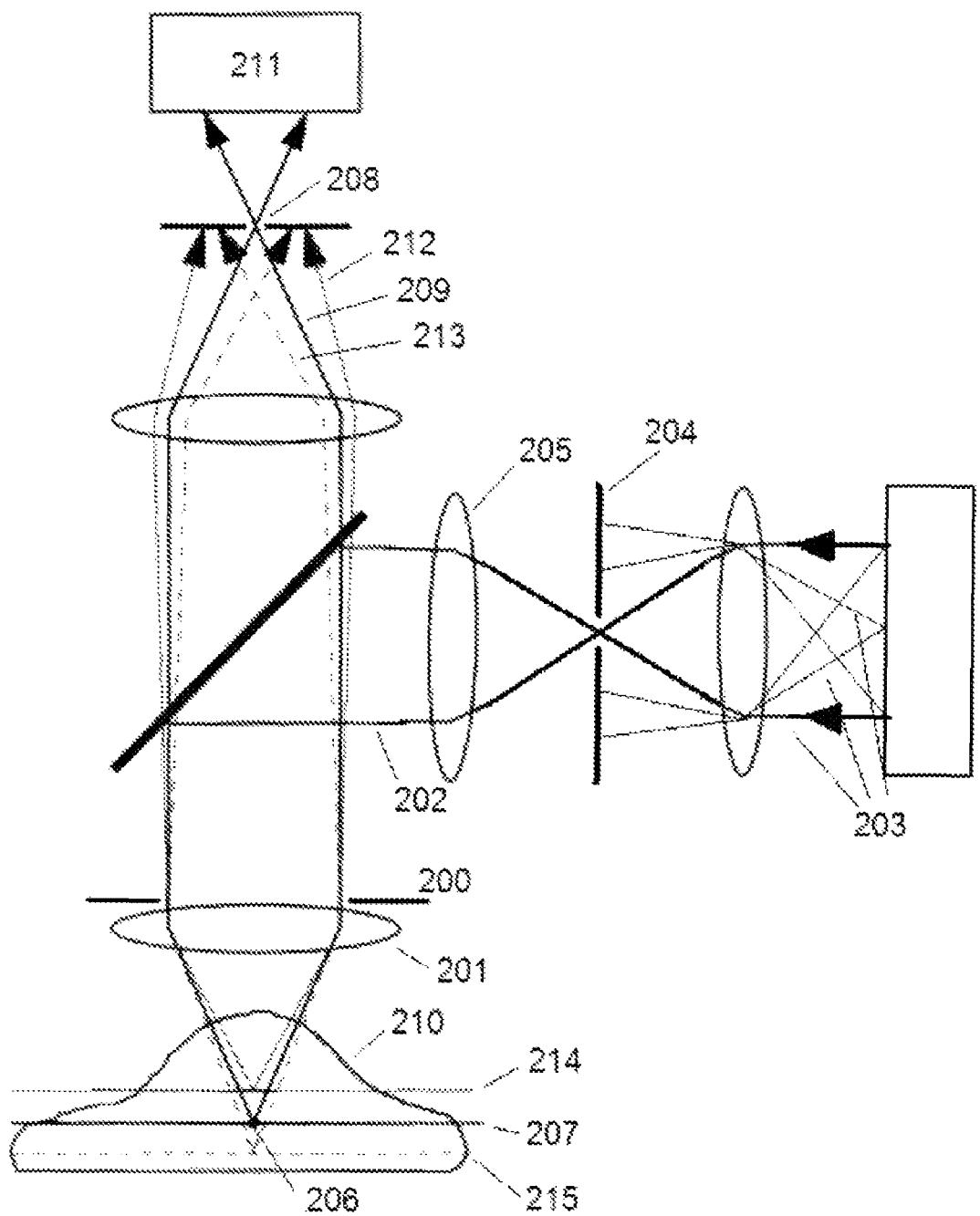
FIG. 2 is a schematic view of a confocal microscopy system.
Figure 3:
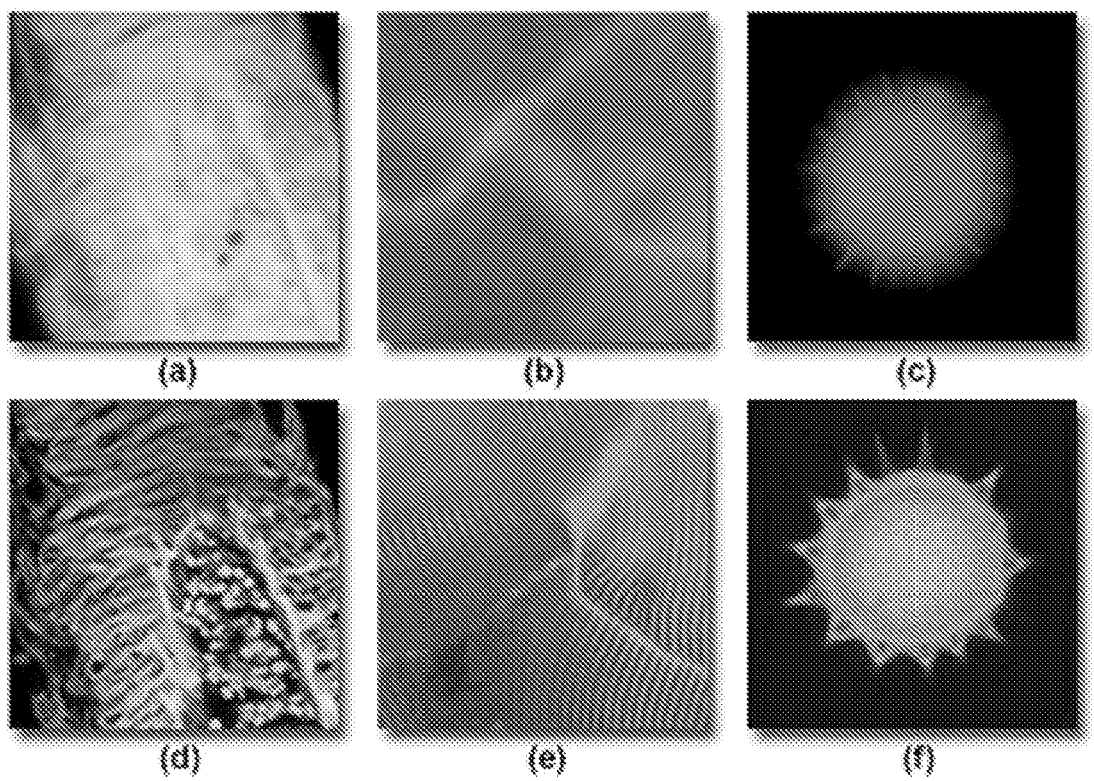
FIGS. 3A, 3B, and 3C are exemplary images obtained with a widefield microscopy system.
FIGS. 3D, 3E, and 3F are exemplary images obtained with a confocal microscopy system.
Figure 4:
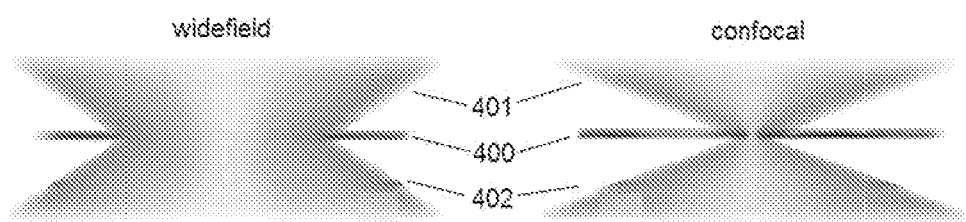
FIG. 4 is a schematic view comparing the illumination regions in widefield microscopy and confocal microscopy.
Figure 5:
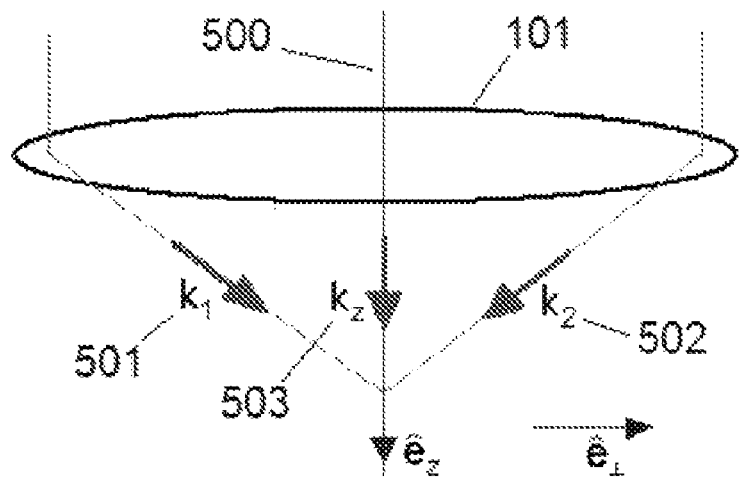
FIG. 5 is a schematic view of an illumination cone produced by focusing plane waves with a single lens.
Figure 6A:
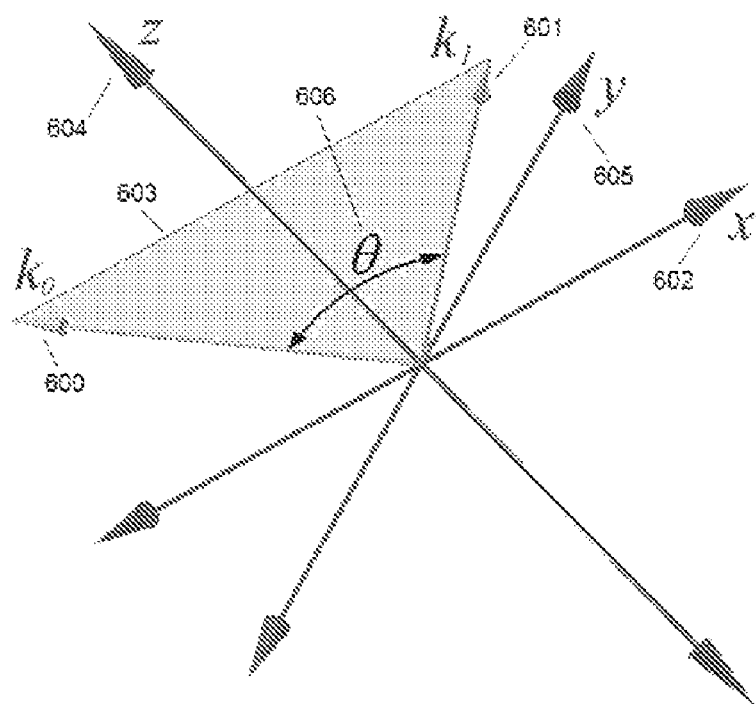
FIG. 6A is a schematic view of the symmetry axes of a one-dimensional optical lattice created by two plane waves.
Figure 6B:
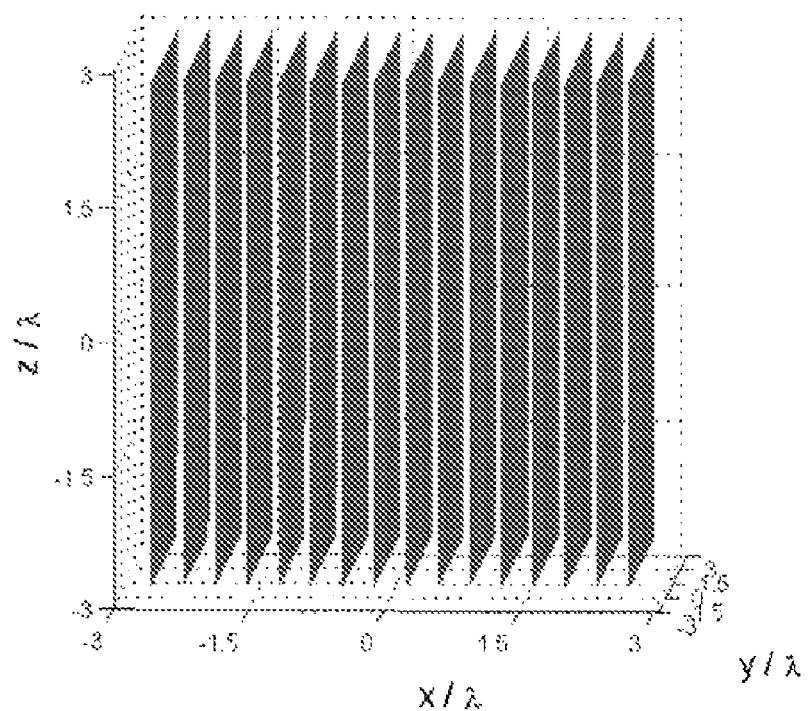
FIG. 6B is a three-dimensional plot of a light intensity having 50% of the maximum light intensity for a one-dimensional optical lattice aligned along the x-axis formed by two perpendicular planes as waves shown in FIG. 6A.
Figure 6C:
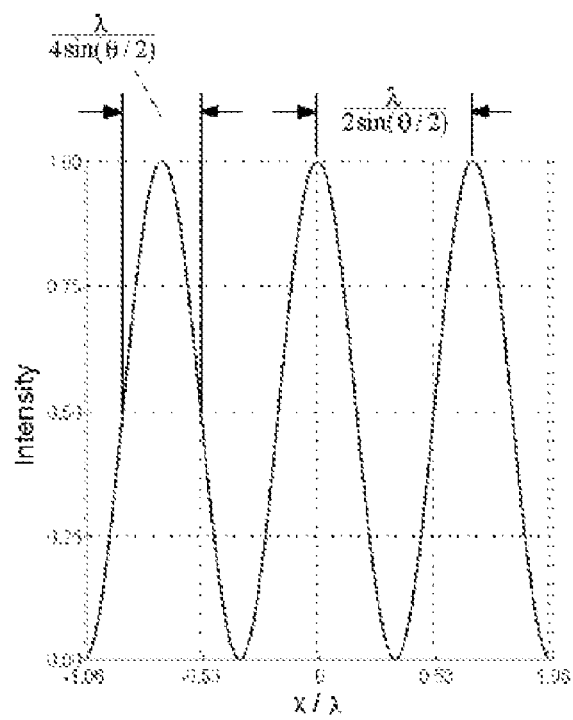
FIG. 6C is a graph of the intensity variation along the x-axis for the optical lattice formed by the plane waves as shown in FIG. 6A.

Referring to FIG. 6A, two electromagnetic (EM) plane waves traveling in the x-z plane of a three-dimensional coordinate system defined by an x-axis 602, a z-axis 604, and a y-axis 605 can be superimposed. Each plane wave can be parameterized by a wavevector $k_0$ and $k_1$, respectively, which defines the propagation direction of the wave and the wavelength of the wave. The magnitude of the wavevector is related to the wavelength of the wave, $\lambda$, by the relationship $|k|=k=2\pi/\lambda$. Because the wavevector is defined by a direction and a magnitude, it is a vector quantity. Vector quantities, as used herein, are written as bold lower-case symbols. Wavevectors $k_0$ and $k_1$ have different directions but identical magnitudes, $|k_0|=|k_1|$, so the two plane waves each have the same wavelength. In addition, the phases of the waves are controlled so that they have a constant phase difference. Because the waves are monochromatic and have a well-defined phase difference, their intersection results in a coherent superposition of the waves. As shown in FIG. 6B, the superposition of the two plane waves yields a one-dimensional pattern of intensity maxima in the combined EM fields of the waves. Such a pattern can be called a one-dimensional optical lattice and is commonly known as a standing wave. As shown in FIG. 6C, the EM field of the one-dimensional lattice varies sinusoidally along the x-axis 602 of the x-z plane 603. Along the z-axis 604 (defined by the line in the x-z plane 603 that bisects the wavevectors 600 and 601), as well as along the y-axis 605 that is perpendicular to both wavevectors 600 and 601, the EM field is uniform.

As shown in FIG. 6C, by altering the angle, $\theta$, between the two wavevectors 600 and 601, the spacing $\Delta x=\lambda/(2\sin(\theta/2))$ of the periodic intensity maxima along the x-axis can be increased by any desired amount from a minimum of $\lambda/2$. Although altering the angle, $\theta$, to increase the distance between adjacent intensity maxima permits signals from adjacent maxima to be more readily resolved, it also reduces the spatial confinement of each high-intensity region. This is the case because the spatial confinement at a local maximum in the light intensity can be defined as the width of a region within which the intensity is at least half of its greatest magnitude. In other words, the spatial confinement of an intensity maximum can be defined as the full width at half magnitude ("FWHM"), such that $FWHM_x = \Delta/2 = \lambda/(4 \sin(\theta/2))$. Thus, for purposes of detecting local maxima (e.g., to create a microscopic image of a portion of a sample of maximum light intensity), increased resolvability of adjacent maxima generally comes at the price of reduced spatial confinement and resolution of individual high-intensity regions. Furthermore, when only two EM plane waves are superimposed, as shown in FIG. 6A, although the intensity maxima are confined along the x-axis, the excitation of local maxima is not confined along the y and z axes. Thus, the three-dimensional microscopy resolution that can be achieved by creating a one-dimensional lattice in a sample is determined primarily by the detection characteristics of the particular microscope in the z- and y-directions, as well as the ability to isolate the signal from a single planar intensity maximum in the x-direction.

Two-Dimensional Lattices

Figure 7A:
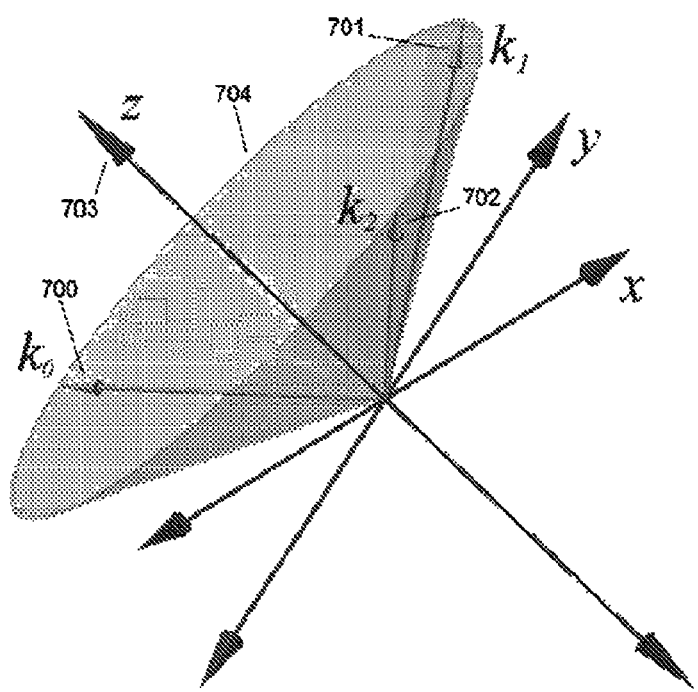
FIG. 7A is a schematic view of symmetry axes for a two-dimensional optical lattice created by three plane waves.
Figure 7B:
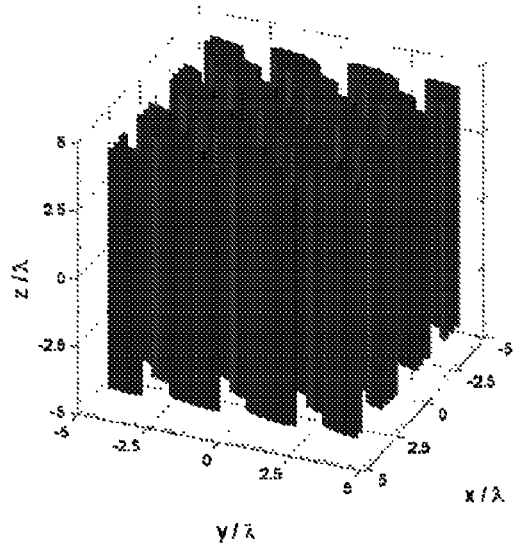
FIG. 7B is a three-dimensional plot of surfaces of light intensity having 50% of the maximum light intensity in the optical lattice formed by the plane waves shown in FIG. 7A.
Figure 7C:
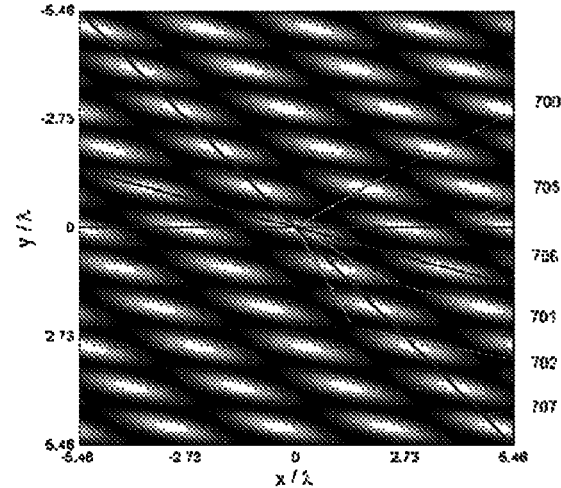
FIG. 7C is a linear grayscale image of the light intensity in the x-y plane for the optical lattice formed by the plane waves shown in FIG. 7A, shown in relation to the constituent wavevectors of the lattice.

Referring to FIG. 7A, a two-dimensional optical lattice can be created by adding a third plane wave having a wavevector, $k_2$, to the superposition of plane waves with wavevectors, $k_0$ and $k_1$, where the three plane waves are monochromatic (i.e., each plane wave has the same wavelength). The optical lattice is located in the plane that is orthogonal to the z-axis 703 of the cone 704 on which all three wavevectors $k_0$, $k_1$, and $k_2$ lie. In particular, FIG. 7B is a three-dimensional plot of surfaces of light intensity having 50% of the maximum light intensity in the optical lattice formed by the plane waves shown in FIG. 7A. FIG. 7B shows the periodic nature of the intensity maxima in an exemplary two-dimensional optical lattice created by the superposition of three z-polarized plane waves, all propagating in the x-y plane. FIG. 7C depicts the intensity maxima of the lattice of FIG. 7B as lighter regions that are shown in relation to the wavevectors $k_0$, $k_1$, and $k_2$ of the constituent plane waves that make up the lattice.

The superposition of exactly three wavevectors $k_0$, $k_1$, and $k_2$ creates only one spatial frequency in each of the three directions 705, 706, and 707 defined by the intersection of the lattice plane with the plane bisecting any pair of wavevectors. Thus, as in the case of a one-dimensional lattice, the spatial confinement (i.e., the intensity full width at half maximum) of high-intensity regions of the lattice is equal to half of the distance between maxima (i.e., half the periodicity of the lattice), in each of the directions 705, 706, and 707. As a result, spatial confinement of individual maxima and periodicity of the lattice can only be adjusted by changing the angle of the cone, shown in FIG. 7A, upon which the three wavevectors $k_0$, $k_1$, and $k_2$ lie (as shown in FIGS. 8B and 8C).

Figure 8A:
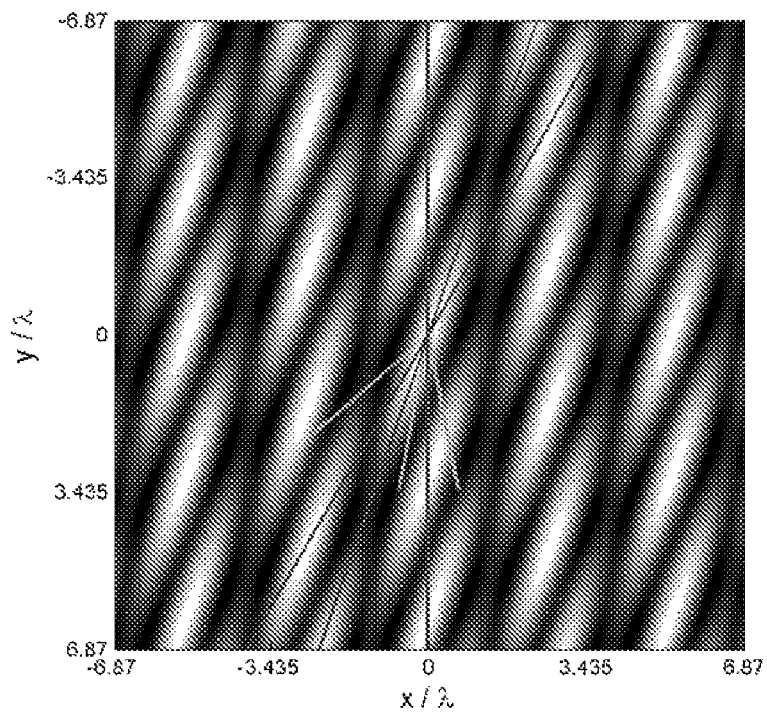
FIG. 8A is a linear grayscale image of the light intensity in the x-y plane for an exemplary two-dimensional lattice of hexagonal symmetry, created by three plane waves propagating in the x-y plane and polarized along the z-axis.
Figure 8B:
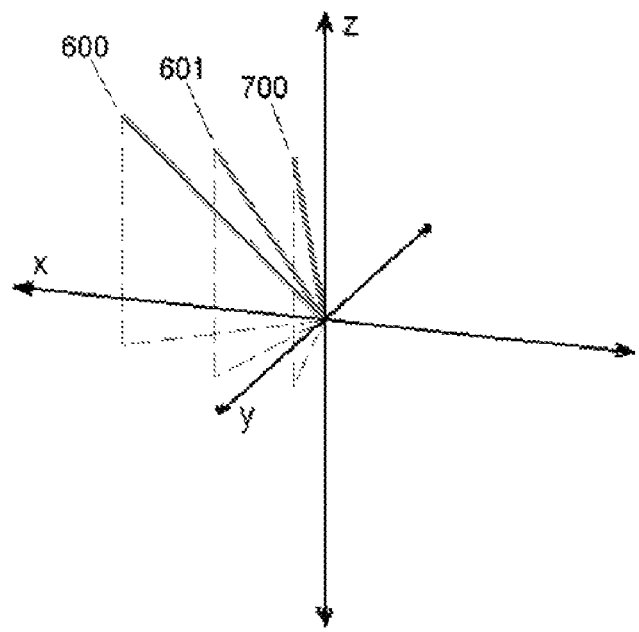
FIG. 8B is a three-dimensional representation of three wavevectors, each oriented at an angle of $\sin^{-1}(2/3)$ with respect to the z-axis, having projections onto the x-y plane in the same directions as the wavevectors of FIG. 8A.
Figure 8C:
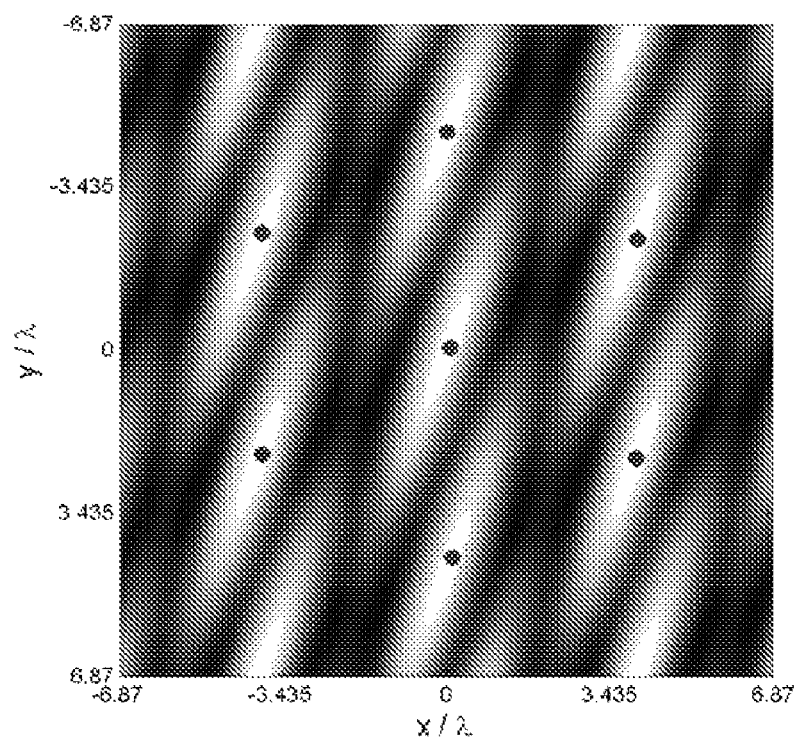
FIG. 8C is a linear grayscale image of the light intensity of a two-dimensional hexagonal lattice created with the wavevectors in FIG. 8B and having a period of 1.5 times the period of the related lattice shown in FIG. 8A.

When certain relationships between the constituent wavevectors of a lattice are satisfied, a lattice of special symmetry can be created that is particularly useful for microscopy, such as, for example, the lattice of hexagonal symmetry shown in FIG. 8A which is formed by the superposition of three wavevectors $k_0$, $k_1$, and $k_2$ that all lie in the x-y plane. FIGS. 8B and 8C show an example of changing the angle of the cone upon which the wavevectors lie. By shifting the wavevectors $k_0$, $k_1$, and $k_2$ that create the lattice in FIG. 8A out of the x-y plane to form an angle of $\sin^{-1}(2/3)$ with respect to the z-axis, as illustrated in FIG. 8B, an optical lattice having a periodicity of 1.5 times greater than the original lattice can be created. The resulting lattice having the higher periodicity is shown in FIG. 8C.

Figure 8D:
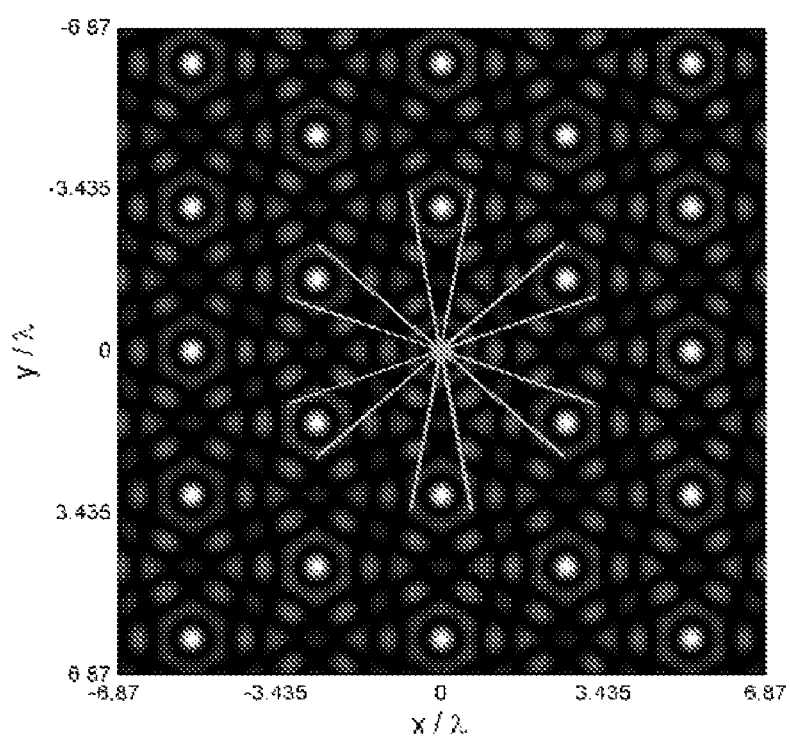
FIG. 8D is a linear grayscale image of the light intensity in the x-y plane for an exemplary two-dimensional optical lattice having the same symmetry, periodicity, and polarization as the lattice shown in FIG. 8A, but having increased light intensity confinement due to the inclusion of twelve plane waves propagating in the x-y plane.

When such lattices are used in optical microscopy, the periodicity of the lattice intensity maxima determines the ease with which the maxima can be resolved at a detector. The periodicity also determines the number of maxima required to cover a given field of view. On the other hand, the spatial confinement of individual maxima determines the spatial resolution of an image of one or more maxima. Although the periodicity of the lattice and the spatial confinement of individual maxima may only be adjusted in tandem for two-dimensional lattices constructed from three plane waves, control of the lattice periodicity and the spatial confinement of individual maxima can be decoupled if more than three plane waves with wavevectors $k_0, k_1 \ldots k_N$ lying on a single cone are used to create the optical lattice. Such lattices formed of four or more plane waves having different wavevectors lying on a cone and having a wavelength x, are hereafter called composite two-dimensional lattices. FIG. 8D, for example, illustrates a composite two-dimensional lattice formed from 12 plane waves that has increased spatial confinement but identical periodicity relative to the exemplary lattice of FIG. 8A. The direction of the 12 constituent wavevectors of the plane waves is explained in more detail below.

Three-Dimensional Lattices

Figure 9A:
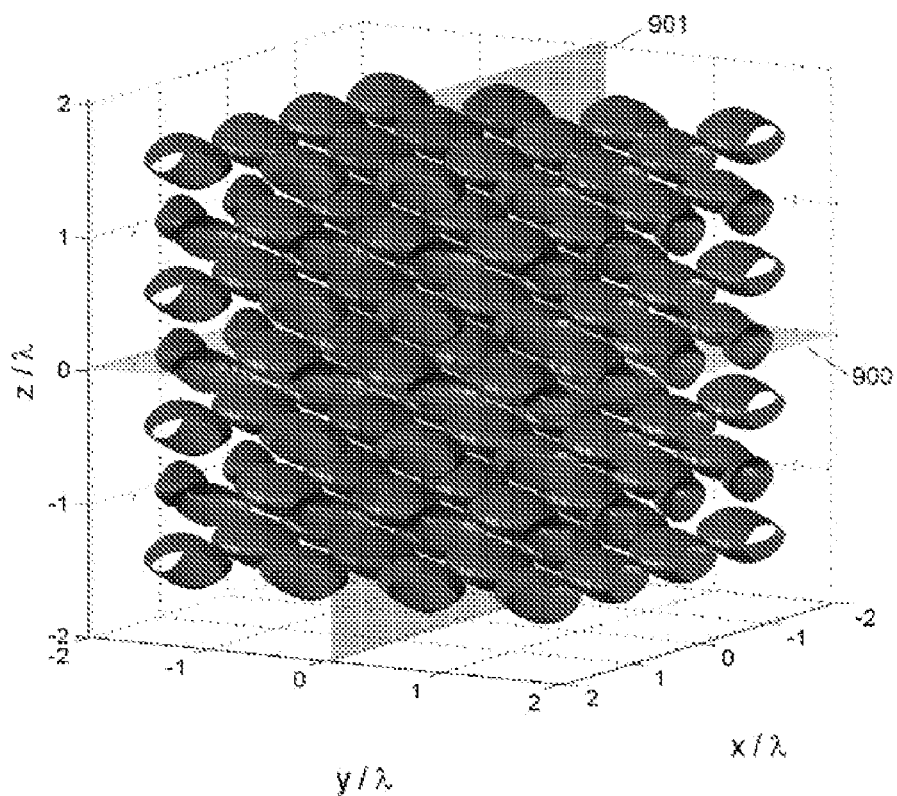
FIG. 9A is a three-dimensional plot of surfaces of light intensity having 50% of the maximum light intensity for an exemplary three-dimensional lattice created by four plane waves.
Figure 9B:
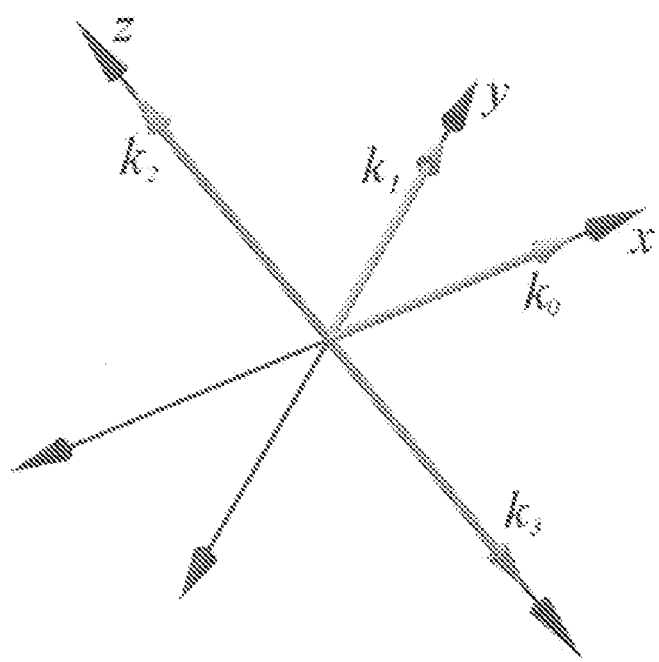
FIG. 9B is a three-dimensional representation of the wavevectors of four plane waves used to create the lattice shown in FIG. 9A.
Figure 9C:
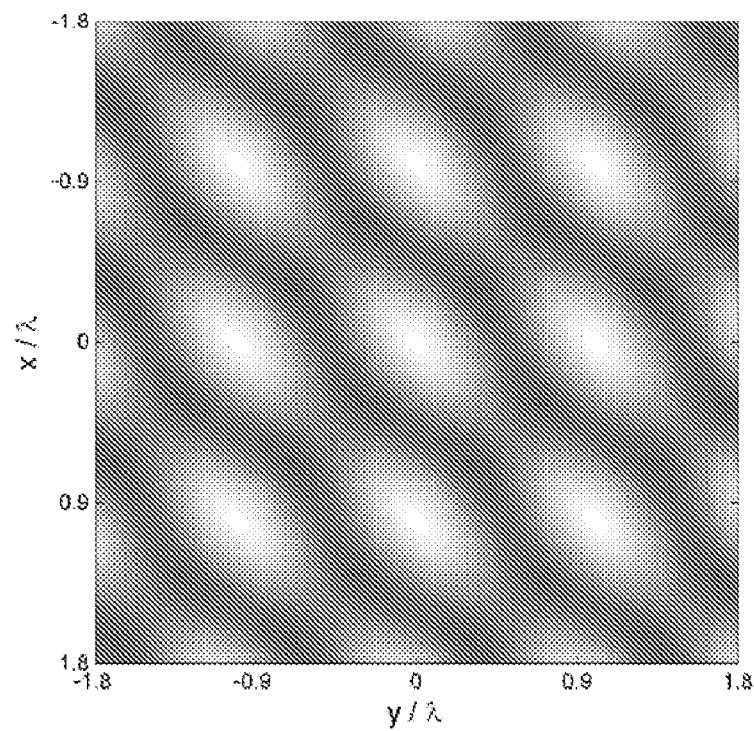
FIGS. 9C and 9D are linear grayscale images of the light intensity in the x-y plane shown by reference numeral 900 and the x-z plane shown by reference numeral 901, respectively, of the optical lattice shown in FIG. 9A.
Figure 9D:
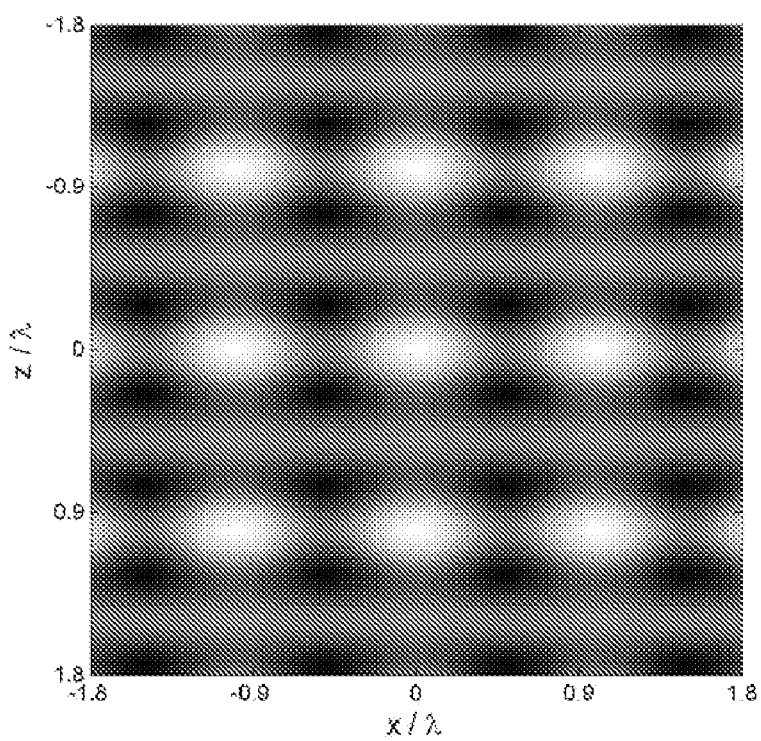
Figure 10A:
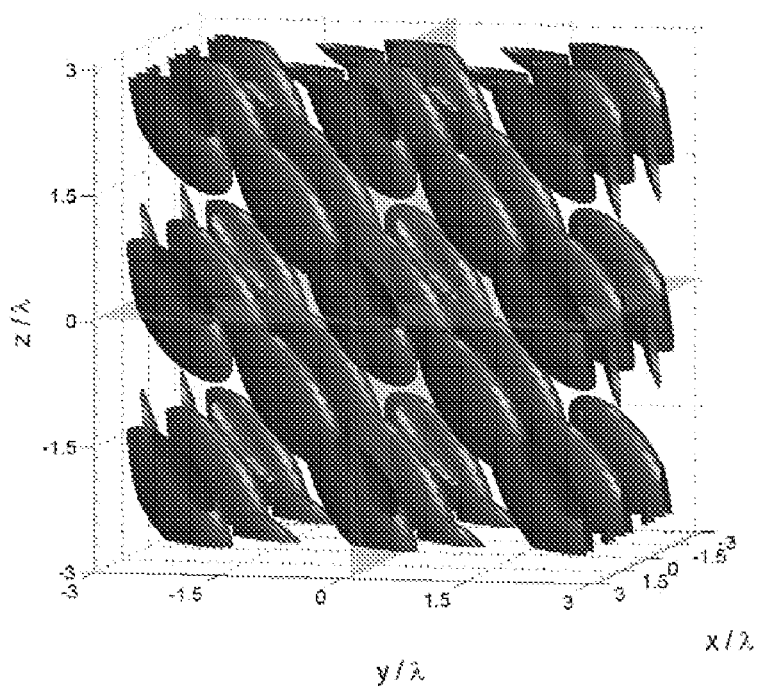
FIG. 10A is a three-dimensional plot of surfaces of light intensity having 50% of the maximum light intensity for an exemplary three-dimensional, body-centered cubic optical lattice created by four plane waves.
Figure 10B:
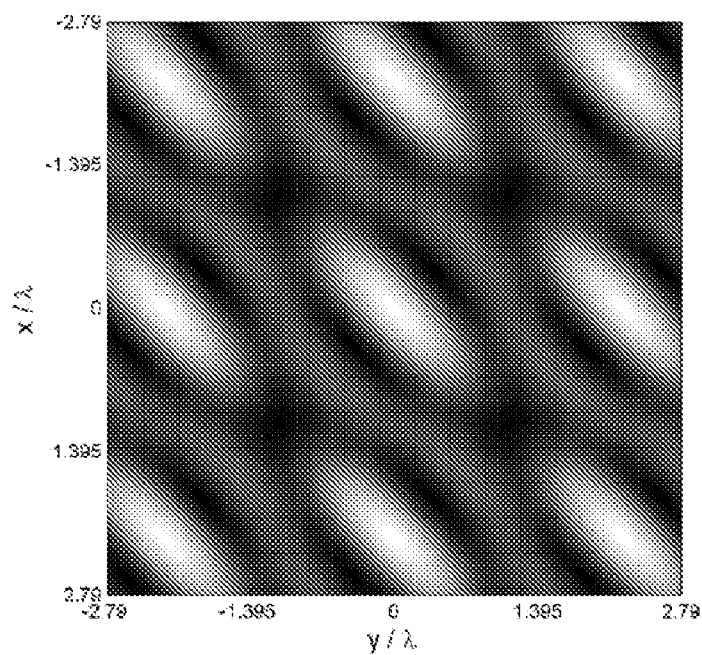
FIGS. 10B and 10C are linear grayscale images of the light intensity in the x-y plane shown by reference numeral 900 and x-z plane shown by reference numeral 901, respectively, of the optical lattice shown in FIG. 10A.
Figure 10C:
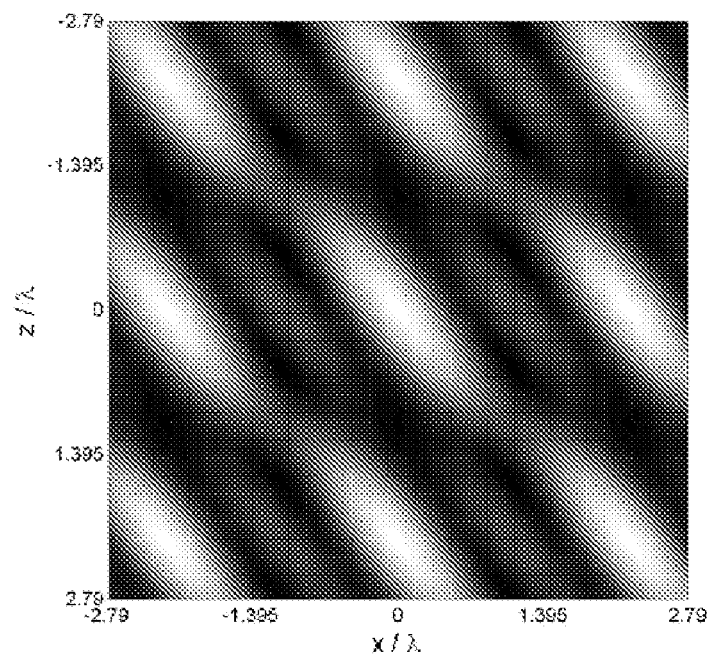
Figure 10D:
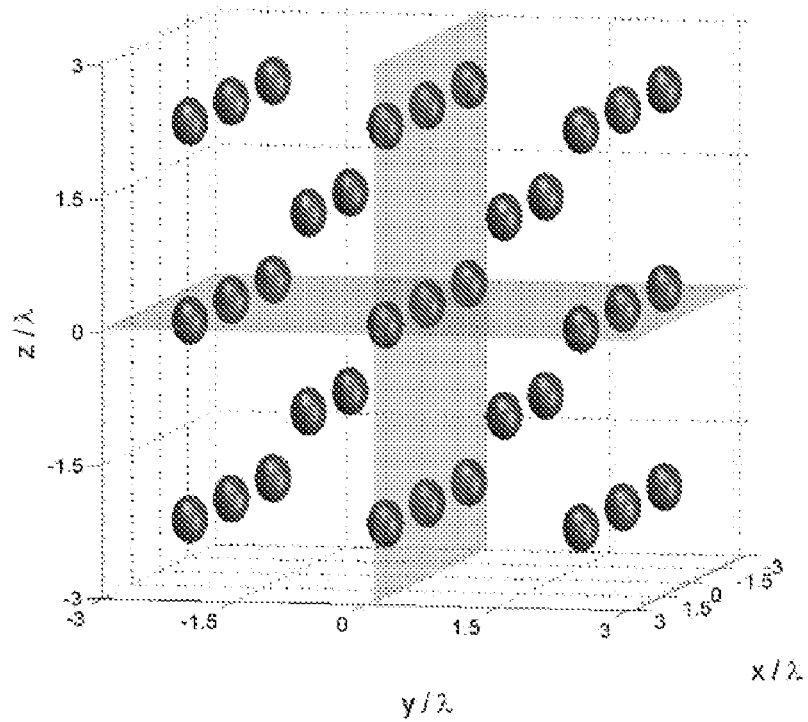
FIG. 10D is a three-dimensional plot of surfaces of light intensity having 50% of the maximum light intensity for a three-dimensional lattice of the same symmetry and periodicity as in FIG. 10A, but with increased intensity confinement because the lattice is created with 24 plane waves.
Figure 10E:
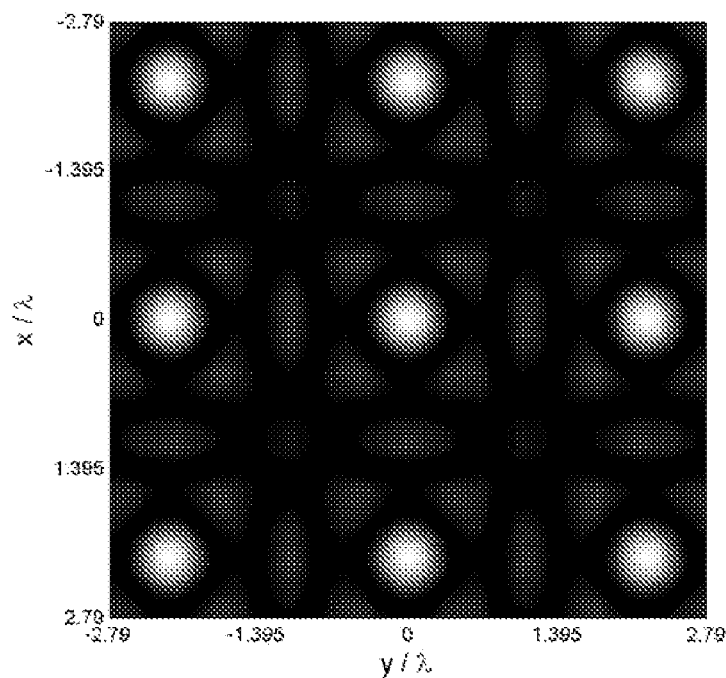
FIGS. 10E and 10F are linear grayscale images of the light intensity in the x-y plane shown by reference numeral 900 and x-z plane shown by reference numeral 901, respectively, of the optical lattice shown in FIG. 10D.
Figure 10F:
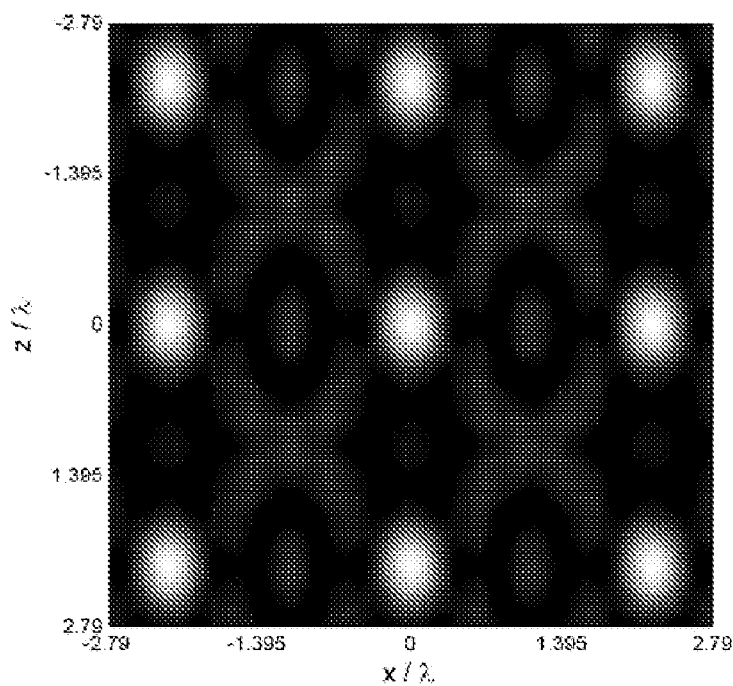

Analogously to the case of two-dimensional lattices described above, the superposition of four or more plane waves results in a three-dimensional lattice when all constituent wavevectors $k_m$ do not lie on one cone, as illustrated in FIG. 9B. As shown in FIG. 9B, wavevectors $k_0$, $k_1$, and $k_2$ fall on the positive x-, y-, and z-axes, respectively, and the wavevector $k_3$ and falls on the negative z-axis. Intensity confinement occurs in all three directions, as shown in intensity maxima of FIG. 9 and as indicated in the intensity maxima in the two-dimensional slice planes 900 and 901 shown in FIG. 9A, which are plotted separately in FIGS. 9C and 9D, respectively. Analogously to two-dimensional optical lattices, when certain relationships between the constituent wavevectors, $k_m$, are satisfied, three-dimensional lattices of special symmetry can be created that are particularly useful for purposes of microscopy. For example, a body-centered cubic three-dimensional lattice (shown in FIG. 10A) can be created from four plane waves having a wavelength, $\lambda$, and wavevectors $k_0$, $k_1$, $k_2$, and $k_z$ arranged as shown in FIG. 9B. Maxima along the two-dimensional planes shown in FIG. 10A are shown in FIGS. 10B and 10C. Also, although periodicity of the lattice and the spatial confinement of the maxima may only be adjusted in tandem for three-dimensional lattices constructed from four plane waves, control of the lattice periodicity and spatial confinement of the intensity maxima can be decoupled if more than four plane waves with wavevectors $k_0, k_1 \ldots k_N$ not all lying on a single cone are used to create the lattice. Such lattices formed of five or more plane waves having a wavelength, $\lambda$, and wavevectors that do not lie on a single cone are hereafter termed composite three-dimensional lattices. The periodicity of the lattice is then decoupled from the spatial intensity confinement of the intensity maxima in the four directions defined by the cone axis associated with every grouping of three wavevectors. For example, FIG. 10D illustrates a three-dimensional lattice, formed from 24 plane waves, that has increased three-dimensional spatial confinement but identical three-dimensional periodicity relative to the exemplary lattice of FIG. 10A. FIGS. 10E and 10F illustrate the intensity maxima of the lattice shown in FIG. 10D viewed in the x-y and x-z planes, respectively.

The Basis Associated with an Optical Lattice

For two-dimensional and three-dimensional lattices, the interrelationship between the wavevectors, $k_0, k_1 \ldots k_N$, of the N+1 constituent plane waves completely determines the symmetry and periodicity of the lattice relative to the wavelength of the plane waves. However, it is the electric field vectors, $e_0, e_1, \ldots e_N$, (and associated magnetic field vectors, $h_m = n(k_m \times e_m)/k$) of these plane waves as well as their wavevectors, $k_0, k_1 \ldots k_N$, that determine the EM field pattern that exists within each primitive cell (i.e., the smallest two- or three-dimensional region that, when repeated, will fill the entire lattice) of the lattice. This EM field pattern, which can be referred to as the basis, is analogous to the arrangement of atoms in each primitive cell of a crystalline solid, such as the arrangement of the sodium and chlorine atoms that exists in every primitive cell of the simple cubic lattice of table salt.

In general, the basis associated with any lattice can be quite complex, leading to an intensity pattern within each unit cell that is unsuitable for microscopy. However, by carefully selecting the relative amplitudes and phases of each of the components of the electric field, $e_m$, for every plane wave in the lattice, the basis can be manipulated so as to be suitably tailored for microscopy applications.

Figure 11A:
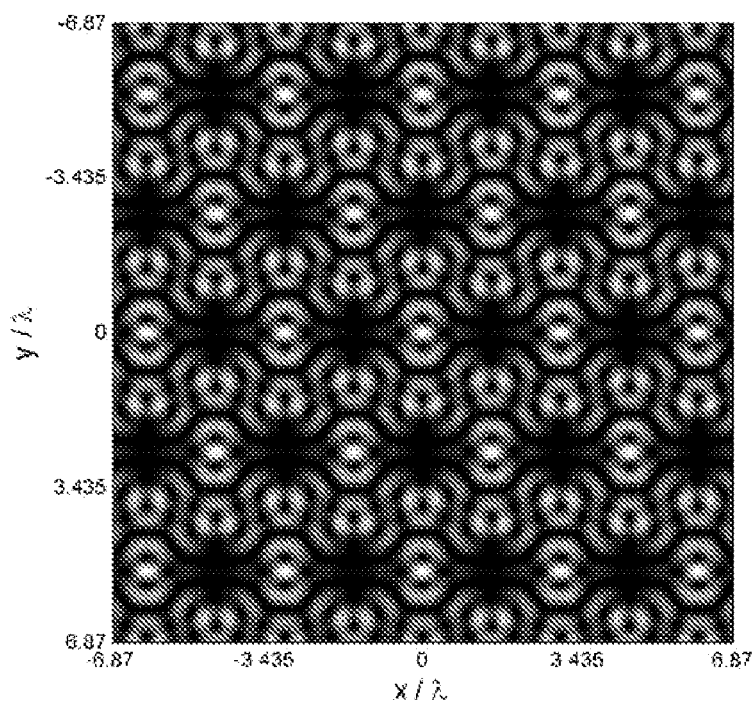
FIG. 11A is a linear grayscale image of the light intensity in the x-y plane for a two-dimensional hexagonal optical lattice that is identical to the lattice whose intensity image is shown in FIG. 8D, except that a different basis is chosen to optimizes the x-component of the polarization at the light intensity maxima.
Figure 11B:
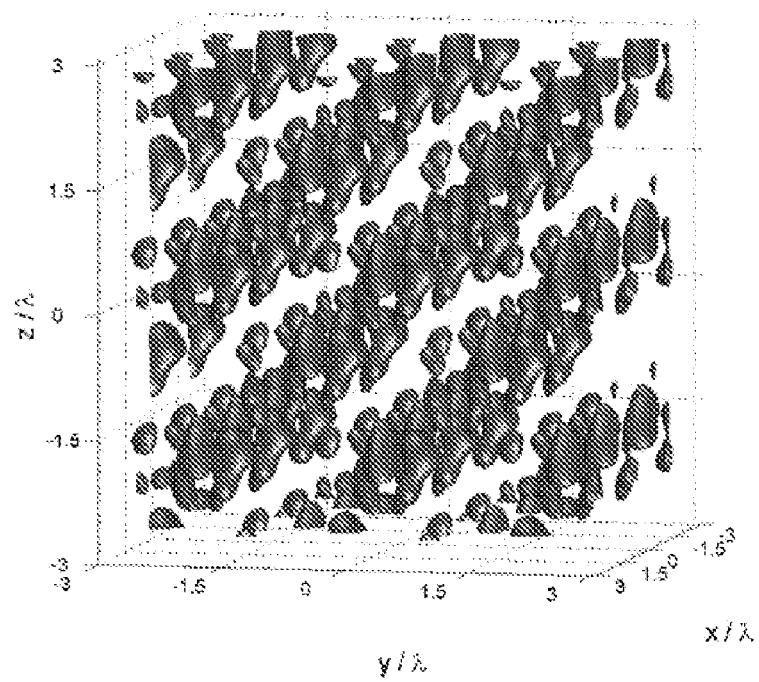
FIG. 11B is a three-dimensional plot of surfaces of light intensity having 50% of the maximum light intensity for in a three-dimensional, body-centered cubic lattice that is identical to the lattice whose light intensity image is shown in FIG. 10D, created from constituent plane waves that are polarized in the same directions as the corresponding waves used to for the lattice for FIG. 10D, except that the phase of each wave is randomly chosen instead of aligned.

A common example of such a basis is a basis consisting of a single dominant, tightly-confined intensity maximum within the primitive cell. For example, the two-dimensional hexagonal lattice represented in FIG. 8D clearly achieves this dominant maximum basis having a single tightly-confined intensity maximum in each cell by using plane waves polarized perpendicularly to their mutual plane of propagation and phases adjusted to achieve maximal constructive interference at the maximum. However, as shown in FIG. 11A, when the same wavevectors used to form the lattice of FIG. 8D but having plane waves polarized to maximize the y-component of the polarization at the intensity maximum, a more complicated basis results in which the intensity is no longer significantly confined to one point within the primitive cell. Similarly, the three-dimensional body-centered cubic lattice depicted in FIG. 11B uses plane waves of the same wavevectors and polarizations as those used to form the lattice in FIG. 10D, but the phases of the plane waves are chosen randomly for the lattice of FIG. 11B instead of being selected to achieve optimal constructive interference at a single point within the primitive cell, as in FIG. 10D. As seen from the comparison of FIGS. 11B and 10D, and from the comparison of FIGS. 11A and 8D, control of the relative phase and polarization, in addition to the wavevectors, of the constituent plane wave of a lattice can be used to control the basis of the lattice and to tailor the basis for particular applications.

Image Formation in Optical Lattice Microscopy

When the basis is selected to achieve a tightly confined intensity maximum in each primitive cell, as exemplified by the two- and three-dimensional lattices shown in FIG. 8D and FIG. 10D, the lattice and basis together are well suited to function as an optical crystal lattice that can provide a multi-point excitation field to excite a sample to be imaged during a microscopy process. Such an excitation field can be exploited in the context of microscopy by conducting parallel scanning of a sample in one or more dimensions, as depicted in the imaging and detection examples shown in FIG. 12 and FIG. 13, respectively. However, in other microscopy applications, such as those in which a microscopy signal is generated from two or more overlapping optical lattices, the formation of different types of bases can be more appropriate.

Figure 12:
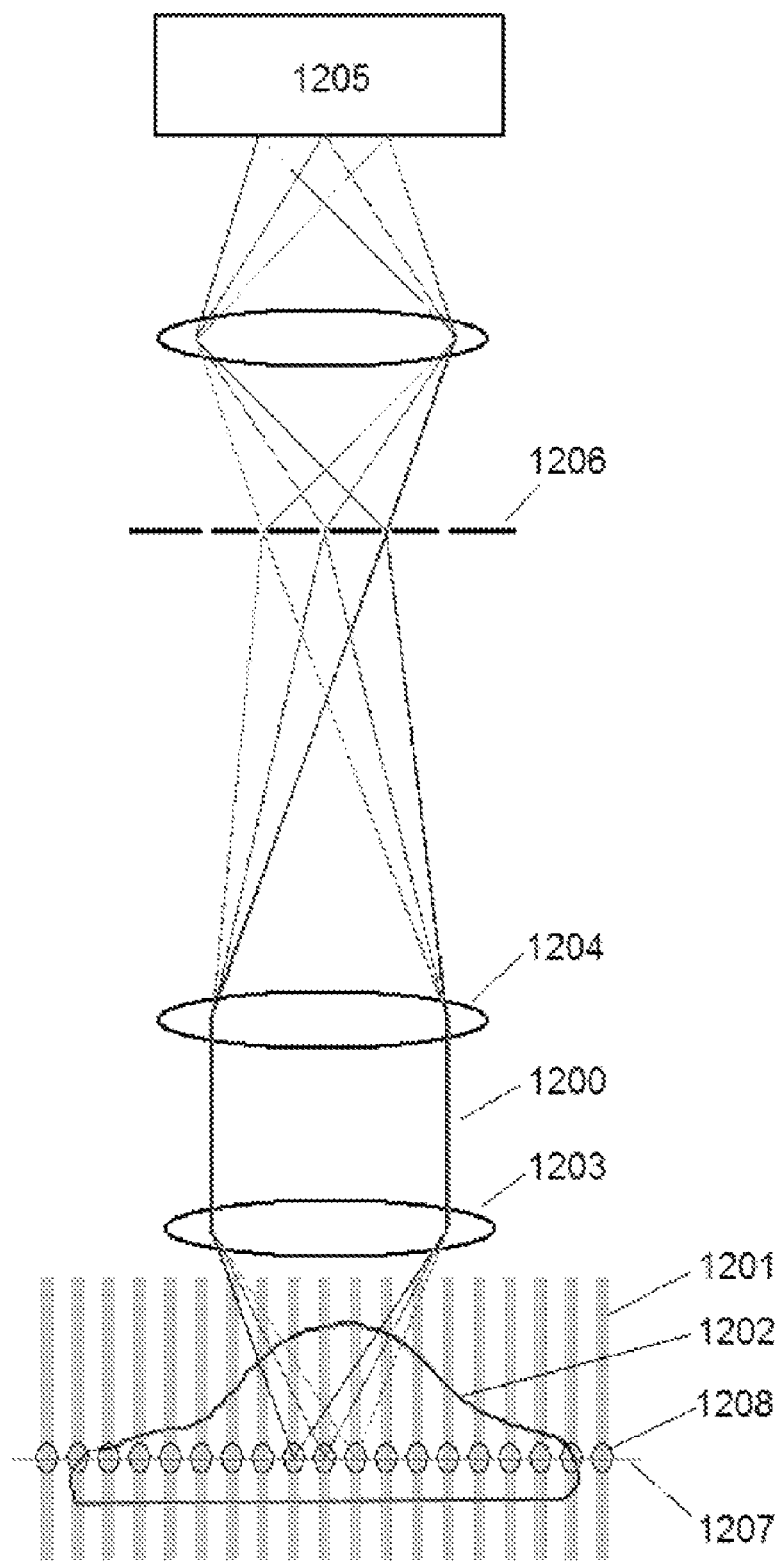
FIG. 12 is a schematic view of an apparatus for detecting a signal generated by a two-dimensional optical lattice.

FIG. 12 illustrates one manner in which microscopy can detect a signal from a multi-point excitation field using a two-dimensional lattice. Signal light 1200 emitted from the interaction of an optical lattice 1201 with a sample 1202 is collected by a lens 1203 and imaged onto a two-dimensional multi-element detector 1205, such as, for example, a charge-coupled device (CCD) array. Lens 1203 may be an infinity-corrected microscope objective and the light 1200 may be imaged with a corresponding tube lens 1204. Prior to detection, the signal light 1200 can be spatially filtered by, for instance, using a pinhole array 1206 of the same symmetry and magnified periodicity as the lattice. Such filtration can block signal light 1200 that is emitted from regions not within the two-dimensionally confined maximum of each primitive cell and can limit detection in the third dimension to regions near the focal plane 1207. Indeed, the pinhole diameters within array 1206 together with the numerical aperture (NA) of the objective lens 1203 and the magnification of the objective 1203/tube lens 1204 pair define a detection point spread function ("PSF") 1208 that characterizes a three-dimensional region from which signal light is predominantly measured within each primitive cell.

Figure 13:
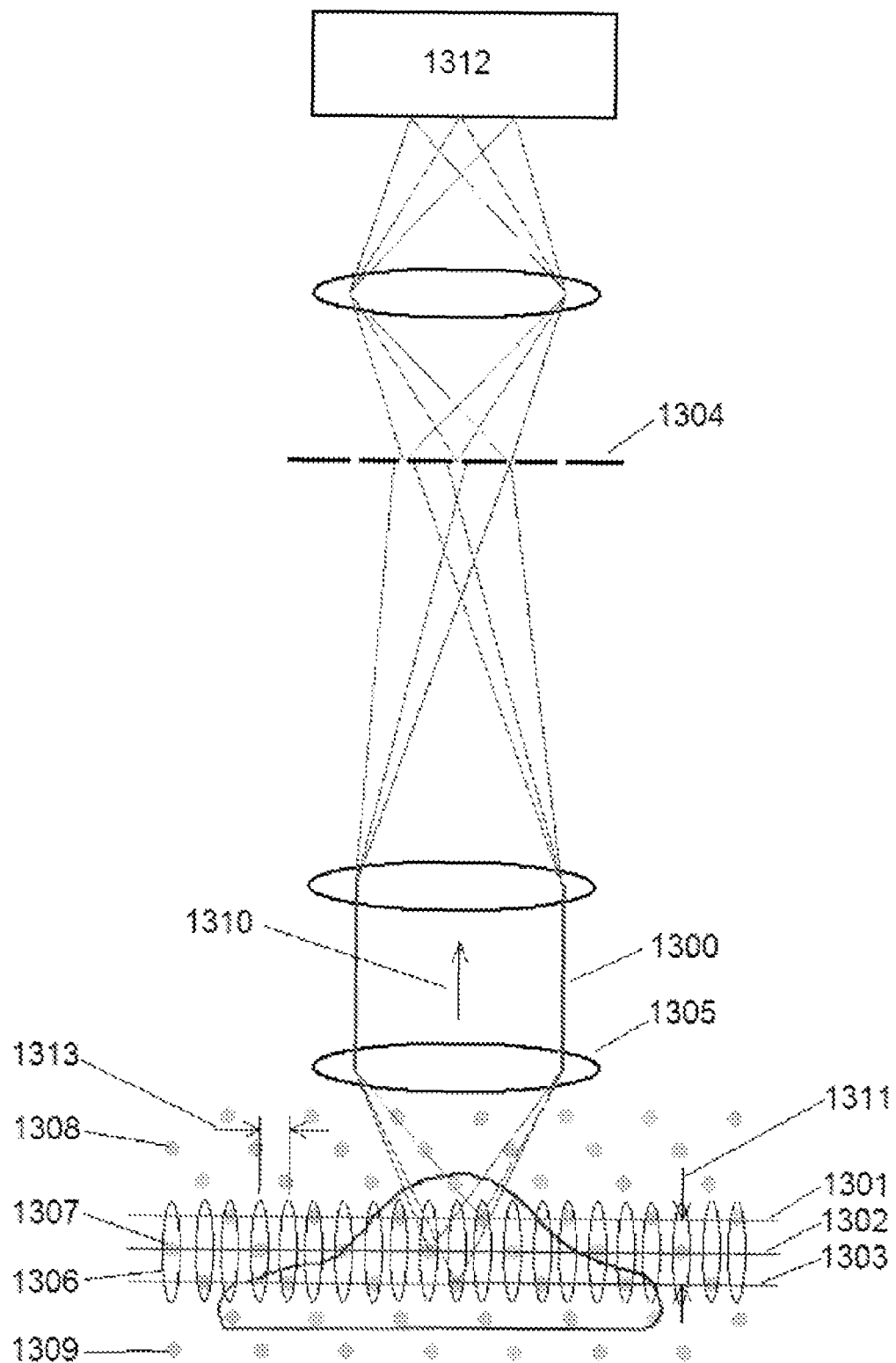
FIG. 13 is a schematic view of an apparatus for detecting a signal generated by a three-dimensional optical lattice.

FIG. 13 illustrates one manner in which microscopy can detect signal from a multi-point excitation field of a three-dimensional lattice. Signal light 1300 emitted from the interaction of a three-dimensional optical lattice 1314 with a sample 1315 is collected by a lens 1305 and imaged onto one or more two-dimensional detectors 1312, such as one or more CCD arrays films or other photosensitive medium. Lens 1305 may be an infinity-corrected microscope objective and the light 1300 may be imaged with a corresponding tube lens 1316. Detection of a signal from a three-dimensional lattice with a basis of isolated intensity maxima (e.g., as shown in FIG. 10D) is rendered more complicated by the fact that the signal 1300 emitted from each maximum (e.g., 1307, 1308, and 1309) must be individually discriminated after originating on multiple, lattice planes (e.g., 1301, 1302, and 1303), and being imaged onto one or more two-dimensional detectors 1312. Therefore, prior to detection, the signal light 1200 can be spatially filtered such that signal light from only the intensity maxima within the desired lattice planes 1302 is detected while signal light from other lattice planes 1301 and 1303 is blocked from reaching the detector 1312. For example, a pinhole array 1304 can act as a spatial filter to pass light emitted from the plane 1302 (i.e., at the focal plane of lens 1305) but to block light from planes 1301 and 1303 (i.e., out of the focal plane of the lens 1305).

The pinhole diameters within array 1304 together with the numerical aperture ("NA") of the objective lens 1305 and the magnification of the objective 1305/tube lens 1316 pair define a detection point spread function ("PSF") 1306 of axial extent that primarily encompasses signal from only one intensity maximum element (e.g., 1308) within a given column 1317 of maxima whose axial projections onto the image plane 1318 are not resolvable transversely to the optical axis 1310. The three-dimensional lattice can be tilted relative to the optical axis 1310 to define the number of lattice planes that fall within the axial bounds 1311 of the detection PSF 1306 and to insure that the intensity maxima within these planes are transversely separated by distances 1313 greater than the transverse extent of the detection PSF, making them individually resolvable. In particular, the lattice can be tilted to an orientation dictated by the Miller indices of the various lattice plane families if it is desirous for the intensity maxima to lie in planes transverse to the optical axis 1310.

Figure 14A:
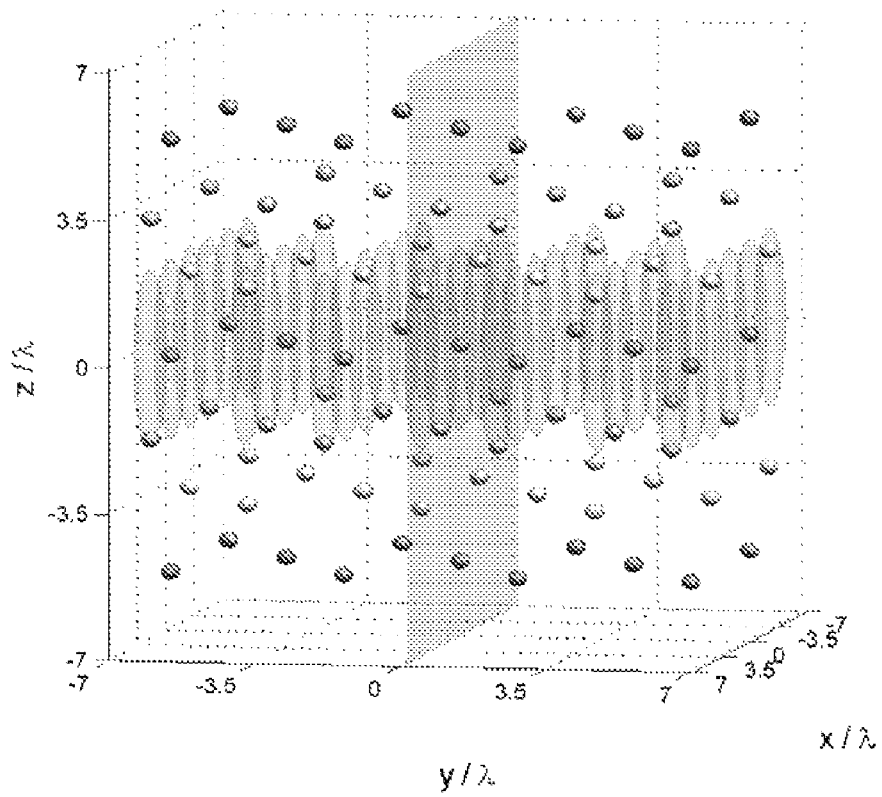
FIG. 14A is a three-dimensional plot of surfaces of light intensity having 50% of the maximum light intensity for a simple cubic optical lattice oriented with the (111) lattice planes parallel to the x-y plane.
Figure 14B:
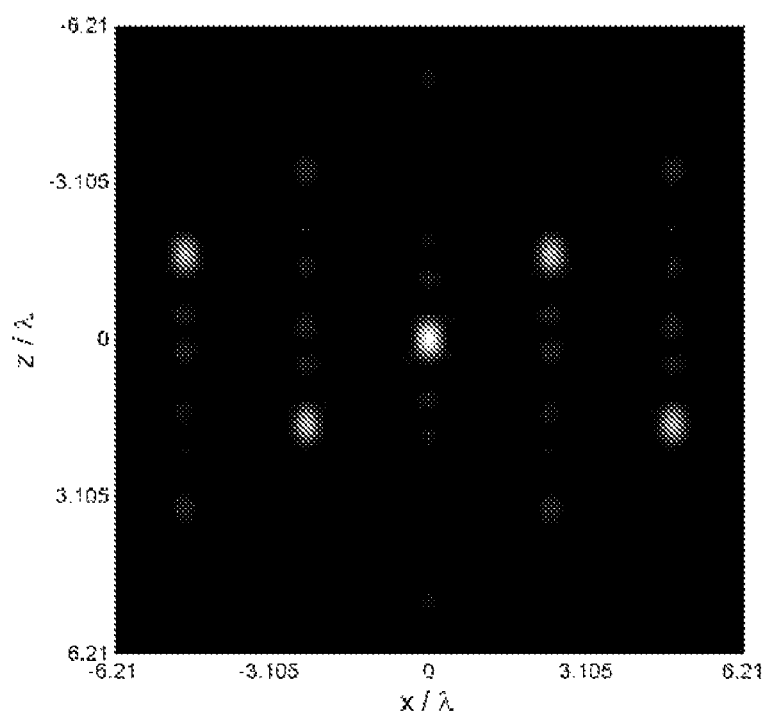
FIG. 14B is a linear grayscale image of the source of a detected signal within the x-z plane due to the convolution of the lattice intensity and the detection efficiency function shown in FIG. 14A.
Figure 14C:
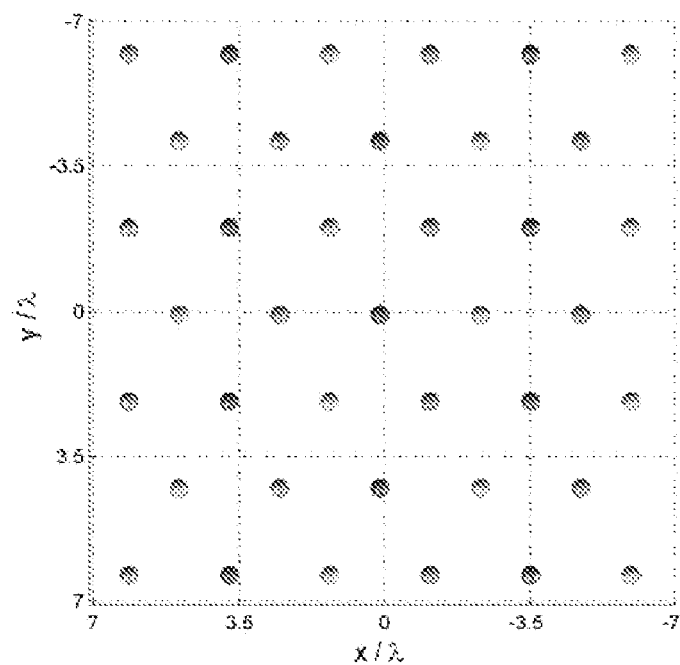
FIG. 14C is a plot of the projection of a filtered signal at the plane of the detector for the arrangement the optical lattice and the detection efficiency shown in FIG. 14A.
Figure 14D:
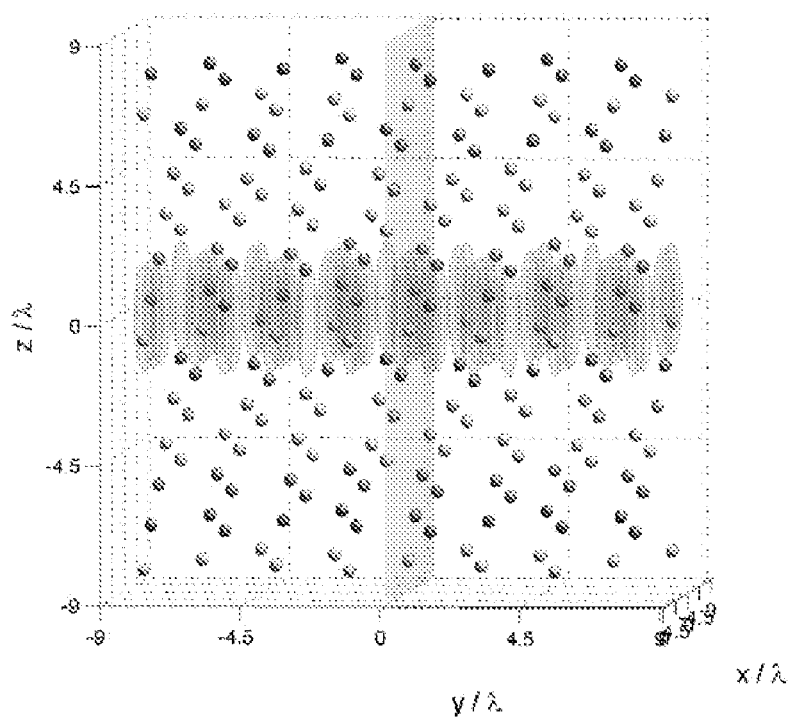
FIG. 14D is a three-dimensional plot of surfaces of light intensity having 50% of the maximum light intensity for a cubic lattice that is the same a the simple cubic lattice as in FIG. 14A, except that the (121) lattice planes are oriented parallel to the x-y plane.
Figure 14E:
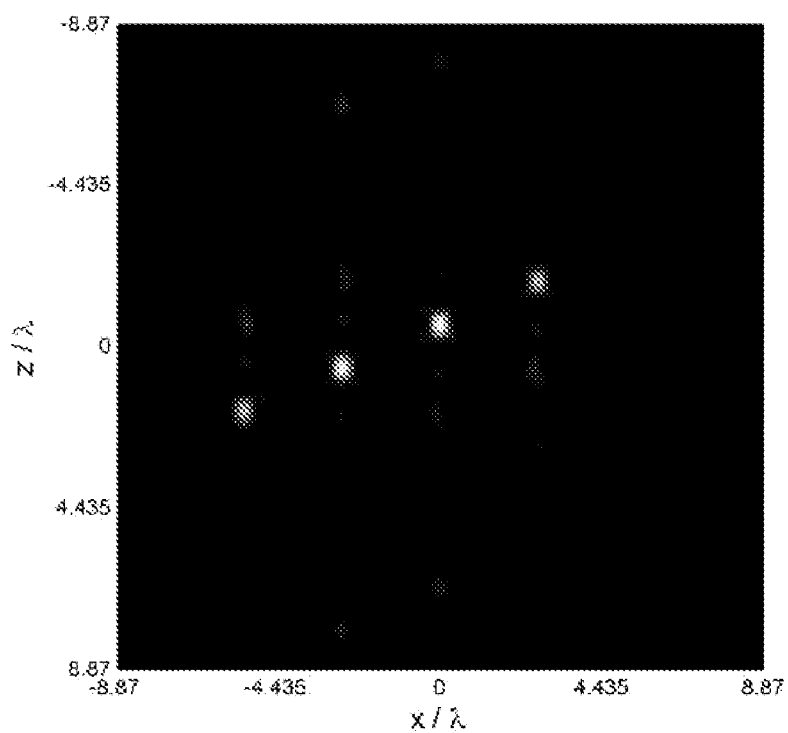
FIG. 14E is a linear grayscale image of the source of the detected signal within the x-z plane due to the convolution of the optical lattice intensity shown in FIG. 14D with the detection efficiency function (i.e., the detection point spread function) from FIG. 14D.
Figure 14F:
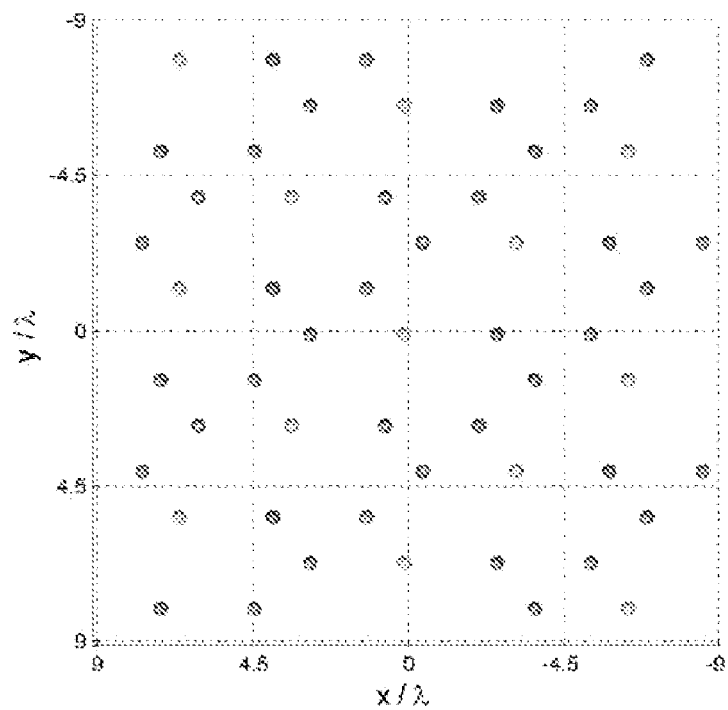
FIG. 14F is a plot of the projection of the filtered signal for the optical lattice and detector efficiency shown in FIG. 14D at the plane of the detector.

FIG. 14A depicts a three-dimensional plot of intensity maxima for an exemplary three-dimensional optical lattice where each three-dimensional detection PSF encompasses signal emitted from a single intensity maximum element of the lattice. FIG. 14B represents the convolution of the intensity maxima with the detection PSF in the x-z plane shown in FIG. 14A, and demonstrates that the detected signal is indeed limited to individual maxima within three adjacent lattice planes. FIG. 14C is a representation of the projection of the lattice at the image plane, and thus indicates the pinhole pattern within the mask 1304 needed to preferentially capture the signal from all intensity maxima in the three desired lattice planes over a region of given transverse extent. FIG. 14D, FIG. 14E, and FIG. 14F are plots similar to FIG. 14A, FIG. 14B, and FIG. 14C, except with the lattice tilted so that the (121) lattice planes are transverse to the optical axis instead of the (111) lattice planes. The pinhole pattern in FIG. 14F is designed to collect signal from four of the six lattice planes having different x-y positions of intensity maxima therein. Many other detection scenarios are also possible, as discussed in more detail herein.

Imaging an Entire Sample

Figure 15A:
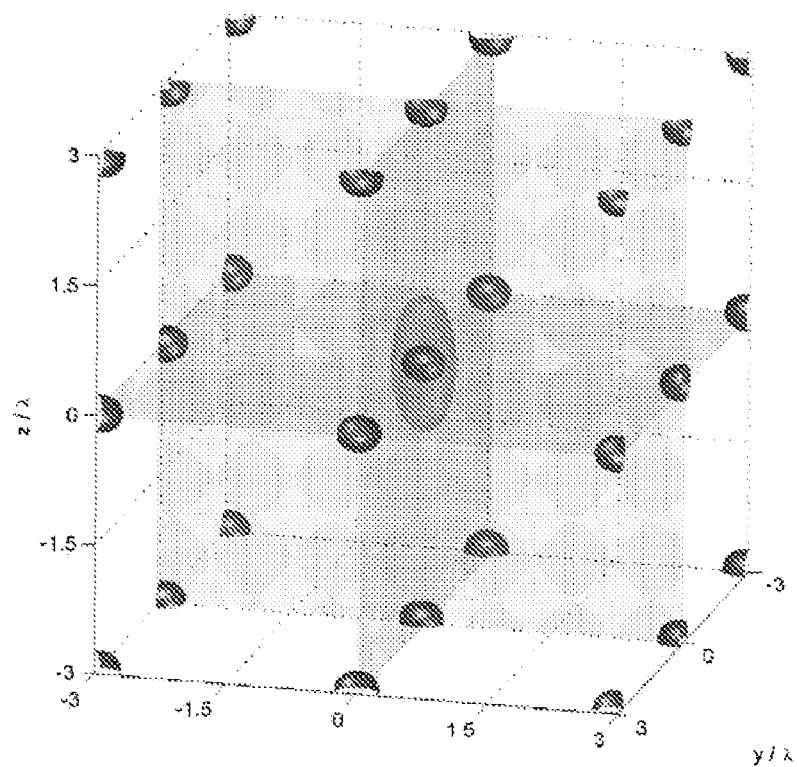
FIG. 15A is a three-dimensional plot of surfaces of light intensity having 50% of the maximum light intensity for a simple cubic lattice with polarization optimized along the x-axis shown.
Figure 15B:
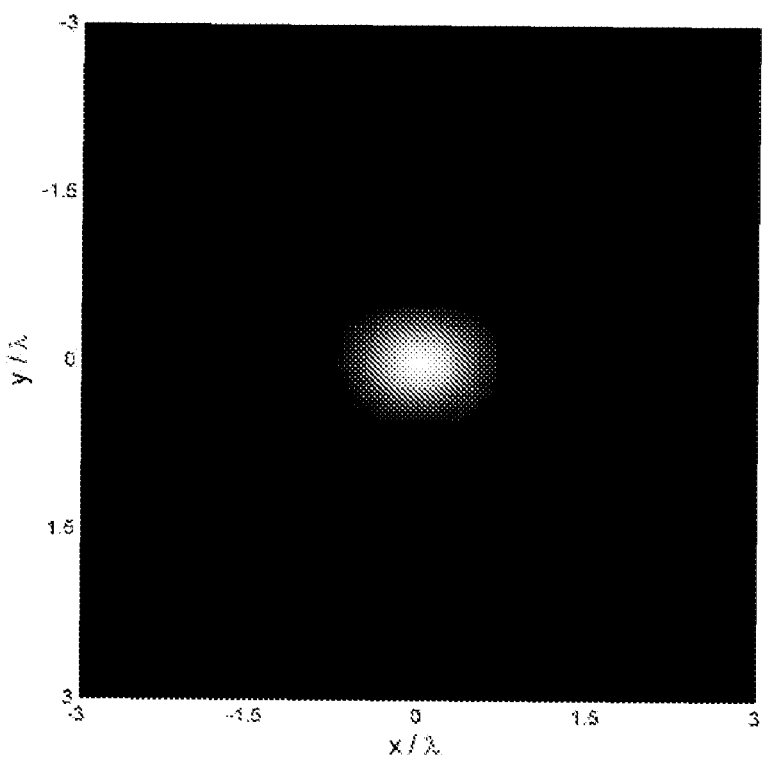
FIGS. 15B, 15C, and 15D are linear grayscale images of the light intensity near the objective focus in the x-y, x-z, and y-z planes, respectively, as shown in FIG. 15A.
Figure 15C:
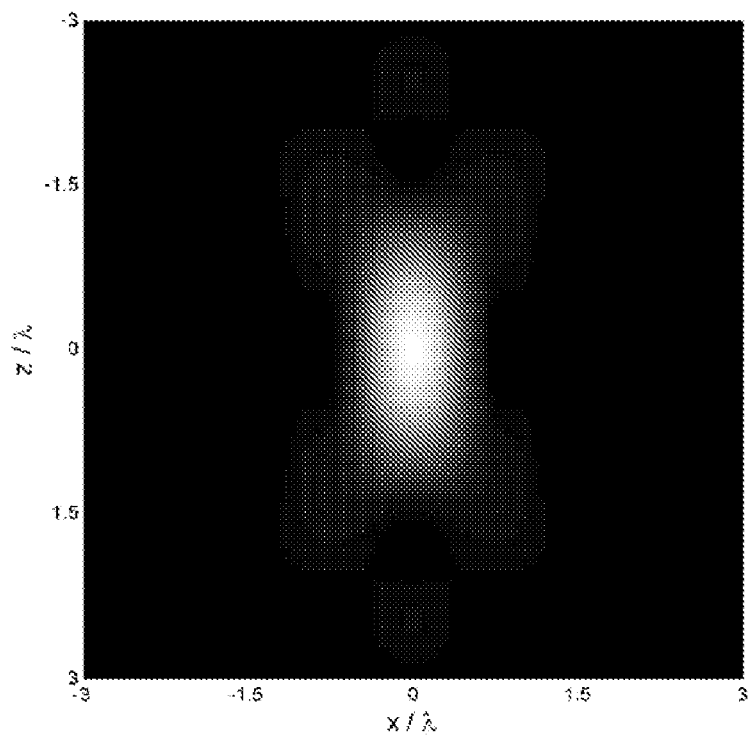
Figure 15D:
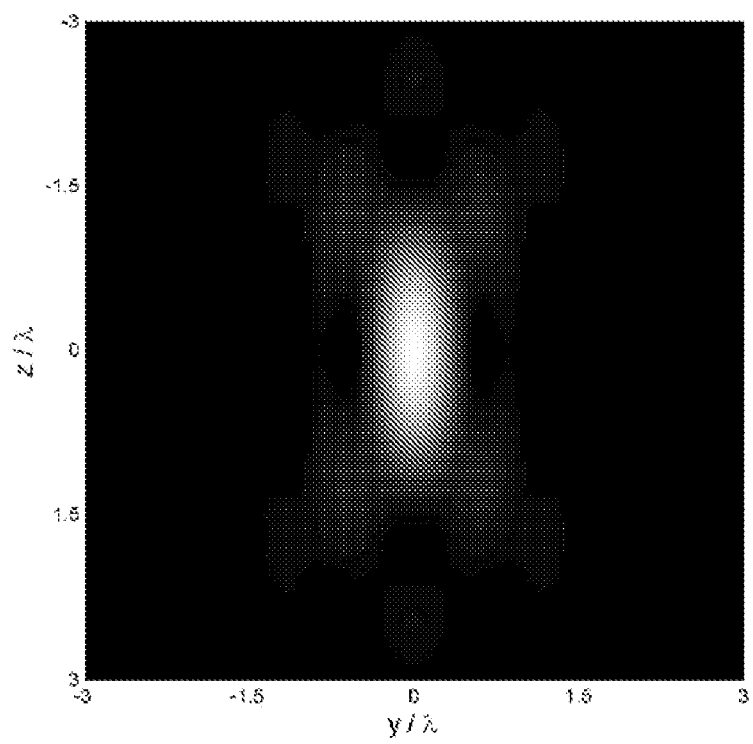
Figure 15E:
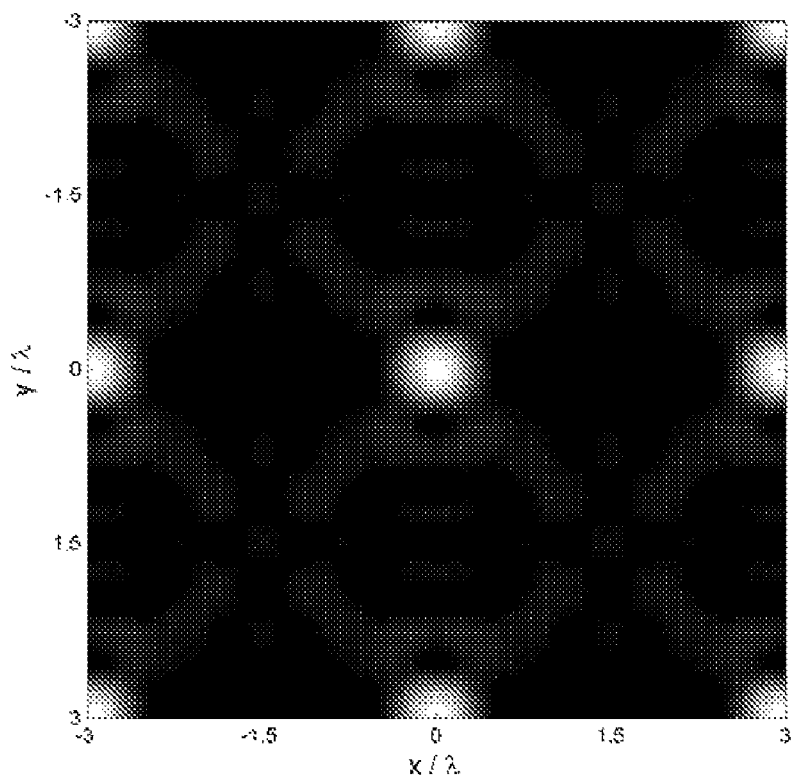
FIGS. 15E, 15F, and 15G are linear grayscale images of the lattice excitation intensity in the x-y, x-z, and y-z planes, respectively, shown in FIG. 15A.
Figure 15F:
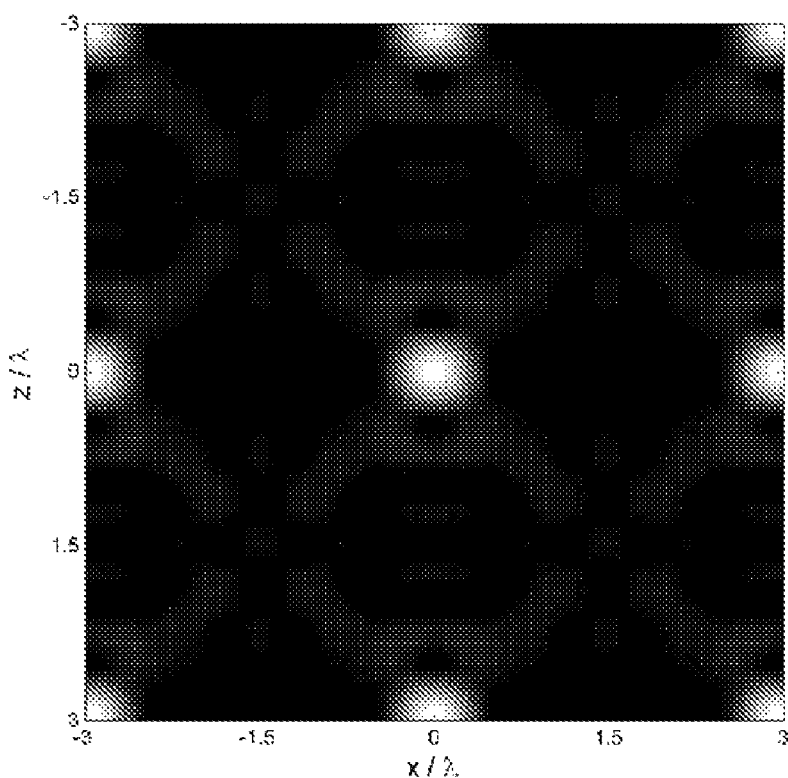
Figure 15G:
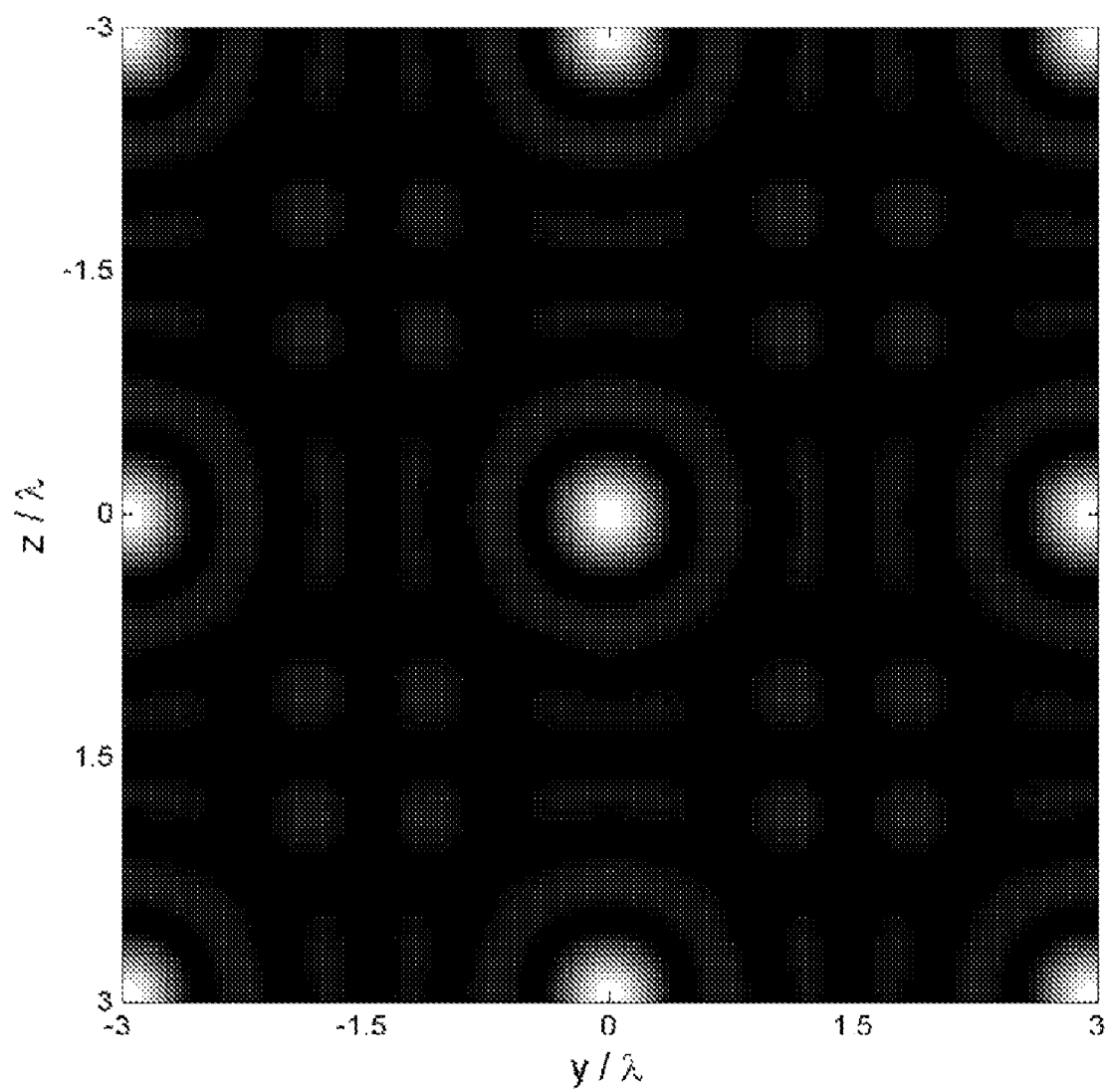

For either a two-dimensional or a three-dimensional lattice with a basis of isolated intensity maxima, an image of the entire two-dimensional or three-dimensional field of view can be generated by scanning the optical lattice and the detection system over the dimensions of a single primitive cell of the lattice relative to a sample, and (2) recording the signal from all maxima at each scan position. Where L lattice points of intensity maxima are detected within the field of view, the signal-limited imaging speed for optical lattice microscopy is L times faster than for single focus confocal microscopy. Also, where an optical lattice has a high degree of symmetry (e.g., a three-dimensional lattice of the cubic crystal group), the intensity maxima can be tightly confined in optical lattice microscopy, such that the lattice has spatial frequencies that approach the diffraction-limited maximum of $(\Delta k \cdot \hat{e}_j)_{max} = 2k$ in all directions, $\hat{e}_j$. Thus, for example, the intensity maxima 1502 of a particular simple cubic lattice shown in FIG. 15A can be significantly smaller than the single maximum 1504 of a confocal system shown in the same figure. This improvement is further demonstrated by comparing the intensity plots in the xy, xz, and yz planes for the lattice in FIGS. 14E, 14F, and 14G with the corresponding plots for the confocal focus in FIGS. 14B, 14C, and 14D.

Optical lattice microscopy can also reduce the rate of photobleaching in a sample, as compared with widefield or confocal fluorescence microscopy, because optical lattice microscopy detects intensity maxima at numerous points throughout a field of view, creates constructive interference leading to strong intensity maxima at such points, and creates partial destructive interference at other points in each primitive cell, such that a greater proportion of the light interacting with a sample results in the generation of detected signal. Optical lattice microscopy can also enhance sensitivity to nanometric structures and processes, such as fluorescence resonance energy transfer ("FRET") between a single pair of molecules, because it can reduce background radiation and improve excitation confinement.

Design and Construction of Ideal Optical Lattices

Introduction

The first step in applying optical lattices to microscopy is to develop methods of identifying the plane wave sets and their wavevectors, $k_m$, and properties of their electric fields, $e_m$, that give rise to lattices and bases of greatest use for a given imaging application. Toward this end, maximal flexibility and effectiveness can be achieved by:

a) determining wavevector sets, $\{k_m\}$, for lattices of any possible desired symmetry;

b) determining different wavevector sets, $\{k_m\}$, corresponding to lattices of the same symmetry but having different wavelength-normalized periodicities;

c) increasing the number of wavevectors used to create a lattice of given symmetry and periodicity in order to increase the spatial frequency content and confinement of the excitation; and d) determining complete descriptions of the electric field properties and wavevectors $\{e_m, k_m\}$ for plane wave sets that optimize one or more basis parameters for a given lattice, such as the intensity or polarization state at a given point in the primitive cell.

Each of the above tasks can be accomplished by considering a mathematical model of optical lattices. The total basis (i.e., the excitation electric field pattern), e(x,t), for a given optical lattice results from the coherent superposition of all of its constituent plane waves. Where the selected plane waves have wavevectors, $k_0, k_1 \ldots k_N$ and electric fields $e_0, e_1 \ldots e_N$, the resulting basis is described by the equation:

$$e(x,t) = \text{Re}\left\{\sum_{n=0}^{N} e_n \exp[i(k_n \cdot x - i\omega t)]\right\}, \quad (3)$$

where, by the coherence condition, $$|k_n|=k=2\pi/\lambda=\omega/c=\text{constant for all values of } n \quad (4)$$

and $\Delta$, $\omega$, and c are the wavelength, angular frequency, and speed of light in the medium, respectively. According to Maxwell's equations, each plane wave must also satisfy the equation:

$$e_n \cdot k_n = 0 \text{ for all values of } n \quad (5)$$

The total excitation intensity is given by the square of the electric field function and can be expressed by the equation:

$$I(x) \propto |e(x,t)|^2 = \sum_{m=0}^{N}\sum_{n=0}^{N} e_m^* \cdot e_n \exp[i(k_n - k_m) \cdot x]. \quad (6)$$

Multidimensional Lattices

The electric fields of the basis of an optical lattice have a spatial periodicity such that the fields repeat themselves in space. The spatial periodicity of the basis described in Equation (3), which can be expressed as e(x+a,t)=e(x,t), is dictated solely by the exp(ik_n·x) terms. As a result, as mentioned above, the symmetry and wavelength-normalized size of an optical lattice depend only upon the wavevectors, $k_n$, associated with the constituent plane waves. However, the complete electromagnetic field pattern, or basis, depends upon both the wavevectors, $k_n$, and the electric fields, $e_n$, of the constituent plane waves. With exactly two plane waves having wavevectors $k_0$ and $k_1$ (i.e., N=1), as illustrated in FIG. 6A, the basis is uniform along the y and z axes and $(k_0-k_1)\cdot\hat{e}_y=0$ and $(k_0-k_1)\cdot\hat{e}_z=0$, where $\hat{e}_y=(k_0\times k_1)/|k_0\times k_1|$ and $\hat{e}_z=(k_0+k_1)/|k_0+k_1|$. In light of Equation (6), the superimposition of two such plane waves yields a one-dimensional lattice described by I(x)=I(x) where $\hat{e}_x=\hat{e}_y\times\hat{e}_z$.

Similarly, as illustrated in FIG. 7A, exactly three plane waves having wavevectors $k_0$, $k_1$, and $k_z$ (i.e., N=2) results in a uniform basis ∀n along the z-axis and $k_n \cdot \hat{e}_z = 0$ for all values where the z-axis is described in the equation:

$$\hat{e}_z = (k_0 \times k_1) + (k_1 \times k_2) + (k_2 \times k_0) / |(k_0 \times k_1) + (k_1 \times k_2) + (k_2 \times k_0)| \quad (7)$$

The superimposition of three such plane waves yields a two-dimensional lattice described by $I(x) = I(x,y)$ and lying in the x-y plane orthogonal to $\hat{e}_z$.

With four or more plane waves (i.e., N≧3), a three-dimensional lattice can be created, provided that there is no axis, $\hat{e}_z$, for which $k_n \cdot \hat{e}_z = 0$ for all values of n. Thus, a D dimensional lattice requires at least D+1 plane waves.

Finding Wavevector Sets for a Given Lattice

Figure 16A:
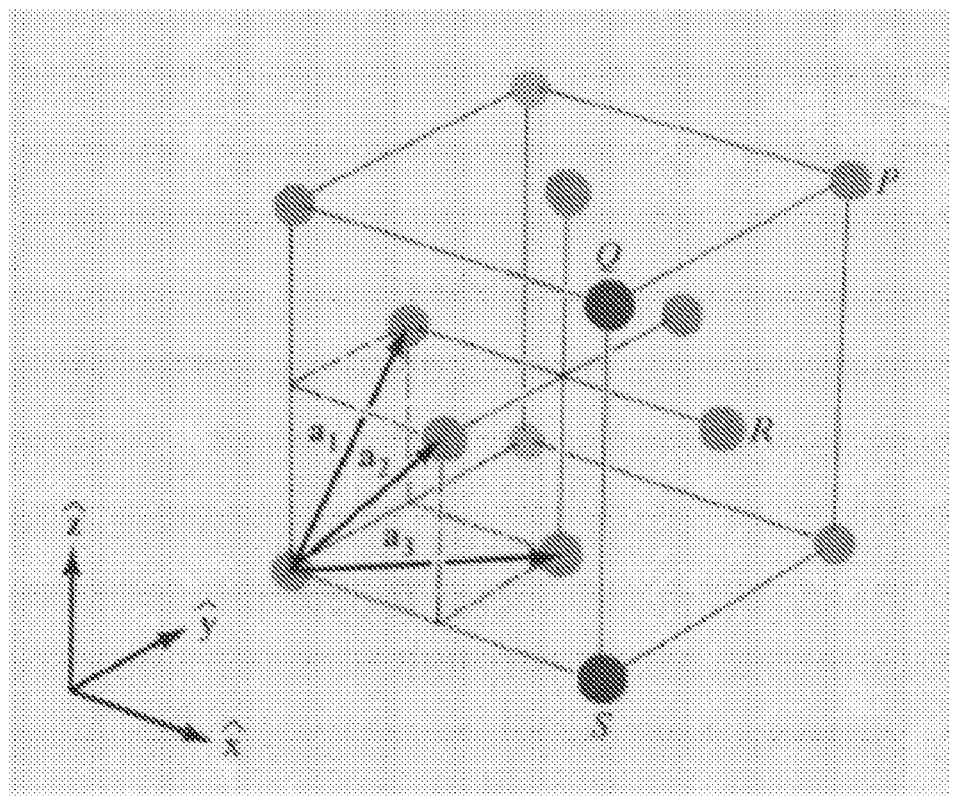
FIG. 16A is a diagram of exemplary primitive vectors $a_1$, $a_2$, $a_3$, for a face-centered cubic three-dimensional lattice.
Figure 16B:
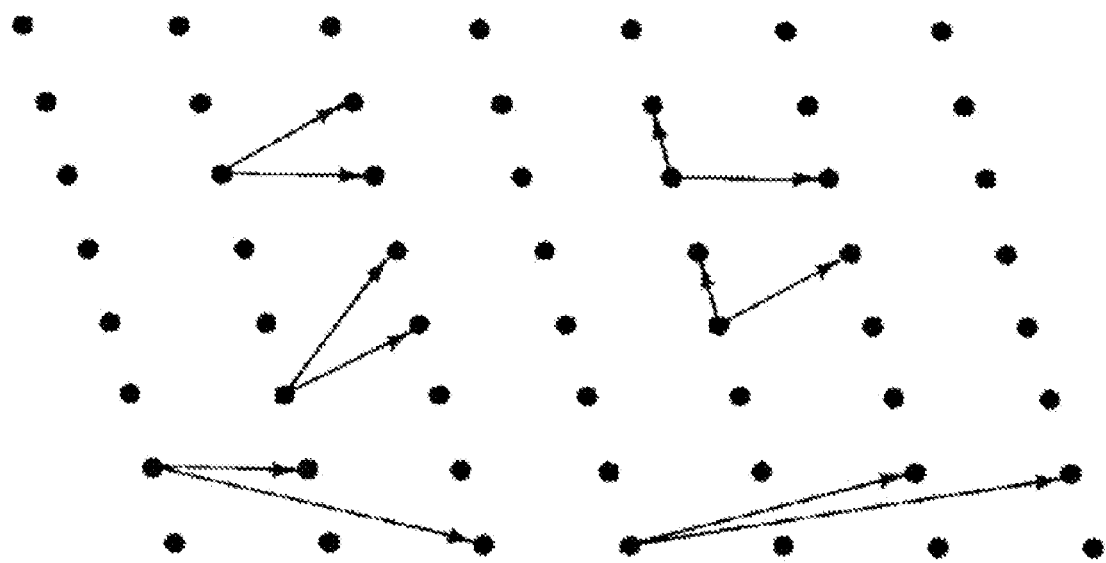
FIG. 16B is a diagram of different valid primitive vectors pairs for a particular oblique two-dimensional lattice.
Figure 17A:
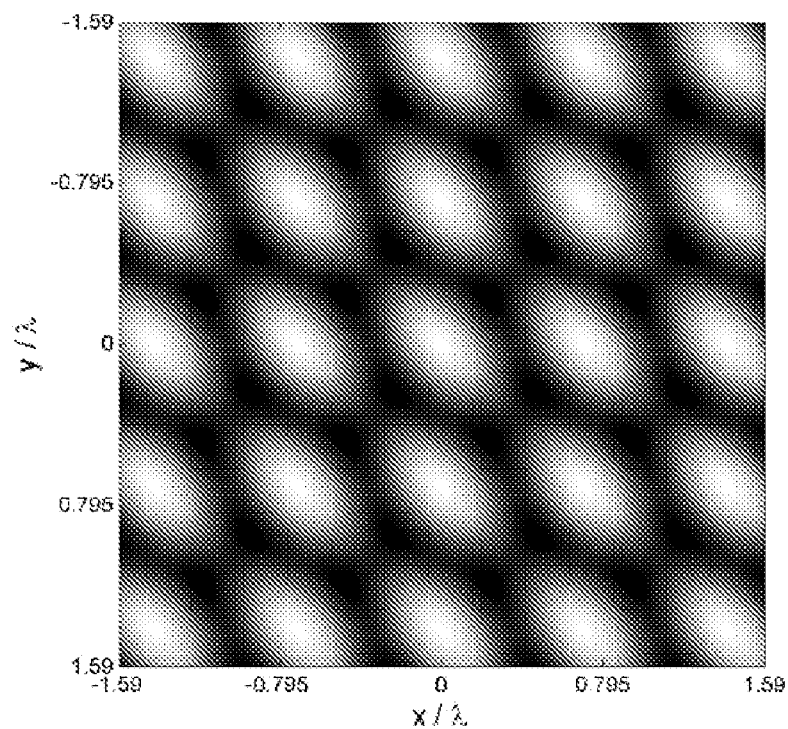
FIGS. 17A, 17B, and 17C are linear grayscale images of the intensity in the x-y plane for exemplary square, centered-rectangular, and hexagonal two-dimensional fundamental lattices, respectively, with all plane waves polarized along the z-axis and propagating in the x-y plane.
Figure 17B:
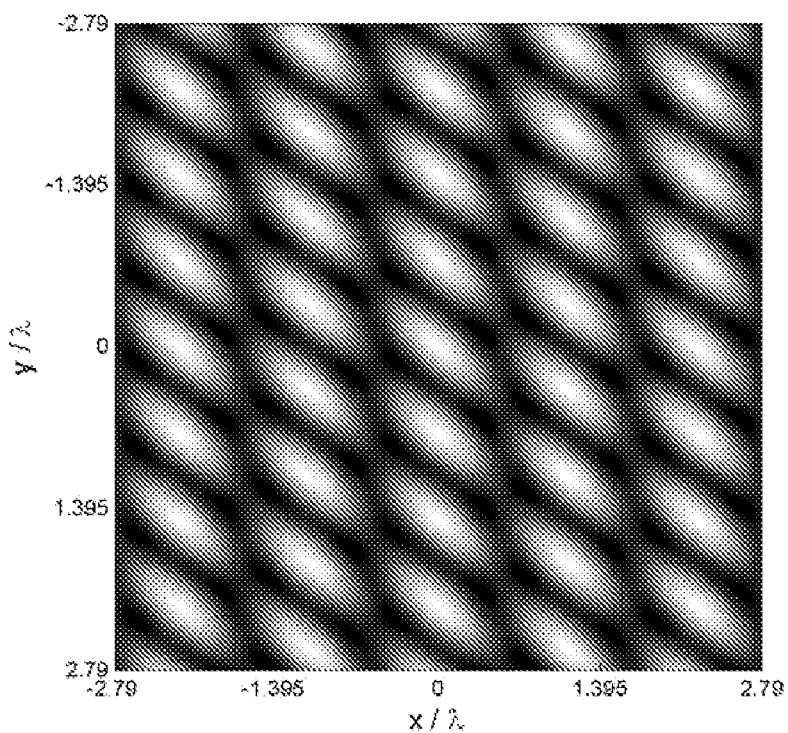
Figure 17C:
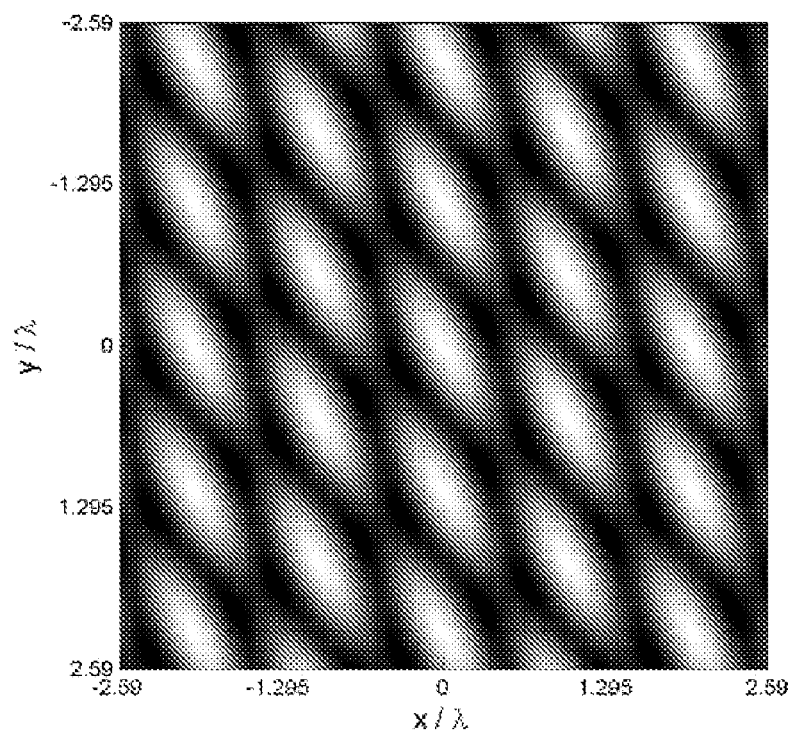
Figure 17D:
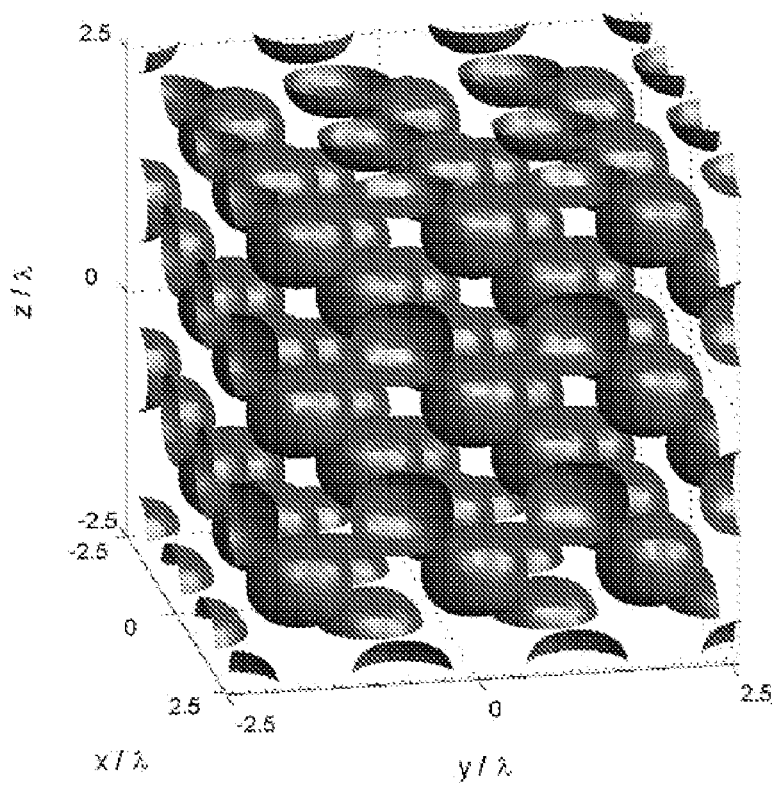
FIGS. 17D, 17E, and 17F are three-dimensional plots of surfaces of light intensity having 50% of the maximum light intensity for exemplary body-centered cubic, monoclinic, and hexagonal three-dimensional fundamental lattices, respectively.
Figure 17E:
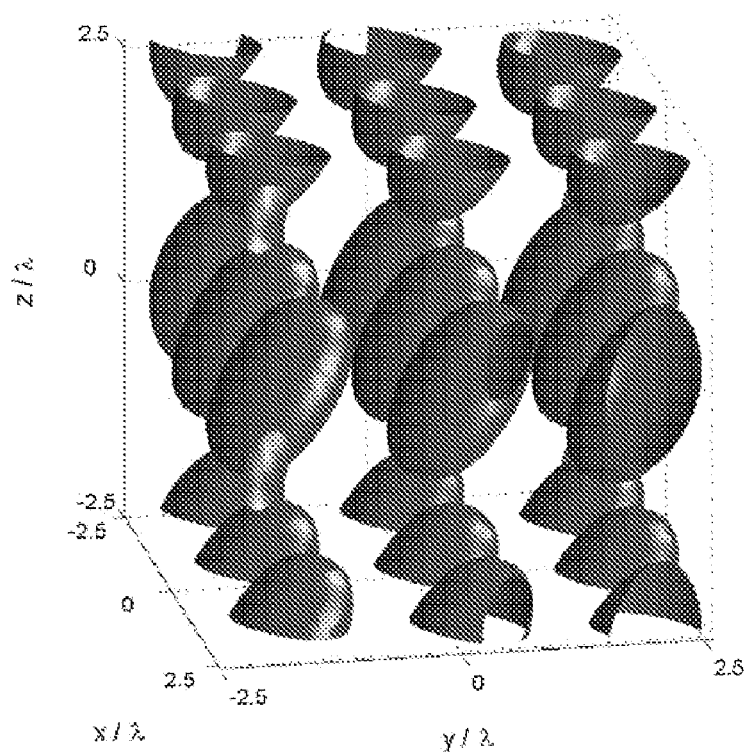
Figure 17F:
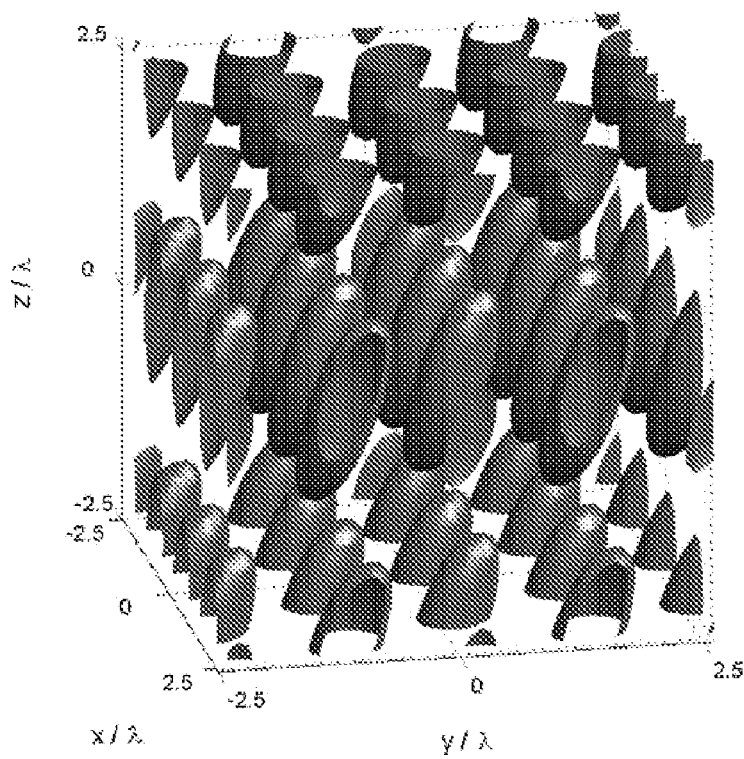

Just as a lattice in solid-state physics is a purely geometrical construct specifying the periodicities and symmetry of the crystal, and the corresponding basis is the physical entity that determines the actual location of the atoms within each primitive cell, an optical lattice is analogously a geometrical construct specifying the periodicities and symmetry of an optical crystal and the corresponding basis is given by the field, $e(x,t)$, that determines the actual intensity pattern within each primitive cell. Crystallography dictates that it is possible to create exactly five two-dimensional lattices, and exactly fourteen three-dimensional lattices, of unique symmetry, which are collectively referred to as Bravais lattices. Bravais Lattices are discussed in K. I. Petsas, et. al, Phys. Rev. A 50, 5173-5189 (1994), which is incorporated herein by reference. Each D-dimensional Bravais lattice (where D=2 or 3) can be characterized by a D-dimensional set of D primitive vectors, $a_n$, that satisfy the necessary and sufficient conditions of both (1) connecting symmetrically identical points and (2) spanning the entire real space lattice (i.e., the direct lattice). FIG. 16B illustrates several valid primitive vector pairs for a particular oblique two-dimensional lattice, and FIG. 16A illustrates an exemplary primitive vector trio for a particular three-dimensional lattice. Where each set of primitive vectors, $a_n$, is expressed as a D×1 column vector, the associated lattice can be characterized by a D×D direct lattice matrix. For example, where D is equal to two or three, respectively, the corresponding direct lattice matrices are given by the equations:

$$A \equiv [a_1 \; a_2] = \begin{bmatrix} a_{1x} & a_{2x} \\ a_{1y} & a_{2y} \end{bmatrix} \quad D = 2 \quad (8a)$$

$$A \equiv [a_1 \; a_2 \; a_3] = \begin{bmatrix} a_{1x} & a_{2x} & a_{3x} \\ a_{1y} & a_{2y} & a_{3y} \\ a_{1z} & a_{2z} & a_{3z} \end{bmatrix} \quad D = 3. \quad (8b)$$

where matrix quantities, as used herein, are written as bold upper-case symbols. The direct lattice matrix, A, is not unique because the choice of primitive vectors, $a_n$, is not unique, which can be seen from the existence of multiple valid primitive vector pairs for the particular two-dimensional lattice illustrated in FIG. 16B.

Every direct (i.e., real space) Bravais lattice has an associated reciprocal (i.e. reciprocal space) lattice that, by definition, is given by the set of all vectors, κ, for which the quantity $\exp(i\kappa \cdot x)$ exhibits the same periodicity as the direct lattice. A reciprocal lattice is also a Bravais lattice, and hence can also be described by an D-dimensional set of D primitive vectors, $b_n$, or by a reciprocal lattice matrix B that is defined similarly to the direct lattice matrix A in Equations (8a) and (8b). For a given set of direct lattice primitive vectors, $\{a_n\}$, it is possible find a set of reciprocal lattice primitive vectors, $\{b_n\}$, that satisfy the condition $b_i \cdot a_j = 2\pi\delta_{ij}$, where i, j=1 . . . D, and where δ is the Dirac delta function and is equal to one when i=j and is equal to zero when i≠j. In matrix form, the reciprocal lattice matrix is described by the equation:

$$B' \cdot A = 2\pi I \quad (9a)$$

or, equivalently:

$$B = 2\pi (A')^{-1} \quad (9b)$$

where I is the D×D identity matrix.

Next Equation (6), which describes the light intensity pattern due to the combination of the interfering individual light beams, can be examined in view of these definitions. There are D(D+1) non-zero wavevector differences, $k_n - k_m$, that can be identified with specific points in a reciprocal lattice, and these wavevector differences can be expressed as integral combinations of N independent primitive vectors, $b_n$. In particular, for the minimum set of N=D+1 plane waves, we can choose:

$$b_n = k_0 - k_n \text{ where } n = 1 \ldots D; \quad (10)$$

that is, the primitive vectors, $b_n$, are given by the difference between a single wavevector, $k_0$, in the minimum set and every other wavevector, $k_n$, in the same set. Combining Equations (4) and (10) then yields:

$$|k_n|^2 = k^2 = |k_0 - b_n|^2 = k^2 - 2b_n' \cdot k_0 + b_n' \cdot b_n \quad (11)$$

or, in matrix form:

$$B' \cdot k_0 = \begin{bmatrix} b_1' \cdot b_1 \\ \vdots \\ b_D' \cdot b_D \end{bmatrix} / 2 \equiv \beta/2 \quad (12)$$

$$D = 2 \text{ or } 3$$

Lastly, Equations (9b) and (12) together yield:

$$k_0 = A \cdot \beta / 4\pi \quad (13)$$

Using the mathematical framework provided by Equations (8), (9b), (10), (12) and (13), a minimum set of wavevectors, $\{k_n\}$, can be selected that generates a two-dimensional or three-dimensional optical lattice of any desired Bravais symmetry, as characterized by a particular direct lattice matrix, A. First, the corresponding reciprocal lattice, B, can be determined using Equation (9b). Second, the column vectors $b_n'$ of B can be used to determine β in light of Equation (12). Third, A and β together can yield the first unknown wavevector, $k_0$, according to Equation (13). Finally, the remaining D wavevectors can be determined using Equation (10).

Direct lattice primitive vectors, $a_n$, are traditionally expressed as vector functions of the lattice constants α, b, and c that describe the lengths of the three sides (for a three-dimensional lattice) of the corresponding conventional unit cell. Such a unit cell has aspect ratios of $\eta \equiv b/a$ and $\xi \equiv c/a$, and inclination angles γ and δ between its sides α to b and α to c, respectively (c, ξ, and δ being relevant only for the three-dimensional case). The direct lattice matrix, A, and, as a result, α, b, c, γ, and δ can be related to the wavelength λ of the excitation waves by squaring both sides of Equation (13) and applying Equation (4) (assuming, for simplicity, that the lattice is not of triclinic symmetry, and hence the c-axis is orthogonal to the αb plane). The result is the equation:

$$\lambda = 8\pi^2 / \sqrt{\beta' \cdot A' \cdot A \cdot \beta} \equiv F(\alpha, b, c, \gamma, \delta) \quad (14)$$

where $F(\alpha,b,c,\gamma,\delta)$ is a function of the lattice constants and inclination angles. Thus, any optical lattice of a given Bravais symmetry, with aspect ratios, $\eta$ and $\xi$, and inclination angles, $\gamma$ and $\delta$, can only exist in discrete sizes relative to the wavelength of light used to create the lattice. These sizes are dictated by the valid choices of A (assuming, for D=2, that the wavevectors, $k_n$, are restricted to a single plane). Furthermore, for any optical lattice, a minimum possible lattice size will always exist, because the lattice basis $e(x,t)$ can have no spatial frequencies greater than $2k$.

Fundamental Lattices

A D-dimensional lattice of a given Bravais type that consists of D+1 plane waves and that has the minimum possible size relative to the light wavelength is referred to herein as a fundamental lattice of that type. In light of Equation (14), fundamental lattices are created by those sets of direct lattice primitive vectors, $\{a_n\}$, for which the quantity $\beta' \cdot A' \cdot A \cdot \beta$ is minimized. Such sets of direct lattice primitive vectors are often geometrically identifiable by those primitive vectors, $a_n$, of minimal length that, to within the constraints of the lattice symmetry, are most nearly orthogonal to one another. Table 1 and Table 2 summarize exemplary fundamental direct lattice matrices, $A_f$, and their corresponding minimum sets of reciprocal lattice vectors, $\{k_n\}$, (expressed as the D×(D+1) matrix, $K_f$) for all two-dimensional and three-dimensional Bravais lattice types. Table 3 and Table 4 summarize the wavelength-normalized sizes, $a/\lambda$, of such lattices in terms of their unit cell aspect ratios $\eta$, $\xi$, and inclination angle, $\gamma$, where appropriate. Finally, FIG. 17 shows intensity plots of several exemplary two-dimensional and three-dimensional fundamental lattices.

TABLE 1

Direct Lattice and Wave Vector Matrices for the Five Fundamental 2D Optical Bravais Lattices

| Lattice Type | $A_f$ | $K_f{}^a$ |
|---|---|---|
| oblique[b] | $\begin{bmatrix} a & b\cos\gamma \\ 0 & b\sin\gamma \end{bmatrix}$ | $\dfrac{\pi}{\sin^2\gamma} \begin{bmatrix} 1/a + \cos\alpha/b & (1-2\sin^2\gamma)/a + \cos\gamma/b & 1/a + \cos\gamma/b \\ \sin\gamma/b & \sin2\gamma/a + \sin\gamma/b & -\sin\gamma/b \end{bmatrix}$ |
| hexagonal | $\begin{bmatrix} a & -a/2 \\ 0 & \sqrt{3}\,a/2 \end{bmatrix}$ | $\pi \begin{bmatrix} \dfrac{2}{3a} & -\dfrac{4}{3a} & \dfrac{2}{3a} \\ \dfrac{2}{\sqrt{3}\,a} & 0 & -\dfrac{2}{\sqrt{3}\,a} \end{bmatrix}$ |
| centered rectangular | $\begin{bmatrix} a/2 & a/2 \\ b/2 & -b/2 \end{bmatrix}$ | $\pi \begin{bmatrix} \dfrac{a}{b^2}+\dfrac{1}{a} & \dfrac{a}{b^2}-\dfrac{1}{a} & \dfrac{a}{b^2}-\dfrac{1}{a} \\ 0 & -2/b & 2/b \end{bmatrix}$ |
| primitive rectangular | $\begin{bmatrix} a & 0 \\ 0 & b \end{bmatrix}$ | $\pi \begin{bmatrix} 1/a & -1/a & 1/a \\ 1/b & 1/b & -1/b \end{bmatrix}$ |
| square | same as primitive rectangular, except b = a | |

[a] $K_f$ is a 2 × 3 matrix, each column of which gives one of the wave vectors, $k_n$, (in Cartesian coordinates) in the minimum plane wave set
[b] $\gamma$ is the angle between the a and b sides of the conventional unit cell

TABLE 2

Direct Lattice and Wave Vector Matrices for the Fourteen Fundamental 3D Optical Bravais Lattices

| Lattice Type | $A_f$ | $K_f{}^a$ |
|---|---|---|
| triclinic | general: $[a_1\ a_2\ a_3]$ | use Eqs. (1), (7), and (9) |
| trigonal[b] | $\begin{bmatrix} a & a\cos\gamma & a\cos\gamma \\ 0 & a\sin\gamma & a\cos\gamma\tan(\gamma/2) \\ 0 & 0 & a\sqrt{1-\dfrac{\cos^2\gamma}{\cos^2(\gamma/2)}} \end{bmatrix}$ | |
| centered monoclinic[b] | $\begin{bmatrix} b\cos\gamma - a & b\cos\gamma + a & b\cos\gamma + a \\ b\sin\gamma & -b\sin\gamma & b\sin\gamma \\ c & c & -c \end{bmatrix}/2$ | $\dfrac{\pi}{a+b\cos\gamma}\begin{bmatrix} \dfrac{1}{\sin^2\gamma} + \left(\dfrac{b\cos\gamma}{c}\right)^2 & \dfrac{1}{\sin^2\gamma} + \left(\dfrac{b\cos\gamma}{c}\right)^2 & \dfrac{\cos2\gamma}{\sin^2\gamma} + \left(\dfrac{b\cos\gamma}{c}\right)^2 & \dfrac{\cos2\gamma}{\sin^2\gamma} + \left(\dfrac{b\cos\gamma}{c}\right)^2 \\ \dfrac{b^2\sin2\gamma}{2c^2} + \dfrac{a}{b\sin\gamma} & \dfrac{b^2\sin2\gamma}{2c^2} - \dfrac{a+2b\cos\gamma}{b\sin\gamma} & \dfrac{b^2\sin2\gamma}{2c^2} + \dfrac{a+2b\cos\gamma}{b\sin\gamma} & \dfrac{b^2\sin2\gamma}{2c^2} - \dfrac{a}{b\sin\gamma} \\ \dfrac{c\cot\gamma}{b\sin\gamma} + \dfrac{a}{c} & \dfrac{c\cot\gamma}{b\sin\gamma} - \dfrac{a+2b\cos\gamma}{c} & \dfrac{c\cot\gamma}{b\sin\gamma} - \dfrac{a}{c} & \dfrac{c\cot\gamma}{b\sin\gamma} + \dfrac{a+2b\cos\gamma}{c} \end{bmatrix}$ |
| simple monoclinic[b] | $\begin{bmatrix} a & b\cos\gamma & 0 \\ 0 & b\sin\gamma & 0 \\ 0 & 0 & c \end{bmatrix}$ | $\dfrac{\pi}{\sin^2\gamma}\begin{bmatrix} 1/a + \cos\alpha/b & (1-2\sin^2\gamma)/a + \cos\gamma/b & 1/a + \cos\gamma/b & 1/a + \cos\gamma/b \\ \sin\gamma/b & \sin2\gamma/a + \sin\gamma/b & -\sin\gamma/b & \sin\gamma/b \\ \dfrac{\sin^2\gamma}{c} & \dfrac{\sin^2\gamma}{c} & \dfrac{\sin^2\gamma}{c} & \dfrac{\sin^2\gamma}{c} \end{bmatrix}$ |

TABLE 2-continued

Direct Lattice and Wave Vector Matrices for the Fourteen Fundamental 3D Optical Bravais Lattices

| Lattice Type | $A_f$ | $K_f{}^a$ |
|---|---|---|
| hexagonal | $\begin{bmatrix} a & -a/2 & 0 \\ 0 & \sqrt{3}a/2 & 0 \\ 0 & 0 & c \end{bmatrix}$ | $\pi \begin{bmatrix} \frac{2}{3a} & -\frac{4}{3a} & \frac{2}{3a} & \frac{2}{3a} \\ \frac{2}{\sqrt{3}a} & 0 & \frac{2}{\sqrt{3}a} & \frac{2}{\sqrt{3}a} \\ 1/c & 1/c & 1/c & -1/c \end{bmatrix}$ |
| face-centered orthorhombic | $\begin{bmatrix} a & -a & 0 \\ 0 & 0 & -b \\ c & c & -c \end{bmatrix}/2$ | $\pi \begin{bmatrix} 0 & -2/a & 2/a & 0 \\ -2/b & 0 & 0 & 2/b \\ \frac{c}{a^2} - \frac{c}{b^2} + \frac{1}{c} & \frac{c}{a^2} - \frac{c}{b^2} - \frac{1}{c} & \frac{c}{a^2} - \frac{c}{b^2} - \frac{1}{c} & \frac{c}{a^2} - \frac{c}{b^2} + \frac{1}{c} \end{bmatrix}$ |
| body-centered orthorhombic | $\begin{bmatrix} -a & a & a \\ b & -b & b \\ c & c & -c \end{bmatrix}/2$ | $\pi \begin{bmatrix} 1/a & 1/a & -1/a & -1/a \\ 1/b & -1/b & 1/b & -1/b \\ 1/c & -1/c & -1/c & 1/c \end{bmatrix}$ |
| base-centered orthorhombic | $\begin{bmatrix} a/2 & a/2 & 0 \\ b/2 & -b/2 & 0 \\ 0 & 0 & c \end{bmatrix}$ | $\pi \begin{bmatrix} \frac{a}{b^2} + \frac{1}{a} & \frac{a}{b^2} - \frac{1}{a} & \frac{a}{b^2} - \frac{1}{a} & \frac{a}{b^2} + \frac{1}{a} \\ 0 & -2/b & 2/b & 0 \\ 1/c & 1/c & 1/c & -1/c \end{bmatrix}$ |
| simple orthorhombic | $\begin{bmatrix} a & 0 & 0 \\ 0 & b & 0 \\ 0 & 0 & c \end{bmatrix}$ | $\pi \begin{bmatrix} 1/a & -1/a & 1/a & 1/a \\ 1/b & 1/b & -1/b & 1/b \\ 1/c & 1/c & 1/c & -1/c \end{bmatrix}$ |
| centered tetragonal | same as body-centered orthorhombic, except b = a | |
| simple tetragonal | same as simple orthorhombic, except b = a | |
| face-centered cubic | $\begin{bmatrix} 0 & -a & a \\ a & 0 & -a \\ a & a & 0 \end{bmatrix}/2$ | $\frac{\pi}{a} \begin{bmatrix} 0 & -2 & 2 & 0 \\ -2 & 0 & 0 & 2 \\ 1 & -1 & -1 & 1 \end{bmatrix}$ |
| body-centered cubic | same as body-centered orthorhombic, except c = b = a | |
| simple cubic | same as simple orthorhombic, except c = b = a | |

[a] $K_f$ is a 3 × 4 matrix, each column of which gives one of the wave vectors, $k_n$, (in Cartesian coordinates) in the minimum plane wave set
[b] $\gamma$ is the angle between the a and b sides of the conventional unit cell

TABLE 3

Wavelength-Normalized Sizes of the Five Fundamental Two-Dimensional Optical Bravais Lattices

| Lattice Type | $a/\lambda^a$ |
|---|---|
| oblique[b] | $\frac{1}{2\sin^2\gamma}\left[1 + \frac{1}{\eta^2} + \frac{2\cos\gamma}{\eta}\right]^{1/2}$ |
| hexagonal | $2/3$ |
| centered rectangular | $(1 + 1/\eta^2)/2$ |
| primitive rectangular | $\sqrt{1+1/\eta^2}/2$ |
| square | $1/\sqrt{2}$ |

[a] $\eta \equiv b/a$ and $\xi \equiv c/a$ are the aspect ratios of the conventional unit cell
[b] $\gamma$ is the angle between the a and b sides of the conventional unit cell

TABLE 4

Wavelength-Normalized Sizes of the Fourteen Fundamental Three-Dimensional Optical Bravais Lattices

| Lattice Type | $a/\lambda^a$ |
|---|---|
| triclinic or trigonal | use Eqs. (1), (7), (9), and (10) |
| centered monoclinic[b] | $\frac{1}{2(1+\eta\cos\gamma)}\left[\left(\frac{1}{\sin^2\gamma} + \left(\frac{\eta\cos\gamma}{\xi}\right)^2\right)^2 + \left(\frac{1}{\eta\sin\gamma} + \frac{\eta^2\sin2\gamma}{2\xi^2}\right)^2 + \left(\frac{1}{\xi} + \frac{\xi\cot\gamma}{\eta\sin\gamma}\right)^2\right]^{1/2}$ |
| simple monoclinic[b] | $\frac{1}{2\sin^2\gamma}\left[1 + \frac{1}{\eta^2} + \frac{2\cos\gamma}{\eta} + \left(\frac{\sin^2\gamma}{\xi}\right)^2\right]^{1/2}$ |
| hexagonal | $\sqrt{4/9 + 1/(2\xi)^2}$ |

TABLE 4-continued

Wavelength-Normalized Sizes of the Fourteen Fundamental Three-Dimensional Optical Bravais Lattices

| Lattice Type | $a/\lambda^a$ |
|---|---|
| face-centered orthorhombic | $\sqrt{4/\eta^2+(\xi-\xi/\eta^2+1/\xi)^2}/2$ |
| base-centered orthorhombic | $\sqrt{(1+1/\eta^2)^2+1/\xi^2}/2$ |
| body-centered or simple orthorhombic | $\sqrt{1+1/\eta^2+1/\xi^2}/2$ |
| centered or simple tetragonal | $\sqrt{2+1/\xi^2}/2$ |
| face-centered cubic | $\sqrt{5}/2$ |
| body-centered or simple cubic | $\sqrt{3}/2$ |

$^a\eta = b/a$ and $\xi = c/a$ are the aspect ratios of the conventional unit cell
$^b\gamma$ is the angle between the a and b sides of the conventional unit cell The characteristics of fundamental optical lattices makes them useful for a variety of microscopy applications. For example, a fundamental lattice contains the minimum possible number of D(D+1) non-zero spatial frequencies, $k_n-k_m$, and the corresponding points in reciprocal space are separated by the largest distances, $|b_i-b_j|$, possible for the given lattice type. Therefore, the signal, $S(x)=I(x)O(x)$, that results from the interaction of a fundamental lattice having an intensity distribution, $I(x)$, with an object of interest having a spatial distribution, $O(x)$, of signal-producing entities yields well-separated D-dimensional regions in reciprocal space that encode the spatial frequencies of $\tilde{O}(k)$ out to a reciprocal distance, $|k_n-k_m|$, beyond the traditional limit of 2k. The D-dimensional regions encoding the spatial frequencies of the object of interest can be recovered by recording a series of images at different phases using structured illumination microscopy techniques, for example, as described in M. Ben-Levi and E. Peleg, U.S. Pat. No. 5,867,604; J. T. Frohn, et al., Proc. Natl. Acad. Sci. USA 97, 7232-7236 (2000); P.T.C. So, et al., J. Opt. Soc. Am. A 18, 2833-2845 (2001); and G. Cragg, et al., U.S. Pat. No. 6,255,642 B1, all of which are incorporated herein by reference. Also, because a fundamental lattice permits the creation of a basis, $e(x,t)$, that has the most rapid spatial variation possible between adjacent maxima and minima, such lattices can be used effectively in nonlinear multiple field techniques such as stimulated emission depletion ("STED"), for example, as described in S. W. Hell and J. Wichmann, Opt. Lett. 19, 780-782 (1994); or S. Hell and J. Wichmann, U.S. Pat. No. 5,731,588, both of which are incorporated herein by reference. Such lattices also can be used effectively in coherent anti-Stokes Raman scattering ("CARS") microscopy, for example, as described in J. Cheng, et al., Biophys. J. 83, 502-509 (2002), which is incorporated herein by reference. The use of a fundamental lattice can also enhance imaging speed in microscopy when such a lattice incorporates a basis of discrete excitation maxima, because the N-dimensional primitive cell that must be scanned to form a complete image is of the smallest possible size.

Sparse Lattices

Although fundamental lattices are useful for many applications, non-fundamental optical lattices, which are of larger periodicity than the fundamental lattice for any given type, can also be useful in microscopy. For example, the individual signals from adjacent intensity maxima can be more easily differentiated in larger period optical lattices, particularly in three-dimensional lattices, because the distances between such maxima can be greater than in fundamental lattices, which can be helpful in overcoming resolution problems during three-dimensional detection. Similarly, non-fundamental lattices can be used to avoid a high density of intensity maxima, where such a density could be excessively perturbative of certain samples. A larger period lattice can also be used to decrease the density of intensity maxima in order to cover the desired field of view at the desired frame rate with a given detector having a fixed number of elements.

Optical lattices that have greater periodicity than fundamental lattices, referred to herein as sparse lattices, can be selected for any desired lattice type by applying Equations (9b), (10), (12), and (13) as described above to yield the D+1 wavevectors, $k_n$, arising from direct lattice primitive vector sets, $\{a_n\}$, and corresponding matrices, A, for which the quantity $\beta' \cdot A' \cdot A \cdot \beta$ is larger than the minimum value associated with the fundamental lattice. The selection of a sparse lattice of a given type (as characterized by the Bravais symmetry, aspect ratios $\eta$ and $\xi$, and inclination angles $\gamma$ and $\delta$ of the lattice) therefore reduces to the selection of additional valid primitive vector sets, $\{a_n\}$. Because any such set, $\{a_n\}$, must span an entire direct lattice, any two such sets, $\{a_{In}\}$ and $\{a_{IIn}\}$, must be integral combinations of one another, so that:

$$a_{IIm} = \sum_{n=1}^{D} c_{mn} a_{In} \quad m = 1 \ldots D \tag{15a}$$

$$a_{Im} = \sum_{n=1}^{D} d_{mn} a_{IIn} \quad m = 1 \ldots D \tag{15b}$$

or, in matrix form:

$$A_{II}' = CA_I' \tag{16a}$$

$$A_I' = DA_{II}' \tag{16b}$$

Thus, the selection of a sparse lattice further reduces to the selection of valid combination matrices, C, that allow new direct lattice matrices, $A_{II}$, to be generated from known direct lattices, $A_I$, including, for example, the fundamental direct lattice matrices, $A_f$, given in Table 1 and Table 2.

Equation (16a) and Equation (16b) collectively indicate that $C^{-1}=D$. Therefore, the matrix $C^{-1}$ has integral elements, as do the matrices C and D. However, the determinant of any matrix with integral elements must be an integer. Furthermore, for any matrix, $|C^{-1}|=1/|C|$. Accordingly, the only valid combination matrices are those for which:

$$|C|=\pm 1. \tag{17}$$

Equation (17) provides for the convenient selection of different sparse lattices and their D+1 constituent wavevectors. Such selection can be achieved by:

a) cycling through different integer possibilities for each of the elements of the combination matrix C and evaluating $|C|$ in each case;

b) determining whether each of the resulting matrices satisfies Equation (17);

c) applying matrices that satisfy Equation (17) to Equation (16a) along with known direct lattice matrices $A_I$ to select additional matrices $A_{II}$;

d) applying Equations (9b), (10), (12), and (13) to $A_{II}$ to select the corresponding wavevectors, $\{k_n\}$, and using Equation (14) to find the wavelength-normalized lattice size for the given $\eta$, $\xi$, and $\gamma$.

Figure 18A:
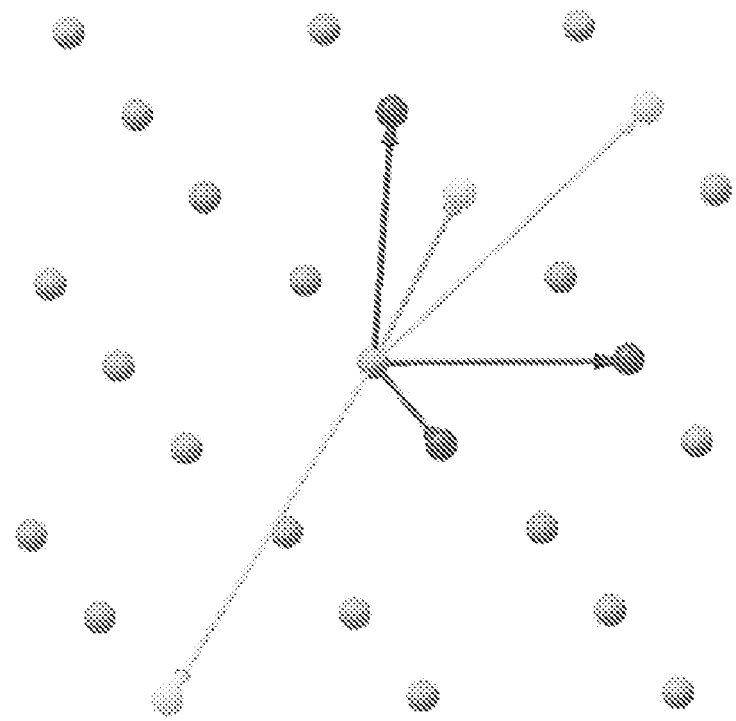
FIG. 18A is a view of a two different sets of primitive vectors for a simple cubic lattice: one set of vectors defines a fundamental lattice, and another set defines a sparse lattice of $\sqrt{59/3}$ greater period.
Figure 18B:
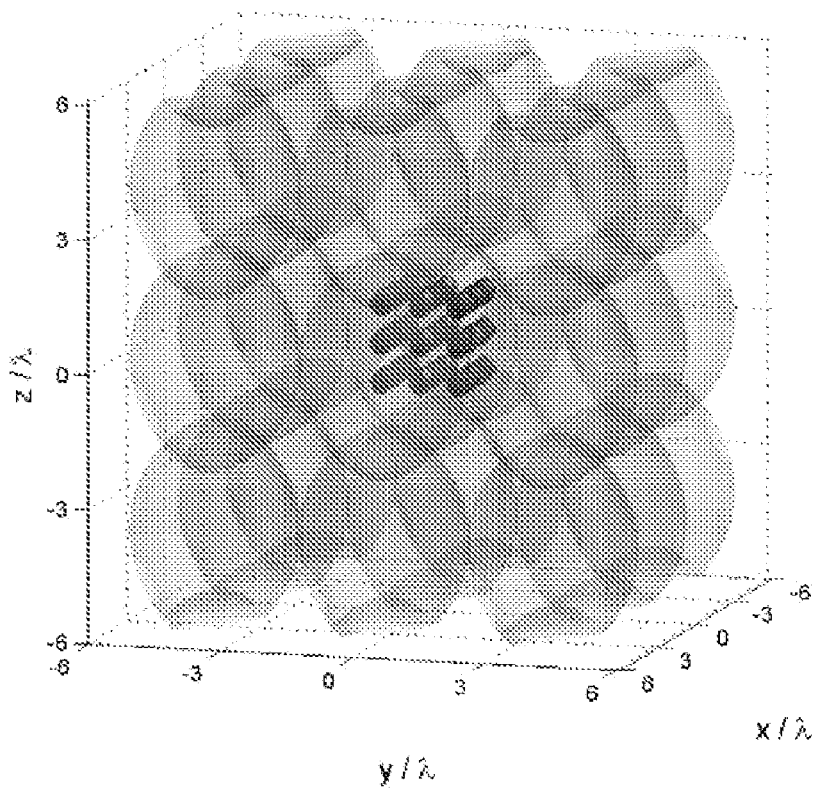
FIG. 18B is a three-dimensional plot of surfaces of light intensity having 50% of the maximum light intensity for the fundamental and sparse lattices shown in FIG. 18A, plotted over ±1.5 intensity periods.

Although sparse lattices can only be selected in discrete sizes, the density of valid solutions for such lattices, particularly in three dimensions, is such that a sparse lattice usually can be selected to approximate many desired sizes larger than that of the fundamental lattice. FIGS. 8A and 10A show exemplary sparse lattices in two-dimensional and three-dimensional, respectively. FIG. 18 illustrates direct lattice primitive vectors and resulting intensity plots to provide for comparison between a fundamental simple cubic lattice and a related sparse lattice having a periodicity that is $\sqrt{59/3}=4.435$ times larger than the periodicity of the fundamental lattice.

New valid combination matrices, C, can be generated from any product of known combination matrices or their inverses. Also, because Equation (17) was derived without reference to any specific Bravais symmetry, a valid combination matrix, C, can be applied to any type of direct lattice matrix, A, during the selection of new sparse lattices.

As the choice of direct lattice primitive vectors, $a_n$, extends to lattice points successively farther from the origin, the number of valid lattice matrices, A, and hence the likely number of differently sized sparse lattices for any given type, increases rapidly. Even when only relatively short primitive vectors are considered (e.g., $C_{mn}=0, \pm 1, \pm 2, \pm 3$ for two dimensions and $C_{mn}=0, \pm 1$ for three dimensions, as used in Tables 5 and 6, respectively), many lattice sizes exist, and the number of different sizes generally increases as lattice symmetry decreases.

Figure 19A:
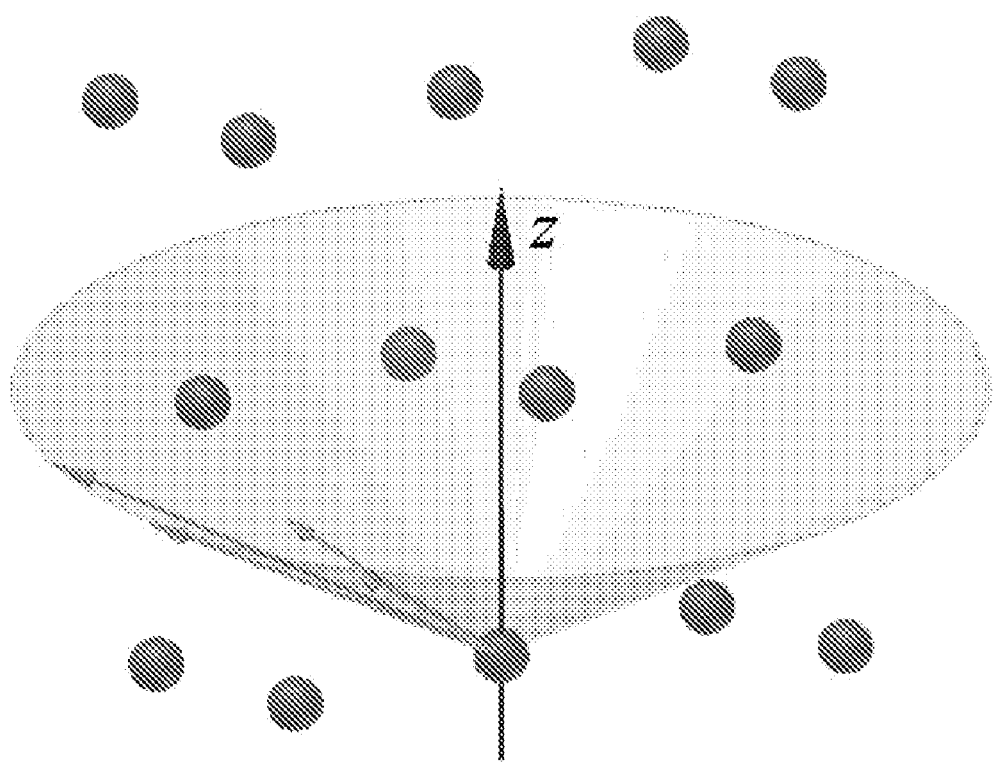
FIG. 19A is a view of four wavevectors of a particular sparse lattice, where three of the wavevectors lie on a cone, and conic axis associated with the wavevectors.
Figure 19B:
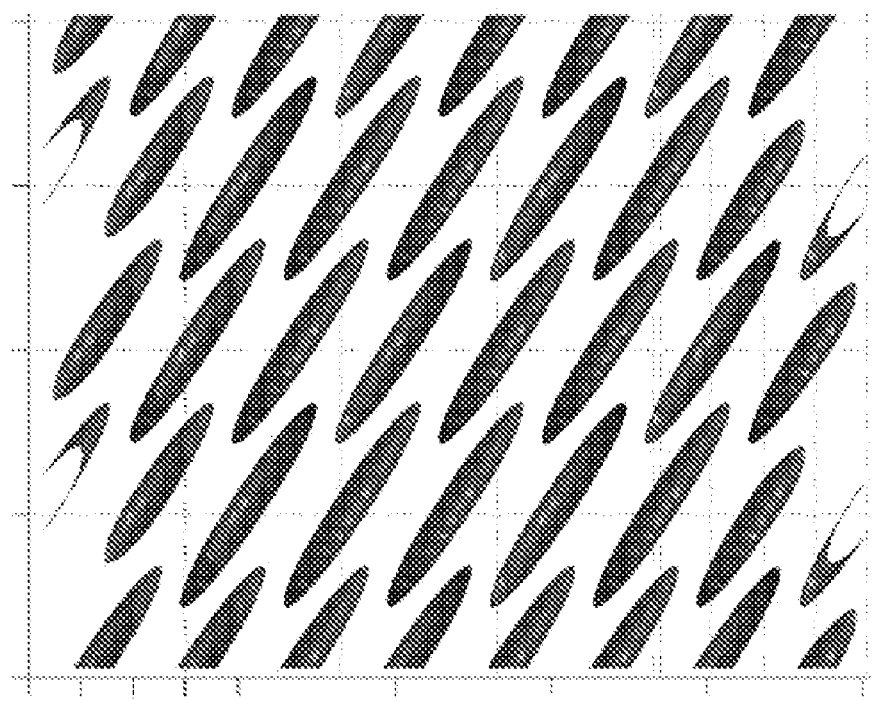
FIGS. 19B and 19C are three-dimensional plots of the surfaces of light intensity having 50% of the maximum light intensity for the sparse lattice resulting from plane waves with the wavevectors shown in FIG. 19A, viewed parallel and perpendicular to the conic axis defined in FIG. 19A, respectively.
Figure 19C:
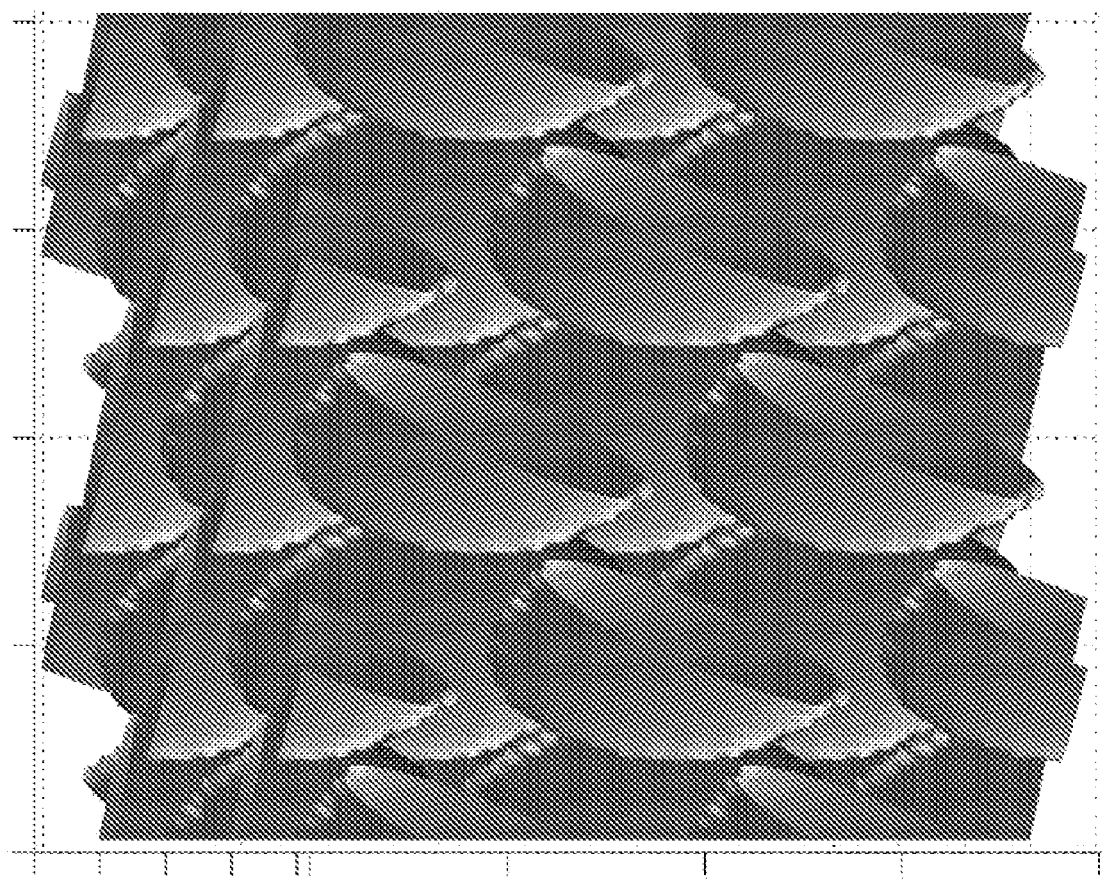

In three dimensions, increasingly sparse lattices can be understood to arise when the four wavevectors $k_0, k_1, k_2, k_3$ in the minimum set all lie near the surface of a single cone, as shown in FIG. 19A. In accordance with the arguments presented in connection with FIG. 7, the result of this wavevector relationship is a pattern that approximates a 2D lattice in the x-y plane perpendicular to the axis, $\hat{e}_z$, of the cone, and that varies slowly along $\hat{e}_z$, as illustrated in FIG. 19B and FIG. 19C, respectively. As with the two-dimensional lattices depicted in FIG. 8B and FIG. 8C, the periodicity of such a sparse lattice within the x-y plane increases as the cone angle decreases.

TABLE 5

Periodicities of Two-Dimensional Sparse Lattices Generated With Combinations of Fundamental Primitive Vectors

| Lattice Type[a] | Number of Sparse Lattice Sizes | Five Smallest a /λ, a = b | Largest a/λ, a = b |
|---|---|---|---|
| square | 10 | $1/\sqrt{2}, \sqrt{5/2}, 5/\sqrt{2}, \sqrt{65/2}, \sqrt{85/2}$ | $\sqrt{1005/2}$ |
| primitive rectangular | 15 | reduces to square for a = b | |
| centered rectangular | 20 | reduces to square for a = b | |
| hexagonal | 12 | $2/3, 2/\sqrt{3}, 2\sqrt{7/3}, 2\sqrt{91}/3, \sqrt{133/3}$ | $14\sqrt{133}/3$ |

[a]for simplicity, only lattice types with fixed unit cell angles are considered here

TABLE 6

Periodicities of Three-Dimensional Sparse Lattices Generated With Combinations of Fundamental Primitive Vectors

| Lattice Type[a] | Number of Sparse Lattice Sizes | Five Smallest a/λ, a = b = c | Largest a/λ, a = b = c |
|---|---|---|---|
| simple | cubic (a = b = c): 10 tetragonal (a = b): 29 orthorhombic: 59 | $\sqrt{3}/2, \sqrt{11}/2, \sqrt{19}/2, \sqrt{27}/2, \sqrt{35}/2$ | $\frac{\sqrt{203}}{2}$ |
| base-centered | orthorhombic: 76 | N.A. | N.A. |
| face-centered | cubic (a = b = c): 60 orthorhombic: 148 | $\sqrt{5}/2, 3/2, \sqrt{11}/2, \sqrt{21}/2, \sqrt{29}/2$ | $\frac{\sqrt{6761}}{2}$ |
| body-centered | cubic (a = b = c): 33 tetragonal (a = b): 113 orthorhombic: 236 | $\sqrt{3}/2, 1, \sqrt{2}, \sqrt{11}/2, \sqrt{5}$ | $\sqrt{689}$ |
| hexagonal | (a = c): 47 (a ≠ c): 50 | $5/6, 7/6, \sqrt{57}/6, \sqrt{65}/6, \sqrt{85}/6$ | $\frac{\sqrt{8157}}{2}$ |

[a]for simplicity, only lattice types with fixed unit cell angles are considered here As wavevectors of a sparse lattice approach the state of lying on a single conic surface, the wavevector differences approach zero in the direction of the conic axis, such that $(k_m-k_n)\cdot\hat{e}_z \to 0$, for all values of m and n. As a result, Equation (10) indicates that all valid reciprocal lattice primitive vectors, $b_b$, lie near the x-y plane. When expressed in this basis, B' has only two effectively non-zero columns. Equation (9a) and Equation (9b) imply that the direct lattice primitive vectors, $a_n$, comprising $A=2\pi(B')^{-1}$ must also lie in this plane. Thus, direct lattice primitive vectors, $a_n$, giving rise to increasingly sparse lattices can be geometrically identified by selecting vectors of increasing length that lie progressively nearer to, but not exactly upon, a single plane.

Composite Lattices

As discussed in conjunction with FIGS. 8A and 10A, sparse lattices contain only one spatial frequency in each of the D+1 directions defined by the possible combinations of D wavevectors from the D+1 element minimum set. Thus, for sparse lattices of increasing size, the resolution and potential confinement of the intensity maxima (with the appropriate basis) becomes increasingly degraded in these directions. More than D+1 plane waves can be used to provide high spatial frequency content in the excitation field in all directions and more symmetric confinement of the intensity maxima regardless of the wavelength-normalized lattice size, for example, as shown in FIGS. 8D and 10D. Such lattices that are composed of more than D+1 plane waves are referred to herein as composite lattices.

Figure 20A:
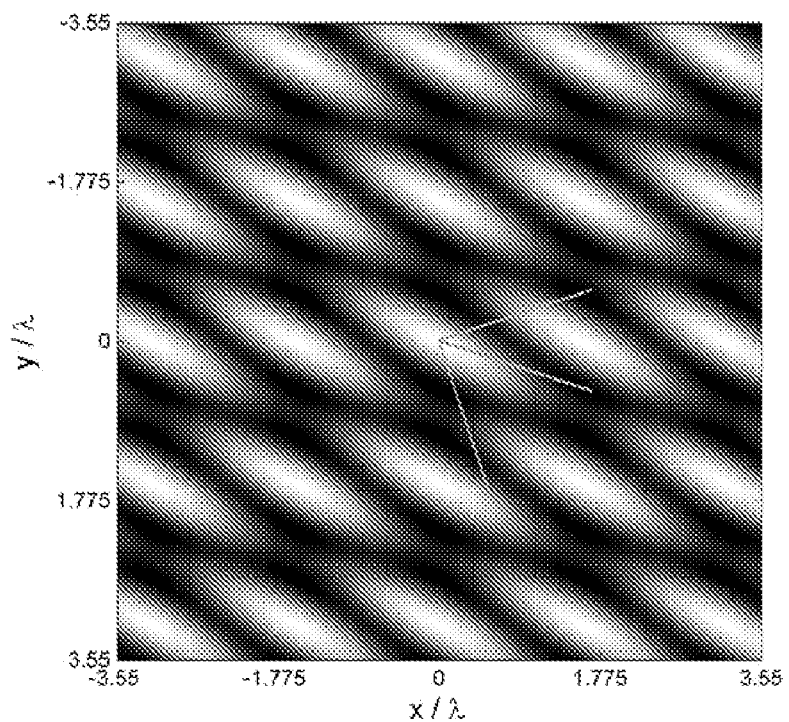
FIGS. 20A and 20B are linear grayscale images of two different size-degenerate, square, sparse, two-dimensional lattices shown in relation to their constituent wavevectors.
Figure 20B:
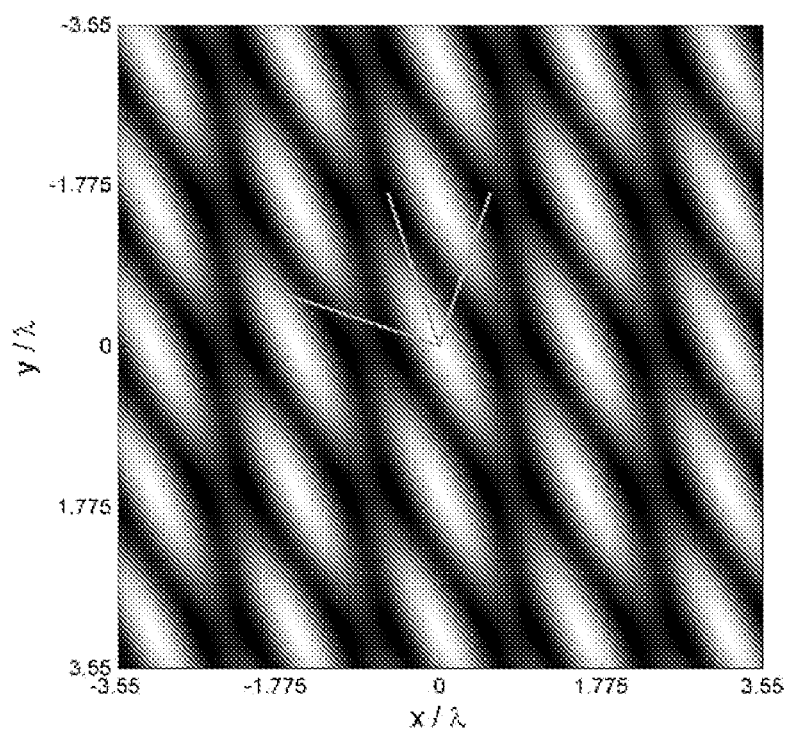
Figure 20C:
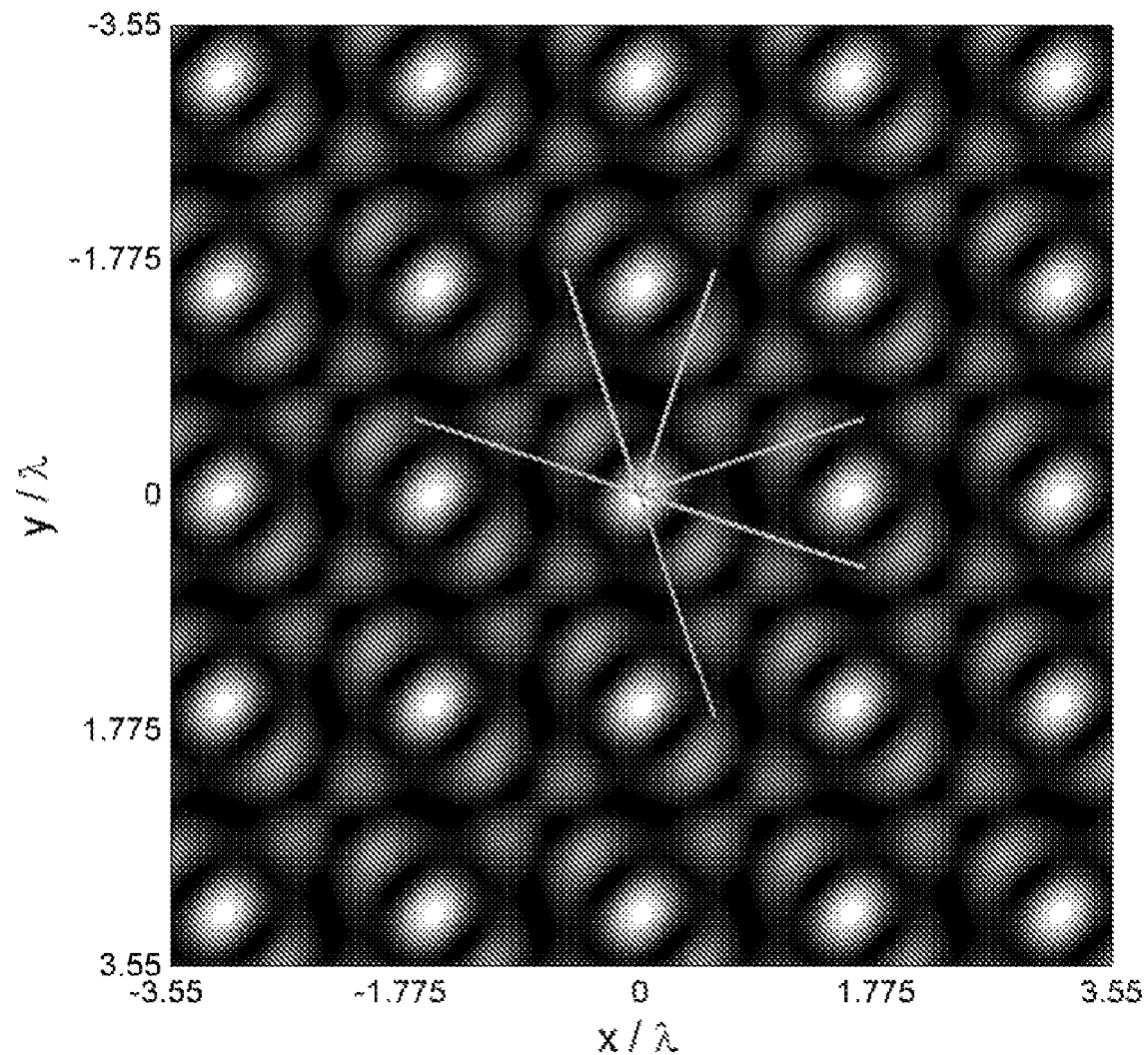
FIG. 20C is an image of the composite square two-dimensional lattice given by the superposition of the wavevectors from FIGS. 20A and 20B.

To construct composite lattices, the Bravais symmetry and periodicity of the lattice must be preserved as additional plane waves are added to an existing set. The selection procedure described above for sparse lattices can typically produce multiple direct lattice matrices, A, and associated wavevector sets, $\{k_n\}$, yielding lattices of identical size and symmetry, but exhibiting differing spatial frequencies, $k_n-k_m$, that define the confinement of the excitation, $[(k_n-k_m)\cdot\hat{e}_j]_{max}$, (i.e., the intensity maxima) in any direction, $\hat{e}_j$, within each primitive cell. FIG. 20A and FIG. 20B show two such lattices of identical size and symmetry that exhibit different directional excitation confinement. Composite lattices can be constructed by superimposing all of the unique plane waves from two or more such "size-degenerate" sparse lattices. FIG. 20C shows the composite lattice that results from the superimposition of the two sparse lattices depicted in FIG. 20A and FIG. 20B.

Any such combination of size-degenerate sparse lattices can be used to generate a composite lattice. However, composite lattices of high excitation confinement and symmetry can be formed systematically where the lattice sets satisfy the equation:

$$A_{II} = MA_I, \quad (18)$$

where:

$$M \cdot M^t = I. \quad (19)$$

For such cases, Equations (9b), (18), and (19) can be combined to yield $B_{II} = MB_I$ and, with the additional use of Equation (12), $\beta_{II} = M\beta_I$. Since $\beta_{II}{}^t \cdot A_{II}{}^t \cdot A_{II} \cdot \beta_{II} = \beta_I{}^t \cdot A_I{}^t \cdot A_I \beta_I$ for such cases, the sparse lattices represented by $A_I$ and $A_{II}$ are indeed, by virtue of Equation (14), size degenerate.

Combining these results with Equations (10) and (13) yields $k_{IIn} = Mk_{In}$. Thus, the geometric effect of the transformation matrix, M, on the direct lattice, reciprocal lattice, and constituent wave vectors is identical. This characteristic may also be observed from the fact that the orthogonality condition expressed in Equation (19) is satisfied by all single and multiplicative combinations of reflections and rotations of the lattice. A composite lattice of increased confinement and basis symmetry within each primitive cell can therefore be created by applying one or more such transformations to the wavevectors of an existing lattice and then superposing all new wavevectors in the transformed set with the original ones. Repeated application of this procedure can further increase the confinement and basis symmetry of a composite lattice, until all possible wavevectors resulting from such transformations are uncovered. Thus, like sparse lattices, composite lattices can have larger primitive cells than fundamental lattices. However, composite lattices can also have greater confinement of individual intensity maxima than sparse lattices of the same Bravais symmetry.

Figure 21A:
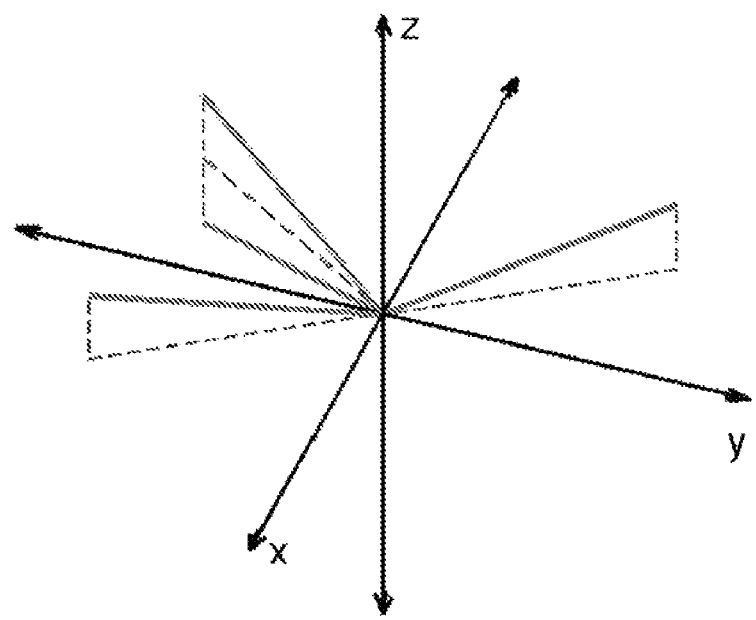
FIG. 21A is a three-dimensional representation of relative wavevector directions for a particular simple orthorhombic fundamental lattice.
Figure 21B:
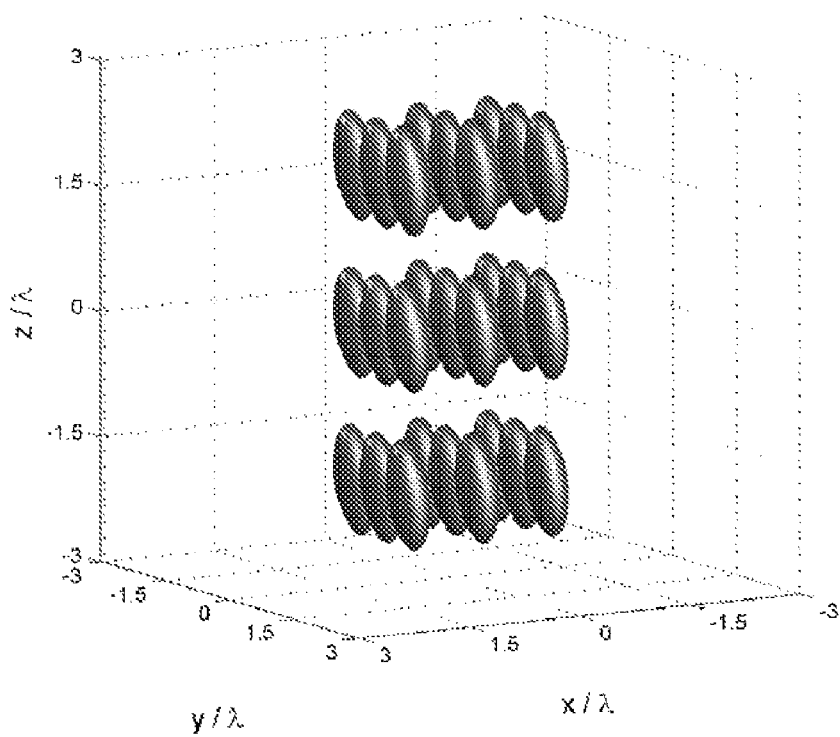
FIG. 21B is a three-dimensional plot of surfaces of light intensity having 50% of the maximum light intensity for a lattice constructed with the wavevectors shown in FIG. 21A.
Figure 21C:
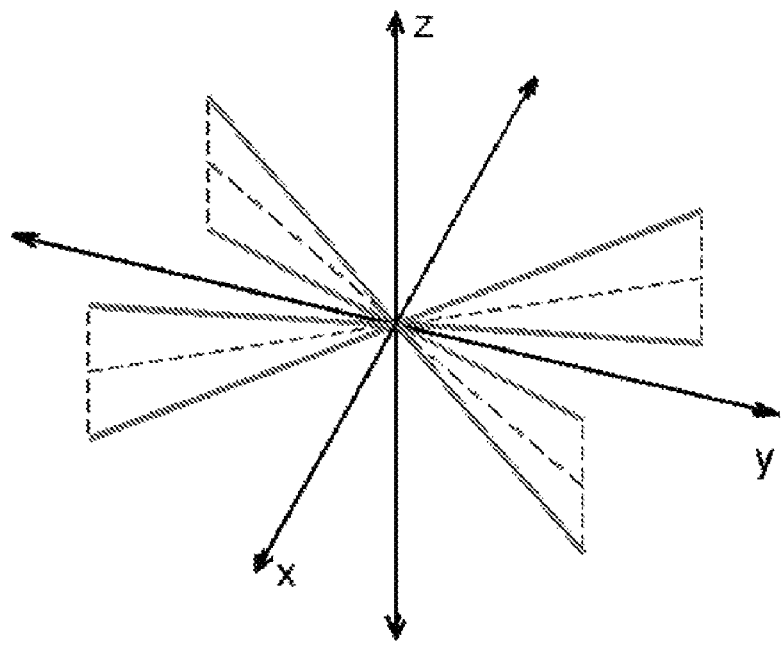
FIG. 21C is a three-dimensional representation of relative wavevector directions for a simple orthorhombic composite lattice obtained by applying all reflection operations about the three principal planes to the wavevectors from FIG. 21A.

However, the Bravais symmetry of a lattice will be preserved only for transformations $A_I \rightarrow A_{II}$ and subsequent superpositions that satisfy Equation (16a) as well as Equations (18) and (19). In other words, Bravais symmetry is only preserved by transformations that map a lattice onto itself. FIG. 21 illustrates one example of this characteristic of composite lattices. The intensity within each cell of the initial simple orthorhombic fundamental lattice depicted in FIG. 21A and FIG. 21B (where $\eta=0.66$ and; $\xi=2.0$) is asymmetric and exhibits poor confinement in several directions. Because the orthorhombic crystal group is characterized by invariance under reflections about the principal planes only, FIGS. 21C and 21D show that when the plane waves resulting from all reflection combinations are superimposed (i.e., eight plane waves in total), the resulting composite lattice maintains the orthorhombic nature of the original lattice, while imposing similar symmetry and improved confinement of the excitation (i.e., on the intensity maxima of the lattice) within the basis.

Figure 21D:
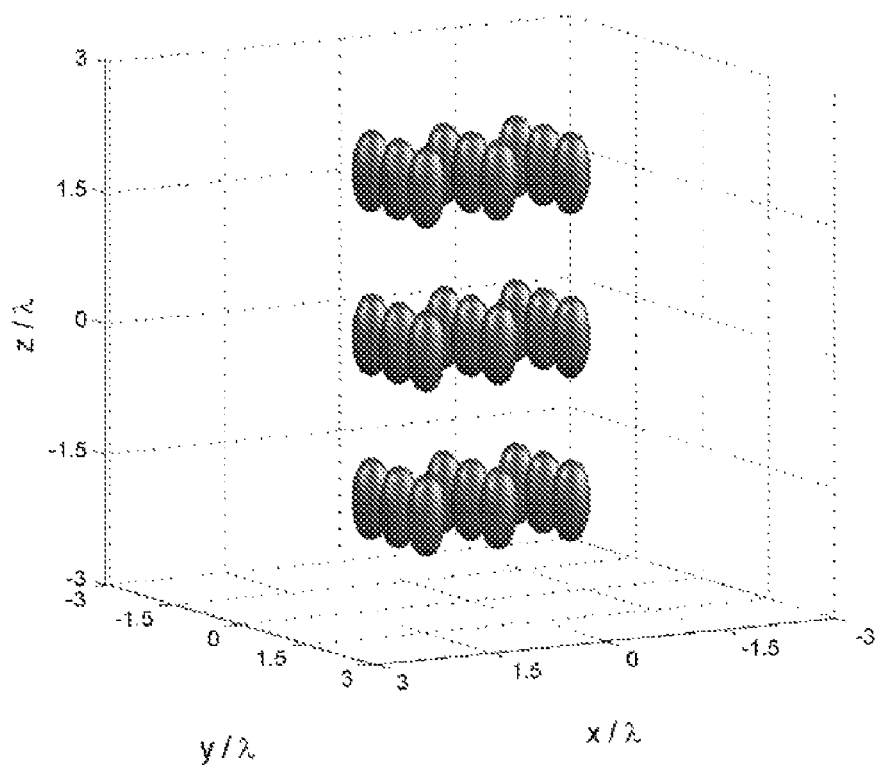
FIG. 21D is a three-dimensional plot of surfaces of light intensity having 50% of the maximum light intensity for a lattice constructed with the wavevectors shown in FIG. 21C.
Figure 21E:
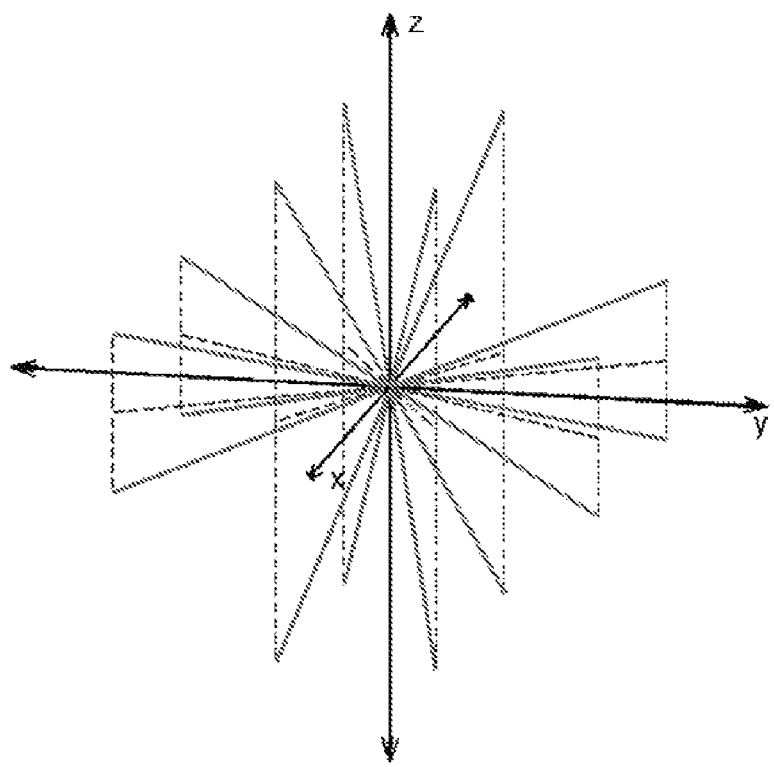
FIG. 21E is a three-dimensional representation of wavevector directions for the simple tetragonal composite lattice obtained by rotating the wavevectors of FIG. 21C 90° about the axis of the lattice and adding the rotated set of vectors to and unrotated set of vectors.
Figure 21F:
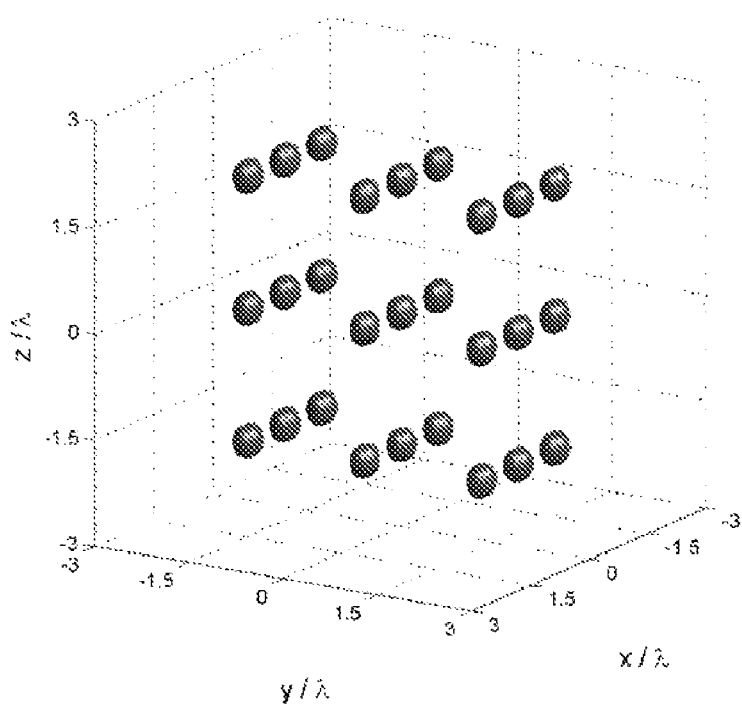
FIG. 21F is a three-dimensional plot of surfaces of light intensity having 50% of the maximum light intensity for a lattice constructed with the wavevectors of FIG. 21E.
Figure 21G:
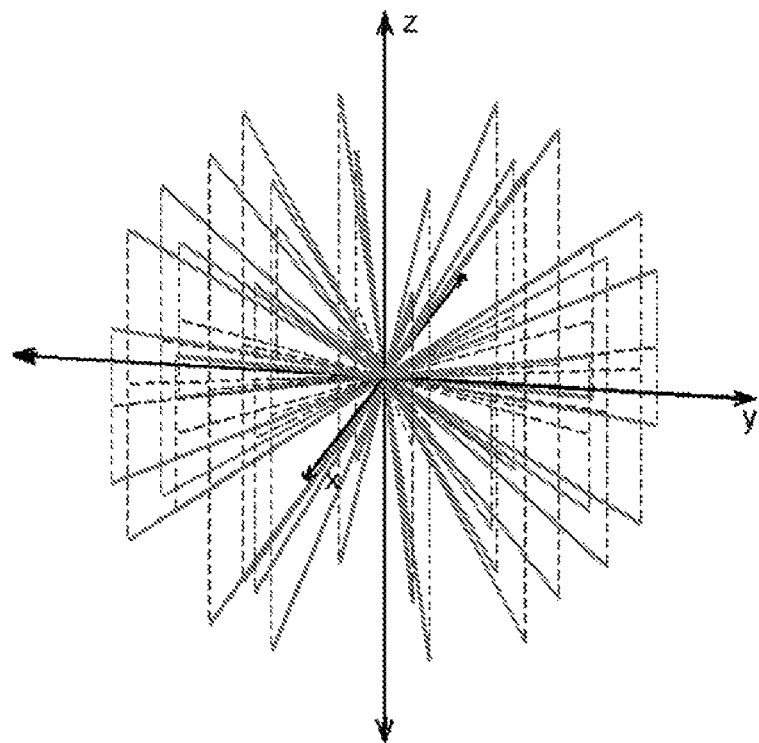
FIG. 21G is a three-dimensional representation of wavevector directions for the body-centered cubic lattice obtained by applying all 90° rotation operations about the three principal axes to the wavevector set of FIG. 21E.
Figure 21H:
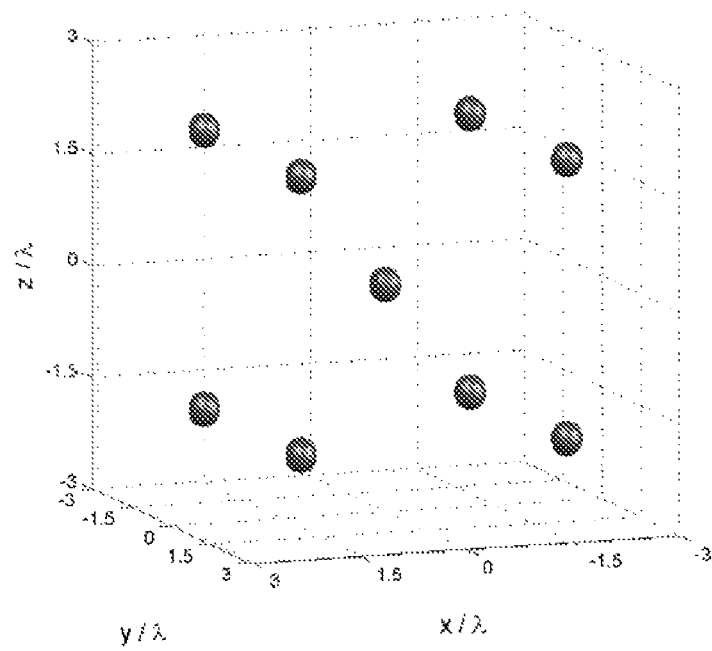
FIG. 21H is a three-dimensional plot of surfaces of light intensity having 50% of the maximum light intensity for a lattice constructed with the wavevectors of FIG. 21G.

The comparatively poor intensity confinement that then remains along the z-axis, as shown in FIG. 21D, can be rectified by superimposing an additional composite set upon the existing set (16 plane waves total as shown in FIG. 21D). The additional composite set can be obtained by rotating the existing set through 90° about the [100] axis of the lattice. The wavevectors that result from such a transformation are illustrated in FIG. 21E. However, as such a transformation is not orthorhombic invariant, the orthorhombic symmetry is destroyed thereby, and the result is a simple tetragonal composite lattice, as shown in FIG. 21F, for which the rotation is allowed. Continuing through all combinations of 90° rotations about the three principal axes, the 48 wavevectors for which are shown in FIG. 21G, similarly destroys the tetragonal symmetry of the composite lattice and eventually leads to the composite body-centered cubic structure shown in FIG. 21H, which has tightly-confined, widely-spaced intensity maxima.

Maximally Symmetric Composite Lattices

A composite lattice is referred to herein as a maximally symmetric composite lattice if it contains all of the unique wavevectors that can be obtained by applying every allowed symmetry transformation to a sparse lattice's D+1 original wavevectors. A maximally symmetric composite lattice exhibits the highest spatial frequency content and greatest basis symmetry for any optical lattice of its type. Of the five Bravais lattice types that can be formed in two dimensions, the hexagonal type has the most allowed symmetry operations and hence yields maximally symmetric composite lattices of the greatest intensity confinement and basis symmetry, as shown, for example, in FIG. 8D. Similarly, the hexagonal type three-dimensional lattice also yields maximally symmetric composite lattices of the greatest confinement and basis symmetry in the [001] plane. However, the greatest overall confinement and basis symmetry in all directions can be achieved by the three three-dimensional lattices of the cubic crystal group, since they permit the same reflection and rotation symmetry operations to be performed in or about all three principal planes. FIG. 10D shows a three-dimensional intensity plot for an exemplary maximally symmetric body-centered cubic lattice of the cubic crystal group.

Figure 22A:
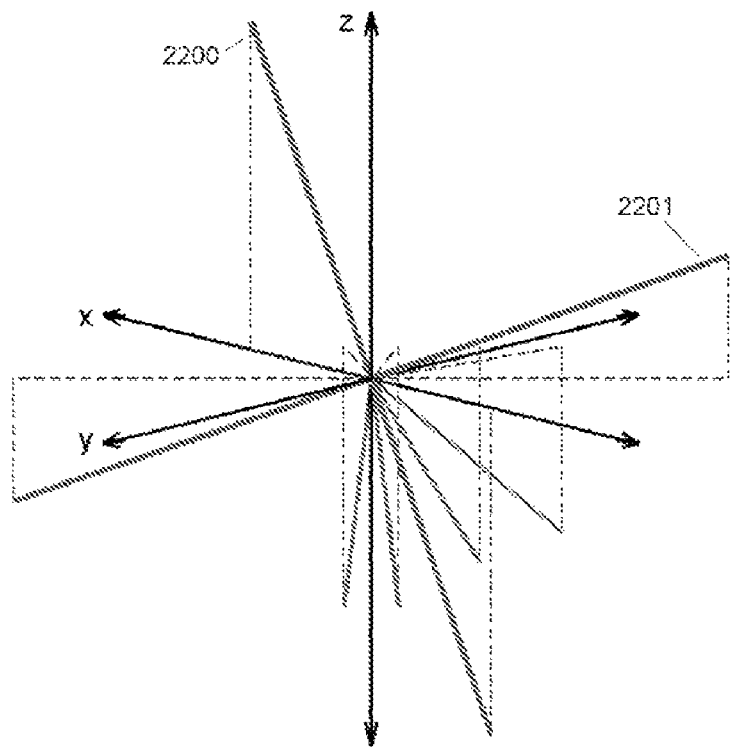
FIG. 22A is a three-dimensional representation of relative wavevector directions and axes of minimum and maximum spatial frequency for a body-centered cubic sparse lattice having an intensity period of $\sqrt{248}\lambda/2$.
Figure 22B:
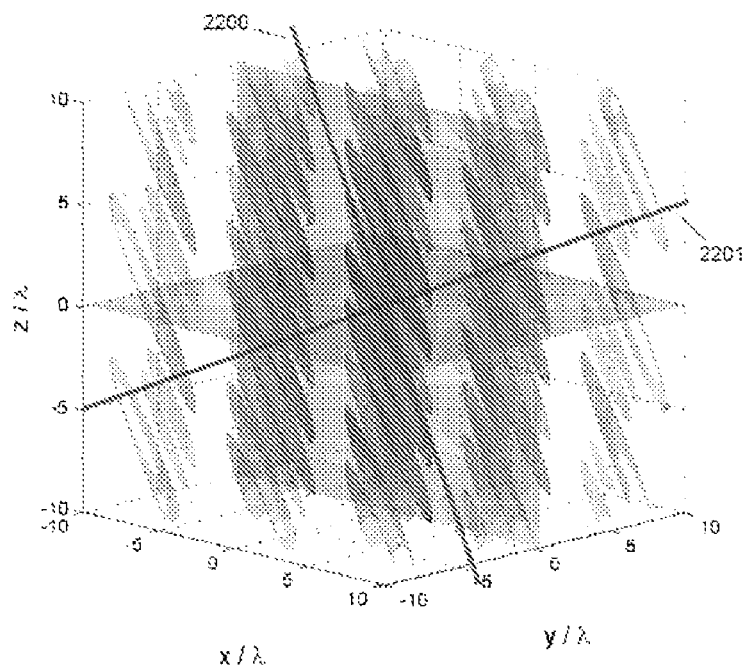
FIG. 22B is a three-dimensional plot of surfaces of light intensity having 50% of the maximum light intensity for a lattice having the wavevector distribution shown in FIG. 22A.
Figure 22C:
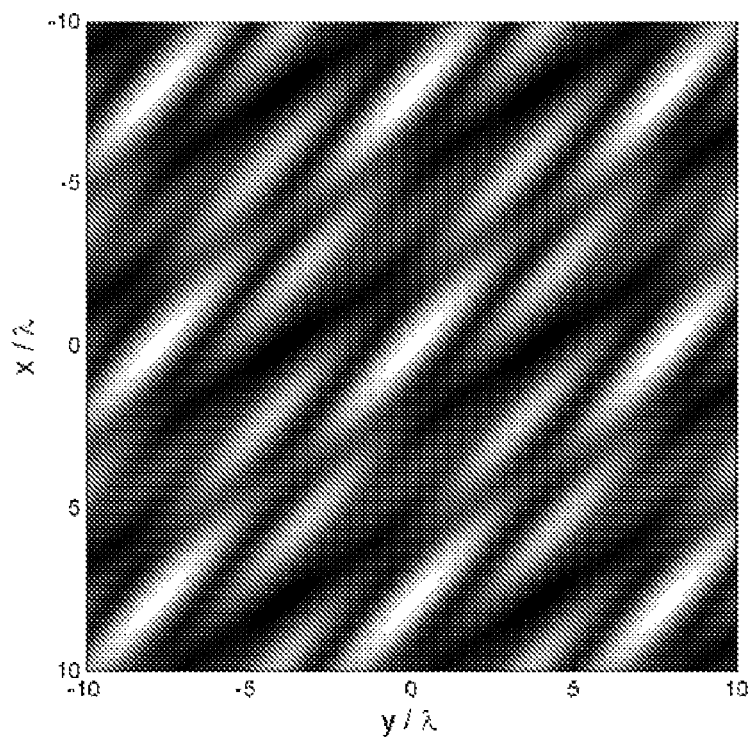
FIGS. 22C and 22D are linear grayscale images of the light intensity in the x-y and x-z planes, respectively, for the lattice formed from the wavevectors shown in FIG. 22A.
Figure 22D:
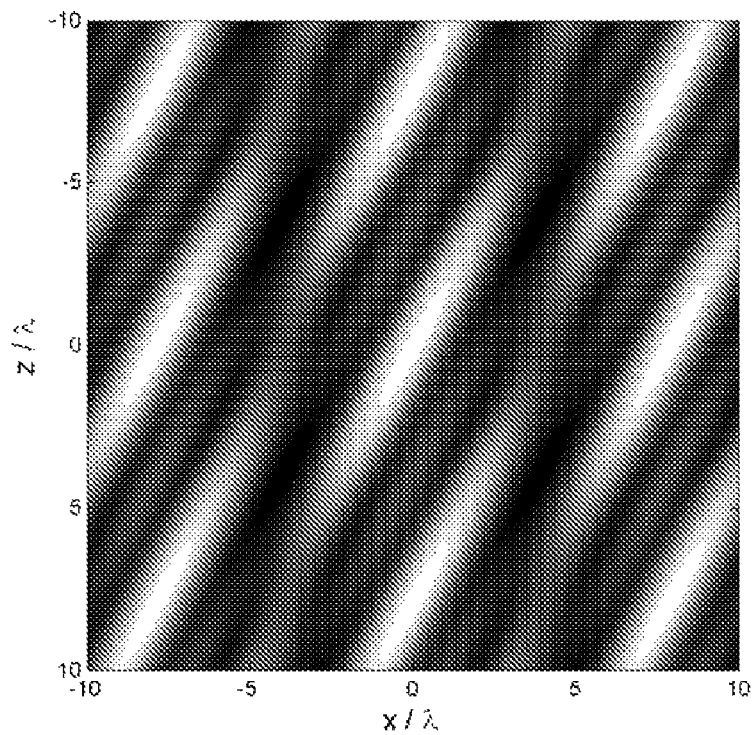
Figure 22E:
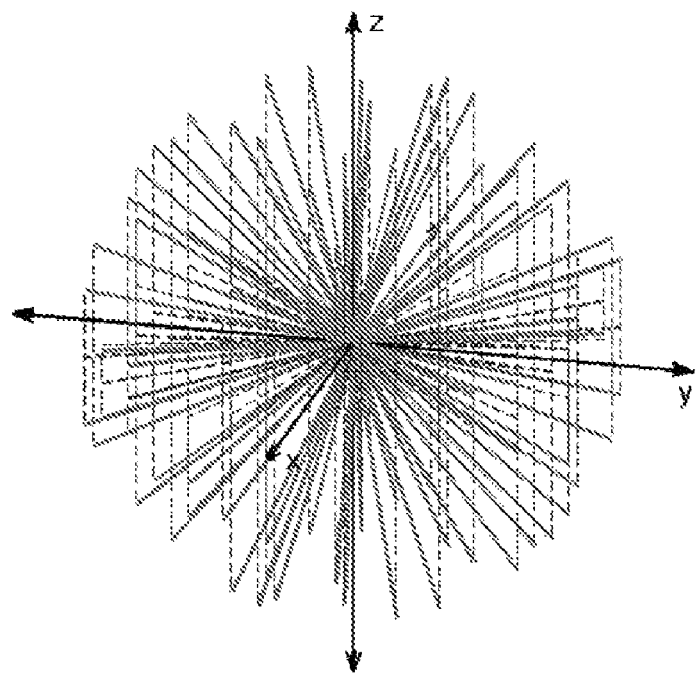
FIG. 22E is a three-dimensional representation of relative wavevector directions for a maximally symmetric lattice of the same body-centered cubic symmetry as shown as in FIGS. 22A, 22B, 22C, and 22D, and having an intensity period of $\sqrt{248}\lambda/2$.

Maximally symmetric cubic lattices can exhibit near-optimal three-dimensional confinement of the excitation at the intensity maxima of the lattice, even when the periodicity of the original sparse lattice is far greater than that of the fundamental lattice. FIGS. 22A, 22B, 22C, and 22D and FIGS. 22E, 22F, 22G, and 22H illustrate this trait for a particular body-centered cubic lattice by depicting a sparse lattice and its maximally symmetric composite lattice, respectively. For the sparse lattice shown in FIG. 22A, the confinement of the intensity maxima, $[(k_n - k_m) \cdot \hat{e}_j]_{max}$, varies from 0.057 k to 0.762 k along the axes, $\hat{e}_j = \hat{e}_{\Delta k \ min}$ 2200 and $\hat{e}_j = \hat{e}_{\Delta k \ max}$ 2201, leading to considerable asymmetry in the basis, which is depicted in FIGS. 22B, 22C, and 22D. The corresponding maximally symmetric composite lattice depicted in FIGS. 22E, 22F, 22G, and 22H has 96 plane waves propagating over a much greater range of directions, so its excitation confinement exhibits less variation (1.78 k to 2.00 k) and more closely approaches the theoretical maximum of 2k in all directions.

Consequently, the selection of maximally symmetric square or hexagonal lattices can be especially appropriate for two-dimensional microscopy applications where a basis is selected to form a confined intensity maximum within each primitive cell. Likewise, the selection of maximally symmetric two-dimensional cubic or hexagonal lattices can be especially appropriate for analogous three-dimensional microscopy applications.

Subset Lattices

Occasionally, however, constraints other than excitation confinement can be of paramount concern in the selection of an optical lattice (e.g., arrangement of the excitation/detection optics, optimization of polarization in a specific direction within the basis). In such circumstances, it can be desirable to select a lattice having a different symmetry, different aspect ratios, and/or having fewer plane waves relative to the maximally symmetric composite lattice of any given type. The latter non-maximally symmetric lattices are referred to herein as subset lattices, as long as they still consist of N>D+1 plane waves, because they are formed by a composite subset of waves from a maximally symmetric composite set.

Design and Construction of the Basis for an Optical Lattice

To apply optical lattices to optical microscopy, it is necessary to identify not only the appropriate lattice types for a given application and the wavevector sets, $\{k_n\}$, with which they can be produced, but also design an appropriate basis field, $e(x,t)$, (which, after all, will ultimately determine the relationship between the sample of interest and the multidimensional images obtained) for the application. As stated previously, this basis field, $e(x,t)$, depends on both the complex electric field, $e_n$, and the wavevector, $k_n$, of every plane wave that contributes to a given lattice.

Figure 22F:
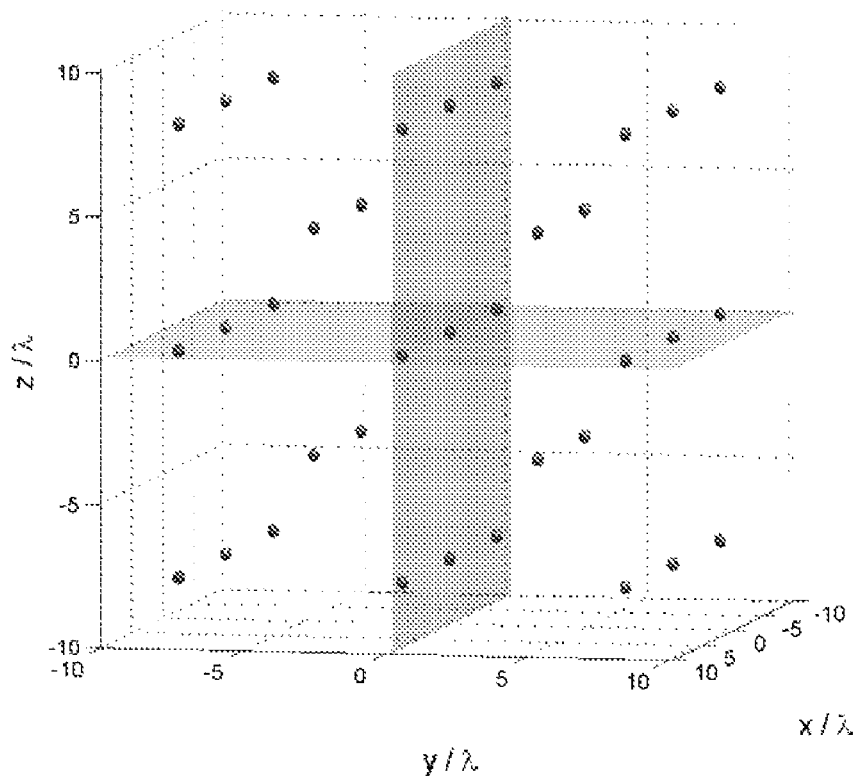
FIG. 22F is a three-dimensional plot of surfaces of 50% of maximum intensity for a lattice with the wavevector distribution shown in FIG. 22E.
Figure 22G:
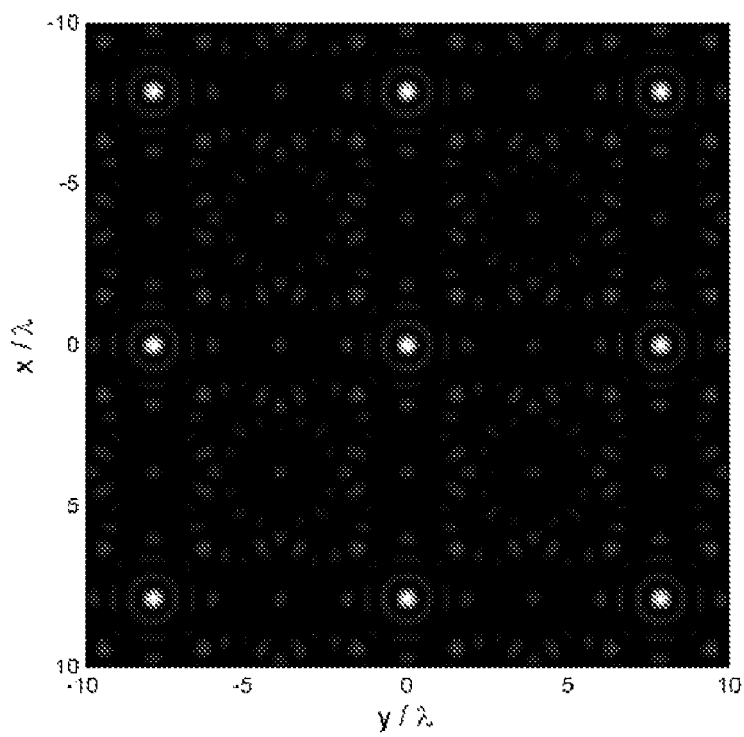
FIGS. 22G and 22H are linear grayscale images of the light intensity in the x-y and x-z planes, respectively, for the lattice formed from the wavevectors shown in FIG. 22F.
Figure 22H:
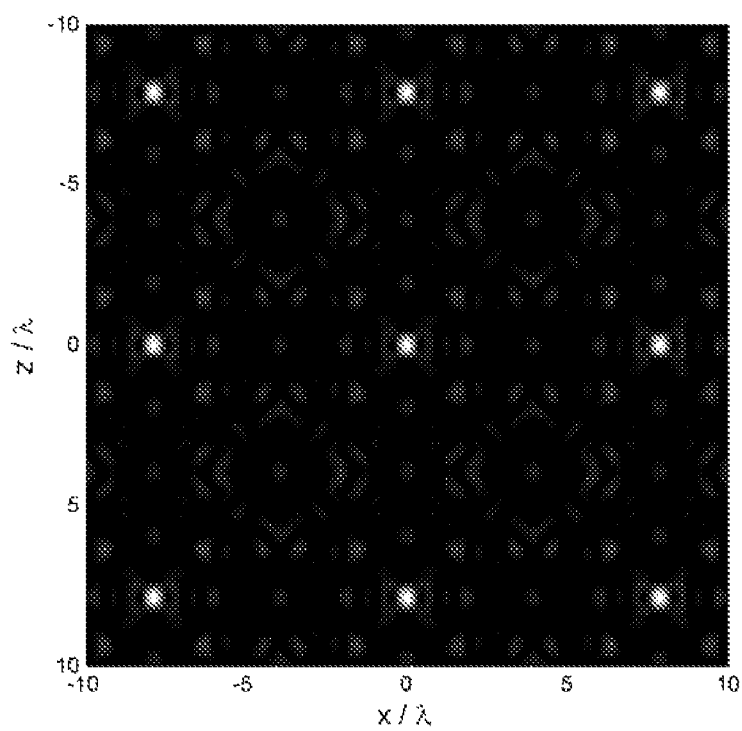

The Basis of Maximal Intensity with Optimized Polarization at a Single Point One specific basis useful for optical microscopy consists of a single dominant, tightly confined intensity maximum within each primitive cell as exemplified by the lattices shown in FIG. 8D, FIG. 10D, and FIG. 22F. This basis as applied to any lattice can serve as a multi-point excitation field for massively parallel multifocal microscopy. Thus, an entire two- or three-dimensional region spanning many periods of the lattice within a sample of interest can be imaged by scanning the lattice and basis relative to the sample over only the dimensions of one primitive cell. In contrast, a confocal microscope imaging the same region would be required to scan over the entire region sequentially.

It is also useful for optical microscopy to control the polarization properties of the basis field, $e(x,t)$. Either alone or in combination with polarization sensitive detection, such control can yield additional insights into the nature of reflective, absorptive, or scattering samples. Furthermore, the absorption of light by molecular markers (e.g., fluorescent molecules) within biological systems, and thus the ultimate signal comprising an image, can depend upon the orientations of these molecules relative to the polarization of the excitation light. Thus, control of the polarization of the excitation light can yield information concerning the former.

A basis can be created satisfying the twin goals of having concentrated intensity at a single point and having substantial control of the polarization at this same point by maximizing a particular desired electric field state, $e_d(x_d,t_d) \equiv e_d$, defined with respect to a unit vector, $\hat{e}_p$, at a given time, $t_d$, and a selected point, $x_d$, within the primitive cell. Considering each constituent plane wave individually, $\hat{e}_p$ and $k_n$ together define a natural orthonormal coordinate system, $\{\hat{e}_{kn}, \hat{e}_{pkn\perp}, \hat{e}_{kn\perp}\}$, for representing $e_n(x,t)$ as:

$$e_n(x,t) = e_n[\cos\chi\exp(i\theta)\hat{e}_{kn\perp} + \sin\chi\exp(i\psi)\hat{e}_{pkn\perp}]\exp[i(k_n\cdot x - \omega t)], \quad (20)$$

where $0 \leq \chi \leq \pi/2$, $-\pi \leq \theta \leq \pi$, $-\pi \leq \phi \leq \pi$, and:

$$\hat{e}_{kn} = k_n/|k_n|, \quad (21a)$$

$$\hat{e}_{pkn\perp} = (\hat{e}_p \times \hat{e}_{kn})/\sin\Omega_n \quad (21b)$$

$$\hat{e}_{kn\perp} = \hat{e}_{kn} \times \hat{e}_{pkn\perp} = (\hat{e}_p - \cos\Omega_n\hat{e}_{kn})/\sin\Omega_n \quad (21c)$$

$$\Omega_n = \cos^{-1}(\hat{e}_p \cdot \hat{e}_{kn}), \text{ and} \quad (21d)$$

$$\hat{e}_{kn\perp} \cdot \hat{e}_p = \sin\Omega_n. \quad (21e)$$

Equation (20) exploits the orthogonality condition expressed in Equation (5). Similarly, $e_d$ can be represented in the related orthonormal coordinate system $\{\hat{e}_p, \hat{e}_{pkn\perp}, \hat{e}_{p\perp}\}$ as:

$$e_d = (\hat{e}_p \cdot e_d)\hat{e}_p + (\hat{e}_{pkn\perp} \cdot e_d)\hat{e}_{pkn\perp} + (\hat{e}_{p\perp} \cdot e_d)\hat{e}_{p\perp} \quad (22)$$

where:

$$\hat{e}_{p\perp} = \hat{e}_{pkn\perp} \times \hat{e}_p = (\hat{e}_{kn} - \cos\Omega_n\hat{e}_p)/\sin\Omega_n, \quad (23a)$$

$$\hat{e}_{kn\perp} \cdot \hat{e}_{p\perp} = \cos\Omega_n \quad (23b)$$

The unit vector, $\hat{e}_{pkn\perp}$, common to both coordinate systems lies along the intersection of the planes orthogonal to $\hat{e}_p$ and $\hat{e}_{kn}$, and $\Omega_n$ is the angle between $\hat{e}_p$ and $\hat{e}_{kn}$.

Since the physical electric field is given by the real part of $e_n(x,t)$, $e_d$ can be maximized by finding the value of $e_n$ for each plane wave, consistent with Equation (5), that maximizes the projection of $e_n(x,t)$ at $x_d$ and $t_d$ onto $e_d$ (i.e., $Re\{e_n^*(x_d,t_d)' \cdot e_d\}$). By manipulating Equations (20)-(23), it can be shown that:

$$Re\{e_n^*(x_d,t_d)' \cdot e_d\} = Re\{[\sin\Omega_n(\hat{e}_p \cdot e_d) - \cos\Omega_n(\hat{e}_{p\perp} \cdot e_d)] \\ [e_n^*(x_d,t_d) \cdot \hat{e}_{kn\perp}] + (\hat{e}_{pkn\perp} \cdot e_d)[e_n^*(x_d,t_d) \cdot \hat{e}_{pkn\perp}]\} \quad (24)$$

As a result, the selection of this basis can be reduced to the matter of finding the components of $e_n(x_d,t_d)$ (and thus $e_n$) along $\hat{e}_{pkn\perp}$ and $\hat{e}_{kn\perp}$ that maximize the quantity represented in Equation (24).

Maximal Intensity with Optimized Linear Polarization

An example that can help to explain the process of finding the plane wave fields $e_n$ that optimize the $e_d$ component of the basis, $e(x,t)$, at the position, $x_d$, and the time, $t_d$, involves maximizing the linear polarization of $e(x_d,t_d)$ in a desired direction $\hat{e}_p$. For such a case:

$$e_d = E\hat{e}_p, \quad (25)$$

which, when taken in conjunction with Equation (20) and Equation (24), yields:

$$Re\{e_n^*(x_d,t_d)' \cdot e_d\} = e_n E \sin\Omega_n \cos\chi \cos(k_n \cdot x_d - \omega t_d + \theta) \quad (26)$$

Since $\Omega_n$ is fixed in Equation (21d), the expression in Equation (26) is maximized for $\chi=0$ and $\theta=-(k_n \cdot x_d - \omega t_d)$. Thus, in light of Equation (20):

$$e_n(x,t) = e_n\hat{e}_{kn\perp}\exp[i(k_n \cdot (x-x_d) - \omega(t-t_d))] \text{ (where } e_d \text{ is linear)} \quad (27)$$

Figure 23:
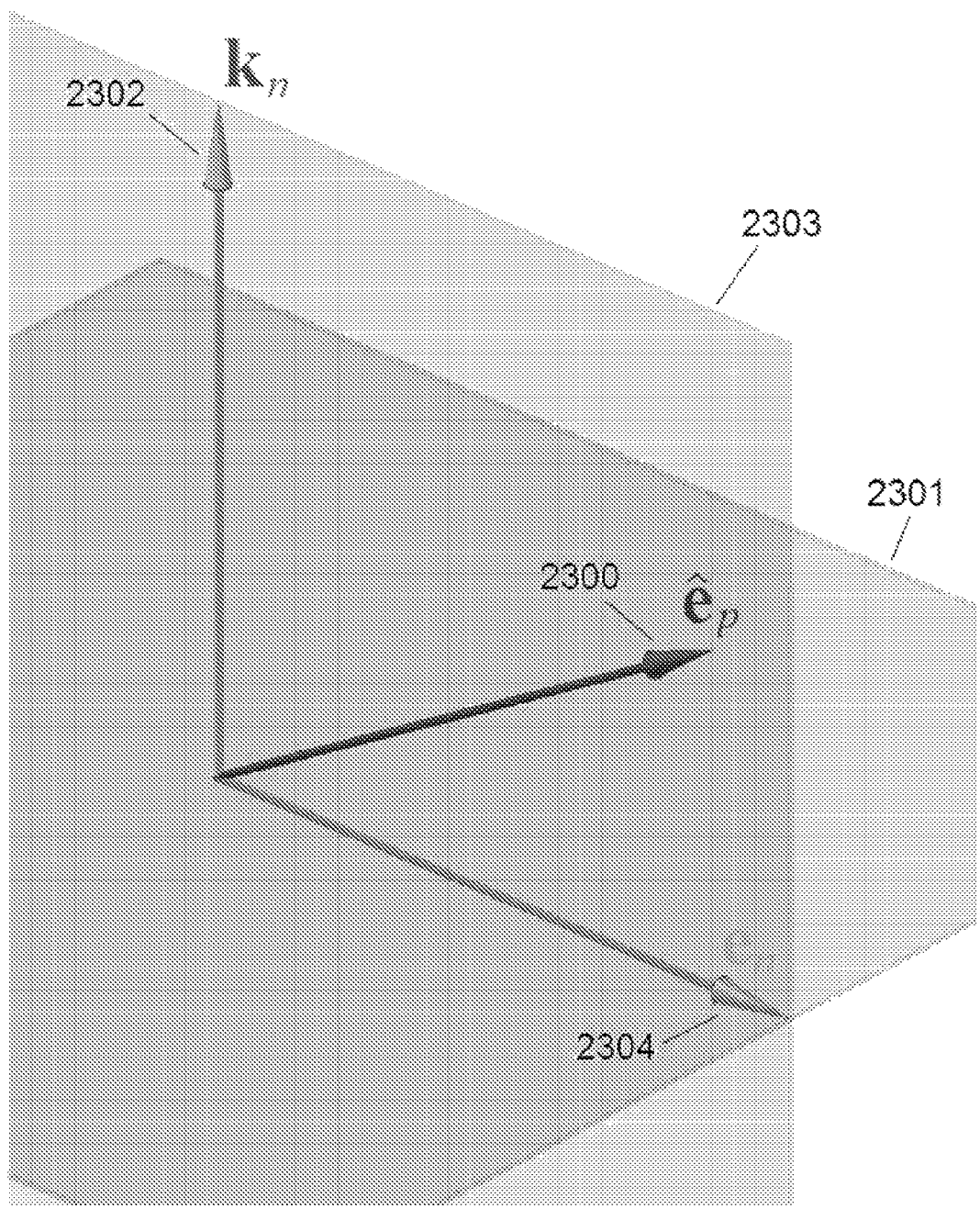
FIG. 23 is a three-dimensional representation of the relative wavevector and electric field directions for a plane wave that optimize the projection of the latter in a desired direction $\hat{e}_p$.

As represented geometrically in FIG. 23, Equation (27) thus implies that linear polarization along the $\hat{e}_p$ axis 2300 is maximized when: (1) each plane wave is linearly polarized along the axis defined by the intersection of the plane 2301 that is perpendicular to the wavevectors, $k_n$, 2302 and the plane 2303 on which $\hat{e}_p$ and $k_n$ both lie; and (2) the phase is selected so that the real part of the field, $e_n$, 2304 is a maximum at $x_d$ and $t_d$.

To conclude this basis-selection example, the relative plane wave amplitudes $e_n$ must still be selected. This can be accomplished in practice simply by only selecting plane waves of equal amplitude, such that:

$$e_n = e_o\hat{e}_{kn\perp}\exp[-i(k_n \cdot x_d - \omega t_d)], \text{ and, for } e_d \text{ linear,} \\ |e_n| = e_o. \quad (28)$$

Figure 24A:
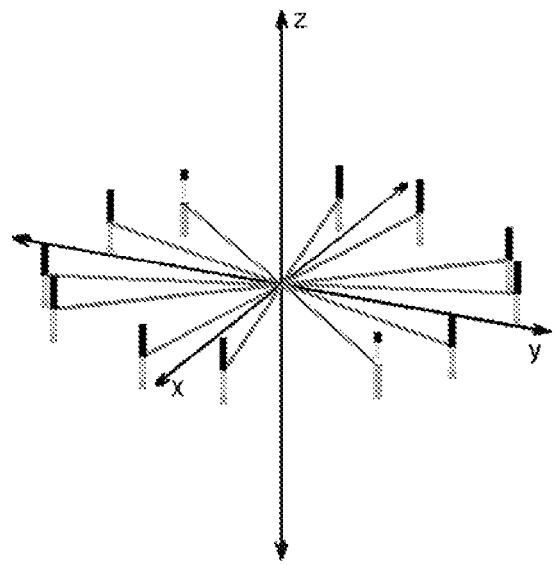
FIG. 24A is a three-dimensional representation of the relative wavevector and electric field directions and real field magnitudes at different times for the plane waves that make up the lattice and basis shown in FIG. 8D.
Figure 24B:
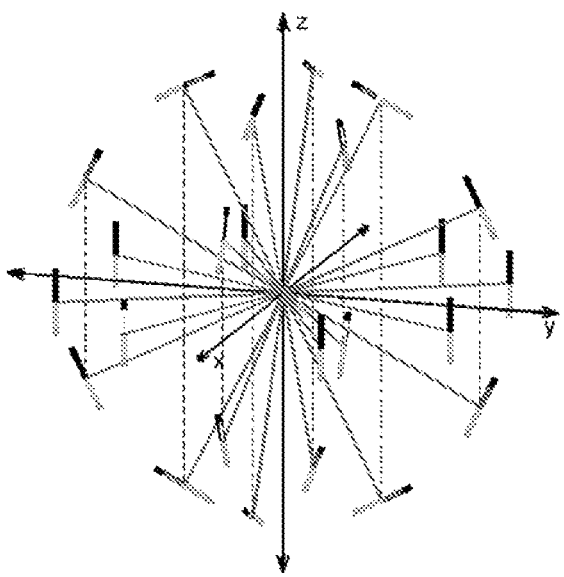
FIG. 24B is a three-dimensional representation of the relative wavevector and electric field directions and real field magnitudes at different times for the plane waves that make up the lattice and basis shown in FIG. 10D.
Figure 24C:
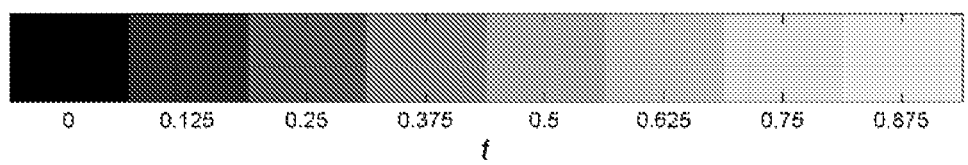
FIG. 24C is a key relating the time within one period of oscillation of the total field to the grayscale shading of the field vectors shown in FIGS. 24B and 24C, and all other figures of this type shown herein.
Figure 25A:
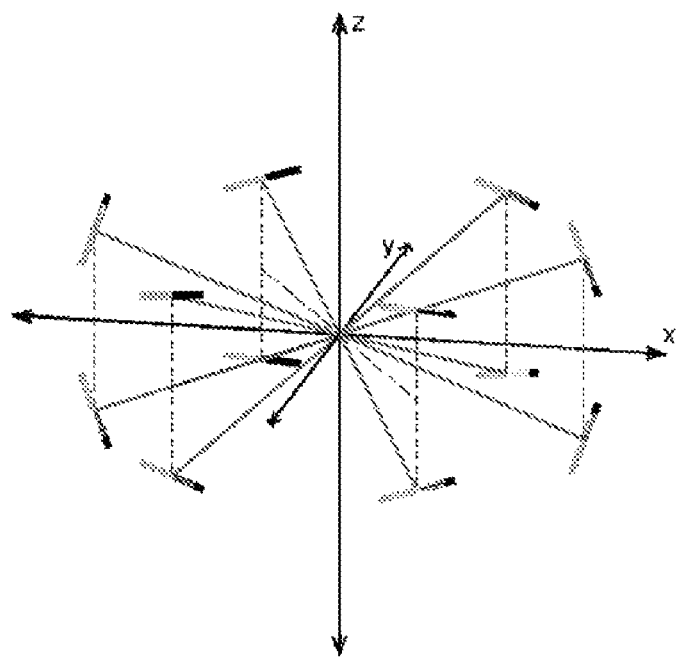
FIG. 25A is a three-dimensional representation of the relative wavevector and electric field directions and real field magnitudes at different times for the plane waves that make up a particular maximally symmetric three-dimensional hexagonal lattice, with a basis chosen to optimize the x-polarization at a point in the primitive cell.
Figure 25B:
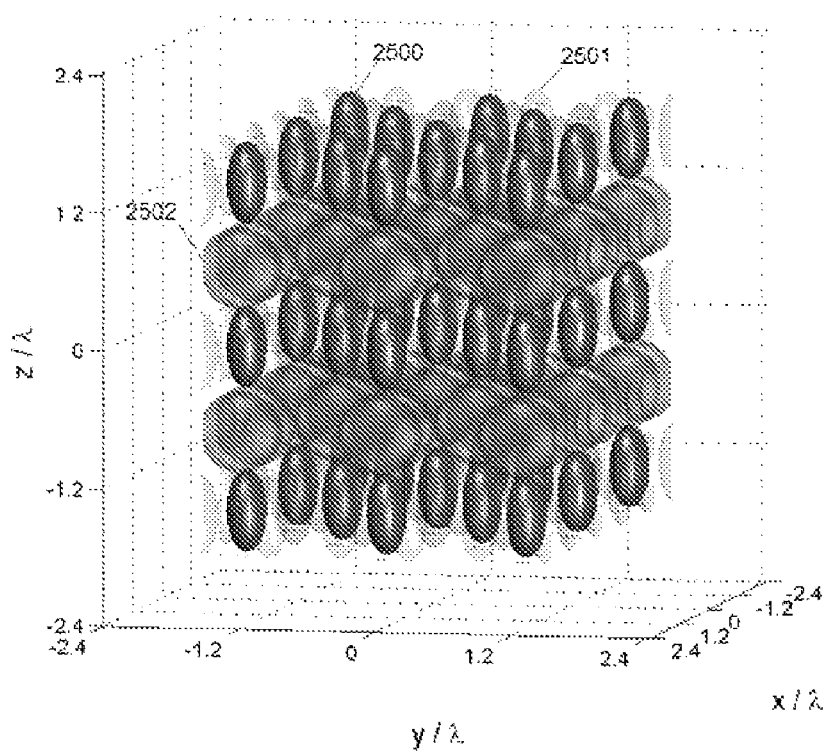
FIG. 25B is a three-dimensional plot of surfaces of light intensity having 50% of the maximum light intensity for each of the individual field components $e(x) \cdot \hat{e}_x$ (opaque), $e(x) \cdot \hat{e}_y$ (light translucent), and $e(x) \cdot \hat{e}_z$ (medium translucent) of the hexagonal lattice and basis obtained with the plane wave properties given in FIG. 25A.
Figure 25C:
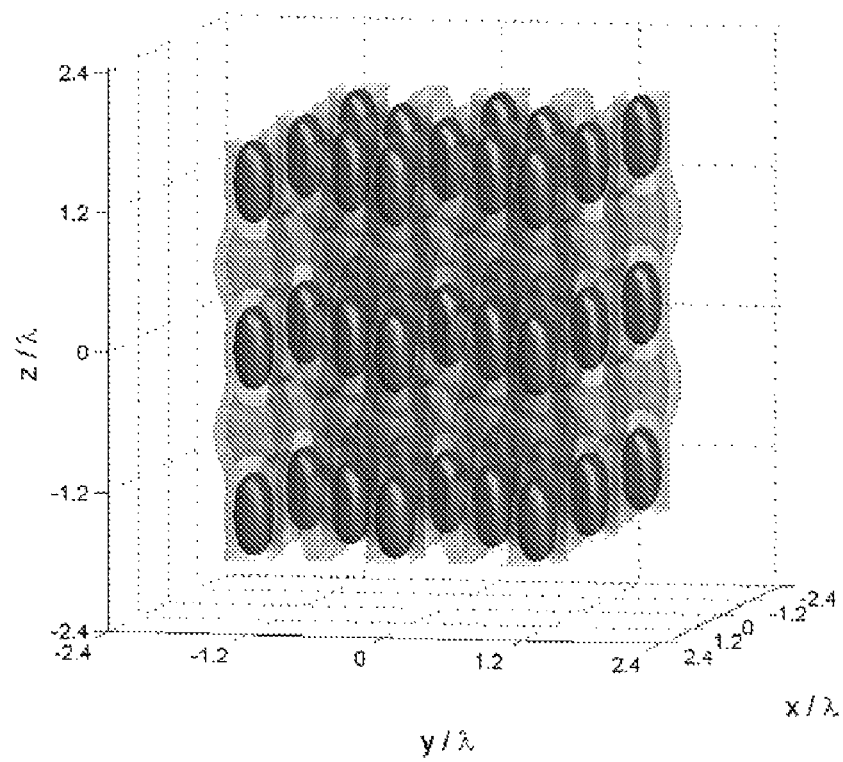
FIG. 25C is a three-dimensional plot of surfaces of 20% (translucent) and 50% (opaque) of the total intensity $|e(x)|^2$ for the lattice and basis of FIGS. 25A and 25B.
Figure 25D:
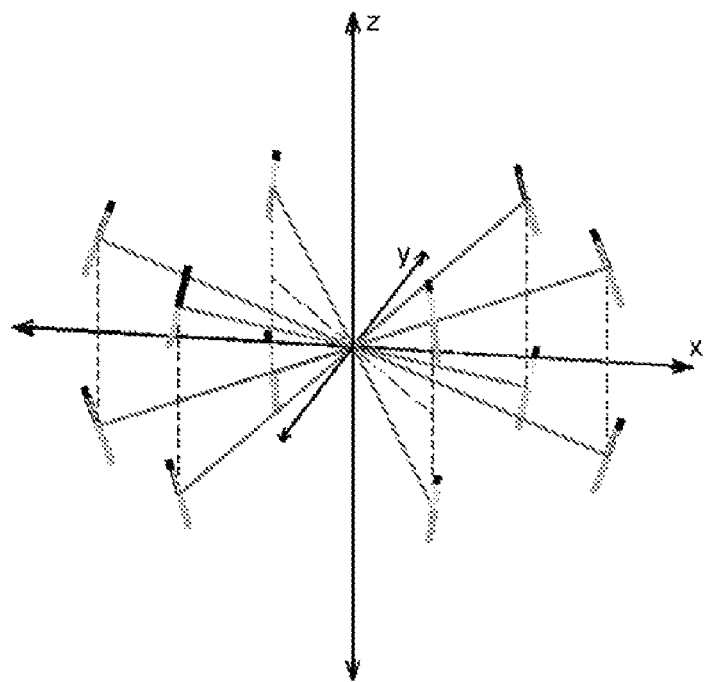
FIG. 25D is a three-dimensional representation of the relative wavevector and electric field directions and real field magnitudes at different times for the plane waves that make up the same maximally symmetric three-dimensional hexagonal lattice as in FIGS. 25A, 25B, and 25C, with a basis chosen to optimize the z-polarization at a point in the primitive cell.
Figure 25E:
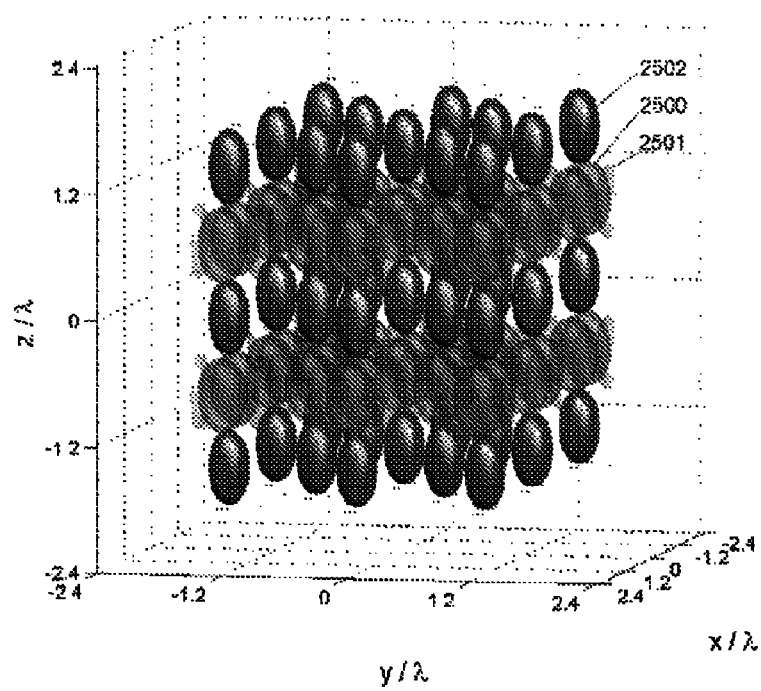
FIG. 25E is a three-dimensional plot of surfaces of light intensity having 50% of the maximum light intensity for each of the individual field components $e(x) \cdot \hat{e}_x$ (medium translucent), $e(x) \cdot \hat{e}_y$ (light translucent), and $e(x) \cdot \hat{e}_z$ (opaque) of the hexagonal lattice and basis obtained with the plane wave properties given in FIG. 25D.
Figure 25F:
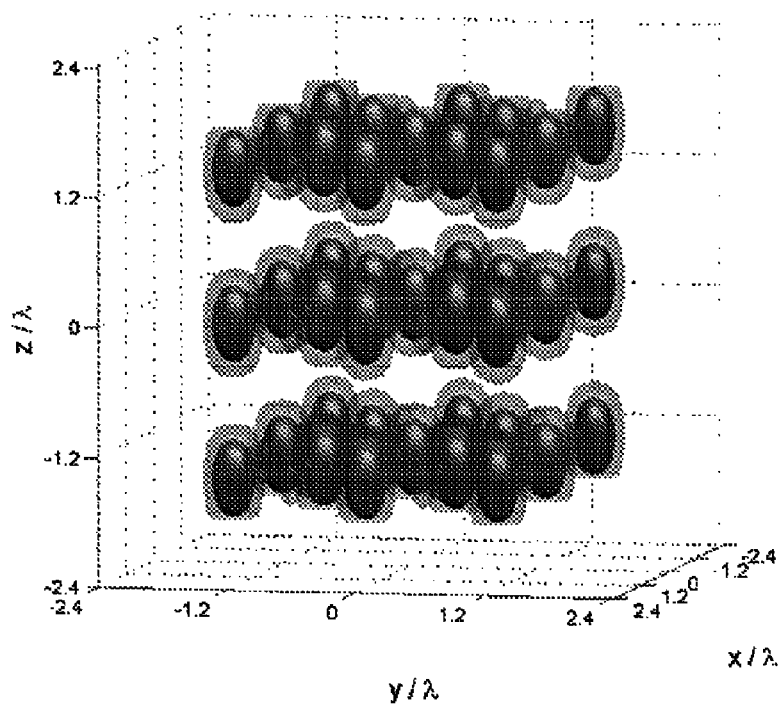
FIG. 25F is a three-dimensional plot of surfaces of 20% (translucent) and 50% (opaque) of the total intensity $|e(x)|^2$ for the lattice and basis of FIGS. 25D and 25E.
Figure 26A:
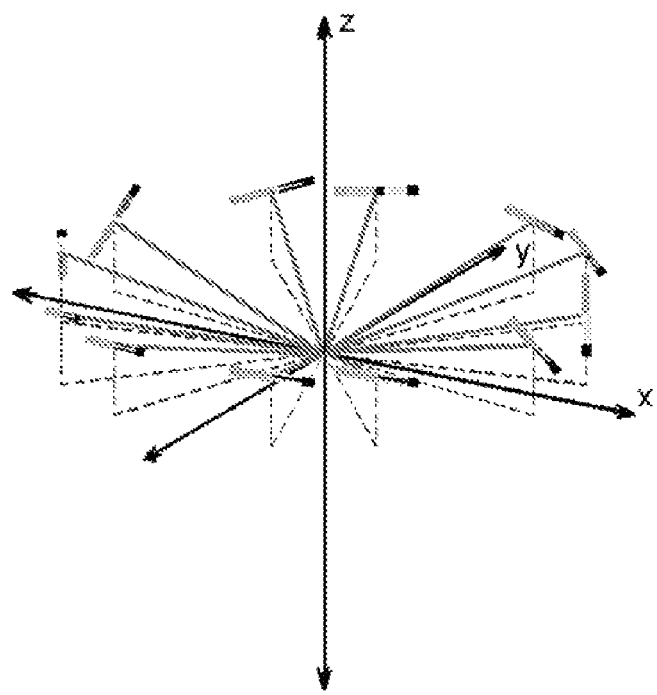
FIGS. 26A and 26C are three-dimensional representations of the relative wavevector and electric field directions and real field magnitudes at different times for the plane waves that make up the two-dimensional hexagonal lattices and bases identical to that in FIGS. 11A and 24A, except that all wavevectors are on cones of half angles 60° and 45°, respectively.
Figure 26B:
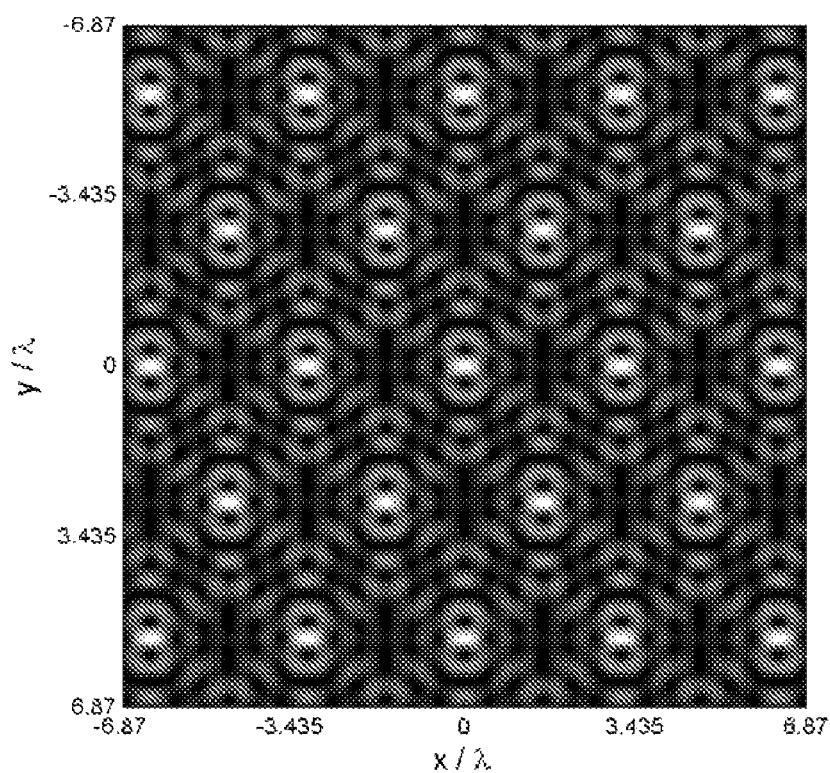
FIGS. 26B and 26D are linear grayscale images of the corresponding lattices for these 60° and 45° cases show in FIGS. 26A and 26C, respectively.
Figure 26C:
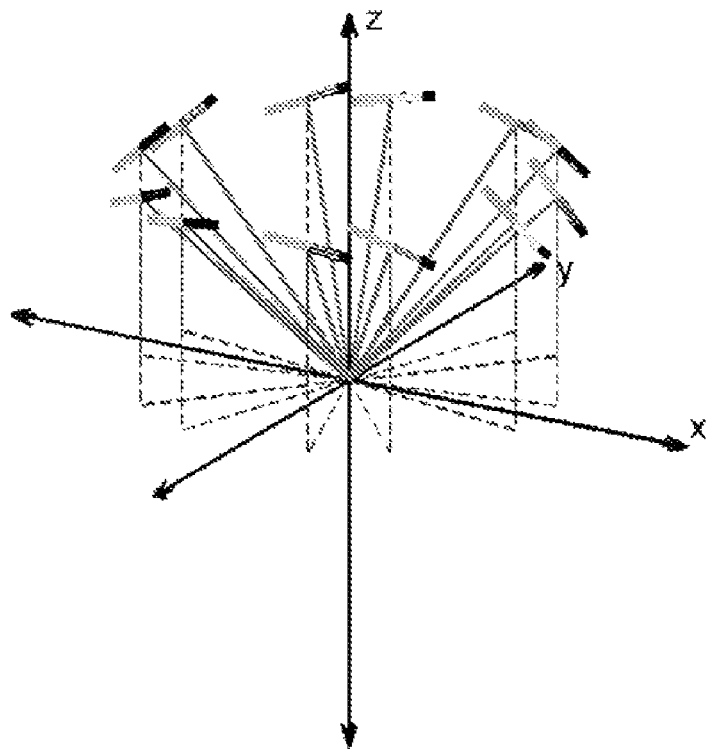
Figure 26D:
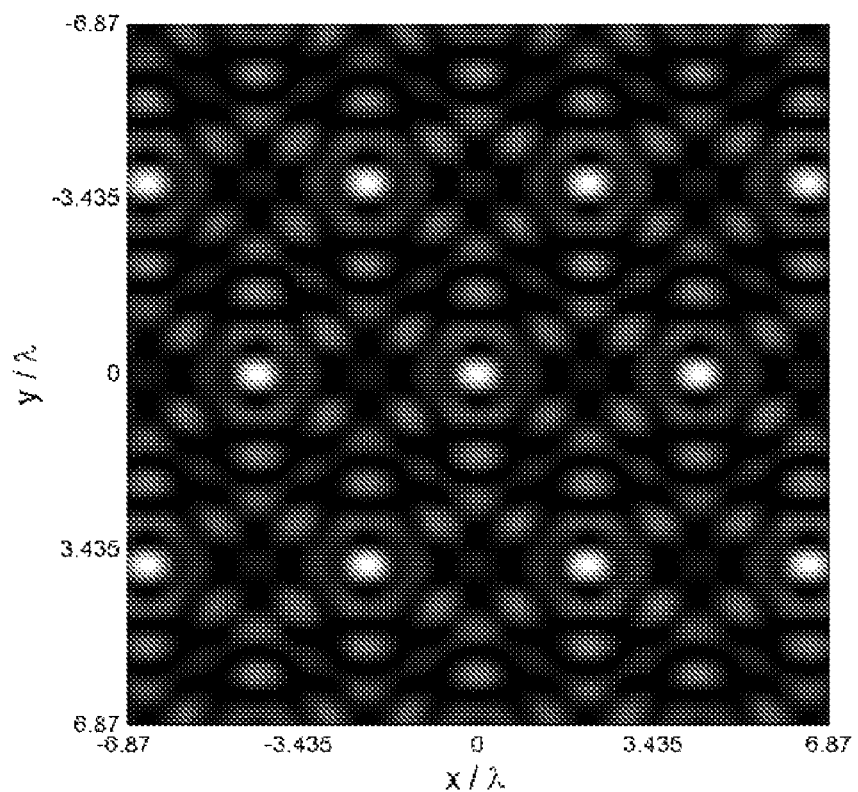

The resulting basis can have a strong intensity maximum at $x=x_d$ within the primitive cell and good contrast with respect to the background intensity elsewhere in the cell, as is the case for the examples shown in FIG. 8D and FIG. 10D. For these examples, the corresponding wavevectors, $k_n$, and the electric field vectors, $e_n(x_d,t)$, are shown in FIG. 24A and FIG. 24B, respectively at eight different times $t_q = t_d + 2\pi q/8\omega$, $q=0 \ldots 7$. The length of each field vector is proportional to its real amplitude at the time, $t_q$. FIG. 24C shows a key relating the time, $t_q$, to the grayscale shade of each field vector for all plots of this type.

Because of the requirement that $k_n \cdot e_n = 0$, the strength of the intensity maxima for the particular basis represented by Equation (28) depends upon the lattice type and its distribution of wavevectors, $k_n$, with the strongest maxima occurring for lattices having $k_n$ more nearly orthogonal to $\hat{e}_p$. The polarization purity at the maxima and the likely intensity contrast elsewhere in the primitive cell also depend upon these same factors. FIG. 8D and FIG. 11A illustrate these points, as FIG. 8D shows strong intensity maxima and high contrast with $\hat{e}_p=\hat{e}_z$ perpendicular to the plane of all $k_n$, and FIG. 11A shows weaker maxima and reduced contrast with $\hat{e}_p=\hat{e}_x$ parallel to the plane of all $k_n$.

FIG. 25 illustrates a similar example for a three-dimensional hexagonal lattice (with $\xi=2$). For $\hat{e}_p\|\hat{e}_x\equiv[100]$, as illustrated in FIG. 25A-C, the directions of the fields, $e_n$, vary sufficiently such that the relative intensities of the field components, $|e(x)\cdot\hat{e}_x|^2$ 2500, $|e(x)\cdot\hat{e}_y|^2$ 2501, and $|e(x)\cdot\hat{e}_z|^2$ 2502 are only $(|e(x)\cdot\hat{e}_x|^2)_{max}/(|e(x)\cdot\hat{e}_y|^2)_{max}\approx 6.08$ and $(|e(x)\cdot\hat{e}_x|^2)_{max}/(|e(x)\cdot\hat{e}_z|^2)_{max}\approx 3.07$, leading to reduced contrast in the overall intensity $|e(x)|^2$. On the other hand, as illustrated in FIGS. 25D-F, for $\hat{e}_p\|\hat{e}_z\equiv[001]$, the field directions, $e_n$, are more nearly aligned, yielding $(|e(x)\cdot\hat{e}_z|^2)_{max}/(|e(x)\cdot\hat{e}_x|^2)_{max}=(|e(x)\cdot\hat{e}_z|^2)_{max}/(|e(x)\cdot\hat{e}_y|^2)_{max}\approx 21.3$, and superior overall contrast.

When the basis represented by Equation (28) is considered in conjunction with Equation (3) and Equation (21), the following result is implicated:

$$e(x_p, t) \cdot \hat{e}_p = \text{Re}\left\{e_o \sum_{n=0}^{N} \sin\Omega_n \exp[i(kx_p\cos\Omega_n - i\omega t + \varphi_n)]\right\} \quad (29)$$

Specifically, when a basis is selected with plane waves of equal amplitude, the highest spatial frequencies along the axis, $\hat{e}_p$, have the least contribution to the total confinement of the intensity maxima. This characteristic is depicted in FIG. 10D, where, despite the symmetric wavevector distribution represented by FIG. 24B, the intensity maxima are less confined along the desired polarization direction. This characteristic can be compensated for by altering the aspect ratio of the optical lattice, where such alteration is permitted by the Bravais symmetry, to increase the wavevector components, $k_n\cdot\hat{e}_p$, along the desired polarization direction. However, as explained above, such alteration will simultaneously reduce the polarization purity and intensity contrast.

Conversely, the polarization purity and the intensity contrast can be improved at the expense of the spatial frequency distribution and the resulting confinement. FIG. 26 illustrates such a scenario, where the wavevector cone angle of the two-dimensional lattice depicted in FIG. 11A is reduced in order to increase the projection of each constituent plane wave field, $e_n$, in a desired direction, $\hat{e}_p\|\hat{e}_x$. Thus, for a lattice with the basis represented by Equation (28), a trade-off occurs between the linear polarization purity and the degree of confinement along the polarization axis. The appropriate balance between the polarization purity and the degree of confinement can be selected on a case-by-case basis in light of the needs of each particular microscopy application.

For any two-dimensional lattice, there exists a particularly symmetric basis of linear polarization wherein $\hat{e}_p$ is along the axis of the cone on which all the constituent wavevectors lie. As a result, all spatial frequencies, $k_m-k_n$, contribute equally to the superposition in Equation (3). In the limit where all the wavevectors lie in a single plane, the highest possible confinement of the intensity maxima within the plane can be achieved, along with excellent contrast, by selecting the basis of Equation (28) with $\hat{e}_p$ perpendicular to the plane. This is the case because, as shown in FIG. 8D, all plane waves exhibit optimal constructive interference at such maxima.

The confinement for a basis of predominately linear polarization can also be improved, as suggested by Equation (29), by selecting plane waves of amplitude $e_n=e_o/\sin\Omega_n$ so that the projection $e_n\cdot\hat{e}_p$ of each plane wave field is identical:

$$e_n=(e_o/\sin\omega_n)\hat{e}_{kn\perp}\exp[-i(k_n\cdot x_d-\omega t_d)] \text{ (for } e_d \text{ linear,}$$
$$|e_n|=e_o/\sin\Omega_n) \quad (30)$$

Figure 27A:
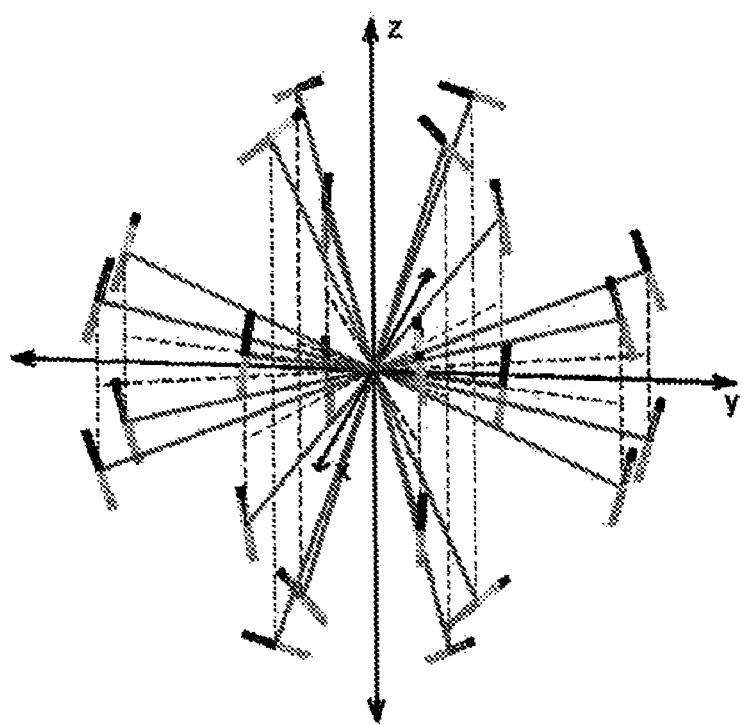
FIGS. 27A and 27C are three-dimensional representations of the relative wavevector and electric field directions and real field magnitudes at different times for the plane waves that comprise a simple cubic lattice of intensity period $\sqrt{11}\lambda/2$, each with a basis chosen to maximize the z-component of the total field at a given point in the primitive cell, but with equal plane wave amplitudes $|e_n|$ in FIG. 27A, and equal projections $|e_n \cdot \hat{e}_z|$ in FIG. 27C.
Figure 27B:
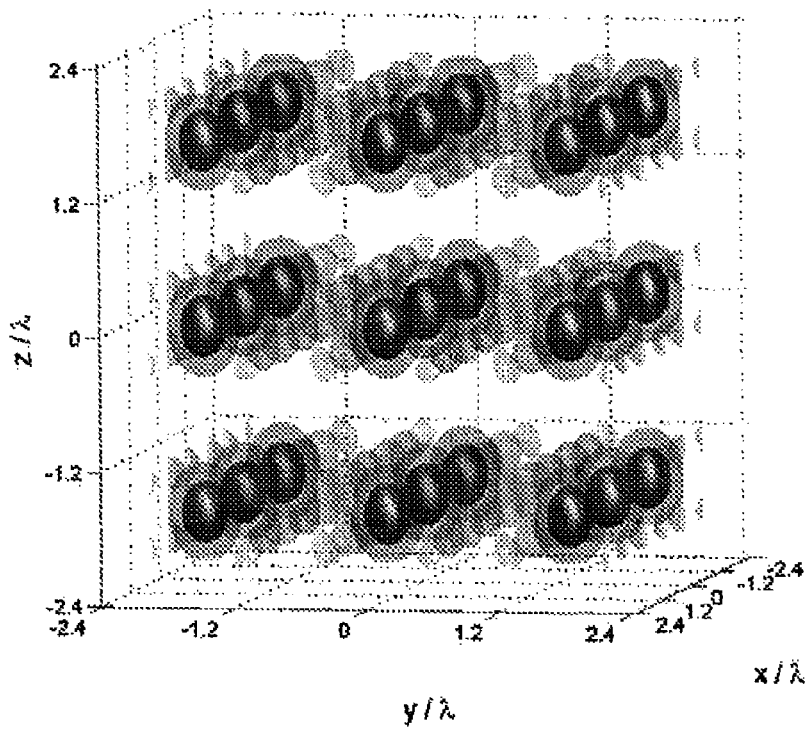
FIGS. 27B and 27D are three-dimensional plots of surfaces of 15% (translucent) and 50% (opaque) of the total intensity $|e(x)|^2$ for the lattice and bases obtained with the plane wave properties shown in FIGS. 27A and 27C, respectively.
Figure 27C:
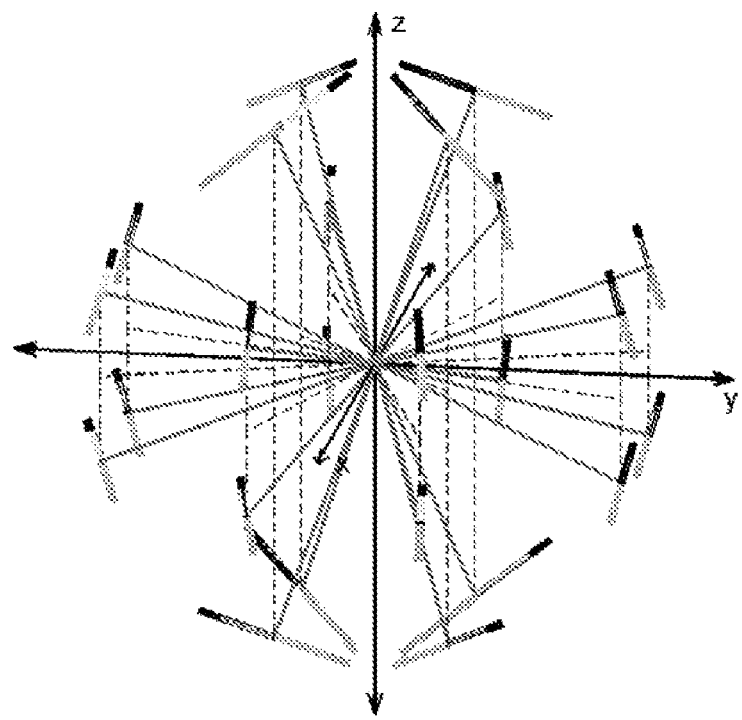
Figure 27D:
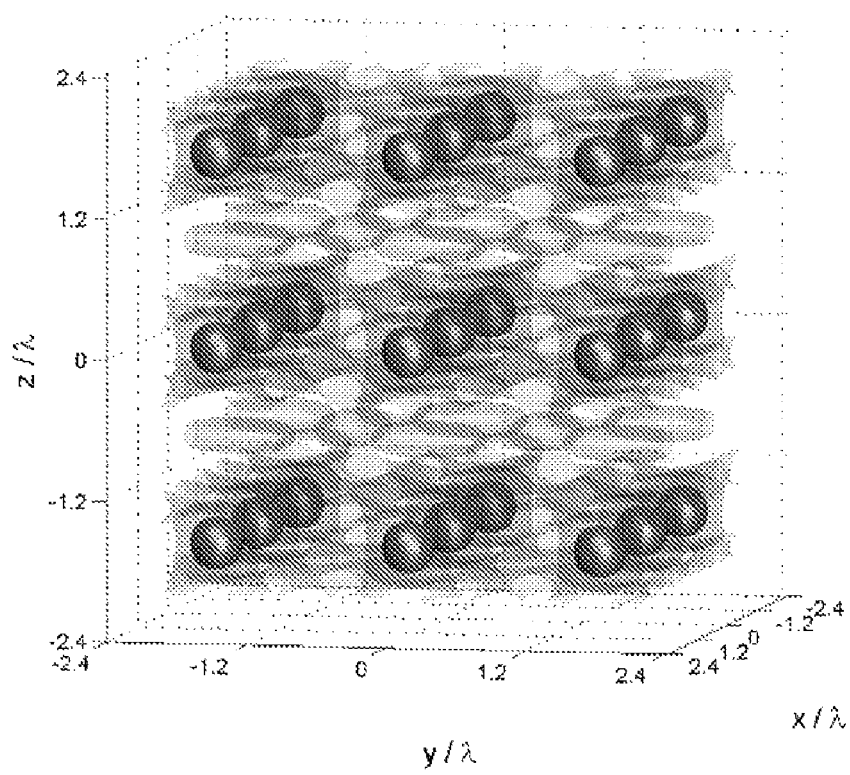

For example, the field vectors and resulting bases represented by Equation (28) and Equation (30) can be compared for a simple cubic lattice of an intensity period, $\sqrt{11}\lambda/2$, as shown in FIGS. 27A-B and FIGS. 27C-D, respectively. Specifically, plane waves are shown with equal amplitudes in FIG. 27A and with equal projections in FIG. 27C. FIG. 27B and FIG. 27D illustrate the resulting confinement symmetry, as opaque surfaces of at least 50% maximum intensity, for plane waves of equal amplitude, and with equal projections, respectively. Although the confinement symmetry can be improved by selecting plane waves with equal projections, the intensity contrast across each primitive cell is significantly reduced, due to less efficient destructive interference at points away from $x=X_d$.

Maximal Intensity with Optimized Circular Polarization

The confinement can also be enhanced by selecting a desired electric field polarization state, $e_d$, at the intensity maxima that corresponds to the desired symmetry. For example, optimization of circular, rather than linear, polarization at the maxima can be represented by:

$$e_d=E\exp(i\theta)(\hat{e}_{pkn\perp}+i\hat{e}_{p\perp})/\sqrt{2}\equiv E\hat{e}_L, \quad (31)$$

which, in conjunction with Equation (20) and Equation (24), yields:

$$Re\{e_n^*(x_d,t_d)\cdot e_d\}=e_nE[-\cos\Omega_n\cos\chi\sin(k_n\cdot x_d-\omega t_d+\theta-\theta)+\sin\chi\cos(k_n\cdot x_d-\omega t_d+\psi-\theta)]\sqrt{2}\equiv G(\chi,\theta,\psi) \quad (32)$$

Equation (32) is maximized for $\partial G/\partial\chi=\partial G/\partial\theta=\partial G/\partial\psi=0$, $\partial^2 G/\partial\chi^2<0$, $\partial^2 G/\partial\theta^2<0$, and $\partial^2 G/\partial\psi^2<0$. Such maximization occurs when $\tan\chi=1/|\cos\Omega_n|$, $\theta=-(k_n\cdot x_d-\omega t_d)-(\cos\Omega_n/|\cos\Omega_n|)\pi/2+\theta$, and $\psi=-(k_n\cdot x_d-\omega t_d)+\theta$. Therefore, by Equation (20):

$$e_n(x,t) = \frac{e_n(-i\cos\Omega_n\hat{e}_{kn\perp}+\hat{e}_{pkn\perp})}{\sqrt{1+\cos^2\Omega_n}} \quad (33)$$

$$\exp[i(k_n\cdot(x-x_d)-\omega(t-t_d)+\vartheta)] \text{(for } e_d \text{ circular).}$$

A simple basis with good intensity contrast can be selected when all plane waves are assigned equal amplitudes:

$$e_n = \frac{e_o(-i\cos\Omega_n\hat{e}_{kn\perp}+\hat{e}_{pkn\perp})}{\sqrt{1+\cos^2\Omega_n}} \quad (34)$$

$$\exp[-i(k_n\cdot x_d-\omega t_d-\vartheta)] \text{(for } e_d \text{ circular, } |e_n|=e_o)$$

Figure 28A:
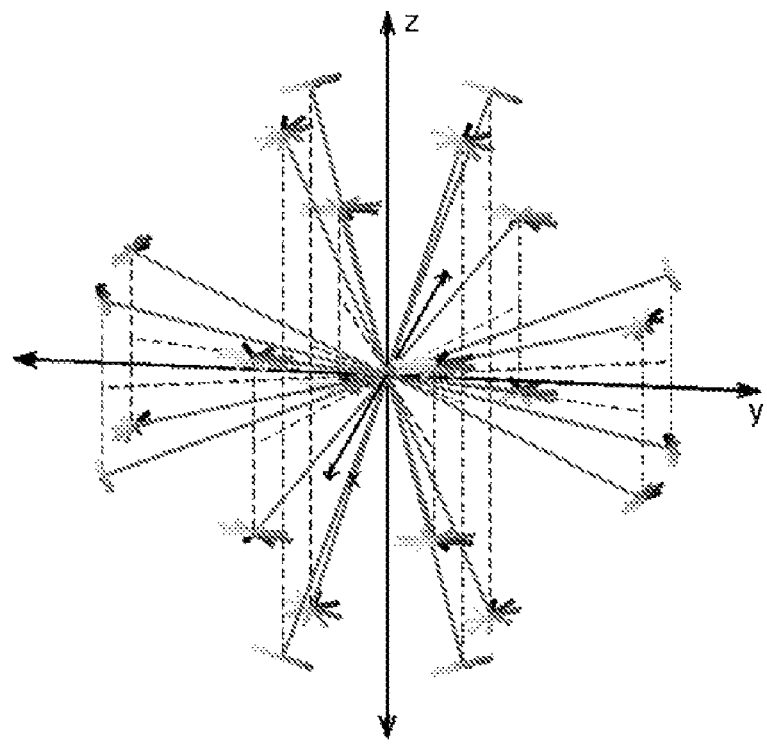
FIG. 28A is a three-dimensional representation of the relative wavevector and electric field directions and real field magnitudes at different times for the plane waves that comprise the same simple cubic lattice as in FIG. 27, but with a basis of generally elliptically polarized plane waves chosen to maximize a given component $\hat{e}_L$ of circular polarization at a particular point in the primitive cell.
Figure 28B:
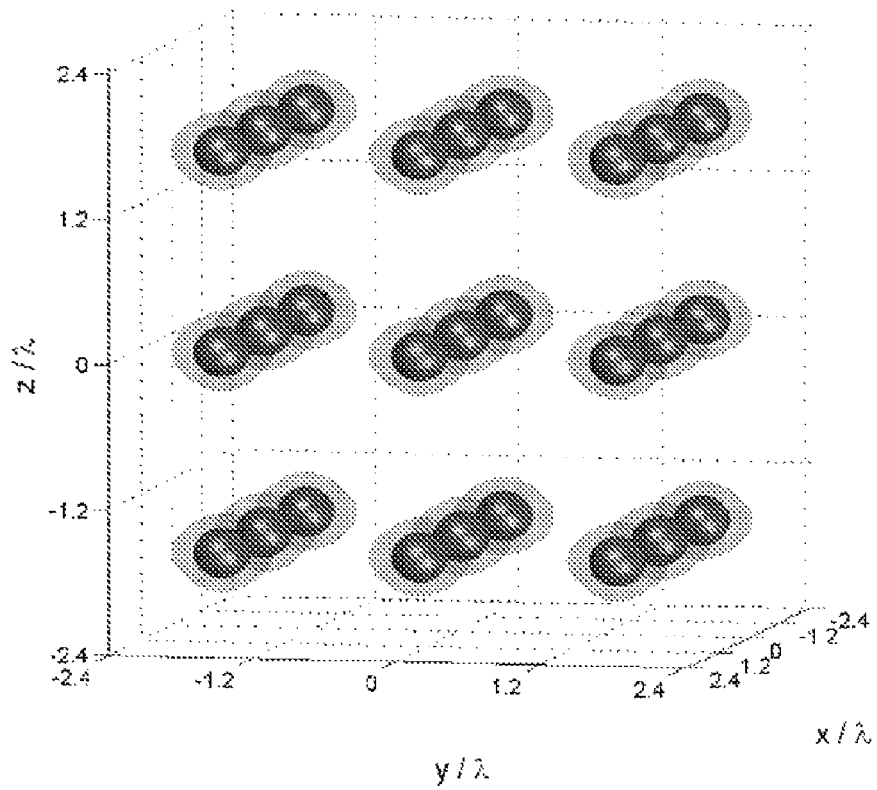
FIG. 28B is a three-dimensional plot of surfaces of 15% (translucent) and 50% (opaque) of the total intensity for the lattice and basis obtained with the plane wave properties of FIG. 28A.

FIG. 28A shows the field vectors that result from applying Equation (34) to the simple cubic lattice depicted in FIG. 27. The field vectors indicate that the $\hat{e}_L$ component of the total field at the intensity maxima is optimized when the plane wave polarization ellipticity varies according to $\cos\Omega_n$, i.e., from circular for $k_n$ parallel to $\hat{e}_p$ to linear for $k_n$ perpendicular to $\hat{e}_p$. The corresponding opaque surfaces of 50% intensity, as shown in FIG. 28B, demonstrate that nearly spherical intensity confinement can be obtained while simultaneously maintaining an intensity contrast (as represented by the translucent surfaces of 15% intensity), which is better than that illustrated in the linear polarization example in FIG. 27B.

The selection of a basis of circularly polarized intensity maxima yields photons in a single state of angular momentum. This can be useful for microscopy applications, because such a basis is better attuned to generating signal from particular quantum constituents within a sample based on specific selection rules for transitions between quantum mechanical states. However, for fields described by Equation (34), the ellipticity of each field, $e_n$, must be manipulated in addition to its orientation and phase. For this reason, it is simpler to maximize circular polarization at the location, $x_d$, and the time, $t_d$, subject to the constraint that each constituent field is linearly polarized, such that:

$$e_n(x,t) = e_n[\cos\chi \hat{e}_{kn\perp} + \sin\chi \hat{e}_{pkn\perp}]\exp[i(k_n \cdot x - \omega t + \theta)]. \quad (35)$$

When considered in conjunction with Equations (24) and (31), Equation (35) yields:

$$Re\{e_n^*(x_d,t_d)\cdot e_d\} = e_n E[-\cos\Omega_n \cos\chi \sin(k_n \cdot x_d - \omega t_d + \theta - \theta) + \sin\chi \cos(k_n \cdot x_d - \omega t_d + \theta - \theta)]/\sqrt{2} \equiv H(\chi,\theta) \quad (36)$$

The absolute maximum among the solutions of $\partial H/\partial\chi = \partial H/\partial\theta = 0$, $\partial^2 H/\partial\chi^2 < 0$, and $\partial^2 H/\partial\theta^2 < 0$ occurs when $\chi = \pi/2$ and $\theta = -(k_n \cdot x_d - \omega t_d) + \theta$. When all plane wave fields are selected with equal amplitudes, Equation (35) yields:

$$e_n = e_o \hat{e}_{pkn\perp} \exp[-i(k_n \cdot x_d - \omega t_d - \theta)] \text{ (for } e_d \text{ circular, } e_n \text{ linear, and } |e_n| = e) \quad (37)$$

Figure 29A:
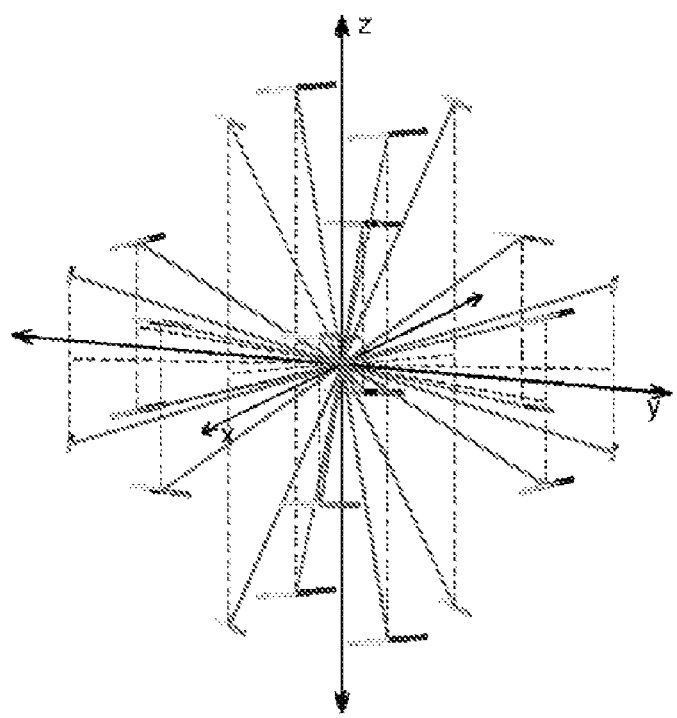
FIG. 29A is a three-dimensional representation of the relative wavevector and electric field directions and real field magnitudes at different times for the plane waves that make up the same simple cubic lattice shown in FIGS. 27 and 28, but with a basis of linearly polarized plane waves chosen to maximize a given component $\hat{e}_L$ of circular polarization at a particular point in the primitive cell.
Figure 29B:
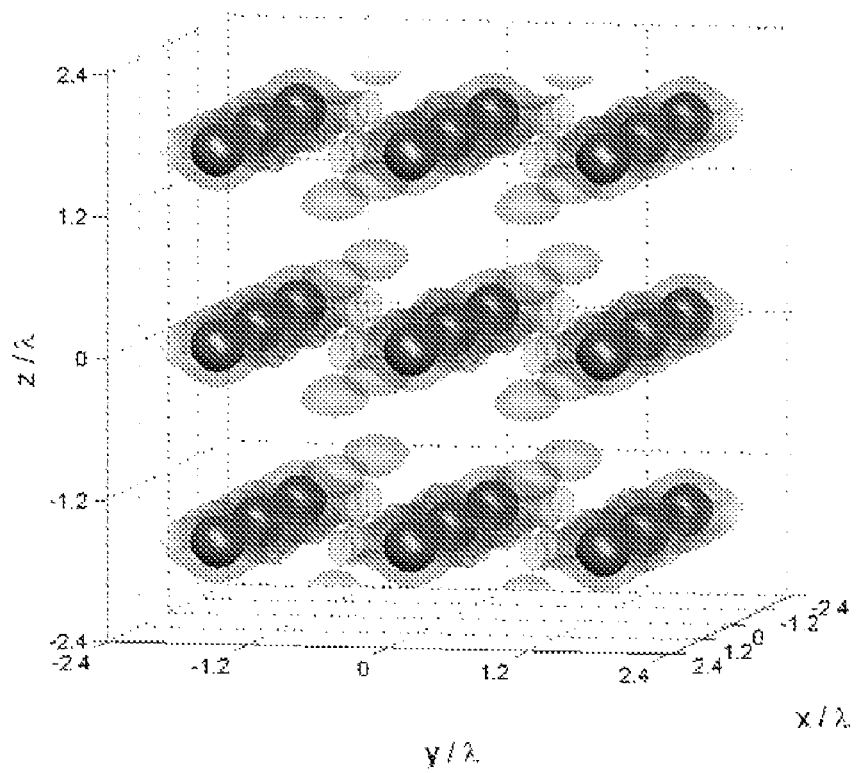
FIG. 29B is a three-dimensional plot of surfaces of 15% (translucent) and 50% (opaque) of the total intensity for the lattice and basis obtained with the plane wave properties of FIG. 29A.

By analogy to the linear polarization case shown in FIG. 23, the circular polarization perpendicular to $\hat{e}_p$ is maximized at the location, $x_d$, when each linear field, $e_n$, is aligned in its allowed plane to lie along the intersection of this plane ($\perp k_n$) with the plane of the desired circular polarization ($\perp \hat{e}_p$). FIG. 29A illustrates this trait where the $e_n$ based on Equation (37) are plotted for the same simple cubic lattice shown in FIG. 27 and FIG. 28. The resulting basis, shown in FIG. 29B, retains the spherically symmetric confinement of intensity maxima evidenced by the more general case of Equation (34), shown in FIG. 28B, but with somewhat reduced contrast with respect to the background due to the linear constraint on each constituent $e_n$.

Generalized Parameter Optimization to Construct a Basis

The basis construction methods discussed in connection with Equations (20)-(37) have the virtue of simplicity, because they depend upon the individual optimization of each plane wave field, $e_n$, after the wavevectors, $k_n$, which dictate the properties of the lattice, have already been determined. Secondary optimization of other parameters such as polarization purity and intensity contrast relative to the background can then be performed by varying the desired polarization state, $e_d$, or the lattice parameters, as illustrated in FIG. 25 and FIG. 26, respectively. In the most general terms, however, the complete electromagnetic field of the lattice, as described in Equation (3), depends upon both the wavevectors, $k_n$, and the fields, $e_n$, of the constituent plane waves. As a result, optimization of any desired property, $\gamma$, (e.g., maximization of the gradient, $\gamma = \nabla(e(x,t)\cdot\hat{e}_i)\cdot\hat{e}_j$, of the $\hat{e}_i$ component of the electric field in the $\hat{e}_j$ direction) can alternatively be performed by finding simultaneous critical values, $\partial\gamma/\partial v_l = 0$ and $\partial^2\gamma/\partial v_l^2 < 0$, for any subset, $\{v_l\}$, of the components of these wavevectors, $k_n$, and fields, $e_n$, or functions thereof under certain specified constraints (e.g., lattice symmetry, relative amplitudes $|e_n|$, etc.).

Exemplary Applications

Selection of an Appropriate Lattice and Basis for Microscopy

The analysis detailed herein suggests that, in a common approach to optical lattice microscopy in which a lattice having intense, highly confined maxima is to be scanned over the dimensions of a primitive cell to generate a complete two-dimensional or three-dimensional image of a sample, care should be taken to appropriately select the lattice symmetry, periodicity, orientation, number of constituent wavevectors, and basis for a particular application. The lattice symmetry should be maximized to the extent possible in light of the sample geometry, the detection strategy, and the desired polarization purity. Cubic and hexagonal lattices, for example, are often useful for this purpose. To enhance the optical confinement, many wavevectors, $k_n$, can be selected from the associated maximally symmetric composite set in accordance with the experimental constraints of the application (e.g., occlusion by an objective nosepiece, excessive aberration through a cover glass).

The wavelength-normalized periodicity can be selected from the discrete possibilities associated with the aforementioned sparse lattice analysis in order to balance considerations such as the ease of signal detection from the individual maxima, the degree of unwanted excitation elsewhere, the desired field of view, and the imaging speed. The plane wave fields, $e_n$, that compose the basis should be selected to achieve the intended signal generation mechanism within the sample. For conventional linear polarization (e.g., birefringence) or fluorescence anisotropy measurements (e.g., determining the orientation of individual molecular fluorophores), the bases represented by Equation (28) and Equation (30) often can be helpful. The basis represented by Equation (28) can be preferred when polarization purity, $|e(x_d)\cdot\hat{e}_p|^2/|e(x_d)|^2$, at the maxima is paramount, and the basis represented by Equation (30) can be preferred when symmetric confinement of the excitation and consequent excitation resolution takes precedence over the increase in background emission (which can be partially removed via pinhole filtering) and related photobleaching. When the total intensity, $|e(x_d)|^2$, is responsible for the desired signal (as in the common case in which a large ensemble of randomly distributed fluorophores exist within each detection region), the basis indicated by Equation (34) can be particularly useful, because it combines near-optimal confinement for cubic lattices in all directions with excellent contrast between the intensity maxima and the background elsewhere in the primitive cells.

Non-Scanning, Massively Parallel Localized Optical Measurements

Lattices of intense, highly confined intensity maxima can also be applied in lieu of scanning to fixed point statistical biophysical techniques, such as, for example, fluorescence correlation spectroscopy ("FCS"), as described, for example, in S. T. Hess, et al., *Biochemistry*, 41, 697-705 (2002), fluorescence photobleaching recovery ("FPR" or "FRAP"), as described, for example, in J. Blonk, et al., *J. Microsc.*, 169, 363-374 (1993), and single molecule detection/fluorescence resonant energy transfer, ("SMD/FRET"), as described, for example, in S. Weiss, *Science*, 283, 1676-1683 (1999) and B. Schuler, et al., *Nature*, 419, 743-747 (2002), all of which are incorporated herein by reference. In FCS, fluctuations in the signal arising from a population of molecules diffusing in and out of a single light excitation focus are analyzed to infer the local diffusion rate of said molecules, which in turn can be indicative of changes in the molecular weight due to ligand/receptor binding. In FPR, a light excitation focus is used to photobleach fluorescent molecules in a localized area, and the time for the fluorescence to recover in the bleached area is indicative of the diffusion rate of molecules in the bleached region.

Currently, FCS, FPR, and SMD/FRET are commonly implemented using the single focus of a confocal microscope, but these techniques can benefit from the massive parallelism and reduced volume at each maximum that is made possible by optical lattice excitation, as opposed to single focus, confocal microscopy. Indeed, the improved intensity confinement and reduction in extraneous photobleaching outside the maxima, which is made possible by the use of optical lattices can significantly enhance sensitivity in SMD studies and permit far longer observations times in a given region with fewer photophysically-induced artifacts.

Figure 30A:
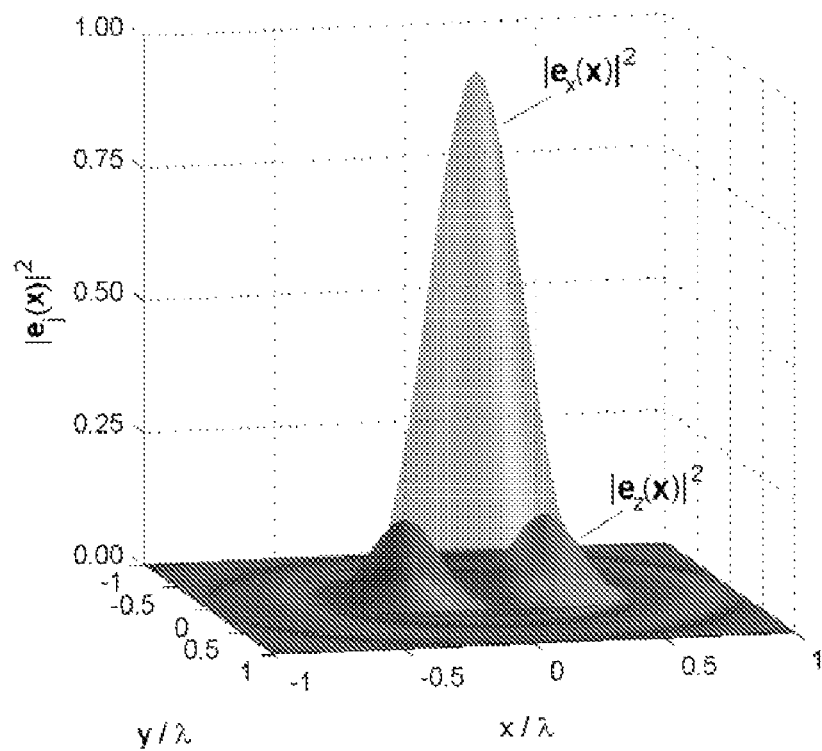
FIGS. 30A, 30B, and 30C are surface plots of the intensity of the x- (light translucent), y- (medium translucent), and z-components (dark translucent) of the electric field in the x-y, x-z, and y-z planes of FIG. 15A near the focus of an NA=1.2 water-immersion microscope objective oriented along the z-axis and illuminated with an x-polarized plane wave.
Figure 30B:
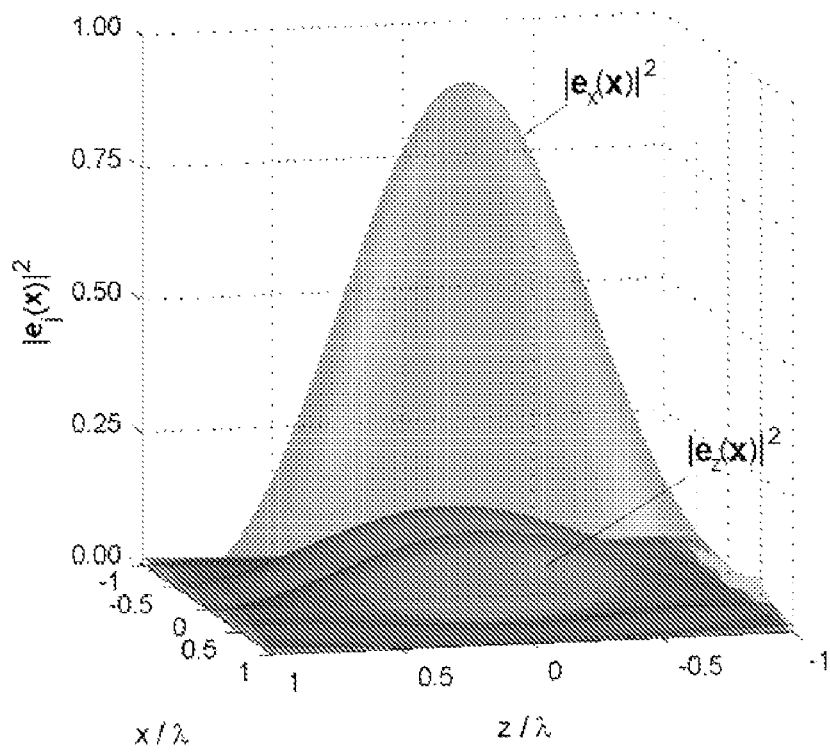
Figure 30C:
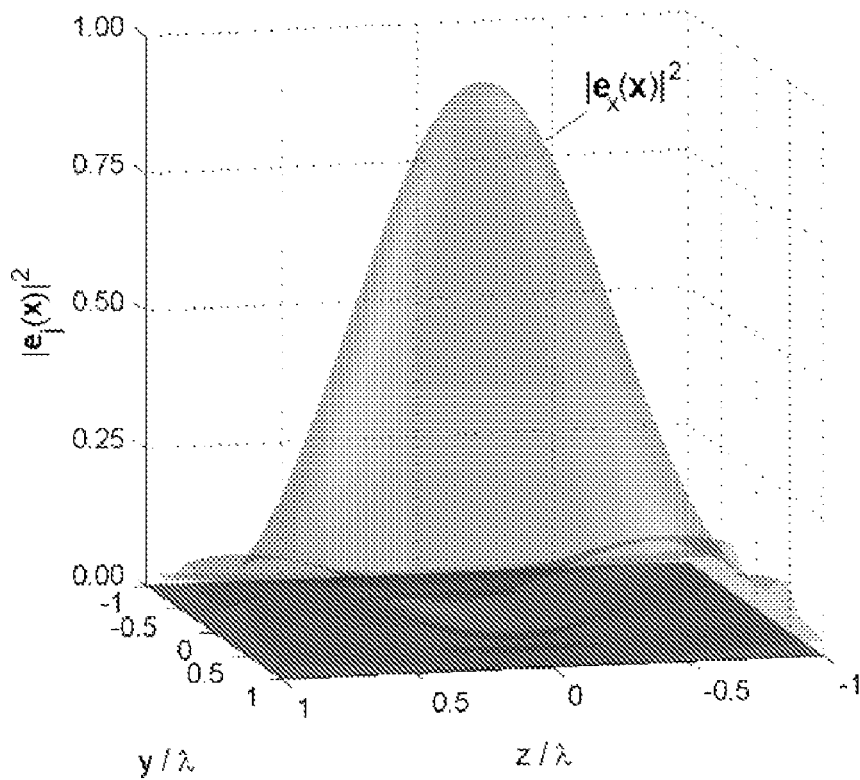
Figure 30D:
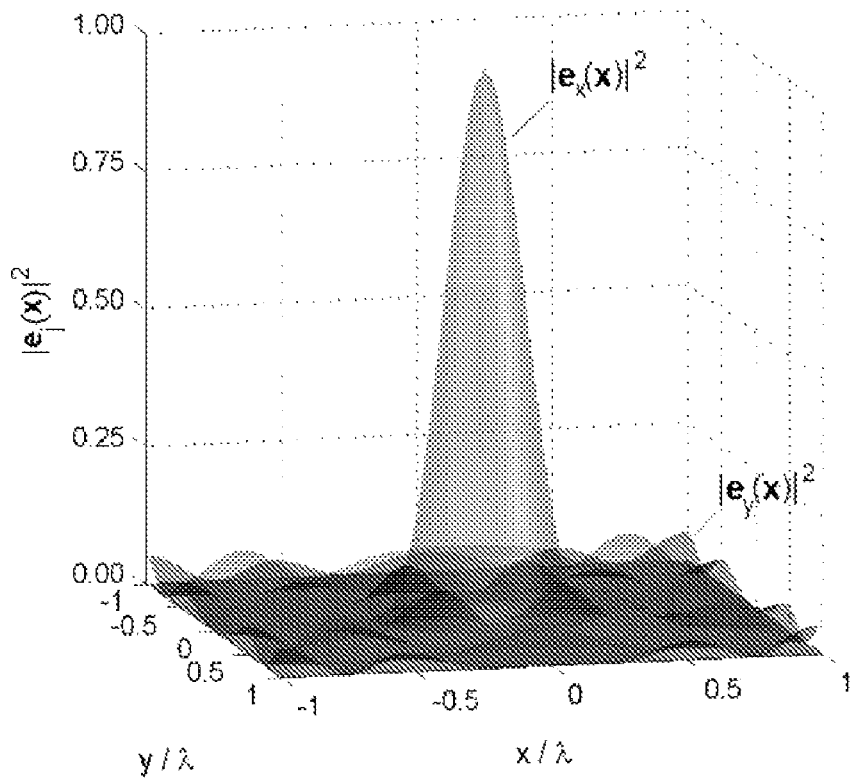
FIGS. 30D, 30E, and 30F are corresponding surface plots of the field components in the x-y, x-z, and y-z planes for a single intensity maximum within a simple cubic lattice (intensity period $\sqrt{35}\lambda/2$) with polarization optimized along the x-axis.
Figure 30E:
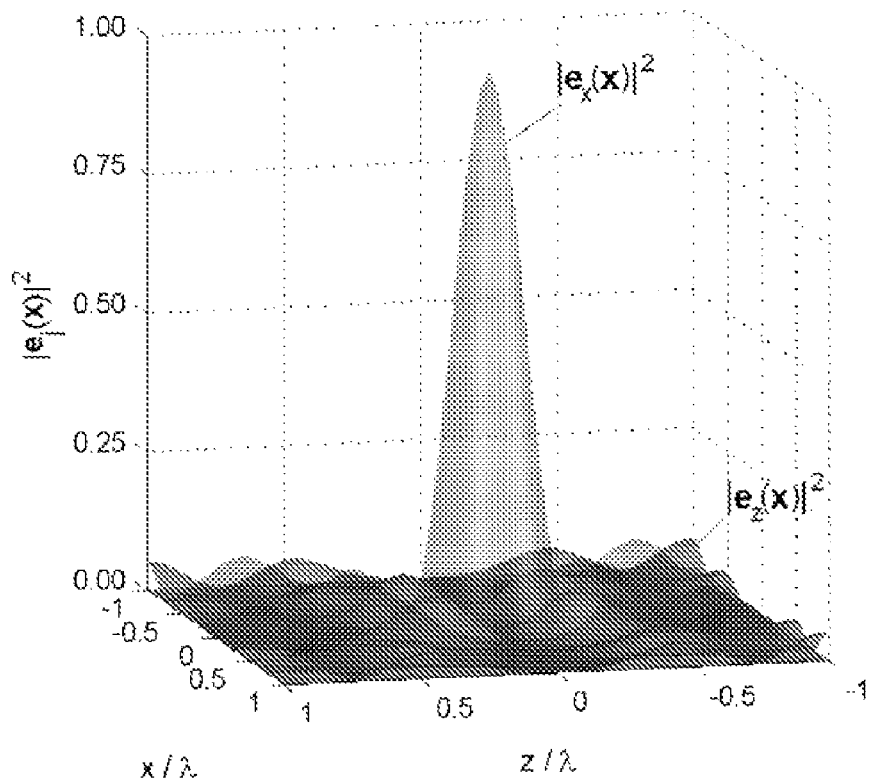
Figure 30F:
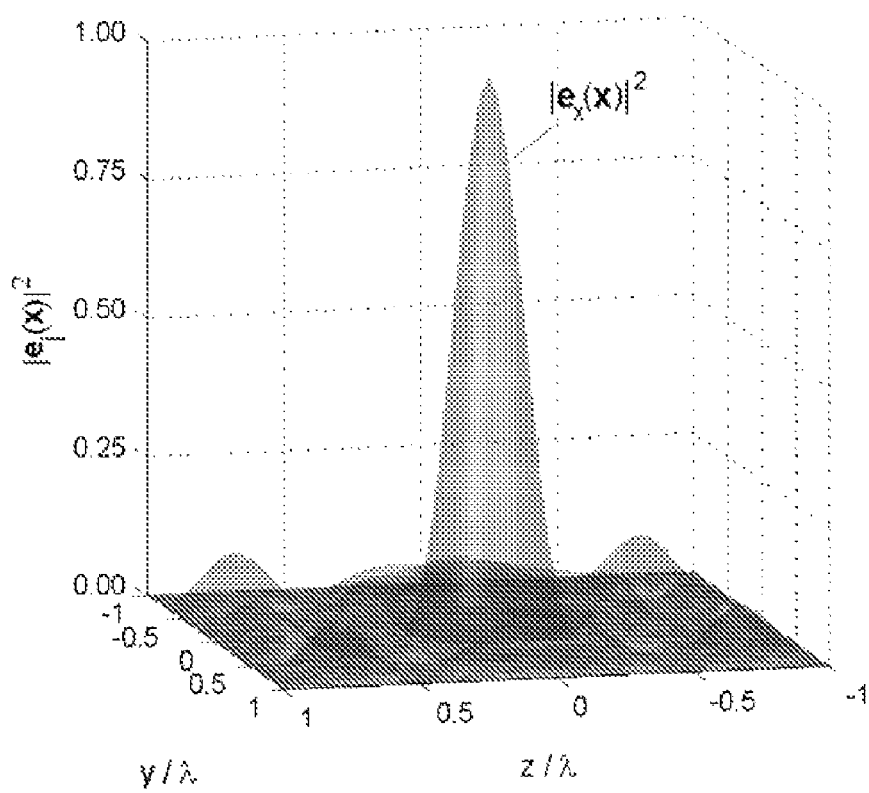

The improved polarization purity that is possible at lattice excitation maxima can be useful for fluorescence anisotropy and single molecule orientation and conformation measurements and can be advantageous compared to the intensity maximum created with confocal microscopy. For example, FIG. 15 compares surface plots of 50 percent maximum intensity within a simple cubic lattice and surface plots of 50 percent maximum intensity within the focal region of a high NA objective lens. FIG. 30 shows the relative intensities and spatial distributions of each of the three orthogonal field components. In the confocal microscopy case, significant side lobes of z-polarization exist on either side of, and partially within, the desired x-polarized central maximum, as shown in FIG. 30A and FIG. 30B. Such side lobes result from a large angle of refraction as marginal rays pass through the objective, which causes rotation of the polarization vector. In contrast, in the lattice microscopy case, secondary maxima of y and z polarization are comparatively smaller, as shown in FIG. 30D and FIG. 30E, because the polarization of each plane wave can be individually manipulated to optimize its contribution to the desired x-polarization at the desired point $x_d$. Furthermore, because the secondary lattice maxima are centered at nodes of the desired field $e(x) \cdot \hat{e}_x$, their contribution to the detected signal can be more readily removed via spatial filtering (e.g., with a pinhole filter). For maximally symmetric lattices of the cubic crystal group, the constituent plane waves propagate in directions, $k_n$, spread over the entire angular sphere, so there is no significant asymmetry in the polarization purity as a function of the desired polarization direction, $\hat{e}_p$. In contrast, for the single focus lens case, the polarization purity is worst for $\hat{e}_p=\hat{e}_z$, because the wavevector distribution is centered about the optical axis.

Lithography

Figure 31A:
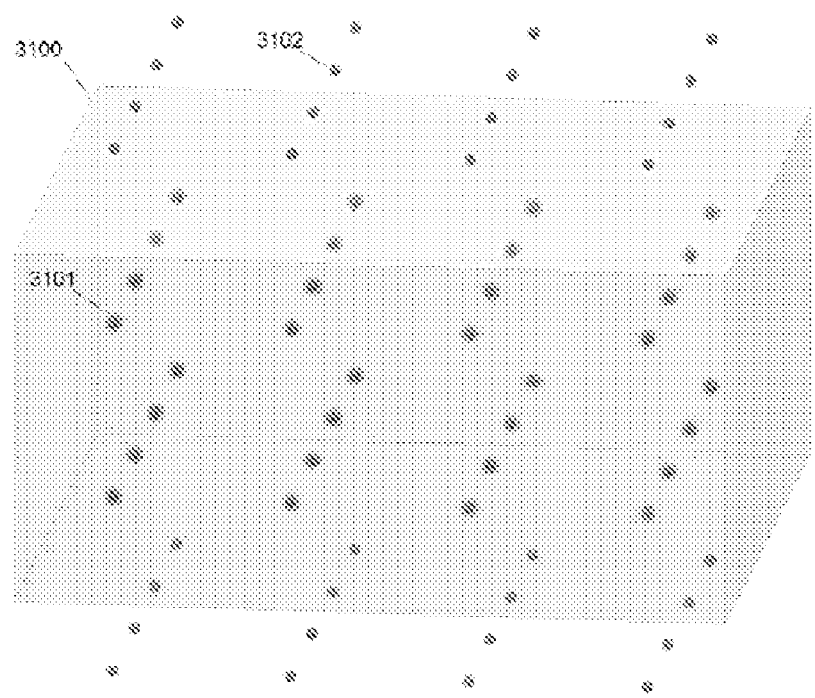
FIGS. 31A and 31B are schematic views of short and long exposures (translucent spheres), respectively, of a photosensitive material with a three-dimensional simple cubic lattice (opaque spheres).
Figure 31B:
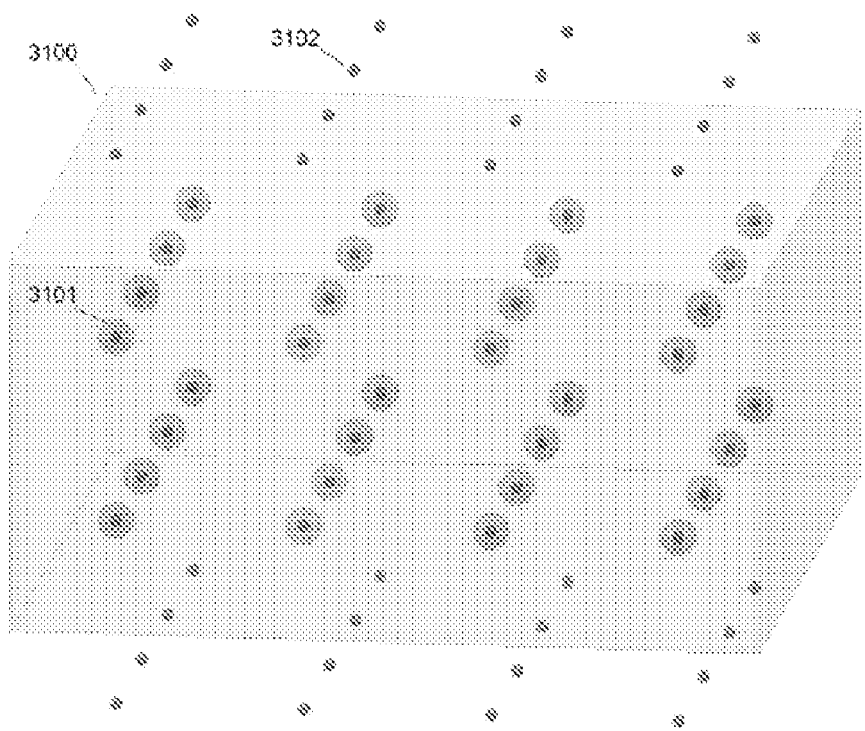

Optical lattices having confined intensity maxima can also be useful for photolithography. As shown in FIG. 31, two-dimensional and three-dimensional lattice structures with a selectable wavelength-normalized periodicity can be rapidly produced in photosensitive materials 3100. With spatially defined excitation, exposed regions 3101 occur at the intensity maxima 3102, the size of which is controlled by adjusting the total exposure dose. Lattice structures can be useful for photonic bandgap applications, or as two-dimensional and three-dimensional holographic filters analogous to the diffractive notch filters currently produced by standing wave methods.

Figure 31C:
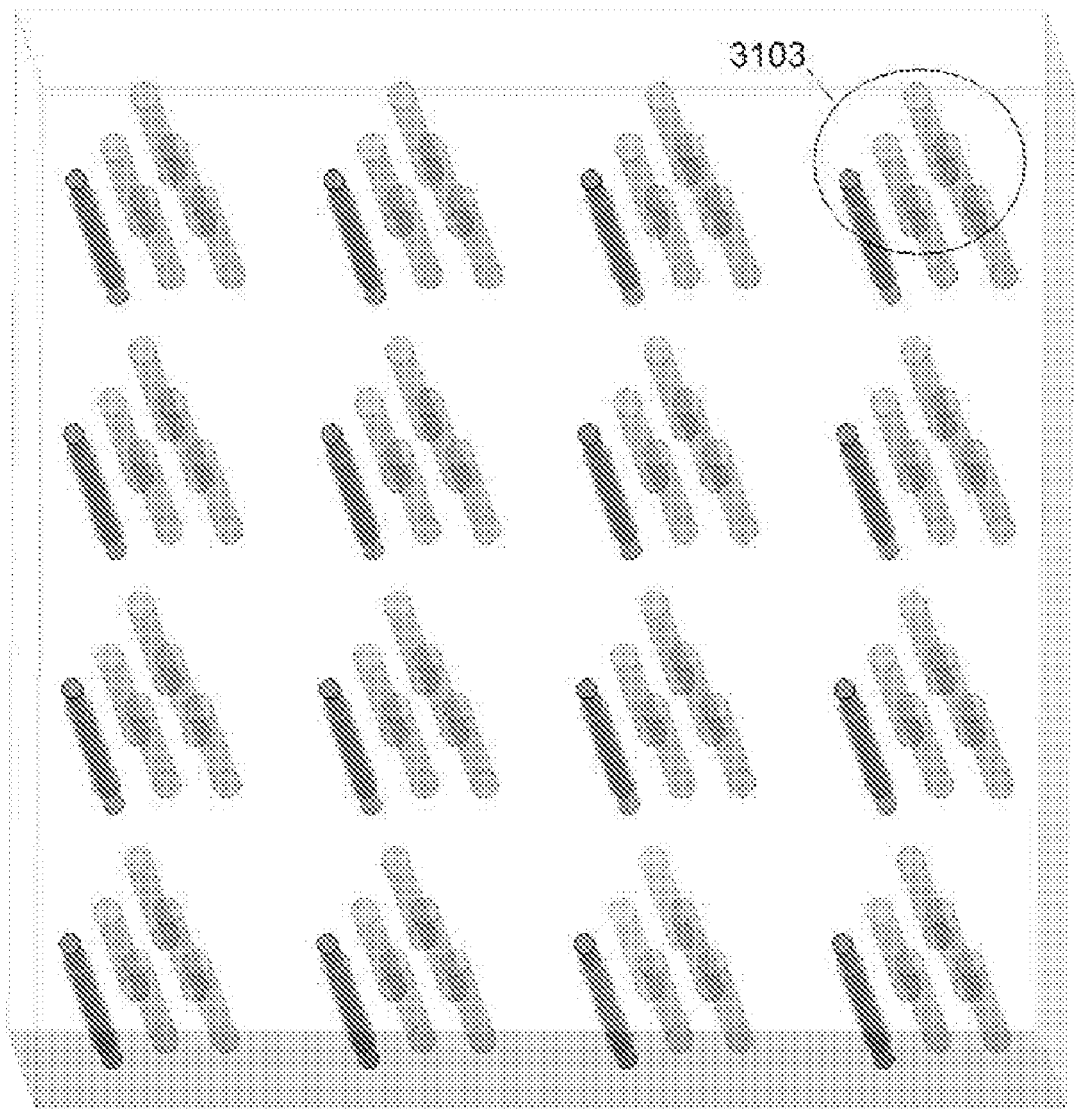
FIG. 31C is a conceptual view of a two-dimensional scattering structure created with six exposures (translucent cylinders) of a two-dimensional square lattice (opaque cylinders) in a photosensitive material.
Figure 32A:
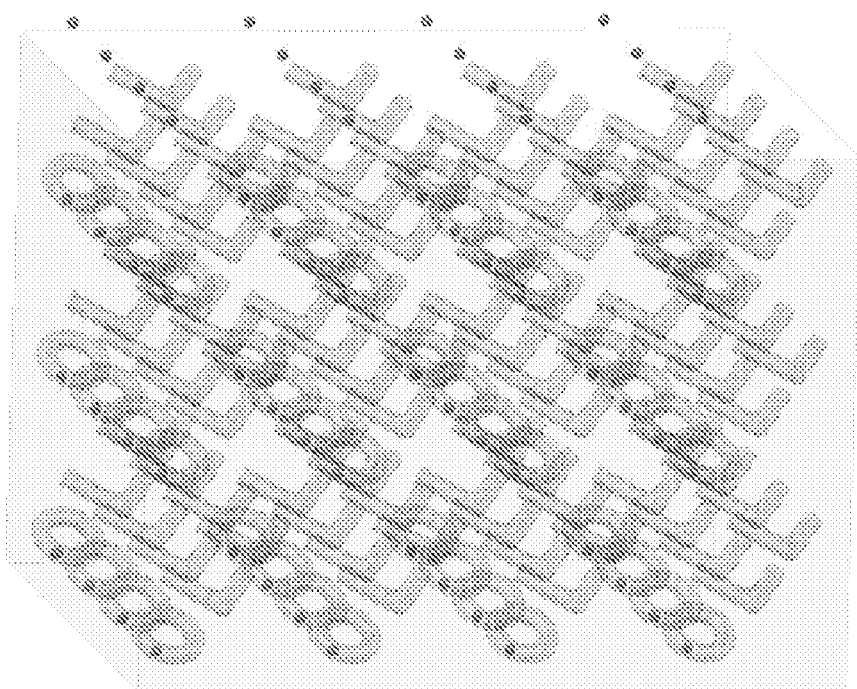
FIG. 32A is a conceptual view of a three-dimensional lattice of an aperiodic pattern (translucent letters) exposed in a photosensitive material (translucent block) by a simple cubic lattice (opaque spheres).
Figure 32B:
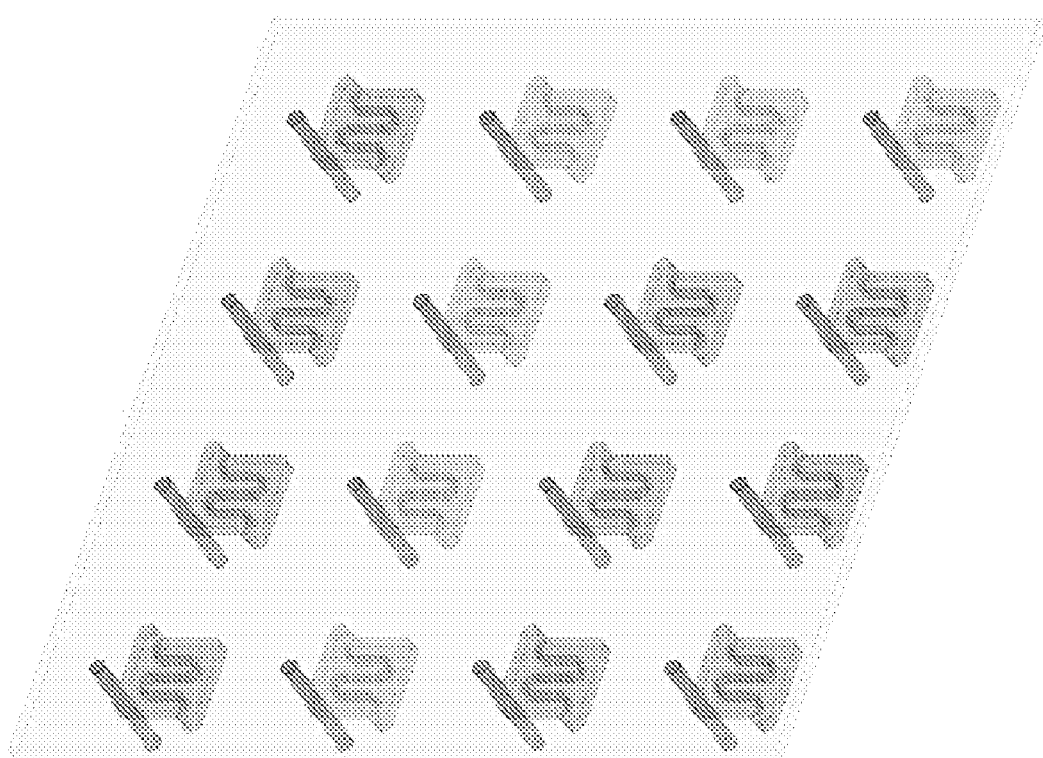
FIG. 32B is a conceptual view of a two-dimensional array of an aperiodic pattern (translucent inter-digitating fingers) exposed in a photosensitive material (translucent layer) using a square lattice (opaque cylinders).
Figure 33A:
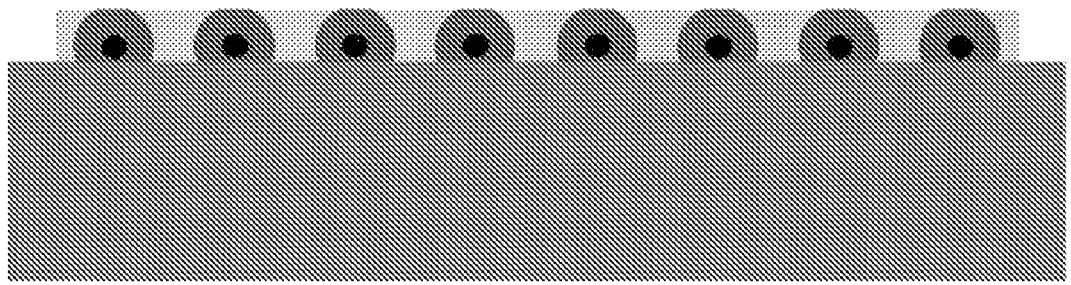
FIG. 33A is a cross-sectional view of the exposure of a two-dimensional lattice of undercut profiles (dark gray) in a photoresist film (light gray) on a substrate (medium gray) to be patterned created with a plane of intensity maxima (black) within a three-dimensional lattice.
Figure 33B:
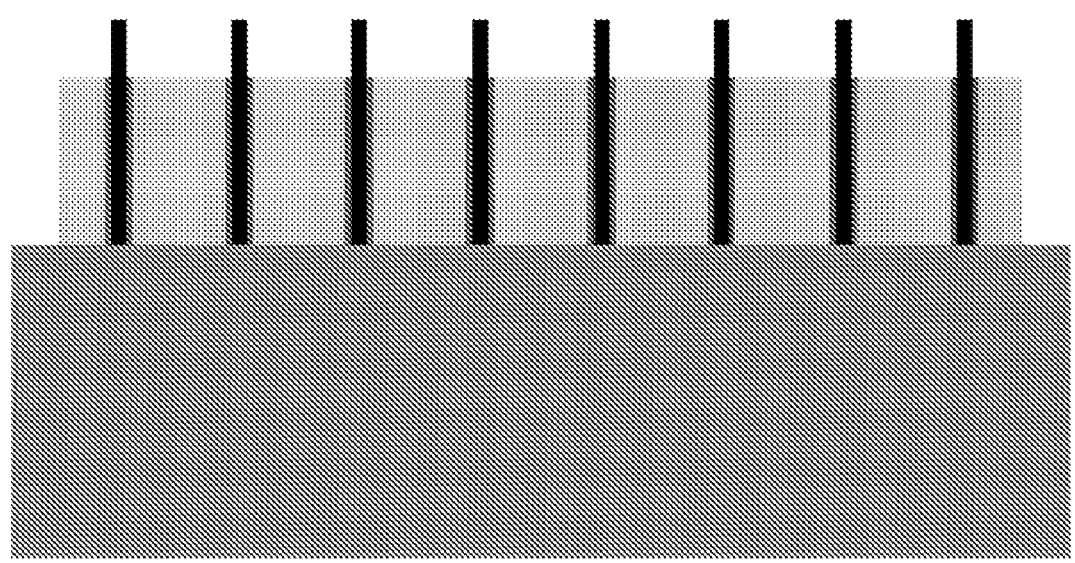
FIG. 33B is a cross-sectional view of the exposure of a two-dimensional lattice high aspect ratio structures (dark gray) in a thick photoresist film (light gray) on a substrate to be patterned created with a two-dimensional lattice of intensity maxima (black).

Referring to FIG. 31C, exposure of the sample at multiple points in each unit cell of the optical lattice can also be used to create more complicated diffractive structures with a basis of specifically tailored scattering regions 3103. As shown in FIG. 32, repeated patterns of any aperiodic structure, which are useful in many lithographic applications, can be created when an optical lattice can be scanned relative to a photosensitive material and the amplitude of the total excitation field, e(x,t), can be fully modulated from point to point. As with microscopy applications, the complete region of interest can be exposed by scanning over the dimensions of a single primitive cell. As shown in FIG. 33A, a three-dimensional lattice can be used to vertically confine the exposure of a planar photoresist layer (for cases where an undercut profile is desired). As shown in FIG. 33B, a two-dimensional lattice can be used to create uniform, high aspect ratio structures.

By utilizing the bases described above, the excitation in each cell of an optical lattice can be confined to nearly the diffraction limit in all desired directions, with minimal unintended exposure elsewhere. Furthermore, the exposed region can be precisely tailored using trepanning operations. Additionally, excitation can be performed through multiple lenses of low or moderate numerical aperture. This trait is beneficial because, as line-widths are further reduced and excitation wavelengths are further shortened in photolithography processes, aberration-free high numerical aperture lenses for traditional widefield lithography are increasingly difficult to design.

Although three-dimensional translucent blocks are depicted in FIGS. 31-33, any photosensitive material can be physically altered via lattice excitation. Such materials include thin-films and fields of surface-adsorbed molecules (whether monolayer or sub-monolayer). In particular, lattice excitation can be useful to improve the areal density and sensitivity in existing array-based assays for high throughput screening and combinatorial chemistry.

Multiphoton Microscopy and Lithography

Another issue of significance for both photolithography and microscopy is the non-zero background intensity remaining even for bases designed to maximize the excitation at a single point in each primitive cell. Such background results in unintentional exposure of surrounding areas in photolithography and unnecessary photobleaching of molecular fluorophores in microscopy. Although these effects are reduced when optical lattices are used as compared with conventional linear (e.g., confocal) microscopy, nonlinear excitation of the lattice and the sample can further reduce the background. For example, application of two-photon absorption as an exemplary nonlinear technique is shown in FIG. 34. The peak absorption wavelength, $\lambda_{abs}$, of the photosensitive material or molecular fluorophores of the sample dictates the excitation confinement and ultimate spatial resolution during either linear excitation (i.e., when $\lambda_{source}=\lambda_{abs}$) or during two-photon excitation (i.e., when $\lambda_{source}=2\lambda_{abs}$), and hence is chosen for the comparison of one- and two-photon lattice excitation in a maximally symmetric body-centered cubic lattice, having a period=$\sqrt{5}\lambda_{source}$, with conventional, single focus two-photon excitation (NA=1.2) in water, as shown in FIG. 34.

Figure 34A:
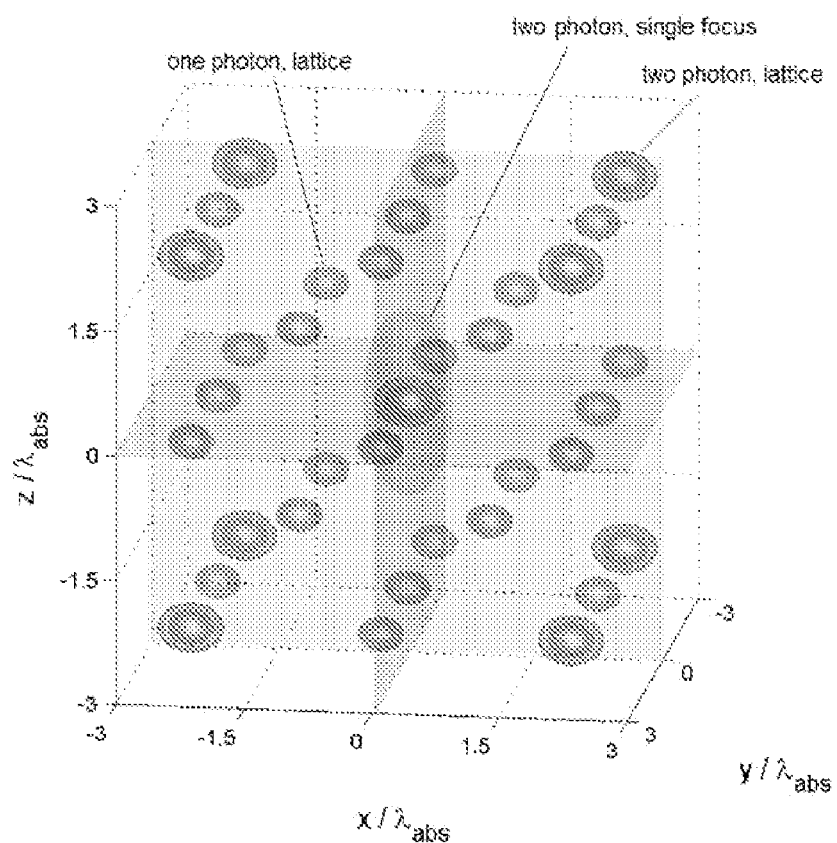
FIG. 34A is a three-dimensional plot of surfaces of 50% of maximum excitation strength for: two photon absorption at the focus of an NA=1.2 water-immersion objective (optical axis $\hat{e}_z$) illuminated by an x-polarized plane wave of wavelength $\lambda_{source}=2\lambda_{abs}$ (light translucent); single photon absorption from a maximally symmetric body-centered cubic lattice of excitation period $\sqrt{5}\lambda_{abs}$, with a basis chosen to optimize $|e(x) \cdot \hat{e}_x|$ at the excitation maxima (medium translucent); and two photon absorption from a body-centered cubic lattice of excitation period $\sqrt{5}\lambda_{source}=2\sqrt{5}\lambda_{abs}$, also with a basis chosen to optimize $|e(x) \cdot \hat{e}_x|$ at the excitation maxima (dark translucent). Continuous plane wave excitation is assumed.
Figure 34B:
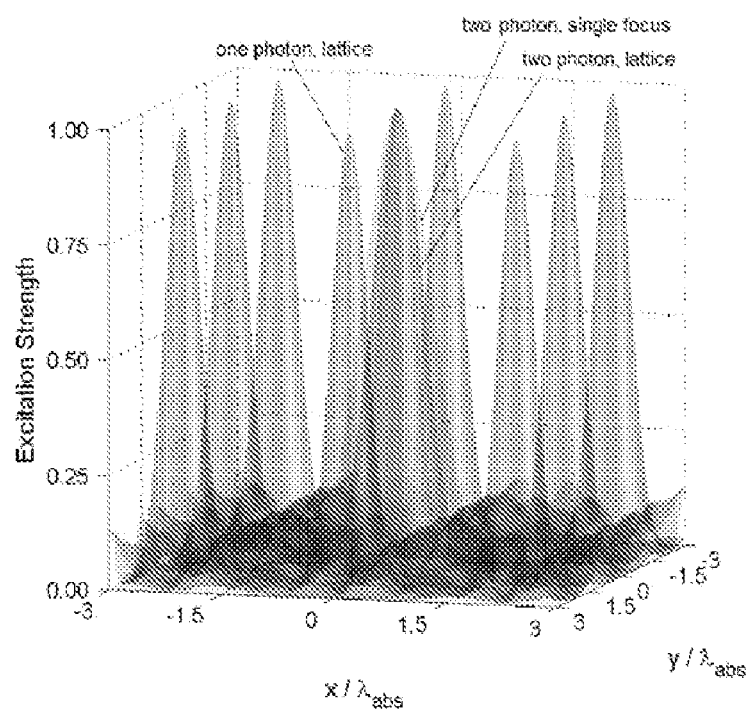
FIGS. 34B, 34C, and 34D are surface plots of the excitation strength in the xy, xz, and yz planes, respectively, for the three excitation scenarios of FIG. 34A.
Figure 34C:
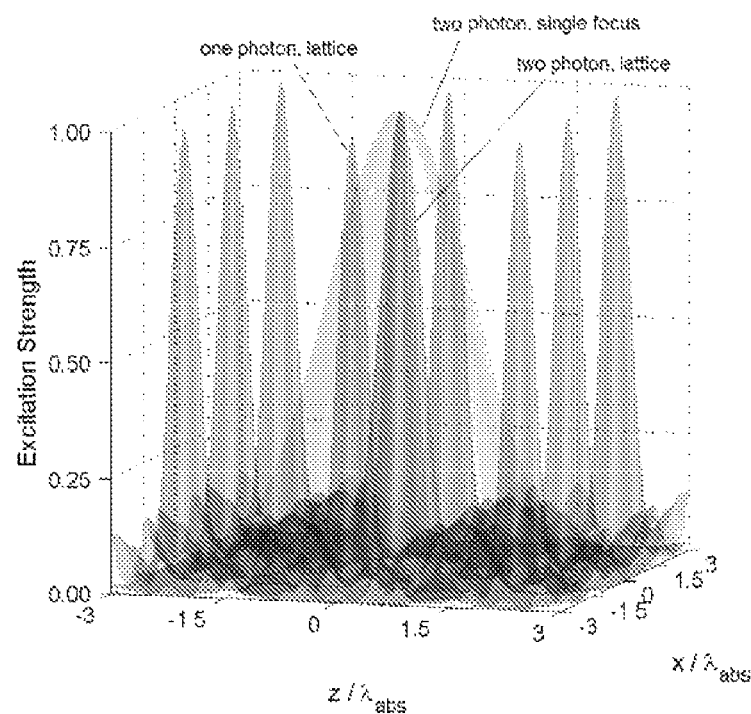
Figure 34D:
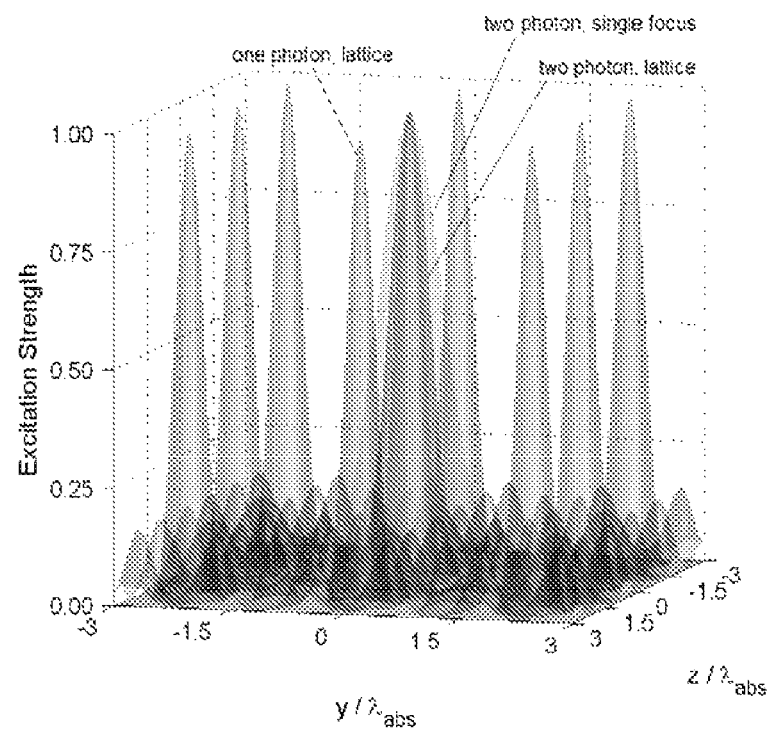

As expected, the dependence of the excitation strength in two-photon absorption on the square of the intensity or on the fourth power of the field amplitude, $|e(x)|^4$ results in a far lower excitation background away from the lattice maxima than in the case of single photon absorption (where the excitation strength is proportional to $|e(x)|^2$), as seen in the lower regions of the planar slice surface plots in FIGS. 34B, 34C, and 34D. However, due to the longer initial wavelength, $\lambda_{source}$, the confinement of the two-photon excitation maxima is inferior to that of the single photon maxima for any given material of peak absorption, $\lambda_{abs}$. Thus, nonlinear excitation generally should be used to reduce the excitation background only in applications where such reduction takes precedence over achieving the highest possible resolution.

The small cross-sections of many nonlinear processes also often demand ultrashort pulsed excitation with high peak power to achieve sufficient signal. However, a temporal pulse of width, $\Delta t$, introduces a frequency spread, $\Delta \omega \approx 1/\Delta t$, that is inconsistent with the perfect coherence necessary for the creation of ideal, infinite lattices. The significance of this effect can be estimated by replacing each continuous constituent plane wave of a given lattice with a wave packet having a sharp leading edge and a tail of exponential decay length, $\tau$, where the leading edge of each packet is assumed to arrive at the same position, $x_d$, at the same time, $t_d$. Mathematically, the fields are given by $$e_n(x, t) = 0, \text{ for } t - t_d < k_n \cdot (x - x_d)/\omega_o \quad (38a)$$

and $$\begin{aligned} e_n(x, t) &= e_n \exp\{[k_n \cdot (x - x_d)/\omega_o \tau - (t - t_d)/\tau]/2\} \\ &\quad \exp\{i[k_n \cdot (x - x_d) - \omega_o(t - t_d)]\} = \\ &\quad e_n \exp\{(i + 1/2\omega_o\tau)[k_n \cdot (x - x_d) - \omega_o(t - t_d)]\}, \\ &\quad \text{for } t - t_d > k_n \cdot (x - x_d)/\omega_o \end{aligned} \quad (38b)$$

Equation (38b) is a solution of the wave equation, and reduces to the continuous plane wave result as $\tau \to \infty$. Furthermore, the frequency spectrum of $|e_n(\omega)|^2$, has a Lorentzian lineshape having full-width-at-half-maximum equal to $1/\tau$ and a center frequency, $\omega_o$, characteristic of a lifetime-limited process. Superposition of all wave packets then gives the effect of the pulsed excitation on the overall lattice field. Integrating over an entire pulse to determine the time-averaged intensity yields, with the aid of Equation (38), $$\begin{aligned} \langle |e(x)|^2 \rangle_t &= (1/\tau) \int_{-\infty}^{\infty} \left| \sum_{n=0}^{N} e_n(x, t) \right|^2 dt \\ &= \sum_{m=0}^{N} \sum_{n=0}^{N} (e_m^* \cdot e_n) \frac{\exp[i(k_n - k_m) \cdot (x - x_d)]}{\exp[-|(k_n - k_m) \cdot (x - x_d)|/2\omega_o \tau]} \end{aligned} \quad (39)$$

Figure 35A:
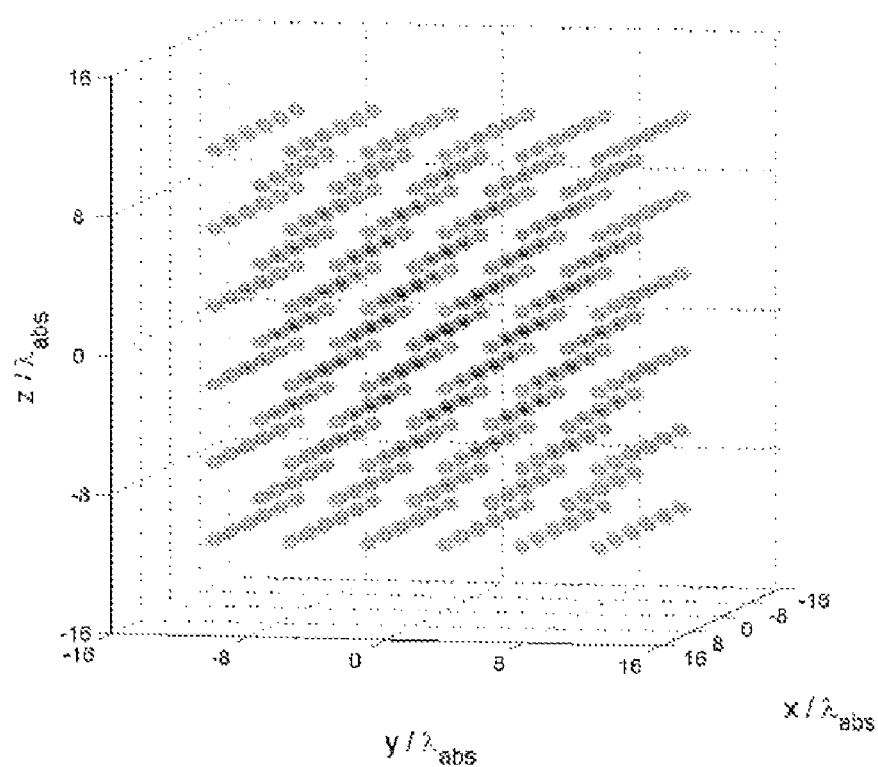
FIG. 35A is a three-dimensional plot of surfaces of 10% (light translucent), 20% (medium translucent), and 50% (opaque) of maximum two-photon excitation strength for the lattice and basis of FIG. 34, except assuming pulsed excitation with wavepackets of frequency-normalized decay time $\omega_o \tau = 31.3$.
Figure 35B:
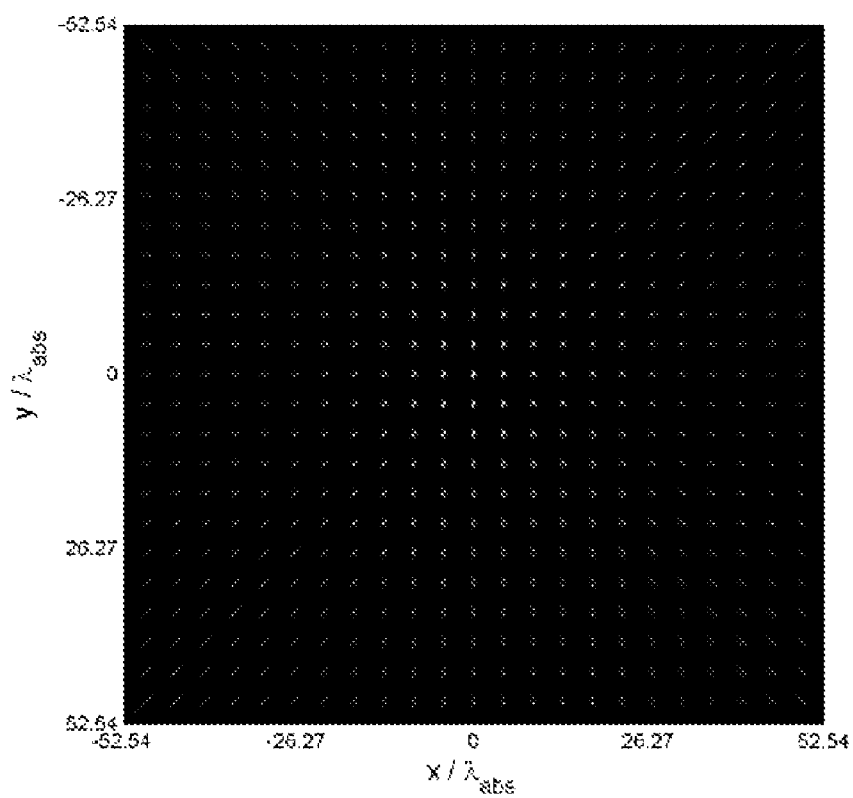
FIGS. 35B, 35C, and 35D are linear grayscale images of the two-photon excitation strength in the xy plane for $\omega_o \tau = 31.3$, $\omega_o \tau = 62.7$, and $\omega_o \tau = 157$, respectively.
Figure 35C:
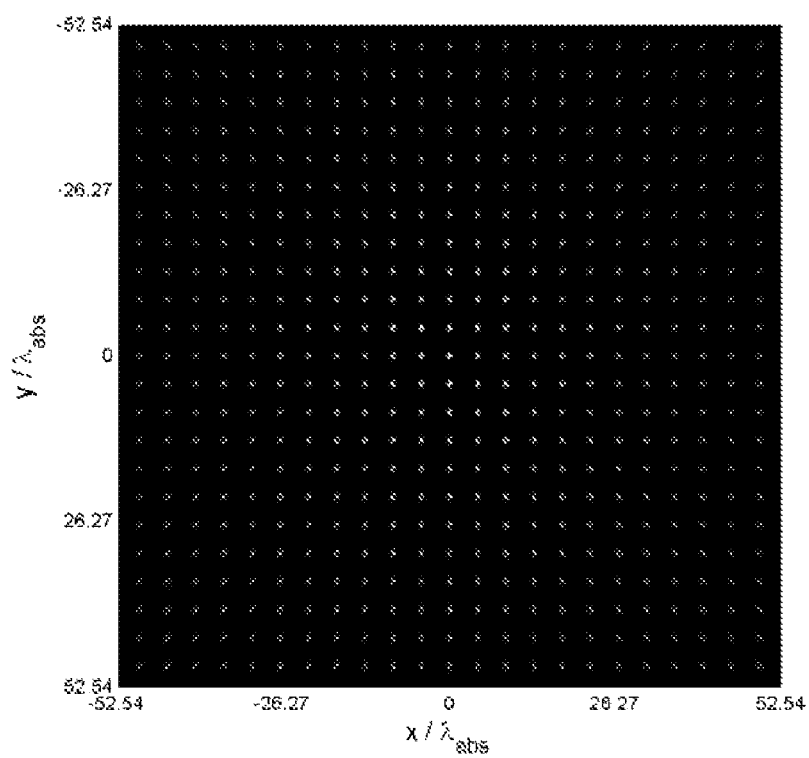
Figure 35D:
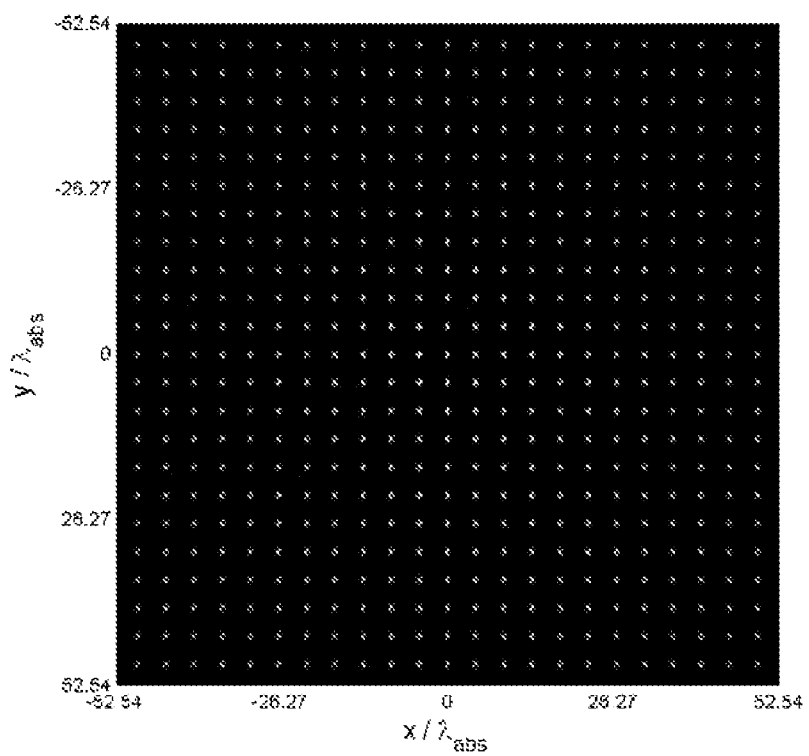
Figure 36A:
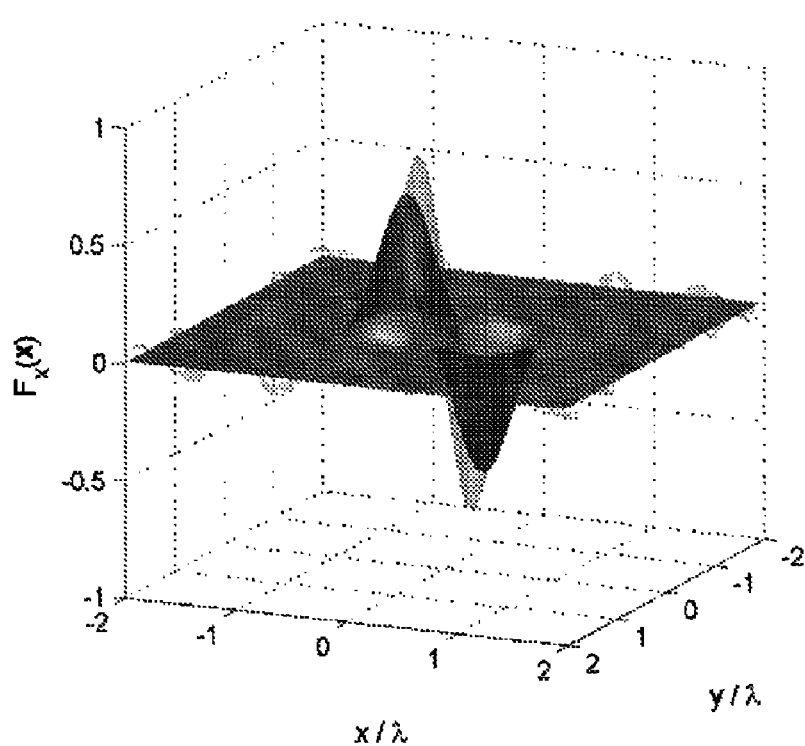
FIGS. 36A and 36B are surface plots of the transverse components of the intensity-normalized optical trapping force in the xy plane for a dielectric particle (k$\alpha$=0.8) at the focus a NA=1.2 water-immersion microscope objective aligned along $\hat{e}_z$ (dark translucent) and at a single intensity maximum within a body-centered cubic lattice of intensity period $\sqrt{26}\lambda$ (light translucent).
Figure 36B:
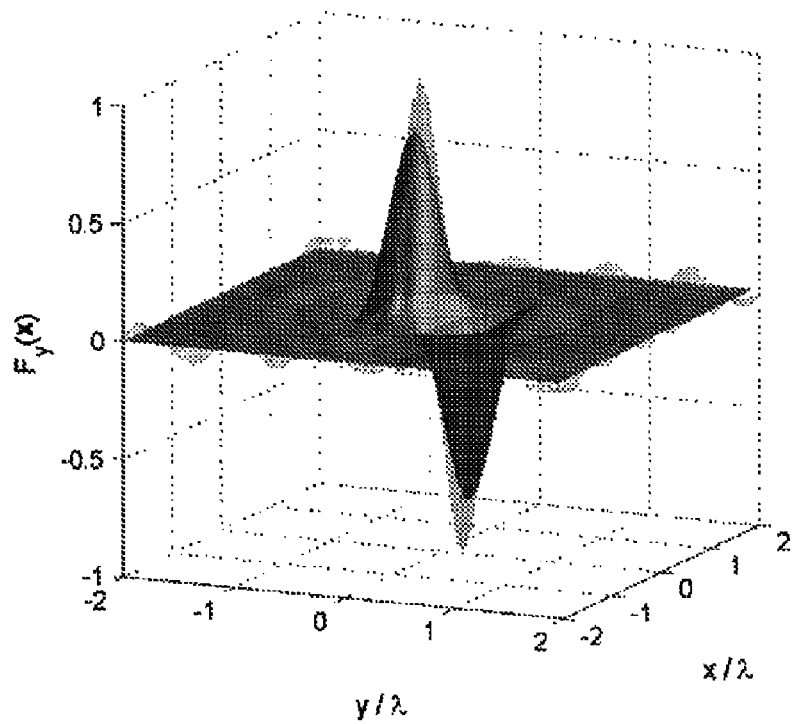
Figure 36C:
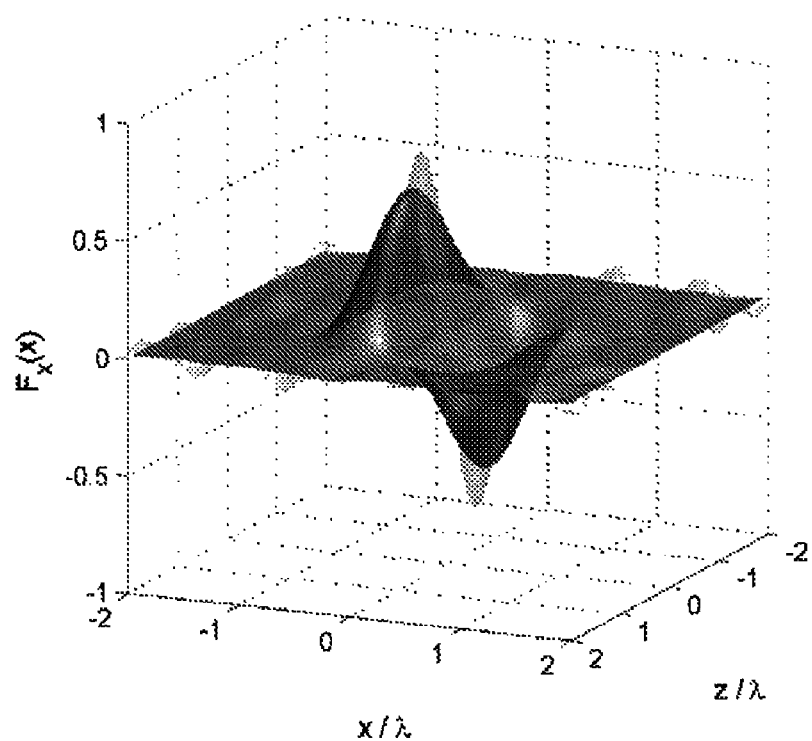
FIGS. 36C and 36D similarly compare the trapping force components $F_x$ and $F_z$ in the xz plane, whereas FIGS. 36E and 36F compare $F_y$ and $F_z$ in the yz plane.
Figure 36D:
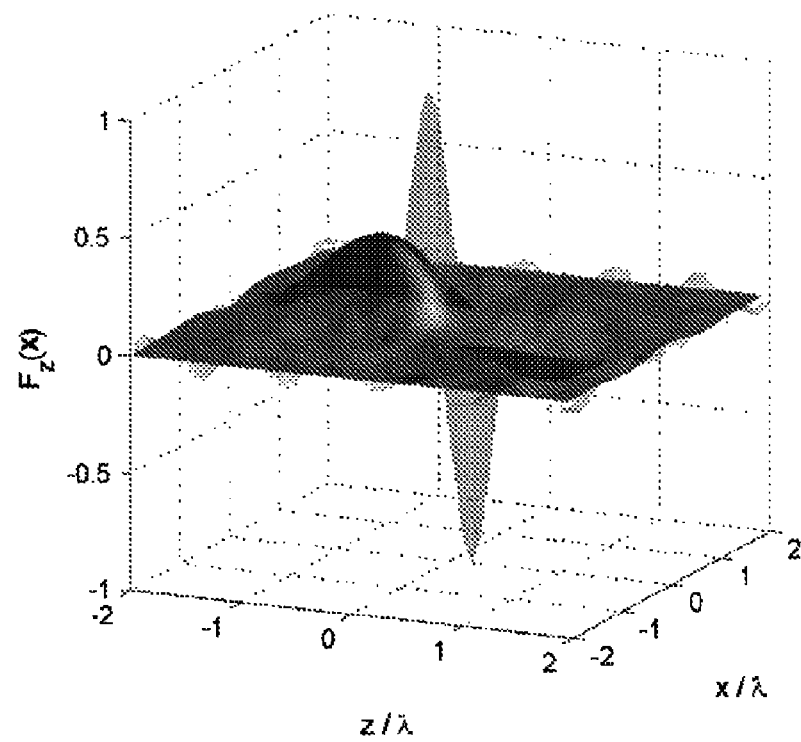
Figure 36E:
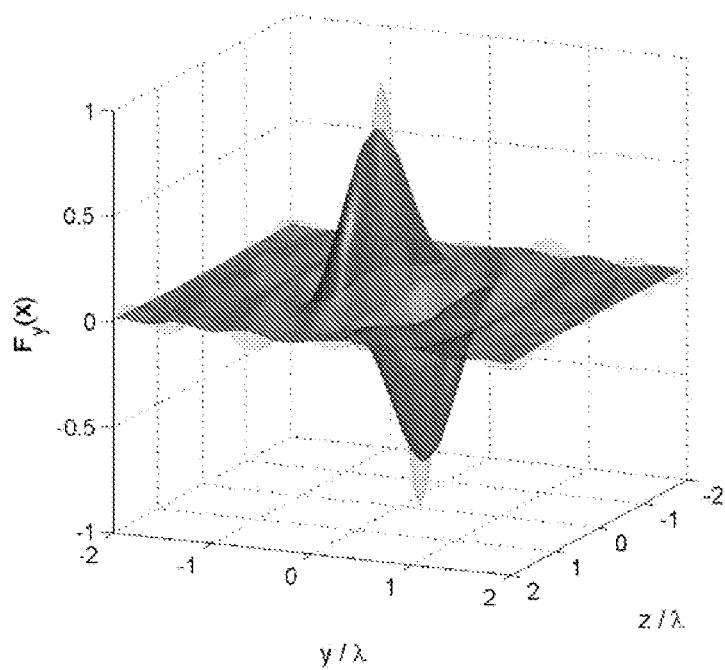
Figure 36F:
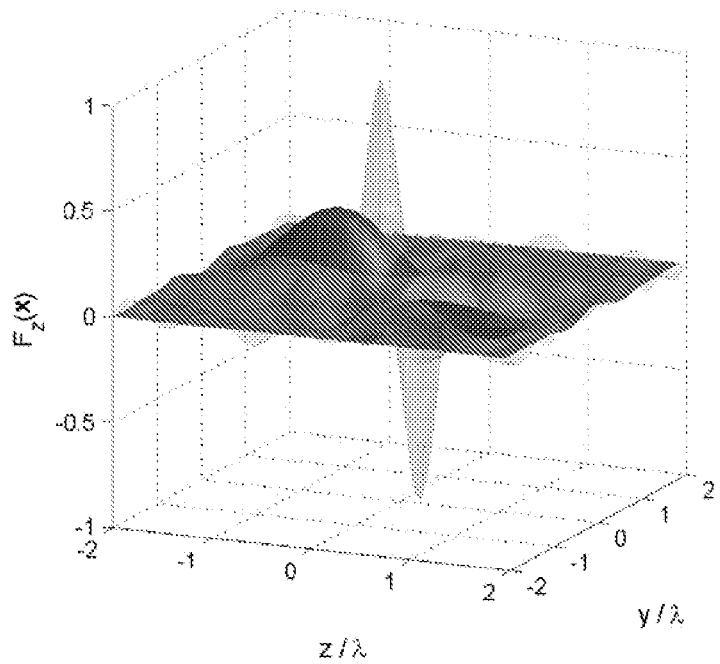

Three-dimensional isosurfaces of the time averaged two-photon excitation strength $\langle |e(x)|^2 \rangle_t^2$ for the body-centered cubic lattice shown in FIG. 34 are plotted in FIG. 35A, where the free-space wavelength, $\lambda_0 = 2\pi c/\omega_0$, is assumed to equal 800 nm and the decay length, $\tau$, is assumed to equal $10^{-14}$ sec (i.e., $\omega_o \tau = 31.3$). Corresponding linear grayscale images showing the two-photon excitation strength in the xy-plane for $\tau = 10^{-14}$, $\tau = 2 \cdot 10^{-14}$, and $\tau = 5 \cdot 10^{-14}$ sec are given in FIGS. 35B, 35C, and 35D, respectively.

Comparison of Equations (6) and (39) and inspection of FIG. 35 reveal two primary effects of the pulsed excitation. First, the excitation strength across the lattice is modified by an envelope having a width, $\Delta w$, that is on order of $c\tau$. Second, the spatial frequencies of the excitation at any point, x, decay fastest along the direction of the radial vector, $x - x_d$, which causes the lattice maxima to become increasingly elongated in this direction with increasing distance from the center of the envelope. However, two-photon excitation in living cells is commonly performed with pulses that are longer than $10^{-13}$ sec, so that these effects become significant (and hence require compensation of the effective excitation PSF) only when the desired field of view is of order 30 µm or larger.

Optical Trapping

Yet another application of optical lattices of confined intensity maxima is optical trapping of matter by the periodic potential wells in the lattice. For a spherical dielectric particle of radius, $\alpha$, and refractive index, $n_p$, in a medium of refractive index, $n_{med}$, the force due to a monochromatic electromagnetic field in the electrostatic limit ($k\alpha \ll 1$) has two contributions: one attractive term due to the gradient of the field:

$$\langle F_\nabla(x) \rangle_t = \langle [p(x, t) \cdot \nabla] e(x, t) \rangle_t \quad (40a)$$

$$= \left( \frac{\varepsilon_{rel} - 1}{\varepsilon_{rel} + 2} \right) \frac{a^3}{4} \nabla |e(x, t)|^2, \varepsilon_{rel} = (n_p/n_{med})^2,$$

and one repulsive term due to Rayleigh scattering:

$$\langle F_{scat}(x) \rangle_t = \frac{n_{med}}{c} \sigma \langle S(x, t) \rangle_t \quad (40b)$$

$$= \frac{n_{med}}{3} k^4 a^6 \left| \frac{\varepsilon_{rel} - 1}{\varepsilon_{rel} + 2} \right|^2 \text{Re}\{e(x) \times h*(x)\},$$

where $\sigma$ is the scattering cross-section of the particle, $S(x,t)$ is the Poynting's vector and, for the lattice electric field, $e(x,t)$, of Equation (3), the corresponding magnetic field, $h(x,t)$, is given by:

$$h(x, t) = n_{med} \sum_{n=0}^{N} (k_n \times e_n) \exp(ik_n \cdot x)/k. \quad (41)$$

Components of the trapping force in the xy, xz, and yz planes are plotted in FIG. 36 for a single trap at the focus of a water-immersion microscope objective having a NA=1.2 and an optical axis, $\hat{e}_z$. Also plotted in FIG. 36 are components of the trapping force in the xy, xz, and yz planes for one of the multiple traps formed by the intensity maxima of a maximally symmetric body-centered cubic lattice of intensity period $\sqrt{26}\lambda$. It is assumed that $k\alpha = 0.8$, $n_p = 1.6$, and x-polarization at the trap is optimized in both cases.

Figure 37A:
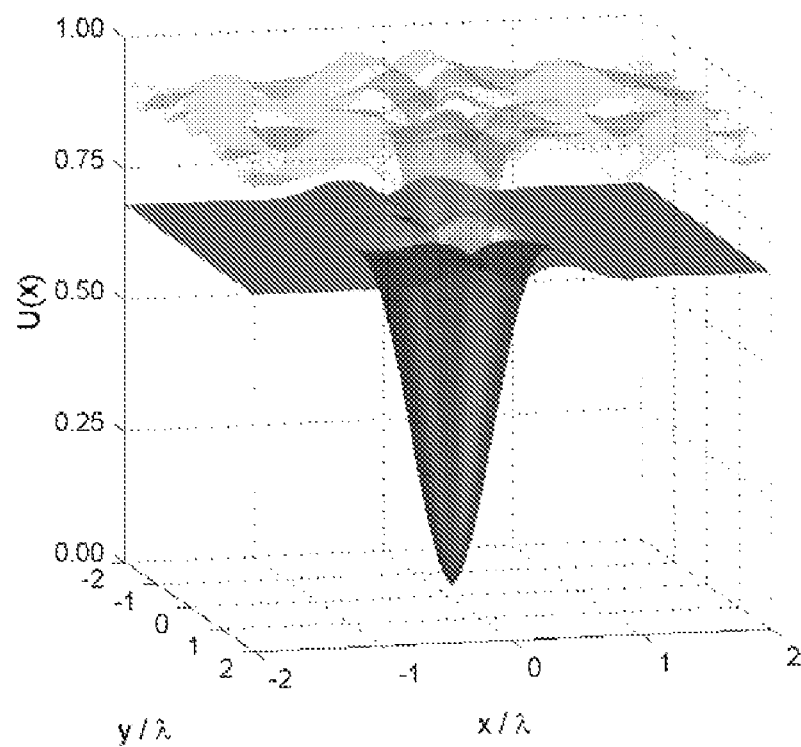
FIGS. 37A-C are surface plots of the optical trapping potential in the xy, xz, and yz planes, respectively, for the objective (dark translucent) and lattice (light translucent) scenarios of FIG. 36.
Figure 37B:
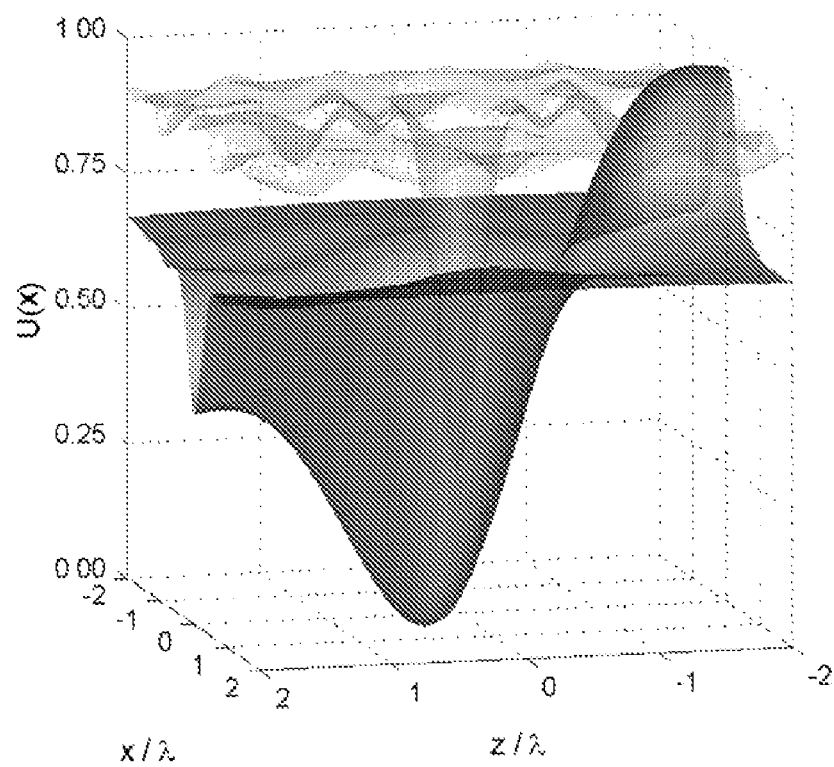
Figure 37C:
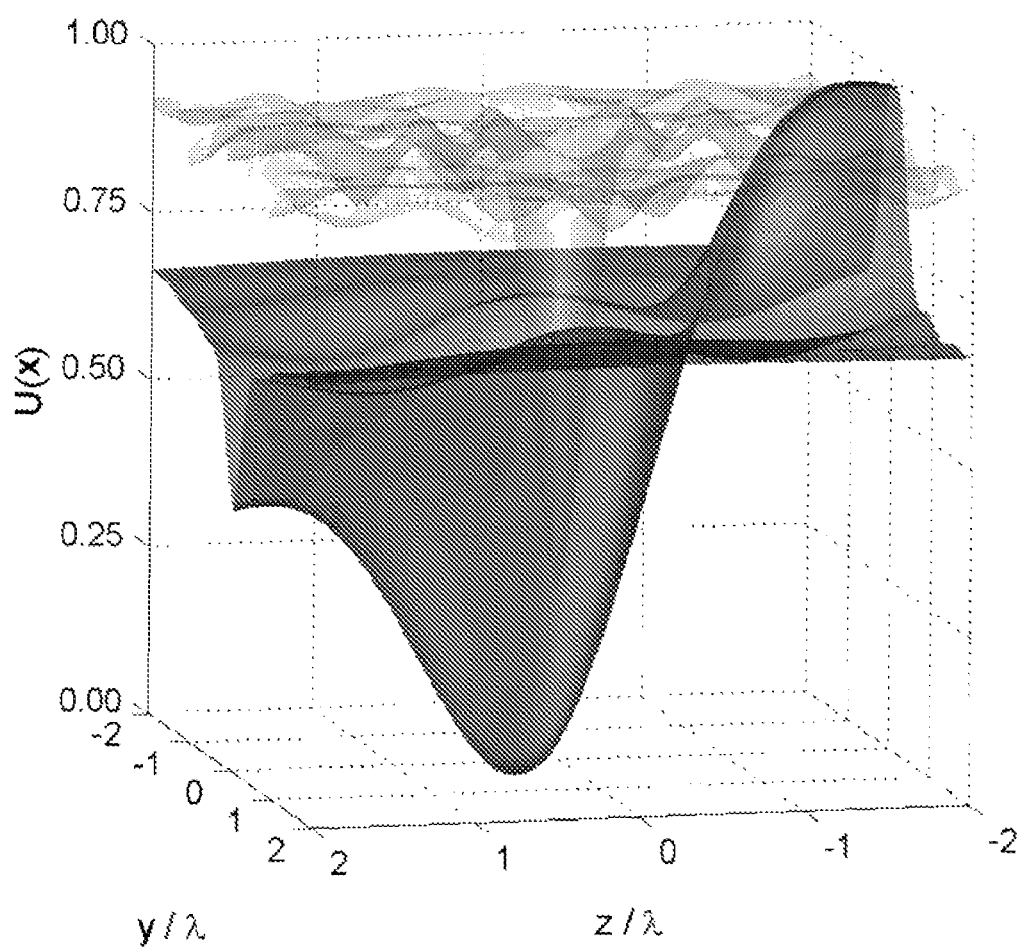

The trapping potential between any two points x and $x_{ref}$ is then given by:

$$U(x) = -\int_{x_{ref}}^{x} [\langle F_\nabla(x) \rangle_t + \langle F_{scat}(x) \rangle_t] \cdot ds, \quad (42)$$

which is plotted in FIG. 37 for the same cases and conditions as used for the traps illustrated in FIG. 36.

FIGS. 36 and 37 reveal several advantages of trapping with a maximally symmetric optical lattice as opposed to a single lens, single focus system. First, the greater confinement of the lattice intensity maxima due to the inclusion of wavevectors from a wider range of directions results in moderate enhancement ($\approx 1.3 \times$) of the peak trapping force in the xy plane, and significant enhancement ($\approx 2.7 \times$) of the gradient contribution to the trapping force along the axis, $\hat{e}_z$. Thus, although the depth of trapping potential minimum for a given peak intensity are similar in the two scenarios, the potential well is significantly narrower in the lattice case, indicating closer confinement to a specific desired position for a dielectric particle of a given kinetic energy. Second, due to the symmetry of the wavevector distribution, the scattering force in the lattice case is zero, whereas in the lens case the overall energy flow $\langle S(x) \rangle$ shifts the potential minimum along $\hat{e}_z$ and reduces the energy necessary for the particle to escape the trap. Indeed, Equations (40) suggest that for a sufficiently large particle, the scattering force dominates in single lens illumination, and the particle will not be confined. Finally, lattice excitation allows an arbitrarily large number of particles to be trapped simultaneously with continuously adjustable spacing in two-dimensions, or with a discrete set of possible periods for a three-dimensional lattice of given symmetry and aspect ratios.

Optical lattice trapping can be used in the conventional fashion to manipulate whole cells or organelles within single cells, as well as to measure intracellular mechanical properties (e.g., effective bending moduli) and the force output of intracellular molecular motors. In addition, however, the multiplicity of traps afforded by lattice excitation can be uniquely used to immobilize a free-floating cell at many points across its interior (e.g., using an infrared wavelength which is not absorbed by the cell) to facilitate imaging with a second lattice at a wavelength chosen to excite the desired target. This eliminates the issues of phase aberrations in beams passing obliquely through the substrate and reflections of beams incident upon the substrate (as discussed below) that must be addressed in the lattice excitation of cultured cells.

Beyond the realm of biology, a dilute beam of individual atoms (e.g., chromium) can be trapped, cooled, and then deposited on a surface using a two-dimensional lattice. This approach has been used with one or two crossed standing waves to create gratings of period of the close order of $\lambda/2$ and linewidths as small as 15 nm (see, e.g., G. Timp, et al., *Phys. Rev. Lett.*, 69, 1636 (1992), which is incorporated herein by reference). As with the lithography examples described herein with reference to FIGS. 31C and 32B, extension to two-dimensional composite lattices permits the creation of arrays of controllable period with a repeated arbitrary pattern in each primitive cell, except at a resolution dictated, not by $\lambda$, but rather by the degree to which the transverse atomic motion has been damped by the lattice. Similarly, atomic cooling in two-dimensional and three-dimensional lattices, which has been used in quantum electronics experiments (e.g., for Bose-Einstein condensation and quantum computing) and typically is performed with fundamental lattices, may also benefit from the narrower trapping potentials and decoupling of the potential depth from the periodicity possible with sparse, composite lattices in general and maximally symmetric composite lattices in particular. As these applications involve selection rules sensitive to specific components of the electromagnetic field, they may also benefit from the basis construction methods outlined above.

Stimulated Emission Depletion Microscopy

Until now the methods of molecular excitation that have been considered, including multiphoton excitation, limit spatial resolution in microscopy to the order of $\sim \lambda_{abs}/(2n_{med})$ dictated by the peak absorption wavelength, $\lambda_{abs}$, of the molecular species and the refractive index, $n_{med}$, of its surrounding medium. Although much can be learned about the structure and function of living cells at this resolution, extension of optical microscopy, and lattice microscopy in particular, well beyond $\lambda_{abs}/(2n_{med})$ can provide a unique non-invasive tool for the study of dynamic intracellular processes in the critical range between macromolecules and organelles.

Additionally, until now the construction of bases that optimize a particular polarization state and hence the intensity at a specific point and time within each primitive cell have been emphasized. However, other types of useful bases also exist and also can be useful for lattice microscopy applications.

Figure 38:
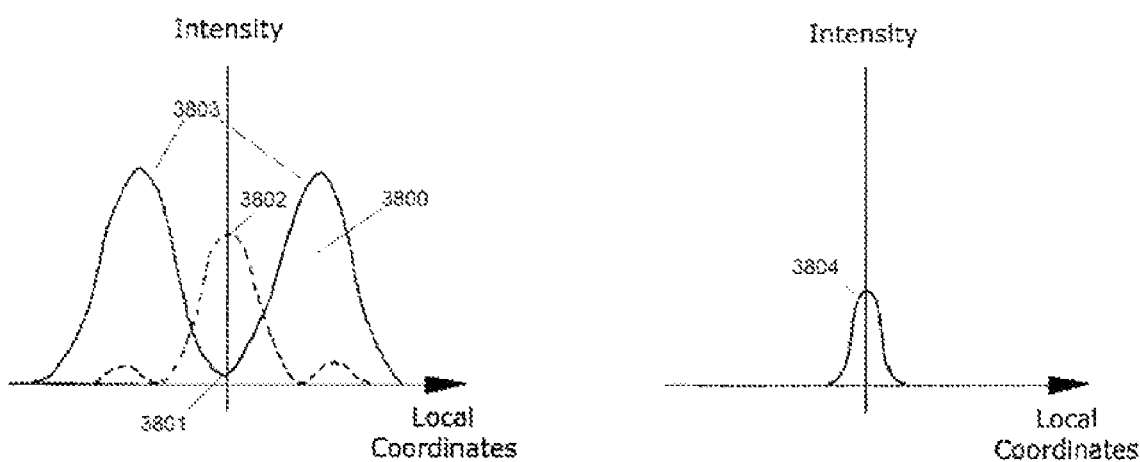
FIG. 38 is a conceptual view of the intensity profiles of an excitation beam, depletion beam, and resulting depleted excitation region in stimulated emission depletion microscopy.
Figure 39A:
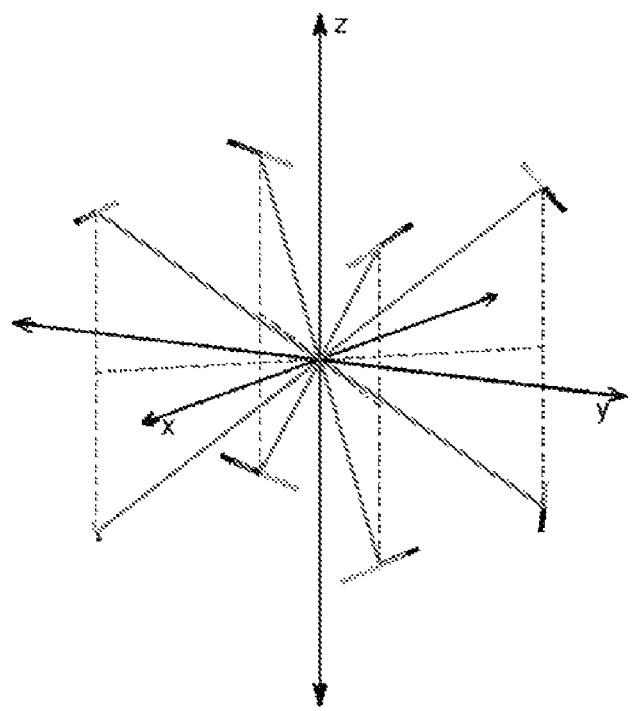
FIG. 39A is a three-dimensional representation of the relative wavevector and electric field directions and real field magnitudes at different times for the plane waves that make up an exemplary body-centered cubic depletion lattice with a basis of three-dimensional nodes for use in stimulated emission depletion microscopy.
Figure 39B:
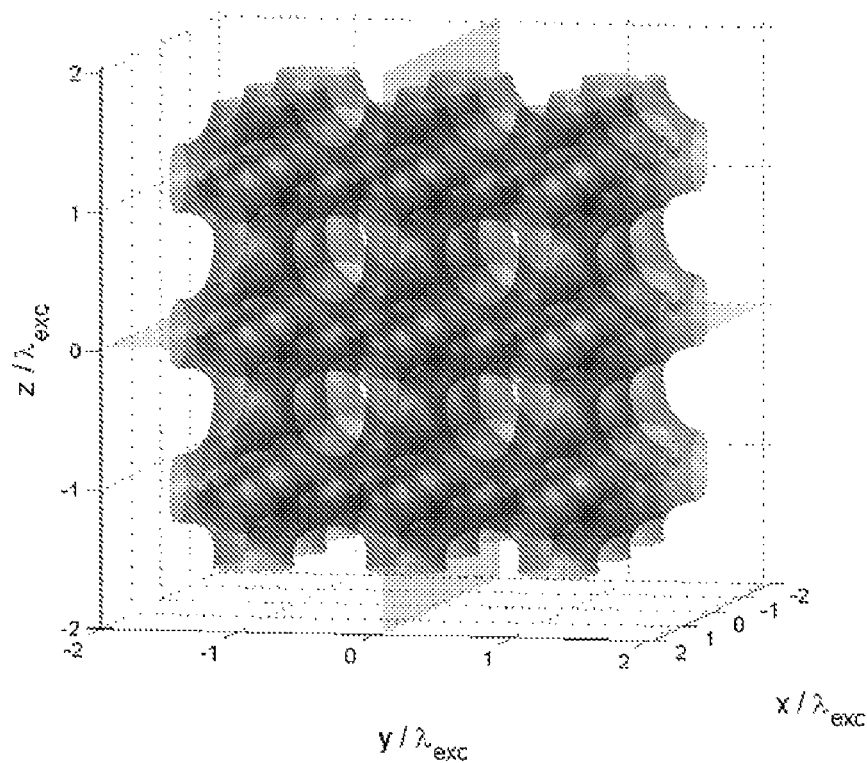
FIG. 39B is a three-dimensional plot of surfaces light intensity (translucent) having 50% of the maximum light intensity for the lattice and basis obtained with the plane wave properties shown in FIG. 39A.
Figure 39C:
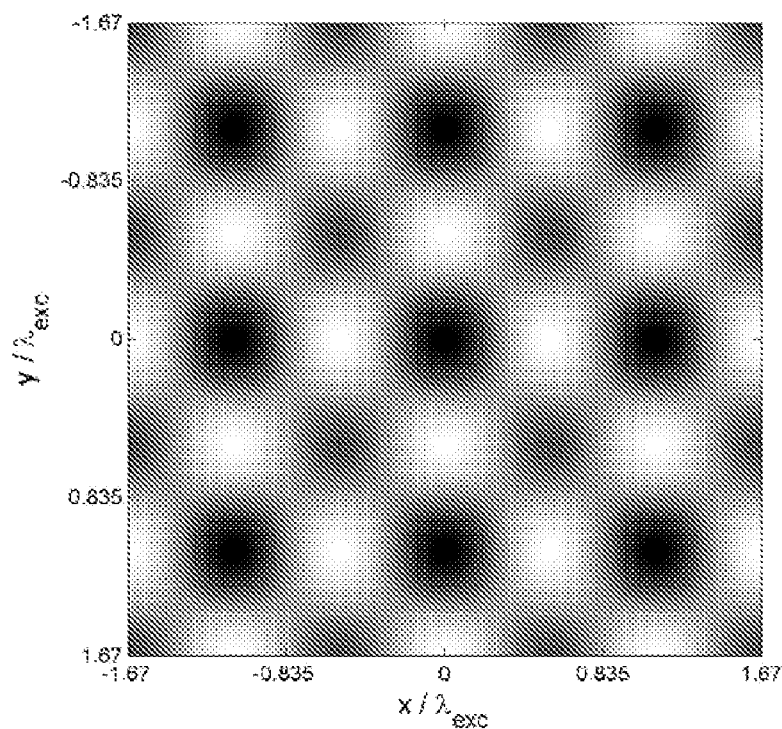
FIGS. 39C, 39D, and 39E are linear grayscale images of the depletion intensity in the x-y, x-z, and y-z planes, respectively, shown in FIG. 39B.
Figure 39D:
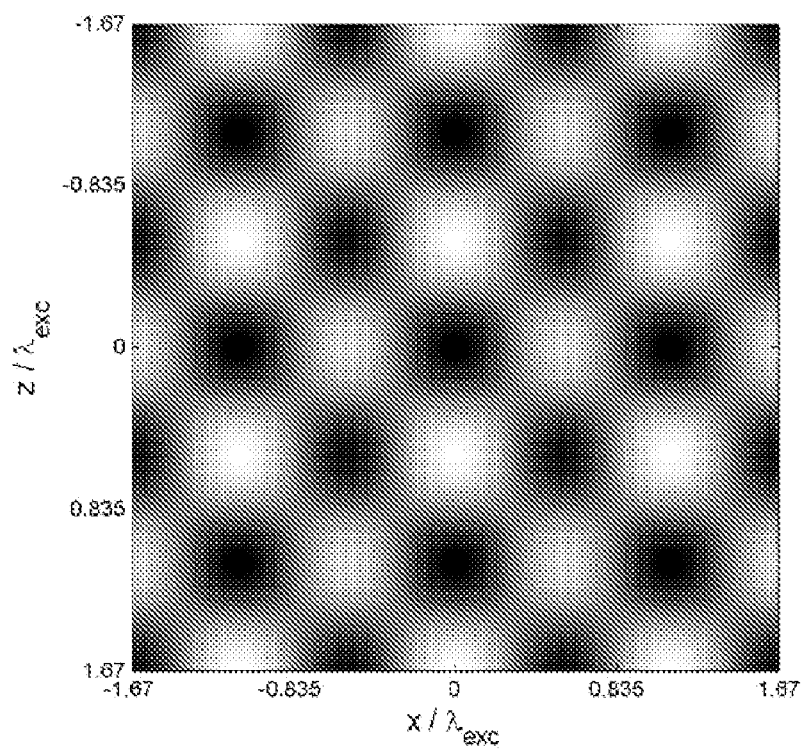
Figure 39E:
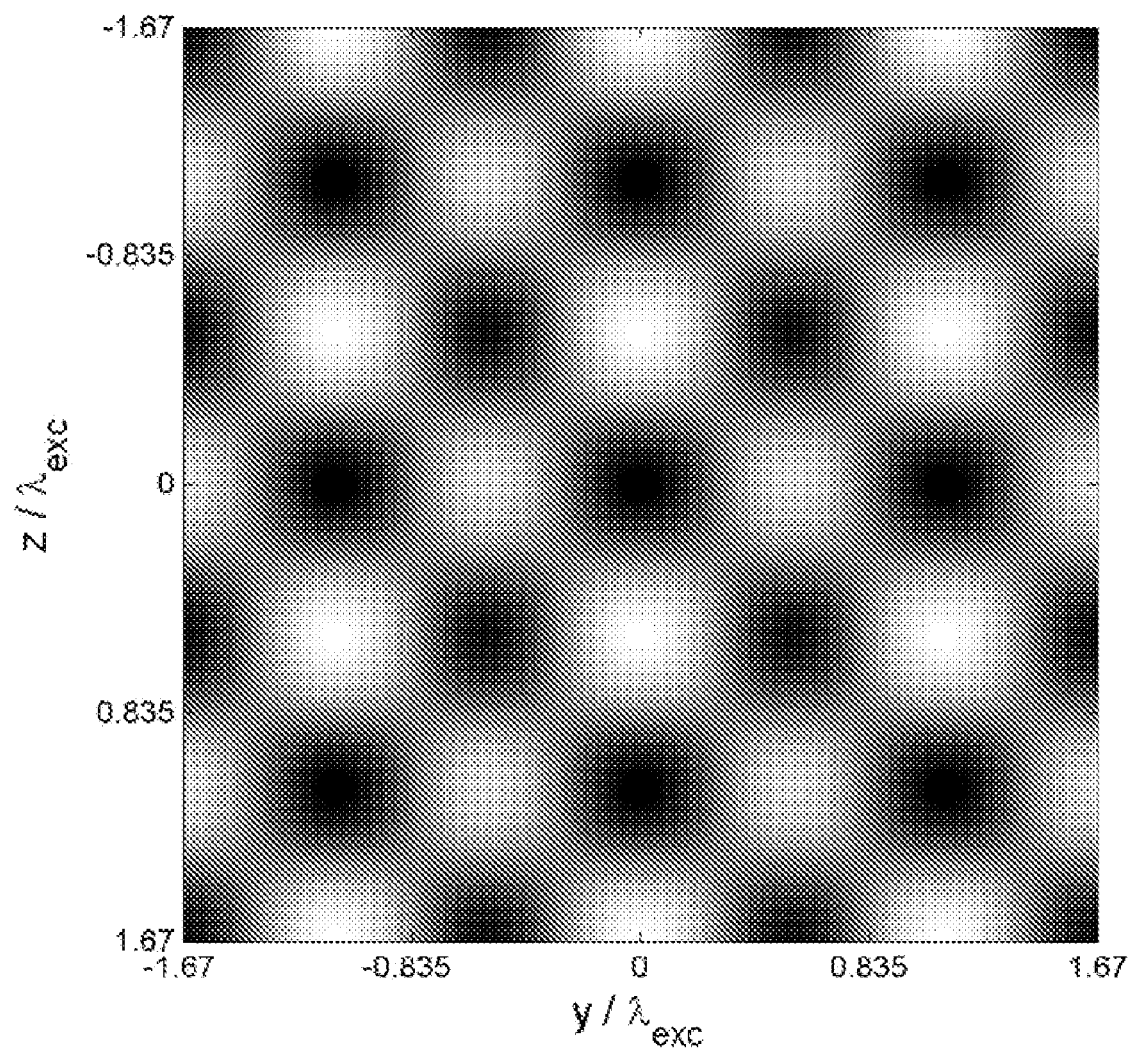
Figure 40A:
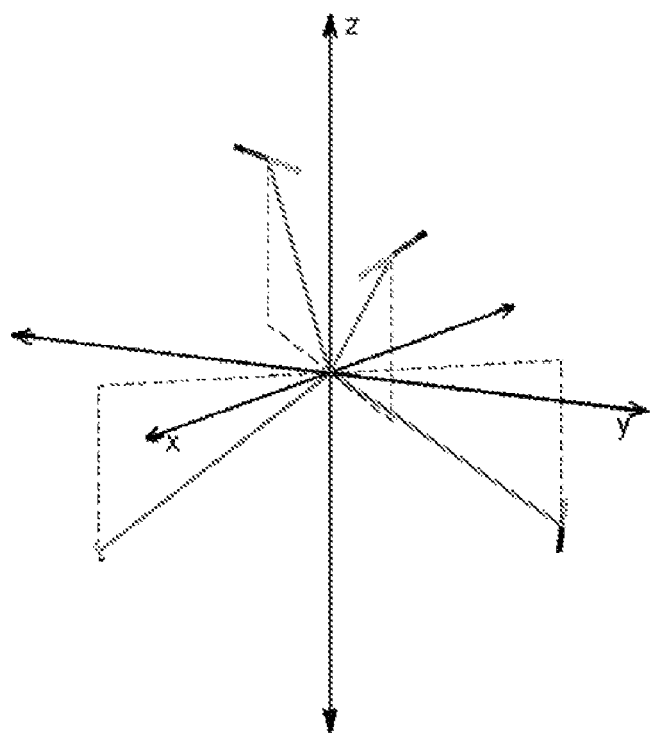
FIGS. 40A, 40F, and 40K are three-dimensional representations of the relative wavevector and electric field directions and real field magnitudes at different times for the plane waves of the three lattices that, when superimposed, make up the depletion lattice shown in FIGS. 39A-39E.
Figure 40B:
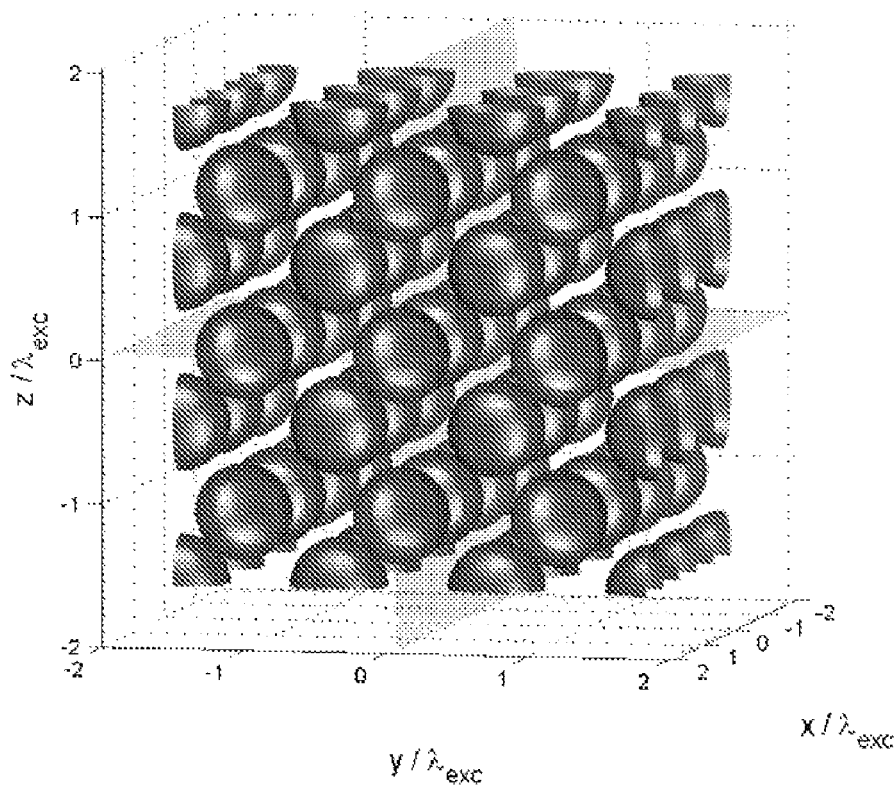
FIGS. 40B, 40G, and 40L are three-dimensional plots of surfaces of light intensity having 50% of the maximum light intensity for the lattices and bases obtained with the plane wave properties of FIGS. 40A, 40F, and 40K, respectively.
Figure 40C:
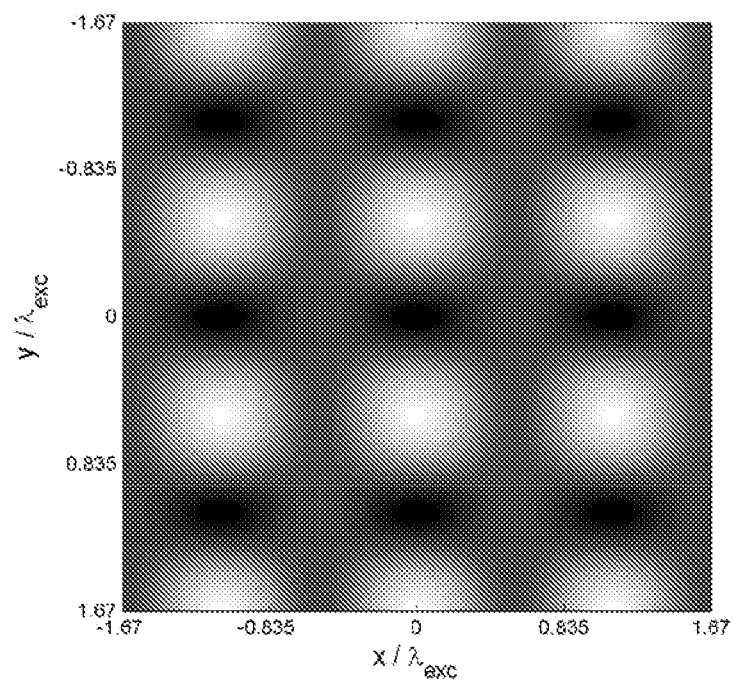
FIGS. 40C, 40D, and 40E are linear grayscale images of the intensity in the x-y, x-z, and y-z planes, respectively, shown in FIG. 40B.
Figure 40D:
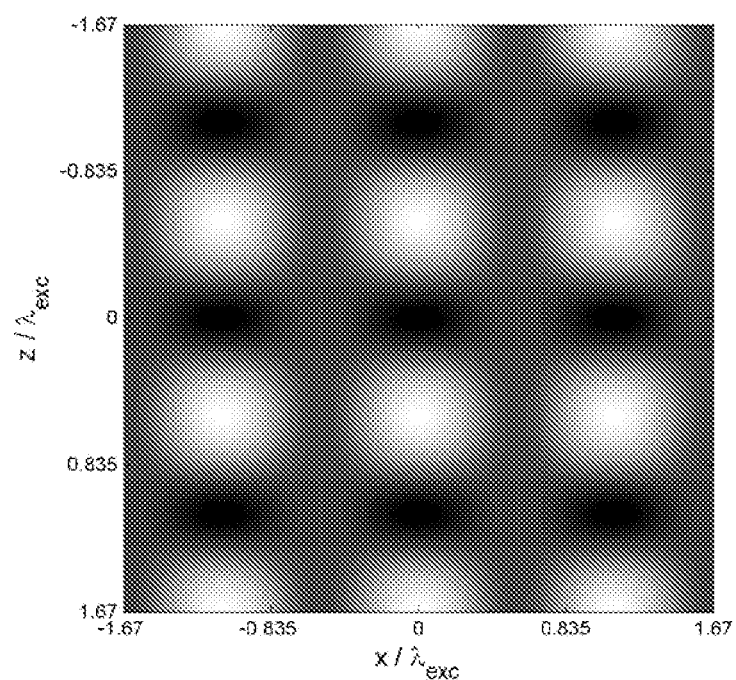
Figure 40E:
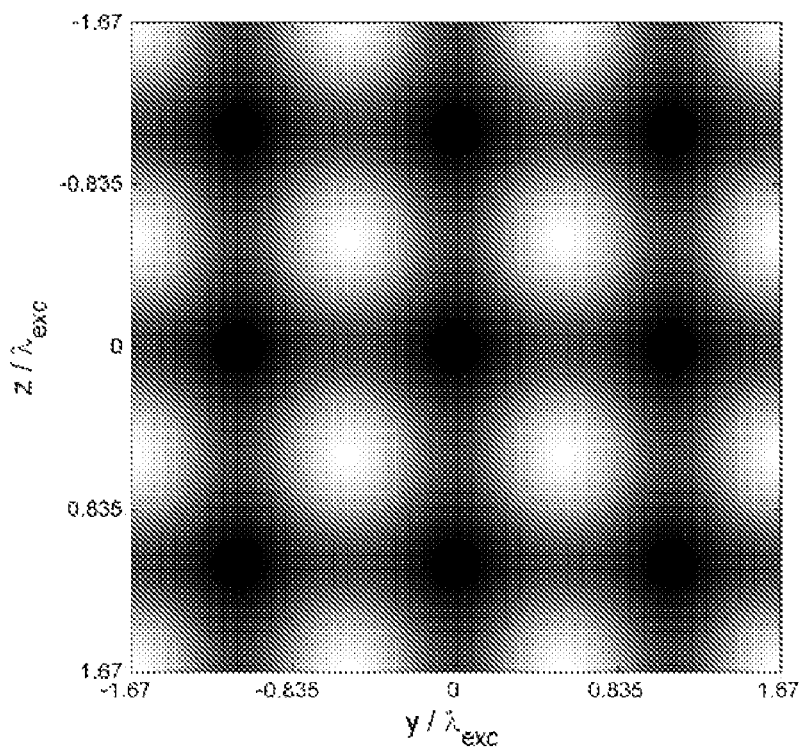
Figure 40F:
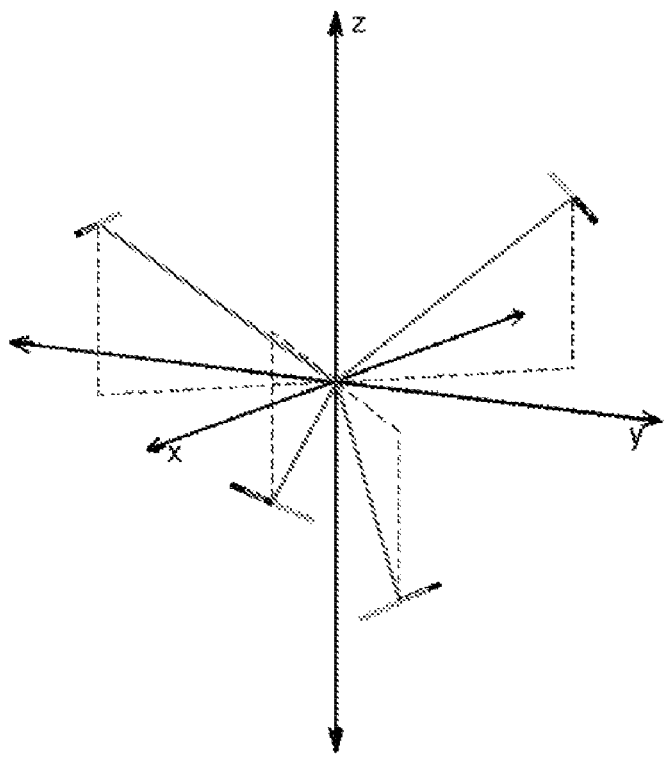
Figure 40G:
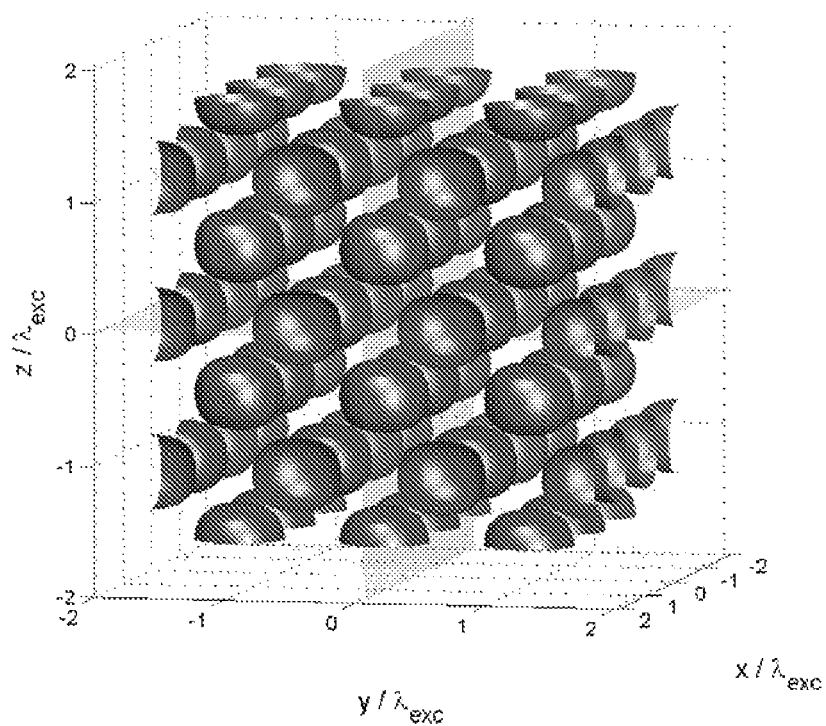
Figure 40H:
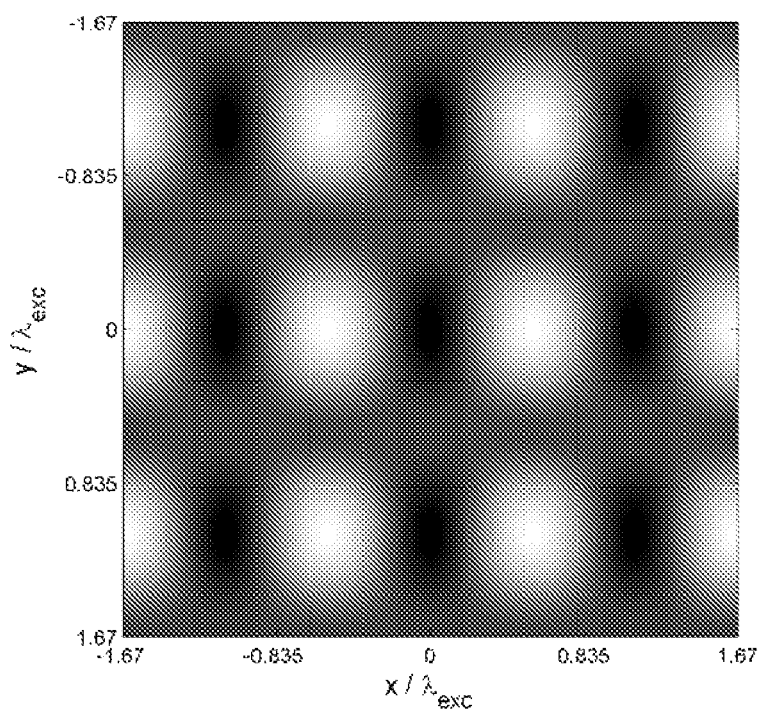
FIGS. 40H, 40I, and 40J are linear grayscale images of the intensity in the x-y, x-z, and y-z planes, respectively, shown in FIG. 40G.
Figure 40I:
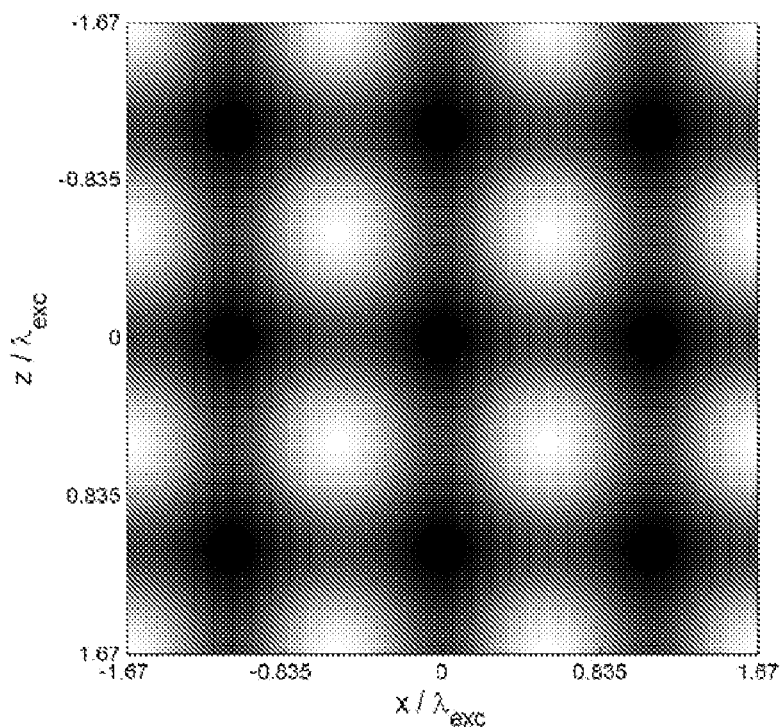
Figure 40J:
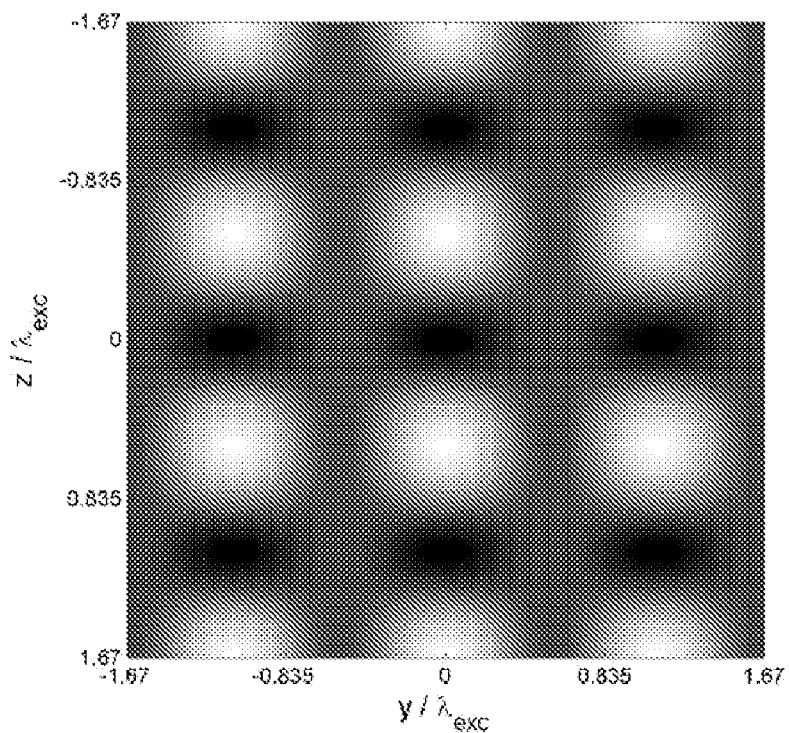
Figure 40K:
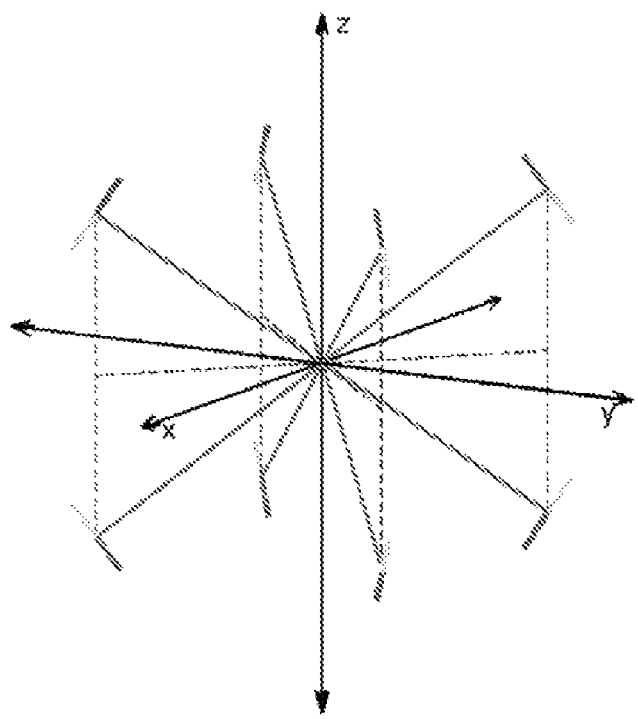
Figure 40L:
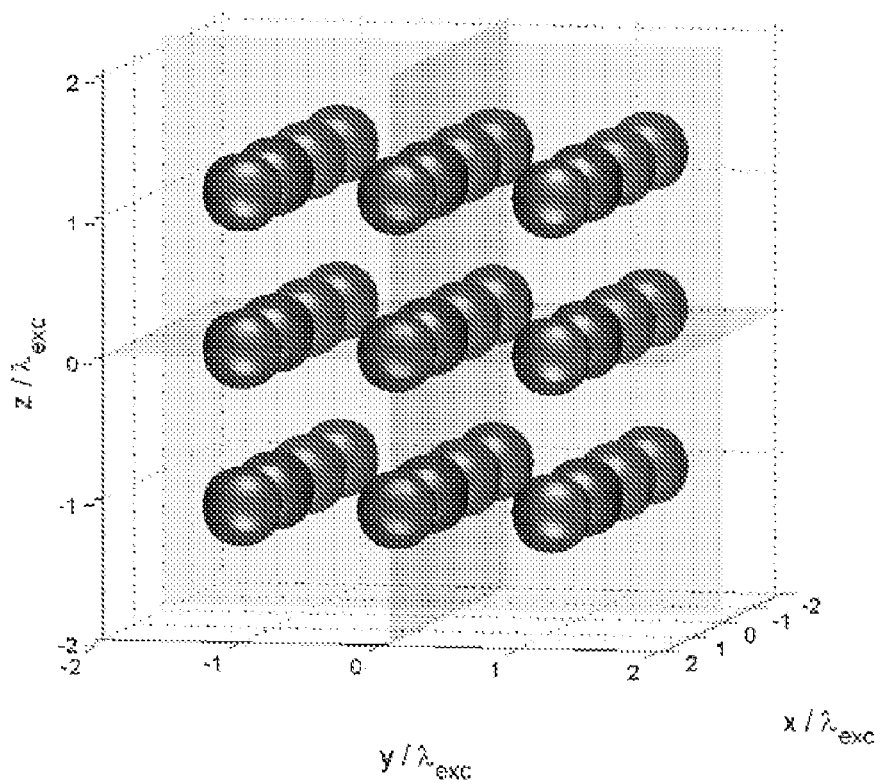
Figure 40M:
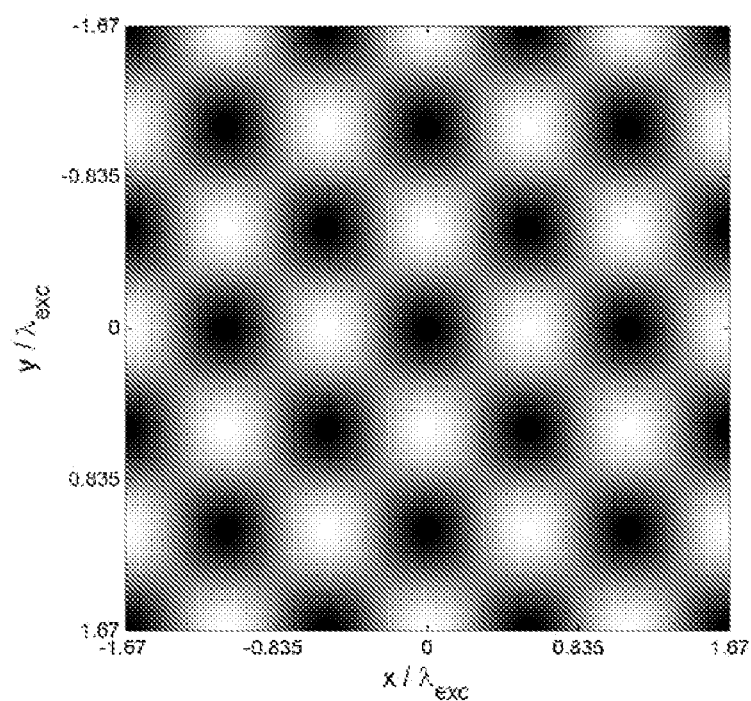
FIGS. 40M, 40N, and 40O are linear grayscale images of the intensity in the x-y, x-z, and y-z planes, respectively, shown in FIG. 40L.
Figure 40N:
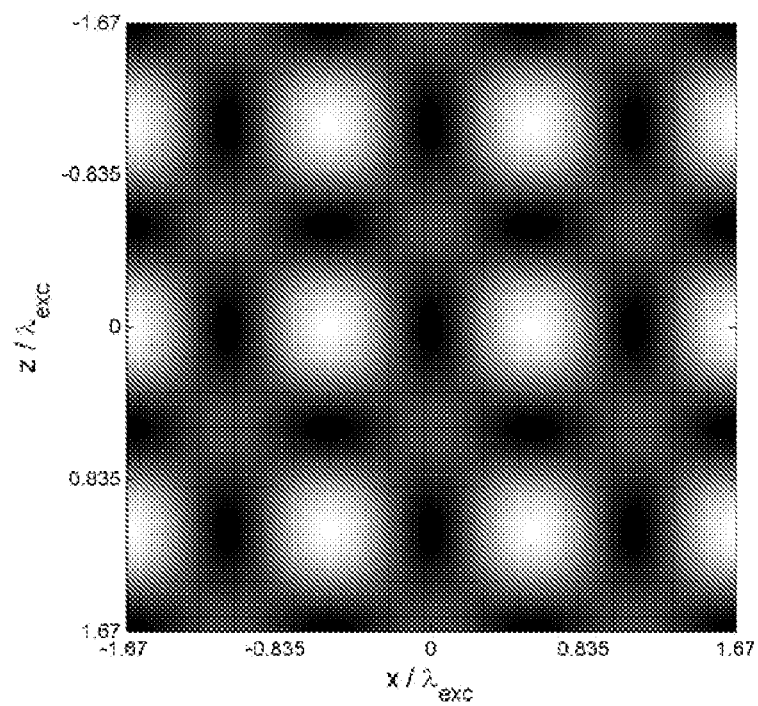
Figure 40O:
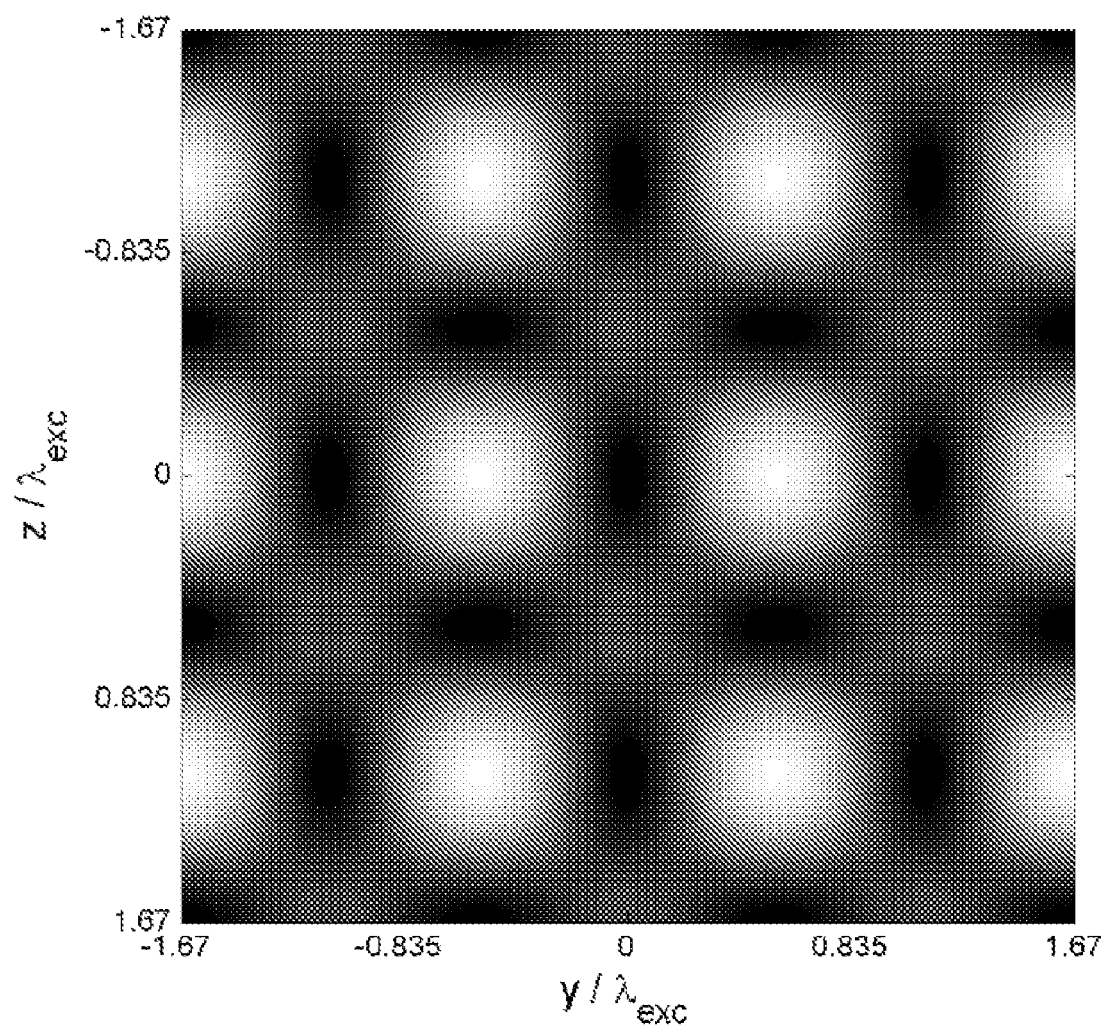
Figure 41A:
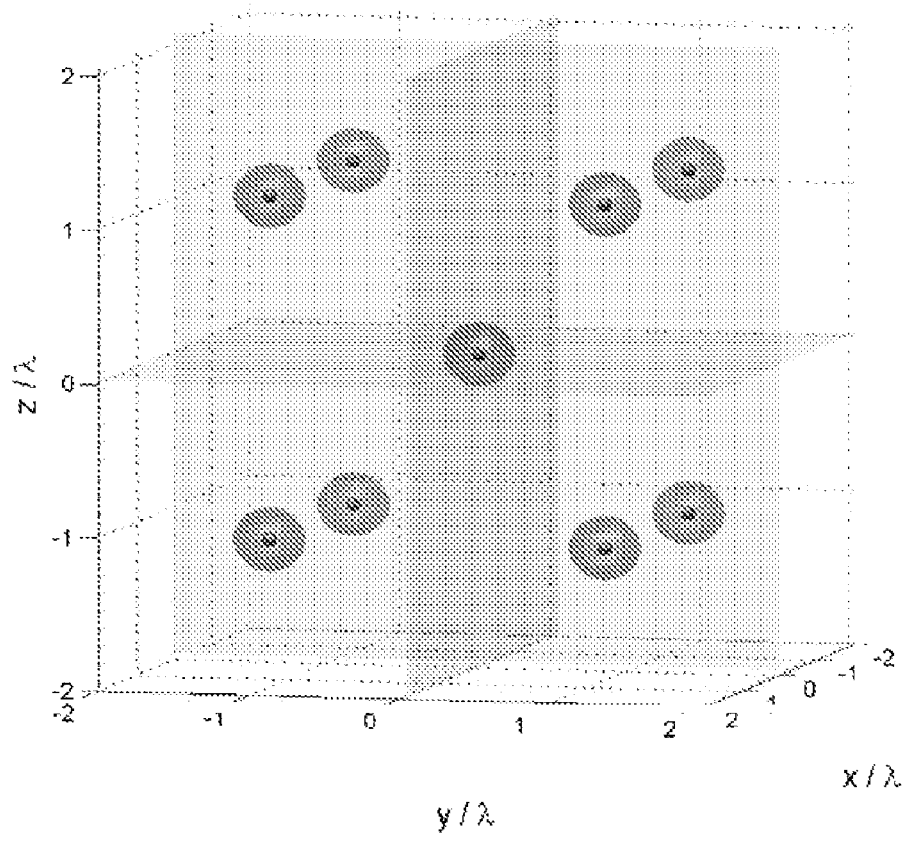
FIG. 41A is a three-dimensional plot of surfaces of light intensity (translucent) having 50% of the maximum intensity for a particular body-centered cubic excitation lattice and surfaces light intensity having 50% of the maximum spontaneous emission intensity (opaque) for the stimulated emission depletion (STED) lattice created by the interaction of both this excitation lattice and the depletion lattice of FIG. 39 with a fluorescent sample.
Figure 41B:
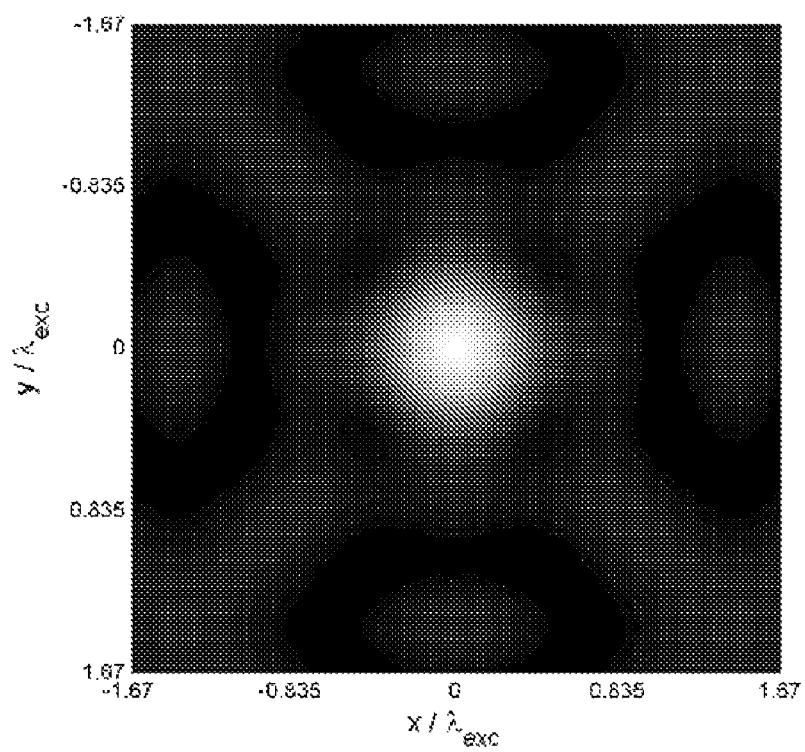
FIGS. 41B, 41C, and 41D are linear grayscale images of the excitation lattice intensity in the x-y, x-z, and y-z planes, respectively, shown in FIG. 41A.
Figure 41C:
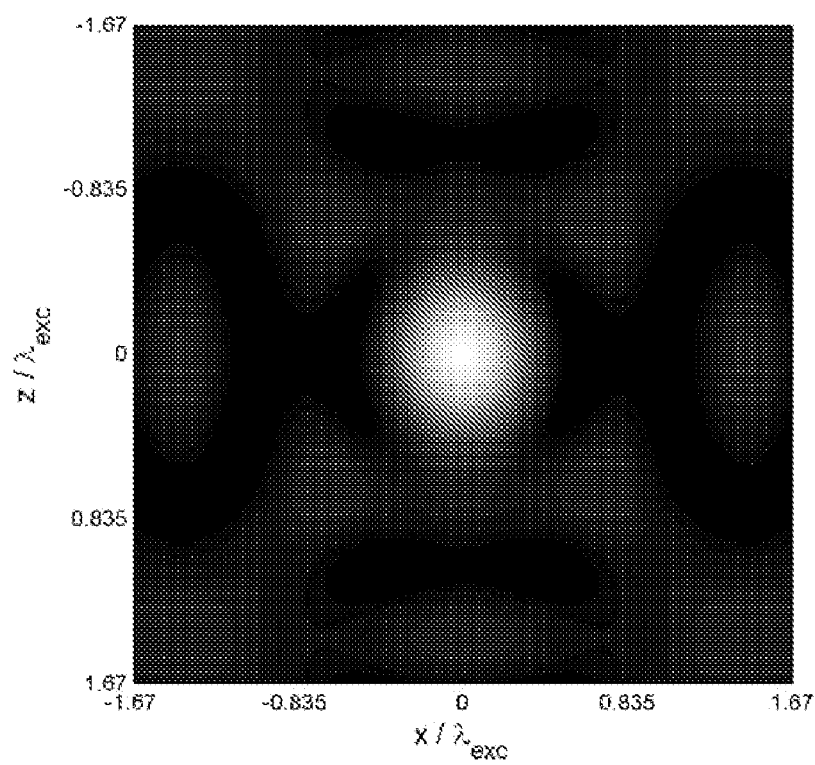
Figure 41D:
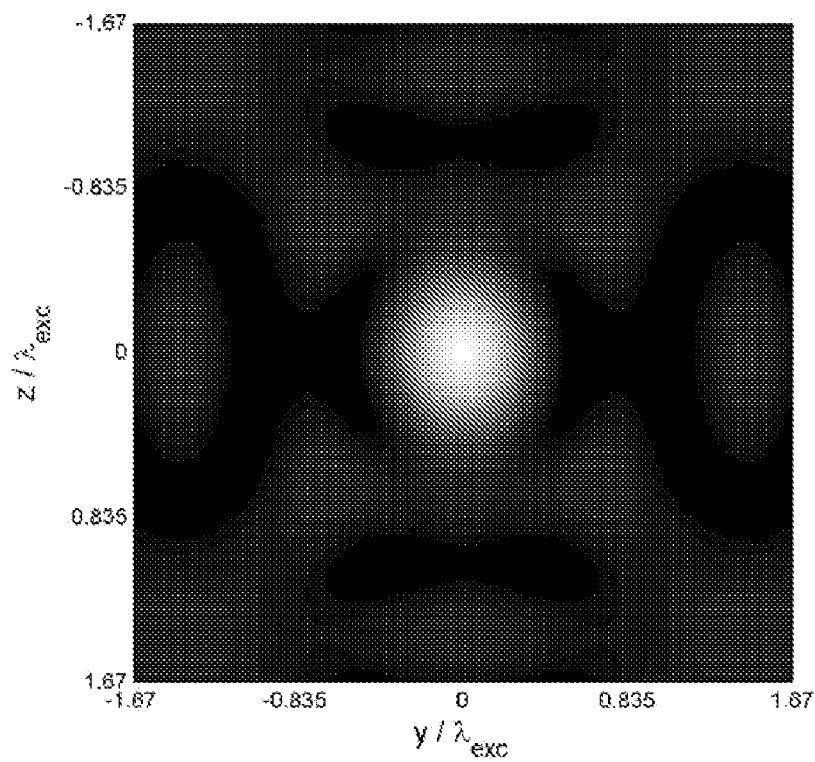
Figure 41E:
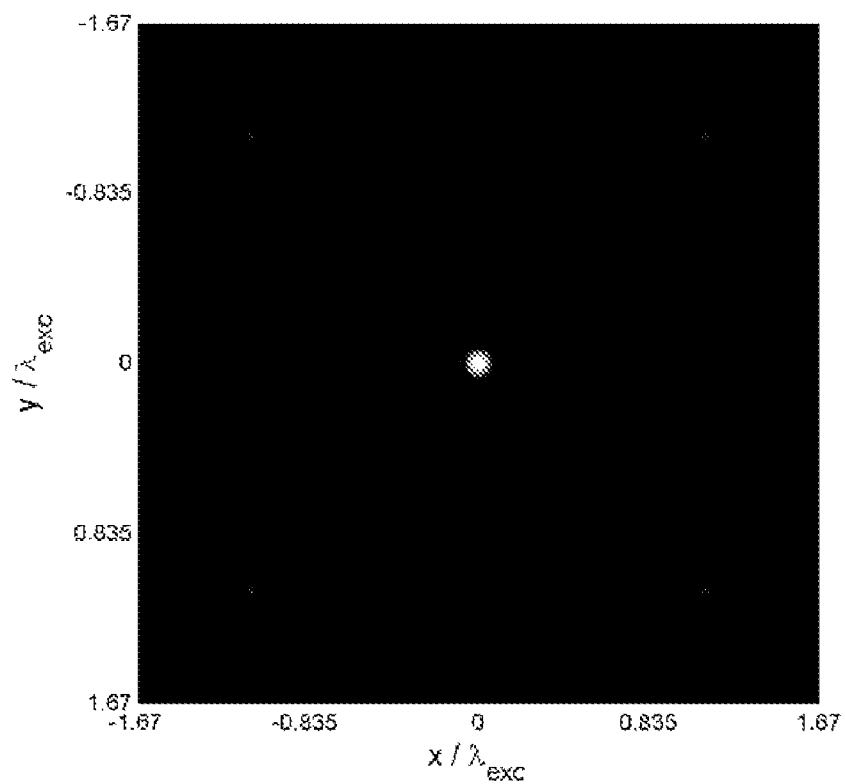
FIGS. 41E, 41F, and 41G are linear grayscale images of the STED lattice spontaneous emission intensity in the x-y, x-z, and y-z planes, respectively, shown in FIG. 41A.
Figure 41F:
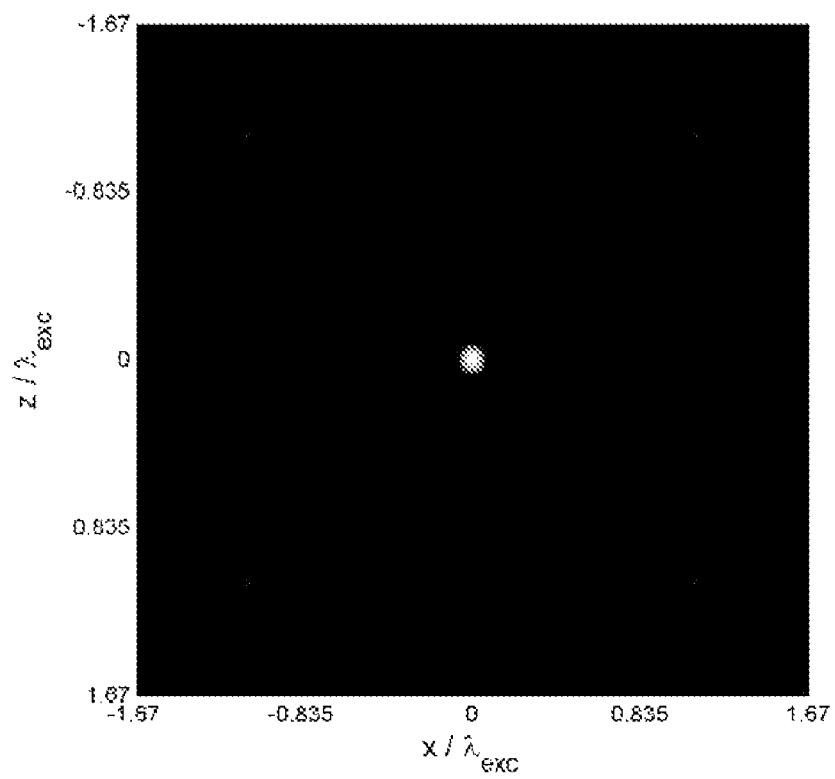
Figure 41G:
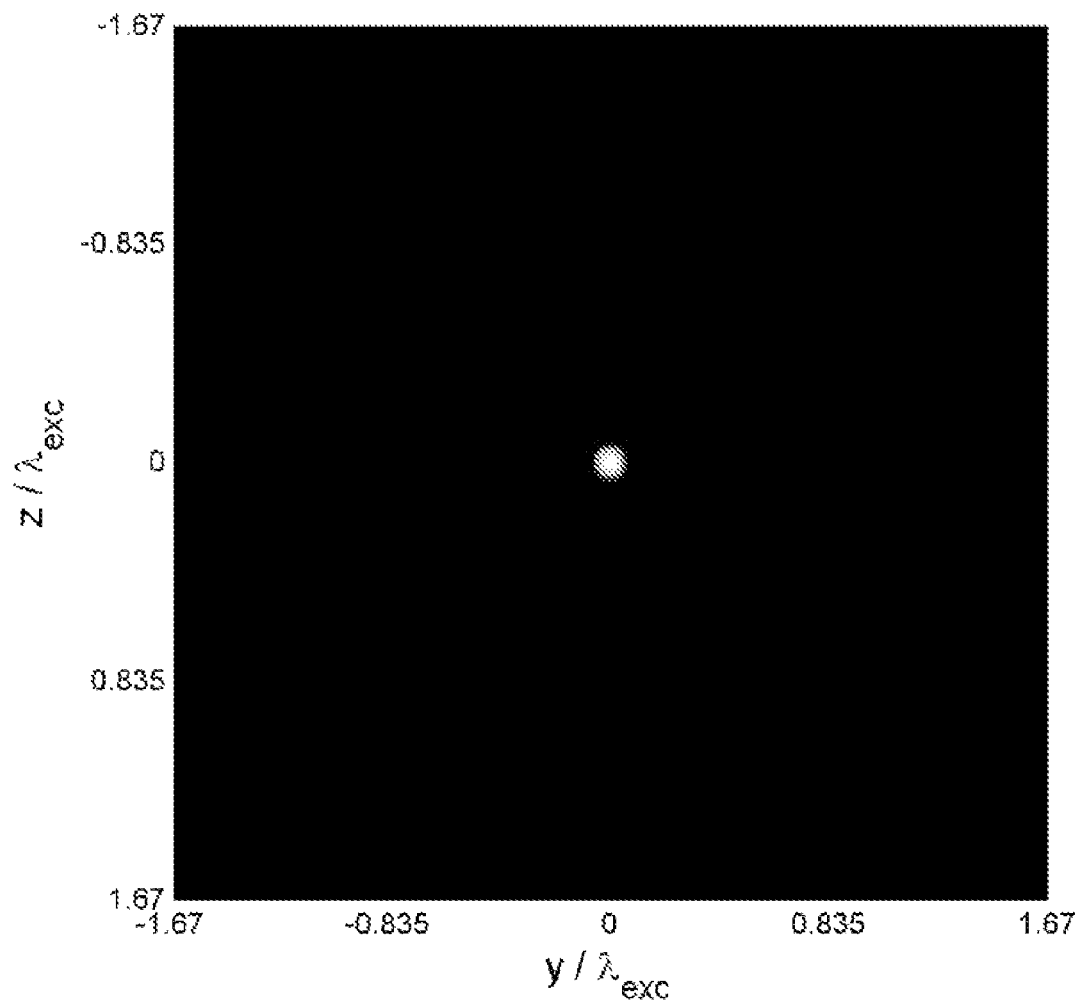

One method adaptable to optical lattice microscopy that can provide significant superresolution and that exemplifies the use of bases other than those founded upon intensity maximization at a point is stimulated emission depletion microscopy ("STED"), described, for example, by S. W. Hell and J. Wichmann, *Opt. Lett.*, 19, 780-782 (1994); and S. Hell and J. Wichmann, U.S. Pat. No. 5,731,588, which are both incorporated herein by reference. As shown in FIG. 38, a brief excitation pulse near the peak absorption wavelength, $\lambda_{abs}$, of a given molecular species can raise such molecules that are near the focal point of a lens to an excited quantum state. On a time scale that is short compared to the fluorescence lifetime of this state, a second pulse near the peak emission wavelength, $\lambda_{depl}$, can then be sent in order to return a fraction of the excited molecules to the ground state via stimulated emission. The molecules remaining in the excited state after the passage of the depletion pulse can be confined to a region 3804 that is small compared to $\lambda_{abs}$ if: (1) the secondary depletion field 3800 is tailored to have a central node 3801 at the maximum of the primary excitation field 3802 with surrounding depletion sidebands 3803; and (2) the relative strengths of the two fields are adjusted accordingly. Such an operation yields an effective PSF consistent with superresolution microscopy.

Therefore, in order to use optical lattice microscopy in conjunction with STED, at least two lattices are needed: an excitation-lattice having intensity maxima as discussed above, and a depletion lattice, as shown in FIG. 39, having a node immediately surrounded by a strong depletion field in each primitive cell.

One exemplary way to create the depletion lattice is to superimpose multiple sub-lattices that have the same periodicity but bases with intensity maxima in different directions relative to a common nodal point. The complete depletion lattice and basis shown in FIG. 39 results from the superposition of three such sub-lattices. The first sub-lattice, as shown in FIGS. 40A, 40B, 40C, 40D, and 40E, is a fundamental body-centered cubic (BCC) lattice having an intensity period, $\tau_{depl} = \sqrt{3} \lambda_{depl}/2$, with a basis given by $e_d \| \hat{e}_p \| \hat{e}_x = [100]$ in Equation (21) and Equation (28), and each $e_n$ phase shifted by an amount, $\Delta\phi_n = -k_n \cdot (\hat{e}_y + \hat{e}_z) \tau_{depl}/2$, to align a nodal point within the primitive cell of the first sub-lattice with a maximum of the excitation lattice. The second sub-lattice, shown in FIGS. 40F, 40G, 40H, 40I, and 40J, is a fundamental BCC lattice obtained by rotating the wavevectors, $k_n$, of the first lattice by 90° about $\hat{e}_z$, and having a basis given by $e_d$ parallel to $\hat{e}_p \| [010] = \hat{e}_y$ in Equation (21) and Equation (28), and with each $e_n$ being phase shifted by an amount, $\Delta\phi_n = -k_n \cdot (\hat{e}_x + \hat{e}_z) \tau_{depl}/2$, to align a nodal point of the second sub-lattice with the corresponding nodal point of the first sub-lattice. The third sub-lattice, shown in FIGS. 40K, 40L, 40M, 40N, and 40O, is a maximally symmetric simple cubic lattice having the same period with a basis given by $e_d$ parallel to $\hat{e}_p \| [001] = \hat{e}_z$ in Equation (21) and Equation (28), and each $e_n$ being phase shifted by and amount, $\Delta\phi = -(k_n \cdot \hat{e}_z) \tau_{depl}/2$, to align a nodal point of the third sub-lattice with those of the other sub-lattices.

To apply optical lattices to STED, the depletion lattice should be of the same Bravais crystal group as the excitation lattice (although of a longer wavelength). The depletion lattice should also have the same defining parameters, $\eta$, $\xi$, and $\gamma$, and the same absolute periodicity as the excitation lattice or some harmonic thereof, (i.e., $\tau_{exc} = m\tau_{depl}$, m=1, 2, ... ), so that some subset of the nodes of the depletion lattice can be aligned with the maxima of the excitation lattice. Thus, the wavelength-normalized periodicities of the two lattices (which only exist in discrete steps) should be selected to match the Stokes shift, $\lambda_{depl}/\lambda_{abs}$, of the target molecular species. An example is shown in FIG. 41, where a maximally symmetric BCC excitation lattice of intensity period, $\tau_{exc} = \sqrt{5} \lambda_{abs}$, (indicated by translucent surfaces of 50% of maximum intensity in FIG. 41A and intensity plots in FIGS. 41B, 41C, and 41D) is used in conjunction with the depletion lattice of FIG. 39 and a species of assumed Stokes shift, $\lambda_{depl}/\lambda_{abs} = \sqrt{5/3} \approx 1.29$. With a depletion pulse of sufficient strength and duration, the result is a final STED lattice (as shown by the opaque surfaces of 50% intensity in FIG. 41A and by the intensity plots in FIGS. 41E, 41F, and 41G) of the same symmetry and periodicity as the excitation lattice, but with emission regions confined on a scale small compared to that of the wavelength. A complete super-resolution image can be generated by scanning such a lattice over the dimensions of a single primitive cell, as described for previous examples.

"Optical Lattice STED" microscopy has several advantages compared to conventional, single focus STED microscopy. First, lattice-based STED microscopy offers massive parallelism for vastly improved imaging speed. Imaging speed is an issue of even greater importance in STED microscopy than in standard, linear fluorescence microscopy, because the size of (and hence the amount of signal from) each post-depletion emission region is so small. Second, the depletion basis of lattice-based STED microscopy offers improved coverage of the desired depletion shell, as well as improved sharpness in the depletion field near the node compared to conventional STED microscopy. Finally, lattice-based STED microscopy offers reduced photobleaching as compared to full-field, single focus lens excitation. Photobleaching is an issue of particular significance for STED microscopy, because the small emission region arising in STED microscopy requires that the illuminated fluorophores undergo many more excitation cycles for a given volume of sample to be imaged than in the convention, single focus microscopy.

The above-described method of superimposing multiple lattices to induce a desired optical response from the sample is not limited to STED. Indeed, any multiple wavelength optical technique can be similarly applied to lattice microscopy, including four wave mixing, coherent anti-Stokes Raman scattering (CARS), and multi-wavelength, multiphoton absorption.

Total Internal Reflection Microscopy

An alternative method capable of achieving resolution beyond $\lambda_{abs}/(2n_{med})$ in living cells is total internal reflection microscopy ("TIRM"), described, for example, by D. Axelrod, et al., *J. Microsc.*, 129, 19-28 (1983), which is incorporated herein by reference. In TIRM, a specimen in a medium of a refractive index, $n_{med}$, in contact with a planar substrate of a higher refractive index, $n_{sub}$, is illuminated with light originating within the substrate and incident upon the medium at an angle, $\theta > \theta_{critical} \equiv \sin^{-1}(n_{med}/n_{sub})$, with respect to the vector, $\hat{e}_z$, that is perpendicular to the substrate/medium interface. As a result, the light is totally reflected from the interface and back into the substrate. However, on the specimen/medium side of the interface, an electromagnetic field is created that propagates parallel to the interface, but that decreases exponentially in amplitude with increasing distance from the interface. This field can excite fluorescence within that portion of the specimen in closest proximity to the interface and can therefore be used to produce images containing information from a significantly narrower section (e.g., ~100 nm) of the specimen than is possible with confocal microscopy, and with much lower photobleaching elsewhere.

Conventional TIRM uses uniform, widefield illumination, so that spatial resolution in the plane of the interface is dictated by the $\sim\lambda_{abs}/(2n\sin\theta_{max}) = \lambda_{abs}/(2 \cdot NA)$ detection resolution of the objective lens used to collect the signal. In prism-based implementations of TIRM, this objective is usually located opposite the substrate (i.e., the prism), due to working distance constraints and the attendant spherical aberration introduced when the prism is in the beam path of the collected light. Thus, $n = n_{med}$, and resolution is limited by the refractive index of the medium (e.g., water, in which $n_{med} = 1.33$). In through-the-objective based implementations of TIRM, the rear pupil of the objective is illuminated only at its periphery, creating a thin, conical illumination shell incident upon at interface at a cone half-angle beyond the critical angle. However, because an ultra-high numerical aperture objective (e.g., NA>1.4) is used to achieve the necessary cone angle, the same objective, when used for detection, gives $n = n_{sub}$ over the path of the collected signal, and hence resolution $n_{sub}/n_{med}$ times greater (e.g., 1.14× for $n_{med}$=1.33 and $n_{sub}$=1.52 (i.e., cover glass)) than when detection occurs from the medium side.

Practical considerations involving lens design and the properties of high refractive index liquids typically preclude extending the detection resolution beyond the limits of NA<1.45 and $n_{sub}$<1.6. However, an appropriate optical lattice, particularly with a basis of well-separated, highly confined intensity maxima, can contribute excitation resolution in TIRM adding to the overall system resolution.

Consider, for example, a subset lattice oriented so that one of the lattice plane families (described by a set Miller indices) is parallel to the substrate/medium interface, and that includes only those plane waves of the corresponding maximally symmetric lattice, or some subset thereof, whose wavevectors, $k_m$, originate in the substrate (i.e., from z<0) and are totally internally reflected at the interface (at z=0):

$$e_m^{sub}(x,t) = e_m^{sub} \exp[i(k_m \cdot x - \omega t)] \quad (43a)$$

$$\theta_m \equiv \cos^{-1}(k_m \cdot \hat{e}_z/k_{sub}) > \theta_{critical} \equiv \sin^{-1}(n_{med}/n_{sub}),$$
$$\theta_m < \pi/2 \quad (43b)$$

Each such plane wave creates an interfacial plane wave whose field amplitude decays exponentially with increasing distance from the substrate/medium interface:

$$e_m^{med}(x,t) = e_m^{med} \exp[-z/\delta(\theta_m)] \exp\{i[(k_m \cdot (\hat{e}_i)_m)(x \cdot (\hat{e}_i)_m) \omega t]\}, \quad (44a)$$

where:

$$\delta(\theta_m) = \frac{(n_{med}/n_{sub})\lambda_{med}}{2\pi\sqrt{\sin^2\theta_m - (n_{med}/n_{sub})^2}}, \quad (44b)$$

$$(\hat{e}_s)_m = (k_m \times \hat{e}_z)/(k_{sub}\sin\theta_m), \quad (44c)$$
$$(\hat{e}_i)_m = \hat{e}_z \times (\hat{e}_s)_m, \text{ and}$$
$$(\hat{e}_{para})_m = (\hat{e}_s)_m \times k_m/k_{sub}.$$

The field, $e_m^{med}$ of each interfacial wave is related to the field, $e_m^{sub}$, of its corresponding substrate wave by the complex Fresnel coefficients for transmission at the interface:

$$e_m^{sub} = [(\hat{e}_s)_m \cdot e_m^{med}](\hat{e}_s)_m/t_s + [\hat{e}_z \cdot e_m^{med}](\hat{e}_{para})_m/t_{para}, \quad (45a)$$

$$t_s = \frac{2\cos\theta_m}{\cos\theta_m + i\sqrt{\sin^2\theta_m - (n_{med}/n_{sub})^2}}, \text{ and} \quad (45b)$$

$$t_{para} = \frac{2(n_{med}/n_{sub})\cos\theta_m}{(n_{med}/n_{sub})^2\cos\theta_m + i\sqrt{\sin^2\theta_m - (n_{med}/n_{sub})^2}}. \quad (45c)$$

Figure 42A:
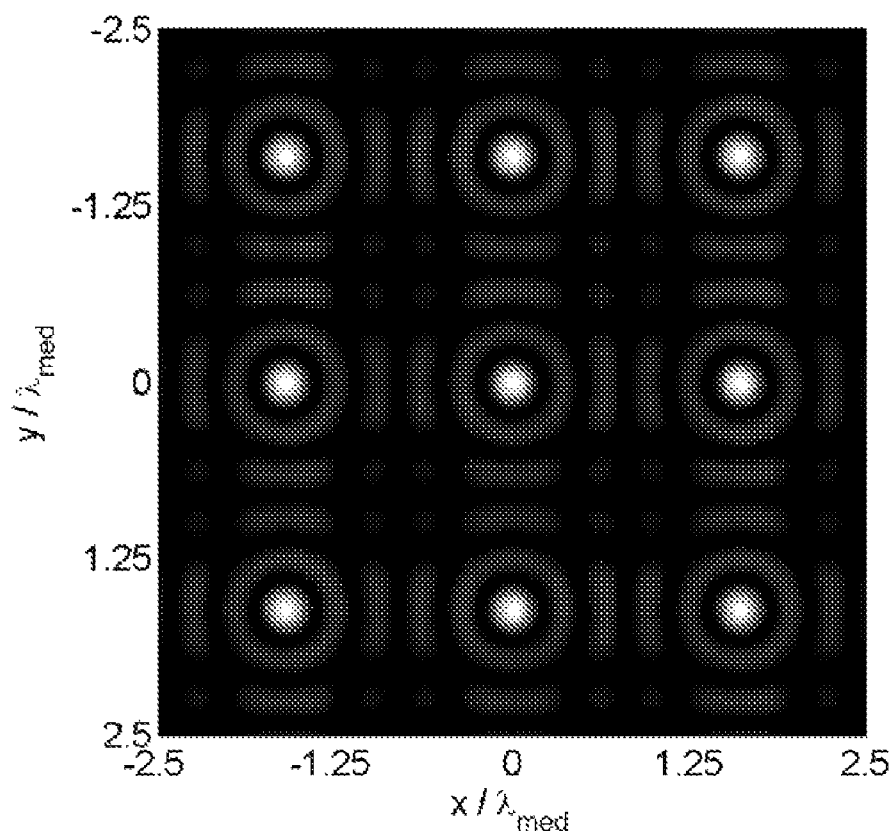
FIG. 42A is a linear grayscale image of the light intensity at the interface between a transparent substrate of refractive index $n_{sub}$=2.45 and a transparent medium of refractive index $n_{med}$=1.33 when illuminated with the sixteen plane waves of the maximally symmetric simple cubic lattice of intensity period $\sqrt{35}\lambda_{sub}/2$ that originate in the substrate and are totally internally reflected at the interface, assuming that the [0 0 1] axis of the lattice is perpendicular to the interface, and that the basis on the medium side of the interface has been chosen to optimize the z-component of the field at the intensity maxima.
Figure 42B:
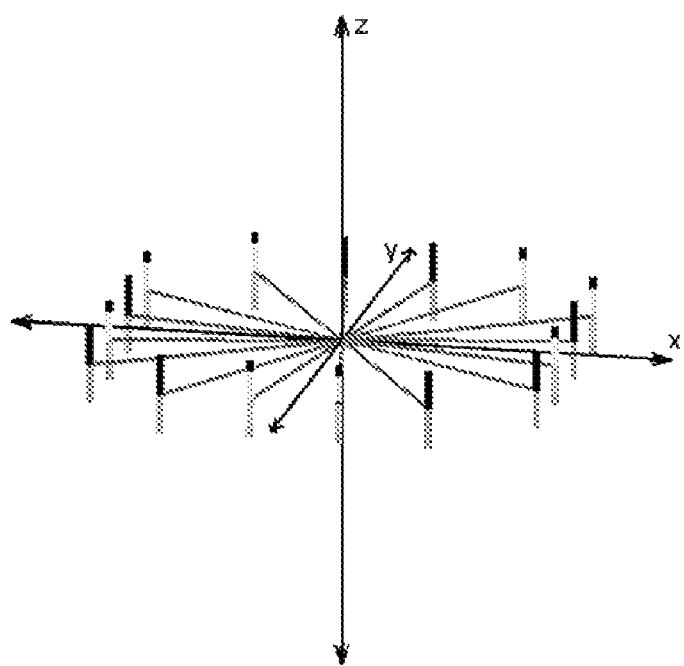
FIG. 42B is a three-dimensional representation of the relative wavevector and electric field directions and real field magnitudes at different times for the sixteen plane waves in the substrate that lead to the interfacial intensity distribution in FIG. 42A.
Figure 42C:
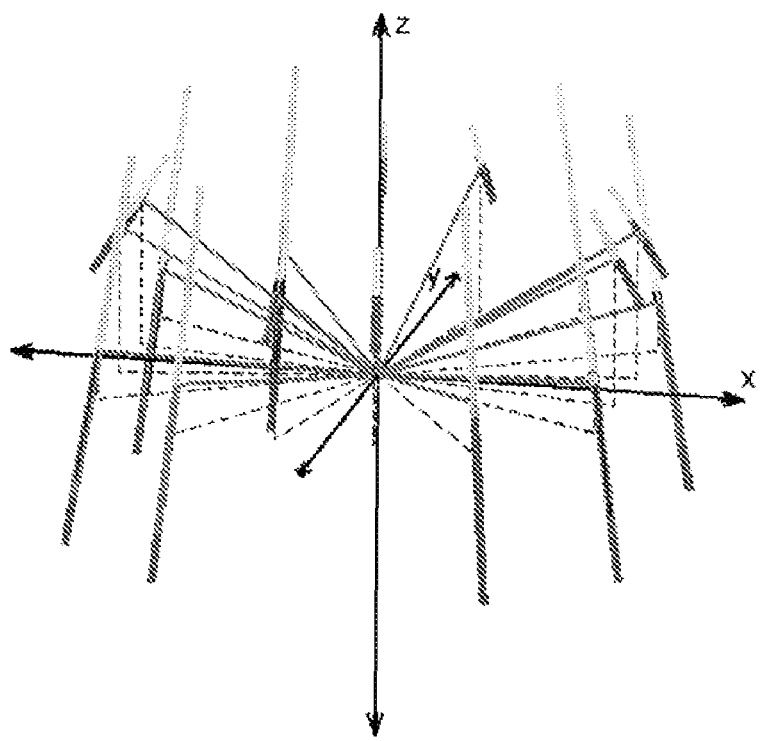
FIG. 42C is a three-dimensional representation of the relative wavevector and electric field directions and real field magnitudes at different times for the sixteen interfacial plane waves arising from the reflection of the substrate waves in FIG. 42B at the interface, and whose superposition yields the interfacial intensity distribution in FIG. 42A.
Figure 42D:
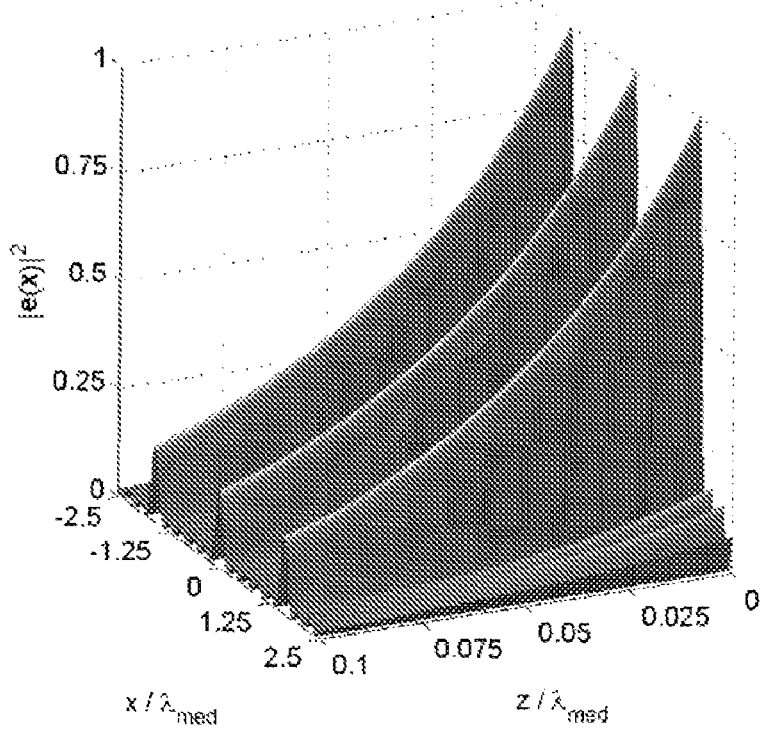
FIG. 42D is a surface plot in the indicating the rate of decay with increasing distance into the medium for points along the x-axis of the intensity pattern in FIG. 42A.

A planar array of isolated yet individually confined intensity maxima can be created at the interface by using, for example, the basis construction methods of Equation (24) or, specifically, the bases leading to Equations (28), (34), or (37), to determine the field, $e_m^{med}$, for each interfacial wave that achieves the desired basis. Equations (45) can then be used to determine the field, $e_m^{sub}$, of each corresponding original plane wave within the substrate. Thus, for example, the two-dimensional array of intensity maxima shown in FIG. 42A is created via superposition of the interfacial plane waves with the wavevectors, $k_m^{med}=(k_m \cdot (\hat{e}_i)_m)(\hat{e}_i)_m$, and the fields, $e_m^{med}$, represented in FIG. 42B, which in turn exist due to excitation within the substrate using plane waves with wavevectors, $k_m$, and fields, $e_m^{sub}$, as represented in FIG. 42C. The intensity within these maxima decays exponentially with increasing distance from the interface as shown in FIG. 42D.

Note that, as demonstrated in FIG. 42A and as implied by Equations (3) and (44), the separation and transverse confinement of the intensity maxima within the medium are the same as if the lattice and basis were constructed entirely within the substrate. Thus, even though the specimen is within the medium, the transverse excitation resolution in optical lattice TIRM is determined by the substrate refractive index, $n_{sub}$. Materials that are substantially transmissive at visible wavelengths and that have exceptionally high refractive indices (e.g., gallium nitride, GaN, with $n_{sub}=2.45$ or gallium phosphide, GaP, with $n_{sub}=3.4$) can therefore be used to attain excitation resolution well in excess of the detection resolution of conventional TIRM.

Figure 43A:
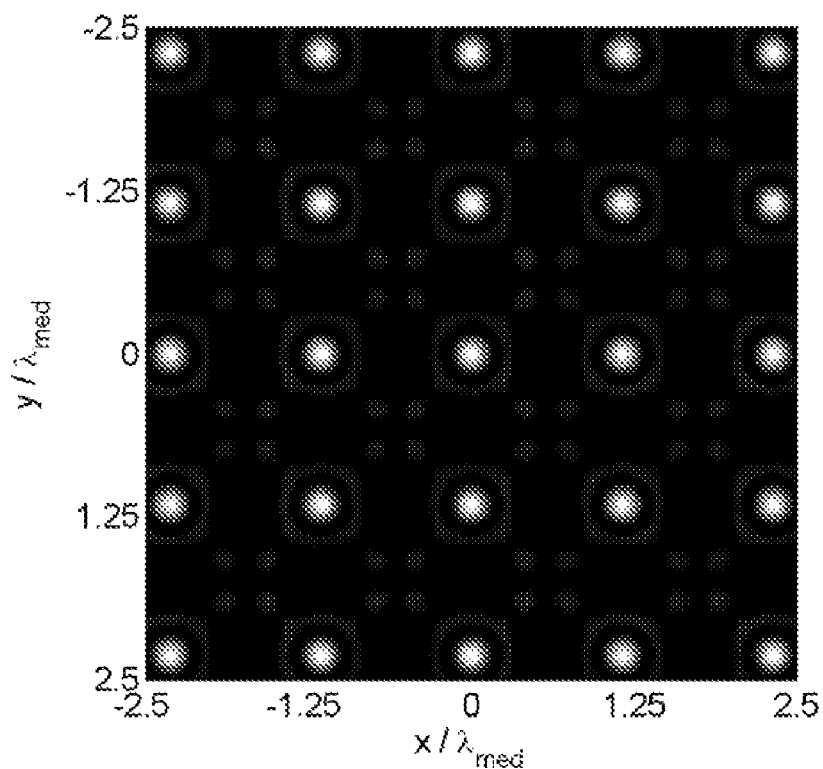
FIG. 43A is a linear grayscale image of the light intensity at the interface between a transparent substrate of refractive index $n_{sub}$=3.4 and a transparent medium of refractive index $n_{med}$=1.33 when illuminated with the twenty-four plane waves of the maximally symmetric simple cubic lattice of intensity period $\sqrt{35}\lambda_{sub}/2$ that originate in the substrate and are totally internally reflected at the interface, assuming that the [0 0 1] axis of the lattice is perpendicular to the interface, and that the basis on the medium side of the interface has been chosen to optimize the z-component of the field at the intensity maxima.
Figure 43B:
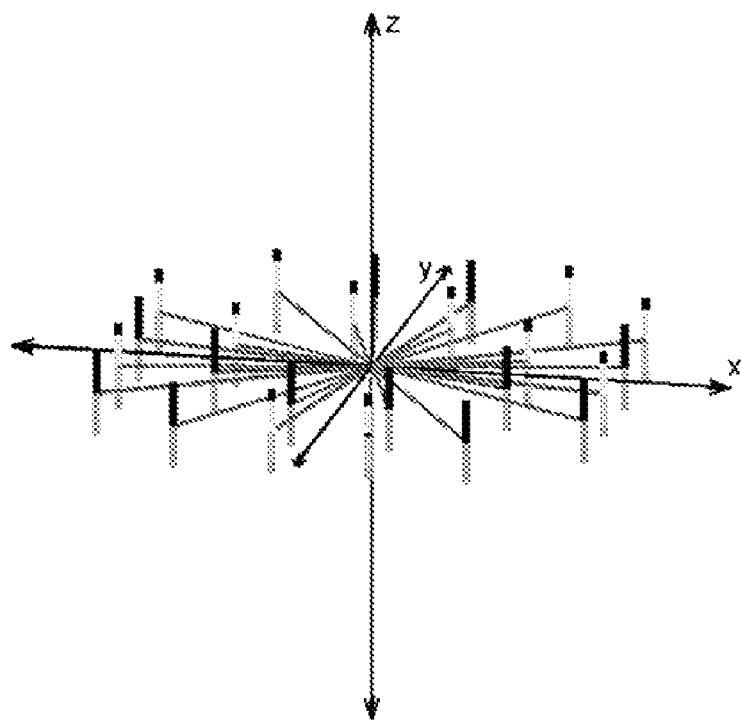
FIG. 43B is a three-dimensional representation of the relative wavevector and electric field directions and real field magnitudes at different times for the twenty-four plane waves in the substrate that lead to the interfacial intensity distribution in FIG. 43A.
Figure 43C:
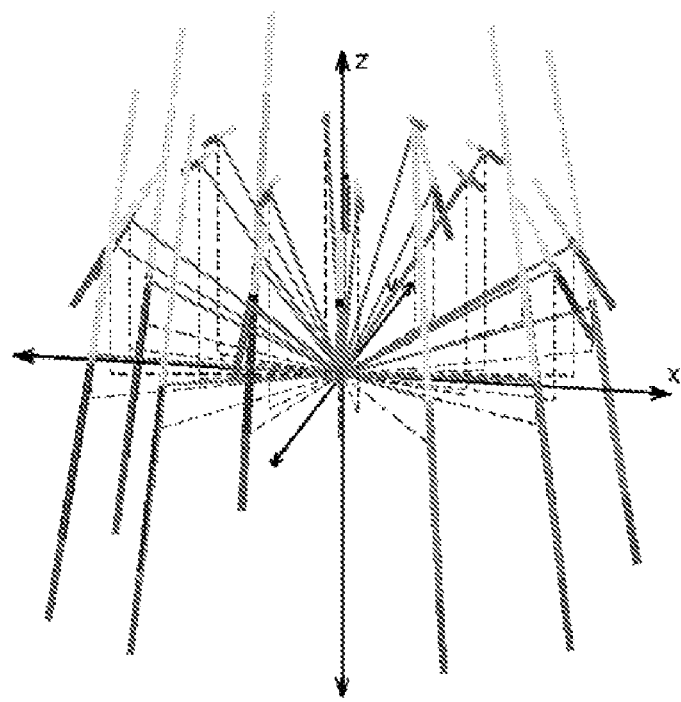
FIG. 43C is a three-dimensional representation of the relative wavevector and electric field directions and real field magnitudes at different times for the twenty-four interfacial plane waves arising from the reflection of the substrate waves in FIG. 43B at the interface, and whose superposition yields the interfacial intensity distribution in FIG. 43A.

Increasing the substrate refractive index, $n_{sub}$, also results in a smaller critical angle, $\theta_{critical}$, which can permit a greater number of plane waves within the maximally composite set to be included in the excitation for a given lattice. As shown in FIG. 43, for example, the same lattice type (i.e., a simple cubic lattice), periodicity in substrate wavelengths ($\sqrt{35}\lambda_{sub}/2$), and basis (e.g., having a polarization maximized along $\hat{e}_z$) is used as in FIG. 42, except that the refractive index of the substrate is increased from $n_{sub}=2.45$ to $n_{sub}=3.4$. As a result, all 24 substrate-originating plane waves of the maximally symmetric lattice are totally internally reflected and hence can be included, as shown in FIG. 43C, rather than only 16 as shown in FIG. 42C. As demonstrated by comparing FIG. 43A to FIG. 42A, this leads to improved intensity contrast relative to the background in the plane of the interface.

Figure 43D:
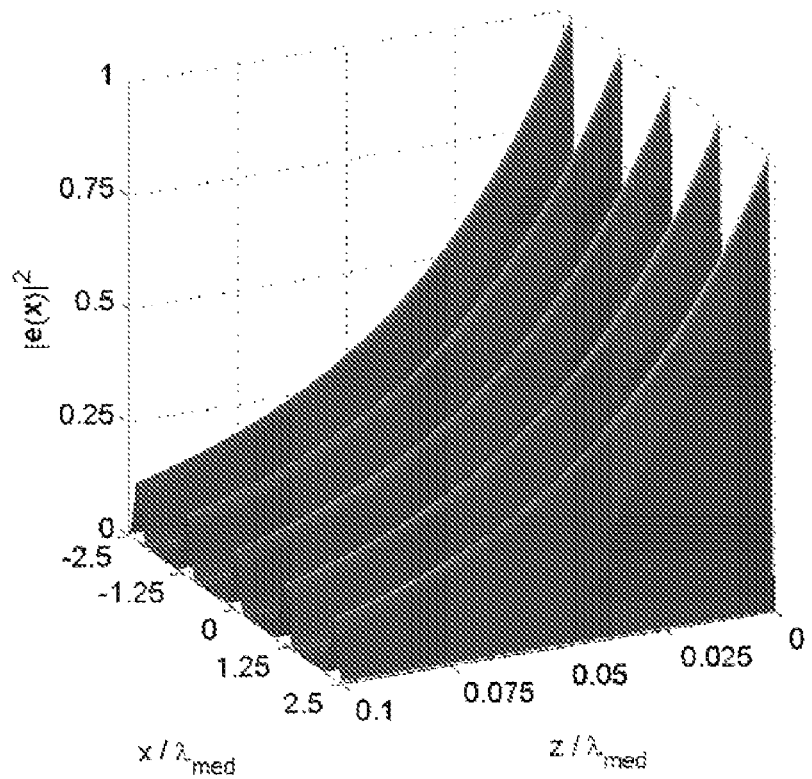
FIG. 43D is a surface plot in the indicating the rate of decay with increasing distance into the medium for points along the x-axis of the intensity pattern in FIG. 43A.
Figure 44A:
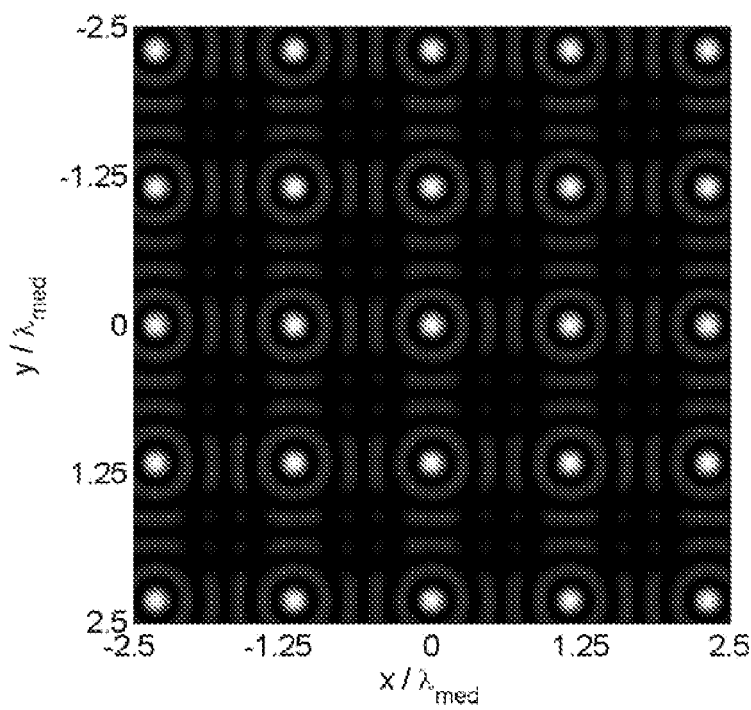
FIG. 44A is a linear grayscale image of the light intensity at the interface between a transparent substrate of refractive index $n_{sub}$=3.4 and a transparent medium of refractive index $n_{med}$=1.33 when illuminated from within the substrate with sixteen plane waves having the same wavevectors $k_m$ as in FIG. 42B, but with polarizations $e_m$ chosen to optimize the z-component of the field at the intensity maxima within the medium for the new substrate index $n_{sub}$=3.4 rather than the substrate index $n_{sub}$=2.45 used in FIG. 42.
Figure 44B:
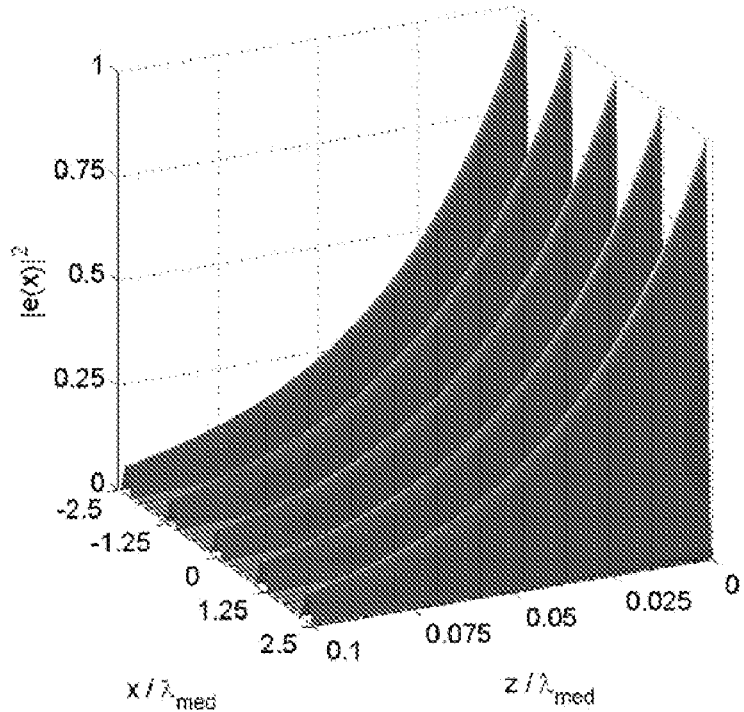
FIG. 44B is a surface plot in the indicating the rate of decay with increasing distance into the medium for points along the x-axis of the intensity pattern in FIG. 44A.

As indicated by Equation (44b), it is also possible to exploit a higher substrate index, $n_{sub}$, to decrease the evanescent decay length of the lattice maxima, and hence create an even sharper excitation band within the sample. For example, FIG. 44B shows the improvement in the axial confinement of the excitation when the lattice consists of the same 16 substrate wavevectors, $k_m$, and the same interfacial basis as in FIG. 42D, except that a higher substrate index of refraction, $n_{sub}=3.4$, rather than $n_{sub}=2.45$ is used. The axial confinement seen in FIG. 44B is also superior to that obtained when $n_{sub}=3.4$ using all 24 waves, as shown in FIG. 43D, because the 8 waves omitted in FIG. 44 have the smallest angles of incidence, $\theta_m$, and, hence, according to Equation (44b), the longest decay lengths, $\delta(\theta_m)$, within the medium. However, the omission of the eight plane waves also reduces the intensity contrast as shown in FIG. 44A, demonstrating a trade-off that exists when three-dimensional lattices having totally internally reflected constituent plane waves at multiple angles of incidence, $\theta_m$, are applied to TIRM.

All the wavevectors, $k_m^{med}$, of any TIRM-generated interfacial optical lattice, by definition, lie in the plane of the interface. Thus, as discussed previously in reference to FIG. 8D and FIG. 11A, the constraint, $k_m^{med} \cdot e_m^{med}=0$ implies that strong intensity maxima, high intensity contrast, and good polarization purity can be achieved for the basis that exists when all interfacial waves are polarized perpendicular to the interface, i.e., when $e_m^{med}$ is parallel to $\hat{e}_z$ for every wave. From Equation (45a), this occurs when every corresponding plane wave within the substrate is polarized within its plane of incidence (i.e., when the plane waves are p-polarized, and $e_m^{sub} \| (\hat{e}_{para})_m$).

Figure 45A:
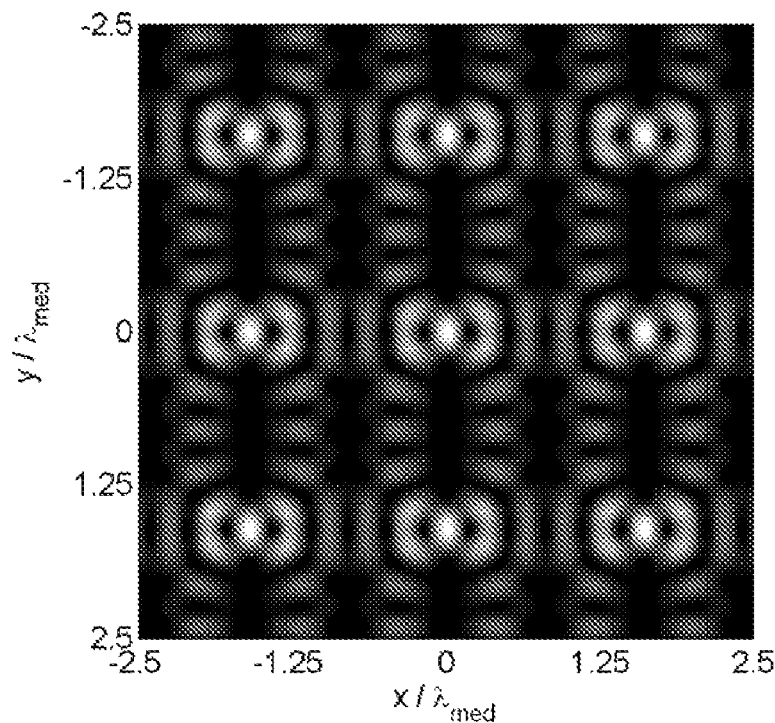
FIG. 45A is a linear grayscale image of the light intensity at the interface between a transparent substrate of refractive index $n_{sub}$=2.45 and a transparent medium of refractive index $n_{med}$=1.33 when illuminated with the sixteen plane waves of the maximally symmetric simple cubic lattice of intensity period $\sqrt{35}\lambda_{sub}/2$ that originate in the substrate and are totally internally reflected at the interface, assuming that the [0 0 1] axis of the lattice is perpendicular to the interface, and that the basis on the medium side of the interface has been chosen to optimize the y-component of the field at the intensity maxima.
Figure 45B:
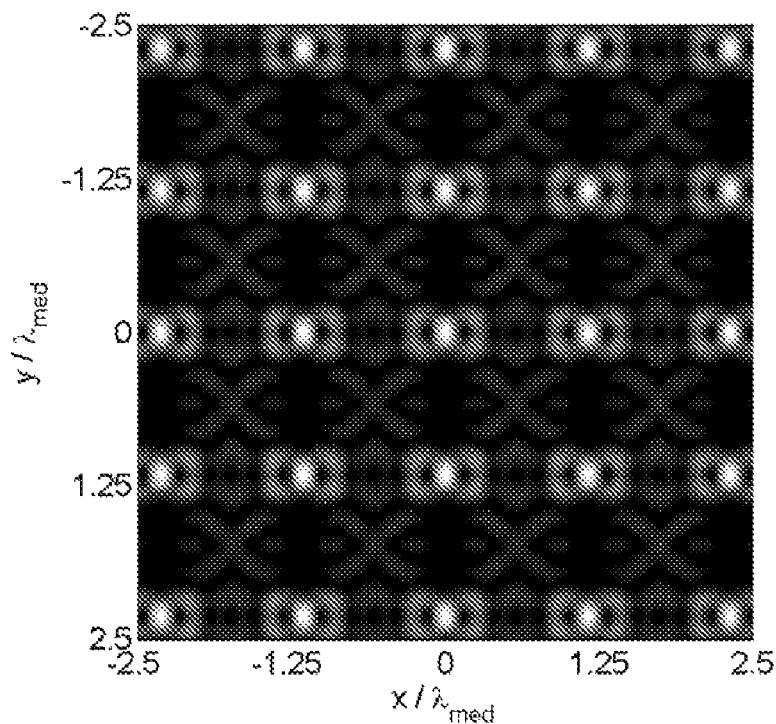
FIG. 45B is a linear grayscale image of the light intensity at the interface between a transparent substrate of refractive index $n_{sub}$=3.4 and a transparent medium of refractive index $n_{med}$=1.33 when illuminated with the twenty-four plane waves of the maximally symmetric simple cubic lattice of intensity period $\sqrt{35}\lambda_{sub}/2$ that originate in the substrate and are totally internally reflected at the interface, assuming that the [0 0 1] axis of the lattice is perpendicular to the interface, and that the basis on the medium side of the interface has been chosen to optimize the y-component of the field at the intensity maxima.

In TIRM applications such as molecular orientation measurements within cellular membranes, bases of other preferred polarization may be needed. FIG. 45A, for example, shows the intensity distribution at the interface for the same lattice, same 16 wavevectors, and same substrate refractive index $n_{sub}=2.45$ as in FIG. 42A, except with a basis chosen to optimize the polarization along the axis, $\hat{e}_x$, at the intensity maxima rather than along the axis, $\hat{e}_z$. Increasing the substrate refractive index to increase the number of allowed wavevectors and therefore the intensity contrast can be particularly effective for bases such as this that have significant desired polarization within the plane of the interface. For example, FIG. 45B shows the contrast improvement under the same conditions as in FIG. 45A, except with $n_{sub}=3.4$ and 24 constituent wavevectors, that is, with the same lattice conditions as in FIG. 43, except with a different basis.

A key advantage of applying two- or three-dimensional sparse composite lattices to TIRM is that, unlike standing wave TIRM (as described, for example, in G. Cragg, et al., U.S. Pat. No. 6,255,642 B1, which is incorporated herein by reference), the confinement of the intensity maxima at the interface can be decoupled from their separation. Therefore, substrates having exceptionally high refractive indices, $n_{sub}$, (e.g., gallium nitride, which has an index of refraction $n_{sub}=2.45$ for light having photon energies of 2.5 eV) can be used to improve the confinement and associated transverse excitation resolution, while the lattice periodicity can be chosen to insure that, even at such high $n_{sub}$, the individual maxima remain resolvable at the more limited resolution of the detection optics, which is a necessary precondition for their collective use as a multi-point excitation array in microscopy.

When a high substrate index, $n_{sub}$, is used, detection of the signal with a high NA objective lens on the medium side of the interface (e.g., NA=1.2 for a good quality water immersion objective) eliminates the need to compensate for aberrations that can be introduced upon passage of the signal through the substrate. The overall transverse resolution is then dominated by the excitation resolution, which is on the order of $\lambda_{abs}/(2 \cdot n_{sub})$, rather than the detection resolution, which is on the order of $\lambda_{abs}/(2 \cdot NA)$. However, even when the through-the-objective configuration is used to both excite the lattice and to detect the signal, and the substrate index, $n_{sub}$, is substantially lower (e.g., when $n_{sub}=1.52$ as when typical cover glass is used for the substrate), the contribution of the excitation resolution provided by the lattice results in slight improvement in the overall transverse resolution compared to conventional TIRM with uniform illumination, assuming the collected light is additionally spatially filtered at the image plane. This effect is analogous to the transverse resolution improvement seen in confocal microscopy compared to widefield microscopy resulting from the combination of point excitation with point detection.

The narrow excitation band within the medium occurring in either conventional or lattice-based TIRM should not be confused with high axial resolution, since axially separated features at the same transverse location are not individually resolved. However, three-dimensional imaging, including high axial resolution, in close proximity to the interface can be implemented in conventional TIRM by recording multiple two-dimensional images at different angles of incidence in the range $\theta_{critical}<\theta<\pi/2$ and processing the resulting data in light of the known decay length, $\delta(\theta)$, (e.g., as given by Equation (44b)) in each image. This technique can also be applied to TIRM with two-dimensional lattice excitation, since all the substrate wavevectors, $k_m$, share the same cone angle, $\theta_m$, and hence the lattice type (although not the periodicity) is preserved when all $\theta_m$ (with $\theta_{critical} < \theta < \pi/2$) are changed in unison. FIG. 46B and FIG. 46D compare the intensity decay within the medium for a particular two-dimensional lattice ($n_{med}=1.33$, $n_{sub}=3.4$) when sin $\theta_m=1$ and sin $\theta_m=1.2$ sin $\theta_{critical}$, respectively. Although the intensity can be made to penetrate arbitrarily far within the medium as $\theta_m \rightarrow \theta_{critical}$, the transverse resolution simultaneously degrades, as seen by comparing FIG. 46A and FIG. 46C, until it is dictated by the refractive index of the medium, $n_{med}$, rather than that of the substrate, $n_{sub}$.

This same multi-angle axial imaging method can also be applied to TIRM with three-dimension lattice excitation, provided that all substrate wavevectors, $k_m$, are rotated so that sin $\theta_m$ changes by the same factor for each wavevector, and the interfacial symmetry is thereby preserved. However, since any three-dimensional lattice contains wavevectors, $k_m$, of at least two different incident angles, $\theta_m$, the total possible range of adjustment will be less than in the two-dimensional case, because both $(\theta_m)_{max} < \pi/2$ and $(\theta_m)_{min} > \theta_{critical}$ are required.

Multidimensional Localization

Another superresolution technique that can benefit from its adaptation to optical lattice microscopy is multidimensional localization, as described, for example, in E. Betzig, *Opt. Lett.*, 20, 237-239 (1995), which is incorporated herein by reference. As shown in FIG. 47A, in multidimensional localization, a plurality of discrete emitters (e.g., individual fluorescent marker molecules within a cell) that are not well resolved in S spatial dimensions in a given optical system are imaged while P independent optical properties that can be expected to vary among the emitters (e.g., polarization or wavelength of the emission) are simultaneously measured at each point. If the resolution in the P dimensions defined by the measured properties is sufficiently high, then, for a given number of emitters within an S dimensional volume defined by the spatial resolution of the system, the emitters can be individually isolated in the S+P multidimensional space formed by the spatial coordinates and the measured parameters, as shown in FIG. 47B. Once isolated, methods such as that described in N. Bobroff, *Rev. Sci. Instrum.*, 57, 1152 (1986), which is incorporated herein by reference, can be used to determine the location of each emitter to an accuracy that, with sufficient signal strength and knowledge of the spatial point spread function of the system, can be far better than the system resolution. Projection of these results back into the spatial dimensions then results in an S-dimensional image of the emitters at a resolution equal to this accuracy, as shown in FIG. 47C.

Optical lattice microscopy can contribute to this process because the volumetric point spread function of the excitation, as demonstrated in FIG. 15, can be significantly smaller than in single focus methods such as confocal microscopy. Thus, a greater spatial density of emitters can be isolated for a given resolution in the measurement of the P independent optical parameters. Furthermore, greater accuracy in the spatial localization, and hence greater resolution in the final image of the isolated emitters, can be achieved for a given signal-to-noise ratio from each emitter.

Since the accuracy of the localization and ultimate spatial resolution improve as this signal-to-noise ratio increases, optical lattice microscopy can also contribute through its ability to collect signal from numerous tightly confined volumes simultaneously. This can be applied to: (1) improve the isolation process by improving the signal-dependent resolution in one or more of the P measured parameters; (2) improve the localization process after isolation and hence the final spatial resolution at a given imaging speed; and (3) increase the imaging speed at a chosen spatial resolution.

Minimizing Deviations from Ideal Lattice Behavior

In an actual experimental setting, a number of factors can contribute to perturb both the wavevectors, $k_n$, and fields, $e_n$, of the idealized plane wave set for a given lattice and basis. It is therefore instructive to estimate their respective impact on the lattice and basis properties and resulting performance for the applications enumerated above. Strategies can then be developed for their amelioration.

Reflection and Refraction at Interfaces

A common scenario in lithography involves exposure of a photosensitive layer (e.g., a photoresist layer, such as, for example, polymethylmethacrylate ("PMMA")) atop a substrate (e.g., silicon), where the photosensitive layer and the substrate have dissimilar optical properties. Similarly, the imaging of cultured cells occurs near a fluid/substrate interface of dissimilar optical properties (e.g., water and glass). At any such interface between regions of dissimilar optical properties, an incident plane wave is generally split into two plane waves: a first plane wave that is specularly reflected back into the originating medium of the wave, and a second plane wave that is transmitted from the first region at an angle of refraction into the other region. The ratio of this division is determined by the Fresnel coefficients for that interface.

For those waves of a lattice originating in a substrate having a refractive index, $n_{sub}$, and transmitted through a planar interface to reach the sample located in a medium of refractive index, $n_{med}$, the wave properties of the wavevectors, $k_m$, and the fields, $e_m$, within the sample can match those dictated by the lattice and basis construction methods described above if the original substrate wave is created with wavevectors, $k_m^{sub}$, and fields, $e_m^{sub}$, such that:

$$k_m^{sub} = k[\sin \theta_m^{sub} (\hat{e}_{para})_m + \cos \theta_m^{sub} \hat{e}_z] \text{ and} \quad (46a)$$

$$e_m^{sub} = ((\hat{e}_s)_m \cdot e_m)(\hat{e}_s)_m/t_s + ((\hat{e}_{para})_m \cdot e_m)(\hat{e}_{para}^{sub})_m/t_{para}, \text{ where:} \quad (46b)$$

$$\theta_m \equiv \cos^{-1}(k_m \cdot \hat{e}_z/k), \theta_m^{sub} = \sin^{-1}[(n_{med}/n_{sub})\sin \theta_m] \text{ (Snell's law)} \quad (46c)$$

$$(\hat{e}_s) = (k_m \times \hat{e}_z)/k \sin \theta_m, (\hat{e}_{para})_m = (\hat{e}_s)_m \times k_m/k, \text{ and} \\ (\hat{e}_{para}^{sub})_m = (\hat{e}_s)_m \times k_m^{sub}/k. \quad (46d)$$

Here the axis, $\hat{e}_z$, is defined perpendicular to the interface, and $t_s, t_{para}$ are the complex Fresnel coefficients for transmission through the interface for the $(\hat{e}_s)_m$ (s-polarized) and $(\hat{e}_{para}^{sub})_m$ (p-polarized) components of the substrate field, respectively. If $(n_{sub}/n_{med})$ sin $\theta_m^{sub} > 1$, then the substrate wave is totally reflected at the interface, and cannot contribute to the lattice at the sample.

For each wave of the lattice originating within the medium of the sample, a reflected wave is created at the interface that, in general, alters the symmetry and periodicity of the lattice as well as the basis. For example, as shown in FIG. 48, a two-dimensional lattice having all its constituent wavevectors on a cone of half-angle, $\theta$, oriented with the cone axis perpendicular to the interface(s) is transformed into a three-dimensional lattice having a single spatial frequency of $2k \cos \theta$ along this axis. If the interfaces are parallel to a mirror plane of the lattice, however, the wavevectors of the reflected waves are also within the maximally symmetric composite set, and hence the symmetry and periodicity is preserved, although the basis is still perturbed, as shown in FIG. 49.

The lattice and interface properties can be tailored in several different ways to minimize the amplitudes of the reflected waves and hence their effect on the basis. First, the lattice can be designed so that some or all of the initial wavevectors are incident on the interface at angles close to reflection minima for their polarizations. In particular, plane waves used to create a two-dimensional lattice in a dielectric medium of refractive index $n_{med}=Re\{n_{med}\}$ perpendicular to a dielectric substrate of refractive index $n_{sub}=Re\{n_{sub}\}$ (e.g., in the case of a two-dimensional lattice within a specimen surrounded by an aqueous environment having $n_{med}=1.33$, cultured on a glass surface having $n_{sub}=1.52$) will exhibit no reflections if the plane wave wavevectors are all incident at an angle equal to Brewster's angle, $\theta_B=\tan^{-1}(n_{sub}/n_{med})$, with respect to the vector normal of the interface plane, $\hat{e}_z$, and if the initial basis is selected to maximize linear polarization perpendicular to the interface as per Equation (28) (so that the fields, $e_n$, are within the plane of incidence for each wave). Second, to reduce reflections at multiple and/or larger angles of incidence, such as is desired for a three-dimensional lattice or a two-dimensional lattice of optimal intensity confinement, a single or multilayer anti-reflection (AR) film can be applied to the interface. For example, a MgF$_2$ film of refractive index, $n_f=1.38$, and thickness, $h=n_m n_f \lambda_m/4\sqrt{(n_f^2-(n_m\sin\theta)^2}$, reduces the amplitude |r| of the reflection coefficient of a p-polarized wave incident at $\theta=80°$ to the vector, $\hat{e}_z$, normal to a water-glass interface from 0.438 to 0.089, and that of an s-polarized wave from 0.539 to 0.029. Thus, the basis can remain relatively unperturbed when it is translated normal to an AR coated interface, as shown in FIGS. 50C and 50F, as compared with the substantial variations due to differing degrees of constructive and destructive interference between the incident and reflected waves as observed with an uncoated water/glass interface as shown in FIGS. 50B and 50E. Third, in those cases where it is impractical to design an AR coating sufficiently effective at all angles of the incident wavevectors of the lattice, it is always possible to simply omit those plane waves exhibiting excessive reflection, although with the concomitant loss of intensity confinement characteristic of subset lattices.

In those cases where the sample medium and the substrate are both substantially transparent (e.g., the water/glass interface common to cultured cells), an alternative approach can be used to produce an unperturbed, translationally invariant lattice. First, the lattice is oriented relative to the interface such that for every incident plane wave originating within the sample medium having wavevector, $$k_m=k[\sin\theta_m(\hat{e}_{para})_m+\cos\theta_m\hat{e}_z], \tag{47}$$

and having the initial basis-dictated field, $e_m$, a reflected wave having a wavevector, $$k_m^r=k[\sin\theta_m(\hat{e}_\square)_m-\cos\theta_m\hat{e}_z], \tag{48a}$$

$$e_m^r=r_s((\hat{e}_s)_m\cdot e_m)(\hat{e}_s)_m-r_{para}((\hat{e}_i)_m\cdot e_m)(\hat{e}_i)_m+r_{para}(\hat{e}_z\cdot e_m)\hat{e}_z, \text{ and } (\hat{e}_i)_m=\hat{e}_z\times(\hat{e}_s)_m \tag{48b}$$

is created that propagates in the same direction, $k_m^r$, as some other wavevector, $k_n$, of the corresponding maximally symmetric composite lattice (where $r_s, r_{para}$ are the complex Fresnel reflection coefficients at the interface for s- and p-polarized waves, respectively). This reflected wave is then superimposed with a wave originating in the substrate with a wavevector, $k_m^{sub}$, and field, $e_m^{sub}$, given by:

$$k_m^{sub}=k[\sin\theta_m^{sub}(\hat{e}_{para})_m-\cos\theta_m^{sub}\hat{e}_z], \sin\theta_m^{sub}=(n_{med}/n_{sub})\sin\theta_m \tag{49a}$$

$$e_m^{sub}=-((\hat{e}_s)_m\cdot e_m^r)(\hat{e}_s)_m/t_s-((\hat{e}_{para}^r)_m\cdot e_m^r)(\hat{e}_{para}^{sub})_m/t_{para} \text{ or} \tag{49b}$$

$$e_m^{sub}=((\hat{e}_s)_m\cdot(e_n-e_m^r))(\hat{e}_s)_m/t_s-((\hat{e}_{para})_m\cdot(e_n-e_m^r))(\hat{e}_{para}^{sub})_m/t_{para}, \tag{49c}$$

$$(\hat{e}_{para}^r)_m=(\hat{e}_s)_m\times k_m^r/k, \tag{50}$$

so that the resulting refracted wave transmitted into the sample medium also propagates in the direction, $k_n$, with a field, $e_n$, such that the combined plane wave, $e_m^r+e_n^t$, field in the medium is either zero (for Equation (49b)) or equal to the ideal basis-dictated field, $e_n$, associated with the wavevector, $k_n$, in the absence of the substrate (for Equation 49c)).

Alternatively, interfacial reflections can be exploited to improve the intensity confinement at the lattice maxima, particularly near opaque substrates, where the reflected plane waves contribute lattice wavevectors that would otherwise originate within the substrate and therefore would be inaccessible. In such cases, the basis should be selected so that the electric field of each reflected wave approximates the field required to optimize the basis polarization at the desired positions of the lattice maxima. However, because the phase relationship between each incident and reflected wave is fixed by the Fresnel reflection coefficients and hence the properties of the interface, in general a different basis polarization will be needed to achieve optimal confinement and intensity strength at every distance from the interface, as demonstrated in FIG. 51.

For a given basis having a desired polarization at the confined intensity maxima, the strength and contrast relative to the background can be further optimized if the electric field of each incident wave, given as, $$e_m(x,t)=e_o\{\sin\chi\exp(i\eta_s)(\hat{e}_s)_m+\cos\chi\exp(i\eta_p)[\sin\theta_m(\hat{e}_i)_m+\cos\theta_m\hat{e}_z]\}\cdot\exp[i(k_m\cdot x-\omega t)] \tag{51}$$

is selected not to maximize its projection, $Re\{e_m^*(x_d,t_d)\cdot e_d\}$, on the desired polarization state, $e_d$, at $x_d$ and $t_d$ as in Equation (24) and the specific examples given by Equations (28), (34), and (37), but rather the projection, $Re\{[(e_m(x_d,t_d)+e_m^r(x_d,t_d))^*]\cdot e_d\}$, of the superposition of this wave with its reflected counterpart, which is given by:

$$e_m^r(x,t)=e_o\{r_s\sin\chi\exp(i\eta_s)(\hat{e}_s)_m+r_p\cos\chi\exp(i\eta_p)[\sin\theta_m(\hat{e}_i)_m-\cos\theta_m\hat{e}_z]\}\cdot\exp[i(k_m^r\cdot x-\omega t)] \tag{52}$$

Because the reflection coefficients, $r_s$ and $r_p$, are generally complex, in the specific case where linear polarization is optimized (i.e., when $e_d=E_o\hat{e}_d$), the projection of the superimposed incident and reflected waves on the desired polarization state is given by:

$$Re\{[(e_m(x_d,t_d)+e_m^r(x_d,t_d))^*]\cdot e_d\}=G(\chi,\eta_s,\eta_p)=e_oE_o\{\sin\chi((\hat{e}_s)_m\cdot\hat{e}_d)[\cos(\phi_m+\eta_s)+Re(r_s)\cos(\phi_m^r+\eta_s)-Im(r_s)\sin(\phi_m^r+\eta_s)]+\cos\chi[(\sin\theta_m(\hat{e}_z\cdot\hat{e}_d)+\cos\theta_m((\hat{e}_{para})_m\cdot\hat{e}_d))\cos(\phi_m+\eta_p)+(\sin\theta_m(\hat{e}_z\cdot\hat{e}_d)-\cos\theta_m((\hat{e}_{para})_m\cdot\hat{e}_d))(Re(r_p)\cos(\phi_m^r+\eta_p)-Im(r_p)\sin(\phi_m^r+\eta_p))]\} \tag{53a}$$

where: $\phi_m=k_m\cdot x_d-\omega t_d$ and $\phi_m^r=k_m^r\cdot x_d-\omega t_d$. (53b)

Application of the maximization conditions, $\partial G/\partial\eta_s=\partial G/\partial\eta_p=\partial G/\partial\chi=0$, then yield, respectively:

$$\eta_s=-\tan^{-1}\left[\frac{\sin\varphi_m+Re(r_s)\sin\varphi_m^r+Im(r_s)\cos\varphi_m^r}{\cos\varphi_m+Re(r_s)\cos\varphi_m^r-Im(r_s)\sin\varphi_m^r}\right]+n_s\pi, \tag{54a}$$

$$\eta_p=-\tan^{-1}\{[(\sin\theta_m(\hat{e}_z\cdot\hat{e}_d)+\cos\theta_m((\hat{e}_{para})_m\cdot\hat{e}_d))\sin\phi_m+(\sin\theta_m(\hat{e}_z\cdot\hat{e}_d)-\cos\theta_m((\hat{e}_{para})_m\cdot\hat{e}_d))(Re(r_p)\sin\phi_m^r+Im(r_p)\cos\phi_m^r)]/[(\sin\theta_m(\hat{e}_z\cdot\hat{e}_d)+\cos\theta_m((\hat{e}_{para})_m\cdot\hat{e}_d))\cos\phi_m+(\sin\theta_m(\hat{e}_z\cdot\hat{e}_d)-\cos\theta_m((\hat{e}_{para})_m\cdot\hat{e}_d))(Re(r_p)\cos\phi_m^r-Im(r_p)\sin\phi_m^r)]\}+n_p\pi, \tag{54b}$$

$$\chi=\tan^{-1}\{[((\hat{e}_s)_m\cdot\hat{e}_d)(\cos(\phi_m+\eta_s)+Re(r_s)\cos(\phi_m^r+\eta_s)-Im(r_s)\sin(\phi_m^r+\eta_s))]/[(\sin\theta_m(\hat{e}_z\cdot\hat{e}_d)+\cos\theta_m((\hat{e}_{para})_m\cdot\hat{e}_d))\cos\phi_m+(\sin\theta_m(\hat{e}_z\cdot\hat{e}_d)-\cos\theta_m((\hat{e}_{para})_m\cdot\hat{e}_d))(Re(r_p)\cos\phi_m^r+\eta_p)-Im(r_p)\sin(\phi_m^r+\eta_p))]\}+n_\chi\pi, \tag{54c}$$

where $n_s$, $n_p$, and $n_\chi$ are even or odd, based on the additional maximization conditions $\partial^2 G/\partial \eta_s^2 < 0$, $\partial^2 G/\partial \eta_p^2 < 0$, and $\partial^2 G/\partial \chi^2 < 0$:

$$\cos(\phi_m + \eta_s) + Re(r_s)\cos(\phi_m^r + \eta_s) - Im(r_s)\sin(\phi_m^r + \eta_s) > 0, \quad (55a)$$

$$(\sin \theta_m(\hat{e}_z \cdot \hat{e}_d) + \cos \theta_m((\hat{e}_{para})_m \cdot \hat{e}_d))\cos(\phi_m + \eta_p) + (\sin \theta_m(\hat{e}_z \cdot \hat{e}_d) - \cos \theta_m((\hat{e}_{para})_m \cdot \hat{e}_d))(Re(r_p)\cos(\phi_m^r + \eta_p) - Im(r_p)\sin(\phi_m^r + \eta_p)) > 0, \text{ and} \quad (55b)$$

$$G(\chi, \eta_s, \eta_p) > 0 \quad (55c)$$

As seen in FIG. 52, such optimization results in somewhat better confinement and intensity strength than the method described above based on the optimization of each incident field alone (e.g., as described in connection with Equation (28)). However, for moderately reflective surfaces, substantial variations in the basis remain under translation of the lattice in a direction normal to the interface. Therefore, for microscopy applications in such cases, the position dependence of the resulting effective point spread function must be taken into account. Similarly, for lithography applications, well-confined exposures may be limited to specific planes parallel to the interface.

Optical Path Length Variations

Creating a stable, well-defined basis for a given lattice, such as those arising from the application of Equation (28) or Equation (34), requires control of the relative phases of all constituent plane waves throughout the region of interest. However, differences in the refractive index along the path traveled by each wave, particularly due to heterogeneity within the sample, can result in significant time- and/or space-dependent phase variations, thereby degrading the basis.

If only a single wave significantly departs from its ideal phase relative to the others, either due to a localized region of differing refractive index (e.g., an organelle) within its path alone, or due to an initial error in its adjustment, then the effect on the basis is often benign. FIG. 53B, for example, shows a worst-case scenario in which one of the plane waves of a maximally symmetric body-centered cubic lattice of intensity period $\sqrt{14}\lambda$, having the largest projection, $e_n \sim e_d$, of all 48 constituent waves onto the desired z-polarization state at the intensity maximum within the primitive cell, is a full 180° out of adjustment with its desired phase at this maximum. The opaque surfaces of at least 50% intensity and the translucent surfaces of at least 20% intensity in FIG. 53B indicate minimal distortion of the resulting basis compared to the corresponding ideal lattice and basis shown in FIG. 53A. Generally, such single-wave phase errors become less significant as the total number of waves within the lattice increases.

FIG. 54A, FIG. 54B, and FIG. 54C demonstrate the effect on the basis when all plane waves of this same lattice experience random phase errors, normally distributed with a mean of zero error and a standard deviation of 30°, 45°, and 60°, respectively. Although spatial filtering in the detection system can be used to isolate the signal of the intensity maximum from the increasing background that is caused by increasing phase errors (presumably induced by sample heterogeneity), these figures suggest that the phase of each wave should be controlled to within about 45°, and ideally to within about 30° or less. Experiments on fixed cells in high-index immersion oil with an alternative interference-based microscope, the I5M, described, for example, in M. G. L. Gustafsson, et al., *J. Microsc.* 195, 10-16 (1999), which is incorporated herein by reference, indicate that, even in this poorly index-matched condition, phase errors of less than 10° are observed when imaging through >3 μm of cellular material. Hence, for most cases of lattice imaging within single cells, no additional corrections to the phases of the individual waves should be required after their initial phase relationships are established. Multiphoton excitation as described in conjunction with FIG. 34 and FIG. 35 can further increase the range of samples for which no additional phase correction is needed, since the wavelength-normalized phase error for a given index variation in the path of each plane wave is q-fold smaller for q-photon excitation at a wavelength of $q\lambda_{abs}$.

Depending on the shape and refractive index distribution within the sample, only a few specific constituent plane waves (e.g., those with the longest path through the sample to reach the region of interest) of a given lattice may exhibit significant phase distortion. In such cases, it may still be possible to avoid resorting to dynamic phase correction either by tilting the lattice to change the paths of these waves through the sample, or by simply omitting the offending waves (although, in this case, some loss of confinement of the intensity maxima along the wavevectors, $k_m$, of the omitted waves must be tolerated).

For thicker tissue samples, in vivo imaging of macroscopic specimens, or exceptionally large and heterogeneous single cells, dynamic correction to the relative phases of the constituent plane waves may be needed. In such cases, existing adaptive optical techniques developed for single focus (e.g., confocal) microscopes and based on maximization of the signal at the focus, can be applied to optimize the phase relationship between all waves at a chosen lattice intensity maximum. Such adaptive methods, which vary the phase of the incoming light at multiple points across the rear pupil of the objective in order to compensate for optical path length differences amongst the various converging rays in the space between the front of the objective and the focal point are described, for example, by M. A. A. Neil, et al., *J. Microsc.*, 200, 105-108 (2000), and M. J. Booth, et al., *Proc. Natl. Acad. Sci.*, 99, 5788-5792 (2002), both of which are incorporated herein by reference. These methods may be even more effective in the case of lattice microscopy, because the phases need be controlled for only a finite set of wavevectors, $k_m$, as opposed to a continuum of wavevectors as in the single focus case.

Additional methods of adaptive phase correction exist that are particularly well suited to optical lattice microscopy. For example, the relative phase of each wave can be interferometrically measured after passage through the specimen to determine the total effective optical path length in each direction, $k_m$. For samples in which the accumulated phase error is approximately proportional to the distance traversed within the specimen, these path length measurements can be used to calculate and correct for an estimated phase error for each wave at the center of the region of interest.

Other options include: (1) briefly blocking all but one "reference" plane wave and, in turn, all but one other plane wave of the lattice, and then adjusting the phase of the latter to position a measured maximum of the resulting standing wave with a chosen lattice intensity maximum; (2) briefly blocking only one or a few plane waves to compare their actual vs. predicted contributions (e.g., as given by Equation (28)) to a chosen lattice intensity maximum, $|e(x_d, t_d)|^2$, and then adjusting their phases accordingly; and (3) phase modulating one or more plane waves by a small amount (e.g., within about ±15°), each at a unique frequency, $f_m$, measuring the frequency spectrum of the signal collected from a chosen lattice intensity maximum, and adjusting the phase of each wave to maximize the $2f_m$ component and/or minimize the $f_m$ of within the spectrum.

Regardless of the method used, once the phases of all plane waves have been corrected at a chosen point to match those of the ideal lattice and basis, phase errors can still accumulate with increasing distance from this point, due to the differing environments experienced by each wave. Nevertheless, the basis characteristics can be substantially improved over a significant volume centered at the correction point by such adaptive methods. If necessary, either the excitation and/or detection can be limited to the volume over which the correction is effective, and larger regions of interest can be imaged by combining data from multiple volumes centered at different correction points within this region.

Experimental Methods of Lattice Excitation

Bound Lattices and Excitation Zones

Thus far, ideal, infinite lattices constructed with ideal, infinite plane waves have been discussed. Such lattices are hereafter termed ideal lattices. However, experimental realization demands that each plane wave be replaced by a beam of finite width, thereby introducing a continuous, albeit localized, distribution of wave vectors in place of each discrete wave vector. Furthermore, for microscopy, it can be useful to intentionally restrict lattices to spatially-limited regions, even regions of microscopic dimensions. Among the reasons to do so are:

a) the fact that nonlinear optical processes, to which lattice microscopy may be fruitfully applied, typically exhibit absorption cross-sections sufficiently small to require excitation intensities accessible only with highly focused illumination;

b) the fact that excitation that occurs beyond the field of view (dictated by the magnification of the detection optics and the size of the detectors) leads to unnecessary photobleaching and potential photodamage within the specimen; and c) the fact that, even with adaptive phase correction methods, lattices will become increasingly distorted as the distance from the correction point increases (in samples of inhomogeneous refractive index).

The region where all finite beams substantially overlap is referred to herein as the excitation zone. The resulting field in the excitation zone can be called an optical lattice or, specifically, a bound lattice, even though the field is not infinite in extent and does not appear identical when viewed from all equivalent lattice points, because the field very closely approximates the symmetry and periodicity of an ideal lattice over any small observation region within the excitation zone, and because the propagation direction, $k_n$, and electric field, $e_n$, of each finite beam are substantially similar to the $k_n$, and $e_n$ of the corresponding plane wave of an ideal lattice.

Creation of Confined Beams

Confined beams to produce optical bound lattices can be produced by shining beams of light through an aperture in an opaque screen or by creating a converging spherical light wave with a lens. A third option—confinement with a reflecting or diffractive structure—is, by Babinet's principle, equivalent to the case of an aperture of the same dimensions. Furthermore, the aperture case is itself equivalent to a lens of the same dimensions and focal length, f, in the limit that $f \to \infty$. Therefore, all these methods of confinement can be considered by analyzing diffraction in the lens case.

When a plane wave, $e_n^i(x,t) = e_n \exp[i(kz - \omega t)]$, $e_n \cdot \hat{e}_z = 0$, is incident from $z<0$ along the axis $\hat{e}_z$ of a circular lens centered at $(x,y)=(0,0)$ in an opaque screen at $z=0$, a confined diffraction field, $e_n(x,t)$, is created in the $z>0$ half space that, for $k\alpha \gg 1$, can be accurately estimated using the generalized Kirchhoff integral:

$$e_n(x, t) = -\frac{ik}{2\pi} \tag{56}$$

$$\int\int [e_W(x', t)]_n \frac{\exp(ik|x - x'|)}{|x - x'|} \left(1 + \frac{i}{k|x - x'|}\right) \frac{\hat{e}_W \cdot (x - x')}{|x - x'|} d^2 x'.$$

The integration is over all points, x', on the spherical wavefront, W, of a radius, f and a solid angle, $\Omega$, subtended by the lens. The unit vector, $\hat{e}_W$, is normal to W, and $[e_W(x',t)]_n$ is given by the projection of the incident field, $e_n^i(x,t)$, onto W.

External Excitation

We first consider the subcase, hereinafter referred to as external excitation, in which each plane wave of the ideal lattice is replaced by a convergent beam radiating from its own lens. The number of lenses is then generally large enough that each lens subtends only a small solid angle, $\Omega$, and the paraxial approximation can be used: $\alpha/f \equiv \sin \alpha \approx \alpha \ll 1$ and $[e_W(x',t)]_n \approx e_n^i(x',y',0,t)$. For points satisfying $\sqrt{x^2+y^2} : O(\alpha)$ and $k\alpha(\alpha/z)^3 \ll 1$, Equation (56) then can be expressed in cylindrical coordinates, $x \equiv (\rho \cos \theta, \rho \sin \theta, z)$, $x' \equiv (\rho' \cos \theta', \rho' \sin \theta', z')$, as:

$$e_n(x, t) \approx e_n \left\{ \begin{array}{c} -i\frac{a}{z} ka \exp\left(\frac{ik\rho^2}{2z}\right) \\ (C(u, v) + iS(u, v)) \end{array} \right\} \exp[i(kz - \omega t)], \tag{57a}$$

where $$C(u, v) = \int_0^1 J_0(v\eta) \cos(u\eta^2/2) \eta d\eta, \tag{57b}$$

$$S(u, v) = \int_0^1 J_0(v\eta) \sin(u\eta^2/2) \eta d\eta$$

$$u(z) = \frac{a}{z} ka, \text{ and } v(\rho, z) = \frac{a}{z} k\rho. \tag{57c}$$

Equations (57) are valid for either the case of aperture illumination or lens illumination. However, in the lens case, it is convenient to recast the result in terms of the axial distance $z_f \equiv z - f$ from the focal point. For distances, $z_f$, sufficiently close to the focus to satisfy the condition, $k\alpha(\alpha/f)(z_f/f)^2 \ll 1$, we find:

$$e_n(x, t) \approx \left\{ \begin{array}{c} -ie\frac{a}{z} ka \exp\left(\frac{ik\rho^2}{2f}\right) \exp(ikf) \\ (C(u_l, v_l) + iS(u_l, v_l)) \end{array} \right\} \exp[i(kz - \omega t)] \tag{58a}$$

where $$u_l(z)(a/f)^2 \cdot k(z - f), \text{ and } v_l(x, y) = \frac{a}{f} k\rho. \tag{58b}$$

Equations (57) and (58) show that the diffracted field in each case has the form of an ideal plane wave traveling along the optical axis, $\hat{e}_z$, modified by a complex multiplier that determines the nature of the field confinement. FIG. 55 compares the amplitude and phase of the complex multiplier for an aperture with $\alpha=30\lambda$ to the amplitude and phase of the complex multiplier for a lens with $\alpha/f=0.012$. Although illumination from either lenses or apertures achieves the desired confinement and can be used to create bound lattices, the lens method achieves superior optical results because, in the neighborhood of the focal point, the variation in the phase is negligible over the entire central amplitude peak. Thus, throughout the excitation zone, the phase relationship between beams of the bound lattice remains nearly identical to the phase relationship between the corresponding plane waves of the ideal lattice, and potential lattice distortion is minimized.

Furthermore, whereas the field emitted from an aperture diverges from the minimum width dictated by the aperture diameter, the field emitted from a lens converges to an intensity at the focal point of $I(0,v)=(2J_1(v)/v)^2 I_o$, yielding a minimum width:

$$2\rho \approx 0.52\lambda/(\alpha/f), \quad (59)$$

which depends only on the wavelength, $\lambda$, and the ratio of the lens diameter, $\alpha$, and the lens focal length, f. Thus, extremely small excitation zones of a width, $2\rho \ll \alpha$, can be created at arbitrarily large distances through appropriate choice of the lens diameter, $\alpha$, and the focal length, f. This simplifies the task of constructing an optical system to produce the large number of beams from diverse angles necessary for most lattices.

An externally excited bound lattice thus can be created by replacing each plane wave of an ideal lattice by a circular lens of low numerical aperture, $n\alpha \approx \alpha/f$, uniformly illuminated at normal incidence, with the optical axis aligned to the plane wave propagation vector, $k_n$, and the complex input polarization, $e_n$, set to achieve the desired basis as described above (e.g., by maximizing the values of Equation (24)). For a maximally symmetric lattice created with identical lenses sharing a common focal point, as shown in FIG. 56A, the resulting excitation zone is approximately spherical, as shown in FIG. 56B. As expected, the minimal phase variation across each beam waist ensures that the actual bound lattice varies from its ideal counterpart primarily due to the overall excitation envelope, i.e., within this envelope the widths of the individual intensity maxima and the contrast relative to the background remain largely unchanged from the ideal case. Furthermore, the size of the excitation zone is consistent with that given by Equation (59), so that zones of differing size can be created by varying the common $n\alpha$ of the lenses as shown in FIG. 57.

The $n\alpha$ of each lens can be increased until the envelope width as given by Equation (59) becomes smaller than the lattice period, at which point the single central lattice point dominates. Indeed, in this limit (e.g., for $\alpha/f \approx 0.32$, for the lattice of FIGS. 56 and 57) the total solid angle, $\Omega_{tot}$, subtended by all N lenses of a maximally symmetric bound lattice is given by:

$$\Omega_{tot} = N\Omega = 2\pi N(1-\sqrt{1-(\alpha/f)^2}), \quad (60)$$

and approaches $4\pi$, and therefore the remaining point exhibits characteristics similar to those at the focus of a $4\pi$ microscope. Similarly, for a subset lattice made up of those beams within the solid angle subtended by a single microscope objective, the central lattice point increasingly mimics the focus of a confocal microscope as $\alpha/f$ increases. However, in either case, the central lattice point exhibits superior polarization purity (e.g., as shown in FIG. 30) and spatial confinement of the intensity compared to these single focus systems. The superior polarization purity is because the polarization of each beam is individually optimized, and the superior intensity confinement is because excitation from solid angles beyond those covered by conventional high NA microscope objectives can be included.

One limitation of external excitation is that, for maximally symmetric three-dimensional lattices, it does not leave a relatively large, unobstructed region for the addition of one or more high NA lenses to detect the resultant signal with reasonable efficiency and spatial resolution. In principle, the signal intercepted by the excitation lenses themselves could be coherently combined in a manner akin to Very Long Baseline Interferometry, thereby achieving high detection resolution at arbitrarily large working distances. Alternatively, the excitation can be limited to subset lattices having constituent plane waves with wavevectors, $k_n$, that travel in directions outside the angles subtended by the collection optics, such as those shown for a single high NA collection objective in FIG. 58. However, the intensity confinement is thereby compromised, as it is for all subset lattices.

Internal Excitation

To optimize both the excitation and detection resolution in an experimentally uncomplicated geometry, the majority of the excitation beams must pass through either one of two opposed, high NA objective lenses that are used for detection of signal from the lattice as well as for its creation. Such an arrangement has an analog with the $4\pi$ microscope, except that illumination at specific, discrete points within the rear pupils of the objectives creates a bound lattice with multiple intensity maxima, as opposed to the single, multi-lobed focus characteristic of the $4\pi$ microscope with uniform full-pupil illumination. Therefore, we now consider the subcase, hereinafter referred to as internal excitation, in which all constituent beams of a bound lattice are transmitted to the excitation zone through the high NA detection optics, as shown in FIG. 59.

As described above, the propagation direction of each beam is given by the wavevector, $k_n$, of the corresponding constituent plane wave of the ideal lattice, and the effective cone half-angle, $n\alpha \equiv \alpha/f \ll 1$, is determined by the desired excitation zone width, as per Equation (59). Ray tracing suggests that a converging beam with these characteristics can be generated in an infinity corrected microscope by introducing an input beam in the afocal region between the objective (having a numerical aperture, NA, a focal length, $F_o$, a rear pupil radius, A, and a refractive index, $n_o$, at its focusing end) and the tube (i.e., imaging) lens (having a focal length, $F_t$) to illuminate a region of radius, $b = n\alpha \cdot F_o = (n\alpha \cdot n/NA) \cdot A$, centered at position, $$x''_{bc} = -[(k_n \cdot \hat{e}_x)\hat{e}_x + (k_n \cdot \hat{e}_y)\hat{e}_y] \quad (61)$$

$$\frac{F_o}{k} = -[(k_n \cdot \hat{e}_x)\hat{e}_x + (k_n \cdot \hat{e}_y)\hat{e}_y]\frac{n}{kNA}A$$

within the rear pupil of the objective lens as shown in FIG. 59C. The bound lattice resulting from the superposition of all converging beams is then derived by determining, in the vicinity of the focal point of the objective, the diffracted field, $e_n(x,t)$, arising from each beam.

To accomplish this, Equation (56) must be evaluated for each localized input beam on the convergent spherical wavefront, W, of radius, $F_o$, emerging from the objective, subtending the large solid angle, $\Omega = 2\pi(1-\sqrt{1-(NA/n)^2})$. Consequently, the paraxial approximation cannot be used as above. However, if the final bound lattice or the region of interest therein is small compared to $F_o$, then $x-x' \approx F_o \hat{e}_w$. Combined with $kF_o \gg 1$, Equation (56) then reduces to, $$e_n(x,t) = -\frac{ik}{2\pi} \int\int [e_W(x',t)]_n \frac{\exp(ik|x-x'|)}{|x-x'|} d^2x' \quad (62)$$

To evaluate Equation (62), the projection, $[e_W(x',t)]_n$, of each input beam, $e_n^i(x'',t)$, onto W must be found. As seen in FIG. 60, the tangential (i.e., s-polarized) component, $(\hat{e}_\phi)_n$, of the input electric field, $e_n^i$, is unchanged by the microscope objective lens (assuming minimal reflection losses), but the radial (i.e., p-polarized) component, $(\hat{e}_\rho)_n$, is rotated by refraction in the lens to the direction, $(\hat{e}_\theta)_n$, at the center, $x_{bc}''$, of the beam. Thus, for the polarization of the diffracted field, $e_n(x,t)$, along the central ray to match the polarization of the corresponding plane wave, $e_n$, of the ideal lattice and desired basis, the input polarization should be given by:

$$e_n^i = [(\hat{e}_\theta)_n \cdot e_n](\hat{e}_\rho)_n + [(\hat{e}_\phi)_n \cdot e_n](\hat{e}_\phi)_n, \text{ where} \quad (63a)$$

$$(\hat{e}_\phi)_n = k_n \times \hat{e}_z / \sqrt{k^2 - (k_n \cdot \hat{e}_z)^2} (\hat{e}_\rho)_n = \hat{e}_z \times (\hat{e}_\phi)_n, \text{ and } (\hat{e}_\theta)_n = k_n \times (e_\phi)_n / k. \quad (63b)$$

Similar arguments can be used to find the field, $[e_W(x',t)]_n$, on W arising from the points, x", within the rear pupil other than $x_{bc}''$. In particular, the input ray at x" can be converted into a convergent ray propagating along $\hat{e}_r(x'')$, where:

$$\hat{e}_r(x'') = \left[ -(\hat{e}_x \cdot x'')\hat{e}_x - (\hat{e}_y \cdot x'')\hat{e}_y + \sqrt{F_o^2 - |x''|^2}\,\hat{e}_z \right] / F_o \quad (64)$$

$$= \left[ \frac{-(\hat{e}_x \cdot x')\hat{e}_x - (\hat{e}_y \cdot x')\hat{e}_y + }{\sqrt{F_o^2 - (\hat{e}_x \cdot x')^2 - (\hat{e}_y \cdot x')^2}\,\hat{e}_z} \right] / F_o$$

$$= \hat{e}_r(x')$$

Along this ray, the input polarization, $e_n^i$, is transformed in the local tangential direction, $\hat{e}_\phi(x')$, and in the radial direction, $\hat{e}_\rho(x')$, analogous to those described above. Thus:

$$[e_W(x',t)]_n = \chi(x',y')\psi_n(x',y') \begin{bmatrix} (\hat{e}_\rho(x') \cdot e_n^i)\hat{e}_\theta(x') + \\ (\hat{e}_\varphi(x') \cdot e_n^i)\hat{e}_\varphi(x') \end{bmatrix}, \quad (65a)$$

where $$\hat{e}_\varphi(x') = \frac{\hat{e}_r(x') \times \hat{e}_z}{\sqrt{1 - (\hat{e}_r(x') \cdot \hat{e}_z)^2}}, \quad (65b)$$

$$\hat{e}_\rho(x') = \hat{e}_z \times \hat{e}_\varphi(x'), \text{ and}$$

$$\hat{e}_\theta(x') = \hat{e}_r(x') \times \hat{e}_\varphi(x'),$$

and where $\psi_n(x',y')=\psi_n(x'')$ gives the variation in amplitude of the input beam across the rear pupil (i.e., $e_n^i(x'',t)=e_n^i\psi_n(x'')\exp(-i\omega t)$), and where $\chi(x',y')$ describes how this amplitude is transformed upon projection onto W.

As seen in FIG. 60, the beam energy, $dE_n(x'') \propto |e_n^i(x'')|^2 dx''dy''$, in area $dx''dy''$ within the rear pupil maps onto the curved element of W at $x'=x''-\sqrt{F_o^2-|x''|^2}\hat{e}_z$ with area $dx'dy'/(\hat{e}_r(x') \cdot \hat{e}_z)$. Hence, energy conservation demands $\chi(x',y') = \sqrt{\hat{e}_r(x') \cdot \hat{e}_z}$. Combining this with Equations (62)-(65), we finally find:

$$e_n(x,t) = \quad (66)$$

$$-\frac{ik}{2\pi}\int\int_{-A}^{A} \Theta\left(\frac{x'^2+y'^2}{A}\right)\{[(\zeta(x',y')x'^2+y'^2)(\hat{e}_x \cdot e_n^i)+(\zeta(x',y')-1)$$

$$x'y'(\hat{e}_y \cdot e_n^i)]\hat{e}_x + [(\zeta(x',y')-1)x'y'(\hat{e}_x \cdot e_n^i)+$$

$$(x'^2+\zeta(x',y')y'^2)(\hat{e}_y \cdot e_n^i)]\hat{e}_y +$$

$$(x'^2+y'^2)\times[x'(\hat{e}_x \cdot e_n^i)\hat{e}_x + y'(\hat{e}_y \cdot e_n^i)\hat{e}_y]\hat{e}_z\}$$

$$\sqrt{\frac{\hat{e}_r(x') \cdot \hat{e}_z}{x'^2+y'^2}}\,\psi(x',y')\frac{\exp(ik|x-x'|)}{|x-x'|}dx'dy'$$

where $\zeta(x',y') = \sqrt{F_o^2 - x'^2 - y'^2}\big/F_o$ and (67)

$\Theta(x) = 1$ for $x \leq 1$, 0 otherwise.

For the special case in which the input beam uniformly illuminates the rear pupil with a linearly polarized plane wave (i.e., $\psi_n(x'')=e_o$), Equation (66) yields a single intensity maximum at the focal point characteristic of a confocal microscope (i.e., as shown in FIGS. 15 and 30).

Input and Convergent Output Beams in Internal Excitation

To model the variation in amplitude of the input beam across the rear pupil, $\psi_n(x'')$, necessary to generate bound lattices, we consider beams of diameter b<A created with an aperture mask, as shown in FIG. 59C, and calculate $\psi_n(x'')$ using Equations (57). The amplitude, $|\psi_n(x'')|$, and phase, $\arg[\psi_n(x'')]$, for one such beam are shown in FIGS. 61A and 61B, respectively. This particular input beam is located in the rear pupil at the position, $x_{bc}''=0.64A(\hat{e}_x+\hat{e}_y)$, necessary to produce one of the eight convergent beams of a maximally symmetric simple cubic bound lattice of intensity period, $\sqrt{3}\lambda/2$, and is chosen because all eight beams, convergent along the wavevector, $k_n=k[\pm 1 \pm 1 \pm 1]/\sqrt{3}$, fit within the two conical acceptance cones of half-angle, $\theta_{max}=\sin^{-1}(1.2/1.33)=64.46°$, defined by opposed NA=1.2 water immersion objectives. The input beam radius, $b=(n\alpha \cdot n/NA)A=0.055$ A, which yields an excitation zone radius, $\rho$: $5\lambda$, according to Equation (59), is chosen to be sufficiently large to highlight any distortions that occur due to passage through the objective lens. Finally, the aperture mask is placed at a distance, $z=2 \cdot \leq 10^4 \lambda \ll \alpha^2/\lambda$ from the rear pupil, which is sufficiently far from the pupil to be outside the path of the collected signal (as shown in FIG. 59C), yet sufficiently close to the rear pupil that the angular wavevector spread, $\Delta k/k$ (which is of order $\lambda/\alpha$), introduced by the confinement of the input beam does not significantly influence the field over the majority of the beam diameter at the plane of the rear pupil.

Figure 61F:
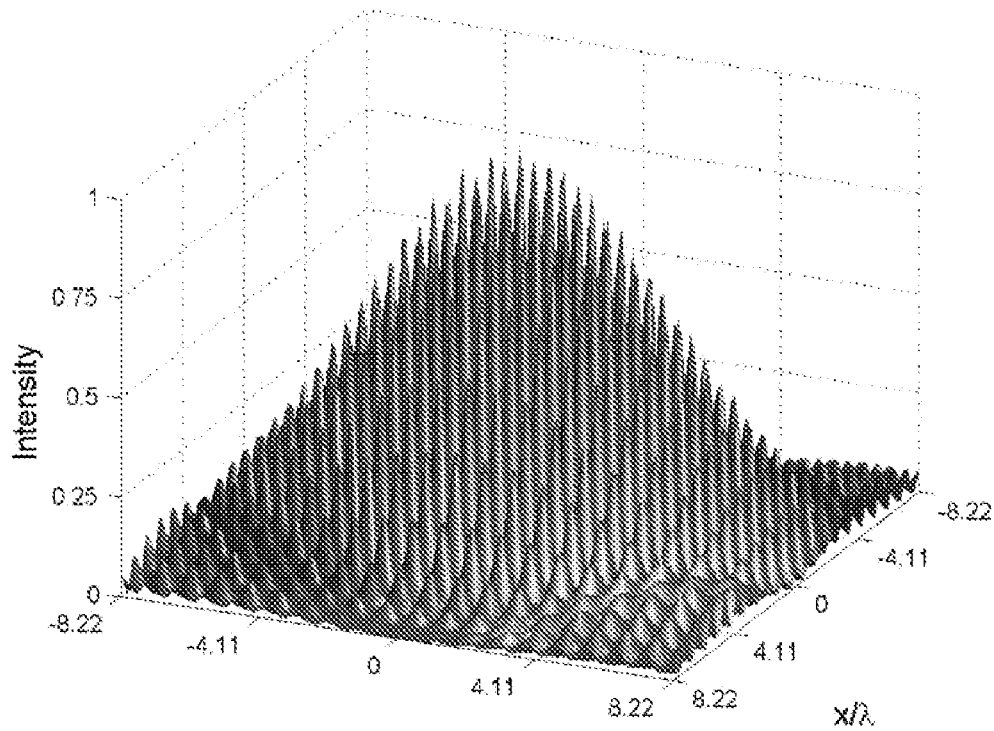

With these parameters, FIGS. 61A and 61B demonstrate that the input beam at the rear pupil remains largely confined to the desired dimensions, with relatively constant phase in the region where the magnitude is large. Beyond this region, rapid phase oscillations occur, as does partial truncation of the beam by the edge of the rear pupil. Nevertheless, FIGS. 61C and 61D demonstrate that the properties of the high amplitude region dominate the resulting convergent beam, as the beam exhibits the appropriate width at the focal point of the objective and phase uniformity across this width necessary to produce the desired bound lattice with minimal distortion, as shown in FIGS. 61E and 61F.

One significant distortion that does occur is the elliptical compression of the convergent beam in the $\hat{e}_\theta$ direction, as shown in FIG. 61C, and subsequent compression of the excitation zone along the $\hat{e}_z$ axis, as shown in FIG. 61E. This occurs, as seen in FIG. 60, when a circular input beam of a radius, b, is projected onto the curved wavefront, W, to create a convergent beam initially stretched by a factor, $k/(k_n \cdot \hat{e}_z)$, based on its location, $x_{bc}"$, within the rear pupil according to Equation (61). The effective numerical aperture, $n\alpha$, is then $b/F_o$, which is as desired in the $\hat{e}_\phi$ direction, but which is higher by a factor, $k/(k_n \cdot \hat{e}_z)$, along the $\hat{e}_\theta$ axis. The result, as per Equation (59), is that the observed convergent beam waist has an ellipticity $(k_n \cdot \hat{e}_z)/k$.

To compensate for this distortion, the width of each input beam can be reduced in its $\hat{e}_\rho$ direction by a factor of $(k_n \cdot \hat{e}_z)/k$ that is appropriate for the beam, as shown in FIG. 62. This model is chosen more for its computational tractability than for its realism, but a comparison of convergent beams and bound lattices calculated with idealized circular apertures agree extremely well with the realistic model illustrated in FIG. 61 in the limit where $z \ll \alpha^2/\lambda$, and hence lends credence to the extension of the idealized model to the elliptical case as well. As expected, elliptical compression of the input beam along the $\hat{e}_\rho$ axis, as shown in FIG. 62A, results in a circular convergent beam waist of the desired size as shown in FIG. 62C, excellent phase uniformity across this beam as shown in FIG. 62D, a bound lattice with a much more circular excitation zone, shown in FIG. 62E, and reduced distortion at the periphery of the excitation zone, as shown in FIG. 62F.

Figure 63F:
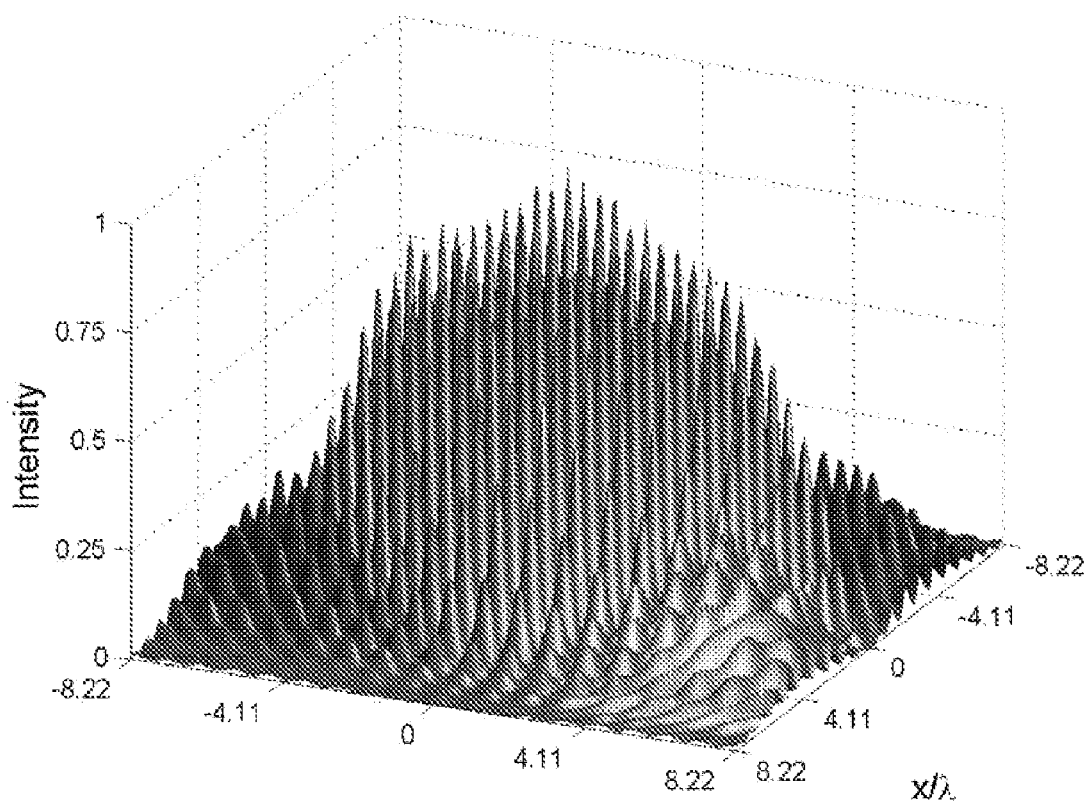

Thus, illumination of the objective rear pupil through apertures of the appropriate shape, size, and location in an opaque mask, as considered in FIGS. 61 and 62 and as shown conceptually in FIG. 59C, can be used to generate internally excited lattices. However, for relatively large excitation zones, apertures are required with diameters that are so small that the resulting input beams expand significantly and become distorted by diffraction for a mask placed outside the path of the collected signal. In such cases, a patterned dichroic mirror or a dichroic mask in close proximity to the rear pupil can be used in lieu of the more distant opaque mask to define the beams. Alternatively, for very large lattices, each input beam can be produced with its own low $n\alpha$ lens, focused at the rear pupil plane of the high NA objective, so that the phase of the beam remains relatively constant over the region of significant amplitude, as shown in FIGS. 63A and 63B. The focal length of each lens, f, can then be chosen to place each lens at the desired distance, and the radius, $\alpha$, of each lens can be selected to produce a beam waist radius, $b \approx 0.26\lambda_o/(\alpha/f)$, at the rear pupil consistent with the creation of an excitation zone of the desired radius, $\rho \approx 0.26\lambda/(b/F_o)$, (i.e., $\alpha/f \approx n\rho/F_o$) at the objective focal point. Each lens can also be illuminated through an elliptical mask to produce a specific elliptical input beam and the ultimate convergent beam shape as discussed above. Because a non-negligible portion of the input beam energy exists in the secondary Airy disk of phase opposite to the primary maximum, as shown in FIGS. 63A and 63B, this method creates a greater amplitude variation in the convergent beam at the objective focal point, shown in FIG. 63C, and hence greater lattice distortion, as shown in FIGS. 63E and 63F. This method is, therefore, best restricted to those internally excited lattices that are too large to exploit the aperture mask method.

Note also that the illumination arrangement shown in FIG. 59C is purely conceptual. In practice, the initial source beam energy can be partitioned into the individual aperture-defined beams by more efficient means, such as with optical waveguides (e.g., optical fibers) having an aperture lithographically defined on the end of each waveguide, or with individual focusing lenses assigned to each aperture having a focal width at the mask that is just large enough to ensure sufficient amplitude and phase uniformity across its assigned aperture.

In addition to providing greater experimental simplicity, the delivery of constituent beams of a bound lattice to the excitation zone via precision, high NA apochromatic microscope objectives can compensate for chromatic and spherical aberration that can occur in lenses of lesser quality. Compensation for chromatic aberration can be used to achieve diffraction-limited performance and correctable dispersion with ultrafast, pulsed excitation (e.g., as shown in FIGS. 34 and 35). Correction for spherical aberration can be used to preserve the amplitude and phase characteristics of each convergent beam, as predicted by Equation (66) and as seen in FIGS. 61C-63C and 61D-63D. This is particularly true for oblique beams of moderate $n\alpha$, as such beams face drastically different optical path lengths across their widths when exciting cover glass mounted specimens, and therefore benefit most from the use of cover glass corrected objectives.

Tailoring the Lattice

Figure 64D:
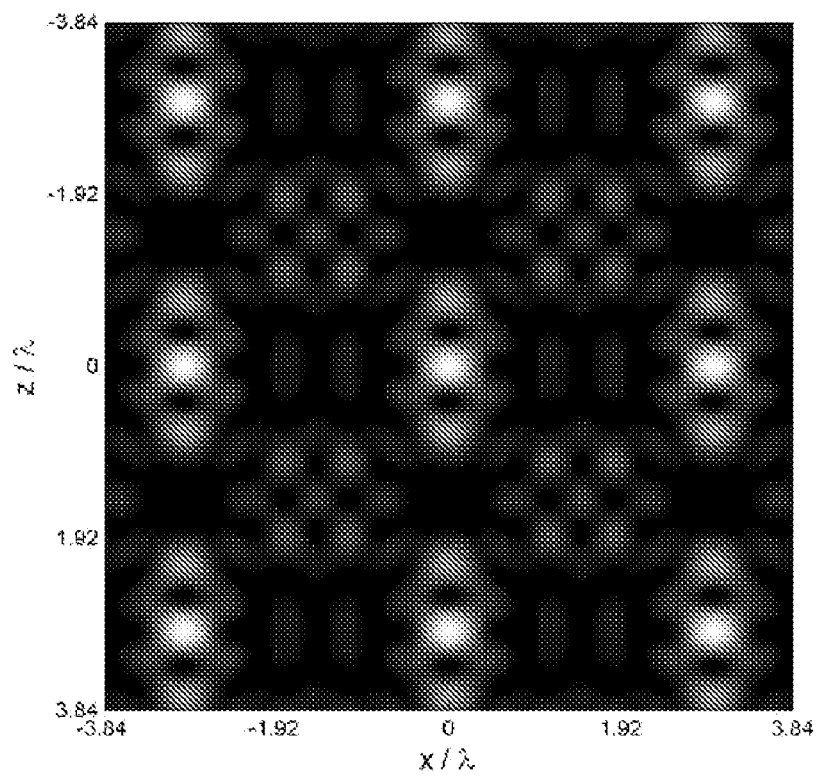

One limitation of creating a lattice with exclusively internal excitation is that opposed water immersion objectives with a numerical aperture at the practical limit, NA=1.2, cover a total solid angle, $\Omega = 4\pi(1-\sqrt{1-(NA/n_{med})^2}) = 2.28\pi$ steradians, that is insufficient to encompass all beams of most maximally symmetric composite lattices, particularly those of the cubic crystal group that produce the greatest intensity confinement at each lattice point. As shown in FIG. 64A, one solution to this problem is to excite only those beams whose central wavevectors, $k_n$, lie within the acceptance cones defined by the objectives, omitting the remaining beams of the maximally symmetric lattice that fall outside these cones. The resultant subset lattice will exhibit reduced transverse confinement, $[(k_m - k_n) \cdot \hat{e}_{x,y}]_{max}$, of the excitation maxima compared to its maximally symmetric counterpart as shown in FIG. 64B, increased background (particularly for a basis that optimizes the $\hat{e}_z$ component of the field at these maxima), as shown in FIGS. 64C and 64D, and greater weighting of the highest longitudinal spatial frequencies, $(k_m - k_n) \cdot \hat{e}_z$. This increased weighting yields, to varying degrees based on the exact lattice type, the multi-lobed excitation profile characteristic of a $4\pi$ microscope, and introduces uncertainty as to the lobe from which a given signal photon originates.

These effects can be ameliorated by first orienting the original lattice, shown in FIG. 65A, with respect to the optical axis, $\hat{e}_z$, so as to maximize the number of beams within the acceptance cones, as demonstrated in FIG. 65B. In the particular case of a maximally symmetric body-centered cubic (BCC) lattice having a period $\lambda$, all six constituent beams of the lattice can be symmetrically placed within the cones via a rotation that maps the [1 1 1] axis onto the optical axis, $\hat{e}_z$. In nearly all other cases however, at least one pair of opposed beams remains within the occlusion region between the objectives for any possible rotation. Nevertheless, because fewer beams are omitted, the rotated subset lattice exhibits confinement that is superior to the subset lattice obtained at the original orientation, as shown in FIG. 65C.

Finally, the parameters of the lattice can be modified to increase the number of wavevectors, $k_n$, within the acceptance cones, as shown in FIG. 66A. In particular, manipulation of the aspect ratio $\xi c/\alpha$, allows the tailoring of maximally symmetric tetragonal lattices (in which the c-axis is parallel to $\hat{e}_z$) at the largest transverse spatial frequency, $2k \cdot NA/n$, that is consistent with internal excitation, as shown in FIG. 66B.

Hybrid Excitation

All these methods of tailoring the lattice lead to reduced intensity confinement and excitation resolution in the xy-plane compared to that of typical maximally symmetric cubic lattices. Furthermore, it is often desirable to choose the lattice orientation on the basis of detection considerations (e.g., as shown in FIGS. 13 and 14) rather than to maximize the number of beams within the acceptance cones (e.g., as shown in FIG. 65). Thus, to combine the high excitation resolution of external excitation with the high detection resolution and collection efficiency of internal excitation, those beams of a given maximally symmetric lattice that fall within the acceptance cone(s) of one or two high NA objectives can be transmitted internally, and those beams that fall outside these cones yet are not occluded by the objective nosepiece(s) can be simultaneously transmitted externally with individual low $n\alpha$ lenses. This approach is hereinafter referred to as hybrid excitation.

FIG. 67 shows an example of hybrid excitation of a maximally symmetric body-centered cubic bound lattice of intensity period $\sqrt{5}\lambda$. To excite 16 of the 24 total beams of this lattice, two opposed NA=1.2 water-immersion objectives are used, as shown in FIG. 67A. The eight beams input at each rear pupil of the two objectives (as shown in FIG. 67B) are elliptically compressed by a factor, $(k_n \cdot \hat{e}_z)/k$, along $\hat{e}_\rho$, as shown in FIG. 62, to achieve a spherical excitation zone. Even so, those beams propagating at $\theta = \cos^{-1}(|k_n \cdot \hat{e}_z/k) = \cos^{-1}(1/\sqrt{5}) = 63.43°$ must be limited to $n\alpha \leq 0.02$ along their major axes to fit within the half-angle of each acceptance cone, $\theta_{max} = \sin^{-1}(NA/n_{med}) = 64.46°$, and thus avoid truncation by the edge of the rear pupil. The polarization of each beam is set according to Equation (63) with the fields, $e_n$, given by Equation (28) to obtain a lattice of predominantly x-polarized intensity maxima.

Despite the short working distances of the objectives, a small secondary acceptance region exists between them, as shown in FIG. 67C. The angular extent of the secondary acceptance region depends upon the working distance of the objectives as well as on the nosepiece geometries. The remaining eight beams of the lattice are transmitted through the secondary acceptance region, with individual $n\alpha = 0.02$ lenses and yields convergent beams similar to those emerging from the objectives. The polarizations of these beams are set to match the fields, $e_n$, of the corresponding plane waves, as determined to achieve the desired basis of predominantly x-polarized intensity maxima. All lenses share a common focal point, and the phase of every beam is adjusted to achieve maximal constructive interference at the focal point.

The resulting hybrid-excited bound lattice, with the internal beams calculated from Equation (66) and the external beams calculated from Equations (58) with the appropriate elliptical input profiles, is shown in FIG. 67D. An expanded view near the center of the excitation zone illustrating near-optimal confinement of the individual maxima and close correspondence to the ideal lattice is given in FIG. 67E. Lastly, an xy slice through the center of the excitation zone is plotted in FIG. 67F, and indicates that the excitation zone has a full-width at half-maximum of $2\rho \approx 29\lambda$, which is in rough agreement with the estimate of $26\lambda$ obtained by Equation (59).

In general, the inclusion of beams that are input through the secondary acceptance region improves the transverse resolution of the optical lattice compared to a lattice created from exclusively internal excitation and additionally reduces the relative signal contributions from axial side lobes. However, even with hybrid excitation, a few beams of many maximally symmetric lattices can fall within the occlusion regions between the primary and secondary acceptance regions. If not in conflict with the desired detection strategy, the lattice can be rotated (e.g., as shown in FIG. 65) or stretched (e.g., as shown in FIG. 66) to minimize the number of such beams.

Experimental Optimization for Hybrid Excitation within Living Cells

When imaging cells that are cultured onto a substrate such as a cover glass, it is not always advisable to include all beams that are possible within the secondary acceptance zone. Highly oblique beams can experience substantial reflections originating within the half space of the sample medium or excessive phase aberration within the substrate. The problem of reflections can be addressed with suitable anti-reflection coatings (e.g., as shown in FIG. 50). The effects of phase aberrations can be addressed with custom-tailored multi-element lenses that individually compensate for the phase aberration in each external beam, phase correction with a spatial light modulator, or by decreasing the $n\alpha$ of each external beam until the effective optical path length is sufficiently uniform for all rays within the beam that intersect the desired excitation zone. For certain lattices, hybrid excitation of cultured cells may not be practical. For example, if all external convergent beams would lie half within the substrate and half within the medium, the beams would be too distorted to create a useful lattice. In such situations, either a different lattice with wavevectors more suitable for hybrid excitation must be selected, or the sample must be immobilized in a different manner that does not distort the constituent beams. A sample can be immobilized, for example, with a patch-clamp pipette positioned so as to not intersect any of the convergent beams, by a mesh of weakly diffracting sub-wavelength fibers, or by a single or multiple point optical trap, such as the lattice traps shown in FIGS. 36 and 37.

Tailoring the Excitation Zone

The bound lattice examples considered thus far exhibit predominantly spherical excitation zone envelopes with widths of about the same order as the sharpness of the zone boundary. However, an ideal excitation zone envelope would exactly cover the region of interest within the sample while exhibiting the characteristics of a three-dimensional step function, i.e., it would have uniform intensity at each lattice point within the envelope and zero intensity elsewhere. The average detected flux (and resultant signal-to-noise ratio) per fluorophore from each equivalent lattice point within the zone would then be constant, the available excitation power would be optimized, and photobleaching outside the zone would be minimized. To more closely approximate this ideal behavior, the position and shape of each convergent beam (the intersection of all of which defines the excitation zone) should be tailored individually for each unique application.

Equation (59) and the results of FIGS. 61 and 62 illustrate how beam shaping can be used to attain a desired zone envelope. First, for every convergent beam associated with a wavevector, $k_n$, of the ideal lattice, the cross-section defined by the intersection of the plane perpendicular to $k_n$ with the center of the desired zone is determined as shown in FIG. 68A. The dimensions of the corresponding input beam at the rear pupil in the $(\hat{e}_\phi)_n$ and $(\hat{e}_\rho)_n$ directions of Equation (63b) are then calculated by applying Equation (59) to the cross-sectional widths in the $(\hat{e}_\phi)_n$ and $(\hat{e}_\theta)_n$ directions, respectively. The input width along $(\hat{e}_\rho)_n$ must also be reduced by a factor of $\hat{e}_k \cdot \hat{e}_z$ to compensate for the elliptical stretching effect conceptually shown in FIG. 60 and demonstrated in FIG. 61.

Figure 68D:
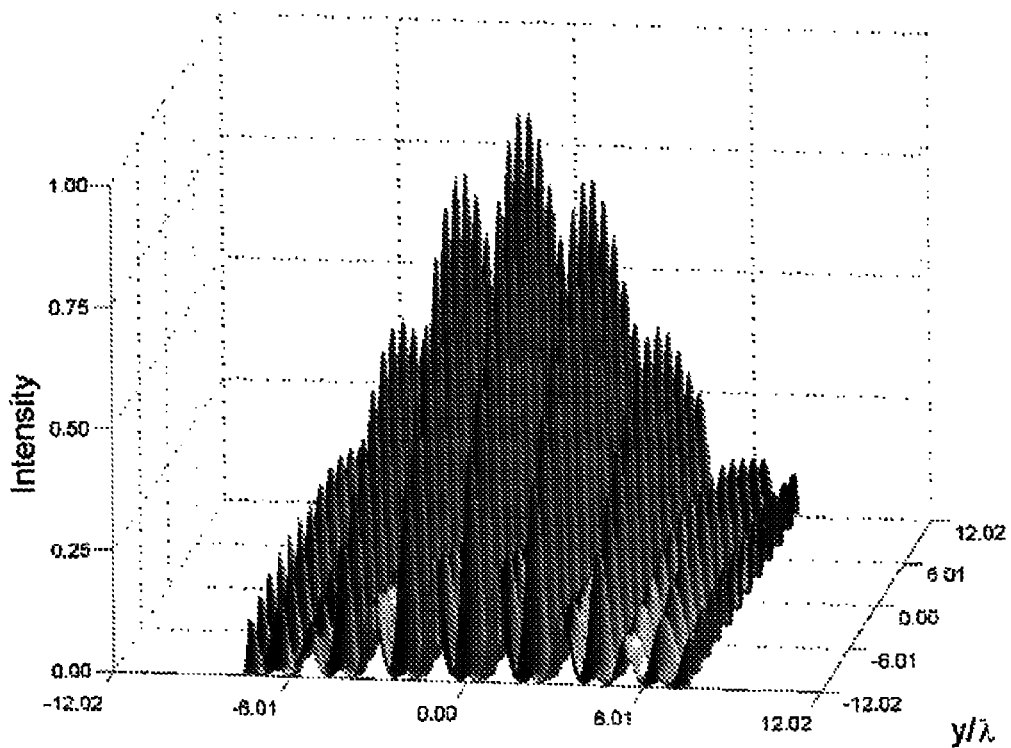

Application of this method to an ellipsoidal excitation zone of a desired aspect ratio 2:6:1 in the x,y,z directions, respectively, is shown in FIG. 68B. The actual aspect ratio is only ~1.5:2.5:1 due to the $[\sin(u_j z_j)/(u_j z_j)]^2$ axial dependence of the intensity near the focus of each convergent beam, which serves to restrict the excitation zone for beams of sufficiently high $n\alpha$. Nevertheless, the xy and yz slice plots in FIGS. 68C and 68D indicate that good confinement of the individual lattice maxima and low background elsewhere is maintained within the excitation zone envelope.

A simple example demonstrating beam positioning to tailor the zone of an externally excited, maximally symmetric cubic bound lattice is shown in FIG. 69. When all beams are of the same $n\alpha$ and share a common focal point, the transverse extent of every beam dictates both the size and sharpness of the zone. However, as shown in FIG. 69A, if each beam is axially displaced from the presumptive center of the zone by an appropriate amount, (e.g., by an amount, $\Delta z=245\lambda$, for $n\alpha=0.08$ for the lattices of FIGS. 56 and 69) while the phase relationship at the lattice maxima is maintained, the distributed foci of the individual beams create a total superimposed field that exhibits the desired lattice properties within a more uniform envelope of increased size ($\approx 22\lambda$ vs. $\approx 10\lambda$) but with relatively unchanged sharpness ($\approx 4.6\lambda$ vs. $3.9\lambda$), as shown in FIG. 69C. On the other hand, contrast relative to the background signal outside this envelope is reduced, since the maxima of the individual beams are not all located at the central lattice point of optimal constructive interference. As explained above, altering the $n\alpha$ will change the size of the envelope, although the axial displacement also must be simultaneously altered on the order of $(n\alpha)^2$ to maintain optimal uniformity within the excitation zone.

The displacement of the foci described above could be achieved by translating each lens or, alternatively, by illuminating each lens with an offset spherical wave, whose field is given by:

$$e_n^i(x'',t) = e_n \exp[i(k|x''-x_s''|-\omega t)](s_o/|x''-x_s''|), x''=0 \text{ at center rear pupil of lens}, \quad (68)$$

rather than the normally incident plane wave assumed in the derivation of Equations (57) and (58) from Equation (56). In the paraxial limit (i.e., for $\alpha/f \ll 1$), this still leads to a convergent beam field $e_n(x,t)$ near the focal point identical in form to the field described by Equation (58a), except with Equation (58b) replaced by:

$$u_f(z) = (\alpha/f)^2 \cdot k((z-f)^2/s-f) \quad (69a)$$

$$v_f(x,y) = (\alpha/f)k\sqrt{(x+fx_s''/s)^2+(y+fy_s''/s)^2} \quad (69b)$$

where $s=|x_s''|$. Thus, the intensity maximum of the beam is axially displaced by a distance, $\Delta z$, from the focal point of the lens for a spherical wave having a curvature, $s=f^2/\Delta z$, and is transversely displaced by a distance $\Delta x$, $\Delta y$ if this wave is centered at:

$$x_s'' = -f[(\Delta x)\hat{e}_x + (\Delta y)\hat{e}_y + \sqrt{f^2-(\Delta x)^2-(\Delta y)^2}\hat{e}_z]/\Delta z. \quad (70)$$

Such a wave could be generated with a second lens, if desired.

Further refinement of the shape and location of the excitation zone envelope is possible by replacing the convergent beam associated with each wavevector of the ideal lattice, $k_n$, with a series of convergent beams propagating in substantially the same direction, but mutually offset in three dimensions. Again, to achieve optimal excitation and detection resolution, hybrid illumination with opposed high NA objectives should be used. The beam sets associated with each wavevector, $k_n$, in the secondary acceptance region between the two objectives can be mutually offset with spherical wave illumination as per Equations (68)-(70). However, similar translation of the internally excited convergent beams via offset spherical wave illumination with confined elliptical input beams at the rear pupils of the objectives requires more intensive analysis. If the spherical wave source is centered at $x_s''$ and the resulting confined input beam is centered at $x_{bc}''$ (Equation (61)), then, from Equation (62) the field of the convergent beam is given by:

$$e_n(x,t) = \quad (71)$$
$$-\frac{ik}{2\pi} \int\int [e_W(x',t)]_n^{plane} \exp[i\Phi_n(x',x_s'')] \frac{\exp(ik|x-x'|)}{|x-x'|} d^2x',$$

where $[e_W(x',t)]_n^{plane}$ is the field on W from Equations (65) assuming normal illumination with a confined, flat-phase beam centered at a position, $x_{bc}''$, and $\Phi_n(x',x_s'')$ is the phase correction due to the offset spherical nature of the wavefronts incident on the rear pupil.

The phase terms, $\Phi_n(x',x_s'')$ and $k|x-x'|$, are most readily estimated by expressing the positions, x, x', and $x_s''$, in the coordinates of Equations (63b) defined by the nominal convergent beam direction, $k_n$, and the objective axis, $\hat{e}_z$. If the input beam is sufficiently small that its major axis half-length satisfies $b \ll \sqrt{s^3\lambda/F_o^2}$, and if the desired excitation zone is sufficiently close to the objective focal point to satisfy $|x| \ll \sqrt{2F_o\lambda}$, the phase terms can be written as:

$$\Phi_n(x',x_s'') = k\sqrt{\begin{array}{c}s^2+(x_\varphi')^2+(x_\rho'+\rho_{bc})^2-\\2x_\varphi''x_\varphi'-2(x_\rho''+\rho_{bc})(x_\rho'+\rho_{bc})\end{array}} \quad (72a)$$
$$\approx ks - \frac{kx_\varphi''}{s}\varepsilon_\varphi' - \frac{k(x_\rho''+\rho_{bc})}{s}\varepsilon_\rho' +$$
$$\frac{k}{2s}[(\varepsilon_\varphi')^2+(\varepsilon_\rho')^2] \text{ and:}$$

$$k|x-x'| \approx k|x'|-kx\cdot x'/|x'| \quad (72b)$$
$$= kF + kx_k - \frac{kx_\varphi}{F_o}\varepsilon_\varphi' + \frac{kx_\theta}{F_o\cos\Gamma}\varepsilon_\rho' -$$
$$\frac{k(x_\theta\tan\Gamma+x_k)}{2F_o^2}[(\varepsilon_\varphi')^2+(\varepsilon_\rho')^2]$$

where $x_\gamma' \equiv x' \cdot (\hat{e}_\gamma)_n$, $\in_\gamma' \equiv (x'-x_{bc}'') \cdot (\hat{e}_\gamma)_n$, $x_\gamma'' \equiv \cdot (\hat{e}_\gamma)_n$ ($\gamma=\varphi,\rho$), $x_\nu \equiv x \cdot (\hat{e}_\nu)_n$ ($\nu=\varphi,\theta$), $x_k \equiv x \sim k_n$, $\Gamma \equiv \cos^{-1}(k_n \cdot \hat{e}_z/k)$, and $x_{bc}'' = -\rho_{bc}(\hat{e}_\rho)_n$.

Combining Equations (71) and (72), we conclude that the focus of the convergent beam will be displaced by a distance, $\Delta x$, relative to the focal point of the objective if the spherical wave has a radius, $s=F_o^2\cos\Gamma/\Delta z$, at $x_{bc}''$ and is centered at:

$$x_s'' = x_{bc}'' - F_o[\Delta x_\phi \cos\Gamma(\hat{e}_\phi)_n \Delta x_\theta(\hat{e}_\rho)_n +$$
$$\sqrt{(F_o^2-\Delta x_\phi^2)\cos^2\Gamma-\Delta x_\theta^2}\hat{e}_z]/\Delta z, \quad (73)$$

where $\Delta x_\nu \equiv \Delta \cdot (\hat{e}_\nu)_n$ ($\nu=\phi,\theta$) and $\Delta z \equiv \Delta x \cdot \hat{e}_z = \Delta x_\theta \sin\Gamma + (\Delta x \cdot k_n)\cos\Gamma/k$. As the confined input beam approaches the center of the rear pupil ($x_{bc}'' \to 0$), Equation (73) reduces to the low $n\alpha$ result of Equation (70), as required. The effect of the wavefront curvature is to displace the focus of the convergent beam along the wavevector, $k_n$, as shown in FIG. 70A, and the effect of the source offsets, $x_\phi''$ and $x_\rho''$, is to displace the focus along directions $(\hat{e}_\phi)_n$ and $(\hat{e}_\theta)_n$, respectively as shown in FIGS. 70B and 70C.

By displacing all external and internal convergent beams to the same position, $\Delta x$, according to Equations (70) and (71), respectively, the entire excitation zone for one set of beams can be translated relative to the foci of the excitation lenses, as demonstrated for the hybrid-excited, maximally symmetric simple cubic bound lattice of an intensity period, $\sqrt{35}\lambda/2$, in FIG. 71*a*. For $|\Delta x| \ll \sqrt{2F_o\lambda}$, such translation occurs without significant distortion of the lattice maxima or increase in background contrast, as demonstrated by the excitation zone slices shown in FIGS. 71B and 71C.

The final tailored excitation zone is created by overlapping M individual excitation zones offset by different amounts, $\Delta x_m$. The lattice maxima within each sub-excitation zone should be offset from those within other such zones by an integer combination of the primitive vectors, $a_n$, so that the superimposed lattice exhibits maximal constructive interference at the overlapped maxima. An example is shown in FIG. 72A, where each sub-lattice has the properties and excitation zone characteristics shown in FIG. 71, and the final excitation zone consists of 11×11×5 sub-lattices overlapped in increments of one intensity period (i.e., $\sqrt{35}\lambda/2$) along the principal axes. The boundary sharpness of this final zone is equal to that of each individual sub-zone (FIG. 72B), and hence dictated by the nα of the individual convergent beams, according to Equation (59). The number of sub-zones and their mutual separations dictates the extent of the zone.

This method would appear to require that each of the N+1 beams of the original ideal lattice be replaced with M convergent beams (i.e., M (N+1) total beams) created with M corresponding input beams, each confined (for internal beams) to the same region, $\psi_n(x'',y'')$, centered at the position, $x_{bc}''$, within the rear pupil, but having different phase factors, $\Phi_n(x'',y'',\Delta x_m)$, resulting in different focal points, $\Delta x_m$, within the final excitation zone. For large, sharply bound zones, this approach becomes increasingly unwieldy. An equivalent but simpler implementation involves using a single input beam for each wavevector, $k_n$, of the ideal lattice, given by the superposition of the associated M input beams. The field of such a beam is given by:

$$e_n^i(x'', t) = e_n^i \psi_n(x'', y'') \left[ \sum_{m=1}^{M} \exp[i\Phi_n(x'', y'', \Delta x_m)] \right] \exp(-i\omega t) \qquad (74)$$

$$\equiv e_n^i \psi_n(x'', y'') \prod_n (x'', y'') \exp(-i\omega t).$$

In principle, the superposition factor, $Å_n(x'',y'')$, can be generated with a spatial light modulator (SLM), and the amplitude factor, $\psi_n(x'',y'')$, can be defined with either the same SLM or an aperture mask as described above. However, FIG. 73 shows that the excitation zone must not be so complex that the resulting amplitude and phase structure of the superposition factor of any input beam exceeds the resolution capabilities of the SLM.

Use of SLMs to define the input beams is also advantageous because it permits: (1) rapid, programmable switching to the internal input beams of different lattices; (2) phase scanning, as discussed below; (3) dynamic adaptive phase correction of refractive index fluctuations within the specimen, as discussed above; and (4) static correction of phase shear within internal or external beams passing through a substrate.

Scanning the Lattice or Sample

Many of the applications described above, such as microscopy and lithography, require translating the lattice relative to the sample. For example, scanning a three dimensional lattice with a basis of isolated, confined intensity maxima relative to the sample over the volume of a single primitive cell can be used to generate a complete three-dimensional image over the generally much larger volume from which signal is collected. In circumstances where even greater imaging speed is required, scanning the lattice in a two-dimensional planar fashion relative to the sample can generate a series of parallel two-dimensions images simultaneously. The scan plane can be in any desired direction as dictated by the features of interest within the sample, and not only in the plane transverse to the axis of objective lens(es) used to collect the signal. However, if the scan plane is parallel to one of the lattice plane families described by the Miller indices of the lattice, then a series of complete images from all such lattice planes within the detection volume can be generated by scanning over only the area of a single primitive cell of the two-dimensional "lattice" defined by those points of the larger three-dimensional lattice that lie within one of the lattice planes.

Lattice translation is also central to other methods of lattice microscopy that depend upon other basis formulations, as described above. In structured illumination microscopy, for example, lattice translation can be used to produce the necessary images at translations of $\neq x_{lmn}=2\pi l/(k_m-k_n)/(3|k_m-k_n|^2)$, for all values of m, n, and l=0, 1, 2. Similarly, in lattice-based stimulated emission depletion microscopy, it can be used to align the nodes of the depletion sub-lattices with the maxima of the excitation lattice.

One effective way of translating a lattice is through control of the phases of all constituent beams. From Equation (3), if a phase shift of $$\Delta \phi_n = -k_n \cdot \Delta x \text{ (modulo } 2\pi) \qquad (75)$$

is added to each plane wave (where $\Delta x$ is the same vector for all values of n), then the entire field becomes:

$$e_{\Delta x}(x, t) = \text{Re}\left\{ \sum_{n=0}^{N} e_n \exp[i(k_n \cdot (x - \Delta x) - i\omega t)] \right\}. \qquad (76)$$

In other words, the field is translated in space in the direction and distance dictated by $\Delta x$ regardless of the details of the lattice type or basis. Thus, the scanning required for the above examples can be performed by modulating the phase of each beam according to Equation (75). Such modulation can be performed by changing the length of the physical path traversed by each beam (e.g., with actuator mounted mirrors), the refractive index within the path traversed by each beam (e.g., via stress or temperature modulation in an optical waveguide), or with a phase sensitive device such as an optical phase modulator (for one beam), or with a spatial light modulator (for a multiplicity of independently controllable beams).

An optical phase modulator with a response time of faster than 1 GHz can be used to provide the phase modulation. Such a fast response time permits rapid scanning and imaging of the sample at speeds consistent with the speed implicit in the massively parallel excitation and detection modes of lattice microscopy. Furthermore, although mechanical scanning of the sample may be performed when the scanning frequency is sufficiently low, scanning the lattice rather than the sample prevents potentially perturbative accelerations from being imposed on the sample. However, if pinhole arrays are employed to spatially filter the collected signal, as shown in FIG. 12 and FIG. 13, it is can be desirable to ensure that the signal from each excitation maximum remains centered upon its assigned pinhole during scanning.

Referring to FIG. 74A, one method of ensuring that the signal 7401 remains centered upon the pinhole array is to scan the pinhole mask 7400 itself. When the pinhole mask 7400 is scanned, the required scan range in the image plane is multiplied by the system magnification and, if axial compensation is desired, by the magnification squared (in the paraxial approximation) along the optical axis 7401. In addition, in many implementations it can be desirable to measure the signal from each pinhole with its own fixed group of detector elements. Such measurement requires translation of the detector 7402 as well (which is a more difficult task due to the relatively high mass of the detector 7402).

Referring to FIG. 74B, a potentially faster method of ensuring that the signal 7401 remains centered is to add a beam deflection device 7403 between a collection objective 7404 and an associated tube lens 7405 in order to introduce a tilt to compensate for the two-dimensional shift 7406 in the projection of the lattice 7407 at the image plane. Exemplary beam deflection devices 7403 include an actuator-mounted mirror or a spatial light modulator programmed to impart a linearly varying phase on the beam prior to its passage through the tube lens 7405.

Referring to FIG. 74C, another method of ensuring that the signal 7401 remains centered in three dimensions is to translate the collection objective 7404 in all directions by the amount necessary to keep the center of the image of each excitation maximum 7407 fixed at the three-dimensional center position of its associated pinhole 7400. This method, although simple, is somewhat speed-limited by the relatively high mass of the objective. For only two-dimensional compensation of the lattice translation, somewhat greater speeds can be achieved by pivoting the objective rather than translating its entire mass.

A combination of phase scanning of the lattice and mechanical scanning of the sample 7408 can also be employed when the scanning frequencies in one or more directions are sufficiently low to justify the latter. The arrangement illustrated in FIG. 74D is particularly useful for this purpose, because only a slight tilt of the low-mass mirror 7403 is needed to achieve transverse compensation, and scanning the sample along the optical axis (at the lowest speed consistent with the desired frame rate) keeps each lattice maximum at a fixed axial position within the detection PSF defined by its associated pinhole.

Example Experimental Methods of Signal Detection in Lattice Microscopy

The methods of optical lattice design and experimental lattice excitation described above are sufficient for applications such as lattice-based lithography and optical trapping. Optical lattice microscopy, however, additionally requires detection of the signal generated by this excitation process, and analysis of the signal in a manner that results in meaningful images.

As discussed above, living cells are dynamically evolving three-dimensional systems, and therefore can be most fruitfully studied with an instrument capable of generating a series of time-resolved three-dimensional spatial images. The signal must therefore be divided into a measurement space of at least four dimensions, requiring both efficient excitation and collection over a large volume in order to generate statistically significant data. Efficiency becomes an even greater issue as the demands on temporal and/or spatial resolution increase in the quest for more detailed understanding of intracellular processes.

In optical lattice excitation with the common basis of one highly confined intensity maximum per primitive cell, factors contributing to the excitation efficiency include: the multitude of excitation maxima (potentially infinite with a finite number of input beams); the potential confinement at each maximum to nearly the limits of diffraction in all directions; the low background and consequent photobleaching outside each maximum; and control over the electromagnetic field properties at each maximum. To take full advantage of this efficiency, the associated lattice detection system should: isolate and then maximize the total amount of signal collected from each maximum; provide the highest possible three-dimensional detection resolution at each maximum (both to increase the overall system resolution and to minimize blur from residual background excitation and adjacent maxima); and be capable of extracting, when desired, the maximum amount of information from each collected photon.

Volumetric Fluorescence Imaging with a Lens

To address these issues, we consider the common scenario in which the signal results from fluorescence emission within a specimen which is collected by an objective lens. With optical lattice excitation, such emission can occur simultaneously at many points throughout a large volume, including (unlike confocal microscopy) points well outside the focal plane of the objective. Thus, we must analyze the general case of spatially resolved detection of the emission from fluorophores anywhere in the vicinity of the objective focal point.

This analysis is initially similar to the objective excitation case considered in conjunction with FIG. 60. Thus, a molecular flourophore at position, x, with respect to the focal point of an objective of focal length, $F_o$, and having a dipole emission axis, $\hat{e}_p$, creates, on the spherical surface, W, of radius, $F_o$, centered at the focal point, an emission electromagnetic field, $e_W$ and $h_W$, of:

$$e_W(x, x'', \hat{e}_p) = e_o r_o \frac{[\hat{e}_p \times (F_o \hat{e}_r^o(x'') + x)] \times (F_o \hat{e}_r^o(x'') + x)}{|F_o \hat{e}_r^o(x'') + x|^3} \exp(ik_o|F_o \hat{e}_r^o(x'') + x|) \quad (77a)$$

$$h_W(x, x'', \hat{e}_p) = -h_o r_o \frac{[\hat{e}_p \times (F_o \hat{e}_r^o(x'') + x)]}{|F_o \hat{e}_r^o(x'') + x|^2} \exp(ik_o|F_o \hat{e}_r^o(x'') + x|) \quad (77b)$$

where $\hat{e}_r^o(x'')$ is given in Equation (64) (the "o" superscript implying the use of the objective focal length $F_o$ in the equation), x" is a point in the rear pupil plane of the objective, $e_o r_o$ and $h_o r_o$ are measures of the molecular dipole moment, and $k_o = 2\pi/\lambda_o = 2\pi n_o/\lambda_{em}$ is the magnitude of the wavevector in the medium (refractive index $n_o$) of the objective for a free space emission wavelength of $\lambda_{em}$.

As before, we restrict our attention to points x satisfying $|x| << \sqrt{2F_o\lambda_o}$ so that we can use the approximation $k_o|F_o\hat{e}_r^o(x'')+x| \approx k_oF_o + k_o\hat{e}_r^o \cdot x$ within the phase terms of Equations (77), and $F_o\hat{e}_r^o(x'')+x \approx F_o\hat{e}_r^o(x'')$ elsewhere. Expressed in the $\{\hat{e}_r^o, \hat{e}_\theta^o, \hat{e}_\phi\}$ orthonormal coordinate system of Equation (65b), Equations (77) then become:

$$e_W(x,x'',\hat{e}_p) \approx -e_o(r_o/F_o)\{[\hat{e}_\phi(x'')\cdot\hat{e}_p]\hat{e}_\phi(x'')+[\hat{e}_\theta^o(x'')\cdot\hat{e}_p]\hat{e}_\theta^o(x'')\}\exp[ik_o(F_o+\hat{e}_r^o(x'')\cdot x)] \quad (78a)$$

$$h_W(x,x'',\hat{e}_p) \approx -h_o(r_o/F_o)\{[\hat{e}_\theta(x'')\cdot\hat{e}_p]\hat{e}_\phi(x'')+[\hat{e}_\phi(x'')\cdot\hat{e}_p]\hat{e}_\theta^o(x'')\}\exp[ik_o(F_o+\hat{e}_r^o(x'')\cdot x)] \quad (78b)$$

On passing through the objective and out the rear pupil, the $\hat{e}_\theta^o(x'')$ components of these fields are rotated by refraction into the $\hat{e}_p$ radial direction of Equation (65b), reversing the process shown in FIG. 60. Also in a reversal of the focusing process considered earlier, the emission energy in an element dW located at $-F_o\hat{e}_r^o$ on the spherical surface W is mapped onto the smaller area $dx''dy''=dW|\hat{e}_r^o(x'')\cdot\hat{e}_z|$ in the rear pupil. Hence, by energy conservation, the rear pupil fields increase in amplitude by a factor of $1/\sqrt{|\hat{e}_r^o(x'')\cdot\hat{e}_z|}$:

$$e_{rp}^o(x, x'', \hat{e}_p) \approx -e_o \frac{r_o}{F_o} \left\{ \begin{array}{l} [\hat{e}_\varphi(x'') \cdot \hat{e}_p]\hat{e}_\varphi(x'') + \\ [\hat{e}_\theta^o(x'') \cdot \hat{e}_p]\hat{e}_\rho(x'') \end{array} \right\} \quad (79a)$$

$$\frac{\exp[ik_o(F_o + \hat{e}_r^o(x'') \cdot x)]}{\sqrt{|\hat{e}_r^o(x'') \cdot \hat{e}_z|}}$$

$$h_{rp}^o(x, x'', \hat{e}_p) \approx -h_o \frac{r_o}{F_o} \left\{ \begin{array}{l} [\hat{e}_\theta^o(x'') \cdot \hat{e}_p]\hat{e}_\varphi(x'') - \\ [\hat{e}_\varphi(x'') \cdot \hat{e}_p]\hat{e}_\rho(x'') \end{array} \right\} \quad (79b)$$

$$\frac{\exp[ik_o(F_o + \hat{e}_r^o(x'') \cdot x)]}{\sqrt{|\hat{e}_r^o(x'') \cdot \hat{e}_z|}}$$

In the afocal space between the collection objective and the imaging tube lens, we consider two different scenarios. First, all the emission may be sent to the tube lens:

$$[e_{rp}^t(x,x'',\hat{e}_p)]_{nopol} = e_{rp}^o(x,x'',\hat{e}_p), \ [h_{rp}^t(x,x'',\hat{e}_p)]_{nopol} = h_{rp}^o(x,x'',\hat{e}_p) \quad (80a)$$

Alternatively, the emission may be divided into orthogonal polarization states before being sent to one or more tube lenses. This situation permits fluorescence anisotropy measurements to be made, including possibly measurements of the dipole orientation of single fluorophores. It can also be helpful in isolating and efficiently measuring the signal from different lattice planes as discussed below. Considering one such polarization state (e.g., with the electric field parallel to $\hat{e}_x$), at the tube lens we have:

$$[e_{rp}^t(x,x'',\hat{e}_p)]_{pol} = [\hat{e}_x \cdot e_{rp}^o(x,x'',\hat{e}_p)]\hat{e}_x, \ [h_{rp}^t(x,x'',\hat{e}_p)]_{pol} = -[\hat{e}_y \cdot h_{rp}^o(x,x'',\hat{e}_p)]\hat{e}_y \quad (80b)$$

To find the image field of the fluorophore in the vicinity of the focal point of the tube lens, we again proceed in a manner similar to the focusing analysis of FIG. 60, except with the lens positioned at $z_t > 0$ with respect to its focal point. Thus, the ray $-\hat{e}_r^o(x'')$ within the diverging wavefront emanating from the fluorophore in the space of the objective lens is transformed into a ray $\hat{e}_r^t(x'')$ within the converging wavefront in the space of the tube lens of:

$$\hat{e}_r^t(x'') = [-(\hat{e}_x \cdot x'')\hat{e}_x - (\hat{e}_y \cdot x'')\hat{e}_y - F_t \alpha_t(x'')\hat{e}_z]/F_t, \ \text{where:} \quad (81a)$$

$$\alpha_t(x'') = \sqrt{1 - [(\hat{e}_x \cdot x'')^2 + (\hat{e}_y \cdot x'')^2]/F_t^2} \quad (81b)$$

and $F_t$ is the focal length of the tube lens. Again, the tangential (i.e., $\hat{e}_\varphi$) components of the rear pupil fields in Equations (80) remain unperturbed except for an amplitude reduction of $\sqrt{|\hat{e}_r^t(x'') \cdot \hat{e}_z|} = \sqrt{\alpha_t(x'')}$ upon passage through the tube lens and projection onto a spherical wavefront W of radius $F_t$, whereas the radial (i.e., $\hat{e}_\rho$) components are additionally rotated to a direction $\hat{e}_\theta^t(x'')$:

$$e_W^t(x, x'', \hat{e}_p) \approx -e_o \frac{r_o}{F_o} \sqrt{\alpha_t(x'')} \quad (82a)$$

$$\left\{ \begin{array}{l} [\hat{e}_\varphi(x'') \cdot e_{rp}^t(x, x'', \hat{e}_p)]\hat{e}_\varphi(x'') + \\ [\hat{e}_\rho(x'') \cdot e_{rp}^t(x, x'', \hat{e}_p)]\hat{e}_\theta^t(x'') \end{array} \right\}$$

$$h_W^t(x, x'', \hat{e}_p) \approx -h_o \frac{r_o}{F_o} \sqrt{\alpha_t(x'')} \quad (82b)$$

$$\left\{ \begin{array}{l} [\hat{e}_\varphi(x'') \cdot h_{rp}^t(x, x'', \hat{e}_p)]\hat{e}_\varphi(x'') + \\ [\hat{e}_\rho(x'') \cdot h_{rp}^t(x, x'', \hat{e}_p)]\hat{e}_\theta^t(x'') \end{array} \right\}$$

where: $\hat{e}_\theta^t(x'') = \hat{e}_\varphi(x'') \times \hat{e}_r^t(x'')$ (83)

The final image fields $e(x,x_t,\hat{e}_p)$ and $h(x,x_t,\hat{e}_p)$ at a point $x_t$ relative to the focal point of the tube lens are then determined by applying the Kirchhoff diffraction formula of Equation (62) to integrate the fields, $e_w^t(x,x'',\hat{e}_p)$ and $h_w^t(x,x'',\hat{e}_p)$, on the surface, W, over all points, x'', in the rear pupil. Combining Equations (62), (64), and (79)-(82) we find at points satisfying $|x_t| \ll \sqrt{2F_t \lambda_t}$:

$$[e(x, x_t, \hat{e}_p)]_{nopol} \approx e_o \frac{ik_t r_o}{2\pi F_o F_t} \exp[i(k_o F_o + k_t F_t)] \quad (84a)$$

$$\int\int \{[\hat{e}_\varphi(x'') \cdot \hat{e}_p]\hat{e}_\varphi(x'') + [\hat{e}_\theta^o(x'') \cdot \hat{e}_p]\hat{e}_\theta^t(x'')\} \times$$

$$\exp\left\{i\left[-\left(\frac{k_o x}{F_o} + \frac{k_t x_t}{F_t}\right)x'' - \left(\frac{k_o y}{F_o} + \frac{k_t y_t}{F_t}\right)y'' - k_o z \alpha_o(x'') + k_t z_t \alpha_t(x'')\right]\right\} \sqrt{\frac{\alpha_t(x'')}{\alpha_o(x'')}} \, dx''dy''$$

$$[h(x, x_t, \hat{e}_p)]_{nopol} \approx h_o \frac{ik_t r_o}{2\pi F_o F_t} \exp[i(k_o F_o + k_t F_t)] \quad (84b)$$

$$\int\int \{[\hat{e}_\theta^o(x'') \cdot \hat{e}_p]\hat{e}_\varphi(x'') - [\hat{e}_\varphi(x'') \cdot \hat{e}_p]\hat{e}_\theta^t(x'')\} \times$$

$$\exp\left\{i\left[-\left(\frac{k_o x}{F_o} + \frac{k_t x_t}{F_t}\right)x'' - \left(\frac{k_o y}{F_o} + \frac{k_t y_t}{F_t}\right)y'' - k_o z \alpha_o(x'') + k_t z_t \alpha_t(x'')\right]\right\} \sqrt{\frac{\alpha_t(x'')}{\alpha_o(x'')}} \, dx''dy''$$

$$[e(x, x_t, \hat{e}_p)]_{pol} \approx e_o \frac{ik_t r_o}{2\pi F_o F_t} \exp[i(k_o F_o + k_t F_t)] \quad (84c)$$

$$\int\int \{[\hat{e}_\varphi(x'') \cdot \hat{e}_p][\hat{e}_\varphi(x'') \cdot \hat{e}_x] + [\hat{e}_\theta^0(x'') \cdot \hat{e}_p][\hat{e}_\rho(x'') \cdot \hat{e}_x]\}$$

$$\{[\hat{e}_\varphi(x'') \cdot \hat{e}_x]\hat{e}_\varphi(x'') + [\hat{e}_\rho(x'') \cdot \hat{e}_x]\hat{e}_\theta^t(x'')\}\sqrt{\frac{\alpha_t(x'')}{\alpha_o(x'')}} \times$$

$$\exp\left\{i\left[-\left(\frac{k_o x}{F_o} + \frac{k_t x_t}{F_t}\right)x'' - \left(\frac{k_o y}{F_o} + \frac{k_t y_t}{F_t}\right)y'' - k_o z \alpha_o(x'') + k_t z_t \alpha_t(x'')\right]\right\} dx''dy''$$

$$[h(x, x_t, \hat{e}_p)]_{pol} \approx h_o \frac{ik_t r_o}{2\pi F_o F_t} \exp[i(k_o F_o + k_t F_t)] \quad (84d)$$

$$\int\int \{-[\hat{e}_\theta^o(x'') \cdot \hat{e}_p][\hat{e}_\varphi(x'') \cdot \hat{e}_y] + [\hat{e}_\varphi(x'') \cdot \hat{e}_p][\hat{e}_\rho(x'') \cdot \hat{e}_y]\}$$

$$\{[\hat{e}_\varphi(x'') \cdot \hat{e}_y]\hat{e}_\varphi(x'') + [\hat{e}_\rho(x'') \cdot \hat{e}_y]\hat{e}_\theta^t(x'')\}\sqrt{\frac{\alpha_t(x'')}{\alpha_o(x'')}} \times$$

$$\exp\left\{i\left[-\left(\frac{k_o x}{F_o} + \frac{k_t x_t}{F_t}\right)x'' - \left(\frac{k_o y}{F_o} + \frac{k_t y_t}{F_t}\right)y'' - k_o z \alpha_o(x'') + k_t z_t \alpha_t(x'')\right]\right\} dx''dy''$$

where $k_t = 2\pi/\lambda_t = 2\pi n_t/\lambda_{em}$, $n_t$ being the refractive index of the medium in the space of the tube lens, $x = x \cdot \hat{e}_x$, $x_t = x_t \cdot \hat{e}_x$, etc., and:

$$\alpha_o(x'') = \sqrt{1 - [(x'')^2 + (y'')^2]/F_o^2} \quad (85)$$

by analogy to Equation (81b).

From Equations (84) we note several key points. First, the image of the fluorophores is inverted in the x and y directions in the space of the tube lens and magnified by a factor of:

$$M = \frac{k_o F_t}{k_t F_o} = \frac{n_o F_t}{n_t F_o} \quad (86)$$

Second, the image is translationally invariant in the x and y directions, meaning that fluorophores at different positions, x, in the same xy plane in the objective space and having identical orientations, $\hat{e}_p$, produce identical images at points, $x_t=-Mx$, in an $x_t y_t$ plane within the image space. Thus, Equations (84) need be evaluated at only one point (e.g., $x_t=(0,0,z_t^{detect})$) to find the detection point spread response (PSF) anywhere in a given plane $z_t=z_t^{detect}$ of a detector. However, the image is generally not translationally invariant in the z direction, except in the special case $F_o=F_t$, or when both lenses are of such low NA that $\alpha_o(x'') \approx 1-[(x'')^2+(y'')^2]/(2F_o^2)$ and $\alpha_t(x'') \approx 1-[(x'')^2+(y'')^2]/(2F_t^2)$. Furthermore, the image will depend upon the orientations of the dipoles over the entire course of the measurement. Therefore, Equations (84) must be evaluated at all z positions of interest covered by the excitation lattice, and under all likely dipole orientation conditions, to determine how the detection process in optical lattice microscopy can be optimized.

To aid in this evaluation, we introduce the substitutions:

$$x_t=-Mx+\rho_t \sin\theta_t \cos\phi_t, \; y_t=-My+\rho_t \sin\theta_t \sin\phi_t, \; z_t=\rho_t \cos\theta_t \quad (87)$$

$$x''=F_o \sin\theta'' \cos\phi'', \; y''=F_o \sin\theta'' \sin\phi'' \quad (88)$$

so that, by Equations (64), (65b), (81), and (83), the unit vectors in Equations (84) become:

$$\hat{e}_\varphi(x'') = -\sin\varphi'' \hat{e}_x + \cos\varphi'' \hat{e}_y \quad (89a)$$

$$\hat{e}_\theta^o(x'') = -\cos\theta'' \cos\varphi'' \hat{e}_x - \cos\theta'' \sin\varphi'' \hat{e}_y - \sin\theta'' \hat{e}_z \quad (89b)$$

$$\hat{e}_\varphi(x'') = -\cos\varphi'' \hat{e}_x - \sin\varphi'' \hat{e}_y \quad (89c)$$

$$\hat{e}_\theta^t(x'') = -\alpha_t(\theta'') \cos\varphi'' \hat{e}_x - \alpha_t(\theta'') \sin\varphi'' \hat{e}_y + \frac{F_0}{F_t} \sin\theta'' \hat{e}_z, \quad (89d)$$

$$\alpha_t(\theta'') = \sqrt{1-\left(\frac{F_o}{F_t}\sin\theta''\right)^2}$$

With these expressions and various trigonometric identities, Equation (84a), for example, can be expressed as:

$$[e(x,x_t,\hat{e}_p)]_{nopol} \approx e_o \frac{ik_t r_o}{4\pi} \frac{F_o}{F_t} \exp[i(k_o F_o + k_t F_t)] \quad (90)$$

$$\int_0^{\theta''_{max}} \exp\{i[-k_o z \cos\theta'' + k_t z_t \alpha_t(\theta'')]\} \times \sqrt{\frac{\alpha_t(\theta'')}{\cos\theta''}}$$

$$\int_0^{2\pi} \exp\left[-i\frac{k_o \rho_t}{M}\sin\theta_t \sin\theta'' \cos(\varphi_t + \varphi'')\right]$$

$$\{[p_x(1+\alpha_t(\theta'')\cos\theta'') - p_x(1-\alpha_t(\theta'')\cos\theta'')\cos 2\varphi'' -$$

$$p_y(1-\alpha_t(\theta'')\cos\theta'')\sin 2\varphi'' + 2p_z\alpha_t(\theta'')\sin\theta'' \cos\varphi'']$$

$$\hat{e}_x + [-p_x(1-\alpha_t(\theta'')\cos\theta'')\sin 2\varphi'' + p_y(1+$$

$$\alpha_t(\theta'')\cos\theta'') + p_y(1-\alpha_t(\theta'')\cos\theta'')\cos 2\varphi'' +$$

$$2p_z\alpha_t(\theta'')\sin\theta'' \sin\varphi'']\hat{e}_y + [-p_x \sin 2\theta'' \cos\varphi'' -$$

$$p_y \sin 2\theta'' \sin\varphi'' - 2p_z \sin^2\theta''](F_o/F_t)\hat{e}_z\}d\varphi'' \sin\theta'' d\theta''$$

where $\theta_{max}''=\sin^{-1}(NA/n_o)$ is the half-angle subtended by the objective, and $p_x=\hat{e}_p \cdot \hat{e}_x$, etc. Similar expressions can be obtained for Equations (84b), (84c), and (84d).

Equation (90) can be reduced to an integral in one dimension by using the integral representation of the Bessel function:

$$\int_0^{2\pi} \exp(im\phi)\exp[-i\eta \cos(\phi-\gamma)]d\phi = 2\pi(-i)^m J_m(\eta)\exp(im\gamma) \quad (91)$$

For further simplicity, we also restrict our attention to the most common case of a high magnification system, where $F_o/F_t \ll 1$. In this case, the $\hat{e}_z$ component of $[e(x,x_t,\hat{e}_p)]_{nopol}$ can be neglected, and, by Equation (89d), we can approximate $\alpha_t(\theta'') \approx 1$ everywhere except within the phase terms of Equation (90). We then find:

$$[e(x, x_t, \hat{e}_p)]_{nopol} \approx e_o \frac{ik_t r_o}{2} \frac{F_o}{F_t} \exp[i(k_o F_o + k_t F_t)] \quad (92a)$$

$$\{[p_x(I_0(\rho_t, z, z_t) + I_2(\rho_t, z, z_t)\cos 2\varphi_t) + p_y I_2(\rho_t, z, z_t)\sin 2\varphi_t -$$

$$2ip_z I_1(\rho_t, z, z_t)\cos\varphi_t]\hat{e}_x + [p_x I_2(\rho_t, z, z_t)\sin 2\varphi_t +$$

$$p_y(I_0(\rho_t, z, z_t) - I_2(\rho_t, z, z_t)\cos 2\varphi_t) -$$

$$2ip_z I_1(\rho_t, z, z_t)\sin\varphi_t]\hat{e}_y\}$$

and proceeding in a similar manner with Equation (84b):

$$[h(x, x_t, \hat{e}_p)]_{nopol} \approx h_o \frac{ik_t r_o}{2} \frac{F_o}{F_t} \exp[i(k_o F_o + k_t F_t)] \quad (92b)$$

$$\{[p_x I_2(\rho_t, z, z_t)\sin 2\varphi_t + p_y(I_0(\rho_t, z, z_t) - I_2(\rho_t, z, z_t)\cos 2\varphi_t) -$$

$$2ip_z I_1(\rho_t, z, z_t)\sin\varphi_t]$$

$$\hat{e}_x + [-p_x(I_0(\rho_t, z, z_t) + I_2(\rho_t, z, z_t)\cos 2\varphi_t) -$$

$$p_y I_2(\rho_t, z, z_t)\sin 2\varphi_t + 2ip_z I_1(\rho_t, z, z_t)\cos\varphi_t\}]\hat{e}_y$$

where:

$$I_0(\rho_t, z, z_t) = \int_0^{\theta''_{max}} (1+\cos\theta'')J_0\left(\frac{k_o\sqrt{\rho_t^2-z_t^2}}{M}\sin\theta''\right) \quad (93a)$$

$$\exp\{i[-k_o z\cos\theta'' + k_t z_t \alpha_t(\theta'')]\}\frac{\sin\theta''}{\sqrt{\cos\theta''}}d\theta''$$

$$I_1(\rho_t, z, z_t) = \int_0^{\theta''_{max}} J_1\left(\frac{k_o\sqrt{\rho_t^2-z_t^2}}{M}\sin\theta''\right) \quad (93b)$$

$$\exp\{i[-k_o z\cos\theta'' + k_t z_t \alpha_t(\theta'')]\}\frac{\sin^2\theta''}{\sqrt{\cos\theta''}}d\theta''$$

$$I_2(\rho_t, z, z_t) = \int_0^{\theta''_{max}} (1-\cos\theta'')J_2\left(\frac{k_o\sqrt{\rho_t^2-z_t^2}}{M}\sin\theta''\right) \quad (93c)$$

$$\exp\{i[-k_o z\cos\theta'' + k_t z_t \alpha_t(\theta'')]\}\frac{\sin\theta''}{\sqrt{\cos\theta''}}d\theta''$$

As expected, in this high magnification, $F_o/F_t \ll 1$ limit, the polarized fields $[e(x,x_t,\hat{e}_p)]_{pol}$ and $[h(x,x_t,\hat{e}_p)]_{pol}$ reduce to the x- and y-components, respectively, of their unpolarized counterparts:

$$[e(x,x_t,\hat{e}_p)]_{pol} = \{[e(x,x_t,\hat{e}_p)]_{nopol} \cdot \hat{e}_x\}\hat{e}_x, \; [h(x,x_t,\hat{e}_p)]_{pol} = \{[h(x,x_t,\hat{e}_p)]_{nopol} \cdot \hat{e}_y\}\hat{e}_y \quad (94)$$

Although these image fields can be directly projected onto a detector (e.g., a CCD camera) to generate a signal, another common situation will involve isolating the signal from the intensity maxima within one or several transversely offset lattice planes perpendicular to $\hat{e}_z$ as shown in FIG. 13 by first projecting the image fields onto a spatial filter (also perpendicular to $\hat{e}_z$) containing transmissive apertures in an opaque mask located at points in the magnified image space corresponding to the locations of the maxima in the object space, and then re-imaging this filtered signal onto the detector. In either situation, the signal per unit time, $\Psi(x,x_t^c,\hat{e}_p,\sigma_t)$, due to a fluorophore at position, x, and orientation, $\hat{e}_p$, measured by a given detector element or through a given aperture centered at $x_t^c$, is given by the electromagnetic field energy that flows across the area $\sigma_t$ of the element or aperture per unit time:

$$\Psi(x,x_t^c,\hat{e}_p,\sigma_t) = -\iint_{\sigma_t @ x_t} \langle S(x,x_t,\hat{e}_p)\rangle_t \cdot \hat{e}_z dx_t dy_t \quad (96a)$$

where $\langle S(x,x_t,\hat{e}_p)\rangle_t$ is the time averaged Poynting vector of the image field at $x_t$ due to the fluorophore:

$$\langle S(x, x_t, \hat{e}_p)\rangle_t = \frac{c}{8\pi}\text{Re}\{e(x, x_t, \hat{e}_p) \times h^*(x, x_t, \hat{e}_p)\} \quad (96b)$$

Also, due to the translational invariance in the xy plane implicit in Equations (84):

$$\Psi(x,x_t^c,\hat{e}_p,\sigma_t) = \Psi(x+x_t^c/M, y+y_t^c/M, z, z_t^c, \hat{e}_p, \sigma_t) = \Psi(x_{rel}, y_{rel}, z, z_t^c, \hat{e}_p, \sigma_t) \quad (96c)$$

Hence, the signal rate, $\Psi(x,x_t^c,\hat{e}_p,\sigma_t)$, needs only to be evaluated as a function of the relative transverse position $x_{rel}=x+x_t^c/M$, $y_{rel}=y+y_t^c/M$ between the fluorophore and the detector or aperture.

The signal rate, $\Psi_o(x,x_t^c,\hat{e}_p)$, normalized to the maximum signal rate at any position, x, is known as the detection point spread function ("PSF"):

$$\text{PSF}_{det}(x,x_t^c,\hat{e}_p,\sigma_t) = \Psi(x,x_t^c,\hat{e}_p,\sigma_t)/\max[|\Psi(x,x_t^c,\hat{e}_p,\sigma_t)|]_x \quad (97a)$$

As the area, $\sigma_t$, increases, the detector element or aperture intercepts more energy from the desired fluorophores near $x_{rel}=y_{rel}=0$ and hence the signal increases. However, the element or aperture also intercepts more energy from fluorophores outside this region, and hence the detection resolution decreases. Before exploring this trade-off, we first consider the high resolution, low-signal limit where the detection element or aperture size, d, is small compared to the magnified emission wavelength within the sample medium, i.e., $d<<\lambda_o/M=\lambda_{em}/(n_o M)$. In this case, Equation (96a) reduces to an integral over a delta function, $\delta(x_t^c)$, centered at $x_t^c$, and, with Equation (97a), yields:

$$\text{PSF}_{det}\begin{pmatrix} x_{rel}, y_{rel} \\ z, z_t^c, \hat{e}_p, \delta \end{pmatrix} = \frac{-\langle S(x_{rel}, y_{rel}, z, z_t^c, \hat{e}_p)\rangle_t \cdot \hat{e}_z}{\max[|\langle S(x_{rel}, y_{rel}, z, z_t^c, \hat{e}_p)\rangle_t \cdot \hat{e}_z|]_x} \quad (97b)$$

Combining Equations (92), (94), (96b) and (97b), we find:

$$[\text{PSF}_{det}(\rho_{rel}, z, z_t^c, \theta_p, \varphi_p - \varphi_{rel}, \delta)]_{nopol} = \quad (98a)$$
$$C\{\sin^2\theta_p[|I_0(\rho_{rel}, z, z_t^c)|^2 + |I_2(\rho_{rel}, z, z_t^c)|^2 +$$
$$2\text{Re}\{I_0(\rho_{rel}, z, z_t^c)I_2^*(\rho_{rel}, z, z_t^c)\}\cos 2(\varphi_p - \varphi_{rel})] +$$
$$4\cos^2\theta_p|I_1(\rho_{rel}, z, z_t^c)|^2 -$$
$$2\text{Re}\{i[I_0(\rho_{rel}, z, z_t^c) + I_2(\rho_{rel}, z, z_t^c)]^* I_1(\rho_{rel}, z, z_t^c)\}$$
$$\sin 2\theta_p \cos(\varphi_p - \varphi_{rel})\}$$

$$[\text{PSF}_{det}(\rho_{rel}, z, z_t^c, \theta_p, \varphi_p, \varphi_{rel}, \delta)]_{pol} = \quad (98b)$$
$$C\{\sin^2\theta_p[|I_0(\rho_{rel}, z, z_t^c)|^2(1 + \cos 2\varphi_p) +$$
$$|I_2(\rho_{rel}, z, z_t^c)|^2(1 + \cos 2(\varphi_p - 2\varphi_{rel})) +$$
$$2\text{Re}\{I_0(\rho_{rel}, z, z_t^c)I_2^*(\rho_{rel}, z, z_t^c)\} \times$$
$$(\cos 2\varphi_{rel} + \cos 2(\varphi_p - \varphi_{rel}))] +$$
$$8|I_1(\rho_{rel}, z, z_t^c)|^2 \cos^2\theta_p \cos^2\varphi_{rel} + 4\sin 2\theta_p \cos$$
$$\varphi_{rel}[\text{Re}\{iI_0(\rho_{rel}, z, z_t^c)I_1^*(\rho_{rel}, z, z_t^c)\}\cos\varphi_p +$$
$$\text{Re}\{iI_1^*(\rho_{rel}, z, z_t^c)I_2(\rho_{rel}, z, z_t^c)\}\cos(\varphi_p - 2\varphi_{rel})]\}$$

where C is a unique normalization constant in each case and:

$$\rho_{rel} = \sqrt{x_{rel}^2 + y_{rel}^2}, \theta_{rel} = \tan^{-1}(y_{rel}/x_{rel}), \theta_p = \cos^{-1}(p_z),$$
$$\phi_p = \tan^{-1}(p_y/p_x) \quad (98c)$$

Equations (98a) and (98b) give the detection point spread function for a fluorophore with a fixed dipole axis, $\hat{e}_p$. The angle, $\theta_p$, is the angle between the dipole axis and the optical axis, $\hat{e}_z$, and $\phi_p$ is the angle between the projection of the dipole axis onto the xy plane and the $\hat{e}_x$ axis within this plane. Equation (98b) assumes this $\hat{e}_x$ axis is defined by the direction of the electric field selected by the polarizing optics in the afocal region between the objective and tube lenses.

It is also common in biological imaging that the fluorophore freely tumble over the course of the measurement, or that many fluorophores can exist with different orientations within the volume defined by the detection resolution of the system. In such cases, the effective detection PSF is given by averaging Equations (98) over all possible orientations:

$$\langle\text{PSF}_{det}(\rho_{rel}, \varphi_{rel}, z, z_t^c, \sigma_t)\rangle_{\Omega_p} = \quad (99)$$
$$\frac{1}{4\pi}\int_{-\pi}^{\pi}\left[\int_0^{2\pi}\text{PSF}_{det}(\rho_{rel}, z, z_t^c, \theta_p, \varphi_p, \varphi_{rel}, \sigma_t)d\varphi_p\right]\sin\theta_p d\theta_p$$

$$[\langle\text{PSF}_{det}(\rho_{rel}, z, z_t^c, \delta)\rangle_{\Omega_p}]_{nopol} = \quad (100a)$$
$$C'[|I_0(\rho_{rel}, z, z_t^c)|^2 + 2|I_1(\rho_{rel}, z, z_t^c)|^2 + |I_2(\rho_{rel}, z, z_t^c)|^2]$$

$$[\langle\text{PSF}_{det}(\rho_{rel}, \varphi_{rel}, z, z_t^c, \delta)\rangle_{\Omega_p}]_{pol} = \quad (100b)$$
$$C'[|I_0(\rho_{rel}, z, z_t^c)|^2 + 2\text{Re}\{I_0(\rho_{rel}, z, z_t^c)I_2^*(\rho_{rel}, z, z_t^c)\}\cos 2\varphi_{rel} +$$
$$|I_2(\rho_{rel}, z, z_t^c)|^2 + 4|I_1(\rho_{rel}, z, z_t^c)|^2 \cos^2\varphi_{rel}]$$

where C' is a new normalization constant in each case.

Detection from a Single Lattice Plane

FIG. 75A is a three-dimensional plot of the detection PSF of Equation (100a) (i.e., no polarizer, orientation averaged, $F_o/F_t<<1$) for a fluorophore in the vicinity of a central plot point $x=-x_t^c/M$, $y=-y_t^c/M$ (i.e., $x_{rel}=y_{rel}=0$) in the focal plane (z=0) of a NA=1.2 water immersion ($n_o=1.33$) signal collection objective, as detected at a point, $x_t, y_t$, in the focal plane ($z_t^c=0$) of the tube lens ($n_t=1.0$). The PSF is plotted as a series of surfaces of 50%, 20%, and 10% detection efficiency, as normalized to the maximum detection efficiency within the plot volume. The decline in the detection efficiency with increasing distance from the point, $x_{rel}=y_{rel}=z=0$, is a measure of the contribution of the detection system to the overall system resolution. In particular, the decline in detection efficiency with increasing distance from the objective focal plane as seen in the xz plot in FIG. 75C demonstrates that a two-dimensional array of small detectors (e.g., pixels within a CCD camera) or small apertures located at the focal plane of the tube lens and having the same symmetry and magnified periodicity as the intensity maxima of a single lattice plane coinciding with the objective focal plane can be used to isolate the signal from only that lattice plane, provided that the spacing between adjacent lattice planes along the optical axis $\hat{e}_z$ is sufficiently large compared to the extent of the detection PSF along $\hat{e}_z$. This is similar to the experimental scenario shown in FIG. 12, except with a three-dimension lattice instead of a two-dimensional one.

If the lattice plane of interest is still orthogonal to $\hat{e}_z$ but is located at a distance, $z_{lp} \neq 0$, from the objective focal plane, it is still possible to isolate the signal from just that plane, provided that the detector or aperture mask is placed at an appropriate corresponding position, $z_t^c \cdot 0$, in the space of the tube lens. When NA<<1 for both the objective and tube lenses, the image fields in Equations (84) and hence the detection PSFs in Equations (98) and (100) become translationally invariant along $\hat{e}_z$, and hence:

$$z_t^c/\lambda_t \approx (F_t/F_o)^2 z_{lp}/\lambda_o \text{ (for NA}_o, \text{NA}_t << 1) \quad (101a)$$

In the more common case where the NA of the objective is chosen to be as high as possible in order to maximize the collection efficiency, the appropriate position, $z_t^c$, can be determined experimentally by translating the detector array or mask along $\hat{e}_z$ until the signal from the desired lattice plane is maximized. For the specific case of NA$_o$=1.2, M=60, n$_o$=1.33, and n$_t$=1.0 used in FIG. 75, an approximate empirical formula valid for $z_{lp}<10\lambda_o$ is:

$$z_t^c/\lambda_t \approx (n_o/n_t)(F_t/F_o)^2 z_{lp}/\lambda_o. \quad (101b)$$

FIGS. 76A-76D show the three-dimensional detection PSF under these conditions when the detector array or aperture mask is located according to Equation (101b), with $z_{lp}=\lambda_o$, $2\lambda_o$, $5\lambda_o$, and $10\lambda_o$, respectively. Although, from the xz slice plots in FIGS. 76I-76L, the actual planes of maximum detection efficiency occur at z=1.0$\lambda_o$, 1.9$\lambda_o$, 4.8$\lambda_o$, and 9.4$\lambda_o$, these results indeed demonstrate that the signal from a single lattice plane can be isolated even when it is not located at the focal plane of the objective.

Compensating for Aberrations Outside the Objective Focal Plane

One issue apparent from FIG. 76 is that the detection PSF degrades, particularly along $\hat{e}_z$, as the detector/mask plane in the image space and the corresponding plane of maximum detection efficiency in the object space move increasingly far from their respective focal planes. This has several negative consequences. First, the three-dimensional overall resolution is degraded due to the lessened contribution from the detection system. Second, more haze is introduced in the eventual images due to increased collection of background emission from the space between lattice planes and the transverse regions near the lattice excitation maxima. Finally, for a given lattice and lattice orientation, the detection PSF will eventually become so elongated that emission from intensity maxima in other lattice planes will contribute to the collected signal, creating overlapped ghost images containing information from other planes in the sample.

The degradation of the detection PSF with increasing z occurs because the path lengths traveled in the objective space by the rays emanating from a given fluorophore increasingly differ as the fluorophore moves farther from the objective focal plane. For example, for a fluorophore on the optical axis, $\hat{e}_z$, the path length difference between the axial ray and any other ray at a relative angle, θ, is given by:

$$\delta OPL_o(\theta) = k_o z(1-\cos\theta) \quad (102a)$$

This expression is clearly evident as a phase term in Equations (92) and (93) for the image fields. As shown in FIGS. 77A-77D, the result is increasing radial phase oscillations in any transverse plane (i.e., increasingly curved wavefronts) in the afocal space between the objective and tube lenses. The tube lens contributes an additional path length difference:

$$\delta OPL_t(\theta) = -k_t z_t(1-\alpha_t(\theta)) \quad (102b)$$

also seen in Equations (93). Therefore, the total path length difference is zero for all rays, and an ideal image of the fluorophore is created, only if z=0 (i.e., the fluorophore is at the objective focal plane) or the NA (and hence the focal length) of both lenses is the same. In this latter case, the ideal image is formed at $z_t/\lambda_t = z_o/\lambda_o$. More generally, however, rays from each unique angle, θ, focus at a different plane, $z_t$, in the image space, creating an increasingly distorted detection PSF with increasing z as shown in FIG. 76.

Extending this argument further, it is possible to compensate completely for this effect as shown in FIG. 78A and therefore achieve the ideal detection PSF (7800) of FIG. 75 at all intensity maxima (7801) in a lattice plane (7802) within the sample (7803) at a distance, $z_{lp}$ (7804) from the objective focal plane (7805) by introducing a phase shift device (7806) (e.g., a static phase shift mask, a spatial light modulator, or a deformable mirror in the afocal space (7807)) to introduce a spatially varying phase shift across the beam (7808) passing between the objective (7809) and tube (7810) lenses that cancels the path length differences caused by these lenses. If the detector (7811) or, as in FIG. 78A, the aperture mask (7812), is located a distance, $z_t^c$ (7813), from the focal plane (7814) of the tube lens (7810), the desired phase correction is given by:

$$\Phi(\rho_A, z_{lp}, z_t^c) = k_o z_{lp} \cos[\theta(\rho_A)] - k_t z_t^c \alpha_t[\theta(\rho_A)] \quad (103)$$
$$= k_o z_{lp} \sqrt{1-(NA_o \rho_A/A)^2} -$$
$$k_t z_t^c \sqrt{1-(NA_t \rho_A/A)^2}$$

where $\rho_A$ is the radial position in the afocal space and A=NA$_o$F$_o$=NA$_t$F$_t$ is the common radius of the rear pupil of the two lenses. Introducing this correction in the form of the multiplicative term, exp[i$\Phi(\rho_A, z_{lp}, z_t^c)$], to Equations (93), we find that the phase term common to these expressions becomes:

$$\exp\{i[-k_o z \cos\theta'' + k_t z_t \alpha_t(\theta'')]\} \Rightarrow \exp\{i[-k_o(z-z_{lp})\cos\theta'' + k_t(z_t-z_t^c)\alpha_t(\theta'')]\} \quad (104)$$

and hence the effect of the correction in Equation (103) is indeed to shift the ideal lattice plane and mask plane positions to z=$z_{lp}$ and $z_t=z_t^c$ in the spaces of the objective and tube lenses, respectively. At high magnification (M=60 in FIGS. 75-78), the correction due to the mask position $z_t^c$ is small compared to that due to the lattice position, $z_{lp}$, as can be seen by comparing the phase patterns at $z_{lp}=\lambda_o$ in FIG. 77A and FIG. 78B, where $z_t^c=0$ and $z_t^c=600\lambda_t$, respectively.

Aperture Mask Optimization

The detection PSF of FIG. 75 assumes an infinitesimal detector element or spatial filtering aperture, and therefore represents a best-case limit to the detection resolution in the objective focal plane, and in any other desired plane when phase correction is used according to Equation (103). In a real situation, however, the area, $\sigma_t$, and shape of the detector element or aperture must be chosen to balance the sharpness of the detection PSF against the absolute strength of the detected signal. In the case of orientation averaged fluorophores and no polarization selection in the afocal region, the optimal PSF, $[\langle PSF_{det}(\rho_{rel},z,z_t^c,\delta)\rangle_{\Omega_p}]_{nopol}$, of Equation (100a) is independent of $\phi_{rel}$, as seen in FIG. 75, suggesting that a circular detector element or aperture be used.

The effect of the size of the detector element or aperture in this case is explored in FIG. 79, using calculations based on a combination of Equations (92), (93), (96), and (97), and the same parameters as in FIG. 75. A radius, $\alpha_t = \sqrt{\sigma_t/\pi} = 0.4\lambda_t$, as shown in FIG. 79C, permits over 50% of the total signal collected by the objective to be measured, with, however, a moderate decrease in the detection resolution versus the optimal PSF of FIG. 75. In fact, because the detection PSF, even in the at $\alpha_t \to 0$ limit of FIG. 75, is significantly larger than the intensity maxima within a maximally symmetric cubic lattice, the overall system resolution (given by the product of the detection PSF with the excitation function) is dominated by the latter, as shown in FIG. 80. Thus, in these cases, where the excitation resolution dominates, the area, $\sigma_t$, and hence the signal detection efficiency can be increased further as shown in FIGS. 79D and 79E until most of the collected emission is detected or until the passage of background emission or crosstalk with the emission from other intensity maxima reaches an undesirable level.

Figure 81A:
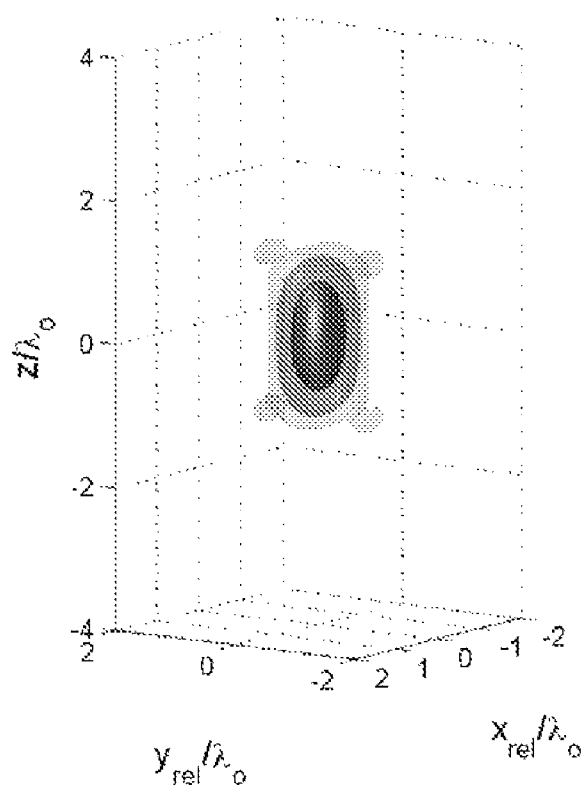
Figure 81B:
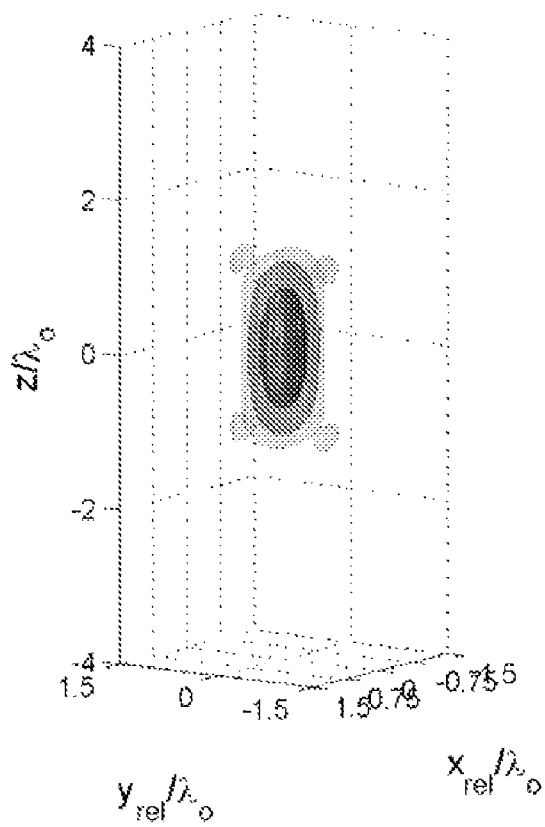
Figure 81C:
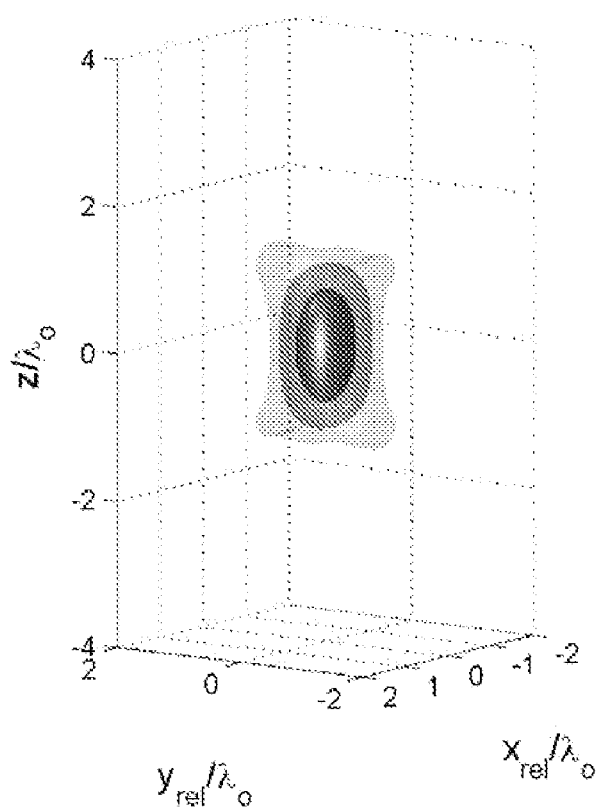
Figure 81D:
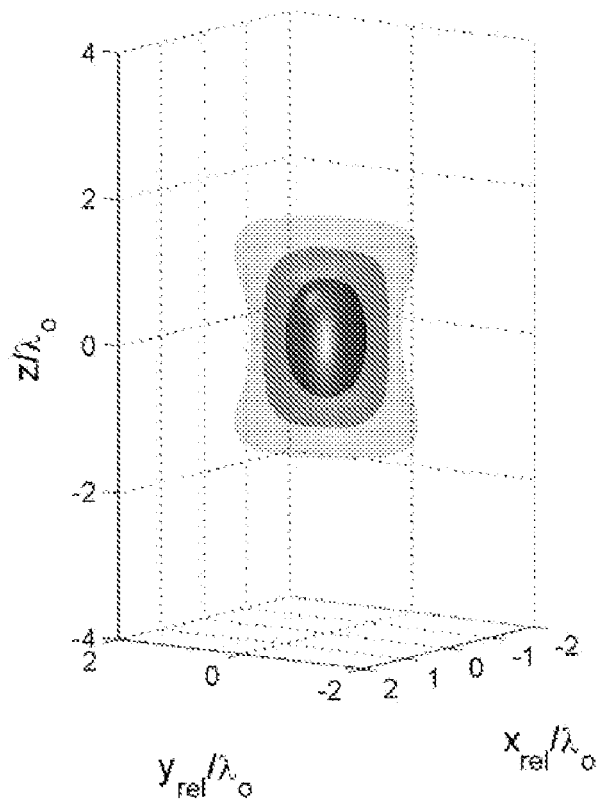
Figure 81E:
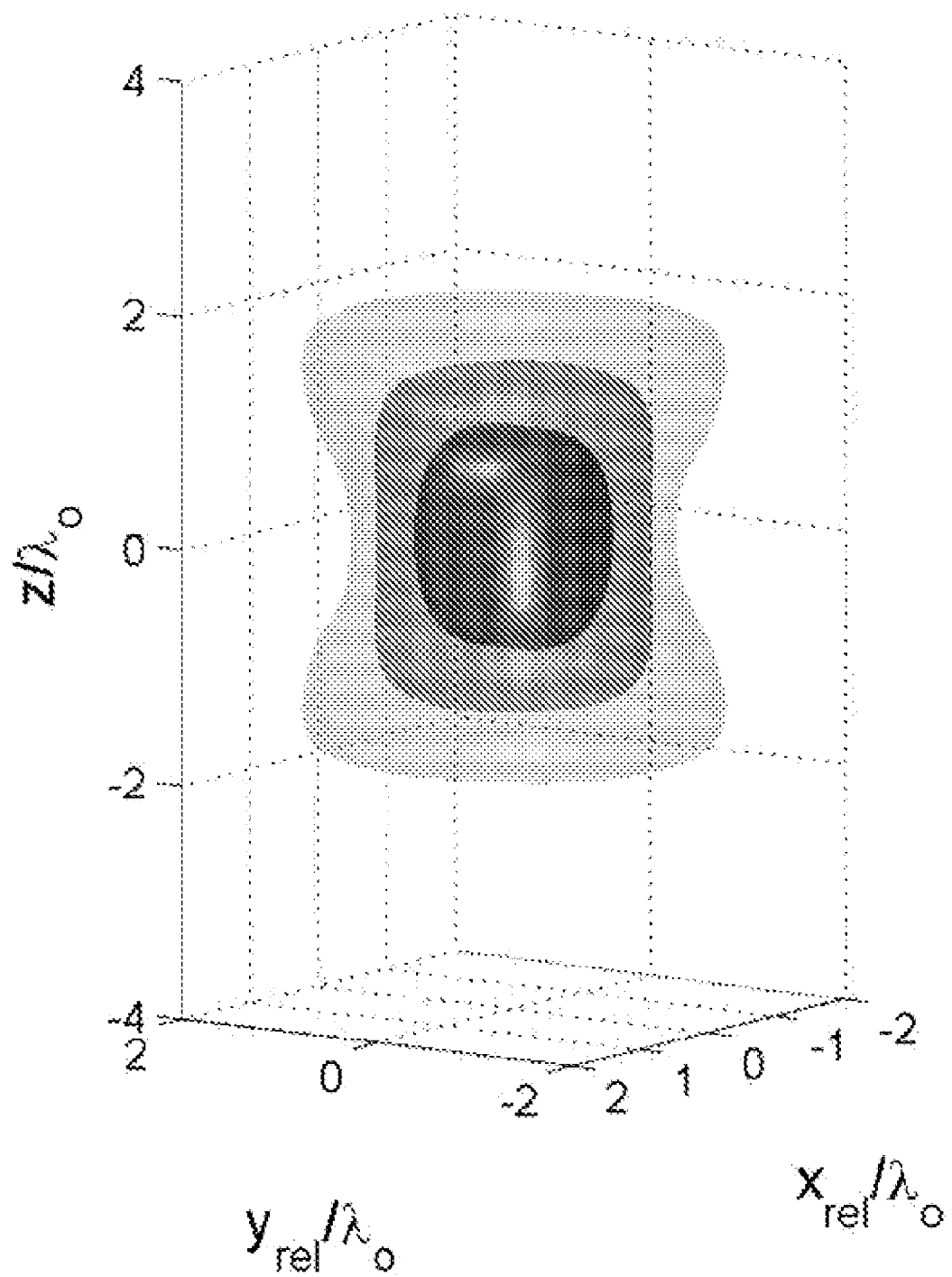

When the orientation-averaged emission is linearly polarized in the afocal region, Equation (100b) and the corresponding plot in FIG. 81A of the optimal detection PSF, $[\langle PSF_{det}(\rho_{rel},\phi_{rel},z,z_t^c,\delta)\rangle_{\Omega_p}]_{pol}$, suggests that an elliptical aperture with major axis parallel to the polarization axis and ellipticity (i.e., major axis/minor axis) of ~1.5 be used. FIGS. 81B-E demonstrate the resulting effect on the extent of the detection PSF and signal detection efficiency for semi-major axis lengths of $0.1M\lambda_t$, $0.2M\lambda_t$, $0.4M\lambda_t$, and $0.6M\lambda_t$, respectively. The overall conclusions concerning the choice of the area, $\sigma_t$, are similar to those in the unpolarized case.

In certain implementations considered below, it is useful for the signal to be circularly polarized in the afocal space. In this case, it can be shown that the optimal detection PSF for orientation-averaged fluorophores is given by the average of the PSFs for two orthogonal linear polarizations. Using Equations (100) we find:

$$[\langle PSF_{det}(\rho_{rel},\phi_{rel},z,z_t^c,\delta)\rangle_{\Omega_p}]_{cincpol} = \{[\langle PSF_{det}(\rho_{rel},\phi_{rel},z,z_t^c,\delta)\rangle_{\Omega_p}]_{pol} + [\langle PSF_{det}(\rho_{rel},\phi_{rel}+\pi/2,z,z_t^c,\delta)\rangle_{\Omega_p}]_{pol}\}/2 = [\langle PSF_{det}(\rho_{rel},z,z_t^c,\delta)\rangle_{\Omega_p}]_{nopol} \quad (105)$$

Thus, the above results for unpolarized detection are applicable to the circularly polarized case as well.

Opposed Objectives and 4π Detection from a Single Lattice Plane

As seen in FIG. 67A, optical lattice microscopy can be implemented with two opposed objective lenses. This not only simplifies the task of delivering the individual beams to the excitation zone, but also permits the resulting signal to be collected over a solid angle twice as large as with a single objective.

Opposed objectives can be used for signal collection in several ways. First, one objective can be used to collect the signal propagating in the $-\hat{e}_z$ direction from a single lattice plane and project it onto a detector or aperture array as shown in FIG. 78A, while the opposite objective can collect the signal propagating in the $+\hat{e}_z$ direction from the same lattice plane and project it onto a second detector or aperture array, in a mirror image of the system in FIG. 78A. The total signal collected from the lattice plane is thereby doubled. The two objectives need not necessarily share the same focal plane, since different phase corrections, $\Phi(\rho_A, z_{lp-}, z_{t-}^c)$ and $\Phi(\rho_A, -z_{lp+}, z_{t+}^c)$, can be applied according to Equation (103) if desired when the lattice plane is a distance, $z_{lp-}$, in the $+\hat{e}_z$ direction from the focal plane of the objective collecting the $-\hat{e}_z$ propagating signal, and a distance, $z_{lp+}$, in the $+\hat{e}_z$ direction from the focal plane of the objective collecting the $+\hat{e}_z$ propagating signal.

Alternatively, each objective can be used to collect the signal from a different lattice plane. The signal collected from each plane is then the same as if a single objective were used. Again, phase corrections of $\Phi(\rho_A, z_{lp1-}, z_{t-}^c)$ and $\Phi(\rho_A, -z_{lp2+}, z_{t+}^c)$ can be applied according to Equation (103) if desired to optimize the detection PSF when the first lattice plane is a distance, $z_{lp1-}$, in the $+\hat{e}_z$ direction from the focal plane of the objective collecting its $-\hat{e}_z$ propagating signal, and the second lattice is a distance, $z_{lp2+}$, in the $+\hat{e}_z$ direction from the focal plane of the objective collecting its $+\hat{e}_z$ propagating signal.

With opposed objectives, it is also possible to superimpose the fields collected by the two objectives from a single lattice plane and coherently detect the resulting signal at one or two detector(s) or aperture array(s). This arrangement is similar to that used to detect the emission from a single point in a conventional 4π microscope, as shown in FIG. 82A, but with several modifications, as shown in FIG. 82B. In either case, the signal from within the sample (8200) is collected with opposed objective lenses (8201) and (8202) and routed with a series of reflective elements, including at least one (8203) (e.g., a movable mirror) capable of adjusting the relative phase of the resulting rear pupil beams (8204) and (8205), so that when the beams are recombined with a beam splitter (8206) or (8207) and imaged with a tube lens (8208), they interfere constructively at an aperture mask (8209) prior to being passed onto a detector (8210). In more recent embodiments of the 4π microscope, and in coherent lattice detection as well, a half wave plate (8211) is inserted in the path of one of the rear pupil beams (8205) and oriented to introduce a 180° phase shift in one (8212) of the two orthogonal components (8212) and (8213) of the electric field of the beam (8205) so that both components can constructively interfere with the corresponding components (8214) and (8215) of the other rear pupil beam (8204) when the phase is appropriately adjusted with reflective element (8203). A polka-dot beam splitter (8207) can be used to insure that the proper phase relationship between parallel component pairs (8212), (8214) and (8213), (8215) is maintained after reflection, rather than the more uncertain relationship that exists when a standard cube beam splitter (8206) is used.

However, a key limitation of the 4π geometry shown in FIG. 82A is that the images produced at the focal plane (8216) of the tube lens (8208) are mirror images of one another, so that the signal from any point (8217) transversely offset from the common focal point (8218) of the objectives (8201) and (8202) is refocused without constructive interference at two points (8219) and (8220) on opposite sides of the axis of the tube lens (8208)—only for signal arising near the common focal point (8218) is constructive interference and the resulting desired 4π detection PSF (8221) achieved, and only for an aperture placed at the corresponding focal point (8222) of the tube lens (8208). To obtain constructive interference and the desired coherent PSF (8223) from multiple excitation maxima (8224) in a given lattice plane (8225), it is necessary to invert the virtual image produced by one of objectives (8201) and (8202) relative to that produced by the other about two orthogonal axes in the plane perpendicular to the axis of beam propagation, so that the recombined images produced by the tube lens (8208) have the same symmetry, and are no longer mirror images of one another. In the particular embodiment shown in FIG. 82B, this is accomplished by replacing mirror (8226) of FIG. 82A with a penta prism (8227) that redirects the beam (8204) through 90° without inverting the virtual image of objective (8201) about either orthogonal axis, and replacing mirror (8228) of FIG. 82A with a roof prism (8229) that redirects beam (8205) through 90° while inverting the virtual image of objective (8202) about both orthogonal axes. A mask (8209) with apertures at each image position corresponding to the excitation maxima (8224) can then be used to spatially filter the coherent signal from each prism prior to passage to a multi-element detector (8210).

Expressed in other terms, the detection PSF for coherent lattice detection in FIG. 82B is translationally invariant in any plane perpendicular to the axis $\hat{e}_z$ of the objectives (for $|x| \ll \sqrt{2F_o\lambda_o}$ and $|x_t| \ll \sqrt{2F_t\lambda_t}$), whereas the detection PSF of the conventional $4\pi$ arrangement in FIG. 82A is not. Thus, transverse alignment of the aperture mask (8209) is far more critical in the $4\pi$ case.

In addition, phase shifters (8230) and (8231), as discussed above, can be inserted in the paths of the rear pupil beams (8204) and (8205) as shown in FIG. 82B to introduce phase corrections, $\Phi(\rho_A, z_{lp-}, z_t^c)$ and $\Phi(\rho_A, -z_{lp+}, z_t^c)$, according to Equation (103) to compensate for aberrations when the desired lattice plane (8225) is a distance, $z_{lp1-}$ (8232), in the $+\hat{e}_z$ direction from the focal plane (8233) of the objective (8201) collecting the $-\hat{e}_z$ propagating signal, and a distance, $z_{lp+}$ (8234), in the $+\hat{e}_z$ direction from the focal plane (8235) of the objective (8202) collecting the $+\hat{e}_z$ propagating signal. These phase shift devices can also be designed to create an optimal detection PSF (8224) when the detector or aperture array is a distance, $z_t^c$ (8236), from the focal plane (8216) of the tube lens (8208). Preferably, they should be inserted in beam paths (8204) and (8205) immediately after objectives (8201) and (8202) so that the beams become more highly collimated, thereby minimizing spherical aberration introduced by the remaining optical elements in the beam paths.

Figure 83D:
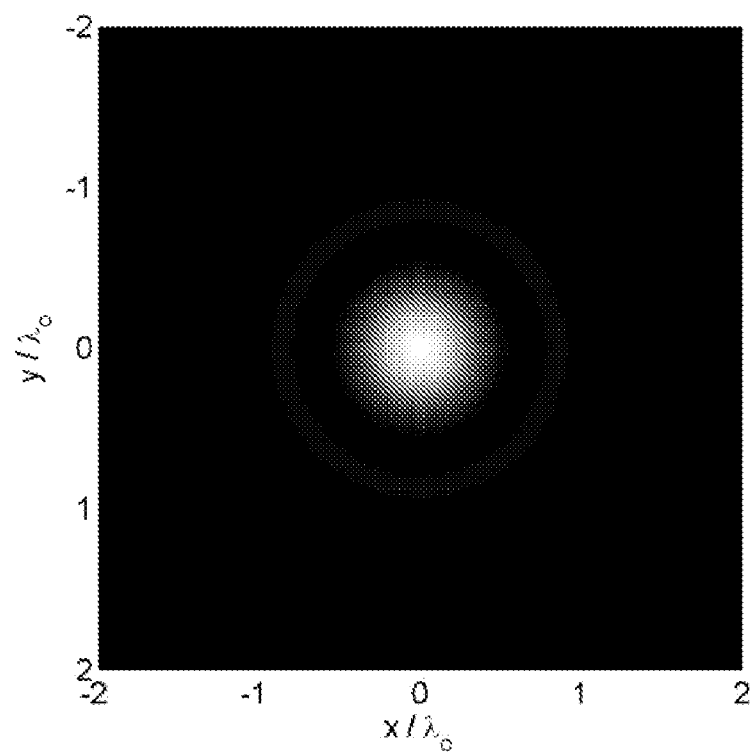
Figure 83E:
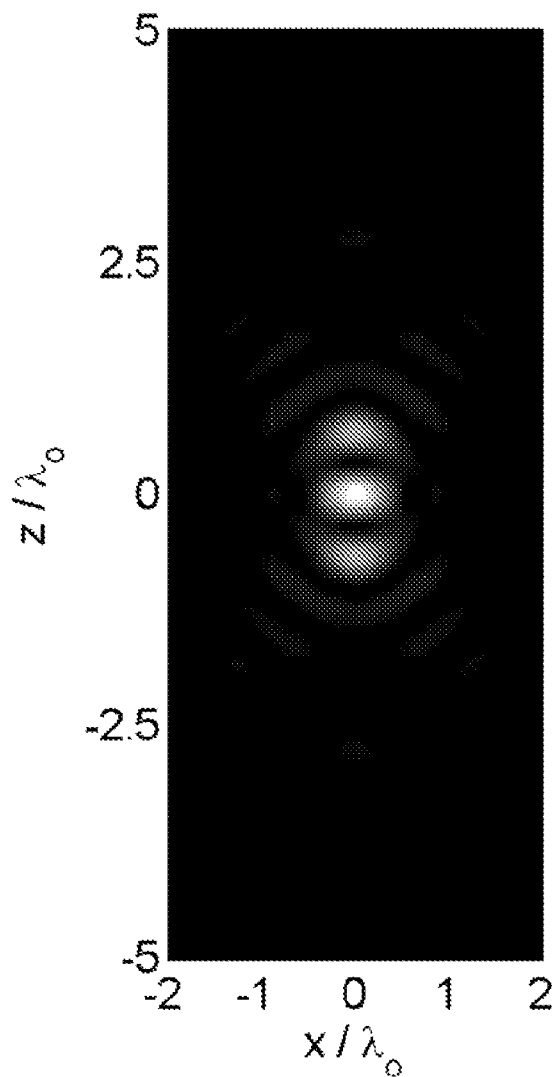
Figure 83F:
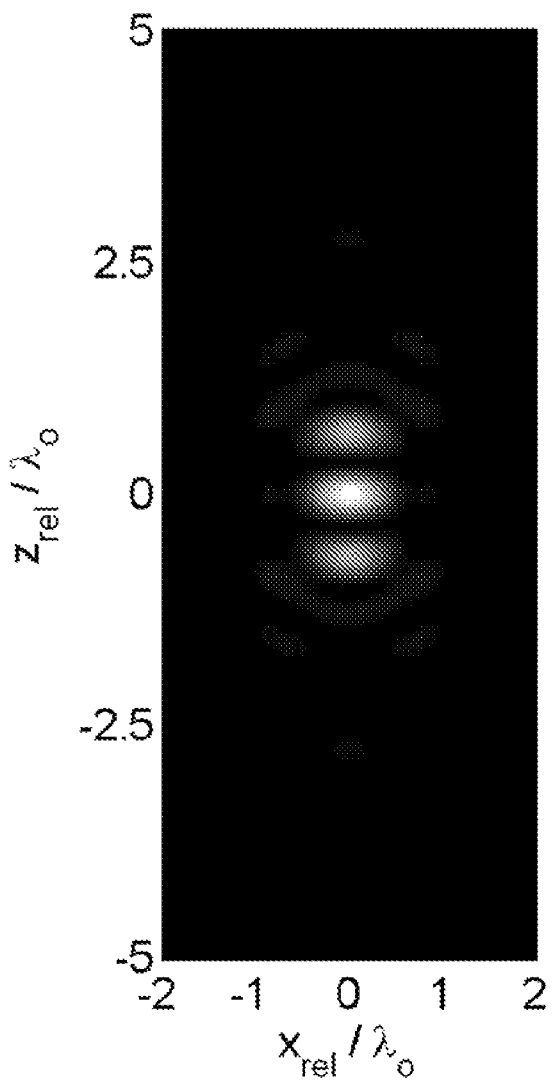

Proceeding in a manner similar to that used to derive Equations (100), we find that when the two rear pupil beams (8204) and (8205) are coherently combined with the relative phase of each of their orthogonal electric field components (8212), (8213) and (8214), (8215) adjusted to achieve maximal constructive interference, the orientation-averaged ideal (i.e., $\sigma_t \ll \lambda_t$) detection PSF with no rear pupil polarizer is:

$$\left[\langle PSF_{det}^{4\pi}(\rho, z, 0, \delta)\rangle_{\Omega_p}\right]_{nopol} = \quad (106a)$$
$$C''\{[\text{Re}\{I_0(\rho, z, 0)\}]^2 + 2[\text{Im}\{I_1(\rho, z, 0)\}]^2 + [\text{Re}\{I_2(\rho, z, 0)\}]^2\}$$

$$\left[\langle PSF_{det}^{CLD}(\rho_{rel}, z, z_t^c, \delta)\rangle_{\Omega_p}\right]_{nopol} = \quad (106b)$$
$$C''\{[\text{Re}\{I_0(\rho_{rel}, z, z_t^c)\}]^2 + 2[\text{Re}\{I_1(\rho_{rel}, z, z_t^c)\}]^2 + [\text{Re}\{I_2(\rho_{rel}, z, z_t^c)\}]^2\}$$

for the $4\pi$ and coherent lattice detection ("CLD") arrangements of FIGS. 82A and 82B, respectively, where C" is a normalization constant. These are shown as three-dimensional plots of detection efficiency isosurfaces in FIGS. 83A and 83B, respectively, and in related two-dimensional plots in the x-y and x-z planes in FIGS. 83C, 83D and 83E, 83F, respectively. The difference in the middle term of Equations (106a) and (106b) is due to the opposite relative symmetry of the superimposed virtual images in the two cases. As seen in FIGS. 83C and 83D, this leads to slightly improved transverse detection resolution in the $4\pi$ case, but at the cost of being valid only at the focal point common to the objectives, as opposed to anywhere in a desired plane.

As seen by comparing FIGS. 75 and 83B, one advantage of coherent lattice detection as shown in FIG. 82B as opposed to single objective detection as shown in FIG. 78A is that the detection resolution along $\hat{e}_z$ and the rejection of out of plane emission are improved. An additional advantage is that the constructive interference in the coherent case results in an electromagnetic field amplitude at the filtering apertures being $\sqrt{2}$ times as large (assuming an equal transmission/reflection ratio at the beam splitter), therefore yielding a signal twice as large. Furthermore, the signal (8237) passing through the other leg of beam splitter (8207) can be imaged with a second tube lens onto a second detector or aperture mask/detector assembly (not shown), so that the total signal is four times as large. Of course, the arrangement in FIG. 78A can be replicated in a mirror image about the lattice plane without coherent recombination of the two rear pupil beams as discussed above to result in a signal twice as large as with a single lens, but half as large as with coherent detection through both beam splitter legs. Although twice the expense of the single lens arrangement, separate detection of the rear pupil fields does not require the same component alignment precision of the coherent system. In short, cost and complexity in the detection arrangement must be weighed against the overall detection efficiency required for any given application.

A number of implementations have been disclosed. However, other additional implementations, features, and advantages are covered by the following claims.

What is claimed is:

1. A method for creating a periodic interference pattern of coherent waves in two or three dimensions, D, the method comprising:
   generating at least D+2 waves, wherein each wave has a substantially identical wavelength, $\lambda$, and travels substantially in a unique direction, $k_i$, wherein the subscript, "i" is an index variable used to indicate a wave;
   directing said waves such that at least a portion of each wave intersects in a common excitation region to create the pattern, wherein:
   the directions, $k_n$, of the waves are selected such that the interference pattern within the excitation region forms a Bravais lattice, wherein the subscript, "n" is an index variable used to indicate a plurality of waves;
   at least one wave travels substantially in a direction, $k_i$, such that one or more symmetry operations characteristic of the Bravais lattice map the direction of the wave, $k_i$, onto a direction of a different wave, $k_j$, wherein the subscript, "j" is an index variable used to indicate a wave that is different from another wave that is indicated by the subscript "i"; and
   the directions of the waves, $k_n$, do not all lie on a D-dimensional set of mutually orthogonal axes.

2. The method of claim 1, wherein the waves are electromagnetic waves.

3. The method of claim 1, wherein the direction, $k_i$, of each wave forms substantially the same angle, $\theta$, with respect to a fixed axis, $\hat{e}_{2D}$.

4. The method of claim 1, wherein for substantially each wave traveling substantially in a unique direction, $k_i$, another wave exists traveling substantially in a direction, $k_j$, that is determined by applying any combination of symmetry operations associated with the Bravais lattice to the direction of the wave $k_i$.

5. The method of claim 2, further comprising controlling a property of at least one wave to enhance an intensity in the interference pattern at a predetermined point in each primitive cell within the excitation region.

6. The method of claim 5, wherein the property is a phase of the at least one wave.

7. The method of claim 5, wherein the property is an amplitude of the at least one wave.

8. The method of claim 2, further comprising controlling a property of at least one wave to enhance a contrast between an intensity at a predetermined point in each primitive cell within the excitation region and an intensity at regions adjacent to the predetermined point within each such primitive cell.

9. The method of claim 8, wherein the property is a phase of the at least one wave.

10. The method of claim 8, wherein the property is an amplitude of the at least one wave.

11. The method of claim 2, further comprising controlling a property of at least one wave to enhance a predetermined component of the polarization of the electric field in the interference pattern at a predetermined point in each primitive cell within the excitation region.

12. The method of claim 2, further comprising controlling a complex electric field polarization, $e_n(x,t)$, of at least one wave to enhance a real part of the wave's complex projection, $Re\{e_n^*(x_d,t_d)' \cdot e_d\}$, at a time, $t_d$, and at a relative point, $x_d$, in each primitive cell within the excitation region onto a complex electric field vector, $e_d$, describing the desired state of a total electric field in the interference pattern at the same time, $t_d$, and the same position, $x_d$.

13. The method of claim 2, further comprising controlling a property of at least one wave to reduce an intensity in the interference pattern at a predetermined point within each primitive cell of the lattice within the excitation region.

14. The method of claim 13, further comprising controlling a property of the at least one wave to enhance an intensity in the interference pattern in at least a portion of a region surrounding the predetermined point in each primitive cell where the intensity has been reduced.

15. The method of claim 1, further comprising controlling a phase of substantially all waves to translate the interference pattern in space.

16. The method of claim 2, further comprising rotating the Bravais lattice and its constituent waves together with respect to a longitudinal axis, $\hat{e}_z$, of a lens in order to increase the number of waves substantially traveling in directions, $k_n$, within the solid angle defined by the numerical aperture of the lens.

17. The method of claim 2, further comprising directing the maximum number of waves traveling in the unique directions, $k_n$, which lie within a solid angle defined by a numerical aperture of a lens through the lens to create the Bravais lattice.

18. The method of claim 2, further comprising controlling the ratios of the lattice constants of the lattice in order to control the number of waves substantially traveling in directions, $k_n$, within the solid angle defined by the numerical aperture of a lens.

19. An optical system for generating an optical lattice in two or three dimensions, D, the optical system comprising:
a source of electromagnetic radiation having a wavelength, $\lambda$;
one or more dividing optical elements configured to divide the radiation into at least D+2 independent excitation beams; and
directing optical elements configured to direct each excitation beam substantially in a unique direction, $k_i$, wherein the subscript, "i" is an index variable used to indicate a beam, such that substantially all the beams intersect to create the optical lattice within an excitation region,
the directions, $k_n$, of the beams are selected such that the interference pattern within the excitation region forms a Bravais lattice, wherein the subscript, "n" is an index variable used to indicate a plurality of beams;
at least one beam travels substantially in a direction, $k_i$, such that one or more symmetry operations characteristic of the Bravais lattice map the direction of the beam, $k_i$, onto a direction of a different beam, $k_j$, wherein the subscript, "j" is an index variable used to indicate a beam that is different from another beam that is indicated by the subscript "i"; and
the directions of the beams, $k_n$, do not all lie on a D-dimensional set of mutually orthogonal axes.

20. The optical system of claim 19, further comprising:
a first lens, having a rear pupil side and an opposite focusing side facing the excitation region, wherein the directing optical elements are configured for directing at least two of the excitation beams into the rear pupil of the lens at distinct beam-center positions, $x_n''$, chosen such that the beams exit from the focusing side of the lens in the unique directions, $k_i$,
wherein the directions, $k_n$, of the beams that exit from the focusing side of the lens lie substantially within a solid angle defined by a numerical aperture of the lens.

21. The optical system of claim 20, wherein the directing optical elements are configured such that the optical lattice includes a Bravais lattice within the excitation region, the Bravais lattice having a symmetry, a shape to the primitive cell defined by the D-dimensional region closest to any chosen lattice point, and a periodicity relative to the wavelength, $\lambda$, that is larger than the smallest periodicity Bravais lattice having the same symmetry and identically defined primitive cell shape that can be created at the wavelength, X, and wherein the directions, $k_n$, of all the beams do not lie on a D-dimensional set of mutually orthogonal axes.

22. The optical system of claim 20, further comprising a first optical element configured to control an effective cross-section of a beam at the plane of the rear pupil.

23. The optical system of claim 22, wherein the first optical element comprises a substantially opaque mask having a substantially transmissive aperture.

24. The optical system of claim 22, wherein the first optical element comprises a diffractive optical element.

25. The optical system of claim 22, wherein the first optical element comprises a spatial light modulator.

26. The optical system of claim 20, further comprising a second optical element adapted for controlling the intensity of at least one of the beams entering the lens.

27. The optical system of claim 20, further comprising a third optical element configured for controlling a phase at the plane of the rear pupil across at least one of the beams entering the lens.

28. The optical system of claim 27, wherein the third optical element comprises a spatial light modulator.

29. The optical system of claim 20, further comprising a fourth optical element configured for controlling a polarization of at least one of the beams entering the lens.

30. The optical system of claim 20, wherein the optical lattice is created at least in part by the intersection of substantially all beams substantially traveling in unique directions, $k_n$, that reside within a solid angle defined by the numerical aperture of the lens and that can be found by applying any combination of symmetry operations of the Bravais lattice to the direction vector, $k_m$, of any other constituent beam of the lattice.

31. The optical system of claim 20, wherein the first lens comprises a high numerical aperture microscope objective having a numerical aperture greater than 0.9.

32. The optical system of claim 31, wherein the microscope objective is adapted for collecting light arising from an interaction of the lattice with a sample that at least partially overlaps with the excitation region.

33. The optical system of claim 31, further comprising at least one additional beam contributing to the creation of the lattice that reaches the excitation zone from outside the objective.

34. The optical system of claim 31, wherein the lattice is a three-dimensional lattice, and is oriented such that multiple lattice planes are oriented substantially parallel to a focal plane of the objective.

35. The optical system of claim 31, wherein the lattice is a two-dimensional lattice, and each beam is directed at substantially the same angle with respect to a longitudinal axis, $\hat{e}_z$, of the objective, and resides within the solid angle defined by its numerical aperture.

36. The optical system of claim 20 further comprising a second lens, having a rear pupil side and an opposite focusing side, wherein the optical elements are configured for directing at least two of the excitation beams through the second lens.

37. The optical system of claim 36, wherein the focusing sides of the first and second lenses oppose one another and their longitudinal axes are substantially parallel.

38. The optical system of claim 36, wherein the first and second lenses comprise high numerical aperture microscope objectives having numerical apertures greater than 0.9.

39. The optical system of claim 38, wherein the microscope objectives are configured for collecting light arising from an interaction of the lattice with the sample that at least partially overlaps with the excitation region.

40. The optical system of claim 38, wherein the optical lattice is created at least in part by the intersection of all beams substantially traveling in unique directions, $k_n$, residing within the total solid angle defined by the numerical apertures of the two objectives and that can be found by applying any combination of the symmetry operations of the Bravais lattice to the direction vector, $k_m$, of any other constituent beam of the lattice.

41. The optical system of claim 38, wherein the directing optical elements direct at least one beam contributing to creation of the lattice to the excitation zone by passing the at least one beam through the space between the two objectives.

42. The optical system of claim 41, wherein the directing optical elements are configured to direct the beams traveling in the unique directions, $k_n$, to generate a lattice that can be found by applying any combination of the symmetry operations of the Bravais lattice to the direction, $k_m$, of any other constituent beam of the lattice and that either reside within the total solid angle defined by the numerical apertures of the two objectives or that travel outside the objectives and that can reach the excitation zone without being substantially occluded by the objectives.

43. The optical system of claim 20, further comprising phase-controlling optical elements configured for introducing a controllable, independent overall phase to substantially every beam that contributes to the lattice.

44. The optical system of claim 43, further comprising:
a sample at least partially overlapping with the excitation region; and
a detector adapted for detecting deviations from a desired basis associated with the lattice,
wherein the phase-controlling optical elements are configured for independently controlling the overall phase of substantially every beam to reduce the detected deviations in the basis by reducing deviations in the phases of the beams relative to one another at a predetermined point within both the sample and the excitation region.

* * * * *

UNITED STATES PATENT AND TRADEMARK OFFICE
CERTIFICATE OF CORRECTION

PATENT NO. : 7,894,136 B2  Page 1 of 1
APPLICATION NO. : 11/719928
DATED : February 22, 2011
INVENTOR(S) : Robert Eric Betzig It is certified that error appears in the above-identified patent and that said Letters Patent is hereby corrected as shown below:

On Title page, in Item (54), in "TITLE", in column 1, line 2, delete "PEDIODIC" and insert -- PERIODIC --, therefor.

In column 1, line 2, delete "PEDIODIC" and insert -- PERIODIC --, therefor.

In column 102, line 49, in claim 1, delete "$k_i$, wherein" and insert -- $k_j$, wherein --, therefor.

In column 104, line 37, in claim 21, delete "X," and insert -- $\lambda$, --, therefor.

Signed and Sealed this
Twenty-sixth Day of April, 2011

David J. Kappos
*Director of the United States Patent and Trademark Office*